US012691172B2

(12) United States Patent
Heeney et al.

(10) Patent No.: US 12,691,172 B2
(45) Date of Patent: Jul. 28, 2026

(54) CORONAVIRUS VACCINES

(71) Applicants: DIOSynVax Ltd, Cambridge (GB);
**The Chancellor, Masters and Scholars
of the University of Cambridge**,
Cambridge (GB)

(72) Inventors: Jonathan Luke Heeney, Cambridge
(GB); Sneha Vishwanath, Cambridge
(GB); George William Carnell,
Cambridge (GB); David Wells,
Hertford (GB); Matteo Ferrari,
Hertford (GB)

(73) Assignees: DIOSynVax Ltd, Hertford (GB);
Cambridge Enterprise Limited,
Cambridge (GB)

( * ) Notice: Subject to any disclaimer, the term of this
patent is extended or adjusted under 35
U.S.C. 154(b) by 700 days.

(21) Appl. No.: 17/916,369

(22) PCT Filed: Apr. 1, 2021

(86) PCT No.: PCT/GB2021/050830
§ 371 (c)(1),
(2) Date: Sep. 30, 2022

(87) PCT Pub. No.: WO2021/198706
PCT Pub. Date: Oct. 7, 2021

(65) Prior Publication Data
US 2024/0285751 A1 Aug. 29, 2024

(30) Foreign Application Priority Data

Apr. 1, 2020 (GB) ...................................... 2004826
Jul. 10, 2020 (GB) ...................................... 2010672
(Continued)

(51) Int. Cl.
*A61K 39/215* (2006.01)
*A61K 39/00* (2006.01)
(Continued)

(52) U.S. Cl.
CPC ............ *A61K 39/215* (2013.01); *A61P 31/14*
(2018.01); *C07K 14/005* (2013.01); *C12N 7/00*
(2013.01);
(Continued)

(58) Field of Classification Search
None
See application file for complete search history.

(56) References Cited

U.S. PATENT DOCUMENTS 10,702,600 B1 7/2020 Ciaramella et al.
11,918,643 B2 * 3/2024 Roth .................. C12N 15/1131
(Continued)

FOREIGN PATENT DOCUMENTS

CN 102690336 A 9/2012
CN 106928326 A1 7/2017
(Continued)

OTHER PUBLICATIONS

International Search Report and Written Opinion dated Sep. 27,
2021 issued in PCT/GB2021/050830.
(Continued)

*Primary Examiner* — David W Berke-Schlessel
(74) *Attorney, Agent, or Firm* — Scully, Scott, Murphy &
Presser, P.C.

(57) ABSTRACT

Designed coronavirus polypeptide sequences are described,
and their use as vaccines against viruses of the coronavirus
family. The designed sequences include designed coronavi-
rus spike(S) proteins and fragments thereof, including
designed S protein receptor binding domain (RBD)
sequence SEQ ID NO:17, designed truncated S protein
(Continued)

sequence SEQ ID NO:15, and designed full length S protein sequence SEQ ID NO:13. Designed coronavirus envelope (E), membrane (M), and nucleocapsid (N) protein sequences are also described, and their use as vaccines. Nucleic acid molecules encoding the polypeptides, vectors, fusion proteins, pharmaceutical compositions, cells, and their use as vaccines against viruses of the coronavirus family are also described.

22 Claims, 68 Drawing Sheets

Specification includes a Sequence Listing.

(30) Foreign Application Priority Data

| Oct. 5, 2020 | (GB) | ..................................... | 2015775 |
|---|---|---|---|
| Feb. 10, 2021 | (GB) | ..................................... | 2101824 |
| Mar. 8, 2021 | (GB) | ..................................... | 2103214 |

(51) Int. Cl.
| | | |
|---|---|---|
| *A61P 31/14* | (2006.01) | |
| *C07K 14/005* | (2006.01) | |
| *C12N 7/00* | (2006.01) | |

(52) U.S. Cl.
CPC ................. *A61K 2039/5256* (2013.01); *C12N 2770/20034* (2013.01)

(56) References Cited

U.S. PATENT DOCUMENTS

| 2006/0121580 A1 | 6/2006 | Crucell |
|---|---|---|
| 2008/0027006 A1 | 1/2008 | Tripet et al. |
| 2010/0150923 A1 | 6/2010 | Jiang et al. |
| 2017/0096455 A1 | 4/2017 | Baric et al. |

FOREIGN PATENT DOCUMENTS

| JP | 2019-169120 A | 10/2019 |
|---|---|---|
| WO | 2015143335 A1 | 9/2015 |
| WO | 2021/156267 A1 | 8/2021 |
| WO | 2021/160346 A1 | 8/2021 |
| WO | 2023/275538 A1 | 1/2023 |

OTHER PUBLICATIONS

Du Lanying et al., "A 219-mer CHO-Expressing Receptor-Binding Domain of SARS-CoV S Protein Induces Potent Immune Responses and Protective Immunity", Viral Immunology (Apr. 1, 2010), vol. 23, No. 2, pp. 211-219, XP055784512, Retrieved from the Internet: URL:https://www.liebertpub.com/doi/pdfplus /10.1089/vim.2009. 0090>.

Yan R. et al., "Structural Basis for the Recognition of SARS-CoV-2 by Full-Length Human ACE2", Science 367:1444-1448 (Mar. 2020).

Yang J. et al., "A Vaccine Targeting the RBD of the S Protein of SARS-CoV-2 Induces Protective Immunity", Nature 586:572-577 (Oct. 22, 2020).

Yip M S et al., "Antibody-Dependent Infection of Human Macrophages by Severe Acute Respiratory Syndrome Coronavirus", Virology Journal 11:82 (2014).

Yu J. et al., "DNA Vaccine Protection Against SARS-CoV-2 in Rhesus Macaques", Science 369:806-811 (Aug. 2020).

Yurkovetskiy L. et al., "Structural and Functional Analysis of the D614G SARS-CoV-2 Spike Protein Variant", Cell 183:739-751 (Oct. 29, 2020).

Zahradnik J. et al., "SARS-CoV-2 RBD In Vitro Evolution Follows Contagious Mutation Spread, Yet Generates an Able Infection Inhibitor", bioRxiv preprint doi: https://doi.org/10.1101/2021.01.06. 425392 (Jan. 29, 2021).

Zahradnik J. et al., "SARS-CoV-2 Variant Prediction and Antiviral Drug Design are Enabled by RBD In Vitro Evolution", Nature Microbiology 6:1188-1198 (Sep. 2021).

Zhang J. et al., "Progress and Prospects on Vaccine Development Against SARS-CoV-2", Vaccines 8:153 (2020).

Zhang L. et al., "Antibody Responses Against SARS Coronavirus are Correlated With Disease Outcome of Infected Individuals", Journal of Medical Virology 78:1-8 (2006).

Zhao J. et al., "Antibody Responses to SARS-CoV-2 in Patients of Novel Coronavirus Disease 2019", medRxiv prepint doi: https:// doi.org/10.1101/2020.03.02.20030189 (Mar. 3, 2020).

Sarwar U.N. et al., "Safety and Immunogenicity of DNA Vaccines Encoding Ebolavirus and Marburgvirus Wild-Type Glycoproteins in a Phase I Clinical Trial", JID 211:549-557 (Feb. 2015).

Self W.H. et al., "Comparative Effectiveness of Moderna, Pfizer-BioNTech, and Janssen (Johnson & Johnson) Vaccines in Preventing COVID-19 Hospitalizations Amond A dults Without Immunocompromising Conditions", MMWR 70( )38):1337-1343 (Sep. 204, 2021).

Seow J. et al., "Longitudinal Evaluation and Decline of Antibody Responses in SARS-CoV-2 Infection", medRxiv preprint doi: https:// doi.org/10.1101/2020.07_09_20148429 (Jul. 11, 2020).

Shaimardanova A.A. et al., "Production and Application of Multicistronic Constructs for Various Human Disease Therapies", Pharmaceutics 11:580 (Nov. 2019).

Shen M-Y et al., "Statistical Potential for Assessment and Prediction of Protein Structures", Protein Science 15:2507-2524 (2006).

Shin M.D. et al., "COVID-19 Vaccine Development and a Potential Nanomaterial Path Forward", Nature Nanotechnology 15:646-655 (2020).

Shi P-Y et al., "Neutralization of N501Y Mutant SARS-CoV-2 by BNT162b2 Vaccine-Elicited Sera", DOI: https://doi.org/10.21203/ rs_3.rs-143532.vl (Jan. 7, 2021).

Siddell S.G., "The Coronaviridae", Plenum Press (10 pages) (1995).

Singh J. et al., "Evolutionary Trajectory of SARS-CoV-2 and Emerging Variants", Virology Journal 18:166 (2021).

Smith T.F. et al., "Comparison of Biosequences", Advances in Applied Mathematics 2:482-489 (1981).

Kruskal J.B., "Time Warps, String Edits and Macromolecules: the Theory and Practice of Sequence Comparison", Sankoff & Kruskal (eds), pp. 1-44, Addison Wesley; programs available from http:// www.ebi.ac.uk/tools/emboss/align (1983).

Kustin T. et al., "Evidence for Increased Breakthrough Rates of SARS-CoV-2 Variants of Concern in BNT162b2- mRNA-Vaccinated Individuals", Nature Medicine 27:1379-1384 (Aug. 2021).

Larkin M.A. et al., "Clustal W and Clustal X Version 2.0", Bioinformatics Applications Note 23(21):2947-2948 (2007).

Larsen M D et al., "Afucosylated Immunoglobulin G Responses are a Hallmark of Enveloped Virus Infections and Show an Exacerbated Phenotype in COVID-19", bioRxiv preprint doi: https://doi.org/10. 1101/2020.05.18.099507 (May 18, 2020).

Le Bert N. et al., "SARS-CoV-2-Specific T Cell Immunity in Cases of COVID-19 and SARS, and Uninfected Controls", Nature 584:457-462 (Aug. 20, 2020).

Letko M. et al., "Functional Assessment of Cell Entry and Receptor Usage for SARS-CoV-2 and Other Lineage B Betacoronaviruses", Nature Microbiology 5:562-569 (Mar. 2020).

Leung K. et al., "Early Transmissibility Assessment of the N501Y Mutant Strains of SARS-CoV-2 in the United Kingdom, Oct. to Nov. 2020", Euro Surveill 26(1):pii=2002106 (2021).

Li Q. et al., "The Impact of Mutations in SARS-Co V-2 Spike on Viral Infectivity and Antigenicity", Cell 182:1284-1294 (Sep. 3, 2020).

Liu K. et al., "Cross-Species Recognition of SARS-CoV-2 to Bat ACE2", PNAS 118(1):e2020216118 (2021).

Loeb M. et al., "Randomized Controlled Trial of Influenza Vaccine in Patients With Heart Failure to Reduce Adverse Vascular Events (IVVE): Rationale and Design", American Heart Journal 212:36-44 (Jun. 2019).

Needleman S.B. et al., "A General Method Applicable to the Search for Similarities in the Amino Acid Sequence of Two Proteins", J. Mol. Biol. 48:443-453 (1970).

(56) References Cited

OTHER PUBLICATIONS

Nieto-Torres J.L. et al., "Severe Acute Respiratory Syndrome Coronavirus Envelope Protein Ion Channel Activity Promotes Virus Fitness and Pathogenesis", *PLoS Pathogens 10*(5):e1004077 (May 2014).

Olival K.J. et al., "Possibility for Reverse Zoonotic Transmission of SARS-CoV-2 to Free-Ranging Wildlife: A Case Study of Bats", *PLoS Pathog 16*(9):e1008758 (Sep. 3, 2020).

Pantaleo G. et al., "Safety and Immunogenicity of a Multivalent HIV Vaccine Comprising Envelope Protein With Either DNA or NYVAC Vectors (HVTN096): A Phase 1b, Double-Blind, Placebo0-Controlled Trial", *Lancet HIV 6*:e737-e749 (2019).

Pardi N. et al., "mRNA Vaccines—A New Era in Vaccinology", *Nature Reviews Drug Discovery 17*:261-279 (Apr. 2018).

Pearson W.R. et al., "Improved Tools for Biological Sequence Comparison", *Proc. Natl. Acad. Sci. USA 85*:2444-2448 (Apr. 1988).

Pedregosa F. et al., "Scikit-Learn: Machine Learning in Python", *Journal of Machine Learning Research 12*:2825-2830 (2011).

Peeples L., "Avoiding Pitfalls in the Pursuit of a COVID-19 Vaccine", *PNAS 117*(15):8218-8221 (Apr. 14, 2020).

Peng Y. et al., "Broad and Strong Memory CD4+ and CD8+ T Cells Induced by SARS-CoV-2 in UK Convalescent COVID-19 Patients", bioRxiv preprint doi: doi: 10.1038/s41599-020-0782-6 (Jun. 8, 2020).

Perez P. et al., "The Combined Vaccination Protocol of DNA/MVA Expressing Zika Virus Structural Proteins as Efficient Inducer of T and B Cell Immune Responses", *Emerging Microbes & Infections 10*(1):1441-1456 (2021).

Long Q-X et al., "Clinical and Immunological Assessment of Asymptomatic SARS-CoV-2 Infections", *Nature Medicine 26*:1200-1204 (Aug. 2020).

Lopez Bernal J. et al., "Effectiveness of the Pfizer-BoNTech and Oxford-AstraZeneca Vaccines on Covid-19 Related Symptoms, Hospital Admissions, and Mortality in Older Adults in England: Test Negative Case-Control Study", *BMJ 373*:n1088 (2021).

Lopez Bernal J. et al., "Effectiveness of Covid-19 Vaccines Against the B.1.617.2 (Delta) Variant", *The New England Journal of Medicine 385*(7):585-594 (Aug. 12, 2021).

Madhi S.A. et al., "Efficacy of the ChAdOx1 nCoV-19 Covid-19 Vaccine Against the B.1.351 Variant", *The New England Journal of Medicine 384*(20):1885-1898 (May 20, 2021).

Martin J.E. et al., "A SARS DNA Vaccine Induces Neutralizing Antibody and Cellular Immune Responses in Healthy Adults in a Phase I Clinical Trial", *Vaccine 26*:6338-6343 (2008).

Martin D.P. et al., "Selection Analysis Identifies Unusual Clustered Mutational Changes in Omicron Lieage BA.1 That Likely Impact Spike Function", bioRxiv preprint doi: https://doi.org/10.1101/2022.01.14.476382 (Jan. 18, 2022).

Menachery V.D. et al., "A SARS-Like Cluster of Circulating Bat Coronaviruses Shows Potential for Human Emergence", *Nature Medicine 21*(12):1508-1513 (Dec. 2015).

Meng B. et al., "Altered TMPRSS2 Usage by SARS-CoV-2 Omicron Impacts Infectivity and Fusogenicity", *Nature 603*:706-714 (Mar. 24, 2022).

Mooij P. et al., "Needle-Free Delivery of DNA: Targeting of Hemagglutinin to MHC Class II Molecules Protects Rhesus Macaques Against H1N1 Influenza", *Vaccine 37*:817-826 (2019).

Montagutelli X. et al., "The B1.351 and P.1 Variants Extend SARS-CoV-2 Host Range to Mice", bioRxiv preprint doi: https://doi.org/10_1101/2021.03_18.436013 (Dec. 2021).

La Vie M. et al., "Glycan Shielding and Modulation of Hepatitis C Virus Neutralizing Antibodies", *Frontiers in Immunology 9*(910):1-9 (Apr. 2018).

Li W. et al., "Animal Origins of the Severe Acute Respiratory Syndrome Coronvirus: Insight from ACE2-S-Protein Interactions", *Journal of Virology 80*(9):4211-4219 (May 2006).

Nguyen L-T et al., "IQ-TREE: A Fast and Effective Stochastic Algorithm for Estimating Maximum-Likelihood Phylogenies", *Mol. Biol. Evol. 32*(1):268-274 (2015).

Pinto D. et al., "Cross-Neutralization of SARS-CoV-2 by a Human Monoclonal SARS-CoV Antibody", *Nature 583*:290-295 (2020).

Eswar N. et al., "Comparative Protein Structure Modeling Using Modeller", *Current Protocols in Protein Science Unit 2.9, Supplemental 50* (Nov. 2007).

GenScript "SARS-CoV-2 Surrogate Virus Neutralization Test Kit", (14 pages) (Jul. 20, 2020).

"WHO Announces Simple, Easy-to-Say Labels for SARS-CoV-2 Variants of Interest and Concern", https://www.who.int/news/item/31-05-2021-who-announces-simple-easy-to-say-labels-for-sars-cov-2-variants-of-interest-and-concern (2021).

Craven J., Regulatory Focus, News Articles, 2020, 3, COVID-19 Vaccine Tracker: https://www.raps.org/news-and-articles/news-articles/2020/3/covid-19-vaccine-tracker (2022).

Chinese Office Action & Search Report dated Mar. 13, 2024 received in Chinese Patent Application No. 202180039232.6, together with an English-language translation.

Japanese Office Action dated Jun. 28, 2025 received in Japanese Patent Application No. 2022-560285, together with an English-language translation.

Vilar S. et al., "One Year of SARS-CoV-2: How Much Has the Virus Changed?", *Biology 10*:91 (2021).

Volz E. et al., "Evaluating the Effects of SARS-CoV-2 Spike Mutation D614G on Transmissibility and Pathogenicity", *Cell 184*:64-75 (Jan. 7, 2021).

Voysey M. et al., "Safety and Efficacy of the ChAdOx1 nCoV-19 Vaccine (AZD1222) Against SARS-CoV-2: An Interim Analysis of Four Randomised Controlled Trials in Brazil South Africa and the UK", *The Lancet 397*:99-111 (Jan. 9, 2021).

Walls A.C. et al., "Structure, Function, and Antigenicity of the SARS-CoV-2 Spike Glycoprotein", *Cell 180*:281-292 (Apr. 16, 2020).

Wan Y. et al., "Molecular Mechanism for Antibody-Dependent Enhancement of Coronavirus Entry", *Journal of Virology 94*(5):e02015-19 (Mar. 2020).

Wang P. et al., "Increased Resistance of SARS-CoV-2 Variant P.1 to Antibody Neutralization", *Cell host & Microbe 29*:747-751 (May 12, 2021).

Wang Y. et al., "mRNA Vaccine: A Potential Therapeutic Strategy", *Molecular Cancer 20*(30):1-23 (2021).

Weisblum Y. et al., "Escape from Neutralizing Antibodies by SARS-CoV-2 Spike Protein Variants", *eLife 9*:e61312 (2020).

Wu K. et al., mRNA-1273 Vaccine Induces Neutralizing Antibodies Against Spike Mutants from Global SARS-CoV-2 Variants, bioRxiv preprint doi: https://doi.org/10.1101/2021.01.25.427948 (Jan. 25, 2021).

Wu Y. et al., "A Noncompeting Pair of Human Neutralizing Antibodies Block DOVID-19 Virus Binding to its Receptor ACE2", *Science 368*:1274-1278 (Jun. 12, 2020).

Planas D. et al., "Sensitivity of Infectious SARS-CoV-2 B.1.1.7 and B.1.351 Variants to Neutralizing Antibodies", *Nature Medicine 27*:917-924 (May 2021).

Polack F.P. et al., "Safety and Efficacy of the BNT162v2 mRNA Covid-19 Vaccine", *The New England Journal of Medicine 383*(27):2603-2615 (2020).

Polack F.P. et al., "Safety and Efficacy of the BNT162 mRNA Covid-19 Vaccine", *The New England Journal of Medicine 383*(27):2603-2615 (Dec. 31, 2020).

Pond S.L.K. et al., "HyPhy: Hypothesis Testing Using Phylogenies", *Bioinformatics Applications Note 21*(5):676-679 (2005).

Raab D. et al., "The GeneOptimizer Algorithm: Using a Sliding Window Approach to Cope With the Vast Sequence Space in Multiparameter DNA Sequence Optimization", *Syst Synth Biol. 4*:215-225 (2010).

Resende P C, "Spike E484K Mutation in the First SARS-CoV-2 Reinfection Case Confirmed in Brazil, 2020", (Jan. 2021), [Posted on www.virological.org on Jan. 10, 2021]) Website printed pdf.

Richert L. et al., "T Cell Immunogenicity, Gene Expression Profile, and Safety of Four Heterologous Prime-Boost Combinations of HIV Vaccine Candidates in Healthy Volunteers: Results of the Randomized Multi-Arm Phase I/II ANRS VRI01 Trial", *The Journal of Immunology 208*:2663-2674 (2022).

(56)                    References Cited

OTHER PUBLICATIONS

Robbiani D.F. et al., "Convergent Antibody Responses to SARS-CoV-2 in Covalescent Individuals", *Nature* 584:437-442 (Aug. 20, 2020).

Sadoff J. et al., "Safety and Efficacy of Single-Dose Ad26.COV2.S Vaccine Against Covid-19", *The New England Journal of Medicine* 384(23):2187-2201 (Jun. 10, 2021).

Sali A. et al., "Comparative Protein Modelling by Satisfaction of Spatial Restraints", *J. Mol. Biol.* 234:779-815 (1993).

Alberer M. et al., "Safety and Immunogenicity of a mRNA Rabies Vaccine in Healthy Adults: An Open-Label, Non-Randomised, Prospective, First-in-Human Phase 1 Clinical Trial", Lancet 390(10101):1511-1520 (Sep. 2017).

Altschul S.F. et al., "Issues in Searching Molecular Sequence Databases", Nature Genetics 6:119-129 (Feb. 1994).

Altschul S.F. et al., "Basic Local Alignment Search Tool", J. Mol. Biol. 215:403-410 (1990).

Amanat F. et al., "A Serological Assay to Detect SARS-CoV-2 Seroconversion in Humans", Nature Medicine 26:1033-1036 (Jul. 2020).

Asbach B. et al., "Priming With a Potent HIV-1 DNA Vaccine Frames the Quality of Immune Responses Prior to a Poxvirus and Protein Boost", Journal of Virology 93(3):e01529-18 (Feb. 2019).

Baden L.R. et al., "Efficacy and Safety of the mRNA-1273 SARS-CoV-2 Vaccine", The New England Journal of Medicine 384(5):403-416 (Feb. 4, 2021).

Barnes C.O. et al., "SARS-CoV-2 Neutralizing Antibody Structures Inform Therapeutic Strategies", Nature 588:682-687 (Dec. 24/31, 2020).

Barouch D.H. et al., "A Human T-Cell Leukemia Virus Type 1 Regulatory Element Enhances the Immunogenicity of Human Immunodeficiency Virus Type 1 DNA Vaccines in Mice and Nonhuman Primates", Journal of Virology 79(14):8828-8834 (Jul. 2005).

Berman H.M. et al., "The Protein Data Bank", Nucleic Acids Research 28(1):235-242 (2000).

Boussif O. et al., "A Versatile Vector for Gene and Oligonucleotide Transfer into Cells in Culture and In Vivo: Polyethylenimine", Proc. Natl. Acad. Sci. USA 92:7297-7301 (Aug. 1995).

Callaway E., "Delta Coronavirus Variant: Scientists Brace for Impact", Nature 595:17-18 (Jul. 1, 2021).

Campanella J.J. et al., "MatGAT: An Application that Generates Similarity/Identity Matrices Using Protein or DNA Sequences", BMC Bioinformatics 4(296) (2003).

Campbell F. et al., "Increased Transmissibility and Global Spread of SARS-CoV-2 Variants of Concern as at Jun. 2021", Euro Surveill 26(24):pii=2100509 (2021).

Carnell G.W. et al., "SARS-CoV-2 Spike Protein Arrested in the Closed State Induces Potent Neutralizing Responses", bioRxiv preprint doi: https://doi.org/10.1101/2021.01.14.426695 (Jan. 14, 2021).

Carnell G.W. et al., "SARS-CoV-2 Spike Protein Stabilized in the Closed State Induces Potent Neutralizing Responses", Journal of Virology 95(15):e00203-21 (Aug. 2021).

Carnell G. et al., "An Optimized Method for Production Using PEI, Titration and Neutralization of SARS-CoV Spike Luciferase Pseudotypes", Bio Protoc. 7(16):e2514 (Aug. 20, 2017).

Chakraborty S. et al., "Symptomatic SARS-CoV-2 Infections Display Specific IgG Fc Structures", medRxiv preprint doi: https://doi.org.10.1101/2020.05.15.20103341 (Nov. 2020).

Choi Y. et al., "Viral Vectors for Vaccine Applications", Clin Exp Vaccine Res 2:97-105 (2013).

Clay C. et al., "Primary Severe Acute Respiratory Syndrome Coronavirus Infection Limits Replication But Not Lung Inflammation Upon Homologous Rechallenge", Journal of Virology 86(8):4234-4244 (Apr. 2012).

Corbett K.S. et al., "SARS-CoV-2 mRNA Vaccine Design Enabled by Prototype Pathogen Preparedness", Nature 586(7830):567-571 (Oct. 2020).

Corpet F., "Multiple Sequence Alignment With Hierarchical Clustering", Nucleic Acids Research 16(22):10881-10890 (1988).

Dai L. et al., "A Universal Design of Betacoronavirus Vaccines Against COVID-19, MERS, and SARS", Cell 182:722-733 (Aug. 6, 2020).

Daly C. et al., "Needle-Free Injectors for Mass Administration of Fractional Dose Inactivated Poliovirus Vaccine in Karachi, Pakistan: A Survey of Caregiver and Vaccinator Acceptability", Vaccine 38:1893-1898 (2020).

Dong N. et al., "Genomic and Protein Structure Modelling Analysis Depicts the Origin and Infectivity of 2019-nCoV, a New Coronavirus Which Caused a Pneumonia Outbreak in Wuhan, China", bioRxiv preprint doi: https://doi.org/10.1101/2020.01.20.913368 (Jan. 22, 2020).

Du L. et al., "Neutralizing Antibodies for the Prevention and Treatment of COVID-19", Cellular & Molecular Immunology 18:2293-2306 (2021).

Du L. et al., "Introduction of Neutralizing Immunogenicity Index to the Rational Design of MERS Coronavirus Subunit Vaccines", Nature Communications 7:13473 (2016).

Fehr A.R. et al., "Coronaviruses: An Overview of Their Replication and Pathogenesis", Coronaviruses: Methods and Protocols, Methods in Molecular Biology 1282:1-23 (2015).

Garcia-Beltran W.F. et al., "Multiple SARS-CoV-2 Variants Escape Neutralization by Vaccine-Induced Humoral Immunity", Cell 184:2372-2383 (Apr. 29, 2021).

Greaney A.J. et al., "Comprehensive Mapping of Mutations to the SARS-CoV-2 Receptor-Binding Domain that Affect Recognition by Polyclonal Human Serum Antibodies", bioRxiv. [Preprint posted online Jan. 4, 2021].

Grifoni A. et al., "Targets of T Cell Responses to SARS-CoV-2 Coronavirus in Humans With COVID-19 Disease and Unexposed Individuals", Cell 181:1489-1501 (Jun. 25, 2020).

Higgins D.G. et al., Fast and Sensitive Multiple Sequence Alignments on a Microcomputer, Comput Appl Biosci. 5(2):151-153 (Apr. 1989).

Higgins D.G. et al., "Clustal: A Package for Performing Multiple Sequence Alignment on a Microcomputer", Gene 73:237-244 (1988).

Hoepel W. et al., "Anti-SARS-CoV-2 IgG from Severely Ill COVID-19 Patients Promotes Macrophage Hyper-Inflammatory Responses", bioRxiv preprint doi: https://doi.org/10.1101/2020.07.13.190140 (Jul. 13, 2020).

Hoffmann M. et al., "SARS-CoV-2 Cell Entry Depends on ACE2 and TMPRSS2 and is Blocked by a Clinically Proven Protease Inhibitor", Cell 181:271-280 (Apr. 16, 2020).

Horby P. et al., Nervtag Note on B.1.1.7 Severity. SAGE Meeting Report (Jan. 21, 2021).

Horspool A.M. et al., "SARS-CoV-2 B. 1.1.7 and B.1.351 Variants of Concern Induce Lethal Disease in K18-hACE2 Transgenic Mice Despite Convalescent Plasma Therapy", bioRxiv preprint doi: https://doi.org/10.1101/2021.05.05.442784 (May 5, 2021).

Hou X. et al., "Lipid Nanoparticles for mRNA Delivery", Nature 6:1078-1094 (Dec. 2021).

Hu B. et al., "Discovery of a Rich Gene Pool of Bat SARS-Related Coronaviruses Provides New Insights into the Origin of SARS Coronavirus", PLoS Pathog 13(11):e1006698 (2017).

Huang A. T. et al., A Systematic Review of Antibody Mediated Immunity to Coronaviruses: Antibody Kinetics, Correlates of Protection, and Association of Antibody Responses With Severity of Disease, medRxiv preprint doi: https://doi.org/10.1101/2020.04.14.20065771 (Apr. 17, 2020).

Hubert B. et al., "The CureVac Vaccine, and a Brief Tour Through Some of the Wonders of Nature", URL https://berthub.eu/articles/posts/curevac-vaccine-and-wonders-of-biology/.(accessed Sep. 15, 2021).

Hunter J.D., "Matplotlib: A 2D Graphics Environment", Computing in Science & Engineering 9(3):90-95(May/Jun. 2007).

Jaume M. et al., "Anti-Severe Acute Respiratory Syndrome Coronavirus Spike Antibodies Trigger Infection of Human Immune Cells via a pH- and Cystein Protease-Independent FcγR Pathway", Journal of Virology 85(20):10582-10597 (Oct. 2011).

Jeong D-E et al., "Assemblies of Putative SARS-CoV2-Spike-Encoding mRNA Sequences for Vaccines BNT-162b2 and mRNA-

(56) References Cited

OTHER PUBLICATIONS

1273", https://virological.org/t/assemblies-of-putative-sars-cov2-spike-encoding-mrna-sequences-for-vaccines-bnt-162b2-and-mrna-1273/663 (2021).

Jo W.K. et al., "The Evolutionary Dynamics of Endemic Human Coronaviruses", Virus Evolution 7(1):veab020 (2021).

Jordan I. et al., "A Deleted Deletion Site in a New Vector Strain and Exceptional Gemomic Stability of Plaque-Purified Modified Vaccina Ankara (MVA)", Virologica Sinica 35:212-226 (2020).

Jordan I. et al., "A Genotype of Modified Vaccinia Ankara (MVA) that Facilitations Replication in Suspension Cultures in Chemically Defined Medium", Viruses 5:321-339 (2013).

Jordan I. et al., "A Chemically Defined Production Process for Highly Attenuated Poxviruses", Biologicals 39:50-58 (2011).

Joseph S. et al., "A Comparative Phase I Study of Combination, Homologous Subtype-C DNA, MVA, and Env gp140 Protein/Adjuvant HIV Vaccines in Two Immunization Regimens", Frontiers in Immunology 8(149):1-14 (Feb. 2017).

Korber B. et al., "Tracking Changes in SARS-CoV-2 Spike: Evidence that D614G Increases Infectivity of the COVID-19 Virus", Cell 182:812-827 (Aug. 20, 2020).

Krivov G.G. et al., "Improved Prediction of Protein Side-Chain Conformations With SCWRL4", Proteins 77(4):778-795 (Dec. 2009).

Tai W. et al., "Characterization of the Receptor-Binding Domain (RBD) of 2019 Novel Coronavirus: Implication for Development of RBD Protein as a Viral Attachment Inhibitor and Vaccine", *Cellular & Molecular Immunology* 17:613-620 (2020).

Tay M Z et al., "The Trinity of COVID-19: Immunity, Inflammation and Intervention", *Nature Review Immunology* 20:363-374 (Jun. 2020).

Teixeira L. et al., "A First-in-Human Phase I Study of INVAC-1, an Optimized Human Telomerase DNA Vaccine in Patients With Advanced Solid Tumors", *Clin Cancer Res.* 26(3):588-597 (Feb. 1, 2020).

Tian F. et al., "Mutation N501Y in RBD of Spike Protein Strengthens the Inter-Action Between COVID-19 and its Receptor ACE2", bioRxiv preprint doi: https://doi.org/10.1101/2021.02.14.431117 (Feb. 15, 2021).

Traggiai E. et al., "An Efficient Method to Make Human Monoclonal Antibodies from Memory B Cells: Potent Neutralization of SARS Coronavirus", *Nature Medicine* 10(8):871-875 (Aug. 2004).

Tse L. V. et al., "The Current and Future State of Vaccines, Antivirals and Gene Therapies Against Emerging Coronaviruses", *Frontiers in Microbiology* 11:658 (Apr. 2020).

Tseng C-T et al., "Immunization With SARS Coronavirus Vaccines Leads to Pulmonary Immunopathology on Challenge With the SARS Virus", *PLoS ONE* 7(4):e35421 (Apr. 2012).

Ura T. et al., "Developments in Viral Vector-Based Vaccines", *Vaccines* 2:624-641 (2014).

Van Derr Spoel D. et al., "Gromacs: Fast, Flexible, and Free", *Journal of Computational Chemistry* 26(16):1701-1718 (Dec. 2005).

Viana R. et al., "Rapid Epidemic Expansion of the SARS-CoV-2 Omicron Variant in Southern Africa", *Nature* 603:679-686 (Mar. 24, 2022).

Zhou B. et al., "SARS-CoV-2 Spike D614G Variant Confers Enhanced Replication and Transmissibility", bioRxiv preprint doi: https://doi.org/10.1101/2020.10.27_357558 (Oct. 27, 2020).

Xiao K. et al., "Isolation and Characterization of 2019-nCoV-Like Coronavirus from Malayan Pangolins", bioRxiv preprint doi: https://doi.org/10.1101/2020.02.17.951335 (Feb. 20, 2020).

Xiong X. et al., "A Thermostable, Closed SARS-CoV-2 Spike Protein Trimer", *Nature Structural & Molecular Biology* 27:934-941 (Oct. 2020).

Xue T. et al., "Single Point Mutations Can Potentially Enhance Infectivity of SARS-CoV-2 Revealed by In Silico Affinity Maturation and SPR Assay", *RSC Adv.* 11:147367 (2021).

Yuan M. et al., "A Highly Conserved Cryptic Epitope in the Receptor Binding Domains of SARS-CoV-2 and SARS-CoV", *Science* 368:630-633 (May 8, 2020).

Watanabe Y. et al., "Structure of the Lassa Virus Glycan Shield Provides a Model for Immunological Resistance", *PNAS* 115(28):7320-7325 (Jul. 10, 2018).

Schymkowitz J. et al., "The FoldX Web Server: An Online Force Field", *Nucleic Acids Research* 33:W382-W388 (2005).

Edgar R.C., "Muscle: A Multiple Sequence Alignment Method With Reduced Time and Space Complexity", *BMC Bioinformatics* 5:113 (2004).

Hatcher E.L. et al., "Virus Variation Resource—Improved Response to Emergent Viral Outbreaks", *Nucleic Acids Research* 45:D482-D490 (2017).

Hwang W.C. et al., "Structural Basis of Neutralization by a Human Anti-Severe Acute Respiratory Syndrome Spike Protein Antibody, 80R", *The Journal of Biological Chemistry* 281(45):34610-34616 (Nov. 10, 2016).

International Search Report and Written Opinion dated Jan. 25, 2023 received in International Application No. PCT/GB2022/052537.

\* cited by examiner

Figure 4

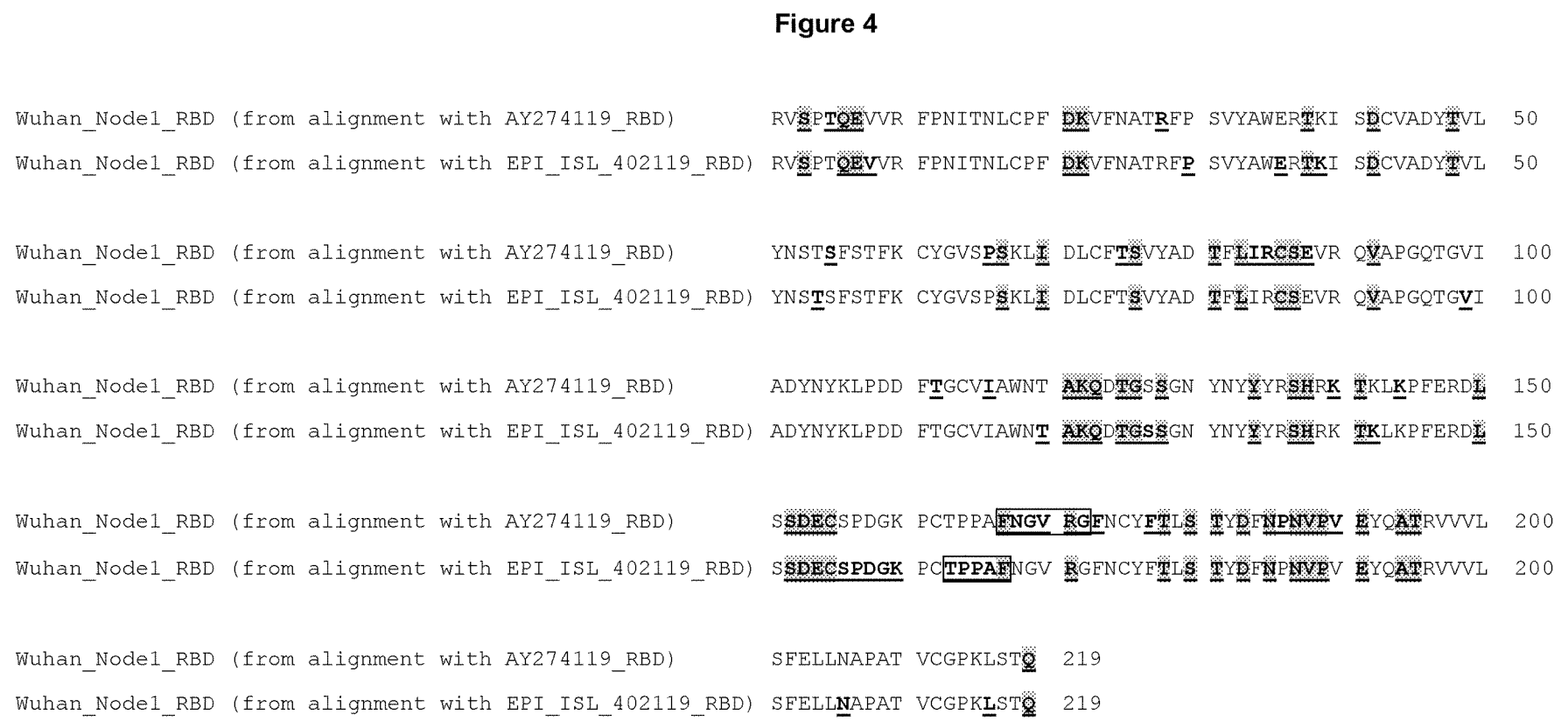

```
Wuhan_Node1_RBD (from alignment with AY274119_RBD)        RVSPTQEVVR FPNITNLCPF DKVFNATRFP SVYAWERTKI SDCVADYTVL   50
Wuhan_Node1_RBD (from alignment with EPI_ISL_402119_RBD)  RVSPTQEVVR FPNITNLCPF DKVFNATRFP SVYAWERTKI SDCVADYTVL   50

Wuhan_Node1_RBD (from alignment with AY274119_RBD)        YNSTSFSTFK CYGVSPSKLI DLCFTSVYAD TFLIRCSEVR QVAPGQTGVI  100
Wuhan_Node1_RBD (from alignment with EPI_ISL_402119_RBD)  YNSTSFSTFK CYGVSPSKLI DLCFTSVYAD TFLIRCSEVR QVAPGQTGVI  100

Wuhan_Node1_RBD (from alignment with AY274119_RBD)        ADYNYKLPDD FTGCVIAWNT AKQDTGSSGN YNYIYRSHRK TKLKPFERDI  150
Wuhan_Node1_RBD (from alignment with EPI_ISL_402119_RBD)  ADYNYKLPDD FTGCVIAWNT AKQDTGSSGN YNYIYRSHRK TKLKPFERDI  150

Wuhan_Node1_RBD (from alignment with AY274119_RBD)        SSDECSPDGK PCTPPAFNGV RGFNCYFILS TYDFNPNVPV EYQATRVVVL  200
Wuhan_Node1_RBD (from alignment with EPI_ISL_402119_RBD)  SSDECSPDGK PCTPPAFNGV RGFNCYFILS TYDFNPNVPV EYQATRVVVL  200

Wuhan_Node1_RBD (from alignment with AY274119_RBD)        SFELLNAPAT VCGPKLSTQ  219
Wuhan_Node1_RBD (from alignment with EPI_ISL_402119_RBD)  SFELLNAPAT VCGPKLSTQ  219
```

Figure 6

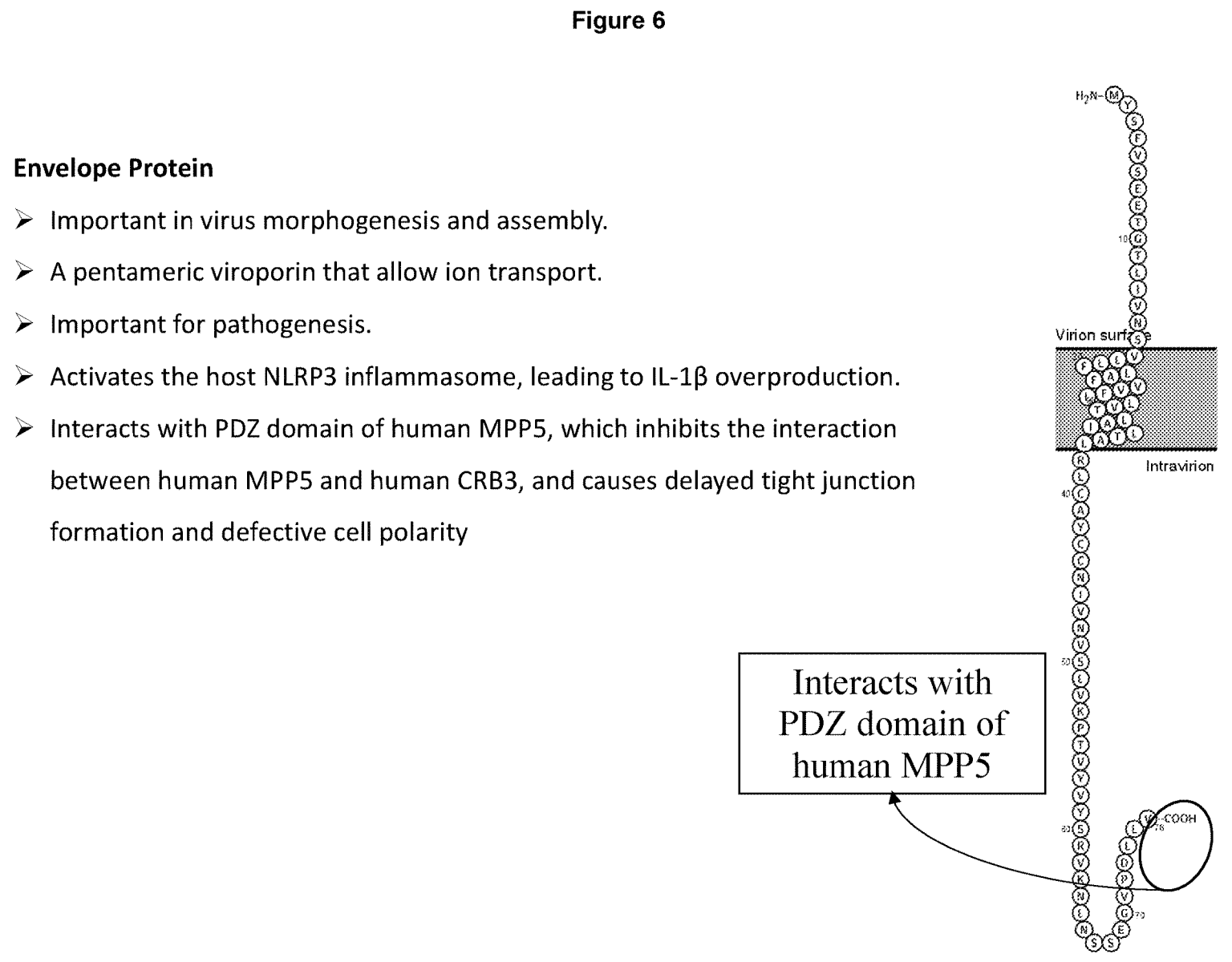

Envelope Protein

⋏ Important in virus morphogenesis and assembly.

⋏ A pentameric viroporin that allow ion transport.

⋏ Important for pathogenesis.

⋏ Activates the host NLRP3 inflammasome, leading to IL-1β overproduction.

⋏ Interacts with PDZ domain of human MPP5, which inhibits the interaction between human MPP5 and human CRB3, and causes delayed tight junction formation and defective cell polarity Interacts with PDZ domain of human MPP5

Figure 8

```
>COV_M_T1_1:MADSNGTITV EELKKLLEQW NLVIGFLFLT WICLLQFAYA NRNRFLYIIK LIFLWLLWPV TLACFVLAAV YRINWITGGI AIAMACIVGL MWLSYFIASF
>COV_M_T2_1:MAD-NGTITV EELKQLLEQW NLVIGFLFLA WIMLLQFAYS NRNRFLYIIK LVFLWLLWPV TLACFVLAAV YRINWVTGGI AIAMACIVGL MWLSYFVASF
>COV_M_T2_2:MADSNGTITV EELKKLLEQW NLVIGFLFLT WICLLQFAYS NRNRFLYIIK LIFLWLLWPV TLACFVLAAV YRINWVTGGI AIAMACIVGL MWLSYFVASF

>COV_M_T1_1:RLFARTRSMW SFNPETNILL NVPLHGTILT RPLLESELVI GAVILRGHLR IAGHHLGRCD IKDLPKEITV ATSRTLSYYK LGASQRVAGD SGFAAYSRYR
>COV_M_T2_1:RLFARTRSMW SFNPETNILL NVPLRGTILT RPLMESELVI GAVILRGHLR MAGHSLGRCD IKDLPKEITV ATSRTLSYYK LGASQRVGTD SGFAAYNRYR
>COV_M_T2_2:RLFARTRSMW SFNPETNILL NVPLRGSIIT RPLMESELVI GAVILRGHLR MAGHSLGRCD IKDLPKEITV ATSRTLSYYK LGASQRVASD SGFAVYNRYR

>COV_M_T1_1:IGNYKLNTDH SSSSDNIALL VQ   1>COV_M_T1_1 (1-222 NC_045512.2 SARS2 reference sequence) (SEQ ID NO:26)
>COV_M_T2_1:IGNYKLNTDH AGSNDNIALL VQ   2>COV_M_T2_1 (1-221 Sarbeco_M_root) (SEQ ID NO:24)
>COV_M_T2_2:IGNYKLNTDH SSSSDNIALL VQ   3>COV_M_T2_2 (1-222 Sarbeco_M_Node88b_epitope_optimised) (SEQ ID NO:25)
```

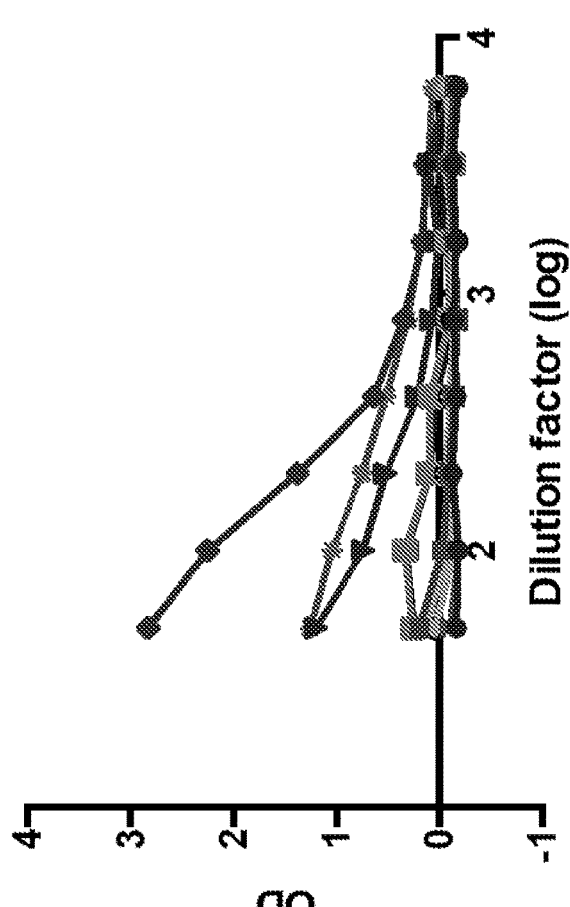
Figure 9

A) SARS1 Spike

B) SARS2 Spike c)

Figure 17
a)
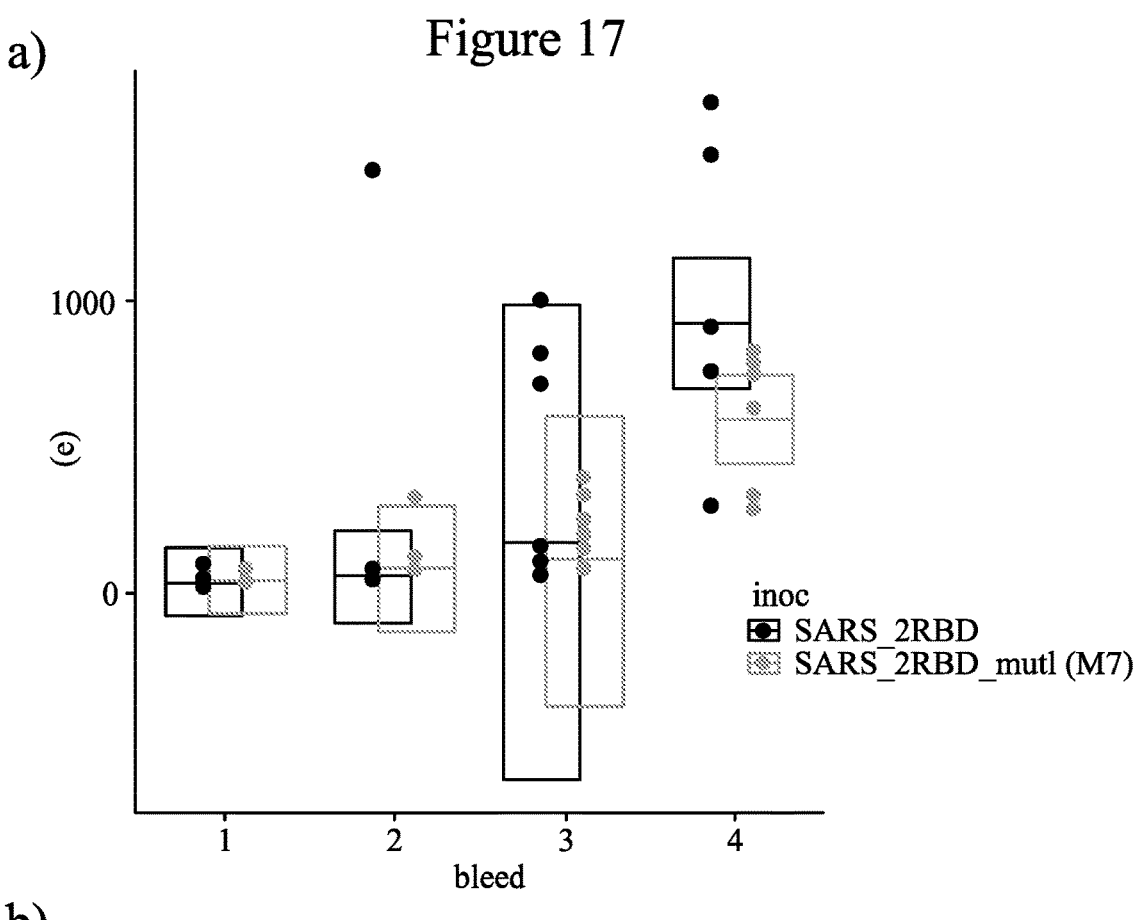
b)
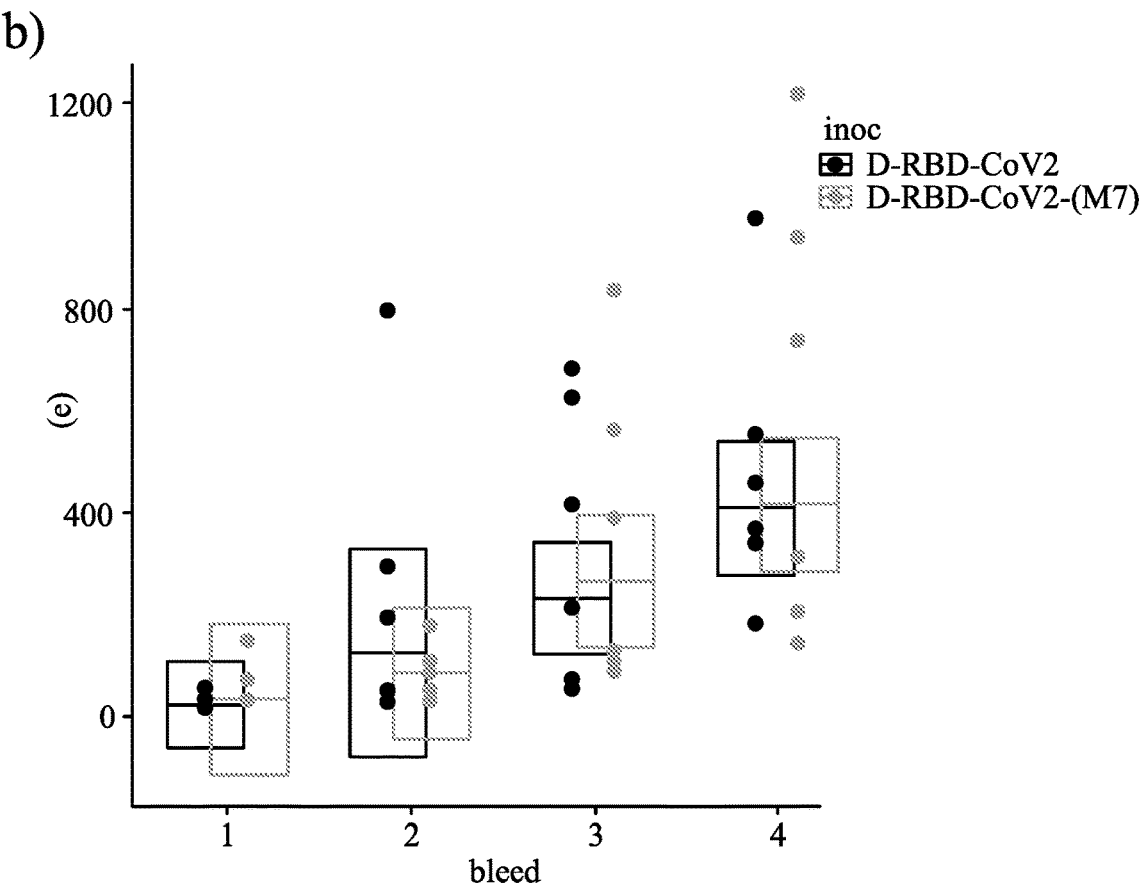

Implicated in antibody response*

Involved in interaction with spike **

N-glycans of CoV-2 Spike Trimer

- N-glycans released from S trimer by PNGaseF digestion
- Permethylated to enhance sensitivity and isomer detection by NSI-MSn
- Detected 64 N-glycan structures Figure 24
Figure 24(1). Sarbecoviruses with the SARS1 and SARS2 clades highlighted along with human or bat host species.
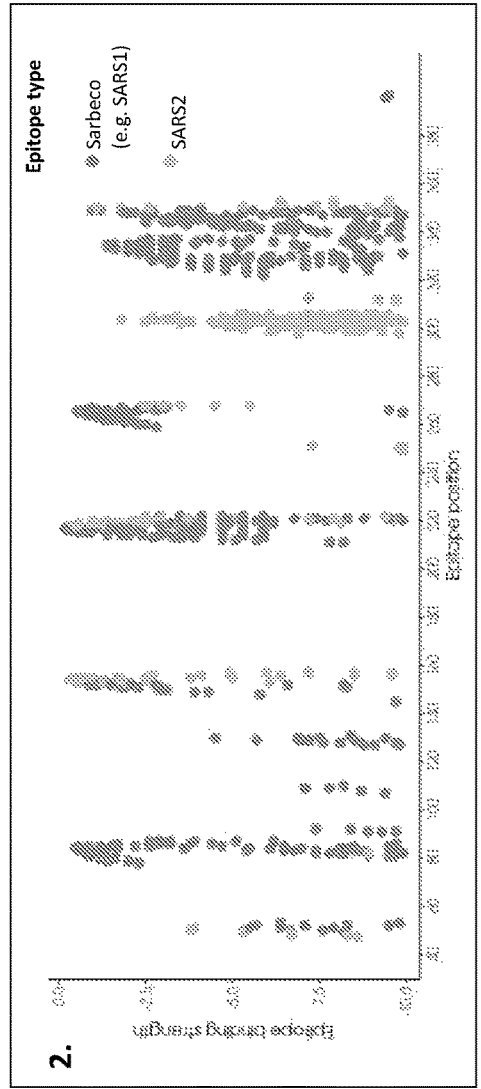
Figure 24(2). Machine learning predicted MHC class II binding (higher is stronger binding) of predicted epitopes within the insert. Lighter grey is for epitopes conserved within SARS2, darker grey are epitopes grafted in from other Sarbecoviruses such as SARS1.

Variant of concerns - UK, South African, and Brazil

| Variant | Mutations |
|---|---|
| UK | 69Δ, 70Δ, 144Δ, N501Y, A570D (B), D614G, P681H, T761I, S982A, D1118H |
| South Africa | K417N, E484K, N501Y. D614G, A701V |
| Japan | L18F, T20N, P26S, D138Y, R190S, D614G, K417T, E484K, N501Y, D614G, H655Y, T1027I |

Top - view

Side - view

Figure 28

Broad coverage of Sarbecoviruses

▷ The immunodominant regions are often virus specific and rarely generate antibody response against related viruses.

▷ Variants often have mutations at immuno-dominant regions in comparison to sub-domain region. (Influenza HA - a classical example).

D

Broad coverage of Sarbecoviruses

Cross-reactivity
epitopes -
SARS1 and SARS2

ACE2 binding region -
Virus specific antibody

Broad coverage of Sarbecoviruses

Introducing glycosylation site at the RBS to immune focus

Figure 33

Summary of the design

| | | |
|---|---|---|
| COV_S_T2_13 | SARS_RBD_anc2 | Redesigned ancestor with new alignment |
| COV_S_T2_14 | SARS_RBD_anc2_mut1 | Anc2 with common epitope A |
| COV_S_T2_15 | SARS_RBD_anc2_mut2 | Anc2 with common epitope B |
| COV_S_T2_16 | SARS_RBD_anc2_mut3 | Anc2 with epitope from SARS2 |
| COV_S_T2_17 | SARS_RBD_anc2_mut4 | Anc2 with common epitope A, RBS mutant |
| COV_S_T2_18 | SARS_RBD_anc2_mut5 | Anc2 with common epitope B, RBS mutant |
| COV_S_T2_19 | SARS_RBD_anc2_TM | Redesigned ancestor with new alignment with TM domain |
| COV_S_T2_20 | SARS_RBD_anc2_mut4_TM | Anc2 with common epitope B, RBS mutant with TM domain |

Figure 34 continued (a) more detailed view of results in left upper panel

Figure 34 continued (b) more detailed view of results in left lower panel

Figure 36
A) Western Blot of sera from immunised mice
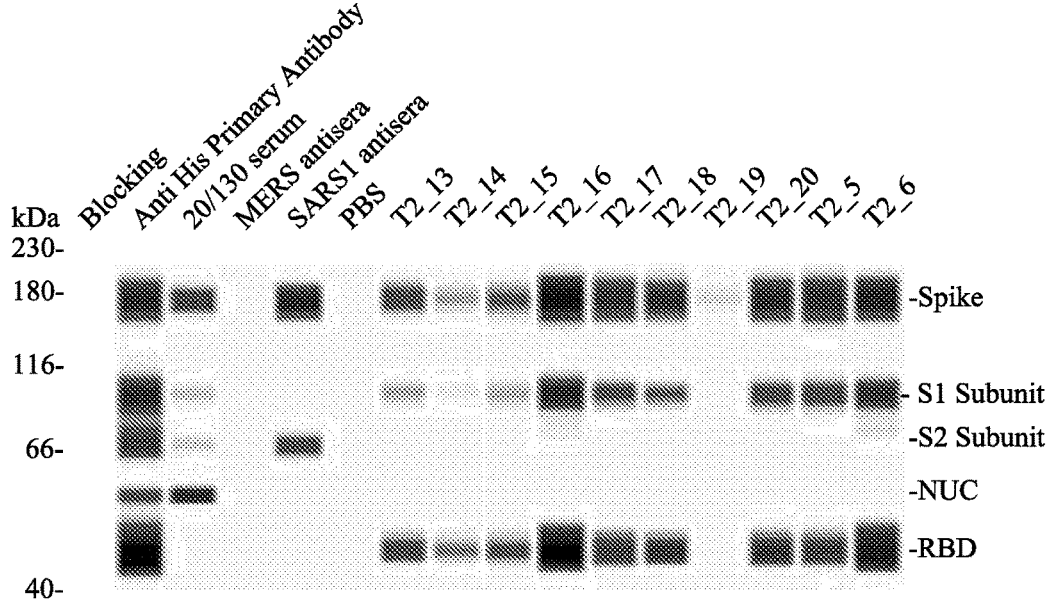
Sera from mice 3<sup>rd</sup> bleed
B) Antibody binding responses of Cell Surface expression bleed 2.
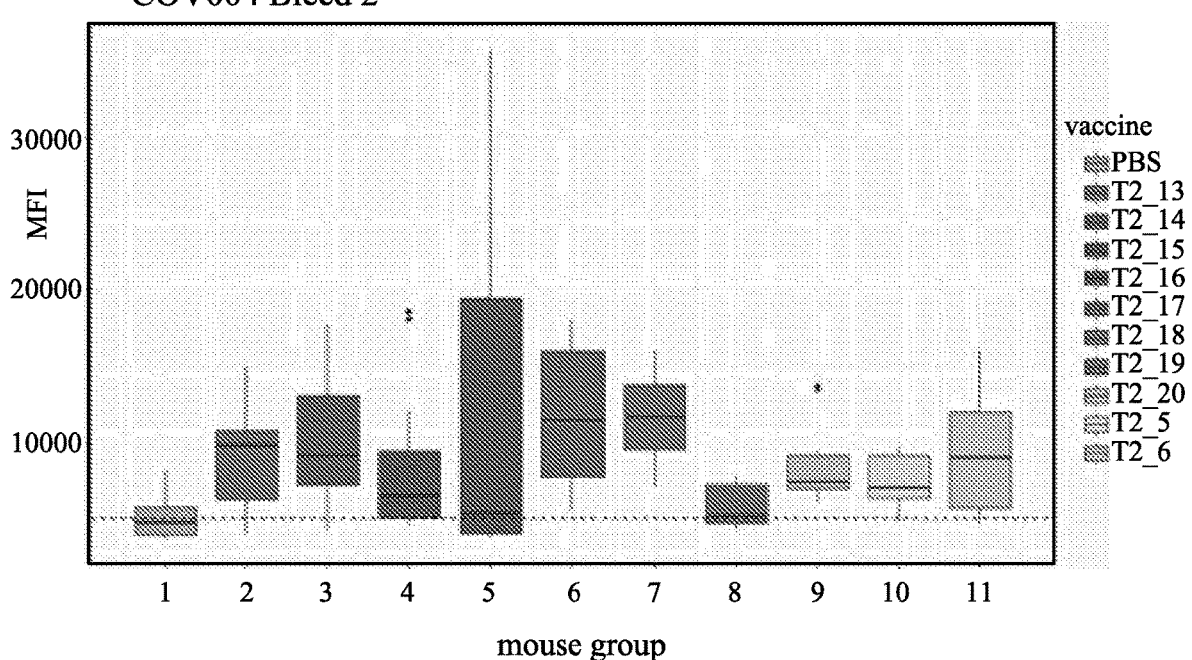

Figure 37

Figure 37 continued
SARS-1
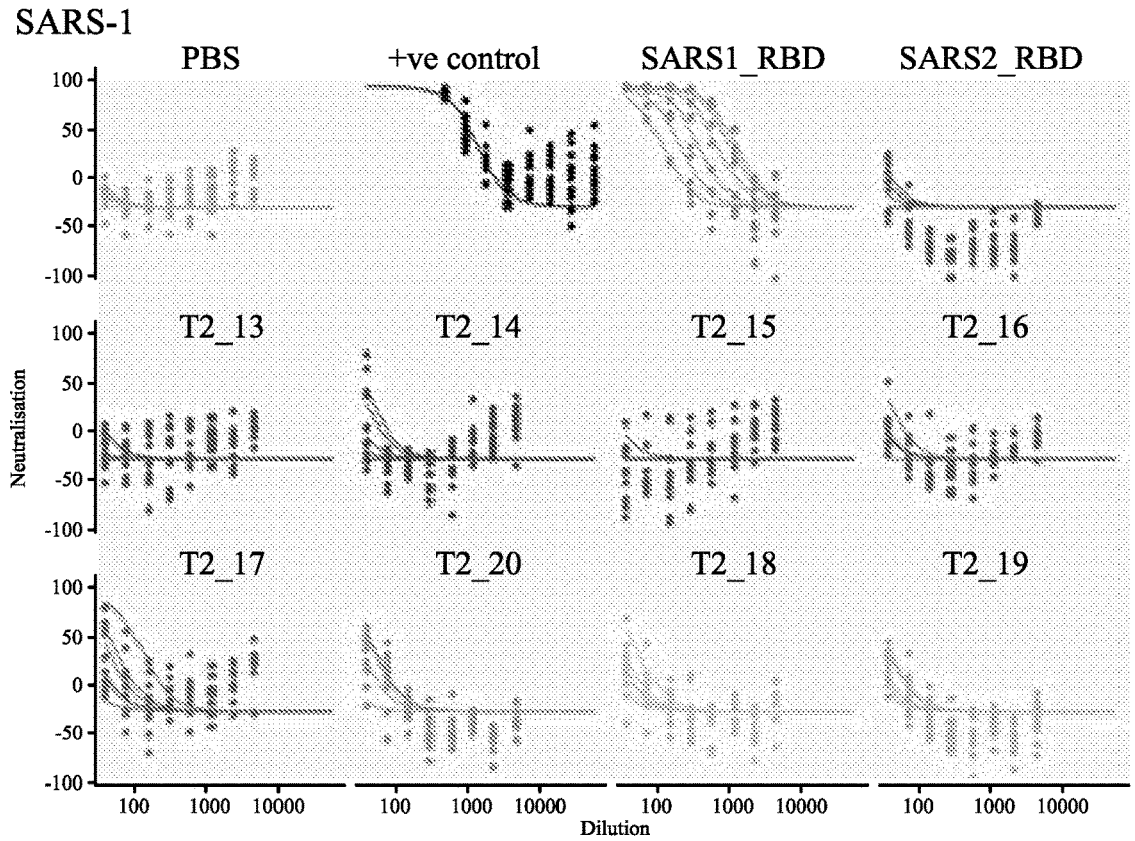
SARS-2
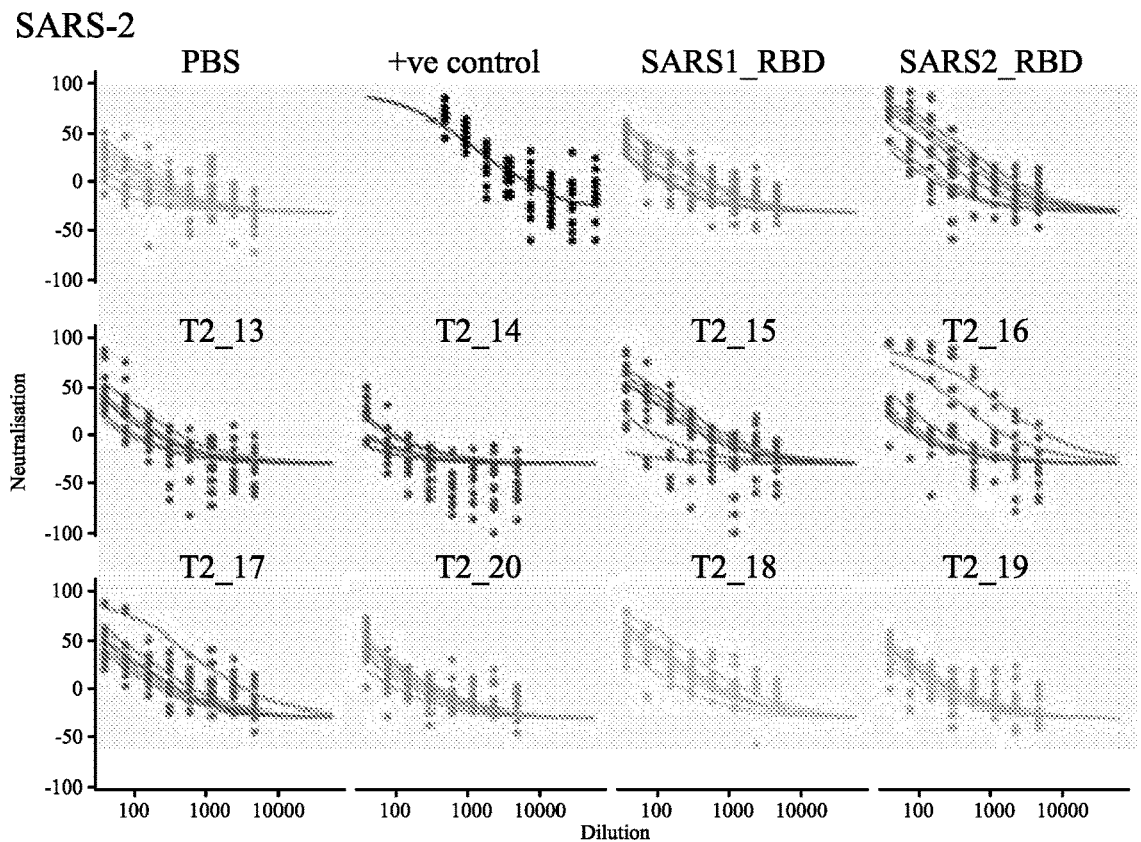

CoV Guinea pigs 001 n=8 per group, 6 immunisation groups; 2 or 3 immunisations 28 days apart.

| Group | Vaccine | Route | Immu 1 (D0) | Immu 2 (D28) | Immu 3 (D56) | Bleed 1 | Bleed 2 | Bleed 3 | Bleed 4 | Bleed 5 |
|---|---|---|---|---|---|---|---|---|---|---|
| 1 | CoV_S_T2_8 | 400 µg s.c. (2mg/mL) | 03/02/2021 | 03/02/2021 | 31/03/2021 | 17/02/2021 | 03/03/2021 | 17/03/2021 | 31/03/2021 | 14/04/2021 |
| 2 | CoV_S_T2_17 | 100 µg Pharmajet (0.5mg/mL) | | | No Immu | | | | | |
| 3 | CoV_S_T2_17 | 100 µg Pharmajet (0.5mg/mL) | | | 31/03/2021 | | | | | |
| 4 | CoV_S_T2_17 | 200 µg Pharmajet (1mg/mL) | | | 31/03/2021 | | | | | |
| 5 | CoV_S_T2_17 | 400 µg Pharmajet (2mg/mL) | | | 31/03/2021 | | | | | |
| 6 | CoV_S_T2_8 | 400 µg Pharmajet (2mg/mL) | | | 31/03/2021 | | | | | |

RBD ELISA Bleed 2 vs SARS1 and SARS-CoV-2

RBD ELISA Bleed 2 vs SARS1 and SARS-CoV-2

Guinea Pig Bleed 2 vs SARS1 RBD ELISA

Figure 40
Neutralisation by pMN Bleed 2 vs SARS1 and SARS-CoV-2 RBD
Guinea Pig Bleed 2 vs SARS-2 PV pMN
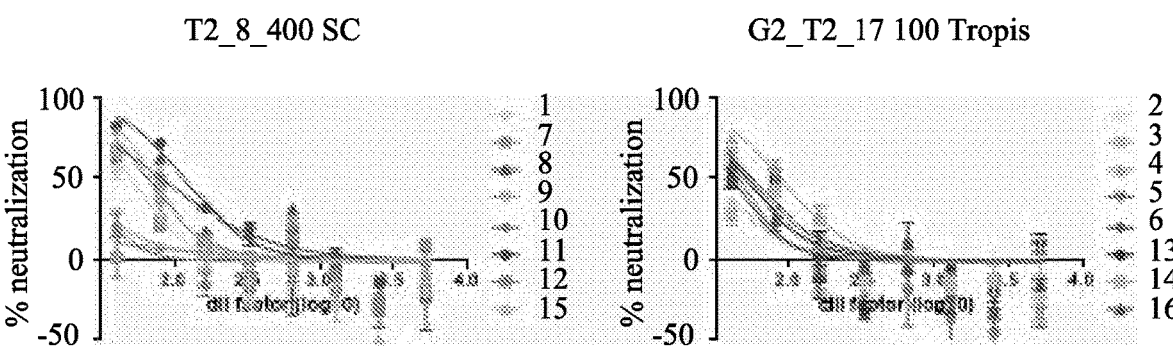
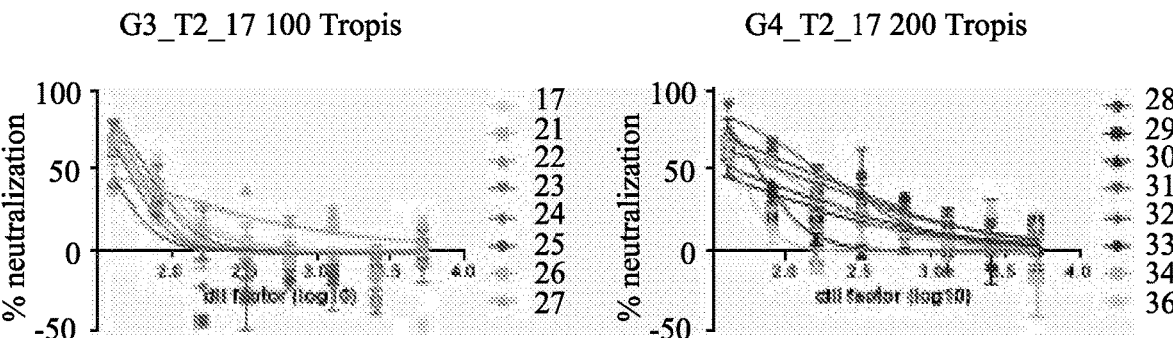
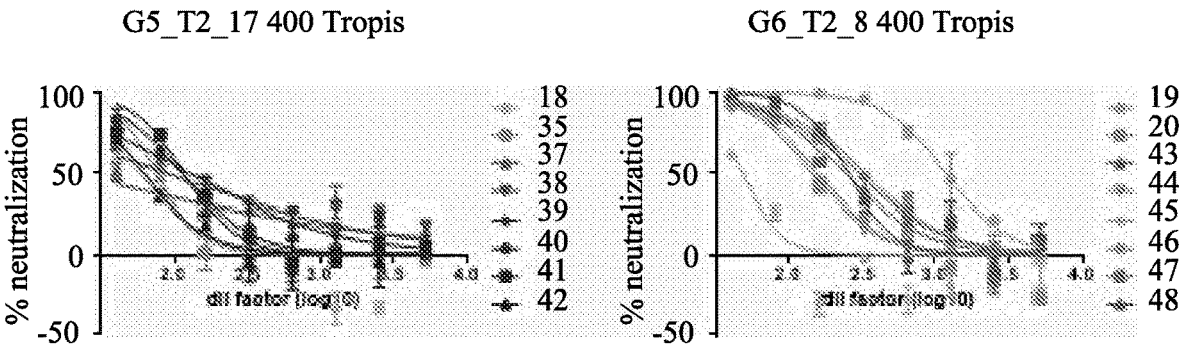

Figure 40 continued
Neutralisation by pMN Bleed 2 vs SARS1 and SARS-CoV-2 RBD
Guinea Pig Bleed 2 vs SARS-1 PV pMN
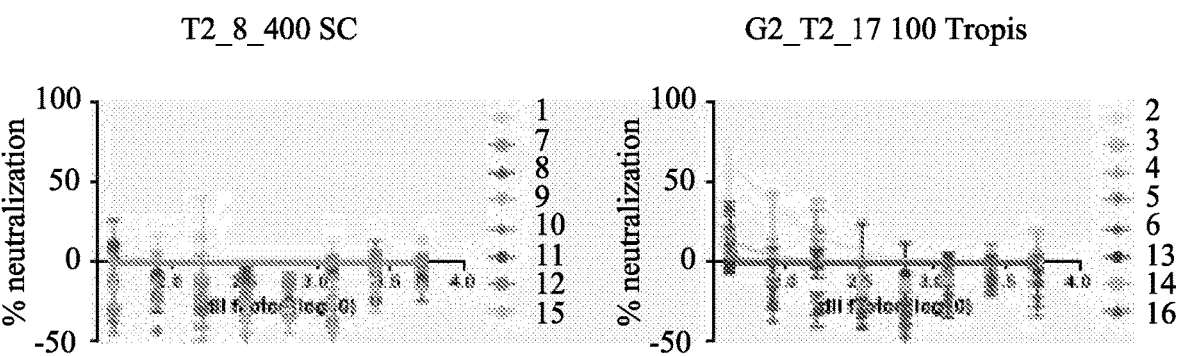
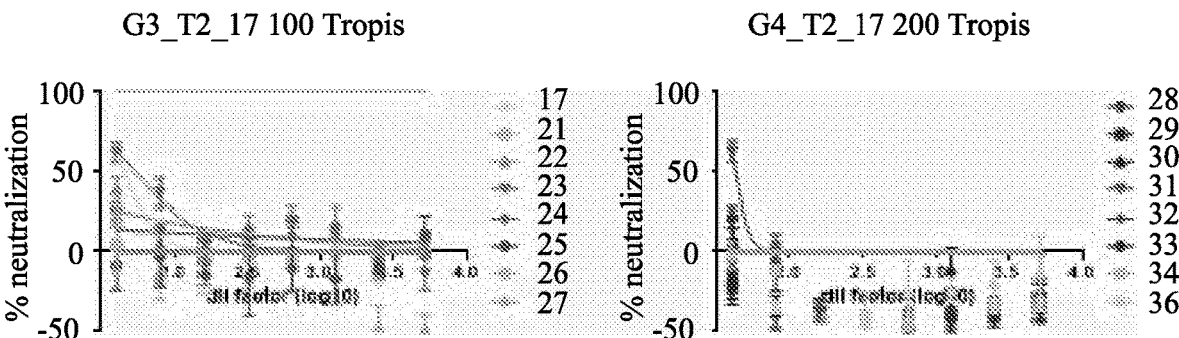
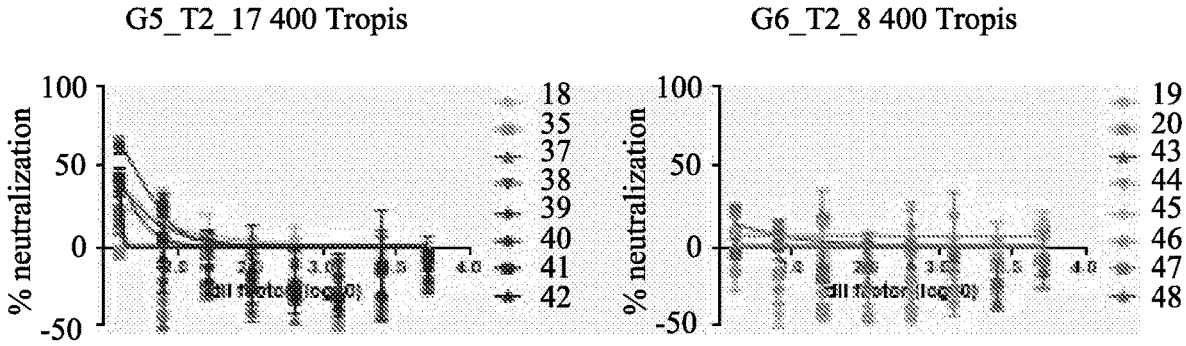

Figure 41
Groups 1, 2 & 3,Neutralisation SARS1 and SARS-CoV-2
by pMN Bleed 2 vs 3 vs SARS1 and SARS-CoV-2 RBD

Figure 41 continued
Groups 1, 2 & 3,Neutralisation SARS1 and SARS-CoV-2
by pMN Bleed 2 vs 3 vs SARS1 and SARS-CoV-2 RBD
pMN Guinea Pig Bleed 2 & 3 vs SARS 1
Bleed 2                                    Bleed 3
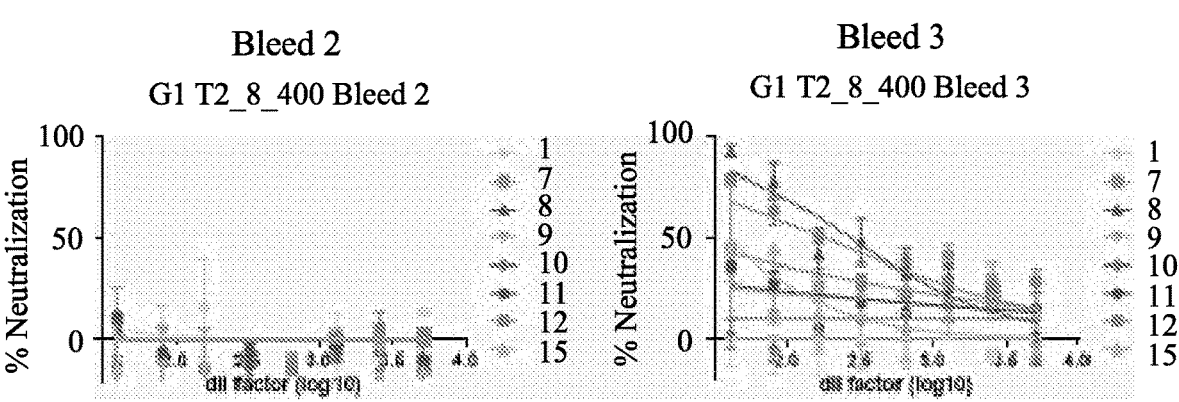
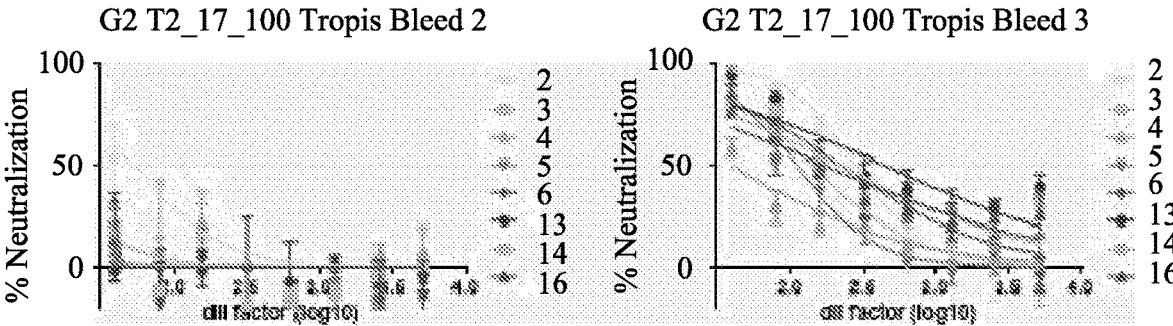
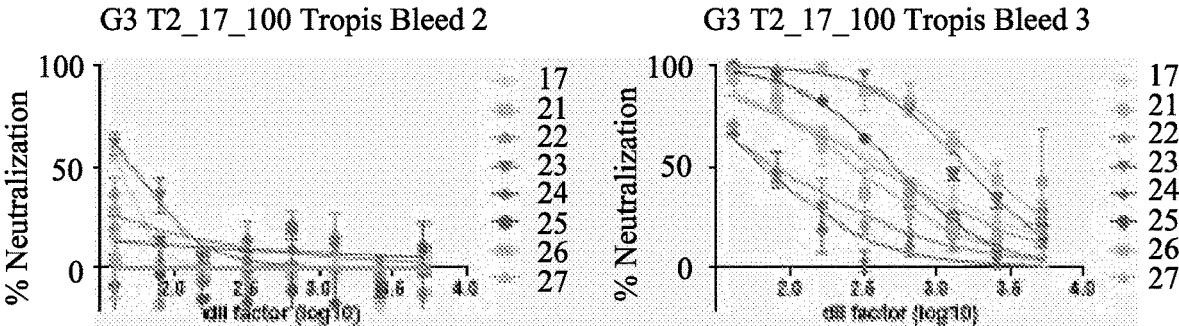

Groups 4, 5 & 6, Neutralisation SARS1 and SARS-CoV-2
by pMN Bleed 2 vs 3 vs SARS1 and SARS-CoV-2 RBD pMN Guinea Pig Bleed 2 & 3 vs SARS2

Figure 42 continued
Groups 4, 5 & 6, Neutralisation SARS1 and SARS-CoV-2
by pMN Bleed 2 vs 3 vs SARS1 and SARS-CoV-2 RBD
pMN Guinea Pig Bleed 2 & 3 vs SARS 1
Bleed 2                                    Bleed 3
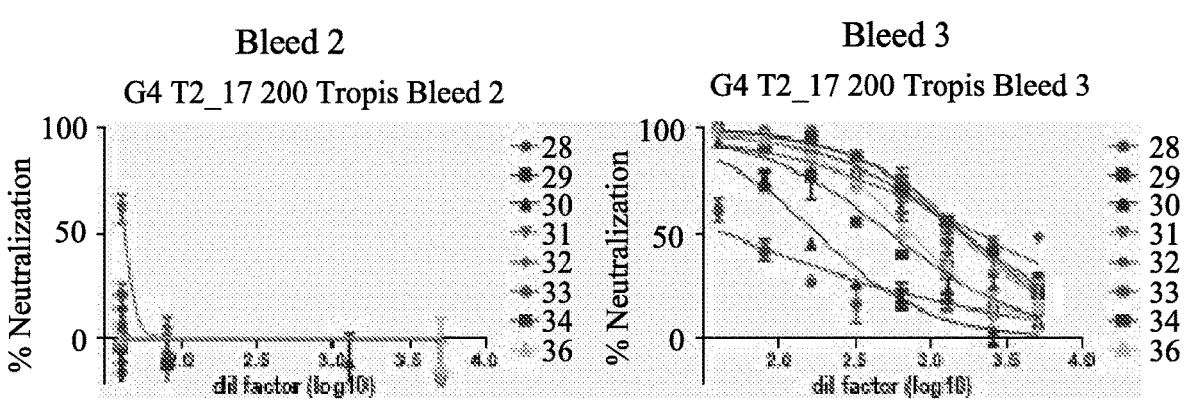
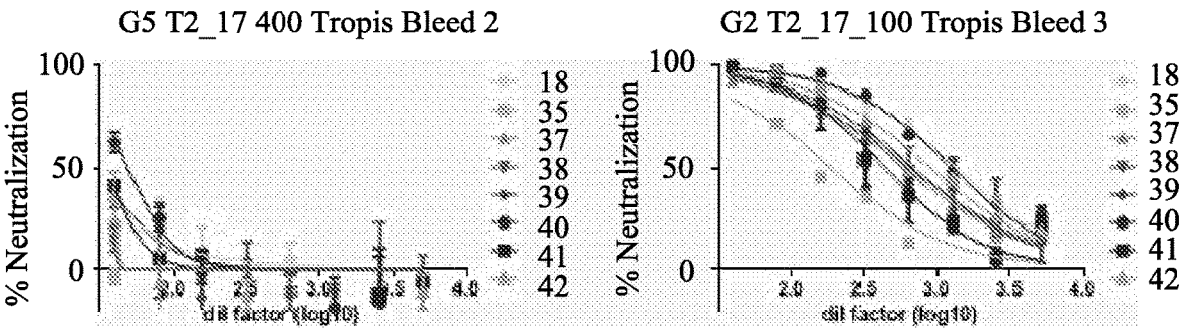
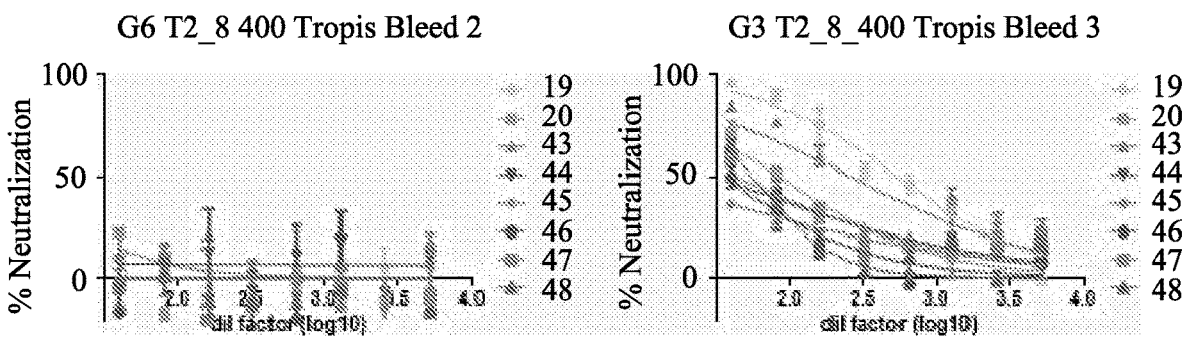

Figure 43
Neutralisation of Variants of Concern B1.351(SA) &
B1.248(p1 BZ) is superior with T2_17 vs T2_8
Normalize of GP BL3 Wuhan
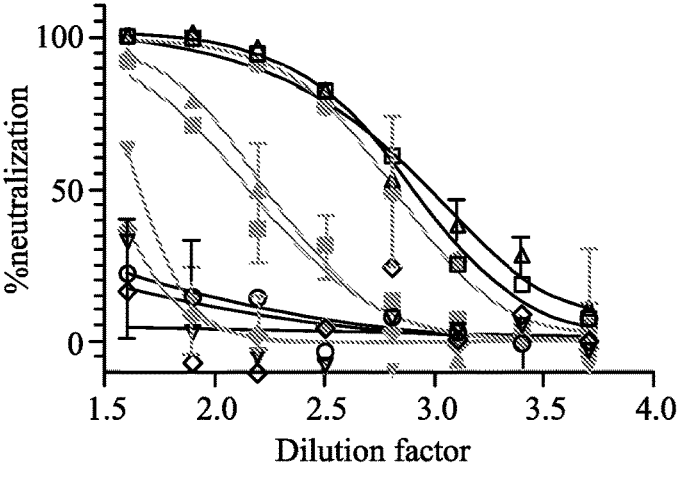
Normalize of GP BL3 B1.248
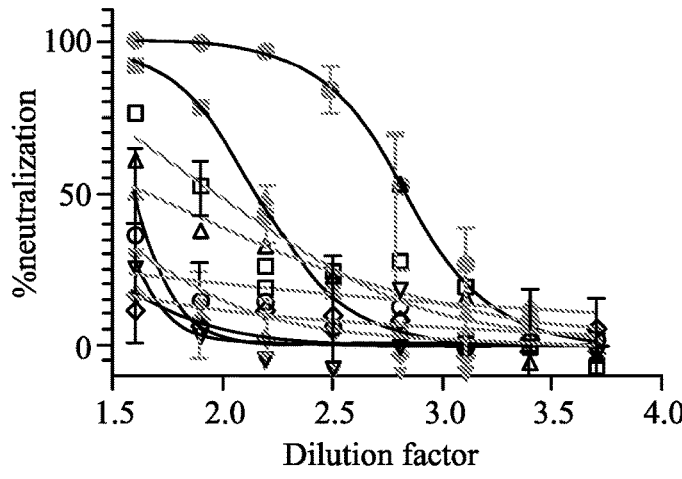
Normalize of GP BL3 B1.351
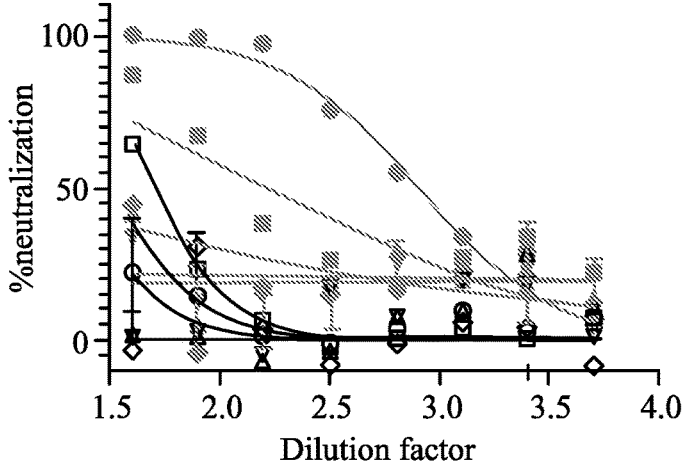
- ···●··· 31 (T2_17)
- ···●··· 34 (T2_17)
- ···●··· 30 (T2_17)
- ···●··· 36 (T2_17)
- ···●··· 28 (T2_17)
- —○— 7 (T2_8)
- —□— 8 (T2_8)
- —△— 11 (T2_8)
- —▽— 9 (T2_8)
- —◇— 1 (T2_8)

```
COV_M_T1_1  MADSNGT ITVEELKKLLEEQWNLVIGFLFLTWICLLQFAYANRNRFLYIIKLIFLWLLWPVTLA  63
COV_M_T1_3  MADSNGT ITVEELKKLLEEQ-----------------------------------------  19
COV_M_T2_1  MAD-NGT ITVEELKQLLEEQWNLVIGFLFLAWIMLLQFAYSNRNRFLYIIKLVFLWLLWPVTLA  62
COV_M_T2_4  MAD--NGT ITVEELKQLLEEQ----------------------------------------  18
COV_M_T2_2  MADSNGT ITVEELKKLLEEQWNLVIGFLFLTWICLLQFAYSNRNRFLYIIKLIFLWLLWPVTLA  63
COV_M_T2_5  MADSNGT ITVEELKKLLEEQ-----------------------------------------  19

COV_M_T1_1  CFVLAAVYR INWITGGIAIAMACLVGLMWLSYFIASFRLFARTRSMWSFNPETNILLNVPLHG  126
COV_M_T1_3  --------- INWTGGIAIAMACLVGLMWLSYFIASFRLFARTRSMWSFNPETNILLNVPLHG  70
COV_M_T2_1  CFVLAAVYR I-VTGGIAIAMACIVGLMWLSYFVASFRLFARTRSMWSFNPETNILLNVPPLRG  125
COV_M_T2_4  CFVLAAVYR INWVTGGIAIAMACIVGLMWLSYFVASFRLFARTRSMWSFFNPETNILLNVPLRG  69
COV_M_T2_2  CFVLAAVYR I-VTGGIAIAMACIVGLMWLSYFVASFRLFARTRSMWSFNPETNILLNVPLRG  126
COV_M_T2_5  --------- -VTGGIAIAMACIVGLMWLSYFVASFRLFARTRSMWSFNPETNILLNVPLRG  70

COV_M_T1_1  THILTRPLLESELVIGAVILRGHLRIAGHHLGRCDIKDLPKEITVATSRTLSYYKLGASQRVAG  189
COV_M_T1_3  THILTRPLLESELVIGAVILRGHLRIAGHHLGRCDIKDLPKEITVATSRTLSYYKLGASQRVAG  133
COV_M_T2_1  THILTRPLMESELVIGAVILRGHLRMAGHSLGRCDIKDLPKEITVATSRTLSYYKLGASQRVGT  188
COV_M_T2_4  THILTRPLMESELVIGAVILRGHLRMAGHSLGRCDIKDLPKEITVATSRTLSYYKLGASQRVGT  132
COV_M_T2_2  SHILTRPLMESELVIGAVILRGHLRMAGHSLGRCDIKDLPKEITVATSRTLSYYKLGASQRVAS  189
COV_M_T2_5  SHILTRPLMESELVIGAVILRGHLRMAGHSLGRCDIKDLPKEITVATSRTLSYYKLGASQRVAS  133

COV_M_T1_1  DSGFAAYSRYRIGNYKLNTDHSSSSDNIALLVQ  222
COV_M_T1_3  DSGFAAYSRYRIGNGKLNTDHSSSSDNIALLVQ  166
COV_M_T2_1  DSGFAAYNRYRIGNYKLNTDHAGSNDNIALLVQ  221
COV_M_T2_4  DSGFAAYNRYRIGNYKLNTDHAGSNDNIALLVQ  165
COV_M_T2_2  DSGFAAYYNRYRIGNGKLNTDHSSSSDNIALLVQ  222
COV_M_T2_5  DSGFAAYYNRYRIGNGKLNTDHSSSSDNIALLVQ  166
```

Figure 48:
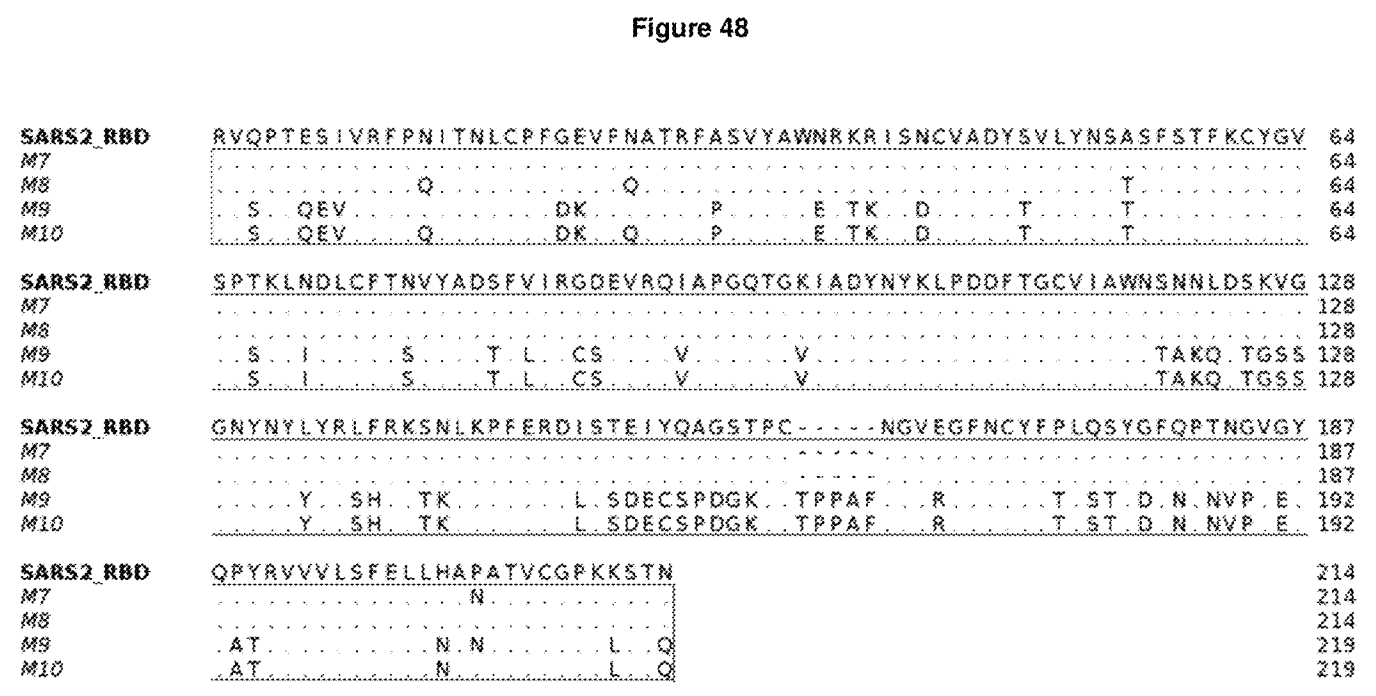

```
SARS2_RBD   RVQPTESIVRFPNITNLCPFGEVFNATRFASVYAWNRKRISNCVADYSVLYNSASFSTFKCYGV   64
M7          ...............................................................   64
M8          ..........Q...........DK......P.......E.TK.D...............T.....   64
M9          .S.QEV....Q...........DK......P.......E.TK.Q...............T.....   64
M10         .S.QEV................................................T.....      64

SARS2_RBD   SPTKLNDLCFTNVYADSFVIRGDEVRQIAPGQTGKIADYNYKLPDDFTGCVIAWNSNNLDSKVG  128
M7          ...............................................................  128
M8          ....S.....T.L..CS.......V.......................................  128
M9          ....L.....T.LL.CS.......V................TAKQ.TGSS..............  128
M10         ....L.....T.LL.CS.......V................TAKQ.TGSS..............  128

SARS2_RBD   GNYNYLYRLFRKSNLKPFERDISTEIYQAGSTPC---NGVEGFNCYFPLQSYGFQPTNGVGY   187
M7          ...........................................................      187
M8          .....Y..SH..TK......L.SDECSPDGK.TPPAF...R.....................    187
M9          .....Y..SH..TK......L.SDECSPDGK.TPPAF...R...T.ST.D.N.NVP.E....   192
M10         .........................................T.ST.D.N.NVP.E....      192

SARS2_RBD   QPYRVVVLSFELLHAPATVCGPKKSTN   214
M7          ..........N................   214
M8          ..AT......N.N..........L.Q.   219
M9          ..AT......N............L.Q.   219
M10         ...........................   219
```

```
EPI_ISL_402130   897  PFAMQMAYRFNGIGVTQNVLYENQKLIANQFNSAIGKIQDSLSSTASALGKLQDVV  952
Super_spike      894  ......................................................  949
X2               893  ......................................................  948

EPI_ISL_402130   953  NQNAQALNTLVKQLSSNFGAISSVLNDILSRLDKVEAEVQIDRLITGRLQSLQTYV 1008
Super_spike      950  .........................PP...........................  1005
X2               949  ......................................................  1004

EPI_ISL_402130  1009  TQQLIRAAEIRASANLAATKMSECVLGQSKRVDFCGKGYHLMSFPQSAPHGVVFLH 1064
Super_spike     1006  ......................................................  1061
X2              1005  ......................................................  1060

EPI_ISL_402130  1065  VTYVPAQEKNFTTAPAICHDGKAHFPREGVFVSNGTHWFVTQRNFYEPQIITTDNT 1120
Super_spike     1062  ......................................................  1117
X2              1061  ......................................................  1116

EPI_ISL_402130  1121  FVSGNCDVVIGIVNNTVYDPLQPELDSFKEELDKYFKNHTSPDVDLGDISGINASV 1176
Super_spike     1118  ......................................................  1173
X2              1117  ......................................................  1172

EPI_ISL_402130  1177  VNIQKEIDRLNEVAKNLNESLIDLQELGKYEQYIKWPWYIWLGFIAGLIAIVMVTI 1232
Super_spike     1174  ......................................................  1229
X2              1173  ......................................................  1228

EPI_ISL_402130  1233  MLCCMTSCCSCLKGCCSCGSCCKFDEDDSEPVLKGVKLHYT 1273
Super_spike     1230  .........................................  1270
X2              1229  .........................................  1269
```

CORONAVIRUS VACCINES

This invention relates to nucleic acid molecules, polypeptides, vectors, cells, fusion proteins, pharmaceutical compositions, and their use as vaccines against viruses of the coronavirus family.

INCORPORATION BY REFERENCE OF SEQUENCE LISTING

The Sequence Listing in an ASCII text file, named as 41402_Sequence_Listing.txt of 239 KB, created on Sep. 30, 2022, and submitted to the United States Patent and Trademark Office via EFS-Web, is incorporated herein by reference.

Coronaviruses (CoVs) cause a wide variety of animal and human disease. Notable human diseases caused by CoVs are zoonotic infections, such as severe acute respiratory syndrome (SARS) and Middle-East respiratory syndrome (MERS). Viruses within this family generally cause mild, self-limiting respiratory infections in immunocompetent humans, but can also cause severe, lethal disease characterised by onset of fever, extreme fatigue, breathing difficulties, anoxia, and pneumonia. CoVs transmit through close contact via respiratory droplets of infected subjects, with varying degrees of infectivity within each strain.

CoVs belong to the Coronaviridae family of viruses, all of which are enveloped. CoVs contain a single-stranded positive-sense RNA genome, with a length of between 25 and 31 kilobases (Siddell S. G. 1995, The Coronaviridae), the largest genome so far found in RNA viruses. The Coronaviridae family are subtyped into four genera: α, β, γ, and δ coronaviruses, based on phylogenetic clustering, with each genus subdivided again into clusters depending on the strain of the virus. For example, within the genus β-CoV (Group 2 CoV), four lineages (a, b, c, and d) are commonly recognized:

Lineage A (subgenus Embecovirus) includes HCoV-OC43 and HCoV-HKU1 (various species)

Lineage B (subgenus Sarbecovirus) includes SARSr-COV (which includes all its strains such as SARS-COV, SARS-COV-2, and Bat SL-CoV-WIV1)

Lineage C (subgenus Merbecovirus) includes *Tylonycteris* bat coronavirus HKU4 (BtCoV-HKU4), *Pipistrellus* bat coronavirus HKU5 (BtCoV-HKU5), and MERS-COV (various species)

Lineage D (subgenus Nobecovirus) includes Rousettus bat coronavirus HKU9 (BtCoV-HKU9)

CoV virions are spherical with characteristic club-shape spike projections emanating from the surface of the virion. The virions contain four main structural proteins: spike(S); membrane (M); envelope (E); and nucleocapsid (N) proteins, all of which are encoded by the viral genome. Some subsets of β-CoVs also comprise a fifth structural protein, hemagglutinin-esterase (HE), which enhances S protein-mediated cell entry and viral spread through the mucosa via its acetyl-esterase activity. Homo-trimers of the S glycoprotein make up the distinctive spike structure on the surface of the virus. These trimers are a class I fusion protein, mediating virus attachment to the host receptor by interaction of the S protein and its receptor. In most CoVs, S is cleaved by host cell protease into two separate polypeptides—S1 and S2. S1 contains the receptor-binding domain (RBD) of the S protein (the exact positioning of the RBD varies depending on the viral strain), while S2 forms the stem of the spike molecule.

FIG. 1 shows SARS S-protein architecture. The N-terminal sequence is responsible for relaying extracellular signals intracellularly. Studies show that the N-terminal region of the S protein is much more diverse than the C-terminal region, which is highly conserved (Dong et al, *Genomic and protein structure modelling analysis depicts the origin and infectivity of 2019-nCoV, a new coronavirus which caused a pneumonia outbreak in Wuhan, China.* 2020). The figure shows the S domain, which comprises S1 and S2 domains, responsible for receptor binding and cell membrane fusion respectively.

RNA viruses generally have very high mutation rates compared to DNA viruses, because viral RNA polymerases lack the proofreading ability of DNA polymerases. This is one reason why the virus is able to transmit from its natural host reservoir to other species, and from human to human, and why it is difficult to make effective vaccines to prevent diseases caused by RNA viruses. In most cases, current vaccine candidates against RNA viruses are limited by the viral strain used as the vaccine insert, which is often chosen based on availability of a wild-type strain rather than by informed design. Technical challenges for developing vaccines for enveloped RNA viruses include: i) viral variation of wild-type field isolate glycoproteins (GPs) provide limited breadth of protection as vaccine antigens; ii) selection of vaccine antigens expressed by the vaccine inserts is highly empirical; immunogen selection is a slow, trial and error process; iii) in an evolving or unanticipated viral epidemic, developing new vaccine candidates is time-consuming and can delay vaccine deployment.

Before 2002, CoVs were only thought to cause mild respiratory problems, and were endemic in the human population, causing 15-30% of respiratory tract infections each year. Since their first discovery in the 1960's, the CoV family has expanded massively and has caused many outbreaks in both humans and animals. The SARS pandemic that occurred in 2002-2003 in the Guangdong Province of China was the most severe disease caused by any coronavirus known to that date. During that period, approximately 8098 cases occurred with 774 deaths (mortality rate~9.6% overall). The mortality rate was ~50% in individuals over 90 years of age. The virus, identified as SARS-COV, a group 2b β-CoV, originated in bats. Two novel virus isolates from bats show more similarity to the human SARS-COV than any other virus identified to date, and bind to the same cellular receptor as human derived SARS-COV-angiotensin converting enzyme 2 (ACE2).

While the SARS-COV epidemic was controlled in 2003, a novel human CoV, a group 2c β-CoV, emerged in the Middle East in 2012. MERS is the causative agent of a series of highly pathogenic respiratory tract infections in the Middle East, with an initial mortality rate of 50%. An estimate of 2,494 cases and 858 deaths caused by MERS has been reported since its emergence, with a total estimated fatality rate by the World Health Organisation (WHO) of 34.4%. Along with SARS-COV, this novel CoV originated from bats, likely with an intermediate host such as dromedary camels contributing to the spread of the outbreak. This virus utilises dipeptidyl peptidase (DPP4) as its receptor, another peptidase receptor. It is currently unclear why CoVs utilise host peptidases as their binding receptor, as entry occurs even in the absence of enzyme activity.

In the beginning of 2020, another novel CoV emerged; severe acute respiratory syndrome coronavirus 2 (SARS-COV-2). The outbreak began in Wuhan, China in late 2019. By 30 Jan. 2020 the WHO declared a global health emergency as the virus had spread to over 25 countries within a month of its emergence. At the time of writing, the number of SARS-CoV-2 infections was increasing exponentially across many countries around the world, nearing 800,000 cases of infection, and causing over 40,000 total confirmed deaths.

Human cases or outbreaks of haemorrhagic fevers caused by coronaviruses occur sporadically and irregularly. The occurrence of outbreaks cannot be easily predicted. With a few exceptions, there is no cure or established drug treatment for CoV infections. Vaccines have only been approved for some CoVs, but these vaccines are not always used because they are either not very effective or in some cases have been reported to promote selection of novel pathogenic CoVs via recombination of circulating strains. By April 2020, several potential vaccines had been developed for SARS-COV but none had been approved for use. A year later, several novel vaccines have had regulatory approval, and a mass vaccination programme is underway. The first mass vaccination programme started in early December 2020, and as of 15 Feb. 2021, the WHO estimates that 175.3 million vaccine doses have been administered. At least 7 different vaccines are being used worldwide. WHO issued an Emergency Use Listing (EUL) for the Pfizer-BioNTech COVID-19 vaccine (BNT162b2) on 31 Dec. 2020. On 15 Feb. 2021, WHO issued EULs for two versions of the AstraZeneca/Oxford COVID-19 vaccine (AZD1222). As of 18 Feb. 2021, the UK had administered 12 million people with their first dose of either of the Pfizer-BioNTech or the AstraZeneca/Oxford vaccine. Both the Pfizer and AstraZeneca vaccine use an mRNA platform encoding the S protein. Pfizer uses a nanoparticle vector for nucleic acid delivery, whereas AstraZeneca uses an adenoviral vector.

There are many hurdles to overcome in the development of an effective vaccine for CoVs. Firstly, immunity, whether it is natural or artificial, does not necessarily prevent subsequent infection (Fehr et al. *Methods Mol Biol.* 2015, 1282:1-23). Secondly, the propensity of the viruses to recombine may pose a problem by rendering the vaccine useless by increasing the genetic diversity of the virus. Additionally, vaccination with the viral S-protein has been shown to lead to enhanced disease in the case of FIPV (feline infectious peritonitis virus), a highly virulent strain of feline CoV. This enhanced pathogenicity of the disease is caused by non-neutralising antibodies that facilitate viral entry into host cells in a process called antibody-dependent enhancement (ADE). After primary infection of one strain of a virus, neutralising antibodies are produced against the same strain of the virus. However, if a different strain infects the host in a secondary infection, non-neutralising antibodies produced during the first infection, which do not neutralise the virus, instead, bind to the virus and then bind to the IgG Fc receptors on immune cells and mediate viral entry into these cells (Wan et al. *Journal of Virology.* 2020, 94 (5): 1-13).

When developing vaccines against viruses that are capable of ADE (or of triggering ADE-like pro-inflammatory responses), it is crucial that epitopes are identified that are responsible for eliciting non-neutralising antibodies, and that these epitopes are either masked by modification or are removed from the vaccine. These non-neutralising epitopes on the S-protein may also result in immune diversion wherein the non-neutralising epitopes outcompete neutralising epitopes for binding to antibodies. The neutralising epitopes are neglected by the immune system which fails to neutralise the antigen. In the case of recombinant RBD vaccines, previously buried surfaces containing non-neutralising immunodominant epitopes may become newly exposed which outcompete epitopes responsible for neutralisation by the immune system.

There is a need, therefore, to provide effective vaccines that induce a broadly neutralising immune response to protect against emerging and re-emerging diseases caused by CoVs, especially β-CoVs, such as SARS-COV and the recent SARS-COV-2. In particular, there is a need to provide vaccines lacking non-neutralising epitopes that may result in virus immune evasion and disease progression by ADE (or ADE-like pro-inflammatory responses).

Designed Coronavirus Spike(s) Protein Sequences (Full-Length, Truncated, and Receptor Binding Domain, RBD)

FIG. 2 shows a multiple sequence alignment of the S-protein (the region around the cleavage site 1) comparing SARS-COV isolate (SARS-COV-1), and closely related bat betacoronavirus (RaTG13) isolate, with four SARS-COV-2 isolates. The SARS-COV S-protein (1269 amino acid residues) shares a high sequence identity (~73%) with the SARS-COV-2 S-protein (1273 amino acid residues). Expansion of cleavage site one (shown as a boxed area in the figure) is observed in all SARS-COV-2 strains so far. The majority of the insertions/substitutions are observed in the subunit 1, with minimal substitutions in the subunit S2, as compared to SARS-COV-1. The C-terminus contains epitopes which elicit non-neutralising antibodies and are responsible for antibody dependent enhancement.

The applicant has generated a novel amino acid sequence for an S-protein, called CoV_T2_1 (also referred to below as Wuhan-Node-1), which has improved immunogenicity (which allows the protein and its derivatives to elicit a broadly neutralising immune response).

The amino acid sequences of the full length S-protein (SEQ ID NO:13) (CoV_T2_1; Wuhan-Node-1), truncated S-protein (tr, missing the C-terminal part of the S2 sequence) (SEQ ID NO: 15) (CoV_T2_4; Wuhan_Node1_tr), and the receptor binding domain (RBD) (SEQ ID NO: 17) (CoV_T2_7; Wuhan_Node1_RBD) (and their respective encoding nucleic acid sequences, SEQ ID NOs: 14, 16, 18) are provided in the examples below.

According to the invention there is provided an isolated polypeptide which comprises an amino acid sequence of SEQ ID NO: 17, or an amino acid sequence which has at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% amino acid identity over its entire length with the amino acid sequence of SEQ ID NO:17.

SEQ ID NO:17 is the amino acid sequence of a novel S-protein RBD designed by the applicant.

There is also provided according to the invention an isolated polypeptide comprising an amino acid sequence of SEQ ID NO: 15, or an amino acid sequence which has at least 81%, 82%, 83%, 84%, 85%, 86%, 87%, 88%, 89%, 90%, 91%, 92%, 93%, 94%, 95%, 96%, 97%, 98%, or 99% amino acid identity over its entire length with the amino acid sequence of SEQ ID NO: 15.

There is also provided according to the invention an isolated polypeptide comprising an amino acid sequence of SEQ ID NO: 13, or an amino acid sequence which has at least 83%, 84%, 85%, 86%, 87%, 88%, 89%, 90%, 91%, 92%, 93%, 94%, 95%, 96%, 97%, 98%, or 99% amino acid identity over its entire length with the amino acid sequence of SEQ ID NO:13.

Examples 6 and 7 below provide amino acid sequence alignments of the novel S-protein RBD amino acid sequence (Wuhan_Node1_RBD (CoV_T2_7) (SEQ ID NO:17)) with the RBD amino acid sequences of SARS-TOR2 isolate AY274119 (AY274119_RBD (COV_T2_5) (SEQ ID NO: 5)), and SARS_COV_2 isolate hCov-19/Wuhan/LVDC-HB-01/2019 (EPI_ISL_402119) (EPI_ISL_402119_RBD (COV_T2_6) (SEQ ID NO:11)), respectively.

As explained in Example 9 below, FIG. 4 shows Wuhan_Node1_RBD (CoV_T2_7) amino acid sequence (SEQ ID NO:17) with amino acid residue differences in bold and underline from the respective alignments with AY274119_RBD (COV_T2_5) (SEQ ID NO:5) and EPI_ISL_402119_RBD (COV_T2_6) (SEQ ID NO:11) amino acid sequences (Examples 6 and 7, respectively). The amino acid residue differences from the two alignments are listed in the table below (the numbering of residue positions corresponds to positions of the Wuhan_Node1_RBD (CoV_T2_7) (SEQ ID NO:17) amino acid sequence. The common differences from the two alignments are at amino acid residues: 3, 6, 7, 21, 22, 38, 42, 48, 67, 70, 76, 81, 83, 86, 87, 92, 121, 122, 123, 125, 126, 128, 134, 137, 138, 141, 150, 152, 153, 154, 155, 167, 171, 178, 180, 181, 183, 185, 187, 188, 189, 191, 194, 195, 219 (shown with grey highlighting in FIG. 4, and shows as centered in Table 1 below):

TABLE 1

| Wuhan_Node1_RBD (CoV_T2_7) residue position | Amino acid residue difference vs AY274119_RBD | Amino acid residue difference vs EPI_ISL_402119_RBD |
|---|---|---|
| 3 | S | S |
| 5 | T | — |
| 6 | Q | Q |
| 7 | E | E |
| 8 | — | V |
| 21 | D | D |
| 22 | K | K |
| 28 | R | — |
| 30 | — | P |
| 36 | — | E |
| 38 | T | T |
| 39 | — | K |
| 42 | D | D |
| 48 | T | T |
| 54 | — | T |
| 55 | S | — |
| 66 | P | — |
| 67 | S | S |
| 70 | I | I |
| 75 | T | — |
| 76 | S | S |
| 81 | T | T |
| 83 | L | L |
| 84 | I | — |
| 85 | R | — |
| 86 | C | C |
| 87 | S | S |
| 88 | E | — |
| 92 | V | V |
| 99 | — | V |
| 112 | T | — |
| 116 | I | — |
| 120 | — | T |
| 121 | A | A |
| 122 | K | K |
| 123 | Q | Q |
| 125 | T | T |
| 126 | G | G |
| 127 | — | S |
| 128 | S | S |
| 134 | Y | Y |
| 137 | S | S |
| 138 | H | H |
| 140 | K | — |
| 141 | T | T |
| 142 | — | K |
| 144 | K | — |
| 150 | L | L |

TABLE 1-continued

| Wuhan_Node1_RBD (CoV_T2_7) residue position | Amino acid residue difference vs AY274119_RBD | Amino acid residue difference vs EPI_ISL_402119_RBD |
|---|---|---|
| 152 | S | S |
| 153 | D | D |
| 154 | E | E |
| 155 | C | C |
| 156 | — | S |
| 157 | — | P |
| 158 | — | D |
| 159 | — | G |
| 160 | — | Y |
| 163 | — | T |
| 164 | — | P |
| 165 | — | P |
| 166 | — | A |
| 167 | F | F |
| 168 | N | — |
| 169 | G | — |
| 170 | V | — |
| 171 | R | R |
| 172 | G | — |
| 173 | F | — |
| 177 | F | — |
| 178 | T | T |
| 180 | S | S |
| 181 | T | T |
| 183 | D | D |
| 185 | N | N |
| 186 | P | — |
| 187 | N | N |
| 188 | V | V |
| 189 | P | P |
| 190 | V | — |
| 191 | E | E |
| 194 | A | A |
| 195 | T | T |
| 206 | — | N |
| 216 | — | L |
| 219 | Q | Q |

Amino acid insertions are at positions 167-172 (compared to AY274119_RBD), and 163-167 (compared to EPI_ISL_402119_RBD) (shown boxed in FIG. 4).

Optionally an isolated polypeptide of the invention comprises at least one of the amino acid residues, at a position corresponding to the amino acid residue position of SEQ ID NO:17, as shown in Table 2 below:

TABLE 2

| Wuhan_Node1_RBD (CoV_T2_7) residue position | Amino acid residue |
|---|---|
| 3 | S |
| 6 | Q |
| 7 | E |
| 21 | D |
| 22 | K |
| 38 | T |
| 42 | D |
| 48 | T |
| 67 | S |
| 70 | I |
| 76 | S |
| 81 | T |
| 83 | L |
| 86 | C |
| 87 | S |
| 92 | V |
| 121 | A |
| 122 | K |
| 123 | Q |
| 125 | T |
| 126 | G |

7

TABLE 2-continued

| Wuhan_Node1_RBD (CoV_T2_7) residue position | Amino acid residue |
|---|---|
| 128 | S |
| 134 | Y |
| 137 | S |
| 138 | H |
| 141 | T |
| 150 | L |
| 152 | S |
| 153 | D |
| 154 | E |
| 155 | C |
| 167 | F |
| 171 | R |
| 178 | T |
| 180 | S |
| 181 | T |
| 183 | D |
| 185 | N |
| 187 | N |
| 188 | V |
| 189 | P |
| 191 | E |
| 194 | A |
| 195 | T |
| 219 | Q |

Optionally an isolated polypeptide of the invention comprises at least five of the amino acid residues, at positions corresponding to the amino acid residue positions of SEQ ID NO:17, as shown in Table 2.

Optionally an isolated polypeptide of the invention comprises at least ten of the amino acid residues, at positions corresponding to the amino acid residue positions of SEQ ID NO:17, as shown in Table 2.

Optionally an isolated polypeptide of the invention comprises at least fifteen of the amino acid residues, at positions corresponding to the amino acid residue positions of SEQ ID NO:17, as shown in Table 2.

Optionally an isolated polypeptide of the invention comprises at least twenty of the amino acid residues, at positions corresponding to the amino acid residue positions of SEQ ID NO:17, as shown in Table 2.

Optionally an isolated polypeptide of the invention comprises at least twenty five of the amino acid residues, at positions corresponding to the amino acid residue positions of SEQ ID NO: 17, as shown in Table 2.

Optionally an isolated polypeptide of the invention comprises at least thirty of the amino acid residues, at positions corresponding to the amino acid residue positions of SEQ ID NO:17, as shown in Table 2.

Optionally an isolated polypeptide of the invention comprises at least thirty five of the amino acid residues, at positions corresponding to the amino acid residue positions of SEQ ID NO: 17, as shown in Table 2.

Optionally an isolated polypeptide of the invention comprises at least forty of the amino acid residues, at positions corresponding to the amino acid residue positions of SEQ ID NO:17, as shown in Table 2.

Optionally an isolated polypeptide of the invention comprises all of the amino acid residues, at positions corresponding to the amino acid residue positions of SEQ ID NO:17, as shown in Table 2.

Optionally an isolated polypeptide of the invention comprises at least one of the amino acid residues, at a position corresponding to the amino acid residue position of SEQ ID NO:17, as shown in Table 3 below:

8

TABLE 3

| Wuhan_Node1_RBD (CoV_T2_7) residue position | Amino acid residue |
|---|---|
| 3 | S |
| 6 | Q |
| 7 | E |
| 8 | V |
| 21 | D |
| 22 | K |
| 30 | P |
| 36 | E |
| 38 | T |
| 39 | K |
| 42 | D |
| 48 | T |
| 54 | T |
| 67 | S |
| 70 | I |
| 76 | S |
| 81 | T |
| 83 | L |
| 86 | C |
| 87 | S |
| 92 | V |
| 99 | V |
| 120 | T |
| 121 | A |
| 122 | K |
| 123 | Q |
| 125 | T |
| 126 | G |
| 127 | S |
| 128 | S |
| 134 | Y |
| 137 | S |
| 138 | H |
| 141 | T |
| 142 | K |
| 150 | L |
| 152 | S |
| 153 | D |
| 154 | E |
| 155 | C |
| 156 | S |
| 157 | P |
| 158 | D |
| 159 | G |
| 160 | K |
| 163 | T |
| 164 | P |
| 165 | P |
| 166 | A |
| 167 | F |
| 171 | R |
| 178 | T |
| 180 | S |
| 181 | T |
| 183 | D |
| 185 | N |
| 187 | N |
| 188 | V |
| 189 | P |
| 191 | E |
| 194 | A |
| 195 | T |
| 206 | N |
| 216 | L |
| 219 | Q |

Optionally an isolated polypeptide of the invention comprises at least five of the amino acid residues, at positions corresponding to the amino acid residue positions of SEQ ID NO:17, as shown in Table 3.

Optionally an isolated polypeptide of the invention comprises at least ten of the amino acid residues, at positions corresponding to the amino acid residue positions of SEQ ID NO:17, as shown in Table 3.

Optionally an isolated polypeptide of the invention comprises at least fifteen of the amino acid residues, at positions corresponding to the amino acid residue positions of SEQ ID NO:17, as shown in Table 3.

Optionally an isolated polypeptide of the invention comprises at least twenty of the amino acid residues, at positions corresponding to the amino acid residue positions of SEQ ID NO:17, as shown in Table 3.

Optionally an isolated polypeptide of the invention comprises at least twenty five of the amino acid residues, at positions corresponding to the amino acid residue positions of SEQ ID NO: 17, as shown in Table 3.

Optionally an isolated polypeptide of the invention comprises at least thirty of the amino acid residues, at positions corresponding to the amino acid residue positions of SEQ ID NO:17, as shown in Table 3.

Optionally an isolated polypeptide of the invention comprises at least thirty five of the amino acid residues, at positions corresponding to the amino acid residue positions of SEQ ID NO: 17, as shown in Table 3.

Optionally an isolated polypeptide of the invention comprises at least forty of the amino acid residues, at positions corresponding to the amino acid residue positions of SEQ ID NO:17, as shown in Table 3.

Optionally an isolated polypeptide of the invention comprises at least forty five of the amino acid residues, at positions corresponding to the amino acid residue positions of SEQ ID NO: 17, as shown in Table 3.

Optionally an isolated polypeptide of the invention comprises at least fifty of the amino acid residues, at positions corresponding to the amino acid residue positions of SEQ ID NO:17, as shown in Table 3.

Optionally an isolated polypeptide of the invention comprises at least fifty five of the amino acid residues, at positions corresponding to the amino acid residue positions of SEQ ID NO: 17, as shown in Table 3.

Optionally an isolated polypeptide of the invention comprises at least sixty of the amino acid residues, at positions corresponding to the amino acid residue positions of SEQ ID NO:17, as shown in Table 3.

Optionally an isolated polypeptide of the invention comprises all of the amino acid residues, at positions corresponding to the amino acid residue positions of SEQ ID NO:17, as shown in Table 3.

Optionally an isolated polypeptide of the invention comprises at least one of the amino acid residues, at a position corresponding to the amino acid residue position of SEQ ID NO:17, as shown in Table 4 below:

TABLE 4

| Wuhan__Node1__RBD (CoV_T2__7) residue position | Amino acid residue |
| --- | --- |
| 3 | S |
| 5 | T |
| 6 | Q |
| 7 | E |
| 2 | D |
| 22 | K |
| 28 | R |
| 38 | T |
| 42 | D |
| 48 | T |
| 55 | S |
| 66 | P |
| 67 | S |
| 70 | I |
| 75 | T |

TABLE 4-continued

| Wuhan__Node1__RBD (CoV_T2__7) residue position | Amino acid residue |
| --- | --- |
| 76 | S |
| 81 | T |
| 83 | L |
| 84 | I |
| 85 | R |
| 86 | C |
| 87 | S |
| 88 | E |
| 92 | V |
| 112 | T |
| 116 | I |
| 121 | A |
| 122 | K |
| 123 | Q |
| 125 | T |
| 126 | G |
| 128 | S |
| 134 | Y |
| 137 | S |
| 138 | H |
| 140 | K |
| 141 | T |
| 144 | K |
| 150 | L |
| 152 | S |
| 153 | D |
| 154 | E |
| 155 | C |
| 167 | F |
| 168 | N |
| 169 | G |
| 170 | V |
| 171 | R |
| 172 | G |
| 173 | F |
| 177 | F |
| 178 | T |
| 180 | S |
| 181 | T |
| 183 | D |
| 185 | N |
| 186 | P |
| 187 | N |
| 188 | V |
| 189 | P |
| 190 | V |
| 191 | E |
| 194 | A |
| 195 | T |
| 219 | Q |

Optionally an isolated polypeptide of the invention comprises at least five of the amino acid residues, at positions corresponding to the amino acid residue positions of SEQ ID NO:17, as shown in Table 4.

Optionally an isolated polypeptide of the invention comprises at least ten of the amino acid residues, at positions corresponding to the amino acid residue positions of SEQ ID NO:17, as shown in Table 4.

Optionally an isolated polypeptide of the invention comprises at least fifteen of the amino acid residues, at positions corresponding to the amino acid residue positions of SEQ ID NO:17, as shown in Table 4.

Optionally an isolated polypeptide of the invention comprises at least twenty of the amino acid residues, at positions corresponding to the amino acid residue positions of SEQ ID NO:17, as shown in Table 4.

Optionally an isolated polypeptide of the invention comprises at least twenty five of the amino acid residues, at positions corresponding to the amino acid residue positions of SEQ ID NO: 17, as shown in Table 4.

Optionally an isolated polypeptide of the invention comprises at least thirty of the amino acid residues, at positions corresponding to the amino acid residue positions of SEQ ID NO:17, as shown in Table 4.

Optionally an isolated polypeptide of the invention comprises at least thirty five of the amino acid residues, at positions corresponding to the amino acid residue positions of SEQ ID NO: 17, as shown in Table 4.

Optionally an isolated polypeptide of the invention comprises at least forty of the amino acid residues, at positions corresponding to the amino acid residue positions of SEQ ID NO:17, as shown in Table 4.

Optionally an isolated polypeptide of the invention comprises at least forty five of the amino acid residues, at positions corresponding to the amino acid residue positions of SEQ ID NO: 17, as shown in Table 4.

Optionally an isolated polypeptide of the invention comprises at least fifty of the amino acid residues, at positions corresponding to the amino acid residue positions of SEQ ID NO:17, as shown in Table 4.

Optionally an isolated polypeptide of the invention comprises at least fifty five of the amino acid residues, at positions corresponding to the amino acid residue positions of SEQ ID NO: 17, as shown in Table 4.

Optionally an isolated polypeptide of the invention comprises at least sixty of the amino acid residues, at positions corresponding to the amino acid residue positions of SEQ ID NO:17, as shown in Table 4.

Optionally an isolated polypeptide of the invention comprises all of the amino acid residues, at positions corresponding to the amino acid residue positions of SEQ ID NO:17, as shown in Table 4.

According to the invention there is also provided an isolated polypeptide, which comprises a coronavirus S protein RBD domain with any, or all of the amino acid residues at positions corresponding to the amino acid residue positions as shown in Table 5 below:

TABLE 5

| S protein RBD residue position | Amino acid residue |
| --- | --- |
| 3 | S |
| 6 | Q |
| 7 | E |
| 21 | D |
| 22 | K |
| 38 | T |
| 42 | D |
| 48 | T |
| 67 | S |
| 70 | I |
| 76 | S |
| 81 | T |
| 83 | L |
| 86 | C |
| 87 | S |
| 92 | V |
| 121 | A |
| 122 | K |
| 123 | Q |
| 125 | T |
| 126 | G |
| 128 | S |
| 134 | Y |
| 137 | S |
| 138 | H |
| 141 | T |
| 150 | L |
| 152 | S |
| 153 | D |

TABLE 5-continued

| S protein RBD residue position | Amino acid residue |
| --- | --- |
| 154 | E |
| 155 | C |
| 167 | F |
| 171 | R |
| 178 | T |
| 180 | S |
| 181 | T |
| 183 | D |
| 185 | N |
| 187 | N |
| 188 | V |
| 189 | P |
| 191 | E |
| 194 | A |
| 195 | T |
| 219 | Q |

According to the invention there is also provided an isolated polypeptide, which comprises a coronavirus S protein RBD domain with any, or all of the amino acid residues at positions corresponding to the amino acid residue positions as shown in Table 6 below:

TABLE 6

| S protein RBD residue position | Amino acid residue |
| --- | --- |
| 3 | S |
| 6 | Q |
| 7 | E |
| 8 | V |
| 21 | D |
| 22 | K |
| 30 | P |
| 36 | E |
| 38 | T |
| 39 | K |
| 42 | D |
| 48 | T |
| 54 | T |
| 67 | S |
| 70 | 1 |
| 76 | S |
| 81 | T |
| 83 | L |
| 86 | C |
| 87 | S |
| 92 | V |
| 99 | V |
| 120 | T |
| 121 | A |
| 122 | K |
| 123 | Q |
| 125 | T |
| 126 | G |
| 127 | S |
| 128 | S |
| 134 | Y |
| 137 | S |
| 138 | H |
| 141 | T |
| 142 | K |
| 150 | L |
| 152 | S |
| 153 | D |
| 154 | E |
| 155 | C |
| 156 | S |
| 157 | P |
| 158 | D |
| 159 | G |
| 160 | K |
| 163 | T |

TABLE 6-continued

| S protein RBD residue position | Amino acid residue |
|---|---|
| 164 | P |
| 165 | P |
| 166 | A |
| 167 | F |
| 171 | R |
| 178 | T |
| 180 | S |
| 181 | T |
| 183 | D |
| 185 | N |
| 187 | N |
| 188 | V |
| 189 | P |
| 191 | E |
| 194 | A |
| 195 | T |
| 206 | N |
| 216 | L |
| 219 | Q |

There is also provided according to the invention an isolated polypeptide, which comprises a coronavirus S protein RBD domain with any, or all of the amino acid residues at positions corresponding to the amino acid residue positions as shown in Table 7 below:

TABLE 7

| S protein RBD residue position | Amino acid residue |
|---|---|
| 3 | S |
| 5 | T |
| 6 | Q |
| 7 | E |
| 21 | D |
| 22 | K |
| 28 | R |
| 38 | T |
| 42 | D |
| 48 | T |
| 55 | S |
| 66 | P |
| 67 | S |
| 70 | I |
| 75 | T |
| 76 | S |
| 81 | T |
| 83 | L |
| 84 | I |
| 85 | R |
| 86 | C |
| 87 | S |
| 88 | E |
| 92 | V |
| 112 | T |
| 116 | I |
| 121 | A |
| 122 | K |
| 123 | Q |
| 125 | T |
| 126 | G |
| 128 | S |
| 134 | Y |
| 137 | S |
| 138 | H |
| 140 | K |
| 141 | T |
| 144 | K |
| 150 | L |
| 152 | S |
| 153 | D |
| 154 | E |
| 155 | C |

TABLE 7-continued

| S protein RBD residue position | Amino acid residue |
|---|---|
| 167 | F |
| 168 | N |
| 169 | G |
| 170 | V |
| 171 | R |
| 172 | G |
| 173 | F |
| 177 | F |
| 178 | T |
| 180 | S |
| 181 | T |
| 183 | D |
| 185 | N |
| 186 | P |
| 187 | N |
| 188 | V |
| 189 | P |
| 190 | V |
| 191 | E |
| 194 | A |
| 195 | T |
| 219 | Q |

Optionally an isolated polypeptide of the invention which comprises a coronavirus S protein RBD domain comprises an amino acid sequence which has at least 70%, 75%, 80%, 85%, 90%, 91%, 92%, 93%, 94%, 95%, 96%, 97%, 98%, or 99% amino acid identity over its entire length with the amino acid sequence of SEQ ID NO:5.

Optionally an isolated polypeptide of the invention which comprises a coronavirus S protein RBD domain comprises an amino acid sequence which has at least 70%, 75%, 80%, 85%, 90%, 91%, 92%, 93%, 94%, 95%, 96%, 97%, 98%, or 99% amino acid identity over its entire length with the amino acid sequence of SEQ ID NO:11.

Further novel S protein RBD sequences are referred to herein as COV_S_T2_13-CoV_S_T2_18 (SEQ ID NOs: 27-32, respectively). CoV_S_T2_13 is the direct output of our design algorithm, and CoV_S_T2_14-COV_S_T2_18 are epitope-enriched versions of CoV_S_T2_13. The amino acid sequences of these designed sequences are provided below, and in Example 12:

```
>COV_S_T2_13
                             (SEQ ID NO: 27)
RVAPTKEVVR FPNITNLCPF GEVFNATRFP SVYAWERKRI
SNCVADYSVL YNSTSFSTFK CYGVSPTKLN DLCFTNVYAD
SFVIRGDEVR QIAPGQTGVI ADYNYKLPDD FTGCVIAWNT
NNLDSTTGGN YNYLYRSLRK SKLKPFERDI SSDIYSPGGK
PCSGVEGFNC YYPLRSYGFF PTNGVGYQPY RVVVLSFELL
NAPATVCGPK LSTD

>COV_S_T2_14
                             (SEQ ID NO: 28)
RVAPTKEVVR FPNITNLCPF GEVFNATKFP SVYAWERKKI
SNCVADYSVL YNSTSFSTFK CYGVSPTKLN DLCFTNVYAD
SFVIRGDEVR QIAPGQTGVI ADYNYKLPDD FTGCVIAWNT
NNIDSTTGGN YNYLYRSLRK SKLKPFERDI SSDIYSPGGK
PCSGVEGFNC YYPLRSYGFF PTNGVGYQPY RVVVLSFELL
NAPATVCGPK LSTD

>COV_S_T2_15
                             (SEQ ID NO: 29)
RVAPTKEVVR FPNITNLCPF GEVFNATRFP SVYAWERKRI
SNCVADYSVL YNSTFFSTFK CYGVSPTKLN DLCFSNVYAD
SFVIRGDEVR QIAPGQTGVI ADYNYKLPDD FMGCVIAWNT
NNLDSTTGGN YNYLYRSLRK SKLKPFERDI SSDIYSPGGK
PCSGVEGFNC YYPLRSYGFF PTNGVGYQPY RVVVLSFELL
NAPATVCGPK LSTD
```

-continued

>COV_S_T2_16

(SEQ ID NO: 30)
RVAPTKEVVR FPNITNLCPF GEVFNATRFP SVYAWERKRI
SNCVADYSVL YNSTSFSTFK CYGVSPTKLN DLCFTNVYAD
SFVIRGDEVR QIAPGQTGKI ADYNYKLPDD FTGCVIAWNT
NNLDSTTGGN YNYLYRLFRK SNLKPFERDI SSDIYQAGST
PCSGVEGFNC YFPLQSYGFQ PTNGVGYQPY RVVVLSFELL
NAPATVCGPK LSTD

>COV_S_T2_17

(SEQ ID NO: 31)
RVAPTKEVVR FPNITNLCPF GEVFNATKFP SVYAWERKKI
SNCVADYSVL YNSTSFSTFK CYGVSPTKLN DLCFTNVYAD
SFVIRGDEVR QIAPGQTGVI ADYNYKLPDD FTGCVIAWNT
NNIDSTTGGN YNYLYRSLRK SKLKPFERDI SSDIYSPGGK
PCSGVEGFNC YYPLRSYGFF PTNGTGYQPY RVVVLSFELL
NAPATVCGPK LSTD

-continued

>COV_S_T2_18

(SEQ ID NO: 32)
RVAPTKEVVR FPNITNLCPF GEVFNATRFP SVYAWERKRI
SNCVADYSVL YNSTFFSTEK CYGVSPTKLN DLCFSNVYAD
SFVIRGDEVR QIAPGQTGVI ADYNYKLPDD FMGCVIAWNT
NNLDSTTGGN YNYLYRSLRK SKLKPFERDI SSDIYSPGGK
PCSGVEGFNC YYPLRSYGFF PTNGTGYQPY RVVVLSFELL
NAPATVCGPK LSTD

Alignment of these sequences with SARS2 Reference sequence (EPI_ISL_402119_RBD (CoV_T2_6) (SEQ ID NO:11)) is shown in Example 12 below.

The amino acid differences of the designed sequences from the SARS2 reference sequence are shown in Table 8.1 below (with differences from the reference sequence in bold, and differences that are common to all the designed sequences underlined):

TABLE 8.1

| SARS2 RBD (CoV_T2_6; SEQ ID NO: 11) residue position | Reference residue | T2_13 residue (SEQ ID NO: 27) | T2_14 residue (SEQ ID NO: 28) | T2_15 residue (SEQ ID NO: 29) | T2_16 residue (SEQ ID NO: 30) | T2_17 residue (SEQ ID NO: 31) | T2_18 residue (SEQ ID NO: 32) |
|---|---|---|---|---|---|---|---|
| 3 | Q | A | A | A | A | A | A |
| 6 | E | K | K | K | K | K | K |
| 7 | S | E | E | E | E | E | E |
| 8 | I | V | V | V | V | V | V |
| 28 | R | R | K | R | R | K | R |
| 30 | A | P | P | P | P | P | P |
| 36 | N | E | E | E | E | E | E |
| 39 | R | R | K | R | R | K | R |
| 54 | A | T | T | T | T | T | T |
| 55 | S | S | S | F | S | S | F |
| 75 | T | T | T | S | T | T | S |
| 99 | K | V | V | V | K | V | V |
| 112 | T | T | T | M | T | T | M |
| 120 | S | T | T | T | T | T | T |
| 123 | L | L | I | L | L | I | L |
| 126 | K | T | T | T | T | T | T |
| 127 | V | T | T | T | T | T | T |
| 137 | L | S | S | S | L | S | S |
| 138 | F | L | L | L | F | L | L |
| 142 | N | K | K | K | N | K | K |
| 152 | T | S | S | S | S | S | S |
| 153 | F | D | D | D | D | D | D |
| 156 | Q | S | S | S | Q | S | S |
| 157 | A | P | P | P | A | P | P |
| 159 | S | G | G | G | S | G | G |
| 160 | T | K | K | K | T | K | K |
| 163 | N | S | S | S | S | S | S |

TABLE 8.1-continued

| SARS2 RBD (CoV_T2_6; SEQ ID NO: 11) residue position | Reference residue | T2_13 residue (SEQ ID NO: 27) | T2_14 residue (SEQ ID NO: 28) | T2_15 residue (SEQ ID NO: 29) | T2_16 residue (SEQ ID NO: 30) | T2_17 residue (SEQ ID NO: 31) | T2_18 residue (SEQ ID NO: 32) |
|---|---|---|---|---|---|---|---|
| 172 | F | Y | Y | Y | F | Y | Y |
| 175 | Q | R | R | R | Q | R | R |
| 180 | Q | F | F | F | Q | F | F |
| 185 | V | V | V | V | V | T | T |
| 201 | H | N | N | N | N | N | N |
| 211 | K | L | L | L | L | L | L |
| 214 | N | D | D | D | D | D | D |
| Total no of differences from reference | — | 27 | 30 | 30 | 16 | 31 | 31 |
| Percentage identity with reference | — | 87.38 | 85.98 | 85.98 | 92.52 | 85.51 | 85.51 |

The amino acid changes common to all of the designed sequences are summarised in Table 8.2 below:

TABLE 8.2

| SARS2 RBD (CoV_T2_6; SEQ ID NO: 11) residue position | Reference residue | Design residue |
|---|---|---|
| 3 | Q | A |
| 6 | E | K |
| 7 | S | E |
| 8 | I | V |
| 30 | A | P |
| 36 | N | E |
| 54 | A | T |
| 120 | S | T |
| 126 | K | T |
| 127 | V | T |
| 152 | T | S |
| 153 | E | D |
| 163 | N | S |
| 201 | H | N |
| 211 | K | L |
| 214 | N | D |

Optional additional changes are summarised in Table 8.3 below:

TABLE 8.3

| SARS2 RBD (CoV_T2_6; SEQ ID NO: 11) residue position | Reference residue | Design residue |
|---|---|---|
| 99 | K | V |
| 137 | L | S |
| 138 | F | S |
| 142 | N | K |
| 156 | Q | S |
| 157 | A | S |
| 159 | S | G |
| 160 | T | K |
| 172 | F | Y |

TABLE 8.3-continued

| SARS2 RBD (CoV_T2_6; SEQ ID NO: 11) residue position | Reference residue | Design residue |
|---|---|---|
| 175 | Q | R |
| 180 | Q | F |

The additional changes listed in Table 8.3 are found in SEQ ID NOs: 27-29, 31, and 32.

Further optional additional changes are summarised in Tables 8.4-8.6 below:

TABLE 8.4

| SARS2 RBD (CoV_T2_6; SEQ ID NO: 11) residue position | Reference residue | Design residue | Found in SEQ ID NO: |
|---|---|---|---|
| 28 | R | K | 28, 31 |
| 39 | R | K | 28, 31 |
| 123 | L | I | 28, 31 |

TABLE 8.5

| SARS2 RBD (CoV_T2_6; SEQ ID NO:11) residue position | Reference residue | Design residue | Found in SEQ ID NO: |
|---|---|---|---|
| 55 | S | F | 29, 32 |
| 75 | T | S | 29, 32 |
| 112 | T | M | 29, 32 |

TABLE 8.6

| SARS2 RBD (CoV_T2_6; SEQ ID NO: 11) residue position | Reference residue | Design residue | Found in SEQ ID NO: |
|---|---|---|---|
| 185 | V | T | 31, 32 |

According to the invention there is provided an isolated polypeptide, which comprises an amino acid sequence according to any of SEQ ID NOs: 27-32.

According to the invention there is also provided an isolated polypeptide comprising an amino acid sequence of SEQ ID NO: 27 (COV_S_T2_13), or an amino acid sequence which has at least 88%, 89%, 90%, 91%, 92%, 93%, 94%, 95%, 96%, 97%, 98%, or 99% amino acid identity over its entire length with the amino acid sequence of SEQ ID NO:27.

According to the invention there is also provided an isolated polypeptide comprising an amino acid sequence of SEQ ID NO: 28 (COV_S_T2_14), or an amino acid sequence which has at least 86%, 87%, 88%, 89%, 90%, 91%, 92%, 93%, 94%, 95%, 96%, 97%, 98%, or 99% amino acid identity over its entire length with the amino acid sequence of SEQ ID NO:28.

According to the invention there is also provided an isolated polypeptide comprising an amino acid sequence of SEQ ID NO: 29 (COV_S_T2_15), or an amino acid sequence which has at least 86%, 87%, 88%, 89%, 90%, 91%, 92%, 93%, 94%, 95%, 96%, 97%, 98%, or 99% amino acid identity over its entire length with the amino acid sequence of SEQ ID NO:29.

According to the invention there is also provided an isolated polypeptide comprising an amino acid sequence of SEQ ID NO: 30 (COV_S_T2_16), or an amino acid sequence which has at least 93%, 94%, 95%, 96%, 97%, 98%, or 99% amino acid identity over its entire length with the amino acid sequence of SEQ ID NO:30.

According to the invention there is also provided an isolated polypeptide comprising an amino acid sequence of SEQ ID NO: 31 (COV_S_T2_17), or an amino acid sequence which has at least 86%, 87%, 88%, 89%, 90%, 91%, 92%, 93%, 94%, 95%, 96%, 97%, 98%, or 99% amino acid identity over its entire length with the amino acid sequence of SEQ ID NO:31.

According to the invention there is also provided an isolated polypeptide comprising an amino acid sequence of SEQ ID NO: 32 (COV_S_T2_18), or an amino acid sequence which has at least 86%, 87%, 88%, 89%, 90%, 91%, 92%, 93%, 94%, 95%, 96%, 97%, 98%, or 99% amino acid identity over its entire length with the amino acid sequence of SEQ ID NO:32.

Optionally a polypeptide of the invention comprising an amino acid sequence of SEQ ID NO:27 (COV_S_T2_13), or an amino acid sequence which has at least 88%, 89%, 90%, 91%, 92%, 93%, 94%, 95%, 96%, 97%, 98%, or 99% amino acid identity over its entire length with the amino acid sequence of SEQ ID NO:27, comprises at least one, or all of the amino acid residues at positions corresponding to the amino acid residue positions of SEQ ID NO:11 as shown in Table 8.2 above.

Optionally a polypeptide of the invention comprising an amino acid sequence of SEQ ID NO: 28 (COV_S_T2_14), or an amino acid sequence which has at least 86%, 87%, 88%, 89%, 90%, 91%, 92%, 93%, 94%, 95%, 96%, 97%, 98%, or 99% amino acid identity over its entire length with the amino acid sequence of SEQ ID NO:28, comprises at least one, or all of the amino acid residues at positions corresponding to the amino acid residue positions as shown in Table 8.2 above.

Optionally a polypeptide of the invention comprising an isolated polypeptide comprising an amino acid sequence of SEQ ID NO: 29 (COV_S_T2_15), or an amino acid sequence which has at least 86%, 87%, 88%, 89%, 90%, 91%, 92%, 93%, 94%, 95%, 96%, 97%, 98%, or 99% amino acid identity over its entire length with the amino acid sequence of SEQ ID NO:29, comprises at least one, or all of the amino acid residues at positions corresponding to the amino acid residue positions as shown in Table 8.2 above.

Optionally a polypeptide of the invention comprising an amino acid sequence of SEQ ID NO: 30 (COV_S_T2_16), or an amino acid sequence which has at least 93%, 94%, 95%, 96%, 97%, 98%, or 99% amino acid identity over its entire length with the amino acid sequence of SEQ ID NO:30, comprises at least one, or all of the amino acid residues at positions corresponding to the amino acid residue positions as shown in Table 8.2 above.

Optionally a polypeptide of the invention comprising an amino acid sequence of SEQ ID NO: 31 (COV_S_T2_17), or an amino acid sequence which has at least 86%, 87%, 88%, 89%, 90%, 91%, 92%, 93%, 94%, 95%, 96%, 97%, 98%, or 99% amino acid identity over its entire length with the amino acid sequence of SEQ ID NO:31, comprises at least one, or all of the amino acid residues at positions corresponding to the amino acid residue positions as shown in Table 8.2 above.

Optionally a polypeptide of the invention comprising an amino acid sequence of SEQ ID NO: 32 (COV_S_T2_18), or an amino acid sequence which has at least 86%, 87%, 88%, 89%, 90%, 91%, 92%, 93%, 94%, 95%, 96%, 97%, 98%, or 99% amino acid identity over its entire length with the amino acid sequence of SEQ ID NO:32, comprises at least one, or all of the amino acid residues at positions corresponding to the amino acid residue positions as shown in Table 8.2 above.

Optionally a polypeptide of the invention comprising an amino acid sequence of SEQ ID NO:27 (COV_S_T2_13), or an amino acid sequence which has at least 88%, 89%, 90%, 91%, 92%, 93%, 94%, 95%, 96%, 97%, 98%, or 99% amino acid identity over its entire length with the amino acid sequence of SEQ ID NO:27, further comprises at least one, or all of the amino acid residues at positions corresponding to the amino acid residue positions as shown in Table 8.3 above.

Optionally a polypeptide of the invention comprising an amino acid sequence of SEQ ID NO: 28 (COV_S_T2_14), or an amino acid sequence which has at least 86%, 87%, 88%, 89%, 90%, 91%, 92%, 93%, 94%, 95%, 96%, 97%, 98%, or 99% amino acid identity over its entire length with the amino acid sequence of SEQ ID NO:28, further comprises at least one, or all of the amino acid residues at positions corresponding to the amino acid residue positions as shown in Table 8.3 above.

Optionally a polypeptide of the invention comprising an amino acid sequence of SEQ ID NO: 29 (COV_S_T2_15), or an amino acid sequence which has at least 86%, 87%, 88%, 89%, 90%, 91%, 92%, 93%, 94%, 95%, 96%, 97%, 98%, or 99% amino acid identity over its entire length with the amino acid sequence of SEQ ID NO:29, further comprises at least one, or all of the amino acid residues at positions corresponding to the amino acid residue positions as shown in Table 8.3 above.

Optionally a polypeptide of the invention comprising an amino acid sequence of SEQ ID NO: 31 (COV_S_T2_17), or an amino acid sequence which has at least 86%, 87%, 88%, 89%, 90%, 91%, 92%, 93%, 94%, 95%, 96%, 97%, 98%, or 99% amino acid identity over its entire length with the amino acid sequence of SEQ ID NO:31, further comprises at least one, or all of the amino acid residues at positions corresponding to the amino acid residue positions as shown in Table 8.3 above.

Optionally a polypeptide of the invention comprising an amino acid sequence of SEQ ID NO: 32 (COV_S_T2_18), or an amino acid sequence which has at least 86%, 87%, 88%, 89%, 90%, 91%, 92%, 93%, 94%, 95%, 96%, 97%, 98%, or 99% amino acid identity over its entire length with the amino acid sequence of SEQ ID NO:32, further comprises at least one, or all of the amino acid residues at positions corresponding to the amino acid residue positions as shown in Table 8.3 above. Optionally a polypeptide of the invention comprising an amino acid sequence of SEQ ID NO: 28 (COV_S_T2_14), or an amino acid sequence which has at least 86%, 87%, 88%, 89%, 90%, 91%, 92%, 93%, 94%, 95%, 96%, 97%, 98%, or 99% amino acid identity over its entire length with the amino acid sequence of SEQ ID NO:28, further comprises at least one, or all of the amino acid residues at positions corresponding to the amino acid residue positions as shown in Table 8.4 above.

Optionally a polypeptide of the invention comprising an isolated polypeptide comprising an amino acid sequence of SEQ ID NO: 29 (COV_S_T2_15), or an amino acid sequence which has at least 86%, 87%, 88%, 89%, 90%, 91%, 92%, 93%, 94%, 95%, 96%, 97%, 98%, or 99% amino acid identity over its entire length with the amino acid sequence of SEQ ID NO:29, further comprises at least one, or all of the amino acid residues at positions corresponding to the amino acid residue positions as shown in Table 8.5 above.

Optionally a polypeptide of the invention comprising an amino acid sequence of SEQ ID NO: 31 (COV_S_T2_17), or an amino acid sequence which has at least 86%, 87%, 88%, 89%, 90%, 91%, 92%, 93%, 94%, 95%, 96%, 97%, 98%, or 99% amino acid identity over its entire length with the amino acid sequence of SEQ ID NO:31, further comprises at least one, or all of the amino acid residues at positions corresponding to the amino acid residue positions as shown in Table 8.4 above.

Optionally a polypeptide of the invention comprising an amino acid sequence of SEQ ID NO: 31 (COV_S_T2_17), or an amino acid sequence which has at least 86%, 87%, 88%, 89%, 90%, 91%, 92%, 93%, 94%, 95%, 96%, 97%, 98%, or 99% amino acid identity over its entire length with the amino acid sequence of SEQ ID NO:31, further comprises at least one, or all of the amino acid residues at positions corresponding to the amino acid residue positions as shown in Table 8.6 above.

Optionally a polypeptide of the invention comprising an amino acid sequence of SEQ ID NO: 32 (COV_S_T2_18), or an amino acid sequence which has at least 86%, 87%, 88%, 89%, 90%, 91%, 92%, 93%, 94%, 95%, 96%, 97%, 98%, or 99% amino acid identity over its entire length with the amino acid sequence of SEQ ID NO:32, further comprises at least one, or all of the amino acid residues at positions corresponding to the amino acid residue positions as shown in Table 8.5 above.

Optionally a polypeptide of the invention comprising an amino acid sequence of SEQ ID NO: 32 (COV_S_T2_18), or an amino acid sequence which has at least 86%, 87%, 88%, 89%, 90%, 91%, 92%, 93%, 94%, 95%, 96%, 97%, 98%, or 99% amino acid identity over its entire length with the amino acid sequence of SEQ ID NO:32, further comprises at least one, or all of the amino acid residues at positions corresponding to the amino acid residue positions as shown in Table 8.6 above.

According to the invention there is also provided an isolated polypeptide which comprises a coronavirus S protein RBD domain with at least one of the amino acid residues at positions corresponding to the amino acid residue positions of SEQ ID NO:11, as shown in Table 8.2 above.

Optionally an isolated polypeptide of the invention which comprises a coronavirus S protein RBD domain with at least one of the amino acid residues at positions corresponding to the amino acid residue positions of SEQ ID NO:11, as shown in Table 8.2 above, comprises at least five amino acid residues at positions corresponding to the amino acid residue positions of SEQ ID NO:11, as shown in Table 8.2 above.

Optionally an isolated polypeptide of the invention which comprises a coronavirus S protein RBD domain with at least one of the amino acid residues at positions corresponding to the amino acid residue positions of SEQ ID NO:11, as shown in Table 8.2 above, comprises at least ten amino acid residues at positions corresponding to the amino acid residue positions of SEQ ID NO:11, as shown in Table 8.2 above.

Optionally an isolated polypeptide of the invention which comprises a coronavirus S protein RBD domain with at least one of the amino acid residues at positions corresponding to the amino acid residue positions of SEQ ID NO:11, as shown in Table 8.2 above, comprises at least fifteen amino acid residues at positions corresponding to the amino acid residue positions of SEQ ID NO:11, as shown in Table 8.2 above.

Optionally an isolated polypeptide of the invention which comprises a coronavirus S protein RBD domain with at least one of the amino acid residues at positions corresponding to the amino acid residue positions of SEQ ID NO:11, as shown in Table 8.2 above, comprises all of the amino acid residues at positions corresponding to the amino acid residue positions of SEQ ID NO: 11, as shown in Table 8.2 above.

Optionally an isolated polypeptide of the invention which comprises a coronavirus S protein RBD domain with at least one, five, ten, fifteen, or all, of the amino acid residues at positions corresponding to the amino acid residue positions of SEQ ID NO:11, as shown in Table 8.2 above further comprises at least one, or all of the amino acid residues at positions corresponding to the amino acid residue positions of SEQ ID NO:11, as shown in Table 8.3 above.

Optionally an isolated polypeptide of the invention which comprises a coronavirus S protein RBD domain with at least one, five, ten, fifteen, or all, of the amino acid residues at positions corresponding to the amino acid residue positions of SEQ ID NO:11, as shown in Table 8.2 above and at least one, or all of the amino acid residues at positions corresponding to the amino acid residue positions of SEQ ID NO:11, as shown in Table 8.3 above, further comprises at least one, or all of the amino acid residues at positions corresponding to the amino acid residue positions of SEQ ID NO:11, as shown in any of Tables 8.4 to 8.6 above.

Optionally an isolated polypeptide of the invention which comprises a coronavirus S protein RBD domain comprises an amino acid sequence which has at least 70%, 75%, 80%, 85%, 90%, 91%, 92%, 93%, 94%, 95%, 96%, 97%, 98%, or 99% amino acid identity over its entire length with the amino acid sequence of SEQ ID NO:5.

Optionally an isolated polypeptide of the invention which comprises a coronavirus S protein RBD domain comprises an amino acid sequence which has at least 70%, 75%, 80%, 85%, 90%, 91%, 92%, 93%, 94%, 95%, 96%, 97%, 98%, or 99% amino acid identity over its entire length with the amino acid sequence of SEQ ID NO:11.

Discontinuous Epitope Sequences of Designed S Protein RBD Sequences COV_S_T2_14-18 (SEQ ID NOs: 28-32)

The sequence alignment in FIG. 44A shows the designed S protein RBD sequences COV_S_T2_13-18 (SEQ ID NOs: 27-32, respectively) aligned. The coloured boxes show the residues of-discontinuous epitopes present in sequences COV_S_T2_14-18 shown in different colour. The changes made relative to the COV_S_T2_13 sequence to provide discontinuous epitopes that elicit a broader or more potent immune response are shown by the boxed regions:

The residues of the discontinuous epitope present in COV_S_T2_14 and COV_S_T2_17 (marked in black) are as follows:

```
i)
residues 13-28;
                    (SEQ ID NO: 57)
NITNLCPFGEVENATK ii)
residues 38-42;
                    (SEQ ID NO: 58)
KKISN iii)
residues 122-123
                    (SEQ ID NO: 59)
NI
```

The residues of the discontinuous epitope present in COV_S_T2_15 and COV_S_T2_18 (marked in purple) are as follows:

```
i)
residues 51-75;
                    (SEQ ID NO: 60)
YNSTFFSTFKCYGVSPTKLNDLCFS ii)
residues 109-112
                    (SEQ ID NO: 61)
DDFM iii)
residues 197-201
                    (SEQ ID NO: 62)
FELLN
```

The residues of the discontinuous epitope present in COV_S_T2_16 (marked in orange) are as follows:

```
i)
residues 85-91;
                    (SEQ ID NO: 63)
RGDEVRQ ii)
residues 97-103;
                    (SEQ ID NO: 64)
TGKIADY iii)
residues 135-142;
                    (SEQ ID NO: 65)
YRLFRKSN iv)
residues 155-160
                    (SEQ ID NO: 66)
YQAGST
```

-continued

```
v)
residues 168-187
                    (SEQ ID NO: 67)
FNCYFPLQSYGFQPTNGVGY
```

The residues of the discontinuous epitope present in COV_S_T2_13, COV_S_T2_15, COV_S_T2_16, and COV_S_T2_18 (vertically adjacent the epitope marked in black) are as follows:

```
(i)
residues 13-28;
                    (SEQ ID NO: 68)
NITNLCPFGEVENATR (ii)
residues 38-42;
                    (SEQ ID NO: 69)
KRISN (iii)
residues 122-123
                    (SEQ ID NO: 70)
NL
```

The residues of the discontinuous epitope present in COV_S_T2_13, COV_S_T2_14, COV_S_T2_16, and COV_S_T2_17 (vertically adjacent the epitope marked in purple) are as follows:

```
(i)
residues 51-75;
                    (SEQ ID NO: 71)
YNSTSFSTFKCYGVSPTKLNDLCFT (ii)
residues 109-112
                    (SEQ ID NO: 72)
DDFT (iii)
residues 197-201
                    (SEQ ID NO: 62)
FELLN
```

The residues of the discontinuous epitope present in COV_S_T2_13, COV_S_T2_14, and COV_S_T2_15 (vertically adjacent the epitope marked in orange) are as follows:

```
(i)
residues 85-91;
                    (SEQ ID NO: 63)
RGDEVRQ (ii)
residues 97-103;
                    (SEQ ID NO: 73)
TGVIADY (iii)
residues 135-142;
                    (SEQ ID NO: 74)
YRSLRKSK (iv)
residues 155-160
                    (SEQ ID NO: 75)
YSPGGK (v)
residues 168-187
                    (SEQ ID NO: 76)
FNCYYPLRSYGFFPTNGVGY
```

The residues of the discontinuous epitope present in COV_S_T2_17 and COV_S_T2_18 (vertically adjacent the epitope marked in orange) are as follows:

```
    (i)
    residues 85-91;
                    (SEQ ID NO: 63)
    RGDEVRQ (ii)
    residues 97-103;
                    (SEQ ID NO: 73)
    TGVIADY (iii)
    residues 135-142;
                    (SEQ ID NO: 74)
    YRSLRKSK (iv)
    residues 155-160
                    (SEQ ID NO: 75)
    YSPGGK (v)
    residues 168-187
                    (SEQ ID NO: 77)
    FNCYYPLRSYGFFPTNGTGY
```

According to the invention there is provided an isolated polypeptide comprising an amino acid sequence with the following discontinuous amino acid sequences:

```
    i)
                    (SEQ ID NO: 57)
    NITNLCPFGEVFNATK;

ii)
                    (SEQ ID NO: 58)
    KKISN;

iii)
                    (SEQ ID NO: 59)
    NI.
```

According to the invention there is provided an isolated polypeptide comprising an amino acid sequence with the following discontinuous amino acid sequences:

```
    i)
                    (SEQ ID NO: 60)
    YNSTFFSTFKCYGVSPTKLNDLCFS;

ii)
                    (SEQ ID NO: 61)
    DDFM;

iii)
                    (SEQ ID NO: 62)
    FELLN.
```

According to the invention there is provided an isolated polypeptide comprising an amino acid sequence with the following discontinuous amino acid sequences:

```
    i)
                    (SEQ ID NO: 63)
    RGDEVRQ;

ii)
                    (SEQ ID NO: 64)
    TGKIADY;
```

```
-continued
    iii)
                    (SEQ ID NO: 65)
    YRLFRKSN;

iv)
                    (SEQ ID NO: 66)
    YQAGST;

v)
                    (SEQ ID NO: 67)
    FNCYFPLQSYGFQPTNGVGY.
```

Optionally one or more residues of the amino acid residues of SEQ ID NOs: 63-67 in a polypeptide of the invention comprising discontinuous amino acid sequences of SEQ ID NOs: 63-67 may be changed (for example, by substitution or deletion) to provide a glycosylation site.

According to the invention there is also provided an isolated polypeptide comprising an amino acid sequence with the following discontinuous amino acid sequences:

```
    (i)
                    (SEQ ID NO: 68)
    NITNLCPFGEVFNATR;

(ii)
                    (SEQ ID NO: 69)
    KRISN;

(iii)
                    (SEQ ID NO: 70)
    NL
```

According to the invention there is provided an isolated polypeptide comprising an amino acid sequence with the following discontinuous amino acid sequences:

```
    (i)
                    (SEQ ID NO: 71)
    YNSTSFSTFKCYGVSPTKLNDLCFT;

(ii)
                    (SEQ ID NO: 72)
    DDFT (iii)
                    (SEQ ID NO: 62)
    FELLN
```

According to the invention there is provided an isolated polypeptide comprising an amino acid sequence with the following discontinuous amino acid sequences:

```
    (i)
                    (SEQ ID NO: 63)
    RGDEVRQ;

(ii)
                    (SEQ ID NO: 73)
    TGVIADY;

(iii)
                    (SEQ ID NO: 74)
    YRSLRKSK;

(iv)
                    (SEQ ID NO: 75)
    YSPGGK (v)
                    (SEQ ID NO: 76)
    FNCYYPLRSYGFFPTNGVGY
```

According to the invention there is provided an isolated polypeptide comprising an amino acid sequence with the following discontinuous amino acid sequences:

```
(i)
                              (SEQ ID NO: 63)
RGDEVRQ;

(ii)
                              (SEQ ID NO: 73)
TGVIADY;

(iii)
                              (SEQ ID NO: 74)
YRSLRKSK;

(iv)
                              (SEQ ID NO: 75)
YSPGGK (v)
                              (SEQ ID NO: 77)
FNCYYPLRSYGFFPTNGTGY
```

Optionally the discontinuous amino acid sequences of each polypeptide of the invention are present in the order recited.

Optionally each discontinuous amino acid sequence is separated by at least 3 amino acid residues from an adjacent discontinuous amino acid sequence.

Optionally each discontinuous amino acid sequence is separated by up to 100 amino acid residues from an adjacent discontinuous amino acid sequence.

Optionally a polypeptide of the invention comprising the recited discontinuous amino acid sequences is up to 250, 500, 750, 1,000, 1,250, or 1,500 amino acid residues in length.

Optionally an isolated polypeptide of the invention comprising an amino acid sequence which has at least 86%, 87%, 88%, 89%, 90%, 91%, 92%, 93%, 94%, 95%, 96%, 97%, 98%, or 99% amino acid identity over its entire length with the amino acid sequence of SEQ ID NO:28, comprises the following discontinuous amino acid sequences:

```
i)
                              (SEQ ID NO: 57)
NITNLCPFGEVFNATK;

ii)
                              (SEQ ID NO: 58)
KKISN;

iii)
                              (SEQ ID NO: 59)
NI
```

Optionally the discontinuous amino acid sequences (i), (ii), and (iii) are at amino acid residue positions corresponding to (i) residues 13-28; (ii) residues 38-42; and (iii) residues 122-123 of SEQ ID NO:28, respectively.

Optionally an isolated polypeptide of the invention comprising an amino acid sequence which has at least 86%, 87%, 88%, 89%, 90%, 91%, 92%, 93%, 94%, 95%, 96%, 97%, 98%, or 99% amino acid identity over its entire length with the amino acid sequence of SEQ ID NO:29, comprises the following discontinuous amino acid sequences:

```
i)
                              (SEQ ID NO: 60)
YNSTFFSTFKCYGVSPTKLNDLCFS;
```

-continued
```
                              (SEQ ID NO: 61)
DDFM;

(SEQ ID NO: 62)
FELLN.
```

Optionally the discontinuous amino acid sequences (i), (ii), and (iii) are at amino acid residue positions corresponding to (i) residues 51-75; (ii) residues 109-112; and (iii) residues 197-201 of SEQ ID NO:29, respectively.

Optionally an isolated polypeptide of the invention comprising an amino acid sequence which has at least 93%, 94%, 95%, 96%, 97%, 98%, or 99% amino acid identity over its entire length with the amino acid sequence of SEQ ID NO:30, comprises the following discontinuous amino acid sequences:

```
i)
                              (SEQ ID NO: 63)
RGDEVRQ;

ii)
                              (SEQ ID NO: 64)
TGKIADY;

iii)
                              (SEQ ID NO: 65)
YRLFRKSN;

iv)
                              (SEQ ID NO: 66)
YQAGST;

v)
                              (SEQ ID NO: 67)
FNCYFPLQSYGFQPTNGVGY.
```

Optionally the discontinuous amino acid sequences (i), (ii), (iii), (iv), and (v) are at amino acid residue positions corresponding to (i) residues 85-91, (ii) residues 97-103, (iii) residues 135-142, (iv) residues 155-160, and (v) residues 168-187 of SEQ ID NO:30, respectively.

Optionally an isolated polypeptide of the invention comprising an amino acid sequence which has at least 86%, 87%, 88%, 89%, 90%, 91%, 92%, 93%, 94%, 95%, 96%, 97%, 98%, or 99% amino acid identity over its entire length with the amino acid sequence of SEQ ID NO:31, comprises the following discontinuous amino acid sequences:

```
i)
                              (SEQ ID NO: 57)
NITNLCPFGEVENATK;

ii)
                              (SEQ ID NO: 58)
KKISN;

iii)
                              (SEQ ID NO: 59)
NI.
```

Optionally the discontinuous amino acid sequences (i), (ii), and (iii) are at amino acid residue positions corresponding to (i) residues 13-28; (ii) residues 38-42; and (iii) residues 122-123 of SEQ ID NO:31, respectively.

Optionally an isolated polypeptide of the invention comprising an amino acid sequence which has at least 86%, 87%, 88%, 89%, 90%, 91%, 92%, 93%, 94%, 95%, 96%, 97%, 98%, or 99% amino acid identity over its entire length with the amino acid sequence of SEQ ID NO:32, comprises the following discontinuous amino acid sequences:

```
i)
                            (SEQ ID NO: 60)
YNSTFFSTFKCYGVSPTKLNDLCFS;

ii)
                            (SEQ ID NO: 61)
DDFM;

iii)
                            (SEQ ID NO: 62)
FELLN.
```

Optionally the discontinuous amino acid sequences (i), (ii), and (iii) are at amino acid residue positions corresponding to (i) residues 51-75; (ii) residues 109-112; and (iii) residues 197-201 of SEQ ID NO:32, respectively.

Optionally an isolated polypeptide of the invention comprising an amino acid sequence which has at least 86%, 87%, 88%, 89%, 90%, 91%, 92%, 93%, 94%, 95%, 96%, 97%, 98%, or 99% amino acid identity over its entire length with the amino acid sequence of SEQ ID NO:29, comprises the following discontinuous amino acid sequences:

```
(i)
                            (SEQ ID NO: 68)
NITNLCPFGEVFNATR;

(ii)
                            (SEQ ID NO: 69)
KRISN;

(iii)
                            (SEQ ID NO: 70)
NL
```

Optionally the discontinuous amino acid sequences (i), (ii), and (iii) are at amino acid residue positions corresponding to (i) residues 13-28; (ii) residues 38-42; and (iii) residues 122-123 of SEQ ID NO:29, respectively.

Optionally an isolated polypeptide of the invention comprising an amino acid sequence which has at least 93%, 94%, 95%, 96%, 97%, 98%, or 99% amino acid identity over its entire length with the amino acid sequence of SEQ ID NO:30, comprises the following discontinuous amino acid sequences:

```
(i)
                            (SEQ ID NO: 68)
NITNLCPFGEVFNATR;

(ii)
                            (SEQ ID NO: 69)
KRISN;

(iii)
                            (SEQ ID NO: 70)
NL
```

Optionally the discontinuous amino acid sequences (i), (ii), and (iii) are at amino acid residue positions corresponding to (i) residues 13-28; (ii) residues 38-42; and (iii) residues 122-123 of SEQ ID NO:30, respectively.

Optionally an isolated polypeptide of the invention comprising an amino acid sequence which has at least 86%, 87%, 88%, 89%, 90%, 91%, 92%, 93%, 94%, 95%, 96%, 97%, 98%, or 99% amino acid identity over its entire length with the amino acid sequence of SEQ ID NO:32, comprises the following discontinuous amino acid sequences:

```
(i)
                            (SEQ ID NO: 68)
NITNLCPFGEVFNATR;

(ii)
                            (SEQ ID NO: 69)
KRISN;

(iii)
                            (SEQ ID NO: 70)
NL
```

Optionally the discontinuous amino acid sequences (i), (ii), and (iii) are at amino acid residue positions corresponding to (i) residues 13-28; (ii) residues 38-42; and (iii) residues 122-123 of SEQ ID NO:32, respectively.

Optionally an isolated polypeptide of the invention comprising an amino acid sequence which has at least 86%, 87%, 88%, 89%, 90%, 91%, 92%, 93%, 94%, 95%, 96%, 97%, 98%, or 99% amino acid identity over its entire length with the amino acid sequence of SEQ ID NO:28, comprises the following discontinuous amino acid sequences:

```
(i)
                            (SEQ ID NO: 71)
YNSTSFSTFKCYGVSPTKLNDLCFT;

(ii)
                            (SEQ ID NO: 72)
DDFT (iii)
                            (SEQ ID NO: 62)
FELLN
```

Optionally the discontinuous amino acid sequences (i), (ii), and (iii) are at amino acid residue positions corresponding to (i) residues 51-75; (ii) residues 109-112; and (iii) residues 197-201 of SEQ ID NO:28, respectively.

Optionally an isolated polypeptide of the invention comprising an amino acid sequence which has at least 93%, 94%, 95%, 96%, 97%, 98%, or 99% amino acid identity over its entire length with the amino acid sequence of SEQ ID NO:30, comprises the following discontinuous amino acid sequences:

```
(i)
                            (SEQ ID NO: 71)
YNSTSFSTFKCYGVSPTKLNDLCFT;

(ii)
                            (SEQ ID NO: 72)
DDFT (iii)
                            (SEQ ID NO: 62)
FELLN
```

Optionally the discontinuous amino acid sequences (i), (ii), and (iii) are at amino acid residue positions corresponding to (i) residues 51-75; (ii) residues 109-112; and (iii) residues 197-201 of SEQ ID NO:30, respectively.

Optionally an isolated polypeptide of the invention comprising an amino acid sequence which has at least 86%, 87%, 88%, 89%, 90%, 91%, 92%, 93%, 94%, 95%, 96%, 97%, 98%, or 99% amino acid identity over its entire length with the amino acid sequence of SEQ ID NO:31, comprises the following discontinuous amino acid sequences:

```
(i)
                            (SEQ ID NO: 71)
YNSTSFSTFKCYGVSPTKLNDLCFT;

(ii)
                            (SEQ ID NO: 72)
DDFT (iii)
                            (SEQ ID NO: 62)
FELLN
```

Optionally the discontinuous amino acid sequences (i), (ii), and (iii) are at amino acid residue positions corresponding to (i) residues 51-75; (ii) residues 109-112; and (iii) residues 197-201 of SEQ ID NO:31, respectively.

Optionally an isolated polypeptide of the invention comprising an amino acid sequence which has at least 86%, 87%, 88%, 89%, 90%, 91%, 92%, 93%, 94%, 95%, 96%, 97%, 98%, or 99% amino acid identity over its entire length with the amino acid sequence of SEQ ID NO:28, comprises the following discontinuous amino acid sequences:

```
(i)
                            (SEQ ID NO: 63)
RGDEVRQ;

(ii)
                            (SEQ ID NO: 73)
TGVIADY;

(iii)
                            (SEQ ID NO: 74)
YRSLRKSK;

(iv)
                            (SEQ ID NO: 75)
YSPGGK v)
                            (SEQ ID NO: 76)
FNCYYPLRSYGFFPTNGVGY
```

Optionally the discontinuous amino acid sequences (i), (ii), and (iii) are at amino acid residue positions corresponding to (i) residues 51-75; (ii) residues 109-112; and (iii) residues 197-201 of SEQ ID NO:28, respectively.

Optionally an isolated polypeptide of the invention comprising an amino acid sequence which has at least 86%, 87%, 88%, 89%, 90%, 91%, 92%, 93%, 94%, 95%, 96%, 97%, 98%, or 99% amino acid identity over its entire length with the amino acid sequence of SEQ ID NO:29, comprises the following discontinuous amino acid sequences:

```
(i)
                            (SEQ ID NO: 63)
RGDEVRQ;

(ii)
                            (SEQ ID NO: 73)
TGVIADY;

(iii)
                            (SEQ ID NO: 74)
YRSLRKSK;

(iv)
                            (SEQ ID NO: 75)
YSPGGK v)
                            (SEQ ID NO: 76)
FNCYYPLRSYGFFPTNGVGY
```

Optionally the discontinuous amino acid sequences (i), (ii), and (iii) are at amino acid residue positions corresponding to (i) residues 51-75; (ii) residues 109-112; and (iii) residues 197-201 of SEQ ID NO:29, respectively.

Optionally an isolated polypeptide of the invention comprising an amino acid sequence which has at least 86%, 87%, 88%, 89%, 90%, 91%, 92%, 93%, 94%, 95%, 96%, 97%, 98%, or 99% amino acid identity over its entire length with the amino acid sequence of SEQ ID NO:31, comprises the following discontinuous amino acid sequences:

```
(i)
                            (SEQ ID NO: 63)
RGDEVRQ;

(ii)
                            (SEQ ID NO: 73)
TGVIADY;

(iii)
                            (SEQ ID NO: 74)
YRSLRKSK;

(iv)
                            (SEQ ID NO: 75)
YSPGGK v)
                            (SEQ ID NO: 76)
FNCYYPLRSYGFFPTNGTGY
```

Optionally the discontinuous amino acid sequences (i), (ii), and (iii) are at amino acid residue positions corresponding to (i) residues 51-75; (ii) residues 109-112; and (iii) residues 197-201 of SEQ ID NO:31, respectively.

Optionally an isolated polypeptide of the invention comprising an amino acid sequence which has at least 86%, 87%, 88%, 89%, 90%, 91%, 92%, 93%, 94%, 95%, 96%, 97%, 98%, or 99% amino acid identity over its entire length with the amino acid sequence of SEQ ID NO:32, comprises the following discontinuous amino acid sequences:

```
(i)
                            (SEQ ID NO: 63)
RGDEVRQ;

(ii)
                            (SEQ ID NO: 73)
TGVIADY;

(iii)
                            (SEQ ID NO: 74)
YRSLRKSK;

(iv)
                            (SEQ ID NO: 75)
YSPGGK v)
                            (SEQ ID NO: 76)
FNCYYPLRSYGFFPTNGTGY
```

Optionally the discontinuous amino acid sequences (i), (ii), and (iii) are at amino acid residue positions corresponding to (i) residues 51-75; (ii) residues 109-112; and (iii) residues 197-201 of SEQ ID NO:32, respectively.

Designed Coronavirus S Protein RBD Sequences with Altered Glycosylation Sites

Masking/de-masking of epitopes has been shown to alter the immune response by masking non-neutralising epitopes, or by de-masking important epitopes in MERS (Du L et. al., *Nat. Comm*, volume 7, Article number: 13473 (2016)). We have prepared additional designed S protein RBD sequences (SARS2 RBD designs M7, M8, M9, and M10) in which we have deleted a glycosylation site of SARS2 RBD sequence, or introduced a glycosylation site to SARS2 RBD sequence. The changes made are illustrated in FIG. 13, and discussed in Example 14 below. Designs M7 and M9 include a glycosylation site introduced at the position indicated by circled number 4 (residue position 203) in FIG. 13. Designs M8 and M10 include a deleted glycosylation site at each of the positions indicated by circled numbers 1 and 2 (residue positions 13 and 25, respectively) in FIG. 13. The M8 design also includes an introduced glycosylation site at the position indicated by circled number 3 (residue position 54).

The amino acid sequences of SARS2 RBD designs M7, M8, M9, and M10 are shown below, and in Example 14:

```
>M7
                                                          (SEQ ID NO: 33)
RVQPTESIVR FPNITNLCPF GEVFNATRFA SVYAWNRKRI SNCVADYSVL YNSASFSTFK CYGVSPTKLN

DLCFTNVYAD SFVIRGDEVR QIAPGQTGKI ADYNYKLPDD FTGCVIAWNS NNLDSKVGGN YNYLYRLFRK

SNLKPFERDI STEIYQAGST PCNGVEGFNC YFPLQSYGFQ PTNGVGYQPY RVVVLSFELL HANATVCGPK

KSTN

>M8
                                                          (SEQ ID NO: 34)
RVQPTESIVR FPQITNLCPF GEVFQATRFA SVYAWNRKRI SNCVADYSVL YNSTSFSTFK CYGVSPTKLN

DLCFTNVYAD SFVIRGDEVR QIAPGQTGKI ADYNYKLPDD FTGCVIAWNS NNLDSKVGGN YNYLYRLFRK

SNLKPFERDI STEIYQAGST PCNGVEGFNC YFPLQSYGFQ PTNGVGYQPY RVVVLSFELL HAPATVCGPK

KSTN

>M9
                                                          (SEQ ID NO: 35)
RVSPTQEVVR FPNITNLCPF DKVFNATRFP SVYAWERTKI SDCVADYTVL YNSTSFSTFK CYGVSPSKLI

DLCFTSVYAD TFLIRCSEVR QVAPGQTGVI ADYNYKLPDD FTGCVIAWNT AKQDTGSSGN YNYYYRSHRK

TKLKPFERDL SSDECSPDGK PCTPPAFNGV RGFNCYFTLS TYDFNPNVPV EYQATRVVVL SFELLNANAT

VCGPKLSTQ

>M10
                                                          (SEQ ID NO: 36)
RVSPTQEVVR FPQITNLCPF DKVFQATRFP SVYAWERTKI SDCVADYTVL YNSTSFSTFK CYGVSPSKLI

DLCFTSVYAD TFLIRCSEVR QVAPGQTGVI ADYNYKLPDD FTGCVIAWNT AKQDTGSSGN YNYYYRSHRK

TKLKPFERDL SSDECSPDGK PCTPPAFNGV RGFNCYFTLS TYDFNPNVPV EYQATRVVVL SFELLNAPAT

VCGPKLSTQ
```

Alignment of these sequences with the SARS2 Reference sequence (EPI_ISL_402119_RBD (CoV_T2_6) (SEQ ID NO:11)) is shown in FIG. 48 and Example 14 below.

The amino acid differences of the designed sequences from the SARS2 reference sequence are shown in Table 9 below (with differences from the reference sequence in bold):

TABLE 9

| Circled number of FIG. 13 | SARS2 RBD (SEQ ID NO: 11) residue position | Reference residue | M7 residue (SEQ ID NO: 33) | M8 residue (SEQ ID NO: 34) | M9 residue (SEQ ID NO: 35) | M10 residue (SEQ ID NO: 36) |
|---|---|---|---|---|---|---|
| | 3 | Q | | | S | S |
| | 6 | E | | | Q | Q |
| | 7 | S | | | E | E |
| | 8 | I | | | V | V |
| 1 | 13 | N | | Q | | Q |
| | 21 | G | | | D | K |
| | 22 | E | | | D | K |

TABLE 9-continued

| Circled number of FIG. 13 | SARS2 RBD (SEQ ID NO: 11) residue position | Reference residue | M7 residue (SEQ ID NO: 33) | M8 residue (SEQ ID NO: 34) | M9 residue (SEQ ID NO: 35) | M10 residue (SEQ ID NO: 36) |
|---|---|---|---|---|---|---|
| 2 | 25 | N | | Q | | Q |
| | 30 | A | | | P | P |
| | 36 | N | | | E | E |
| | 38 | K | | | T | K |
| | 39 | R | | | T | K |
| | 42 | N | | | D | D |
| | 48 | S | | | T | T |
| 3 | 54 | A | | T | T | T |
| | 67 | T | | | S | S |
| | 70 | N | | | I | I |
| | 76 | N | | | S | S |
| | 81 | S | | | T | T |
| | 83 | V | | | L | L |
| | 86 | G | | | C | C |
| | 87 | D | | | S | S |
| | 92 | I | | | V | V |
| | 99 | K | | | V | V |
| | 120 | S | | | T | T |
| | 121 | N | | | A | A |
| | 122 | N | | | K | K |
| | 123 | L | | | Q | Q |
| | 125 | S | | | T | T |
| | 126 | K | | | G | G |
| | 127 | V | | | S | S |
| | 128 | G | | | S | S |
| | 134 | L | | | Y | Y |
| | 137 | L | | | S | S |
| | 138 | F | | | H | H |
| | 141 | S | | | T | T |
| | 142 | N | | | K | K |
| | 150 | I | | | L | L |
| | 152 | T | | | S | S |
| | 153 | E | | | D | D |
| | 154 | I | | | E | E |
| | 155 | Y | | | C | C |
| | 156 | Q | | | S | S |
| | 157 | A | | | P | P |

TABLE 9-continued

| Circled number of FIG. 13 | SARS2 RBD (SEQ ID NO: 11) residue position | Reference residue | M7 residue (SEQ ID NO: 33) | M8 residue (SEQ ID NO: 34) | M9 residue (SEQ ID NO: 35) | M10 residue (SEQ ID NO: 36) |
|---|---|---|---|---|---|---|
| | 158 | G | | | D | D |
| | 159 | S | | | G | G |
| | 160 | T | | | K | K |
| | * | — | | | T | T |
| | * | — | | | P | P |
| | * | — | | | P | P |
| | * | — | | | A | A |
| | * | — | | | F | F |
| | 166 | E | | | R | R |
| | 173 | P | | | T | T |
| | 175 | Q | | | S | S |
| | 176 | S | | | T | T |
| | 178 | G | | | D | D |
| | 180 | Q | | | N | N |
| | 182 | T | | | N | N |
| | 183 | N | | | V | V |
| | 184 | G | | | P | P |
| | 186 | E | | | E | E |
| | 189 | P | | | A | A |
| | 190 | Y | | | T | T |
| | 201 | H | | | N | N |
| 4 | 203 | P | N | | N | — |
| | 211 | K | | | L | L |
| | 214 | Q | | | D | Q |
| Total no of differences from reference | | | 1 | 3 | 66 | 67 |
| Percentage identity with reference | | | 99.53% | 98.60% | 69.12% | 68.69% |

*Residues inserted between amino acid residue positions 162 and 163 of SEQ ID NO: 11.

According to the invention there is provided an isolated polypeptide, which comprises an amino acid sequence according to SEQ ID NO:33, 34, 35, or 36.

According to the invention there is also provided an isolated polypeptide comprising an amino acid sequence of SEQ ID NO: 34 (M8), or an amino acid sequence which has at least 99% amino acid identity over its entire length with the amino acid sequence of SEQ ID NO:34.

Optionally a polypeptide of the invention comprising an amino acid sequence of SEQ ID NO:34 (M8), or an amino acid sequence which has at least 99% amino acid identity over its entire length with the amino acid sequence of SEQ ID NO:34, comprises at least one, or all of the following amino acid residues at positions corresponding to the amino acid residue positions of SEQ ID NO:11: 13Q, 25Q, 54T.

According to the invention there is also provided an isolated polypeptide which comprises a coronavirus S protein RBD domain with at least one of the following amino acid residues at positions corresponding to the amino acid residue positions of SEQ ID NO:11: 13Q, 25Q, 54T, 203N.

According to the invention there is also provided an isolated polypeptide comprising an amino acid sequence of SEQ ID NO: 35 (M9), or an amino acid sequence which has at least 70% amino acid identity over its entire length with the amino acid sequence of SEQ ID NO:35.

Optionally an isolated polypeptide of the invention which comprises an amino acid sequence of SEQ ID NO: 35 (M9), or an amino acid sequence which has at least 70% amino acid identity over its entire length with the amino acid sequence of SEQ ID NO:35, comprises at least one, or all of the amino acid residues at positions corresponding to the amino acid residue positions as shown in Table 9.1 below.

TABLE 9.1

| SARS2 RBD (SEQ ID NO: 11) residue position | M9 residue (SEQ ID NO: 35) |
|---|---|
| 3 | S |
| 6 | Q |
| 7 | E |
| 8 | V |
| 21 | D |
| 22 | D |
| 30 | P |
| 36 | E |
| 38 | T |
| 39 | T |
| 42 | D |
| 48 | T |
| 54 | T |
| 67 | S |
| 70 | I |
| 76 | S |
| 81 | T |
| 83 | L |
| 86 | C |
| 87 | S |
| 92 | V |
| 99 | V |
| 120 | T |
| 121 | A |
| 122 | K |
| 123 | Q |
| 125 | T |
| 126 | G |
| 127 | S |
| 128 | S |
| 134 | Y |
| 137 | S |
| 138 | H |
| 141 | T |
| 142 | K |
| 150 | L |
| 152 | S |
| 153 | D |
| 154 | E |
| 155 | C |
| 156 | S |
| 157 | P |
| 158 | D |
| 159 | G |
| 160 | K |
| * | T |
| * | P |
| * | P |
| * | A |
| * | F |
| 166 | R |
| 173 | T |
| 175 | S |
| 176 | T |
| 178 | D |
| 180 | N |
| 182 | N |
| 183 | V |
| 184 | P |
| 186 | E |
| 189 | A |

TABLE 9.1-continued

| SARS2 RBD (SEQ ID NO: 11) residue position | M9 residue (SEQ ID NO: 35) |
|---|---|
| 190 | T |
| 201 | N |
| 203 | N |
| 211 | L |
| 214 | Q |

Optionally an isolated polypeptide of the invention which comprises an amino acid sequence of SEQ ID NO: 35 (M9), or an amino acid sequence which has at least 70% amino acid identity over its entire length with the amino acid sequence of SEQ ID NO:35, comprises at least one, or both of the following amino acid residues at positions corresponding to the amino acid residue positions of SEQ ID NO:11: 54T, 203N.

Residues for insertion between amino acid residue positions 162 and 163 of SEQ ID NO:11

According to the invention there is also provided an isolated polypeptide comprising an amino acid sequence of SEQ ID NO: 36 (M10), or an amino acid sequence which has at least 69% amino acid identity over its entire length with the amino acid sequence of SEQ ID NO:36.

Optionally an isolated polypeptide of the invention which comprises an amino acid sequence of SEQ ID NO: 36 (M10), or an amino acid sequence which has at least 69% amino acid identity over its entire length with the amino acid sequence of SEQ ID NO:36, comprises at least one, or all of the amino acid residues at positions corresponding to the amino acid residue positions as shown in Table 9.2 below.

TABLE 9.2

| SARS2 RBD (SEQ ID NO: 11) residue position | M10 residue (SEQ ID NO: 36) |
|---|---|
| 3 | S |
| 6 | Q |
| 7 | E |
| 8 | V |
| 13 | Q |
| 21 | K |
| 22 | K |
| 25 | Q |
| 30 | P |
| 36 | E |
| 38 | K |
| 39 | K |
| 42 | D |
| 48 | T |
| 54 | T |
| 67 | S |
| 70 | I |
| 76 | S |
| 81 | T |
| 83 | L |
| 86 | C |
| 87 | S |
| 92 | V |
| 99 | V |
| 120 | T |
| 121 | A |
| 122 | K |
| 123 | Q |
| 125 | T |
| 126 | G |
| 127 | S |
| 128 | S |

41

TABLE 9.2-continued

| SARS2 RBD (SEQ ID NO: 11) residue position | M10 residue (SEQ ID NO: 36) |
|---|---|
| 134 | Y |
| 137 | S |
| 138 | H |
| 141 | T |
| 142 | K |
| 150 | L |
| 152 | S |
| 153 | D |
| 154 | E |
| 155 | C |
| 156 | S |
| 157 | P |
| 158 | D |
| 159 | G |
| 160 | K |
| * | T |
| * | P |
| * | P |
| * | A |
| * | F |
| 166 | R |
| 173 | T |
| 175 | S |
| 176 | T |
| 178 | D |
| 180 | N |
| 182 | N |
| 183 | V |
| 184 | P |
| 186 | E |
| 189 | A |
| 190 | T |
| 201 | N |
| 211 | L |
| 214 | Q |

* Residues from insertion between amino acid residue positions 162 and 163 of SEQ ID NO: 11.

Optionally an isolated polypeptide of the invention which comprises an amino acid sequence of SEQ ID NO: 36 (M10), or an amino acid sequence which has at least 69% amino acid identity over its entire length with the amino acid sequence of SEQ ID NO:36, comprises at least one, or all of the following amino acid residues at positions corresponding to the amino acid residue positions of SEQ ID NO:11: 13Q, 25Q, 54T.

Residues for insertion between amino acid residue positions 162 and 163 of SEQ ID NO:11

The effect of glycosylation of the RBD protein is believed to be important. We have found that M7 and wild-type SARS2 RBD DNA (believed to result in expression of glycosylated RBD protein) is superior to recombinant SARS2 RBD protein (non-glycosylated, or sparsely glycosylated) in inducing neutralising responses to SARS2. Example 28 below describes Mass spectroscopy data obtained to study glycosylation of SARS-COV-2 (SARS2) RBD proteins in supernatants derived from HEK cells transfected with pEVAC plasmid encoding SARS-COV-2 RBD sequences, compared with recombinant SARS-COV-2 RBD proteins (see FIGS. 21 and 22). It was concluded from the results that there are two main glycosylated forms of the proteins obtained from the supernatants, in comparison to purified (recombinant) protein. The purified protein is non-glycosylated or sparsely glycosylated. This difference in glycosylation is believed to be important, as the glycosylation sites surround the epitope region and are conserved in most sarbecoviruses. These glycosylation sites are also important for interaction with some of the antibodies.

Optionally a polypeptide of the invention comprising an amino acid sequence of a designed coronavirus spike(S) protein (full-length, truncated, or RBD) comprises at least one glycosylation site in the RBD sequence.

Optionally a polypeptide of the invention comprising an amino acid sequence of a designed coronavirus spike(S) protein (full-length, truncated, or RBD) comprises at least two glycosylation sites in the RBD sequence.

Optionally a polypeptide of the invention comprising an amino acid sequence of a designed coronavirus spike(S) protein (full-length, truncated, or RBD) comprises at least three glycosylation sites in the RBD sequence.

Optionally a polypeptide of the invention comprising an amino acid sequence of a designed coronavirus spike(S) protein (full-length, truncated, or RBD) comprises a glycosylation site located within the last 10 amino acids of the RBD sequence, preferably at a residue position corresponding to residue position 203 of the RBD sequence.

According to the invention there is also provided an isolated polypeptide, which comprises an amino acid sequence of a SARS2 RBD with a glycosylation site located within the last 10 amino acids of the SARS2 RBD sequence, preferably at a residue position corresponding to residue position 203 of the RBD sequence.

We have also found that immunisation of mice with a wild-type SARS1 S protein, or RBD protein, or a wild-type SARS2 S protein, or RBD protein, induced antibodies that bind SARS2 RBD.

There is also provided according to the invention an isolated polypeptide comprising an amino acid sequence of SEQ ID NO:5.

There is also provided according to the invention an isolated polypeptide comprising an amino acid sequence of SEQ ID NO:11.

A conventional way to produce cross-reactive antigens is to generate a consensus sequence based on natural diversity. Antigenic sequences encoded by nucleic acid sequences of the invention described herein account for sampling bias and coevolution between sites. The result is a realistic molecule which induces an immune response to a range of viruses. As a further refinement, we enrich the antigenic sequences for known and predicted epitopes. We have developed an algorithm to select the combination of epitopes that maximise population protection against a range of target viruses. This algorithm identifies conserved epitopes whilst penalising redundancy and ensuring that the selected epitopes are bound by a range of common MHC alleles.

To avoid disease enhancement we modify the antigens, deleting regions associated with immunopathology, often referred to as antibody dependent enhancement (ADE) and/or complement triggered, or virus triggered proinflammatory responses. In order to validate these modifications, we have developed assays to screen against such ADE-like effects. Using assays modified from Yip et al. (Yip et al. "Antibody-dependent infection of human macrophages by severe acute respiratory syndrome coronavirus", Virol J. 2014; 11:82; Jaume et al. "Anti-Severe Acute Respiratory Syndrome Coronavirus Spike Antibodies Trigger Infection of Human Immune Cells via a pH-and Cysteine Protease-Independent Fc□R Pathway" Journal Of Virology, October 2011, p. 10582-10597), non-neutralising antibodies to the non-RBD site of the S protein that allow SARS-COV-1 to enter non-ACE2 expressing immune cells, which bear Fc-γ-RII, can be identified.

After designing antigens, DNA sequences encoding them are optimised for expression in mammalian cells. In this DNA form, multiple synthetic genes of the target antigens are inserted into a DNA plasmid vector (for example, pEVAC-see FIG. 3), which is used for both in vitro and in vivo immune screening.

Designed Coronavirus Full-Length S Protein Sequence to Protect Against COVID-19 Variants Multiple SARS-COV-2 variants are circulating globally. Several new variants emerged in the fall of 2020, most notably:

In the United Kingdom (UK), a new variant of SARS-COV-2 (known as 201/501Y.V1, VOC 202012/01, or B.1.1.7) emerged with a large number of mutations. This variant has since been detected in numerous countries around the world, including the United States (US). In January 2021, scientists from UK reported evidence that suggests the B.1.1.7 variant may be associated with an increased risk of death compared with other variants, although more studies are needed to confirm this finding. This variant was reported in the US at the end of December 2020.

Brazil, who were tested during routine screening at Haneda airport outside Tokyo, Japan. This variant has 17 unique mutations, including three in the receptor binding domain of the spike protein. This variant was detected in the US at the end of January 2021.

Scientists are working to learn more about these variants to better understand how easily they might be transmitted and the effectiveness of currently authorized vaccines against them. New information about the virologic, epidemiologic, and clinical characteristics of these variants is rapidly emerging.

As described in more detail in Example 30 below, we have designed a new full-length S protein sequence (referred to as "VOC Chimera", or COV_S_T2_29) for use as a COVID-19 vaccine insert to protect against variants B.1.1.7, P.1, and B.1.351. The amino acid sequence of the designed full-length S protein sequence is given below, and in Example 30:

```
>COV_S_T2_29 (VOC chimera)
                                                      (SEQ ID NO: 53)
MFVFLVLLPL VSSQCVNFTN RTQLPSAYTN SFTRGVYYPD KVFRSSVLHS TQDLFLPFFS      60

NVTWFHAISG TNGTKRFDNP VLPFNDGVYF ASTEKSNIIR GWIFGTTLDS KTQSLLIVNN     120

ATNVVIKVCE FQFCNDPFLG VYHKNNKSWM ESEFRVYSSA NNCTFEYVSQ PFLMDLEGKQ     180

GNFKNLREFV FKNIDGYFKI YSKHTPINLV RDLPQGFSAL EPLVDLPIGI NITRFQTLLA     240

LHRSYLTPGD SSSGWTAGAA AYYVGYLQPR TFLLKYNENG TITDAVDCAL DPLSETKCTL     300

KSFTVEKGIY QTSNFRVQPT ESIVRFPNIT NLCPFGEVFN ATRFASVYAW NRKRISNCVA     360

DYSVLYNSAS FSTFKCYGVS PTKLNDLCFT NVYADSFVIR GDEVRQIAPG QTGNIADYNY     420

KLPDDFTGCV IAWNSNNLDS KVGGNYNYLY RLFRKSNLKP FERDISTEIY QAGSTPCNGV     480

KGFNCYFPLQ SYGFQPTYGV GYQPYRVVVL SFELLHAPAT VCGPKKSTNL VKNKCVNFNF     540

NGLTGTGVLT ESNKKFLPFQ QFGRDIADTT DAVRDPQTLE ILDITPCSFG GVSVITPGTN     600

TSNQVAVLYQ GVNCTEVPVA IHADQLTPTW RVYSTGSNVF QTRAGCLIGA EHVNNSYECD     660

IPIGAGICAS YQTQTNSHRR ARSVASQSII AYTMSLGAEN SVAYSNNSIA IPTNFTISVT     720

TEILPVSMTK TSVDCTMYIC GDSTECSNLL LQYGSFCTQL NRALTGIAVE QDKNTQEVFA     780

QVKQIYKTPP IKDFGGFNFS QILPDPSKPS KRSFIEDLLF NKVTLADAGF IKQYGDCLGD     840

IAARDLICAQ KFNGLTVLPP LLTDEMIAQY TSALLAGTIT SGWTFGAGAA LQIPFAMQMA     900

YRFNGIGVTQ NVLYENQKLI ANQFNSAIGK IQDSLSSTAS ALGKLQDVVN QNAQALNTLV     960

KQLSSNFGAI SSVLNDILSR LDPPEAEVQI DRLITGRLQS LQTYVTQQLI RAAEIRASAN    1020

LAATKMSECV LGQSKRVDFC GKGYHLMSFP QSAPHGVVFL HVTYVPAQEK NFTTAPAICH    1080

DGKAHFPREG VFVSNGTHWF VTQRNFYEPQ IITTDNTFVS GNCDVVIGIV NNTVYDPLQP    1140

ELDSFKEELD KYFKNHTSPD VDLGDISGIN ASVVNIQKEI DRLNEVAKNL NESLIDLQEL    1200

GKYEQYIKWP WYIWLGFIAG LIAIVMVTIM LCCMTSCCSC LKGCCSCGSC CKFDEDDSEP    1260

VLKGVKLHYT                                                          1270
```

In South Africa, another variant of SARS-COV-2 (known as 20H/501Y.V2 or B.1.351) emerged independently of B.1.1.7. This variant shares some mutations with B.1.1.7. Cases attributed to this variant have been detected in multiple countries outside of South Africa. This variant was reported in the US at the end of January 2021.

In Brazil, a variant of SARS-COV-2 (known as P.1) emerged that was first was identified in four travelers from Alignment of this sequence with SARS2 Reference sequence (EPI_ISL_402130 (Wuhan strain) (SEQ ID NO:52)) is shown in Example 30 below.

The amino acid differences of the designed sequence COV_S_T2_29 (SEQ ID NO:53) from the SARS2 reference sequence (SEQ ID NO:52) are shown in Table 9.3 below:

TABLE 9.3

| SARS2 S protein residue position (SEQ ID NO: 52) | SARS2 Reference amino acid residue (SEQ ID NO: 52) | COV_S_T2_29 amino acid residue (SEQ ID NO: 53) |
|---|---|---|
| 18 | L | F |
| 20 | T | N |
| 26 | P | S |
| 69 | H | — (deletion) |
| 70 | V | — (deletion) |
| 144 | Y | — (deletion) |
| 417 | K | N |
| 484 | E | K |
| 501 | N | Y |
| 614 | D | G |
| 681 | P | H |
| 986 | K | P |
| 987 | V | P |

According to the invention there is provided an isolated polypeptide, which comprises an amino acid sequence of SEQ ID NO:53.

According to the invention there is also provided an isolated polypeptide comprising an amino acid sequence of SEQ ID NO:53, or an amino acid sequence which has at least 99% amino acid identity over its entire length with the amino acid sequence of SEQ ID NO:53.

Optionally a polypeptide of the invention comprising an amino acid sequence of SEQ ID NO: 53, or an amino acid sequence which has at least 99% amino acid identity over its entire length with the amino acid sequence of SEQ ID NO:53, comprises at least one, or all of the amino acid residues or deletions, at positions corresponding to the amino acid residue positions of SEQ ID NO:52, as shown in Table 9.4 below:

TABLE 9.4

| SARS2 S protein residue position (SEQ ID NO: 52 | COV_S_T2_29 amino acid residue (SEQ ID NO: 53) |
|---|---|
| 18 | F |
| 20 | N |
| 26 | S |
| 69 | — (deletion) |
| 70 | — (deletion |
| 144 | — (deletion) |
| 417 | N |
| 484 | K |
| 501 | Y |
| 614 | G |
| 681 | H |
| 986 | P |
| 987 | P |

Optionally a polypeptide of the invention comprising an amino acid sequence of SEQ ID NO: 53, or an amino acid sequence which has at least 99% amino acid identity over its entire length with the amino acid sequence of SEQ ID NO:53, comprises at least five of the amino acid residues or deletions, at positions corresponding to the amino acid residue positions of SEQ ID NO:52, as shown in Table 9.4.

Optionally a polypeptide of the invention comprising an amino acid sequence of SEQ ID NO: 53, or an amino acid sequence which has at least 99% amino acid identity over its entire length with the amino acid sequence of SEQ ID NO:53, comprises at least ten of the amino acid residues or deletions, at positions corresponding to the amino acid residue positions of SEQ ID NO:52, as shown in Table 9.4.

Optionally a polypeptide of the invention comprising an amino acid sequence of SEQ ID NO: 53, or an amino acid sequence which has at least 99% amino acid identity over its entire length with the amino acid sequence of SEQ ID NO:53, comprises amino acid residue P at position 986, and amino acid residue P at position 987, corresponding to the amino acid residue positions of SEQ ID NO:52, and at least one, or all of the amino acid residues or deletions, at positions corresponding to the amino acid residue positions of SEQ ID NO:52, as shown in Table 9.5 below:

TABLE 9.5

| SARS2 S protein residue position SEQ ID NO: 52 | COV_S_T2_29 amino acid residue (SEQ ID NO: 53) |
|---|---|
| 18 | F |
| 20 | N |
| 26 | S |
| 69 | — (deletion) |
| 70 | — (deletion) |
| 144 | — (deletion) |
| 417 | N |
| 484 | K |
| 501 | Y |
| 614 | G |
| 681 | H |

According to the invention there is also provided an isolated polypeptide which comprises a coronavirus S protein with at least one, or all of the amino acid residues or deletions, at positions corresponding to the amino acid residue positions of SEQ ID NO:52, as shown in Table 9.4 above.

Optionally an isolated polypeptide of the invention which comprises at least one of the amino acid residues or deletions, at positions corresponding to the amino acid residue positions of SEQ ID NO:52, as shown in Table 9.4 above, comprises at least five of the amino acid residues or deletions, at positions corresponding to the amino acid residue positions of SEQ ID NO: 52, as shown in Table 9.4 above.

Optionally an isolated polypeptide of the invention which comprises at least one of the amino acid residues or deletions, at positions corresponding to the amino acid residue positions of SEQ ID NO:52, as shown in Table 9.4 above, comprises at least ten of the amino acid residues or deletions, at positions corresponding to the amino acid residue positions of SEQ ID NO:52, as shown in Table 9.4 above.

Optionally the coronavirus S protein comprises an amino acid sequence which has at least 70%, 75%, 80%, 85%, 90%, 91%, 92%, 93%, 94%, 95%, 96%, 97%, 98%, or 99% amino acid identity over its entire length with the amino acid sequence of SEQ ID NO:52.

Optionally an isolated polypeptide of the invention which comprises at least one of the amino acid residues or deletions, at positions corresponding to the amino acid residue positions of SEQ ID NO:52, as shown in Table 9.4 above, comprises amino acid residue P at position 986, and amino acid residue P at position 987, corresponding to the amino acid residue positions of SEQ ID NO:52, and at least one, or all of the amino acid residues or deletions, at positions corresponding to the amino acid residue positions of SEQ ID NO:52, as shown in Table 9.5 above.

Designed Coronavirus S Protein Sequence in Closed State to Protect Against COVID-19 Variants, and Predicted Future Variants The majority of SARS-COV-2 vaccines in use or in advanced clinical development are based on the viral spike protein(S) as their immunogen. S is present on virions as pre-fusion trimers in which the receptor binding domain (RBD) is stochastically open or closed. Neutralizing antibodies have been described that act against both open and closed conformations. The long-term success of vaccination strategies will depend upon inducing antibodies that provide long-lasting broad immunity against evolving, circulating SARS-COV-2 strains, while avoiding the risk of antibody dependent enhancement as observed with other Coronavirus vaccines.

Carnell et al. ("*SARS-COV-2 spike protein arrested in the closed state induces potent neutralizing responses*"; https://doi.org/10.1101/2021.01.14.426695, posted 14 Jan. 2021) have assessed the results of immunization in a mouse model using an S protein trimer that is arrested in the closed state to prevent exposure of the receptor binding site and therefore interaction with the receptor. The authors compared this with a range of other modified S protein constructs, including representatives used in current vaccines. They found that all trimeric S proteins induce a long-lived, strongly neutralizing antibody response as well as T-cell responses. Notably, the protein binding properties of sera induced by the closed spike differed from those induced by standard S protein constructs. Closed S proteins induced more potent neutralising responses than expected based on the degree to which they inhibit interactions between the RBD and ACE2. The authors conclude that these observations suggest that closed spikes recruit different, but equally potent, virus-inhibiting immune responses than open spikes, and that this is likely to include neutralizing antibodies against conformational epitopes present in the closed conformation.

We have appreciated that the amino acid changes of the designed S protein sequences disclosed herein (and especially of SEQ ID NO:53 as described in Example 30) may optionally be present in a designed S protein that is arrested in the closed state, and thereby further improve the antibody response of the designed sequences. In particular, use of such structural constraints may reduce immunodominance to key regions, and spread the antibody response to focus on other, or less immunodominant sites.

Example 31 below describes optional additional amino acid changes that may be made to a designed S protein sequence to allow it to form a closed structure.

Optionally a designed S protein sequence of the invention may comprise cysteine residues at positions corresponding to positions 413 and 987 of the full length S protein sequence. For example, G413C and V987C.

For example, a designed S protein sequence of the invention may comprise the following amino acid sequence (SEQ ID NO:54) (with cysteine residues at positions 410 and 984, which correspond to positions 413 and 987, respectively, of SEQ ID NO:52):

```
MFVFLVLLPL  VSSQCVNFTN  RTQLPSAYTN  SFTRGVYYPD  KVFRSSVLHS  TQDLFLPFFS      60

NVTWFHAISG  TNGTKRFDNP  VLPFNDGVYF  ASTEKSNIIR  GWIFGTTLDS  KTQSLLIVNN     120

ATNVVIKVCE  FQFCNDPFLG  VYHKNNKSWM  ESEFRVYSSA  NNCTFEYVSQ  PFLMDLEGKQ     180

GNFKNLREFV  FKNIDGYFKI  YSKHTPINLV  RDLPQGFSAL  EPLVDLPIGI  NITRFQTLLA     240

LHRSYLTPGD  SSSGWTAGAA  AYYVGYLQPR  TFLLKYNENG  TITDAVDCAL  DPLSETKCTL     300

KSFTVEKGIY  QTSNFRVQPT  ESIVRFPNIT  NLCPFGEVFN  ATRFASVYAW  NRKRISNCVA     360

DYSVLYNSAS  FSTFKCYGVS  PTKLNDLCFT  NVYADSFVIR  GDEVRQIAPC  QTGNIADYNY     420

KLPDDFTGCV  IAWNSNNLDS  KVGGNYNYLY  RLFRKSNLKP  FERDISTEIY  QAGSTPCNGV     480

KGFNCYFPLQ  SYGFQPTYGV  GYQPYRVVVL  SFELLHAPAT  VCGPKKSTNL  VKNKCVNFNF     540

NGLTGTGVLT  ESNKKFLPFQ  QFGRDIADTT  DAVRDPQTLE  ILDITPCSFG  GVSVITPGTN     600

TSNQVAVLYQ  GVNCTEVPVA  IHADQLTPTW  RVYSTGSNVF  QTRAGCLIGA  EHVNNSYECD     660

IPIGAGICAS  YQTQTNSHRR  ARSVASQSII  AYTMSLGAEN  SVAYSNNSIA  IPTNFTISVT     720

TEILPVSMTK  TSVDCTMYIC  GDSTECSNLL  LQYGSFCTQL  NRALTGIAVE  QDKNTQEVFA     780

QVKQIYKTPP  IKDFGGFNFS  QILPDPSKPS  KRSFIEDLLF  NKVTLADAGF  IKQYGDCLGD     840

IAARDLICAQ  KFNGLTVLPP  LLTDEMIAQY  TSALLAGTIT  SGWTFGAGAA  LQIPFAMQMA     900

YRFNGIGVTQ  NVLYENQKLI  ANQFNSAIGK  IQDSLSSTAS  ALGKLQDVVN  QNAQALNTLV     960

KQLSSNFGAI  SSVLNDILSR  LDPCEAEVQI  DRLITGRLQS  LQTYVTQQLI  RAAEIRASAN    1020

LAATKMSECV  LGQSKRVDFC  GKGYHLMSFP  QSAPHGVVFL  HVTYVPAQEK  NFTTAPAICH    1080

DGKAHFPREG  VFVSNGTHWF  VTQRNFYEPQ  IITTDNTFVS  GNCDVVIGIV  NNTVYDPLQP    1140

ELDSFKEELD  KYFKNHTSPD  VDLGDISGIN  ASVVNIQKEI  DRLNEVAKNL  NESLIDLQEL    1200

GKYEQYIKWP  WYIWLGFIAG  LIAIVMVTIM  LCCMTSCCSC  LKGCCSCGSC  CKFDEDDSEP    1260

VLKGVKLHYT                                                              1270
```

According to the invention there is provided an isolated polypeptide, which comprises an amino acid sequence of SEQ ID NO:54.

According to the invention there is also provided an isolated polypeptide comprising an amino acid sequence of SEQ ID NO:54, or an amino acid sequence which has at least 99% amino acid identity over its entire length with the amino acid sequence of SEQ ID NO:54.

Optionally a polypeptide of the invention comprising an amino acid sequence of SEQ ID NO: 54, or an amino acid sequence which has at least 99% amino acid identity over its entire length with the amino acid sequence of SEQ ID NO:54, comprises at least one, or all of the amino acid residues or deletions, at positions corresponding to the amino acid residue positions of SEQ ID NO:52, as shown in Table 9.4 below:

TABLE 9.4

| SARS2 S protein residue position (SEQ ID NO: 52) | COV_S_T2_29 amino acid residue (SEQ ID NO: 53) |
| --- | --- |
| 18 | F |
| 20 | N |
| 26 | S |
| 69 | — (deletion) |
| 70 | — (deletion) |
| 144 | — (deletion |
| 417 | N |
| 484 | K |
| 501 | Y |
| 614 | G |
| 681 | H |
| 986 | P |
| 987 | P |

Optionally a polypeptide of the invention comprising an amino acid sequence of SEQ ID NO: 54, or an amino acid sequence which has at least 99% amino acid identity over its entire length with the amino acid sequence of SEQ ID NO:54, comprises at least five of the amino acid residues or deletions, at positions corresponding to the amino acid residue positions of SEQ ID NO:52, as shown in Table 9.4.

Optionally a polypeptide of the invention comprising an amino acid sequence of SEQ ID NO: 54, or an amino acid sequence which has at least 99% amino acid identity over its entire length with the amino acid sequence of SEQ ID NO:54, comprises at least ten of the amino acid residues or deletions, at positions corresponding to the amino acid residue positions of SEQ ID NO:52, as shown in Table 9.4.

Optionally a polypeptide of the invention comprising an amino acid sequence of SEQ ID NO: 54, or an amino acid sequence which has at least 99% amino acid identity over its entire length with the amino acid sequence of SEQ ID NO:54, comprises at least one, or all of the amino acid residues or deletions, at positions corresponding to the amino acid residue positions of SEQ ID NO:52, as shown in Table 9.5 below:

Optionally a polypeptide of the invention comprising an amino acid sequence of SEQ ID NO: 54, or an amino acid sequence which has at least 99% amino acid identity over its entire length with the amino acid sequence of SEQ ID NO:54, comprises amino acid residue P at position 986 corresponding to the amino acid residue positions of SEQ ID NO:52, and at least one, or all of the amino acid residues or deletions, at positions corresponding to the amino acid residue positions of SEQ ID NO:52, as shown in Table 9.5 below:

TABLE 9.5

| SARS2 S protein residue position (SEQ ID NO: 52) | COV_S_T2_29 amino acid residue (SEQ ID NO: 53) |
| --- | --- |
| 18 | F |
| 20 | N |
| 26 | S |
| 69 | — (deletion) |
| 70 | — (deletion) |
| 144 | — (deletion) |
| 417 | N |
| 484 | K |
| 501 | Y |
| 614 | G |
| 681 | H |

According to the invention there is also provided an isolated polypeptide which comprises a coronavirus S protein comprising cysteine amino acid residues at positions corresponding to positions 413 and 987 of SEQ ID NO:52, and at least one, or all of the amino acid residues or deletions, at positions corresponding to the amino acid residue positions of SEQ ID NO:52, as shown in Table 9.5 above.

Optionally an isolated polypeptide of the invention which comprises cysteine amino acid residues at positions corresponding to positions 413 and 987 of SEQ ID NO:52, and at least one of the amino acid residues or deletions, at positions corresponding to the amino acid residue positions of SEQ ID NO:52, as shown in Table 9.5 above, comprises at least five of the amino acid residues or deletions, at positions corresponding to the amino acid residue positions of SEQ ID NO:52, as shown in Table 9.5 above.

Optionally an isolated polypeptide of the invention which comprises cysteine amino acid residues at positions corresponding to positions 413 and 987 of SEQ ID NO:52, and at least one of the amino acid residues or deletions, at positions corresponding to the amino acid residue positions of SEQ ID NO:52, as shown in Table 9.5 above, comprises at least ten of the amino acid residues or deletions, at positions corresponding to the amino acid residue positions of SEQ ID NO:52, as shown in Table 9.5 above.

Optionally an isolated polypeptide of the invention which comprises cysteine amino acid residues at positions corresponding to positions 413 and 987 of SEQ ID NO:52, and at least one of the amino acid residues or deletions, at positions corresponding to the amino acid residue positions of SEQ ID NO:52, as shown in Table 9.5 above, comprises amino acid residue P at position 986.

We have also appreciated that any SARS-COV-2 spike protein may be modified to include cysteine residues at positions corresponding to positions 413 and 987 of SEQ ID NO:52 to allow it to form a spike protein arrested in the closed state, in accordance with Carnell et al. (supra), and thereby elicit more potent neutralising responses compared with the corresponding unmodified protein. For example, Jeong et al. (https://virological.org/t/assemblies-of-putative-sars-cov2-spike-encoding-mrna-sequences-for-vaccines-bnt-162b2-and-mrna-1273/663-version 0.2Beta Mar. 30, 2021) have recently reported experimental sequence information for the RNA components of the initial Moderna (https://pubmed.ncbi.nlm.nih.gov/32756549/) and Pfizer/ BioNTech (https://pubmed.ncbi.nlm.nih.gov/33301246/) COVID-19 vaccines, allowing a working assembly of the former and a confirmation of previously reported sequence information for the latter RNA (see the sequences provided in FIGS. 1 and 2 of the document). Spike protein encoded by such sequence may be modified to include cysteine residues at positions corresponding to positions 413 and 987 of SEQ ID NO:52.

According to the invention there is also provided an isolated polypeptide which comprises a coronavirus S protein comprising cysteine amino acid residues at positions corresponding to positions 413 and 987 of SEQ ID NO:52.

Optionally the coronavirus S protein comprises an amino acid sequence which has at least 70%, 75%, 80%, 85%, 90%, 91%, 92%, 93%, 94%, 95%, 96%, 97%, 98%, or 99% amino acid identity over its entire length with the amino acid sequence of SEQ ID NO:52.

SARS-COV-2 is continually evolving, with more contagious mutations spreading rapidly. Zahradník et al., 2021 ("*SARS-COV-2 RBD in vitro evolution follows contagious mutation spread, yet generates an able infection inhibitor*"; doi: https://doi.org/10.1101/2021.01.06.425392, posted 29 Jan. 2021) recently reported using in vitro evolution to affinity maturate the receptor-binding domain (RBD) of the spike protein towards ACE2 resulting in the more contagious mutations, S477N, E484K, and N501Y, to be among the first selected, explaining the convergent evolution of the "European" (20E-EU1), "British" (501.V1), "South African" (501.V2), and "Brazilian" variants (501.V3). The authors report that further in vitro evolution enhancing binding by 600-fold provides guidelines towards potentially new evolving mutations with even higher infectivity. For example, Q498R epistatic to N501Y.

We have also appreciated that the designed S protein sequences (RBD, truncated, or full-length) disclosed herein (and especially in the sections entitled "Designed Coronavirus full-length S protein sequence to protect against COVID-19 variants", and "Designed Coronavirus S protein sequence in closed state to protect against COVID-19 variants, and predicted future variants" above, and in Examples 30 and 31 below) may optionally also include amino acid substitutions at one or more residue positions predicted to be mutated in future COVID-19 variants with a vaccine escape response, for example at one or more (or all) of positions 446, 452, 477, and 498 (for example, G446R, S477N, Q498R, especially Q498R).

Optionally an isolated polypeptide of the invention includes amino acid changes at one or more (or all) of the following positions (corresponding to amino acid residue positions of SEQ ID NO: 52): 446, 452, 477, and 498 (for example, G446R, S477N, Q498R, especially Q498R).

Optionally an isolated polypeptide of the invention includes amino acid changes at positions (corresponding to amino acid residue positions of SEQ ID NO:52): Q498R and N501Y.

Designed Coronavirus Envelope (E) Protein Sequences

We have also generated novel amino acid sequences for coronavirus Envelope (E) protein. FIG. 6 shows an amino acid sequence of the SARS Envelope (E) protein (SEQ ID NO:21), and illustrates key features of the sequence. As described in Example 10 below, FIG. 7shows a multiple sequence alignment of coronavirus E protein sequences, comparing sequences for isolates of NL63 and 229E (alpha-coronaviruses), and HKU1, MERS, SARS, and SARS2 (beta-coronaviruses). The alignment shows that the C-terminal end of the E protein for the SARS2 and SARS sequences (beta-coronaviruses of subgenus Sarbeco) includes a deletion, compared with the other sequences, and that the SARS2 E protein sequence includes a deletion, and an Arginine (positively charged) amino acid residue, compared with the SARS sequence.

The novel amino acid sequences for coronavirus E protein are called COV_E_T2_1 (a designed Sarbecovirus sequence) (SEQ ID NO:22) and COV_E_T2_2 (a designed SARS2 sequence) (SEQ ID NO:23):

```
>COV_E_T2_1
                                        (SEQ ID NO: 22)
MYSFVSEETG TLIVNSVLLF LAFVVFLLVT LAILTALRLC
AYCCNIVNVS LVKPTFYVYS RVKNLNSSQG VPDLLV

>COV_E_T2_2
                                        (SEQ ID NO: 23)
MYSFVSEETG TLIVNSVLLF LAFVVFLLVT LAILTALRLC
AYCCNIVNVS LVKPTFYVYS RVKNLNSSR- VPDLLV
```

As shown in FIG. 45A, alignment of the SARS2 reference E protein sequence in FIG. 7 with these designed sequences highlights that there are four amino acid differences between the SARS2 reference E protein sequence and the COV_E_T2_1 designed sequence (SEQ ID NO: 22), and two amino acid differences between the SARS2 reference E protein sequence and the COV_E_T2_2 designed sequence (SEQ ID NO:23).

The C-terminal sequence of the COV_E_T2_2 sequence is identical to the SARS2 reference sequence. The C-terminal of the E protein is one of the identified epitopes for E-protein, so the amino acid deletion and the substitution with an Arginine residue present in the SARS2 reference sequence (compared with the SARS reference sequence in FIG. 6) have been retained in the COV_E_T2_2 designed sequence. The amino acid differences at the other positions are optimised to maximise induction of an immune response that recognises all Sarbeco viruses.

The amino acid differences are summarised in the table below:

TABLE 10.1

| SARS2 E protein residue position | SARS2 Reference Amino acid residue | COV_E_T2_1 Amino acid residue | COV_E_T2_2 Amino acid residue |
|---|---|---|---|
| 36 | V | A | A |
| 55 | S | T | T |
| 69 | R | Q | R |
| 70 | — | G | — |

There is also provided according to the invention an isolated polypeptide which comprises an amino acid sequence of SEQ ID NO:22, or an amino acid sequence which has at least 95%, 96%, 97%, 98%, or 99% amino acid identity over its entire length with the amino acid sequence of SEQ ID NO:22.

Optionally an isolated polypeptide of the invention which comprises an amino acid sequence of SEQ ID NO:22, or an amino acid sequence which has at least 95%, 96%, 97%, 98%, or 99% amino acid identity over its entire length with the amino acid sequence of SEQ ID NO:22, comprises one or both amino acid residues, at positions corresponding to the amino acid residue positions of SEQ ID NO:22, as shown in the table below:

TABLE 10.2

| SARS2 E protein residue position | COV_E_T2_1 Amino acid residue |
|---|---|
| 36 | A |
| 55 | T |

Optionally an isolated polypeptide of the invention which comprises an amino acid sequence of SEQ ID NO:22, or an amino acid sequence which has at least 95%, 96%, 97%, 98%, or 99% amino acid identity over its entire length with the amino acid sequence of SEQ ID NO:22, comprises any, at least two, at least three, or all, of the amino acid residues, at positions corresponding to the amino acid residue positions of SEQ ID NO:22, as shown in the table below:

TABLE 10.3

| SARS2 E protein residue position | COV_E_T2_1 Amino acid residue |
|---|---|
| 36 | A |
| 55 | T |
| 69 | Q |
| 70 | G |

There is also provided according to the invention an isolated polypeptide, which comprises an amino acid sequence of SEQ ID NO:23, or an amino acid sequence which has at least 98%, or 99% amino acid identity over its entire length with the amino acid sequence of SEQ ID NO:23.

Optionally an isolated polypeptide of the invention which comprises an amino acid sequence of SEQ ID NO:23, or an amino acid sequence which has at least 98%, or 99% amino acid identity over its entire length with the amino acid sequence of SEQ ID NO:23, comprises one or both amino acid residues, at positions corresponding to the amino acid residue positions of SEQ ID NO:23, as shown in the table below:

TABLE 10.4

| SARS2 E protein residue position | COV_E_T2_2 Amino acid residue |
|---|---|
| 36 | A |
| 55 | T |

According to the invention there is also provided an isolated polypeptide, which comprises a coronavirus E protein with one or both of the amino acid residues at positions corresponding to the amino acid residue positions as shown in the table below:

TABLE 10.5

| E protein residue position | Amino acid residue |
|---|---|
| 36 | A |
| 55 | T |

According to the invention there is also provided an isolated polypeptide, which comprises a coronavirus E protein with any, at least two, at least three, or all, of the amino acid residues at positions corresponding to the amino acid residue positions as shown in the table below:

TABLE 10.6

| E protein residue position | Amino acid residue |
|---|---|
| 36 | A |
| 55 | T |
| 69 | Q |
| 70 | G |

Optionally an isolated polypeptide of the invention which comprises a coronavirus E protein comprises an amino acid sequence which has at least 70%, 75%, 80%, 85%, 90%, 91%, 92%, 93%, 94%, 95%, 96%, 97%, 98%, or 99% amino acid identity over its entire length with the amino acid sequence of SEQ ID NO:21.

In the alignment shown in FIG. 45A, residue 36 of the SARS2 reference sequence is shown as V, but is actually A (as correctly shown in FIG. 7 and SEQ ID NO:21). FIG. 45B shows the alignment of SEQ ID NO:21 with the designed sequences and highlights that there are three amino acid differences between the alternative SARS2 reference E protein sequence and the COV_E_T2_1 designed sequence (SEQ ID NO:22), and one amino acid difference between the SARS2 reference E protein sequence and the COV_E_T2_2 designed sequence (SEQ ID NO:23).

The amino acid differences are summarised in the table below:

TABLE 10.7

| SARS2 E protein residue position | SARS2 Reference Amino acid residue | COV_E_T2_1 Amino acid residue | COV_E_T2_2 Amino acid residue |
|---|---|---|---|
| 55 | S | T | T |
| 69 | R | Q | R |
| 70 | — | G | — |

There is also provided according to the invention an isolated polypeptide which comprises an amino acid sequence of SEQ ID NO:22 (COV_E_T2_1), or an amino acid sequence which has at least 97%, 98%, or 99% amino acid identity over its entire length with the amino acid sequence of SEQ ID NO:22.

Optionally an isolated polypeptide of the invention which comprises an amino acid sequence of SEQ ID NO:22, or an amino acid sequence which has at least 97%, 98%, or 99% amino acid identity over its entire length with the amino acid sequence of SEQ ID NO:22, comprises the amino acid residue, at a position corresponding to the amino acid residue position of SEQ ID NO: 22, as shown in the table below:

TABLE 10.8

| SARS2 E protein residue position | COV_E_T2_1 Amino acid residue |
|---|---|
| 55 | T |

Optionally an isolated polypeptide of the invention which comprises an amino acid sequence of SEQ ID NO:22, or an amino acid sequence which has at least 97%, 98%, or 99% amino acid identity over its entire length with the amino acid sequence of SEQ ID NO:22, comprises any, at least two, or all, of the amino acid residues, at positions corresponding to the amino acid residue positions of SEQ ID NO:22, as shown in the table below:

TABLE 10.9

| SARS2 E protein residue position | COV_E_T2_1 Amino acid residue |
| --- | --- |
| 55 | T |
| 69 | Q |
| 70 | G |

There is also provided according to the invention an isolated polypeptide, which comprises an amino acid sequence of SEQ ID NO:23, or an amino acid sequence which has at least 99% amino acid identity over its entire length with the amino acid sequence of SEQ ID NO:23.

Optionally an isolated polypeptide of the invention which comprises an amino acid sequence of SEQ ID NO:23, or an amino acid sequence which has at least 99% amino acid identity over its entire length with the amino acid sequence of SEQ ID NO:23, comprises an amino acid residues, at a position corresponding to the amino acid residue position of SEQ ID NO:23, as shown in the table below:

TABLE 10.10

| SARS2 E protein residue position | COV_E_T2_2 Amino acid residue |
| --- | --- |
| 55 | T |

According to the invention there is also provided an isolated polypeptide, which comprises a coronavirus E protein with the amino acid residue at a position corresponding to the amino acid residue position as shown in the table below:

TABLE 10.11

| E protein residue position | Amino acid residue |
| --- | --- |
| 55 | T |

According to the invention there is also provided an isolated polypeptide, which comprises a coronavirus E protein with any, at least two, or all, of the amino acid residues at positions corresponding to the amino acid residue positions as shown in the table below:

TABLE 10.12

| E protein residue position | Amino acid residue |
| --- | --- |
| 55 | T |
| 69 | Q |
| 70 | G |

Optionally an isolated polypeptide of the invention which comprises a coronavirus E protein comprises an amino acid sequence which has at least 70%, 75%, 80%, 85%, 90%, 91%, 92%, 93%, 94%, 95%, 96%, 97%, 98%, or 99% amino acid identity over its entire length with the amino acid sequence of SEQ ID NO:21.

SARS-COV envelope (E) gene encodes a 76-amino acid transmembrane protein with ion channel (IC) activity, an important function in virus-host interaction. Infection of mice with viruses lacking or displaying E protein IC activity revealed that activation of the inflammasome pathway, and the exacerbated inflammatory response induced by SARS-COV, was decreased in infections by ion channel-deficient viruses (Nieto-Torres et al., 2014, Severe Acute Respiratory Syndrome Coronavirus Envelope Protein Ion Channel Activity Promotes Virus Fitness and Pathogenesis. PLOS Pathog 10 (5): e1004077).

We have made new E protein designs Cov_E_T2_3, CoV_E_T2_4 and CoV_E_T2_5, which correspond to new designs of SARS2 reference (SEQ ID NO:41), COV_E_T2_1 (SEQ ID NO:22), and CoV._E_T2_2 (SEQ ID NO:23) (see Example 10), respectively. These new designs have a point mutation, N15A, which abrogates the ion channel activity, but does not influence the stability of the structure. Nieto-Torres et al., supra, discusses this mutation as well as the toxicity and inflammatory action of SARS E on the host cell.

The amino acid sequence of SARS2 envelope protein reference (SEQ ID NO:41) is:

```
                                      (SEQ ID NO: 41)
MYSFVSEETG TLIVNSVLLF LAFVVFLLVT LAILTALRLC

AYCCNIVNVS LVKPSFYVYS RVKNLNSSRV PDLLV
```

The amino acid sequences of the new E protein designs are shown below, and in Example 25:

```
>COV_E_T2_3 (SARS2_mutant)
                                      (SEQ ID NO: 42)
MYSFVSEETG TLIVASVLLF LAFVVFLLVT LAILTALRLC
AYCCNIVNVS LVKPSFYVYS RVKNLNSSR-VPDLLV >COV_E_T2_4 (Env1_mutant)
                                      (SEQ ID NO: 43)
MYSFVSEETG TLIVASVLLF LAFVVFLLVT LAILTALRLC
AYCCNIVNVS LVKPTFYVYS RVKNLNSSQG VPDLLV >COV_E_T2_5 (Env2_mutant)
                                      (SEQ ID NO: 44)
MYSFVSEETG TLIVASVLLF LAFVVFLLVT LAILTALRLC
AYCCNIVNVS LVKPTFYVYS RVKNLNSSR-VPDLLV
```

Alignment of the E protein designs with SARS2 E protein reference sequence is shown in FIG. 45C.

The amino acid differences of the designed sequences from the SARS2 reference sequence (SEQ ID NO: 41) are shown in the table below (with differences from the reference sequence in bold):

TABLE 10.13

| SARS2 E protein (SEQ ID NO:41) residue position | SARS2 Reference Amino acid residue (SEQ ID NO:41) | COV_E_T2_1 Amino acid residue (SEQ ID NO:22) | COV_E_T2_2 Amino acid residue (SEQ ID NO:23) | COV_E_T2_3 Amino acid residue (SEQ ID NO:42) | COV_E_T2_4 Amino acid residue (SEQ ID NO:43) | COV_E_T2_5 Amino acid residue (SEQ ID NO:44) |
| --- | --- | --- | --- | --- | --- | --- |
| 15 | N | N | N | A | A | A |
| 55 | S | T | T | S | T | T |
| 69 | R | Q | R | R | Q | R |
| 70 | — | G | — | — | G | — |

TABLE 10.13-continued

| SARS2 E protein (SEQ ID NO:41) residue position | SARS2 Reference Amino acid residue (SEQ ID NO:41) | COV_E_T2_1 Amino acid residue (SEQ ID NO:22) | COV_E_T2_2 Amino acid residue (SEQ ID NO:23) | COV_E_T2_3 Amino acid residue (SEQ ID NO:42) | COV_E_T2_4 Amino acid residue (SEQ ID NO:43) | COV_E_T2_5 Amino acid residue (SEQ ID NO:44) |
|---|---|---|---|---|---|---|
| Total no of differences from reference | — | 3 | 1 | 1 | 4 | 2 |
| Percentage identity with reference | — | 96 | 98.67 | 98.67 | 94.67 | 97.33 |

According to the invention there is provided an isolated polypeptide, which comprises an amino acid sequence according to any of SEQ ID NOs: 36-38.

According to the invention there is also provided an isolated polypeptide comprising an amino acid sequence of SEQ ID NO:42 (COV_E_T2_3), or an amino acid sequence which has at least 99% amino acid identity over its entire length with the amino acid sequence of SEQ ID NO: 42.

Optionally a polypeptide of the invention comprising an amino acid sequence of SEQ ID NO:42 (COV_E_T2_3), or an amino acid sequence which has at least 99% amino acid identity over its entire length with the amino acid sequence of SEQ ID NO:42, comprises amino acid residue A at a position corresponding to amino acid residue position 15 of SEQ ID NO:41.

According to the invention there is also provided an isolated polypeptide comprising an amino acid sequence of SEQ ID NO:43 (COV_E_T2_4), or an amino acid sequence which has at least 95%, 96%, 97%, 98%, or 99% amino acid identity over its entire length with the amino acid sequence of SEQ ID NO:43.

Optionally a polypeptide of the invention comprising an amino acid sequence of SEQ ID NO:43 (COV_E_T2_4), or an amino acid sequence which has at least 95%, 96%, 97%, 98%, or 99% amino acid identity over its entire length with the amino acid sequence of SEQ ID NO:43, comprises at least one, or all of the following amino acid residues at positions corresponding to the amino acid residue positions of SEQ ID NO:41: 15A, 55T, 69Q, 70G.

According to the invention there is also provided an isolated polypeptide comprising an amino acid sequence of SEQ ID NO:44 (COV_E_T2_5), or an amino acid sequence which has at least 98%, or 99% amino acid identity over its entire length with the amino acid sequence of SEQ ID NO:44.

Optionally a polypeptide of the invention comprising an amino acid sequence of SEQ ID NO:44 (COV_E_T2_5), or an amino acid sequence which has at least 98%, or 99% amino acid identity over its entire length with the amino acid sequence of SEQ ID NO:44, comprises at least one, or all of the following amino acid residues at positions corresponding to the amino acid residue positions of SEQ ID NO:41: 15A, 55T.

According to the invention there is also provided an isolated polypeptide which comprises a coronavirus E protein with at least one of the following amino acid residues at positions corresponding to the amino acid residue positions of SEQ ID NO:41: 15A, 55T, 69Q, 70G.

Optionally an isolated polypeptide of the invention which comprises a coronavirus E protein, comprises the following amino acid residues at positions corresponding to the amino acid residue positions of SEQ ID NO:41: 15A, 55T.

Optionally an isolated polypeptide of the invention which comprises a coronavirus E protein comprises an amino acid sequence which has at least 70%, 75%, 80%, 85%, 90%, 91%, 92%, 93%, 94%, 95%, 96%, 97%, 98%, or 99% amino acid identity over its entire length with the amino acid sequence of SEQ ID NO:21.

Designed Coronavirus Membrane (M) Protein Sequences

The applicant has also generated novel amino acid sequences for coronavirus Membrane (M) protein:

COV_M_T2_1 Sarbecovirus root ancestor (SEQ ID NO:24);

COV_M_T2_2 Epitope optimised version of SARS2 clade ancestor Node88b (D4 removed), SARS2 equivalent of B cell epitope from start and end added, and then T cell epitopes added whilst observing coevolving site constraints (SEQ ID NO:25).

The amino acid sequences of these designed sequences are:

>COV_M_T2_1/1-221 Sarbeco_M_root:

```
                                      (SEQ ID NO: 24)
MADNGTITVE ELKQLLEQWN LVIGFLFLAW IMLLQFAYSN

RNRFLYIIKL VFLWLLWPVT LACFVLAAVY RINWVTGGIA

IAMACIVGLM WLSYFVASFR LFARTRSMWS FNPETNILLN

VPLRGTILTR PLMESELVIG AVIIRGHLRM AGHSLGRCDI

KDLPKEITVA TSRTLSYYKL GASQRVGTDS GFAAYNRYRI

GNYKLNTDHA GSNDNIALLV Q
```

>COV_M_T2_2/1-222
Sarbeco_M_Node88b_epitope_optimised:

```
                                      (SEQ ID NO: 25)
MADSNGTITV EELKKLLEQW NLVIGFLFLT WICLLQFAYS

NRNRFLYIIK LIFLWLLWPV TLACFVLAAV YRINWVTGGI

AIAMACIVGL MWLSYFVASF RLFARTRSMW SFNPETNILL

NVPLRGSIIT RPLMESELVI GAVILRGHLR MAGHSLGRCD

IKDLPKEITV ATSRTLSYYK LGASQRVASD SGFAVYNRYR

IGNYKLNTDH SSSSDNIALL VQ
```

As described in Example 11 below, FIG. 8 shows alignment of a SARS2 reference M protein sequence (SEQ ID NO:26) with the designed sequences. The alignment shown in FIG. 8 highlights the amino acid differences between the SARS2 reference M protein sequence and the COV_M_T2_1 and COV_M_T2_2 designed sequences, as shown in the table below:

TABLE 11.1

| SARS2 M reference protein residue position (SEQ ID NO: 26) | SARS2 Reference Amino acid residue (SQ ID NO: 26) | COV_M_T2_1 Amino acid residue (SEQ ID NO: 24) | COV_M_T2_2 Amino acid residue (SEQ ID NO: 25) |
|---|---|---|---|
| 4 | S | — | S |
| 15 | K | Q | K |
| 30 | T | A | T |
| 33 | C | M | C |
| 40 | A | S | S |
| 52 | I | V | I |
| 76 | I | V | V |
| 87 | L | I | I |
| 97 | I | V | V |
| 125 | H | R | R |
| 127 | T | T | S |
| 134 | L | M | M |
| 145 | L | I | L |
| 151 | I | M | M |
| 155 | H | S | S |
| 188 | A | G | A |
| 189 | G | T | S |
| 195 | A | A | V |
| 197 | S | N | N |
| 211 | S | A | S |
| 212 | S | G | S |
| 214 | S | N | S |

According to the invention there is also provided an isolated polypeptide which comprises an amino acid sequence of SEQ ID NO:24, or an amino acid sequence which has at least 91%, 92%, 93%, 94%, 95%, 96%, 97%, 98%, or 99% amino acid identity over its entire length with the amino acid sequence of SEQ ID NO:24.

Optionally an isolated polypeptide of the invention which comprises an amino acid sequence of SEQ ID NO:24, or an amino acid sequence which has at least 91%, 92%, 93%, 94%, 95%, 96%, 97%, 98%, or 99% amino acid identity over its entire length with the amino acid sequence of SEQ, ID NO: 24, comprises at least one of the amino acid residues, at a position corresponding to the amino acid residue position of SEQ ID NO:26, as shown in the table below:

TABLE 11.2

| SARS2 M protein residue position | COV_M_T2_1 Amino acid residue |
|---|---|
| 40 | S |
| 76 | V |
| 87 | I |
| 97 | V |
| 125 | R |
| 134 | M |
| 151 | M |
| 155 | S |
| 197 | N |

Optionally an isolated polypeptide of the invention which comprises an amino acid sequence of SEQ ID NO:24, or an amino acid sequence which has at least 91%, 92%, 93%, 94%, 95%, 96%, 97%, 98%, or 99% amino acid identity over its entire length with the amino acid sequence of SEQ' ID NO: 24, comprises at least five of the amino acid residues, at positions corresponding to the amino acid residue positions of SEQ ID NO:26, as shown in Table 11.2.

Optionally an isolated polypeptide of the invention which comprises an amino acid sequence of SEQ ID NO:24, or an amino acid sequence which has at least 91%, 92%, 93%, 94%, 95%, 96%, 97%, 98%, or 99% amino acid identity over its entire length with the amino acid sequence of SEQ ID NO:24, comprises all of the amino acid residues, at positions corresponding to the amino acid residue positions of SEQ ID NO:26, as shown in Table 11.2.

Optionally an isolated polypeptide of the invention which comprises an amino acid sequence of SEQ ID NO:24, or an amino acid sequence which has at least 91%, 92%, 93%, 94%, 95%, 96%, 97%, 98%, or 99% amino acid identity over its entire length with the amino acid sequence of SEQ ID NO:24, comprises at least one of the amino acid residues, at a position corresponding to the amino acid residue position of SEQ ID NO:26, as shown in the table below:

TABLE 11.3

| SARS2 M protein residue position | COV_M_T2_1 Amino acid residue |
|---|---|
| 4 | — (deletion) |
| 15 | Q |
| 30 | A |
| 33 | M |
| 40 | S |
| 52 | V |
| 76 | V |
| 87 | I |
| 97 | V |
| 125 | R |
| 134 | M |
| 145 | I |
| 151 | M |
| 155 | S |
| 188 | G |
| 189 | T |
| 197 | N |
| 211 | A |
| 212 | G |
| 214 | N |

Optionally an isolated polypeptide of the invention which comprises an amino acid sequence of SEQ ID NO:24, or an amino acid sequence which has at least 91%, 92%, 93%, 94%, 95%, 96%, 97%, 98%, or 99% amino acid identity over its entire length with the amino acid sequence of SEQ ID NO: 24, comprises at least five of the amino acid residues, at positions corresponding to the amino acid residue positions of SEQ ID NO:26, as shown in Table 11.3.

Optionally an isolated polypeptide of the invention which comprises an amino acid sequence of SEQ ID NO:24, or an amino acid sequence which has at least 91%, 92%, 93%, 94%, 95%, 96%, 97%, 98%, or 99% amino acid identity over its entire length with the amino acid sequence of SEQ ID NO: 24, comprises at least ten of the amino acid residues, at positions corresponding to the amino acid residue positions of SEQ ID NO:26, as shown in Table 11.3.

Optionally an isolated polypeptide of the invention which comprises an amino acid sequence of SEQ ID NO:24, or an amino acid sequence which has at least 91%, 92%, 93%, 94%, 95%, 96%, 97%, 98%, or 99% amino acid identity over its entire length with the amino acid sequence of SEQ ID NO:24, comprises at least fifteen of the amino acid residues, at positions corresponding to the amino acid residue positions of SEQ ID NO:26, as shown in Table 11.3.

Optionally an isolated polypeptide of the invention which comprises an amino acid sequence of SEQ ID NO:24, or an amino acid sequence which has at least 91%, 92%, 93%, 94%, 95%, 96%, 97%, 98%, or 99% amino acid identity over its entire length with the amino acid sequence of SEQ ID NO:24, comprises all of the amino acid residues, at positions corresponding to the amino acid residue positions of SEQ ID NO:26, as shown in Table 11.3.

There is also provided according to the invention an isolated polypeptide which comprises an amino acid sequence of SEQ ID NO:25, or an amino acid sequence which has at least 95%, 96%, 97%, 98%, or 99% amino acid identity over its entire length with the amino acid sequence of SEQ ID NO:25.

Optionally an isolated polypeptide of the invention which comprises an amino acid sequence of SEQ ID NO:25, or an amino acid sequence which has at least 95%, 96%, 97%, 98%, or 99% amino acid identity over its entire length with the amino acid sequence of SEQ ID NO:25, comprises at least one of the amino acid residues, at a position corresponding to the amino acid residue positions of SEQ ID NO:25, as shown in the table below:

TABLE 11.4

| SARS2 M protein residue position | COV_M_T2_2 Amino acid residue |
| --- | --- |
| 40 | S |
| 76 | V |
| 87 | I |
| 97 | V |
| 125 | R |
| 134 | M |
| 151 | M |
| 155 | S |
| 197 | N |

Optionally an isolated polypeptide of the invention which comprises an amino acid sequence of SEQ ID NO:25, or an amino acid sequence which has at least 95%, 96%, 97%, 98%, or 99% amino acid identity over its entire length with the amino acid sequence of SEQ ID NO:25, comprises at least five of the amino acid residues, at positions corresponding to the amino acid residue positions of SEQ ID NO:25, as shown in Table 11.4.

Optionally an isolated polypeptide of the invention which comprises an amino acid sequence of SEQ ID NO:25, or an amino acid sequence which has at least 95%, 96%, 97%, 98%, or 99% amino acid identity over its entire length with the amino acid sequence of SEQ ID NO:25, comprises all of the amino acid residues, at positions corresponding to the amino acid residue positions of SEQ ID NO:25, as shown in Table 11.4.

Optionally an isolated polypeptide of the invention which comprises an amino acid sequence of SEQ ID NO:25, or an amino acid sequence which has at least 95%, 96%, 97%, 98%, or 99% amino acid identity over its entire length with the amino acid sequence of SEQ ID NO:25, comprises at least one of the amino acid residues, at a position corresponding to the amino acid residue position of SEQ ID NO:25, as shown in the table below:

TABLE 11.5

| SARS2 M protein residue position | COV_M_T2_2 Amino acid residue |
| --- | --- |
| 40 | S |
| 76 | V |
| 87 | I |

TABLE 11.5-continued

| SARS2 M protein residue position | COV_M_T2_2 Amino acid residue |
| --- | --- |
| 97 | V |
| 125 | R |
| 127 | S |
| 134 | M |
| 151 | M |
| 155 | S |
| 189 | S |
| 195 | V |
| 197 | N |

Optionally an isolated polypeptide of the invention which comprises an amino acid sequence of SEQ ID NO:25, or an amino acid sequence which has at least 95%, 96%, 97%, 98%, or 99% amino acid identity over its entire length with the amino acid sequence of SEQ ID NO:25, comprises at least five of the amino acid residues, at positions corresponding to the amino acid residue positions of SEQ ID NO:25, as shown in Table 11.5.

Optionally an isolated polypeptide of the invention which comprises an amino acid sequence of SEQ ID NO:25, or an amino acid sequence which has at least 95%, 96%, 97%, 98%, or 99% amino acid identity over its entire length with the amino acid sequence of SEQ ID NO:25, comprises at least ten of the amino acid residues, at positions corresponding to the amino acid residue positions of SEQ ID NO:25, as shown in Table 11.5.

Optionally an isolated polypeptide of the invention which comprises an amino acid sequence of SEQ ID NO:25, or an amino acid sequence which has at least 95%, 96%, 97%, 98%, or 99% amino acid identity over its entire length with the amino acid sequence of SEQ ID NO:25, comprises all of the amino acid residues, at positions corresponding to the amino acid residue positions of SEQ ID NO:25, as shown in Table 11.5.

According to the invention there is also provided an isolated polypeptide, which comprises a coronavirus M protein with any, or all of the amino acid residues at positions corresponding to the amino acid residue positions as shown in the table below:

TABLE 11.6

| M protein residue position | Amino acid residue |
| --- | --- |
| 40 | S |
| 76 | V |
| 87 | I |
| 97 | V |
| 125 | R |
| 134 | M |
| 151 | M |
| 155 | S |
| 197 | N |

According to the invention there is also provided an isolated polypeptide, which comprises a coronavirus M protein with any, or all of the amino acid residues at positions corresponding to the amino acid residue positions as shown in the table below:

TABLE 11.7

| M protein residue position | Amino acid residue |
|---|---|
| 4 | — (deletion) |
| 15 | Q |
| 30 | A |
| 33 | M |
| 40 | S |
| 52 | V |
| 76 | V |
| 87 | I |
| 97 | V |
| 125 | R |
| 134 | M |
| 145 | I |
| 151 | M |
| 155 | S |
| 188 | G |
| 189 | T |
| 197 | N |
| 211 | A |
| 212 | G |
| 214 | N |

According to the invention there is also provided an isolated polypeptide, which comprises a coronavirus M protein with any, or all of the amino acid residues at positions corresponding to the amino acid residue positions as shown in the table below:

TABLE 11.8

| M protein residue position | Amino acid residue |
|---|---|
| 40 | S |
| 76 | V |
| 87 | I |
| 97 | V |
| 125 | R |
| 134 | M |
| 151 | M |
| 155 | S |
| 197 | N |

According to the invention there is also provided an isolated polypeptide, which comprises a coronavirus M protein with any, or all of the amino acid residues at positions corresponding to the amino acid residue positions as shown in the table below:

TABLE 11.9

| M protein residue position | Amino acid residue |
|---|---|
| 40 | S |
| 76 | V |
| 87 | I |
| 97 | V |
| 125 | R |
| 127 | S |
| 134 | M |
| 151 | M |
| 155 | S |
| 189 | S |
| 195 | V |
| 197 | N |

Optionally an isolated polypeptide of the invention which comprises a coronavirus M protein comprises an amino acid sequence which has at least 70%, 75%, 80%, 85%, 90%, 91%, 92%, 93%, 94%, 95%, 96%, 97%, 98%, or 99% amino acid identity over its entire length with the amino acid sequence of SEQ ID NO:26.

We have made further new M protein designs (COV_M_T2_3, COV_M_T2_4, COV_M_T2_5)). In these designs, we have deleted the first and the second transmembrane region of the membrane protein to abrogate its interaction with the S protein:

The string construct with S, M and E was showing higher order aggregates.

Abrogation of interaction between S and M—can reduce aggregation.

M-del constructs (Cov_M_T2_(3-5)) designed to abrogate the interaction with S.

FIG. 20 shows an illustration of the M protein. Interaction between the M, E and N proteins is important for viral assembly. The M protein also binds to the nucleocapsid, and this interaction promotes the completion of virion assembly. These interactions have been mapped to the C-terminus of the endo-domain of the M protein, and the C-terminal domain of the N-protein. In FIG. 20, * denotes identification of immunodominant epitopes on the membrane protein of the Severe Acute Respiratory Syndrome-Associated Coronavirus, and ** denotes mapping of the Coronavirus membrane protein domains involved in interaction with the Spike protein.

The amino acid sequences of the new M protein designs are given below:

```
>COV_M_T2_3
                                  (SEQ ID NO: 48)
MADSNGTITV EELKKLLEQI TGGIAIAMAC LVGLMWLSYF

IASFRLFART RSMWSFNPET NILLNVPLHG TILTRPLLES

ELVIGAVILR GHLRIAGHHL GRCDIKDLPK EITVATSRTL

SYYKLGASQR VAGDSGFAAY SRYRIGNGKL NTDHSSSSDN

IALLVQ

>COV_M_T2_4
                                  (SEQ ID NO: 49)
MADNGTITVE ELKQLLEQVT GGIAIAMACI VGLMWLSYFV

ASFRLFARTR SMWSFNPETN ILLNVPLRGT ILTRPLMESE

LVIGAVIIRG HLRMAGHSLG RCDIKDLPKE ITVATSRTLS

YYKLGASQRV GTDSGFAAYN RYRIGNGKLN TDHAGSNDNI

ALLVQ

>COV_M_T2_5
                                  (SEQ ID NO: 50)
MADSNGTITV EELKKLLEQV TGGIAIAMAC IVGLMWLSYF

VASFRLFART RSMWSFNPET NILLNVPLRG SIITRPLMES

SYYKLGASQR VASDSGFAVY ELVIGAVILR GHLRMAGHSL

GRCDIKDLPK EITVATSRTL NRYRIGNGKL NTDHSSSSDN

IALLVQ
```

Sequence alignment of the new M protein designs (COV_M_T2_3, COV_M_T2_4, COV_M_T2_5) with the previous M protein designs (COV_M_T1_1, COV_M_T2_1, COV_M_T2_2) is shown in FIG. 46:

The amino acid differences of the designed sequences from the SARS2 M protein reference sequence are shown in the table below (with differences from the reference sequence in bold):

TABLE 11.10

| SARS2 M protein residue position (SEQ ID NO:26) | SARS2 Reference Amino acid residue (COV_M_T1_1) (SEQ ID NO:26) | COV_M_T2_1 Amino acid residue (SEQ ID NO:24) | COV_M_T2_2 Amino acid residue (SEQ ID NO:25) | COV_M_T2_3 Amino acid residue (SEQ ID NO:48) | COV_M_T2_4 Amino acid residue (SEQ ID NO:49) | COV_M_T2_5 Amino acid residue (SEQ ID NO:50) |
|---|---|---|---|---|---|---|
| 4 | S | Deleted | S | S | Deleted | S |
| 15 | K | Q | K | K | Q | K |
| 20-75 | | | | Deleted | Deleted | Deleted |
| 30 | T | A | T | | | |
| 33 | C | M | C | | | |
| 40 | A | S | S | | | |
| 52 | I | V | I | | | |
| 76 | I | V | V | I | V | V |
| 87 | L | I | I | I | I | I |
| 97 | I | V | V | I | V | V |
| 125 | H | R | R | H | R | R |
| 127 | T | T | S | T | T | S |
| 129 | L | L | I | L | L | I |
| 134 | L | M | M | L | M | M |
| 145 | L | I | L | L | I | L |
| 151 | I | M | M | I | M | M |
| 155 | H | S | S | H | S | S |
| 188 | A | G | A | A | G | A |
| 189 | G | T | S | G | T | S |
| 195 | A | A | V | A | A | V |
| 197 | S | N | N | S | N | N |
| 204 | Y | Y | Y | G | G | G |
| 211 | S | A | S | S | A | S |
| 212 | S | G | S | S | G | S |
| 214 | S | N | S | S | N | S |
| Total no of differences from reference | — | 20 | 13 | 57 | 73 | 69 |
| Percentage identity with reference | — | 90.99% | 94.14% | 74.32% | 67.12% | 68.92% |

According to the invention there is also provided an isolated polypeptide which comprises an amino acid sequence of SEQ ID NO:48, or an amino acid sequence which has at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% amino acid identity over its entire length with the amino acid sequence of SEQ ID NO:48.

Optionally an isolated polypeptide of the invention which comprises an amino acid sequence of SEQ ID NO:48, or an amino acid sequence which has at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% amino acid identity over its entire length with the amino acid sequence of SEQ ID NO:48, comprises a deletion of amino acid residues at positions corresponding to positions 20-75 of SEQ ID NO:26.

Optionally an isolated polypeptide of the invention which comprises an amino acid sequence of SEQ ID NO:48, or an amino acid sequence which has at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% amino acid identity over its entire length with the amino acid sequence of SEQ ID NO:48, comprises amino acid residue G at a position corresponding to amino acid residue position 204 of SEQ ID NO:26.

According to the invention there is also provided an isolated polypeptide which comprises an amino acid sequence of SEQ ID NO:49, or an amino acid sequence which has at least 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% amino acid identity over its entire length with the amino acid sequence of SEQ ID NO:49.

Optionally an isolated polypeptide of the invention which comprises an amino acid sequence of SEQ ID NO:49, or an amino acid sequence which has at least 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% amino acid identity over its entire length with the amino acid sequence of SEQ ID NO:49, comprises a deletion of amino acid residues at positions corresponding to positions 20-75 of SEQ ID NO:26.

Optionally an isolated polypeptide of the invention which comprises an amino acid sequence of SEQ ID NO:49, or an amino acid sequence which has at least 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% amino acid identity over its entire length with the amino acid sequence of SEQ ID NO:49, comprises at least one, or all, of the amino acid residues, at a position corresponding to the amino acid residue position of SEQ ID NO:26, as shown in the table below:

TABLE 11.11

| SARS2 M protein residue position (SEQ ID NO: 26) | Amino acid residue |
|---|---|
| 20-75 | Deleted |
| 76 | V |
| 87 | I |
| 97 | V |
| 125 | R |
| 134 | M |
| 151 | M |
| 155 | S |

TABLE 11.11-continued

| SARS2 M protein residue position (SEQ ID NO: 26) | Amino acid residue |
|---|---|
| 189 | T |
| 197 | N |
| 204 | G |

Optionally an isolated polypeptide of the invention which comprises an amino acid sequence of SEQ ID NO:49, or an amino acid sequence which has at least 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% amino acid identity over its entire length with the amino acid sequence of SEQ ID NO:49, comprises at least one, or all, of the amino acid residues, at a position corresponding to the amino acid residue position of SEQ ID NO:26, as shown in the table below:

TABLE 11.12

| SARS2 M protein residue position (SEQ ID NO: 26) | COV_M_T2_4 Amino acid residue (SEQ ID NO: 49) |
|---|---|
| 4 | Deleted |
| 15 | Q |
| 20-75 | Deleted |
| 76 | V |
| 87 | I |
| 97 | V |
| 125 | R |
| 134 | M |
| 145 | I |
| 151 | M |
| 155 | S |
| 188 | G |
| 189 | T |
| 197 | N |
| 204 | G |
| 211 | A |
| 212 | G |
| 214 | N |

According to the invention there is also provided an isolated polypeptide which comprises an amino acid sequence of SEQ ID NO:50, or an amino acid sequence which has at least 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% amino acid identity over its entire length with the amino acid sequence of SEQ ID NO:50.

Optionally an isolated polypeptide of the invention which comprises an amino acid sequence of SEQ ID NO:50, or an amino acid sequence which has at least 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% amino acid identity over its entire length with the amino acid sequence of SEQ ID NO:50, comprises a deletion of amino acid residues at positions corresponding to positions 20-75 of SEQ ID NO:26.

Optionally an isolated polypeptide of the invention which comprises an amino acid sequence of SEQ ID NO:50, or an amino acid sequence which has at least 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% amino acid identity over its entire length with the amino acid sequence of SEQ ID NO:50, comprises at least one, or all, of the amino acid residues, at a position corresponding to the amino acid residue position of SEQ ID NO: 26, as shown in the table below:

TABLE 11.11

| SARS2 M protein residue position (SEQ ID NO: 26) | Amino acid residue |
|---|---|
| 20-75 | Deleted |
| 76 | V |
| 87 | I |
| 97 | V |
| 125 | R |
| 134 | M |
| 151 | M |
| 155 | S |
| 189 | T |
| 197 | N |
| 204 | G |

Optionally an isolated polypeptide of the invention which comprises an amino acid sequence of SEQ ID NO:50, or an amino acid sequence which has at least 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% amino acid identity over its entire length with the amino acid sequence of SEQ ID NO:50, comprises at least one, or all, of the amino acid residues, at a position corresponding to the amino acid residue position of SEQ ID NO: 26, as shown in the table below:

TABLE 11.13

| SARS2 M protein residue position (SEQ ID NO: 26) | COV_M_T2_5 Amino acid residue (SEQ ID NO: 50) |
|---|---|
| 20-75 | Deleted |
| 76 | V |
| 87 | I |
| 97 | V |
| 125 | R |
| 127 | S |
| 129 | I |
| 134 | M |
| 151 | M |
| 155 | S |
| 189 | S |
| 195 | V |
| 197 | N |
| 204 | G |

According to the invention there is also provided an isolated polypeptide, which comprises a coronavirus M protein with any, or all of the amino acid residues at positions corresponding to the amino acid residue positions as shown in the table below:

TABLE 11.11

| SARS2 M protein residue position (SEQ ID NO: 26) | Amino acid residue |
|---|---|
| 20-75 | Deleted |
| 76 | V |
| 87 | I |
| 97 | V |

TABLE 11.11-continued

| SARS2 M protein residue position (SEQ ID NO: 26) | Amino acid residue |
|---|---|
| 125 | R |
| 134 | M |
| 151 | M |
| 155 | S |
| 189 | T |
| 197 | N |
| 204 | G |

According to the invention there is also provided an isolated polypeptide, which comprises a coronavirus M protein with any, or all of the amino acid residues at positions corresponding to the amino acid residue positions as shown in the table below:

TABLE 11.12

| SARS2 M protein residue position (SEQ ID NO: 26) | COV_M_T2_4 Amino acid residue (SEQ ID NO: 49) |
|---|---|
| 4 | Deleted |
| 15 | Q |
| 20-75 | Deleted |
| 76 | V |
| 87 | I |
| 97 | V |
| 125 | R |
| 134 | M |
| 145 | I |
| 151 | M |
| 155 | S |
| 188 | G |
| 189 | T |
| 197 | N |
| 204 | G |
| 211 | A |
| 212 | G |
| 214 | N |

According to the invention there is also provided an isolated polypeptide, which comprises a coronavirus M protein with any, or all of the amino acid residues at positions corresponding to the amino acid residue positions as shown in the table below:

TABLE 11.13

| SARS2 M protein residue position (SEQ ID NO: 26) | COV_M_T2_5 Amino acid residue (SEQ ID NO: 50) |
|---|---|
| 20-75 | Deleted |
| 76 | V |
| 87 | I |
| 97 | V |
| 125 | R |
| 127 | S |
| 129 | I |
| 134 | M |
| 151 | M |
| 155 | S |
| 189 | S |
| 195 | V |
| 197 | N |
| 204 | G |

Optionally an isolated polypeptide of the invention which comprises a coronavirus M protein comprises an amino acid sequence which has at least 70%, 75%, 80%, 85%, 90%, 91%, 92%, 93%, 94%, 95%, 96%, 97%, 98%, or 99% amino acid identity over its entire length with the amino acid sequence of SEQ ID NO:26.

Designed Coronavirus Nucleoprotein (N) Sequences

We have made new N protein designs, COV_N_T2_1 (SEQ ID NO:46) and COV_N_T2_2 (SEQ ID NO: 47). The amino acid sequences of these designs is shown below, and in Example 15. Sequence COV_N_T2_2 was designed using a methodology and algorithm which selected predicted epitopes to include based on their conservation across the sarbecoviruses (whilst minimising redundancy), the frequency and number of MHC alleles the epitope is restricted by the predicted epitope quality, and a handful of user specified weightings.

```
>YP_009724397.2/1-419 nucleocapsid phosphoprotein
(SARS-COV-2](reference sequence)
                              (SEQ ID NO: 45)
MSDNGPQ-NQ RNAPRITFGG PSDSTGSNQN GERSGARSKQ
RRPQGLPNNT ASWFTALTQH GKEDLKFPRG QGVPINTNSS
PDDQIGYYRR ATRRIRGGDG KMKDLSPRWY FYYLGTGPEA
GLPYGANKDG IIWVATEGAL NTPKDHIGTR NPANNAAIVL
QLPQGTTLPK GFYAEGSRGG SQASSRSSSR SRNSSRNSTP
GSSRGTSPAR MAGNGGDAAL ALLLLDRLNQ LESKMSGKGQ
QQQGQTVTKK SAAEASKKPR QKRTATKAYN VTQAFGRRGP
EQTQGNFGDQ ELIRQGTDYK HWPQIAQFAP SASAFFGMSR
IGMEVTPSGT WLTYTGAIKL DDKDPNFKDQ VILLNKHIDA
YKTFPPTEPK KDKKKKADET QALPQRQKKQ QTVTLLPAAD
LDDFSKQLQQ SMSSA--DST QA >COV_N_T2 1/1-418 Node1b 321-323 deleted
                              (SEQ ID NO: 46)
MSDNGPQ-NQ RSAPRITFGG PSDSTDNNQN GERSGARPKQ
RRPQGLPNNT ASWFTALTQH GKEDLRFPRG QGVPINTNSG
KDDQIGYYRR ATRRVRGGDG KMKELSPRWY FYYLGTGPEA
ALPYGANKEG IVWVATEGAL NTPKDHIGTR NPNNNAAIVL
QLPQGTTLPK GFYAEGSRGG SQASSRSSSR SRGNSRNSTP
GSSRGTSPAR MASGGGDTAL ALLLLDRLNQ LESKVSGKGQ
QQQGQTVTKK SAAEASKKPR QKRTATKQYN VTQAFGRRGP
EQTQGNFGDQ ELIRQGTDYK HWPQIAQFAP SASAFFGMSR
---EVTPSGT WLTYHGAIKL DDKDPQFKDN VILLNKHIDA
YKTFPPTEPK KDKKKKADEA QPLPQRQKKQ PTVILLPAAD
LDDFSKQLQN SMSGASADST QA >COV_N_T2 2/1-417 epitope optimised 321-323
deleted
                              (SEQ ID NO: 47)
MTDNGQQ-GP RNAPRITF-G VSDNFDNNQD GGRSGARPKQ
RRPQGLPNNT ASWFTALTQH GKEDLRFPRG QGVPINTNSS
PDDQIGYYRR ATRRIRGGDG KMKDLSPRWY FYYLGTGPEA
ALPYGANKEG IVWVATEGAL NTPKDHIGTR NPNNNAAIVL
QLPQGTTLPK GFYAEGSRGG SQASSRSSSR SRNSSRNSTP
GSSRGTSPAR NLQAGGDTAL ALLLLDRLNQ LESKMSGKGQ
QQQGQTVTKK SAAEASKKPR QKRTATKQYN VTQAFGRRGP
EQTQGNEGDQ ELIRQGTDYK QWPQIAQFAP SASAFFGMSR
---EVTPSGT WLTYTGAIKL DDKDPQFKDN VILLNKHIDA
YKTFPPTEPK KDKKKKADEA QPLPQRQKKQ QTVTLLPAAD
LDDFSRQLQN SMSGASADST QA
```

Alignment of the N protein designs with SARS2 N protein reference sequence is shown in FIG. 47.

The amino acid differences of the designed sequences from the SARS2 reference sequence are shown in the Table 12.1 below (with differences from the reference sequence in bold, and differences that are common to all the designed sequences underlined):

TABLE 12.1

| SARS2 N protein reference (SEQ ID NO: 45) residue position | SARS2 Reference amino acid residue | N_T2_1 amino acid residue (SEQ ID NO: 46) | N_T2_2 amino acid residue (SEQ ID NO: 47) |
|---|---|---|---|
| 2 | S | S | T |
| 6 | P | P | Q |
| 8 | N | N | G |
| 9 | Q | Q | P |
| 11 | N | S | N |
| 18 | G | G | — |
| 20 | P | P | V |
| 23 | S | S | N |
| 24 | T | T | F |
| 25 | G | D | D |
| 26 | S | N | N |
| 29 | N | N | D |
| 31 | E | E | G |
| 37 | S | P | P |
| 65 | K | R | R |
| 79 | S | G | S |
| 80 | P | K | P |
| 94 | I | V | I |
| 103 | D | E | D |
| 120 | G | A | A |
| 128 | D | E | E |
| 131 | I | V | V |
| 152 | A | N | N |
| 192 | N | G | N |
| 193 | S | N | S |
| 211 | A | A | L |
| 212 | G | S | Q |
| 213 | N | G | A |
| 217 | A | T | T |
| 234 | M | V | M |
| 267 | A | Q | Q |
| 300 | H | H | Q |
| 320 | I | — | — |
| 321 | G | — | — |
| 322 | M | — | — |
| 334 | T | H | T |
| 345 | N | Q | Q |
| 349 | Q | N | N |
| 379 | T | A | A |
| 390 | Q | P | Q |
| 406 | K | K | R |
| 409 | Q | N | N |
| 413 | S | G | G |
| *415* | — | *S* | *S* |
| *416* | — | *A* | *A* |
| Total no of differences from reference | — | 31 | 35 |
| Percentage identity with reference | — | 92.60 | 91.65 |

Positions 415 and 416 of the SARS2 N protein reference residue position column are italicised as they are not residues of the reference sequences, but include insertions in the N_T2_1 and N_T2_2 sequences.

The amino acid changes common to both of the designed sequences are summarised in the table below:

TABLE 12.2

| SARS2 N (SEQ ID NO: 45) residue position | Amino acid residue of designed sequences (SEQ ID Nos: 46, 47) |
|---|---|
| 26 | N |
| 37 | P |
| 65 | R |
| 120 | A |
| 128 | E |
| 131 | V |
| 152 | N |
| 217 | T |
| 267 | Q |
| 345 | Q |
| 349 | N |
| 379 | A |
| 409 | N |
| 413 | G |
| 415 | S (insertion) |
| 416 | A (insertion) |

Optional additional changes are summarised in the table below:

TABLE 12.3

| SARS2 N protein (SEQ ID NO: 45) residue position | Amino acid residue of designed sequence (SEQ ID NO: 46) |
|---|---|
| 11 | S |
| 79 | G |
| 80 | K |
| 94 | V |
| 103 | E |
| 192 | G |
| 193 | N |
| 212 | S |
| 213 | G |
| 234 | V |
| 320 | — |
| 321 | — |
| 322 | — |
| 334 | H |
| 390 | P |

Alternative optional additional changes are summarised in the table below:

TABLE 12.4

| SARS2 N protein (SEQ ID NO: 45) residue position | Amino acid residue (SEQ ID NO: 47) |
|---|---|
| 2 | T |
| 6 | Q |
| 8 | G |
| 9 | P |
| 18 | — |
| 20 | V |
| 23 | N |
| 24 | F |
| 25 | D |
| 29 | D |
| 31 | G |

TABLE 12.4-continued

| SARS2 N protein (SEQ ID NO: 45) residue position | Amino acid residue (SEQ ID NO: 47) |
|---|---|
| 211 | L |
| 212 | Q |
| 213 | A |
| 300 | Q |
| 320 | — |
| 321 | — |
| 322 | — |
| 406 | R |

According to the invention there is provided an isolated polypeptide which comprises an amino acid sequence of SEQ ID NO:46 (COV_N_T2_1), or an amino acid sequence which has at least 93%, 94%, 95%, 96%, 97%, 98%, or 99% amino acid identity over its entire length with the amino acid sequence of SEQ ID NO:46.

Optionally a polypeptide of the invention comprising an isolated polypeptide comprising an amino acid sequence of SEQ ID NO:46, or an amino acid sequence which has at least 93%, 94%, 95%, 96%, 97%, 98%, or 99% amino acid identity over its entire length with the amino acid sequence of SEQ ID NO:46, further comprises at least one, or all of the amino acid residues at positions corresponding to the amino acid residue positions as shown in Table 12.2 above.

Optionally a polypeptide of the invention comprising an isolated polypeptide comprising an amino acid sequence of SEQ ID NO:46, or an amino acid sequence which has at least 93%, 94%, 95%, 96%, 97%, 98%, or 99% amino acid identity over its entire length with the amino acid sequence of SEQ ID NO:46, further comprises at least one, or all of the amino acid residues at positions corresponding to the amino acid residue positions as shown in Table 12.3 above.

According to the invention there is also provided an isolated polypeptide which comprises an amino acid sequence of SEQ ID NO:47 (COV_N_T2_2), or an amino acid sequence which has at least 92%, 93%, 94%, 95%, 96%, 97%, 98%, or 99% amino acid identity over its entire length with the amino acid sequence of SEQ ID NO:47.

Optionally a polypeptide of the invention comprising an isolated polypeptide comprising an amino acid sequence of SEQ ID NO:47, or an amino acid sequence which has at least 92%, 93%, 94%, 95%, 96%, 97%, 98%, or 99% amino acid identity over its entire length with the amino acid sequence of SEQ ID NO:47, further comprises at least one, or all of the amino acid residues at positions corresponding to the amino acid residue positions as shown in Table 12.2 above.

Optionally a polypeptide of the invention comprising an isolated polypeptide comprising an amino acid sequence of SEQ ID NO:47, or an amino acid sequence which has at least 92%, 93%, 94%, 95%, 96%, 97%, 98%, or 99% amino acid identity over its entire length with the amino acid sequence of SEQ ID NO:47, further comprises at least one, or all of the amino acid residues at positions corresponding to the amino acid residue positions as shown in Table 12.4 above.

According to the invention there is also provided an isolated polypeptide, which comprises a coronavirus N protein with at least one, or all of the amino acid residues at positions corresponding to the amino acid residue positions of SEQ ID NO:45 as shown in Table 12.2 above.

Optionally an isolated polypeptide of the invention which comprises a coronavirus N protein with at least one, or all of the amino acid residues at positions corresponding to the amino acid residue positions of SEQ ID NO:45, as shown in Table 12.2 above, comprises at least five amino acid residues at positions corresponding to the amino acid residue positions of SEQ ID NO: 45, as shown in Table 12.2 above.

Optionally an isolated polypeptide of the invention which comprises a coronavirus N protein with at least one, or all of the amino acid residues at positions corresponding to the amino acid residue positions of SEQ ID NO:45, as shown in Table 12.2 above, comprises at least ten amino acid residues at positions corresponding to the amino acid residue positions of SEQ ID NO: 45, as shown in Table 12.2 above.

Optionally an isolated polypeptide of the invention which comprises a coronavirus N protein with at least one, or all of the amino acid residues at positions corresponding to the amino acid residue positions of SEQ ID NO:45, as shown in Table 12.2 above, comprises at least fifteen amino acid residues at positions corresponding to the amino acid residue positions of SEQ ID NO: 45, as shown in Table 12.2 above.

Optionally an isolated polypeptide of the invention which comprises a coronavirus N protein with at least one, or all of the amino acid residues at positions corresponding to the amino acid residue positions of SEQ ID NO:45, as shown in Table 12.2 above, comprises at least one, or all of the amino acid residues at positions corresponding to the amino acid residue positions of SEQ ID NO:45, as shown in Table 12.3 above.

Optionally an isolated polypeptide of the invention which comprises a coronavirus N protein with at least one, or all of the amino acid residues at positions corresponding to the amino acid residue positions of SEQ ID NO:45, as shown in Table 12.2 above, comprises at least five of the amino acid residues at positions corresponding to the amino acid residue positions of SEQ ID NO: 45, as shown in Table 12.3 above.

Optionally an isolated polypeptide of the invention which comprises a coronavirus N protein with at least one, or all of the amino acid residues at positions corresponding to the amino acid residue positions of SEQ ID NO:45, as shown in Table 12.2 above, comprises at least ten of the amino acid residues at positions corresponding to the amino acid residue positions of SEQ ID NO: 45, as shown in Table 12.3 above.

Optionally an isolated polypeptide of the invention which comprises a coronavirus N protein with at least one, or all of the amino acid residues at positions corresponding to the amino acid residue positions of SEQ ID NO:45, as shown in Table 12.2 above, comprises at least one, or all of the amino acid residues at positions corresponding to the amino acid residue positions of SEQ ID NO:45, as shown in Table 12.4 above.

Optionally an isolated polypeptide of the invention which comprises a coronavirus N protein with at least one, or all of the amino acid residues at positions corresponding to the amino acid residue positions of SEQ ID NO:45, as shown in Table 12.2 above, comprises at least five of the amino acid residues at positions corresponding to the amino acid residue positions of SEQ ID NO: 45, as shown in Table 12.4 above.

Optionally an isolated polypeptide of the invention which comprises a coronavirus N protein with at least one, or all of the amino acid residues at positions corresponding to the amino acid residue positions of SEQ ID NO:45, as shown in Table 12.2 above, comprises at least ten of the amino acid residues at positions corresponding to the amino acid residue positions of SEQ ID NO: 45, as shown in Table 12.4 above.

Optionally an isolated polypeptide of the invention which comprises a coronavirus N protein with at least one, or all of the amino acid residues at positions corresponding to the amino acid residue positions of SEQ ID NO:45, as shown in Table 12.2 above, comprises at least fifteen of the amino acid residues at positions corresponding to the amino acid residue positions of SEQ ID NO:45, as shown in Table 12.4 above.

Optionally an isolated polypeptide of the invention which comprises a coronavirus N protein comprises an amino acid sequence which has at least 70%, 75%, 80%, 85%, 90%, 91%, 92%, 93%, 94%, 95%, 96%, 97%, 98%, or 99% amino acid identity over its entire length with the amino acid sequence of SEQ ID NO:45.

Polypeptides of the invention are particularly advantageous because they can elicit a broadly neutralising immune response to several different types of coronavirus, in particular several different types of □-coronavirus. Polypeptides of the invention comprising an amino acid sequence of SEQ ID NO:15 (or an amino acid sequence which has at least 81%, 82%, 83%, 84%, 85%, 86%, 87%, 88%, 89%, 90%, 91%, 92%, 93%, 94%, 95%, 96%, 97%, 98%, or 99% amino acid identity over its entire length with the amino acid sequence of SEQ ID NO:15), or SEQ ID NO:17 (or an amino acid sequence which has at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% amino acid identity over its entire length with the amino acid sequence of SEQ ID NO:17) are also advantageous because they lack non-neutralising epitopes that may result in virus immune evasion and disease progression by ADE (or ADE-like pro-inflammatory responses).

Similarly, polypeptides of the invention comprising a novel designed coronavirus E protein amino acid sequence (for example, an amino acid sequence of SEQ ID NO:22, or an amino acid sequence which has at least 95%, 96%, 97%, 98%, or 99% amino acid identity over its entire length with the amino acid sequence of SEQ ID NO:22, or an amino acid sequence of SEQ ID NO:23, or an amino acid sequence which has at least 98%, or 99% amino acid identity over its entire length with the amino acid sequence of SEQ ID NO:23), or a coronavirus M protein amino acid sequence (for example, an amino acid sequence of SEQ ID NO:24, or an amino acid sequence which has at least 91%, 92%, 93%, 94%, 95%, 96%, 97%, 98%, or 99% amino acid identity over its entire length with the amino acid sequence of SEQ ID NO:24, or an amino acid sequence of SEQ ID NO:25, or an amino acid sequence which has at least 95%, 96%, 97%, 98%, or 99% amino acid identity over its entire length with the amino acid sequence of SEQ ID NO:25) are advantageous because they lack non-neutralising epitopes that may result in virus immune evasion and disease progression by ADE (or ADE-like pro-inflammatory responses).

A polypeptide of the invention may include one or more conservative amino acid substitutions. Conservative amino acid substitutions are those substitutions that, when made, least interfere with the properties of the original polypeptide, that is, the structure and especially the function of the protein is conserved and not significantly changed by such substitutions. Examples of conservative substitutions are shown below:

| Original Residue | Conservative Substitutions |
| --- | --- |
| Ala | Ser |
| Arg | Lys |
| Asn | Gln, His |
| Asp | Glu |

-continued

| Original Residue | Conservative Substitutions |
| --- | --- |
| Cys | Ser |
| Gin | Asn |
| Glu | Asp |
| His | Asn; Gln |
| Ile | Leu, Val |
| Leu | Ile; Val |
| Lys | Arg; Gln; |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain.

The substitutions which in general are expected to produce the greatest changes in protein properties will be non-conservative, for instance changes in which (a) a hydrophilic residue, for example, serine or threonine, is substituted for (or by) a hydrophobic residue, for example, leucine, isoleucine, phenylalanine, valine or alanine; (b) a cysteine or proline is substituted for (or by) any other residue; (c) a residue having an electropositive side chain, for example, lysine, arginine, or histidine, is substituted for (or by) an electronegative residue, for example, glutamate or aspartate; or (d) a residue having a bulky side chain, for example, phenylalanine, is substituted for (or by) one not having a side chain, for example, glycine.

The term "broadly neutralising immune response" is used herein to mean an immune response elicited in a subject that is sufficient to inhibit (i.e. reduce), neutralise or prevent infection, and/or progress of infection, of a virus within the coronavirus family. Optionally a broadly neutralising immune response is sufficient to inhibit, neutralise or prevent infection, and/or progress of infection, of more than one type of β-coronavirus (for example, SARS-COV, and SARS-COV-2). Optionally a broadly neutralising immune response is sufficient to inhibit, neutralise or prevent infection, and/or progress of infection, of more than one type of β-coronavirus within the same β-coronavirus lineage (for example, more than one type of β-coronavirus within the subgenus Sarbecovirus, such as SARS-COV, SARS-COV-2, and Bat SL-CoV-WIV1). Optionally a broadly neutralising immune response is sufficient to inhibit, neutralise or prevent infection, and/or progress of infection, of coronaviruses of different β-coronavirus lineages, such as lineage B (for example, SARS-COV, and SARS-COV-2) and lineage C (for example, MERS-COV). Optionally a broadly neutralising immune response is sufficient to inhibit, neutralise or prevent infection, and/or progress of infection, of most or all different β-coronaviruses. Optionally a broadly neutralising immune response is sufficient to inhibit, neutralise or prevent infection, and/or progress of infection, of most or all different viruses of the coronavirus family.

The immune response may be humoral and/or a cellular immune response. A cellular immune response is a response of a cell of the immune system, such as a B-cell, T-cell, macrophage or polymorphonucleocyte, to a stimulus such as an antigen or vaccine. An immune response can include any cell of the body involved in a host defence response, including for example, an epithelial cell that secretes an interferon or a cytokine. An immune response includes, but is not limited to, an innate immune response or inflammation.

Optionally a polypeptide of the invention induces a protective immune response. A protective immune response refers to an immune response that protects a subject from infection or disease (i.e. prevents infection or prevents the development of disease associated with infection). Methods of measuring immune responses are well known in the art and include, for example, measuring proliferation and/or activity of lymphocytes (such as B or T cells), secretion of cytokines or chemokines, inflammation, or antibody production.

Optionally a polypeptide of the invention is able to induce the production of antibodies and/or a T-cell response in a human or non-human animal to which the polypeptide has been administered (either as a polypeptide or, for example, expressed from an administered nucleic acid expression vector).

Optionally a polypeptide of the invention is a glycosylated polypeptide.

Nucleic Acid Molecules

According to the invention there is also provided an isolated nucleic acid molecule encoding a polypeptide of the invention, or the complement thereof.

There is also provided according to the invention an isolated nucleic acid molecule comprising a nucleotide sequence that is at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical over its entire length to a nucleic acid molecule of the invention encoding a polypeptide of the invention, or the complement thereof.

Optionally an isolated nucleic acid molecule of the invention comprises a nucleotide sequence of SEQ ID NO:18, 16, or 14, or a nucleotide sequence that is at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical with a nucleotide sequence of SEQ ID NO: 18, 16, or 14 over its entire length, or the complement thereof.

According to the invention there is also provided an isolated nucleic acid molecule which comprises a nucleotide sequence encoding a polypeptide of the invention comprising an amino acid sequence of SEQ ID NO:33, 34, 35, or 36.

Optionally the nucleotide sequence encoding a polypeptide comprising an amino acid sequence of SEQ ID NO:33, 34, 35, or 36 comprises a nucleotide sequence of SEQ ID NO:37, 38, 39, or 40, respectively.

According to the invention there is also provided an isolated nucleic acid molecule which comprises a nucleotide sequence encoding an isolated polypeptide of the invention comprising an amino acid sequence of SEQ ID NO: 34 (M8), or an amino acid sequence which has at least 99% amino acid identity over its entire length with the amino acid sequence of SEQ ID NO:34.

According to the invention there is also provided an isolated nucleic acid molecule which comprises a nucleotide sequence encoding an isolated polypeptide which comprises a coronavirus S protein RBD domain with at least one of the following amino acid residues at positions corresponding to the amino acid residue positions of SEQ ID NO:11: 13Q, 25Q, 54T, 203N.

According to the invention there is also provided an isolated nucleic acid molecule which comprises a nucleotide sequence encoding an isolated polypeptide comprising an amino acid sequence of SEQ ID NO: 35 (M9), or an amino acid sequence which has at least 70% amino acid identity over its entire length with the amino acid sequence of SEQ ID NO:35.

According to the invention there is also provided an isolated nucleic acid molecule which comprises a nucleotide sequence encoding an isolated polypeptide comprising an amino acid sequence of SEQ ID NO: 36 (M10), or an amino acid sequence which has at least 69% amino acid identity over its entire length with the amino acid sequence of SEQ ID NO:36.

We have found that immunisation of mice with nucleic acid (in particular, DNA) encoding SARS2 truncated S protein induces production of antibodies that are able to bind SARS2 spike protein (see Example 17, FIG. 10).

According to the invention there is provided an isolated nucleic acid molecule encoding a SARS2 truncated S protein of amino acid sequence SEQ ID NO:9 (COV_T2_3).

Optionally the isolated nucleic acid molecule encoding a SARS2 truncated S protein of amino acid sequence SEQ ID NO:9 (CoV_T2_3) comprises a nucleotide sequence of SEQ ID NO:10.

We have also found that immunisation of mice with nucleic acid (in particular, DNA) encoding SARS2 S protein RBD induces production of antibodies that are able to neutralise SARS2 pseudotype virus (see Example 18, FIG. 11).

We have also found that M7 and wild-type SARS2 RBD DNA (believed to result in expression of glycosylated RBD protein) is superior to recombinant SARS2 RBD protein (non-glycosylated, or sparsely glycosylated) in inducing neutralising responses to SARS2.

According to the invention there is provided an isolated nucleic acid molecule encoding a SARS2 S protein RBD of amino acid sequence SEQ ID NO: 11 (CoV_T2_6).

Optionally the isolated nucleic acid molecule encoding a SARS2 S protein RBD of amino acid sequence SEQ ID NO:11 (CoV_T2_6) comprises a nucleotide sequence of SEQ ID NO:12.

We have also found that nucleic acid (in particular, DNA) encoding the designed M7 SARS2 S protein RBD has especially advantageous effects. In particular, we have found that:

immunisation of mice with a DNA vaccine comprising nucleic acid encoding M7 SARS2 RBD (SEQ ID NO:33) induced an immune response with stronger binding to SARS2 RBD than wild-type SARS2 RBD (see Example 20, and FIG. 14);

immunisation of mice with a DNA vaccine encoding M7 SARS2 RBD (SEQ ID NO:33) elicits a neutralising immune response more rapidly than a DNA vaccine encoding wild-type SARS2 RBD (see Example 21, and FIG. 15);

immunisation of mice with a DNA vaccine encoding M7 SARS2 RBD (SEQ ID NO:33) induces a more neutralising response than a DNA vaccine encoding wild-type SARS2 RBD in sera collected from bleeds at weeks 1 and 2 (see Example 22, and FIGS. 16, 17);

supernatant comprising M7 SARS2 RBD competes effectively with three ACE2 binding viruses for ACE2 cell entry (see Example 23, and FIG. 18); and T cell responses were induced by a DNA vaccine encoding M7 SARS2 RBD (SEQ ID NO: 33) that were reactive against peptides of an RBD peptide pool, but not against full length RBD or medium (see Example 24, and FIG. 19).

There is also provided according to the invention an isolated nucleic acid molecule comprising a nucleotide sequence of SEQ ID NO:37.

Sequence Identity

The similarity between amino acid or nucleic acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a given gene or protein will possess a relatively high degree of sequence identity when aligned using standard methods. Methods of alignment of sequences for comparison are well known in the art. Various programs and alignment algorithms are described in: Smith and Waterman, Adv. Appl. Math. 2:482, 1981; Needleman and Wunsch, J. Mol. Biol. 48:443, 1970; Pearson and Lipman, Proc. Natl. Acad. Sci. U.S.A. 85:2444, 1988; Higgins and Sharp, Gene 73:237-244, 1988; Higgins and Sharp, CABIOS 5:151-153, 1989; Corpet et al., Nucleic Acids' Research 16:10881-10890, 1988; and Pearson and Lipman, Proc. Natl. Acad. Sci. U.S.A. 85:2444, 1988. Altschul et al., Nature Genet. 6:119-129, 1994. The NCBI Basic Local Alignment Search Tool (BLAST™) (Altschul et al., J. Mol. Biol. 215:403-410, 1990) is available from several sources, including the National Center for Biotechnology Information (NCBI, Bethesda, MD) and on the Internet, for use in connection with the sequence analysis programs blastp, blastn, blastx, tblastn and tblastx.

Sequence identity between nucleic acid sequences, or between amino acid sequences, can be determined by comparing an alignment of the sequences. When an equivalent position in the compared sequences is occupied by the same nucleotide, or amino acid, then the molecules are identical at that position. Scoring an alignment as a percentage of identity is a function of the number of identical nucleotides or amino acids at positions shared by the compared sequences. When comparing sequences, optimal alignments may require gaps to be introduced into one or more of the sequences to take into consideration possible insertions and deletions in the sequences. Sequence comparison methods may employ gap penalties so that, for the same number of identical molecules in sequences being compared, a sequence alignment with as few gaps as possible, reflecting higher relatedness between the two compared sequences, will achieve a higher score than one with many gaps. Calculation of maximum percent identity involves the production of an optimal alignment, taking into consideration gap penalties.

Suitable computer programs for carrying out sequence comparisons are widely available in the commercial and public sector. Examples include MatGat (Campanella et al., 2003, BMC Bioinformatics 4:29; program available from bitincka.com/ledion/matgat), Gap (Needleman & Wunsch, 1970, J. Mol. Biol. 48:443-453), FASTA (Altschul et al., 1990, J. Mol. Biol. 215:403-410; program available from www.ebi.ac.uk/fasta), Clustal W 2.0 and X 2.0 (Larkin et al., 2007, Bioinformatics 23:2947-2948; program available from www.ebi.ac.uk/tools/clustalw2) and EMBOSS Pairwise Alignment Algorithms (Needleman & Wunsch, 1970, supra; Kruskal, 1983, In: Time warps, string edits and macromolecules: the theory and practice of sequence comparison, Sankoff & Kruskal (eds), pp 1-44, Addison Wesley; programs available from www.ebi.ac.uk/tools/emboss/align). All programs may be run using default parameters.

For example, sequence comparisons may be undertaken using the "needle" method of the EMBOSS Pairwise Alignment Algorithms, which determines an optimum alignment (including gaps) of two sequences when considered over their entire length and provides a percentage identity score. Default parameters for amino acid sequence comparisons ("Protein Molecule" option) may be Gap Extend penalty: 0.5, Gap Open penalty: 10.0, Matrix: Blosum 62.

The sequence comparison may be performed over the full length of the reference sequence.

Corresponding Positions

Sequences described herein include reference to an amino acid sequence comprising an amino acid residue "at a position corresponding to an amino acid residue position" of another sequence. Such corresponding positions may be identified, for example, from an alignment of the sequences using a sequence alignment method described herein, or another sequence alignment method known to the person of ordinary skill in the art.

Vectors

There is also provided according to the invention a vector comprising a nucleic acid molecule of the invention.

Optionally a vector of the invention comprises a nucleic acid molecule encoding a polypeptide of the invention which comprises an amino acid sequence of SEQ ID NO: 17, or an amino acid sequence which has at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% amino acid identity over its entire length with the amino acid sequence of SEQ ID NO: 17.

Optionally a vector of the invention comprises a nucleic acid molecule encoding a polypeptide of the invention which comprises an amino acid sequence of SEQ ID NO: 15, or an amino acid sequence which has at least 81%, 82%, 83%, 84%, 85%, 86%, 87%, 88%, 89%, 90%, 91%, 92%, 93%, 94%, 95%, 96%, 97%, 98%, or 99% amino acid identity over its entire length with the amino acid sequence of SEQ ID NO:15.

Optionally a vector of the invention comprises a nucleic acid molecule encoding a polypeptide of the invention which comprises an amino acid sequence of SEQ ID NO: 13, or an amino acid sequence which has at least 83%, 84%, 85%, 86%, 87%, 88%, 89%, 90%, 91%, 92%, 93%, 94%, 95%, 96%, 97%, 98%, or 99% amino acid identity over its entire length with the amino acid sequence of SEQ ID NO:13.

Optionally a vector of the invention comprises a nucleic acid molecule encoding a polypeptide of the invention which comprises an amino acid sequence of SEQ ID NO: 27 (COV_S_T2_13), or an amino acid sequence which has at least 88%, 89%, 90%, 91%, 92%, 93%, 94%, 95%, 96%, 97%, 98%, or 99% amino acid identity over its entire length with the amino acid sequence of SEQ ID NO:27.

Optionally a vector of the invention comprises a nucleic acid molecule encoding a polypeptide of the invention which comprises an amino acid sequence of SEQ ID NO: 28 (COV_S_T2_14), or an amino acid sequence which has at least 86%, 87%, 88%, 89%, 90%, 91%, 92%, 93%, 94%, 95%, 96%, 97%, 98%, or 99% amino acid identity over its entire length with the amino acid sequence of SEQ ID NO:28.

Optionally a vector of the invention comprises a nucleic acid molecule encoding a polypeptide of the invention which comprises an amino acid sequence of SEQ ID NO: 29 (COV_S_T2_15), or an amino acid sequence which has at least 86%, 87%, 88%, 89%, 90%, 91%, 92%, 93%, 94%, 95%, 96%, 97%, 98%, or 99% amino acid identity over its entire length with the amino acid sequence of SEQ ID NO:29.

Optionally a vector of the invention comprises a nucleic acid molecule encoding a polypeptide of the invention which comprises an amino acid sequence of SEQ ID NO: 30 (COV_S_T2_16), or an amino acid sequence which has at least 93%, 94%, 95%, 96%, 97%, 98%, or 99% amino acid identity over its entire length with the amino acid sequence of SEQ ID NO:30.

Optionally a vector of the invention comprises a nucleic acid molecule encoding a polypeptide of the invention which comprises an amino acid sequence of SEQ ID NO: 31 (COV_S_T2_17), or an amino acid sequence which has at least 86%, 87%, 88%, 89%, 90%, 91%, 92%, 93%, 94%, 95%, 96%, 97%, 98%, or 99% amino acid identity over its entire length with the amino acid sequence of SEQ ID NO:31.

Optionally a vector of the invention comprises a nucleic acid molecule encoding a polypeptide of the invention which comprises an amino acid sequence of SEQ ID NO: 32 (COV_S_T2_18), or an amino acid sequence which has at least 86%, 87%, 88%, 89%, 90%, 91%, 92%, 93%, 94%, 95%, 96%, 97%, 98%, or 99% amino acid identity over its entire length with the amino acid sequence of SEQ ID NO:32.

Optionally a vector of the invention comprises a nucleic acid molecule encoding a polypeptide of the invention which comprises an amino acid sequence of SEQ ID NO: 33.

Optionally a vector of the invention comprises a nucleic acid molecule encoding a polypeptide of the invention which comprises an amino acid sequence of SEQ ID NO: 34, or an amino acid sequence which has at least 99% amino acid identity over its entire length with the amino acid sequence of SEQ ID NO:34.

Optionally a vector of the invention comprises a nucleic acid molecule encoding a polypeptide of the invention which comprises an amino acid sequence of SEQ ID NO:22, or an amino acid sequence which has at least 95%, 96%, 97%, 98%, or 99% amino acid identity over its entire length with the amino acid sequence of SEQ ID NO:22.

Optionally a vector of the invention comprises a nucleic acid molecule encoding a polypeptide of the invention which comprises an amino acid sequence of SEQ ID NO:23, or an amino acid sequence which has at least 98%, or 99% amino acid identity over its entire length with the amino acid sequence of SEQ ID NO:23.

Optionally a vector of the invention comprises a nucleic acid molecule encoding a polypeptide of the invention which comprises an amino acid sequence of SEQ ID NO:42 (COV_E_T2_3), or an amino acid sequence which has at least 99% amino acid identity over its entire length with the amino acid sequence of SEQ ID NO:42.

Optionally a vector of the invention comprises a nucleic acid molecule encoding a polypeptide of the invention which comprises an amino acid sequence of SEQ ID NO:43 (COV_E_T2_4), or an amino acid sequence which has at least 95%, 96%, 97%, 98%, or 99% amino acid identity over its entire length with the amino acid sequence of SEQ ID NO:43.

Optionally a vector of the invention comprises a nucleic acid molecule encoding a polypeptide of the invention which comprises an amino acid sequence of SEQ ID NO:44 (COV_E_T2_5), or an amino acid sequence which has at least 98%, or 99% amino acid identity over its entire length with the amino acid sequence of SEQ ID NO:44.

Optionally a vector of the invention comprises a nucleic acid molecule encoding a polypeptide of the invention which comprises an amino acid sequence of SEQ ID NO:24, or an amino acid sequence which has at least 91%, 92%, 93%, 94%, 95%, 96%, 97%, 98%, or 99% amino acid identity over its entire length with the amino acid sequence of SEQ ID NO:24.

Optionally a vector of the invention comprises a nucleic acid molecule encoding a polypeptide of the invention which comprises an amino acid sequence of SEQ ID NO:25, or an amino acid sequence which has at least 95%, 96%, 97%, 98%, or 99% amino acid identity over its entire length with the amino acid sequence of SEQ ID NO:25.

Optionally a vector of the invention comprises a nucleic acid molecule encoding a polypeptide of the invention which comprises an amino acid sequence of SEQ ID NO:46 (COV_N_T2_1), or an amino acid sequence which has at least 93%, 94%, 95%, 96%, 97%, 98%, or 99% amino acid identity over its entire length with the amino acid sequence of SEQ ID NO:46.

Optionally a vector of the invention comprises a nucleic acid molecule encoding a polypeptide of the invention which comprises an amino acid sequence of SEQ ID NO:47 (COV_N_T2_2), or an amino acid sequence which has at least 92%, 93%, 94%, 95%, 96%, 97%, 98%, or 99% amino acid identity over its entire length with the amino acid sequence of SEQ ID NO:47.

Optionally a vector of the invention further comprises a promoter operably linked to the nucleic acid.

Optionally the promoter is for expression of a polypeptide encoded by the nucleic acid in mammalian cells.

Optionally the promoter is for expression of a polypeptide encoded by the nucleic acid in yeast or insect cells.

Optionally a vector of the invention comprises more than one nucleic acid molecule encoding a different polypeptide of the invention. Advantageously, a vector of the invention comprises a nucleic acid molecule of the invention encoding a designed coronavirus S protein (full length, truncated, or RBD) of the invention and/or a nucleic acid molecule of the invention encoding a designed coronavirus E protein of the invention and/or a nucleic acid molecule of the invention encoding a designed coronavirus M protein of the invention.

Optionally a vector of the invention comprises more than one nucleic acid molecule encoding a different polypeptide of the invention. Advantageously, a vector of the invention comprises a nucleic acid molecule of the invention encoding a designed coronavirus S protein (full length, truncated, or RBD) of the invention and/or a nucleic acid molecule of the invention encoding a designed coronavirus E protein of the invention and/or a nucleic acid molecule of the invention encoding a designed coronavirus M protein of the invention and/or a nucleic acid molecule of the invention encoding a designed coronavirus N protein of the invention Optionally a vector of the invention comprises a nucleic acid molecule of the invention encoding a designed coronavirus S protein (full length, truncated, or RBD) of the invention and a nucleic acid molecule of the invention encoding a designed coronavirus E protein of the invention.

Optionally a vector of the invention comprises a nucleic acid molecule of the invention encoding a designed coronavirus S protein (full length, truncated, or RBD) of the invention and a nucleic acid molecule of the invention encoding a designed coronavirus M protein of the invention.

Optionally a vector of the invention comprises a nucleic acid molecule of the invention encoding a designed coronavirus S protein (full length, truncated, or RBD) of the invention and a nucleic acid molecule of the invention encoding a designed coronavirus N protein of the invention.

Optionally a vector of the invention comprises a nucleic acid molecule of the invention encoding a designed coronavirus E protein of the invention and a nucleic acid molecule of the invention encoding a designed coronavirus M protein of the invention.

Optionally a vector of the invention comprises a nucleic acid molecule of the invention encoding a designed coronavirus E protein of the invention and a nucleic acid molecule of the invention encoding a designed coronavirus N protein of the invention.

Optionally a vector of the invention comprises a nucleic acid molecule of the invention encoding a designed coronavirus S protein (full length, truncated, or RBD) of the invention and a nucleic acid molecule of the invention encoding a designed coronavirus E protein of the invention and a nucleic acid molecule of the invention encoding a designed coronavirus M protein of the invention.

Optionally a vector of the invention comprises a nucleic acid molecule of the invention encoding a designed coronavirus S protein (full length, truncated, or RBD) of the invention and a nucleic acid molecule of the invention encoding a designed coronavirus E protein of the invention and a nucleic acid molecule of the invention encoding a designed coronavirus N protein of the invention.

Optionally a vector of the invention comprises a nucleic acid molecule of the invention encoding a designed coronavirus E protein of the invention and a nucleic acid molecule of the invention encoding a designed coronavirus M protein of the invention and a nucleic acid molecule of the invention encoding a designed coronavirus N protein of the invention.

Optionally a vector of the invention comprises a nucleic acid molecule of the invention encoding a designed coronavirus S protein (full length, truncated, or RBD) of the invention and a nucleic acid molecule of the invention encoding a designed coronavirus E protein of the invention and a nucleic acid molecule of the invention encoding a designed coronavirus M protein of the invention and a nucleic acid molecule of the invention encoding a designed coronavirus N protein of the invention.

Optionally a vector of the invention comprises:
a nucleic acid molecule encoding a polypeptide of the invention which comprises an amino acid sequence of SEQ ID NO: 17, or an amino acid sequence which has at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% amino acid identity over its entire length with the amino acid sequence of SEQ ID NO:17; and
a nucleic acid molecule encoding a polypeptide of the invention which comprises an amino acid sequence of SEQ ID NO:22, or an amino acid sequence which has at least 95%, 96%, 97%, 98%, or 99% amino acid identity over its entire length with the amino acid sequence of SEQ ID NO:22, or a nucleic acid molecule encoding a polypeptide of the invention which comprises an amino acid sequence of SEQ ID NO:23, or an amino acid sequence which has at least 98%, or 99% amino acid identity over its entire length with the amino acid sequence of SEQ ID NO:23.
Optionally a vector of the invention comprises:
a nucleic acid molecule encoding a polypeptide of the invention which comprises an amino acid sequence of SEQ ID NO: 17, or an amino acid sequence which has at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% amino acid identity over its entire length with the amino acid sequence of SEQ ID NO:17; and
a nucleic acid molecule encoding a polypeptide of the invention which comprises an amino acid sequence of SEQ ID NO:24, or an amino acid sequence which has at least 91%, 92%, 93%, 94%, 95%, 96%, 97%, 98%, or 99% amino acid identity over its entire length with the amino acid sequence of SEQ ID NO:24, or a nucleic acid molecule encoding a polypeptide of the invention which comprises an amino acid sequence of SEQ ID NO:25, or an amino acid sequence which has at least 95%, 96%, 97%, 98%, or 99% amino acid identity over its entire length with the amino acid sequence of SEQ ID NO:25.
Optionally a vector of the invention comprises:
a nucleic acid molecule encoding a polypeptide of the invention which comprises an amino acid sequence of SEQ ID NO:22, or an amino acid sequence which has at least 95%, 96%, 97%, 98%, or 99% amino acid identity over its entire length with the amino acid sequence of SEQ ID NO:22, or a nucleic acid molecule encoding a polypeptide of the invention which comprises an amino acid sequence of SEQ ID NO:23, or an amino acid sequence which has at least 98%, or 99% amino acid identity over its entire length with the amino acid sequence of SEQ ID NO:23; and
a nucleic acid molecule encoding a polypeptide of the invention which comprises an amino acid sequence of SEQ ID NO:24, or an amino acid sequence which has at least 91%, 92%, 93%, 94%, 95%, 96%, 97%, 98%, or 99% amino acid identity over its entire length with the amino acid sequence of SEQ ID NO:24, or a nucleic acid molecule encoding a polypeptide of the invention which comprises an amino acid sequence of SEQ ID NO:25, or an amino acid sequence which has at least 95%, 96%, 97%, 98%, or 99% amino acid identity over its entire length with the amino acid sequence of SEQ ID NO:25.
Optionally a vector of the invention comprises:
a nucleic acid molecule encoding a polypeptide of the invention which comprises an amino acid sequence of SEQ ID NO: 17, or an amino acid sequence which has at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% amino acid identity over its entire length with the amino acid sequence of SEQ ID NO:17; and
a nucleic acid molecule encoding a polypeptide of the invention which comprises an amino acid sequence of SEQ ID NO:22, or an amino acid sequence which has at least 95%, 96%, 97%, 98%, or 99% amino acid identity over its entire length with the amino acid sequence of SEQ ID NO:22, or a nucleic acid molecule encoding a polypeptide of the invention which comprises an amino acid sequence of SEQ ID NO:23, or an amino acid sequence which has at least 98%, or 99% amino acid identity over its entire length with the amino acid sequence of SEQ ID NO:23; and
a nucleic acid molecule encoding a polypeptide of the invention which comprises an amino acid sequence of SEQ ID NO:24, or an amino acid sequence which has at least 91%, 92%, 93%, 94%, 95%, 96%, 97%, 98%, or 99% amino acid identity over its entire length with the amino acid sequence of SEQ ID NO:24, or a nucleic acid molecule encoding a polypeptide of the invention which comprises an amino acid sequence of SEQ ID NO:25, or an amino acid sequence which has at least 95%, 96%, 97%, 98%, or 99% amino acid identity over its entire length with the amino acid sequence of SEQ ID NO:25.

Optionally a vector of the invention which further comprises, for each nucleic acid molecule of the vector encoding a polypeptide, a separate promoter operably linked to that nucleic acid molecule.

Optionally the, or each promoter is for expression of a polypeptide encoded by the nucleic acid molecule in mammalian cells.

Optionally the, or each promoter is for expression of a polypeptide encoded by the nucleic acid molecule in yeast or insect cells.

Optionally the vector is a vaccine vector.

Optionally the vector is a viral vaccine vector, a bacterial vaccine vector, an RNA vaccine vector, or a DNA vaccine vector.

A nucleic acid molecule of the invention may comprise a DNA or an RNA molecule. For embodiments in which the nucleic acid molecule comprises an RNA molecule, it will be appreciated that the molecule may comprise an RNA sequence that is at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical with, or identical with, any of SEQ ID NOs: 18, 16, or 14, in which each 'T' nucleotide is replaced by 'U', or the complement thereof.

For example, it will be appreciated that where an RNA vaccine vector comprising a nucleic acid of the invention is provided, the nucleic acid sequence of the nucleic acid of the invention will be an RNA sequence, so may comprise for example an RNA nucleic acid sequence that is at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical with, or identical with, any of SEQ ID NOs: 18, 16, or 14 in which each 'T' nucleotide is replaced by 'U', or the complement thereof.

Viral vaccine vectors use live viruses to deliver nucleic acid (for example, DNA or RNA) into human or non-human animal cells. The nucleic acid contained in the virus encodes one or more antigens that, once expressed in the infected human or non-human animal cells, elicit an immune response. Both humoral and cell-mediated immune responses can be induced by viral vaccine vectors. Viral vaccine vectors combine many of the positive qualities of nucleic acid vaccines with those of live attenuated vaccines. Like nucleic acid vaccines, viral vaccine vectors carry nucleic acid into a host cell for production of antigenic proteins that can be tailored to stimulate a range of immune responses, including antibody, T helper cell (CD4+ T cell), and cytotoxic T lymphocyte (CTL, CD8+ T cell) mediated immunity. Viral vaccine vectors, unlike nucleic acid vaccines, also have the potential to actively invade host cells and replicate, much like a live attenuated vaccine, further activating the immune system like an adjuvant. A viral vaccine vector therefore generally comprises a live attenuated virus that is genetically engineered to carry nucleic acid (for example, DNA or RNA) encoding protein antigens from an unrelated organism. Although viral vaccine vectors are generally able to produce stronger immune responses than nucleic acid vaccines, for some diseases viral vectors are used in combination with other vaccine technologies in a strategy called heterologous prime-boost. In this system, one vaccine is given as a priming step, followed by vaccination using an alternative vaccine as a booster. The heterologous prime-boost strategy aims to provide a stronger overall immune response. Viral vaccine vectors may be used as both prime and boost vaccines as part of this strategy. Viral vaccine vectors are reviewed by Ura et al., 2014 (Vaccines 2014, 2, 624-641) and Choi and Chang, 2013 (Clinical and Experimental Vaccine Research 2013; 2:97-105).

Optionally the viral vaccine vector is based on a viral delivery vector, such as a Poxvirus (for example, Modified Vaccinia Ankara (MVA), NYVAC, AVIPOX), herpesvirus (e.g. HSV, CMV, Adenovirus of any host species), Morbillivirus (e.g. measles), Alphavirus (e.g. SFV, Sendai), Flavivirus (e.g. Yellow Fever), or Rhabdovirus (e.g. VSV)-based viral delivery vector, a bacterial delivery vector (for example, Salmonella, E. coli), an RNA expression vector, or a DNA expression vector.

Optionally the nucleic acid expression vector is a nucleic acid expression vector, and a viral pseudotype vector.

Optionally the nucleic acid expression vector is a vaccine vector.

Optionally the nucleic acid expression vector comprises, from a 5' to 3' direction: a promoter; a splice donor site (SD); a splice acceptor site (SA); and a terminator signal, wherein the multiple cloning site is located between the splice acceptor site and the terminator signal.

Optionally the promoter comprises a CMV immediate early 1 enhancer/promoter (CMV-IE-E/P) and/or the terminator signal comprises a terminator signal of a bovine growth hormone gene (Tbgh) that lacks a KpnI restriction endonuclease site.

Optionally the nucleic acid expression vector further comprises an origin of replication, and nucleic acid encoding resistance to an antibiotic. Optionally the origin of replication comprises a pUC-plasmid origin of replication and/or the nucleic acid encodes resistance to kanamycin.

Optionally the vector is a pEVAC-based expression vector.

Optionally the nucleic acid expression vector comprises a nucleic acid sequence of SEQ ID NO: 20 (pEVAC). The pEVAC vector has proven to be a highly versatile expression vector for generating viral pseudotypes as well as direct DNA vaccination of animals and humans. The pEVAC expression vector is described in more detail in Example 8 below. FIG. 3 shows a plasmid map for pEVAC.

There is also provided according to the invention an isolated cell comprising or transfected with a vector of the invention.

There is also provided according to the invention a fusion protein comprising a polypeptide of the invention.

Pharmaceutical Compositions

According to the invention there is also provided a pharmaceutical composition comprising a polypeptide of the invention, and a pharmaceutically acceptable carrier, excipient, or diluent.

Optionally a pharmaceutical composition of the invention comprises more than one different polypeptide of the invention.

Advantageously, a pharmaceutical composition of the invention comprises a designed coronavirus S protein (full length, truncated, or RBD) of the invention and/or a designed coronavirus E protein of the invention and/or a designed coronavirus M protein of the invention.

Advantageously, a pharmaceutical composition of the invention comprises a designed coronavirus S protein (full length, truncated, or RBD) of the invention and/or a designed coronavirus E protein of the invention and/or a designed coronavirus M protein of the invention and/or a designed coronavirus N protein of the invention.

Optionally a pharmaceutical composition of the invention comprises a designed coronavirus S protein (full length, truncated, or RBD) of the invention and a designed coronavirus E protein of the invention.

Optionally a pharmaceutical composition of the invention comprises a designed coronavirus S protein (full length, truncated, or RBD) of the invention and a designed coronavirus M protein of the invention.

Optionally a pharmaceutical composition of the invention comprises a designed coronavirus S protein (full length, truncated, or RBD) of the invention and a designed coronavirus N protein of the invention.

Optionally a pharmaceutical composition of the invention comprises a designed coronavirus E protein of the invention and a designed coronavirus M protein of the invention.

Optionally a pharmaceutical composition of the invention comprises a designed coronavirus E protein of the invention and a designed coronavirus N protein of the invention.

Optionally a pharmaceutical composition of the invention comprises a designed coronavirus S protein (full length, truncated, or RBD) of the invention and a designed coronavirus E protein of the invention and a designed coronavirus M protein of the invention.

Optionally a pharmaceutical composition of the invention comprises a designed coronavirus S protein (full length, truncated, or RBD) of the invention and a designed coronavirus E protein of the invention and a designed coronavirus N protein of the invention.

Optionally a pharmaceutical composition of the invention comprises a designed coronavirus E protein of the invention and a designed coronavirus M protein of the invention and a designed coronavirus N protein of the invention.

Optionally a pharmaceutical composition of the invention comprises:

a polypeptide of the invention which comprises an amino acid sequence of SEQ ID NO: 17, or an amino acid sequence which has at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% amino acid identity over its entire length with the amino acid sequence of SEQ ID NO:17; and a polypeptide of the invention which comprises an amino acid sequence of SEQ ID NO: 22, or an amino acid sequence which has at least 95%, 96%, 97%, 98%, or 99% amino acid identity over its entire length with the amino acid sequence of SEQ ID NO:22, or a polypeptide of the invention which comprises an amino acid sequence of SEQ ID NO:23, or an amino acid sequence which has at least 98%, or 99% amino acid identity over its entire length with the amino acid sequence of SEQ ID NO:23.

Optionally a pharmaceutical composition of the invention comprises:

a polypeptide of the invention which comprises an amino acid sequence of SEQ ID NO: 17, or an amino acid sequence which has at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% amino acid identity over its entire length with the amino acid sequence of SEQ ID NO:17; and a polypeptide of the invention which comprises an amino acid sequence of SEQ ID NO: 24, or an amino acid sequence which has at least 91%, 92%, 93%, 94%, 95%, 96%, 97%, 98%, or 99% amino acid identity over its entire length with the amino acid sequence of SEQ ID NO: 24, or a polypeptide of the invention which comprises an amino acid sequence of SEQ ID NO: 25, or an amino acid sequence which has at least 95%, 96%, 97%, 98%, or 99% amino acid identity over its entire length with the amino acid sequence of SEQ ID NO:25.

Optionally a pharmaceutical composition of the invention comprises:

a polypeptide of the invention which comprises an amino acid sequence of SEQ ID NO: 22, or an amino acid sequence which has at least 95%, 96%, 97%, 98%, or 99% amino acid identity over its entire length with the amino acid sequence of SEQ ID NO:22, or a polypeptide of the invention which comprises an amino acid sequence of SEQ ID NO:23, or an amino acid sequence which has at least 98%, or 99% amino acid identity over its entire length with the amino acid sequence of SEQ ID NO:23; and a polypeptide of the invention which comprises an amino acid sequence of SEQ ID NO: 24, or an amino acid sequence which has at least 91%, 92%, 93%, 94%, 95%, 96%, 97%, 98%, or 99% amino acid identity over its entire length with the amino acid sequence of SEQ ID NO: 24, or a polypeptide of the invention which comprises an amino acid sequence of SEQ ID NO: 25, or an amino acid sequence which has at least 95%, 96%, 97%, 98%, or 99% amino acid identity over its entire length with the amino acid sequence of SEQ ID NO:25.

Optionally a pharmaceutical composition of the invention comprises:

a polypeptide of the invention which comprises an amino acid sequence of SEQ ID NO: 17, or an amino acid sequence which has at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% amino acid identity over its entire length with the amino acid sequence of SEQ ID NO:17; and a polypeptide of the invention which comprises an amino acid sequence of SEQ ID NO: 22, or an amino acid sequence which has at least 95%, 96%, 97%, 98%, or 99% amino acid identity over its entire length with the amino acid sequence of SEQ ID NO:22, or a polypeptide of the invention which comprises an amino acid sequence of SEQ ID NO:23, or an amino acid sequence which has at least 98%, or 99% amino acid identity over its entire length with the amino acid sequence of SEQ ID NO:23; and a polypeptide of the invention which comprises an amino acid sequence of SEQ ID NO: 24, or an amino acid sequence which has at least 91%, 92%, 93%, 94%, 95%, 96%, 97%, 98%, or 99% amino acid identity over its entire length with the amino acid sequence of SEQ ID NO: 24, or a polypeptide of the invention which comprises an amino acid sequence of SEQ ID NO: 25, or an amino acid sequence which has at least 95%, 96%, 97%, 98%, or 99% amino acid identity over its entire length with the amino acid sequence of SEQ ID NO:25.

According to the invention there is also provided a pharmaceutical composition comprising a nucleic acid of the invention, and a pharmaceutically acceptable carrier, excipient, or diluent.

Optionally a pharmaceutical composition of the invention comprises more than one nucleic acid molecule of the invention encoding a different polypeptide of the invention.

Advantageously, a pharmaceutical composition of the invention comprises a nucleic acid molecule of the invention encoding a designed coronavirus S protein (full length, truncated, or RBD) of the invention and/or a nucleic acid molecule of the invention encoding a designed coronavirus E protein of the invention and/or a nucleic acid molecule of the invention encoding a designed coronavirus M protein of the invention.

Advantageously, a pharmaceutical composition of the invention comprises a nucleic acid molecule of the invention encoding a designed coronavirus S protein (full length, truncated, or RBD) of the invention and/or a nucleic acid molecule of the invention encoding a designed coronavirus E protein of the invention and/or a nucleic acid molecule of the invention encoding a designed coronavirus M protein of the invention and/or a nucleic acid molecule of the invention encoding a designed coronavirus N protein of the invention.

Optionally a pharmaceutical composition of the invention comprises a nucleic acid molecule of the invention encoding a designed coronavirus S protein (full length, truncated, or RBD) of the invention and a nucleic acid molecule of the invention encoding a designed coronavirus E protein of the invention.

Optionally a pharmaceutical composition of the invention comprises a nucleic acid molecule of the invention encoding a designed coronavirus S protein (full length, truncated, or RBD) of the invention and a nucleic acid molecule of the invention encoding a designed coronavirus M protein of the invention.

Optionally a pharmaceutical composition of the invention comprises a nucleic acid molecule of the invention encoding a designed coronavirus S protein (full length, truncated, or RBD) of the invention and a nucleic acid molecule of the invention encoding a designed coronavirus N protein of the invention.

Optionally a pharmaceutical composition of the invention comprises a nucleic acid molecule of the invention encoding a designed coronavirus E protein of the invention and a nucleic acid molecule of the invention encoding a designed coronavirus M protein of the invention.

Optionally a pharmaceutical composition of the invention comprises a nucleic acid molecule of the invention encoding a designed coronavirus E protein of the invention and a nucleic acid molecule of the invention encoding a designed coronavirus N protein of the invention.

Optionally a pharmaceutical composition of the invention comprises a nucleic acid molecule of the invention encoding a designed coronavirus S protein (full length, truncated, or RBD) of the invention and a nucleic acid molecule of the invention encoding a designed coronavirus E protein of the invention and a nucleic acid molecule of the invention encoding a designed coronavirus M protein of the invention.

Optionally a pharmaceutical composition of the invention comprises a nucleic acid molecule of the invention encoding a designed coronavirus S protein (full length, truncated, or RBD) of the invention and a nucleic acid molecule of the invention encoding a designed coronavirus E protein of the invention and a nucleic acid molecule of the invention encoding a designed coronavirus N protein of the invention.

Optionally a pharmaceutical composition of the invention comprises a nucleic acid molecule of the invention encoding a designed coronavirus E protein of the invention and a nucleic acid molecule of the invention encoding a designed coronavirus M protein of the invention and a nucleic acid molecule of the invention encoding a designed coronavirus N protein of the invention.

Optionally a pharmaceutical composition of the invention comprises:

a nucleic acid molecule encoding a polypeptide of the invention which comprises an amino acid sequence of SEQ ID NO: 17, or an amino acid sequence which has at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% amino acid identity over its entire length with the amino acid sequence of SEQ ID NO:17; and a nucleic acid molecule encoding a polypeptide of the invention which comprises an amino acid sequence of SEQ ID NO:22, or an amino acid sequence which has at least 95%, 96%, 97%, 98%, or 99% amino acid identity over its entire length with the amino acid sequence of SEQ ID NO:22, or a nucleic acid molecule encoding a polypeptide of the invention which comprises an amino acid sequence of SEQ ID NO:23, or an amino acid sequence which has at least 98%, or 99% amino acid identity over its entire length with the amino acid sequence of SEQ ID NO:23.

Optionally a pharmaceutical composition of the invention comprises:

a nucleic acid molecule encoding a polypeptide of the invention which comprises an amino acid sequence of SEQ ID NO: 17, or an amino acid sequence which has at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% amino acid identity over its entire length with the amino acid sequence of SEQ ID NO:17; and a nucleic acid molecule encoding a polypeptide of the invention which comprises an amino acid sequence of SEQ ID NO:24, or an amino acid sequence which has at least 91%, 92%, 93%, 94%, 95%, 96%, 97%, 98%, or 99% amino acid identity over its entire length with the amino acid sequence of SEQ ID NO:24, or a nucleic acid molecule encoding a polypeptide of the invention which comprises an amino acid sequence of SEQ ID NO:25, or an amino acid sequence which has at least 95%, 96%, 97%, 98%, or 99% amino acid identity over its entire length with the amino acid sequence of SEQ ID NO:25.

Optionally a pharmaceutical composition of the invention comprises:

a nucleic acid molecule encoding a polypeptide of the invention which comprises an amino acid sequence of SEQ ID NO:22, or an amino acid sequence which has at least 95%, 96%, 97%, 98%, or 99% amino acid identity over its entire length with the amino acid sequence of SEQ ID NO:22, or a nucleic acid molecule encoding a polypeptide of the invention which comprises an amino acid sequence of SEQ ID NO:23, or an amino acid sequence which has at least 98%, or 99% amino acid identity over its entire length with the amino acid sequence of SEQ ID NO:23; and a nucleic acid molecule encoding a polypeptide of the invention which comprises an amino acid sequence of SEQ ID NO:24, or an amino acid sequence which has at least 91%, 92%, 93%, 94%, 95%, 96%, 97%, 98%, or 99% amino acid identity over its entire length with the amino acid sequence of SEQ ID NO:24, or a nucleic acid molecule encoding a polypeptide of the invention which comprises an amino acid sequence of SEQ ID NO:25, or an amino acid sequence which has at least 95%, 96%, 97%, 98%, or 99% amino acid identity over its entire length with the amino acid sequence of SEQ ID NO:25.

Optionally a pharmaceutical composition of the invention comprises:

a nucleic acid molecule encoding a polypeptide of the invention which comprises an amino acid sequence of SEQ ID NO: 17, or an amino acid sequence which has at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% amino acid identity over its entire length with the amino acid sequence of SEQ ID NO:17; and a nucleic acid molecule encoding a polypeptide of the invention which comprises an amino acid sequence of SEQ ID NO:22, or an amino acid sequence which has at least 95%, 96%, 97%, 98%, or 99% amino acid identity over its entire length with the amino acid sequence of SEQ ID NO:22, or a nucleic acid molecule encoding a polypeptide of the invention which comprises an amino acid sequence of SEQ ID NO:23, or an amino acid sequence which has at least 98%, or 99% amino acid identity over its entire length with the amino acid sequence of SEQ ID NO:23; and a nucleic acid molecule encoding a polypeptide of the invention which comprises an amino acid sequence of SEQ ID NO:24, or an amino acid sequence which has at least 91%, 92%, 93%, 94%, 95%, 96%, 97%, 98%, or 99% amino acid identity over its entire length with the amino acid sequence of SEQ ID NO:24, or a nucleic acid molecule encoding a polypeptide of the invention which comprises an amino acid sequence of SEQ ID NO:25, or an amino acid sequence which has at least 95%, 96%, 97%, 98%, or 99% amino acid identity over its entire length with the amino acid sequence of SEQ ID NO:25.

According to the invention there is also provided a pharmaceutical composition comprising a vector of the invention, and a pharmaceutically acceptable carrier, excipient, or diluent.

Optionally a pharmaceutical composition of the invention further comprises an adjuvant for enhancing an immune response in a subject to the polypeptide, or to a polypeptide encoded by the nucleic acid, of the composition.

Optionally a pharmaceutical composition of the invention further comprises an adjuvant for enhancing an immune response in a subject to the polypeptides, or to polypeptides encoded by the nucleic acids, of the composition.

There is also provided according to the invention a pseudotyped virus comprising a polypeptide of the invention.

Methods of Treatment and Uses

There is also provided according to the invention a method of inducing an immune response to a coronavirus in a subject, which comprises administering to the subject an effective amount of a polypeptide of the invention, a nucleic acid of the invention, a vector of the invention, or a pharmaceutical composition of the invention.

There is also provided according to the invention a method of immunising a subject against a coronavirus, which comprises administering to the subject an effective amount of a polypeptide of the invention, a nucleic acid of the invention, a vector of the invention, or a pharmaceutical composition of the invention.

There is further provided according to the invention a polypeptide of the invention, a nucleic acid of the invention, a vector of the invention, or a pharmaceutical composition of the invention, for use as a medicament.

There is further provided according to the invention a polypeptide of the invention, a nucleic acid of the invention, a vector of the invention, or a pharmaceutical composition of the invention, for use in the prevention, treatment, or amelioration of a coronavirus infection.

There is also provided according to the invention use of a polypeptide of the invention, a nucleic acid of the invention, a vector of the invention, or a pharmaceutical composition of the invention, in the manufacture of a medicament for the prevention, treatment, or amelioration of a coronavirus infection.

Optionally the coronavirus is a β-coronavirus.

Optionally the β-coronavirus is a lineage B or C β-coronavirus.

Optionally the β-coronavirus is a lineage B β-coronavirus.

Optionally the lineage B β-coronavirus is SARS-COV or SARS-COV-2.

Optionally the lineage C β-coronavirus is MERS-COV.

Administration

Any suitable route of administration may be used. Methods of administration include, but are not limited to, intradermal, intramuscular, intraperitoneal, parenteral, intravenous, subcutaneous, vaginal, rectal, intranasal, inhalation or oral. Parenteral administration, such as subcutaneous, intravenous or intramuscular administration, is generally achieved by injection. Injectables can be prepared in conventional forms, either as liquid solutions or suspensions, solid forms suitable for solution or suspension in liquid prior to injection, or as emulsions. Injection solutions and suspensions can be prepared from sterile powders, granules, and tablets of the kind previously described. Administration can be systemic or local.

Compositions may be administered in any suitable manner, such as with pharmaceutically acceptable carriers. Pharmaceutically acceptable carriers are determined in part by the particular composition being administered, as well as by the particular method used to administer the composition. Preparations for parenteral administration include sterile aqueous or nonaqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Administration can be accomplished by single or multiple doses. The dose administered to a subject in the context of the present disclosure should be sufficient to induce a beneficial therapeutic response in a subject over time, or to inhibit or prevent infection. The dose required will vary from subject to subject depending on the species, age, weight and general condition of the subject, the severity of the infection being treated, the particular composition being used and its mode of administration. An appropriate dose can be determined by one of ordinary skill in the art using only routine experimentation.

Pharmaceutically Acceptable Carriers

Pharmaceutically acceptable carriers include, but are not limited to, saline, buffered saline, dextrose, water, glycerol, ethanol, and combinations thereof. The carrier and composition can be sterile, and the formulation suits the mode of administration. The composition can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, and magnesium carbonate. Any of the common pharmaceutical carriers, such as sterile saline solution or sesame oil, can be used. The medium can also contain conventional pharmaceutical adjunct materials such as, for example, pharmaceutically acceptable salts to adjust the osmotic pressure, buffers, preservatives and the like. Other media that can be used with the compositions and methods provided herein are normal saline and sesame oil.

In some embodiments, the compositions comprise a pharmaceutically acceptable carrier and/or an adjuvant. For example, the adjuvant can be alum, Freund's complete adjuvant, a biological adjuvant or immunostimulatory oligonucleotides (such as CpG oligonucleotides).

The pharmaceutically acceptable carriers (vehicles) useful in this disclosure are conventional. Remington's Pharmaceutical Sciences, by E. W. Martin, Mack Publishing Co., Easton, PA, 15th Edition (1975), describes compositions and formulations suitable for pharmaceutical delivery of one or more therapeutic compositions, such as one or more influenza vaccines, and additional pharmaceutical agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Optionally a polypeptide, nucleic acid, or composition of the invention is administered intramuscularly.

Optionally a polypeptide, nucleic acid, or composition of the invention is administered intramuscularly, intradermally, subcutaneously by needle or by gene gun, or electroporation.

Embodiments of the invention are now described, by way of example only, with reference to the accompanying drawings, in which.

Figure 5:
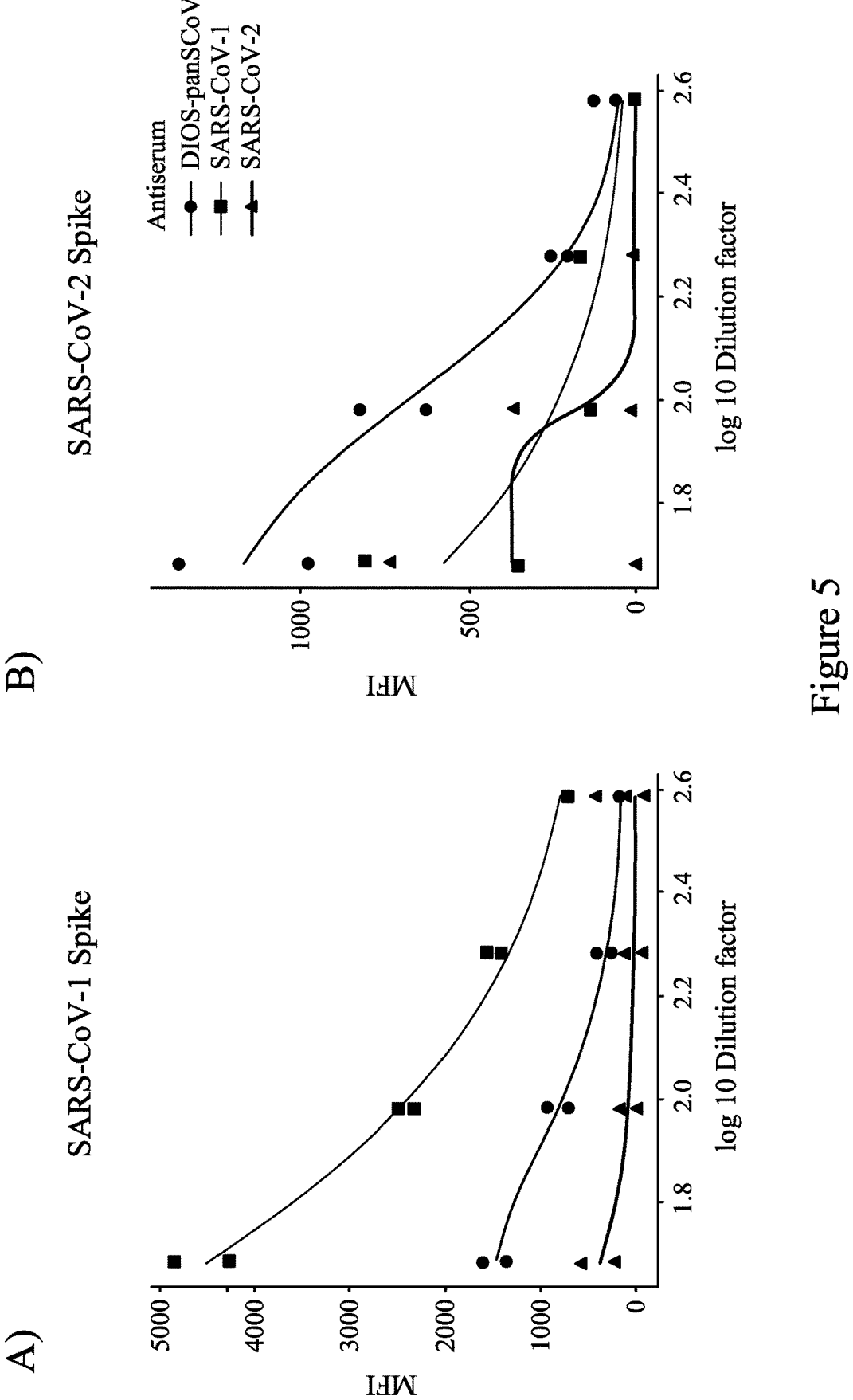
Figure 7:
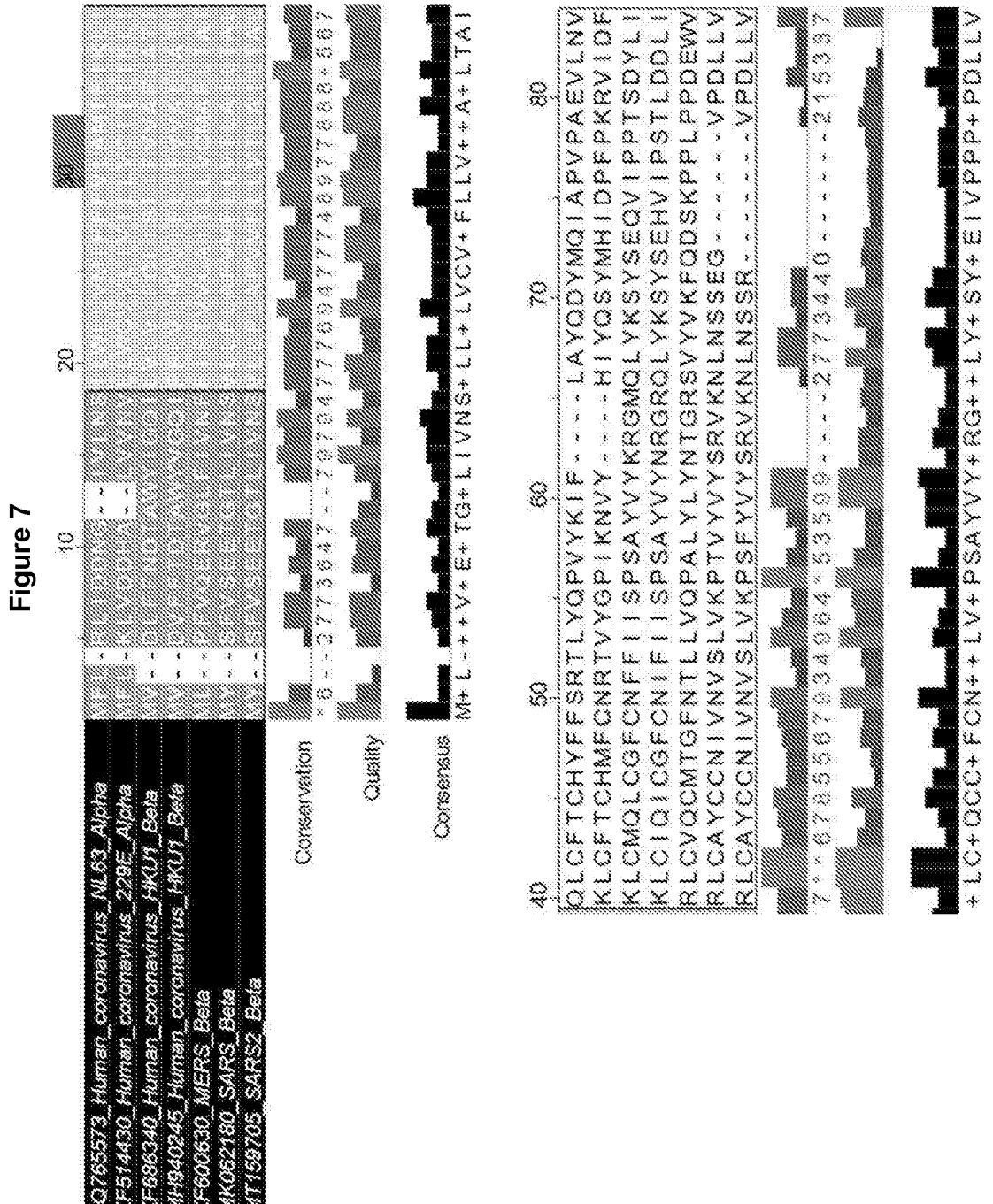
Figure 7:
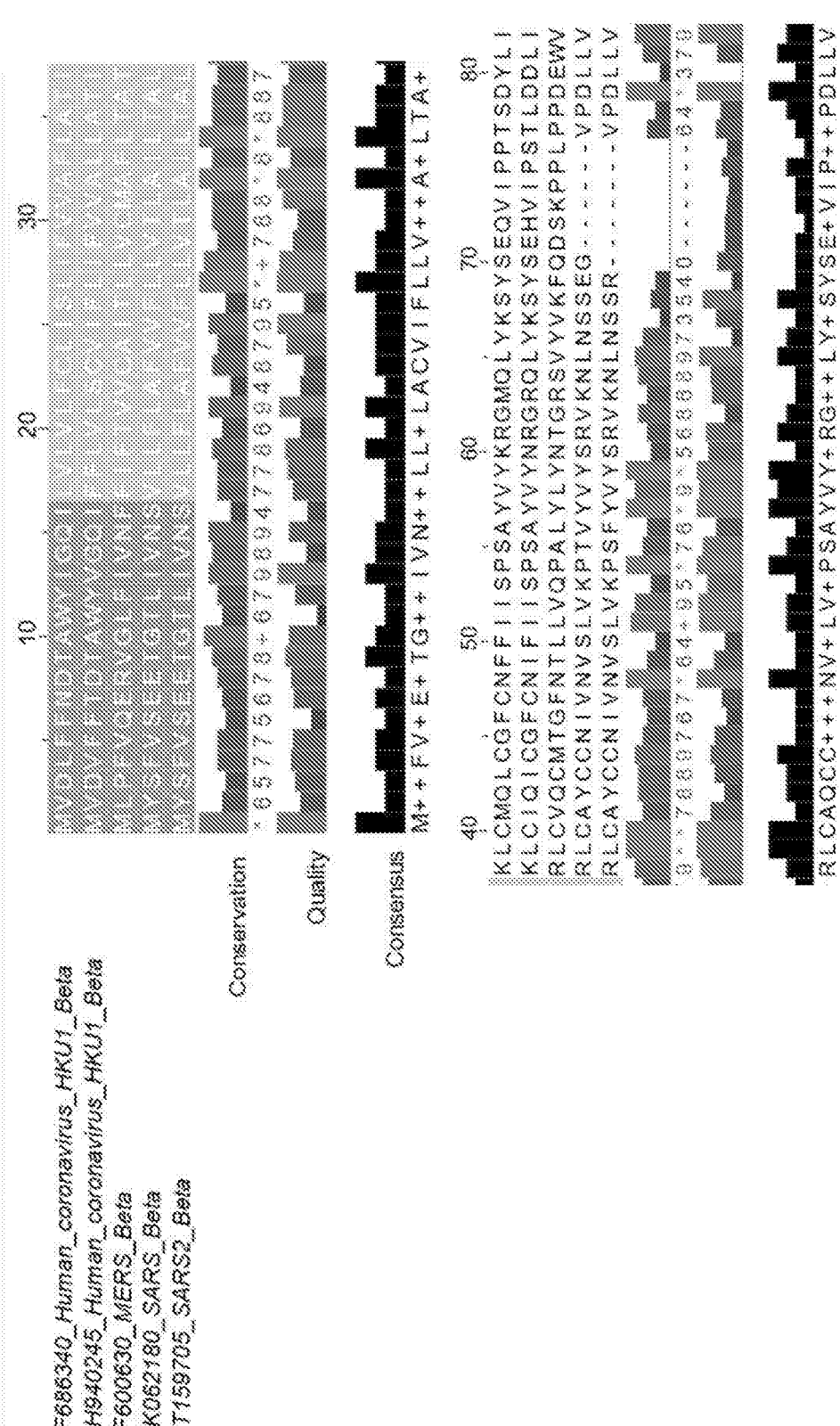
Figure 7:
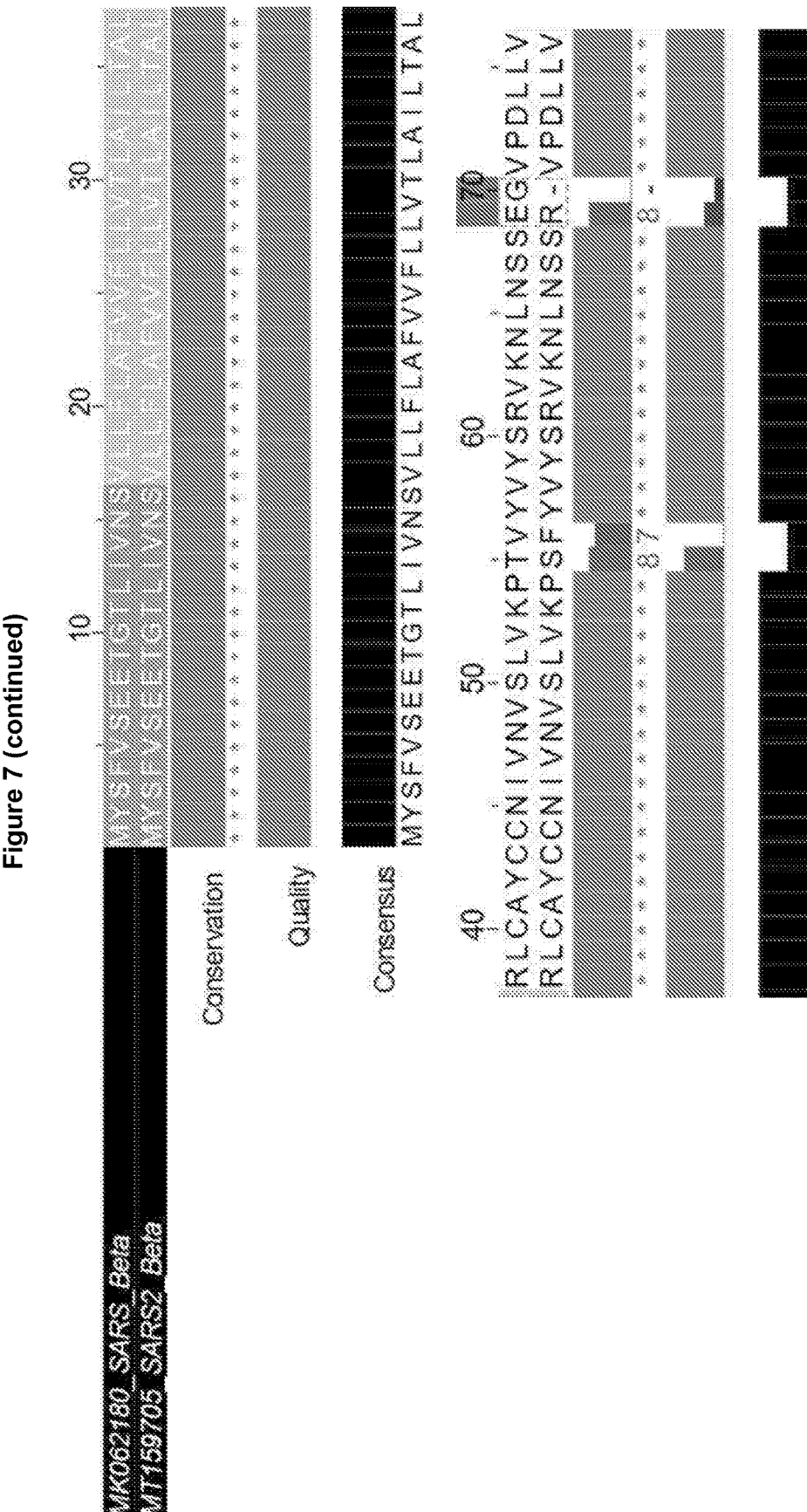
Figure 10:
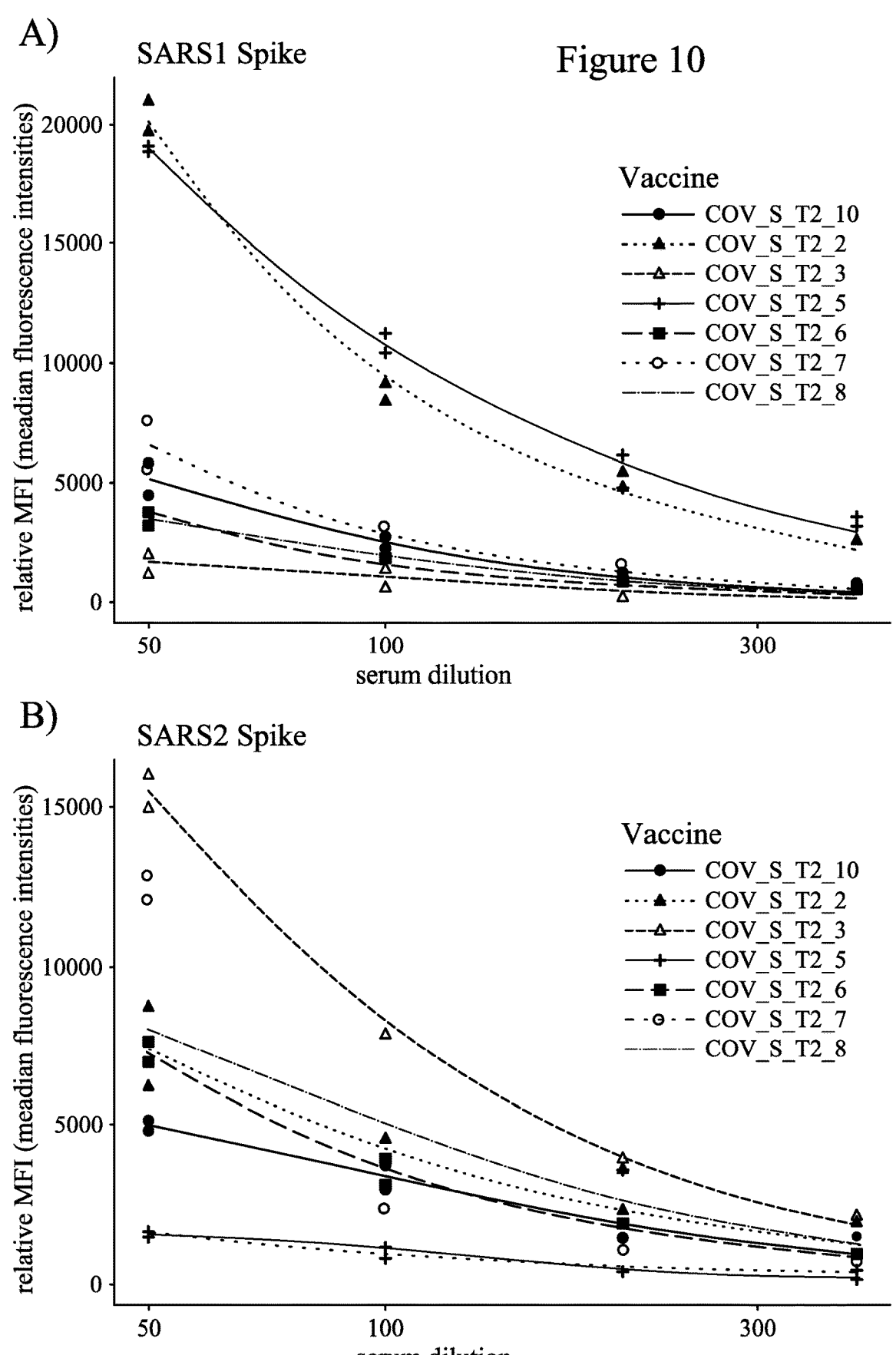
Figure 11:
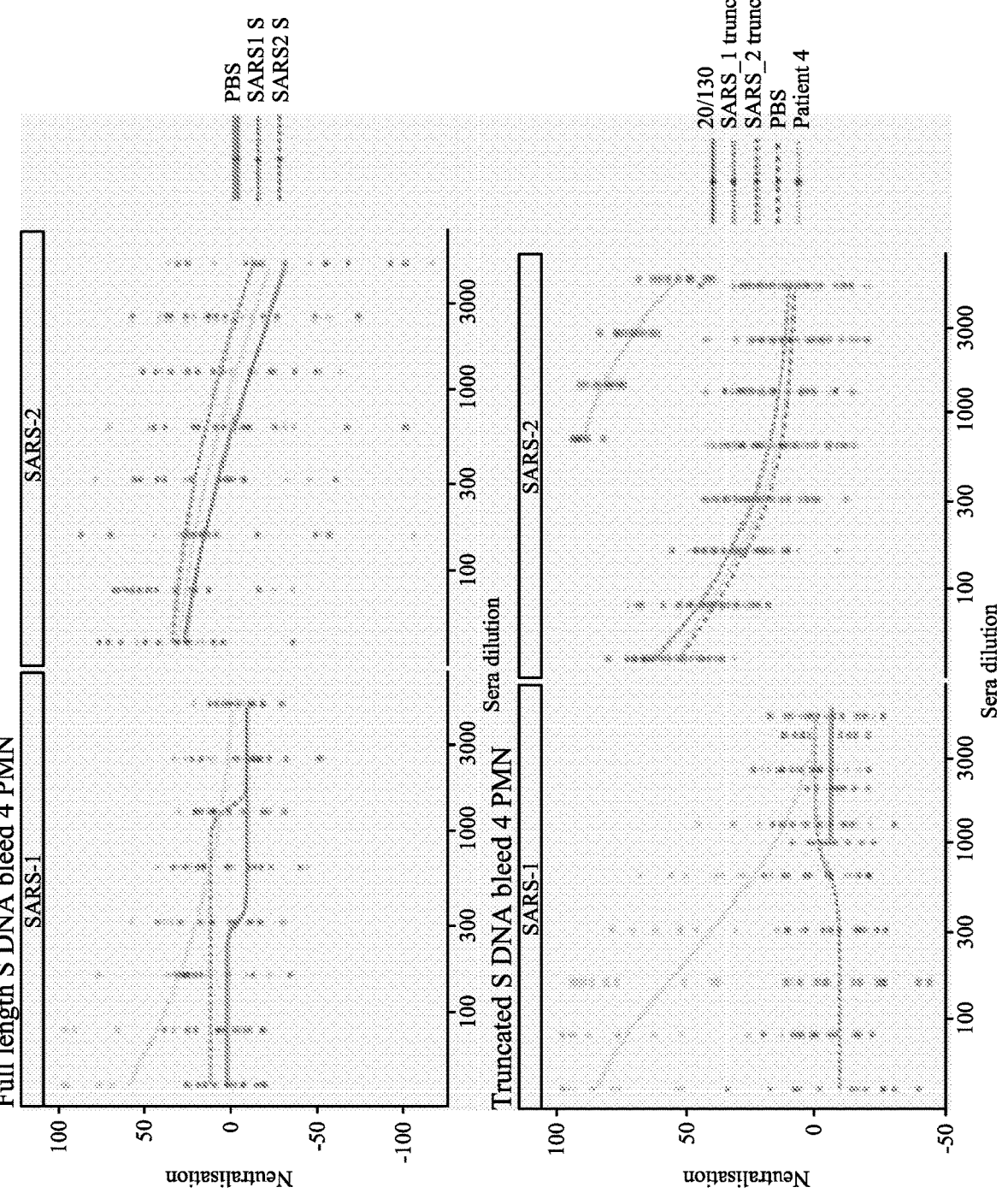
Figure 11:
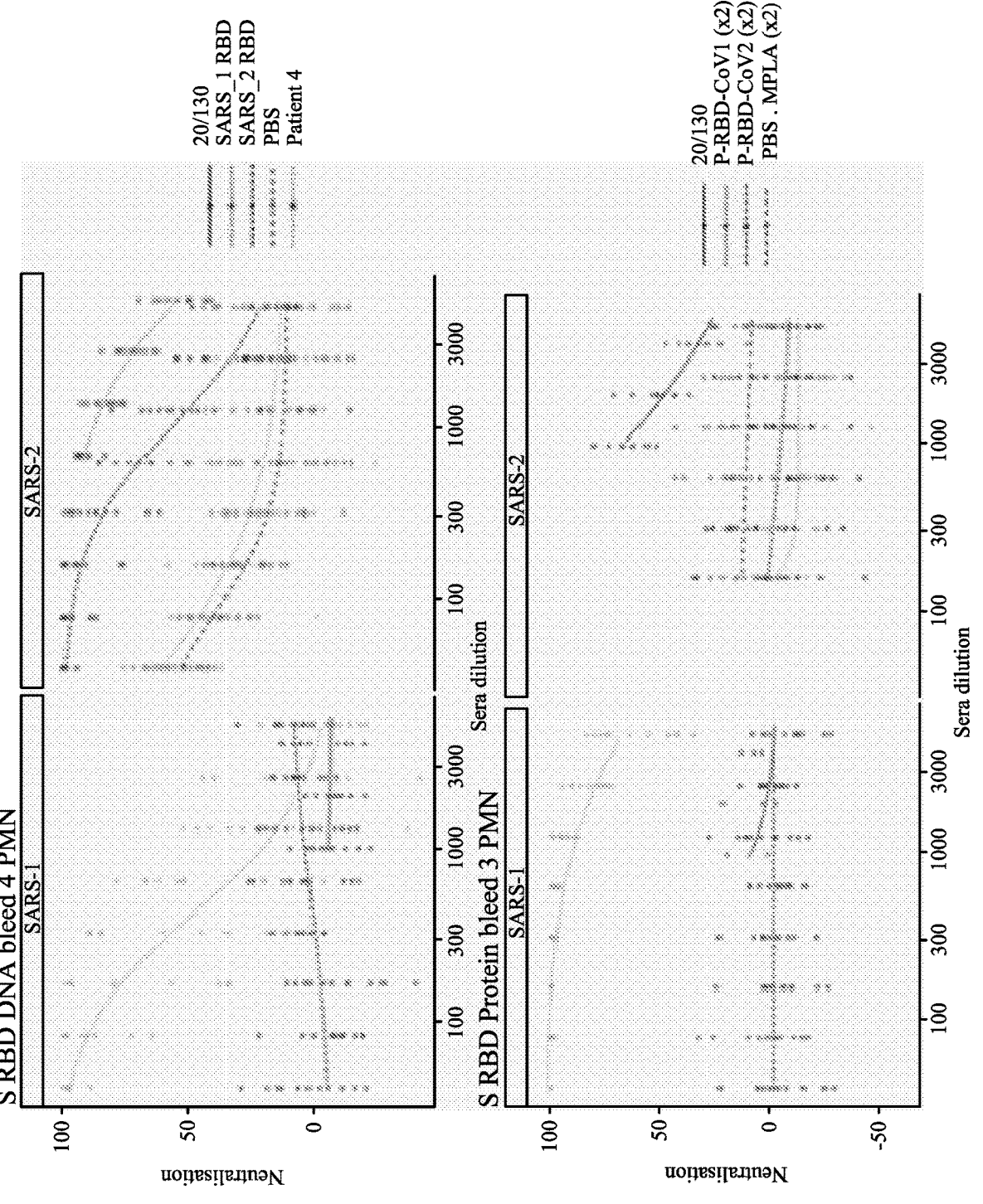
Figure 12:
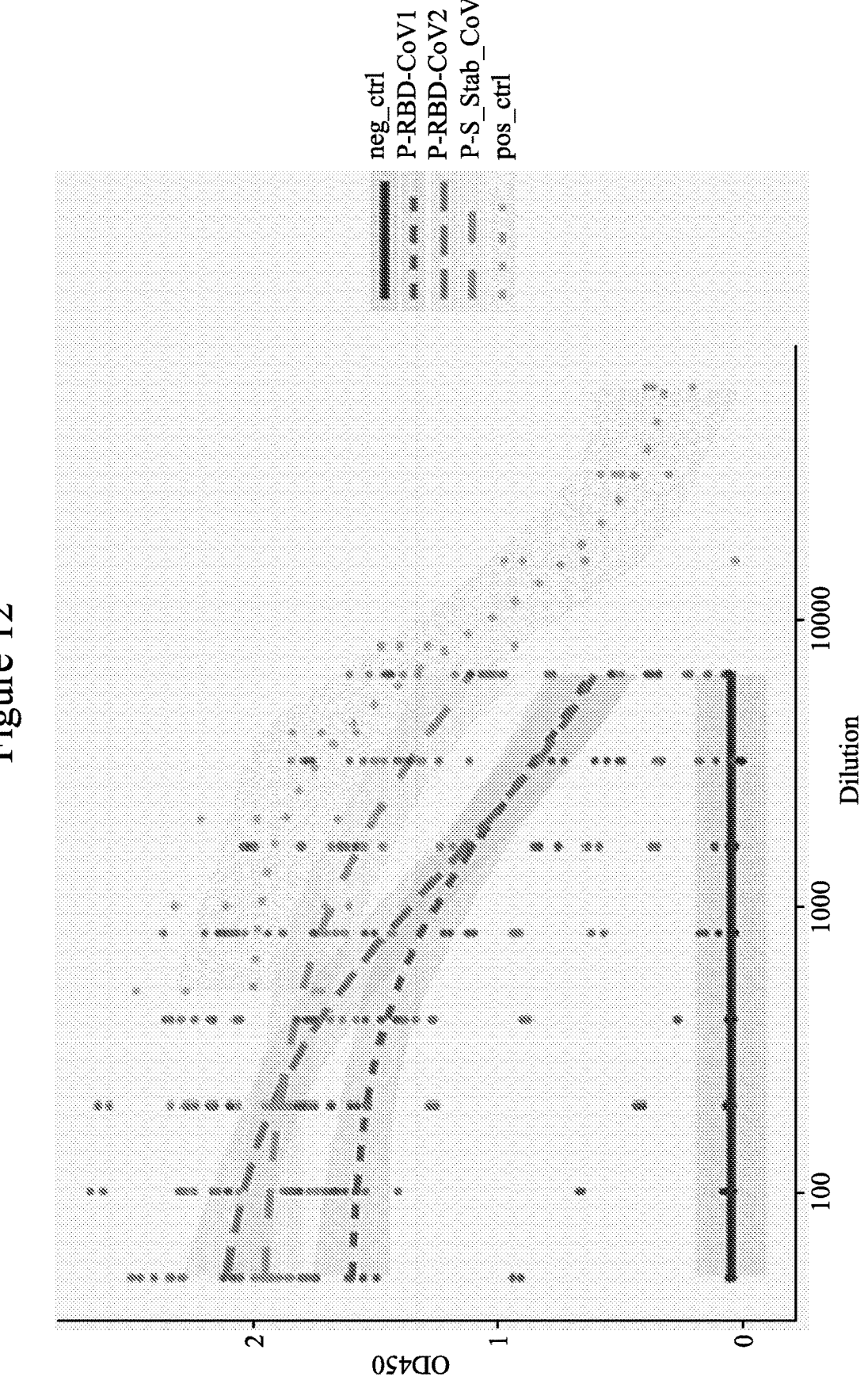
Figure 13:
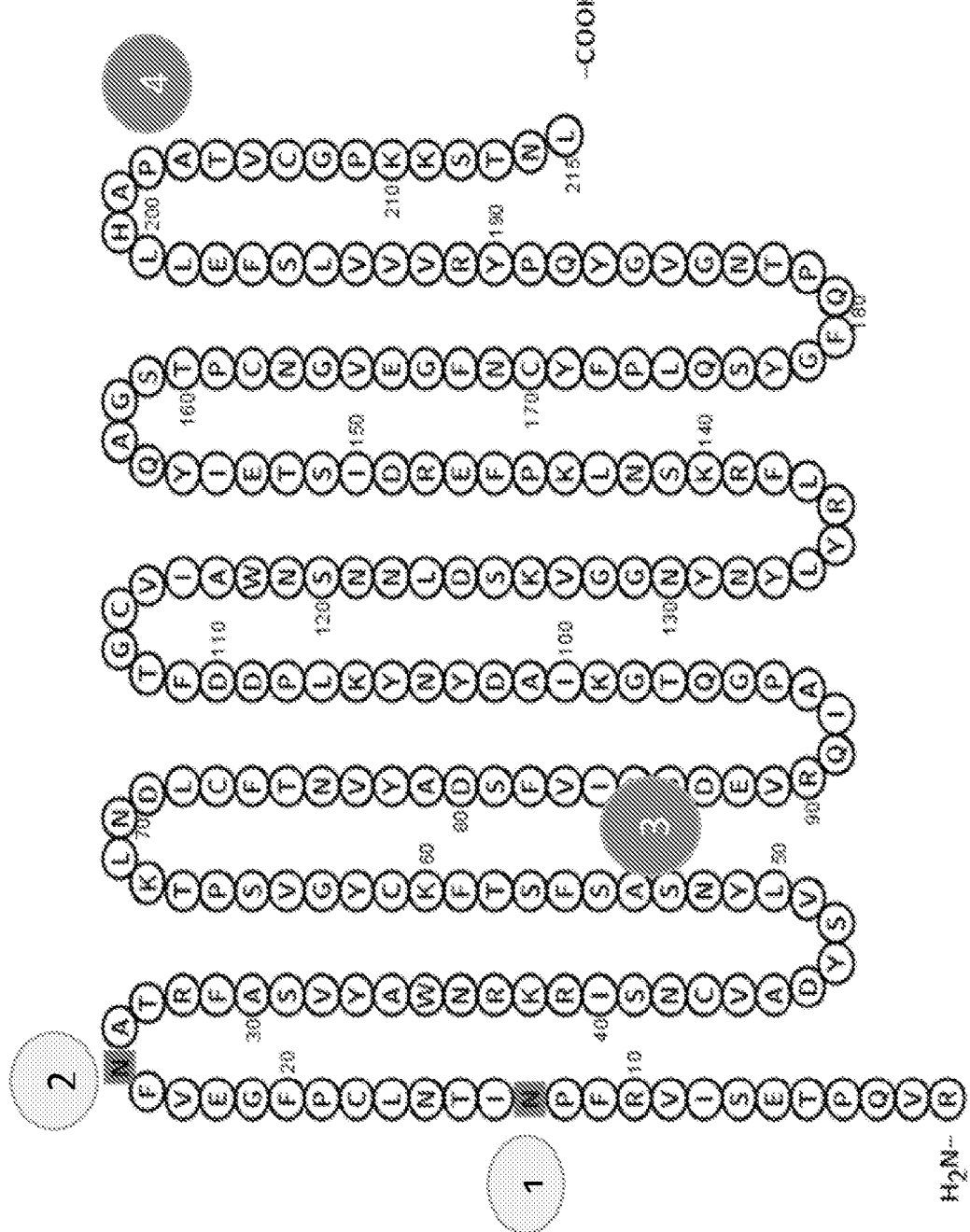
Figure 14:
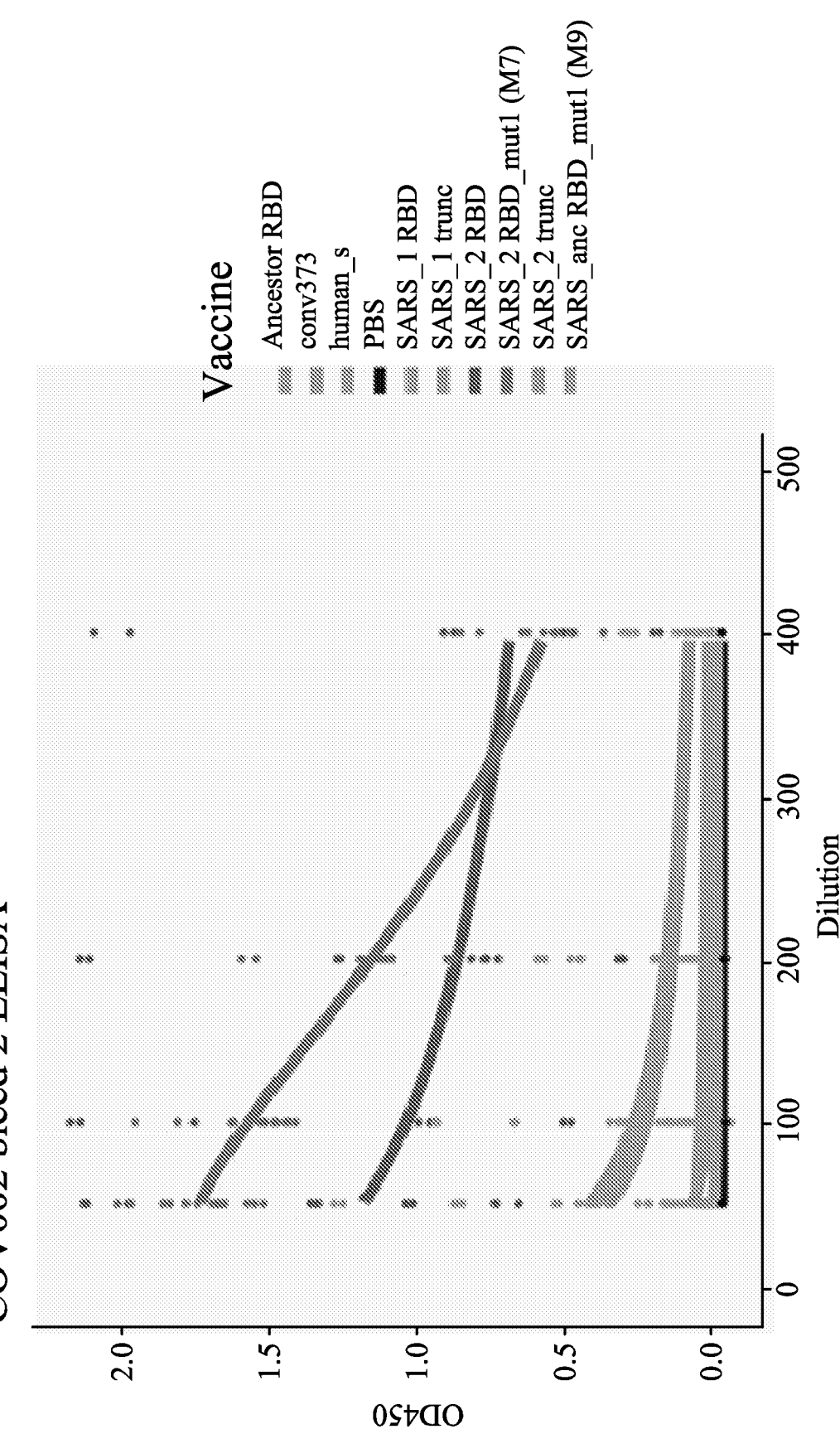
Figure 15:
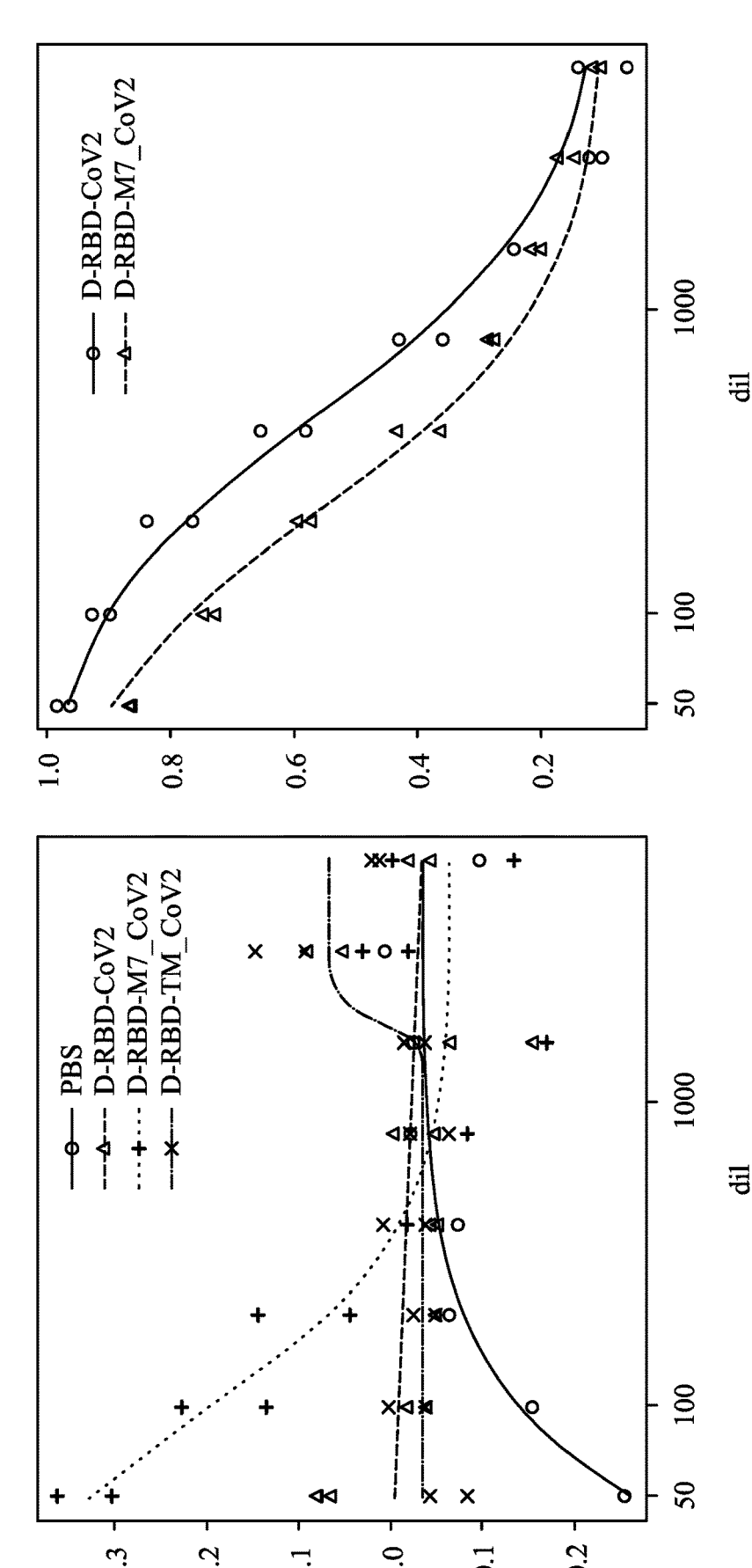
Figure 16:
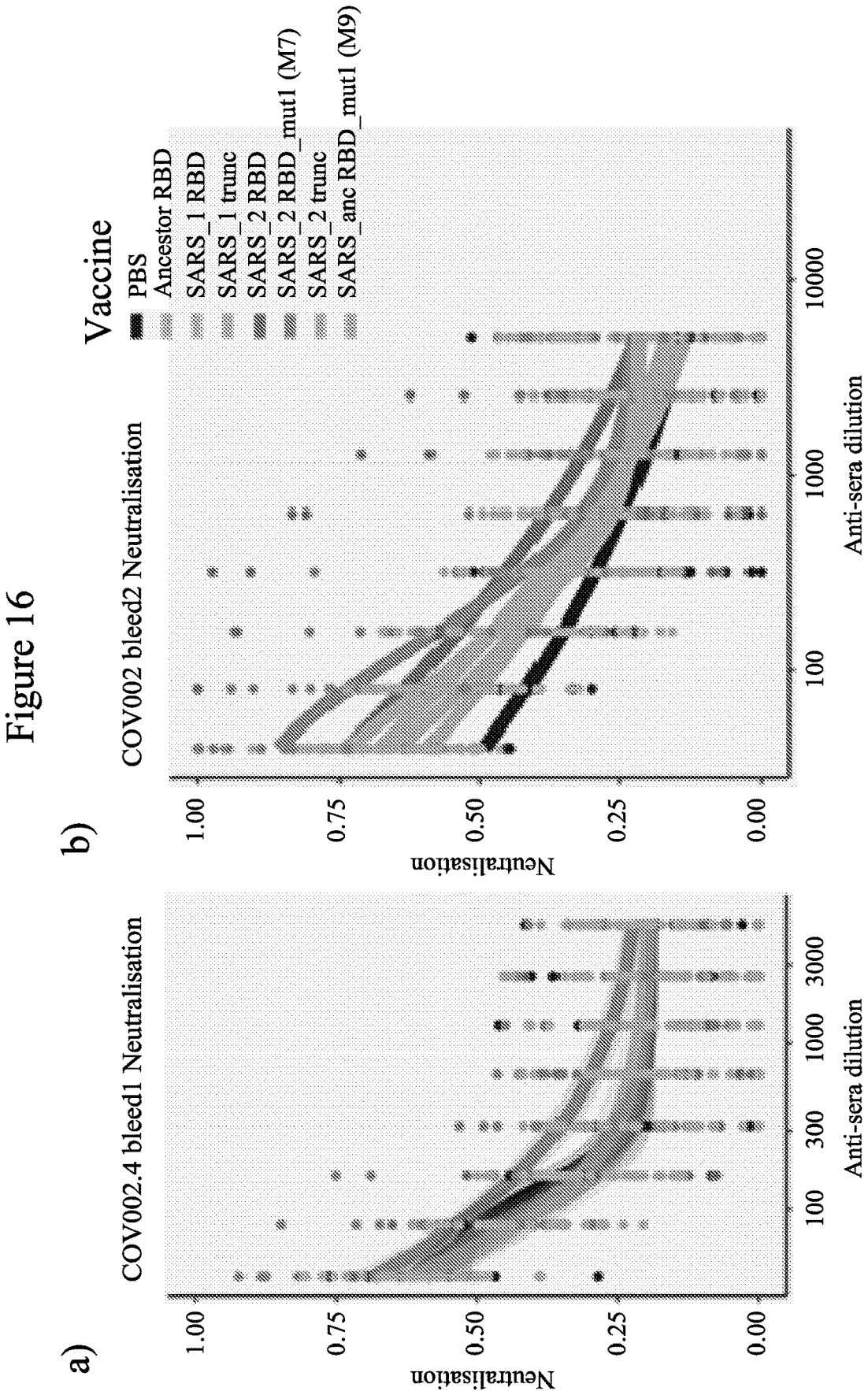
Figure 16:
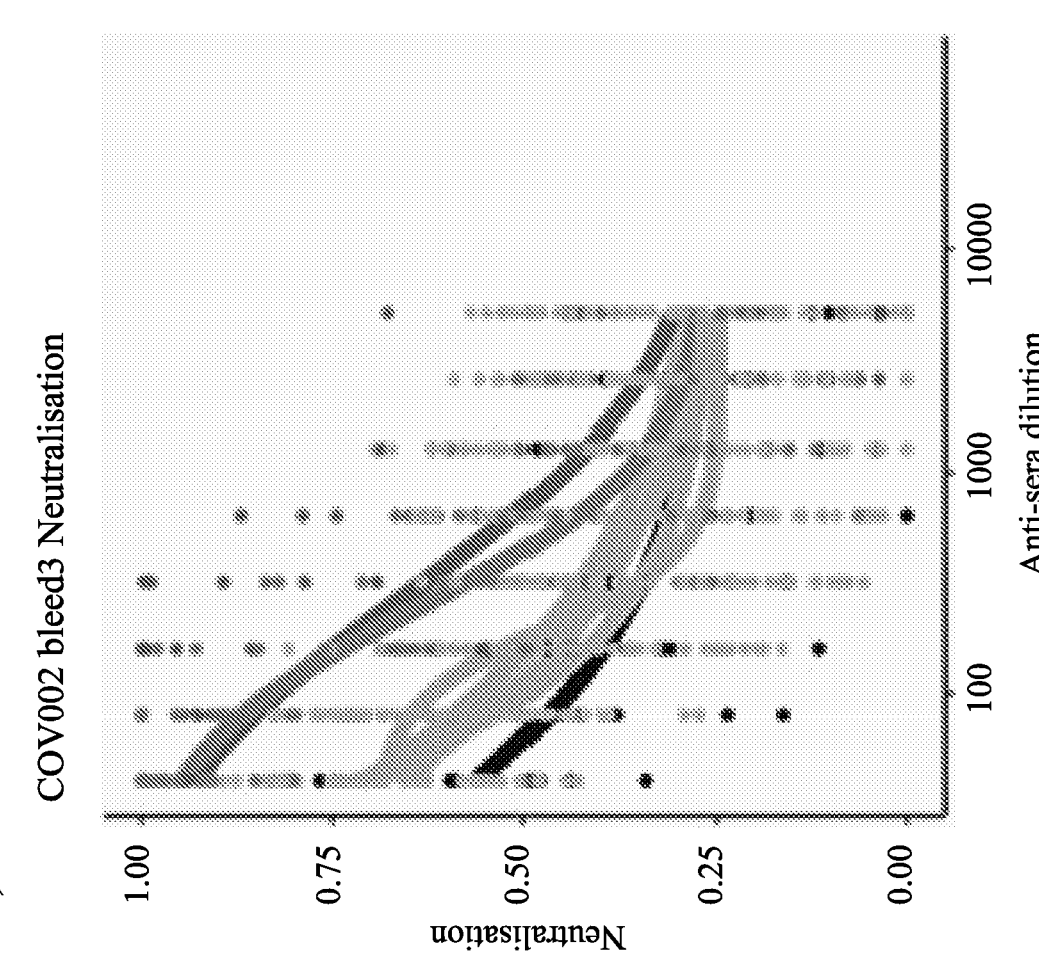
Figure 18:
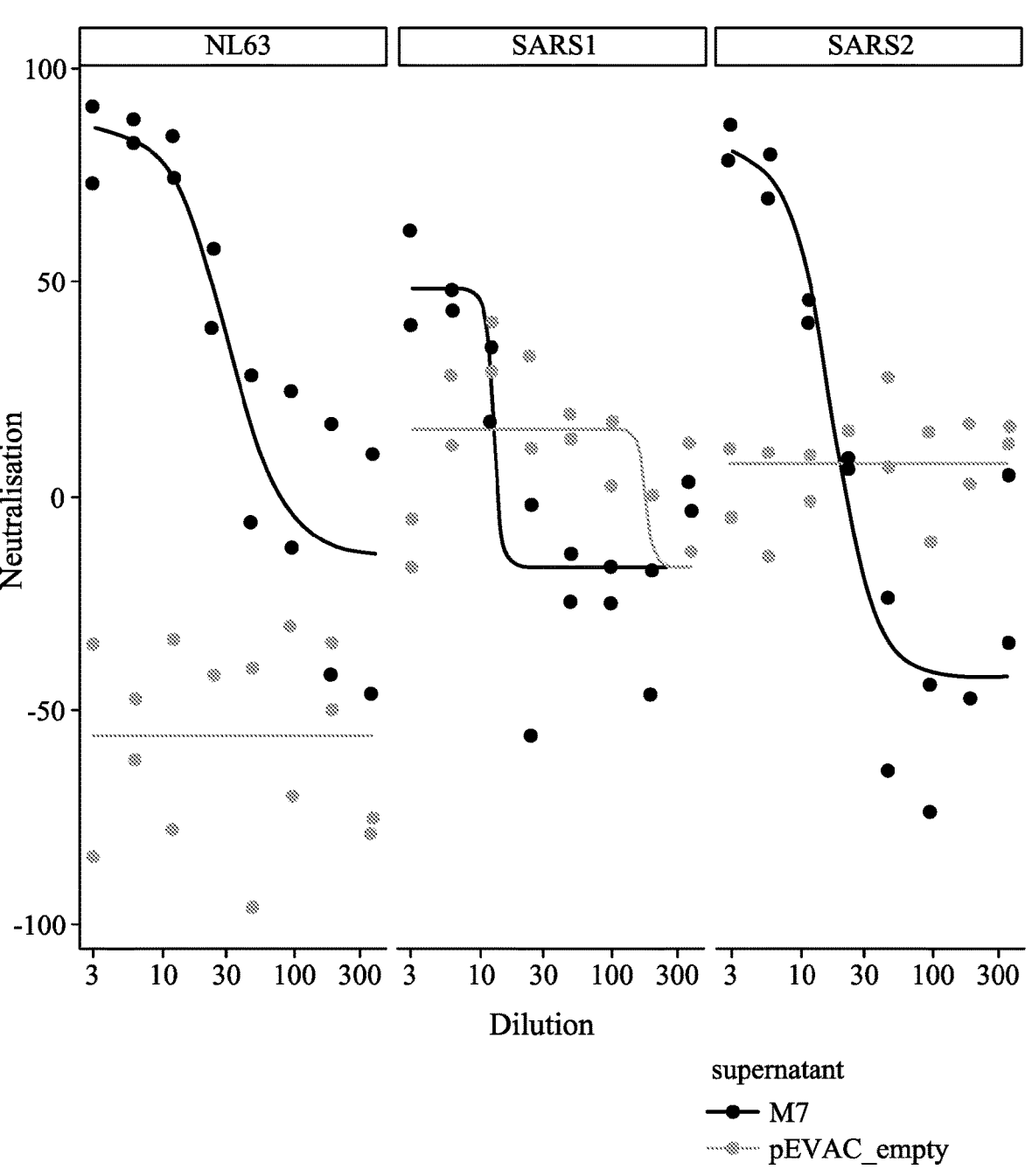
Figure 19:
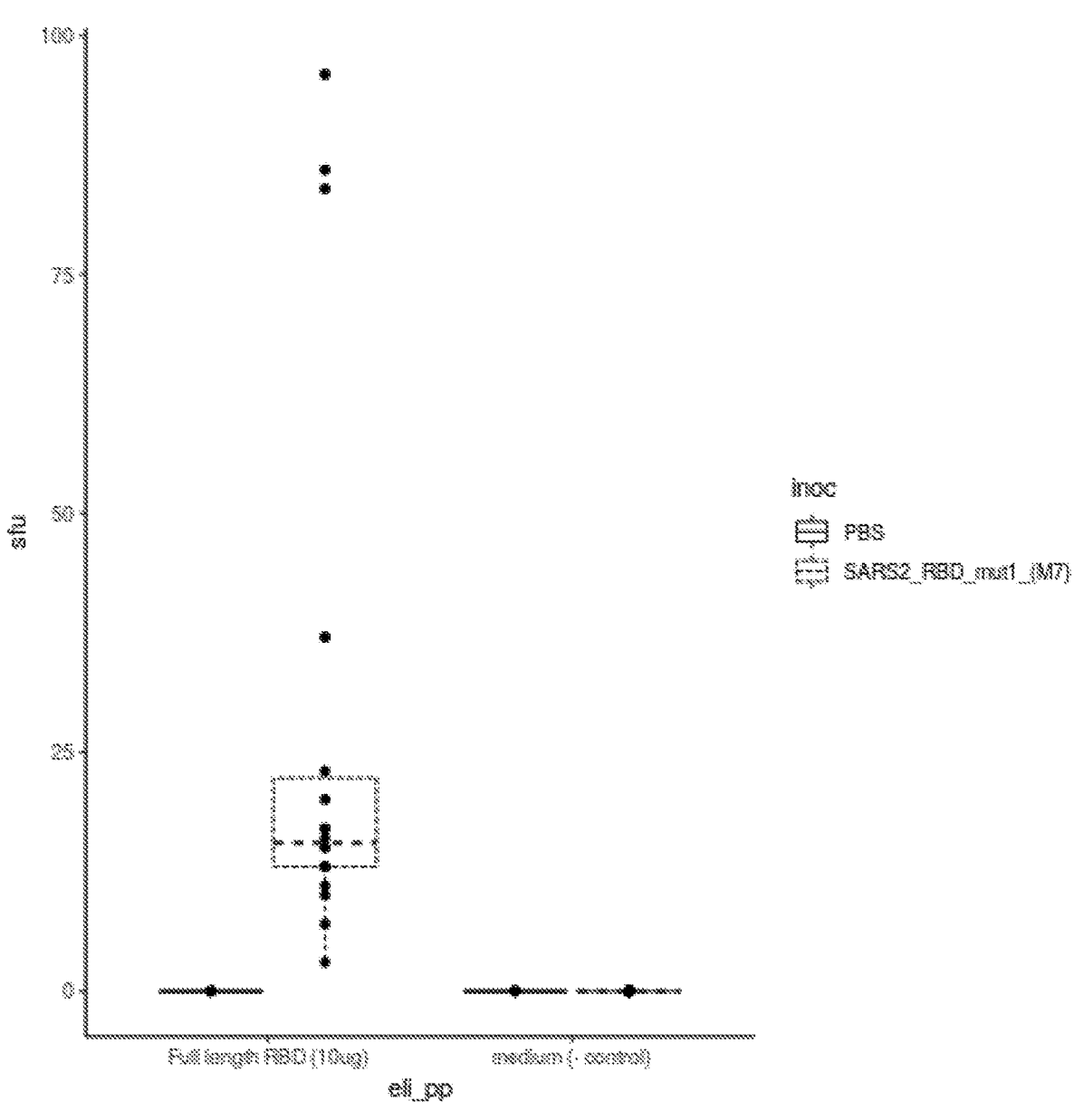
Figure 20:
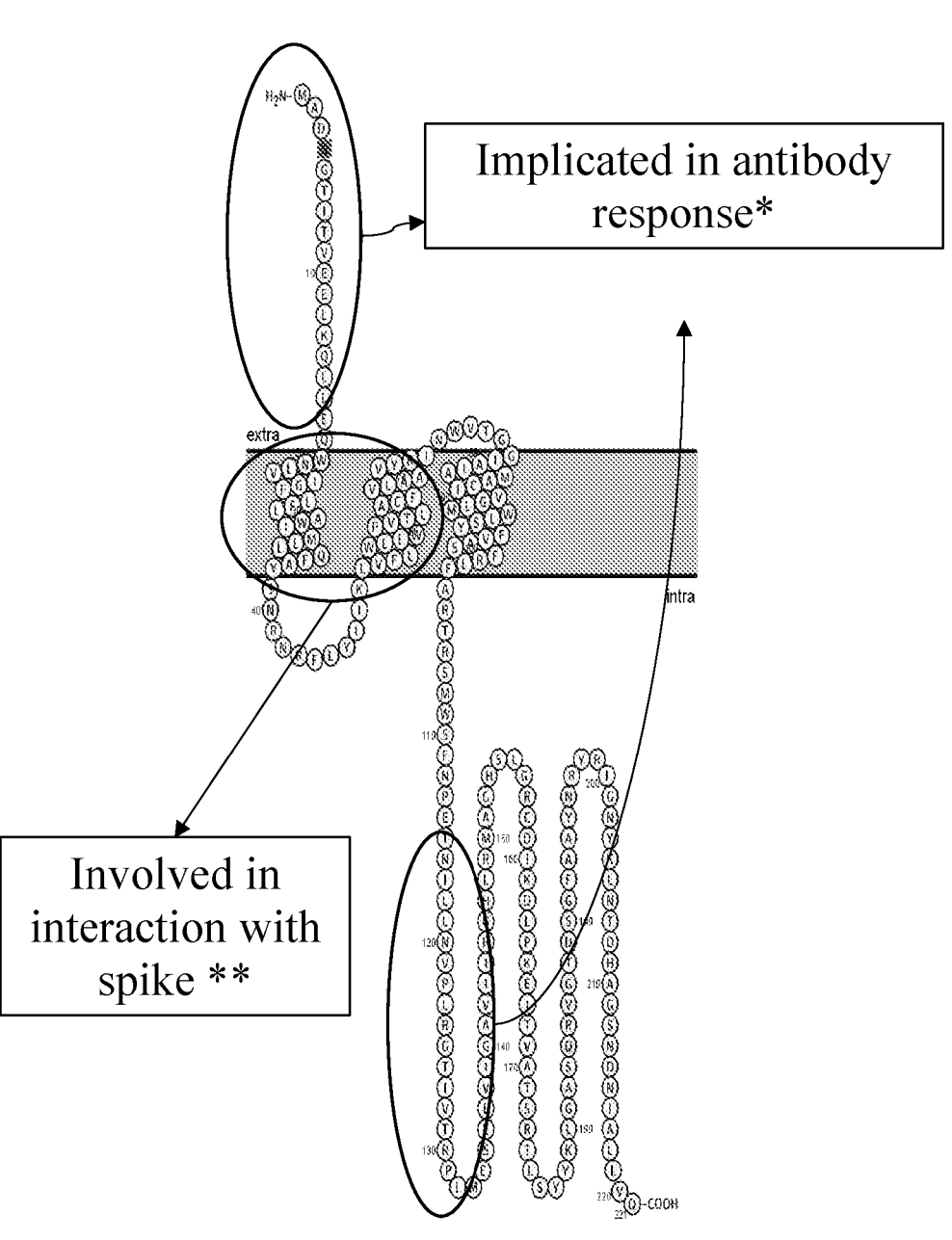
Figure 21:
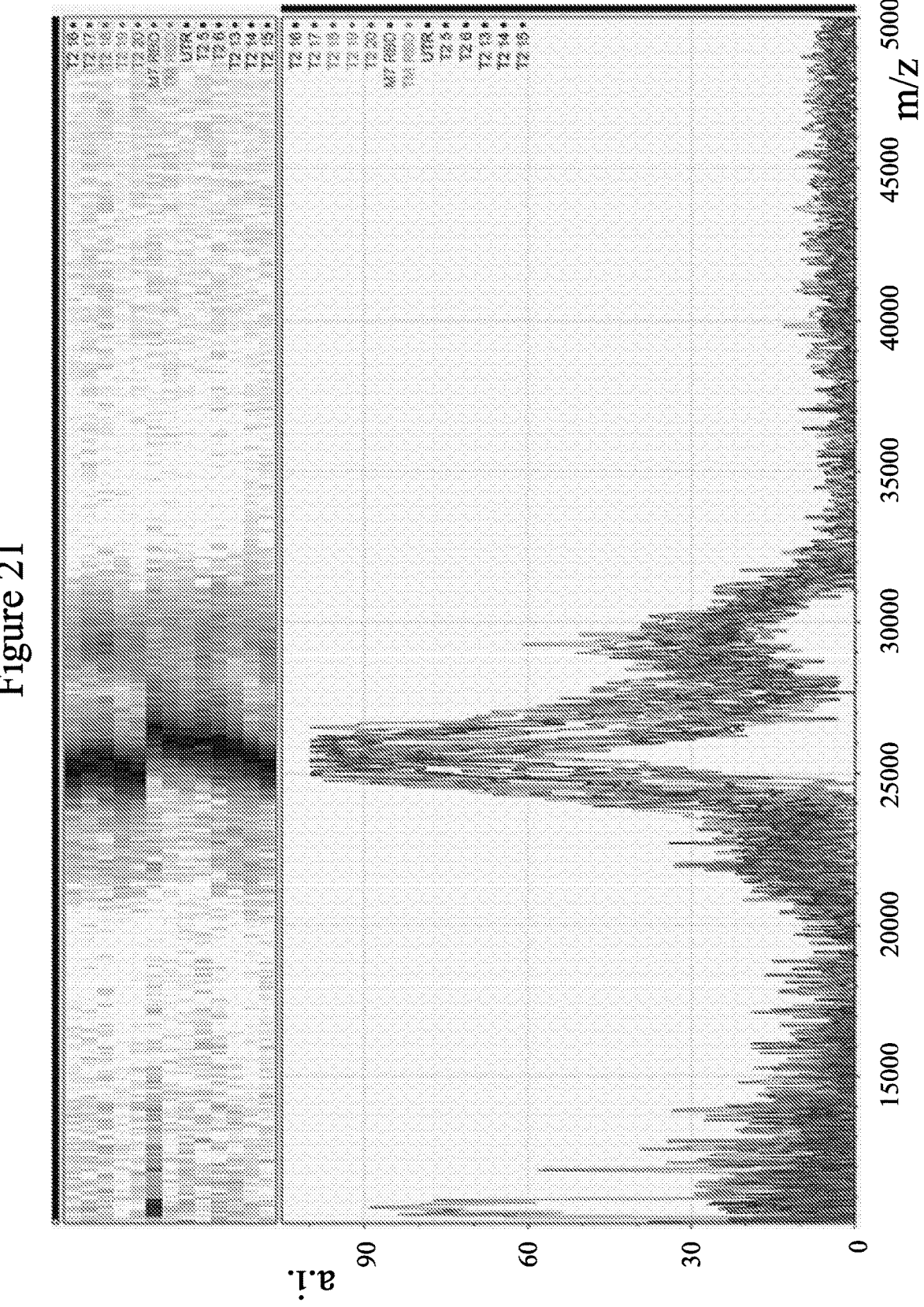
Figure 22:
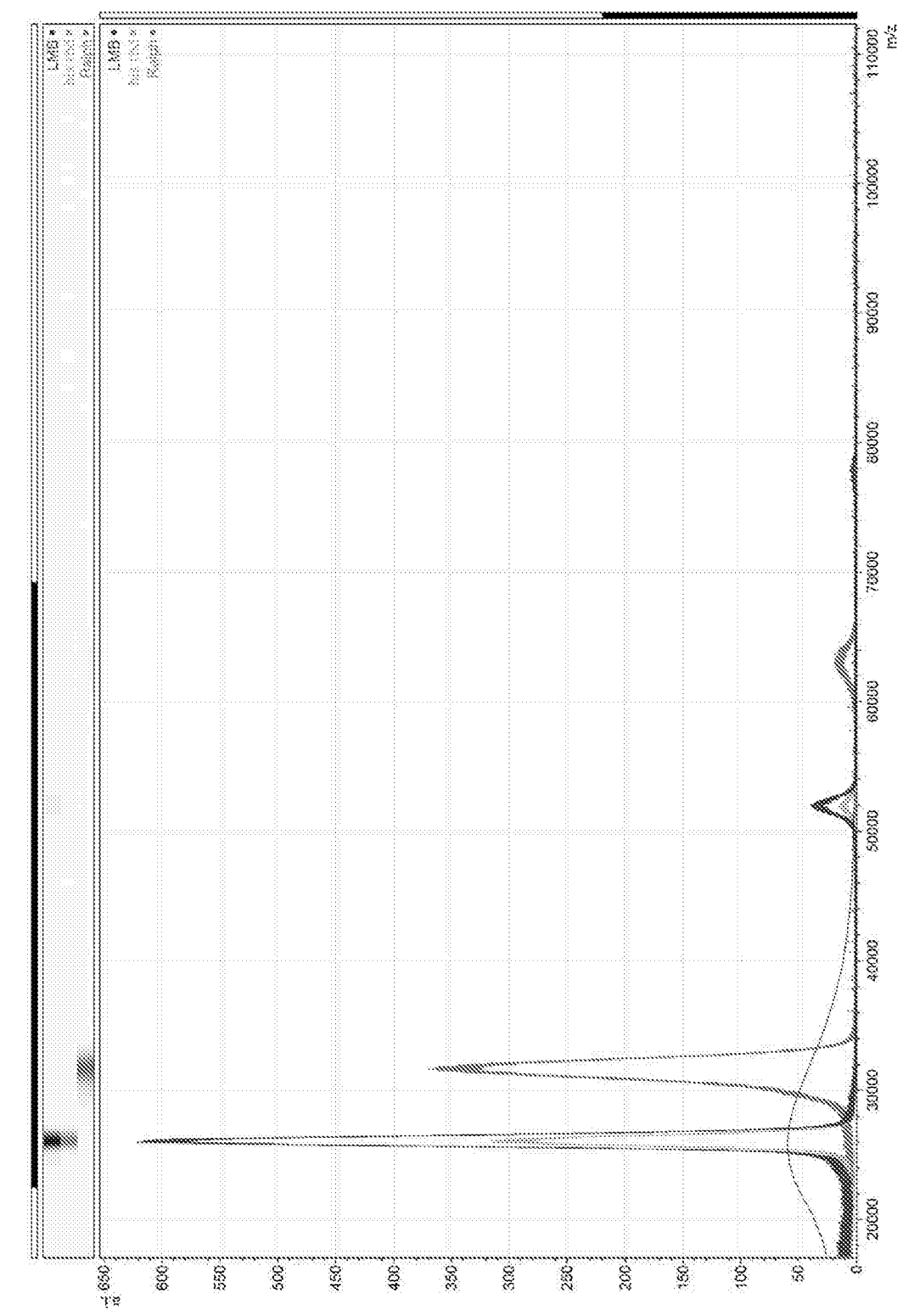
Figure 23:
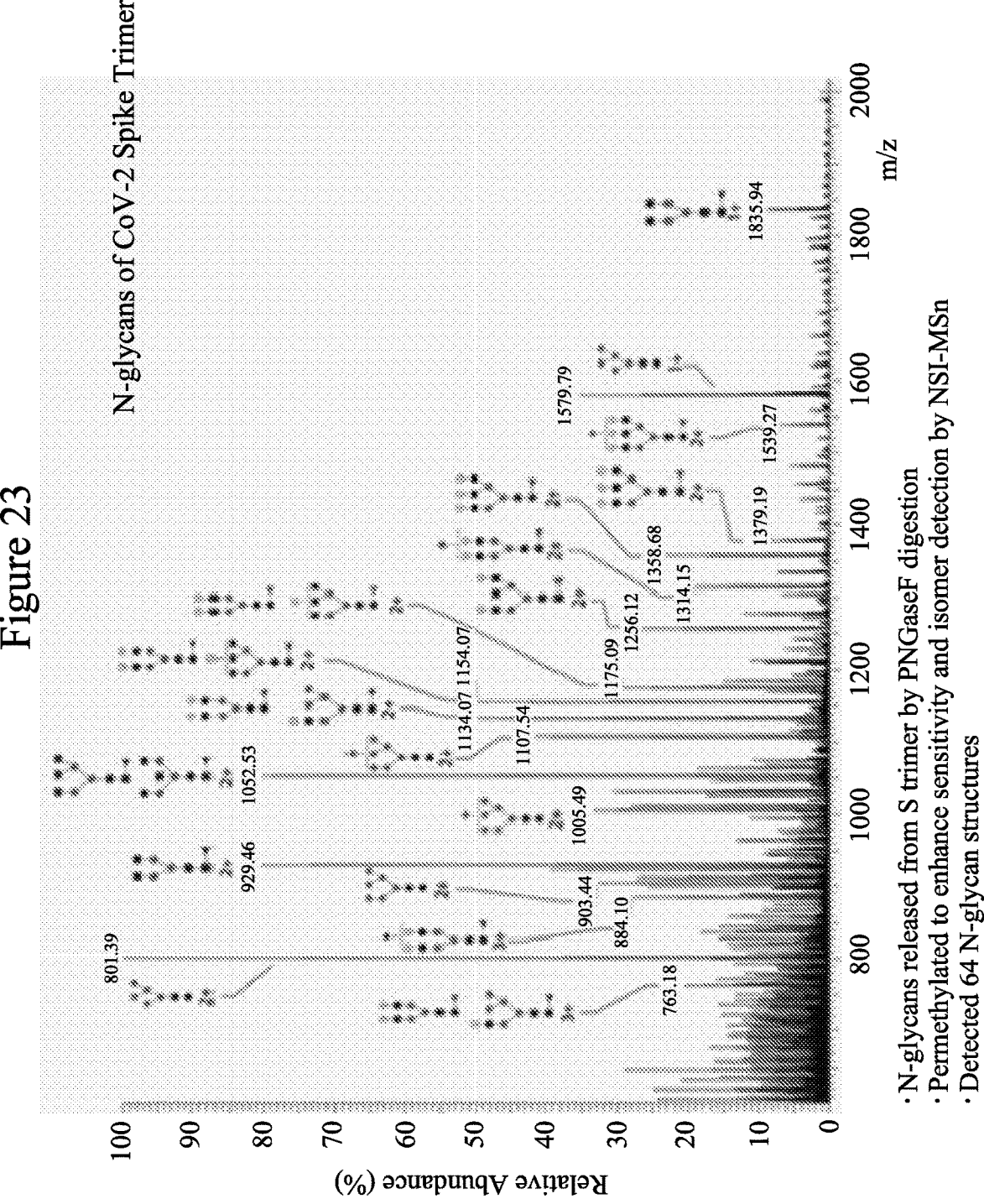
Figure 25:
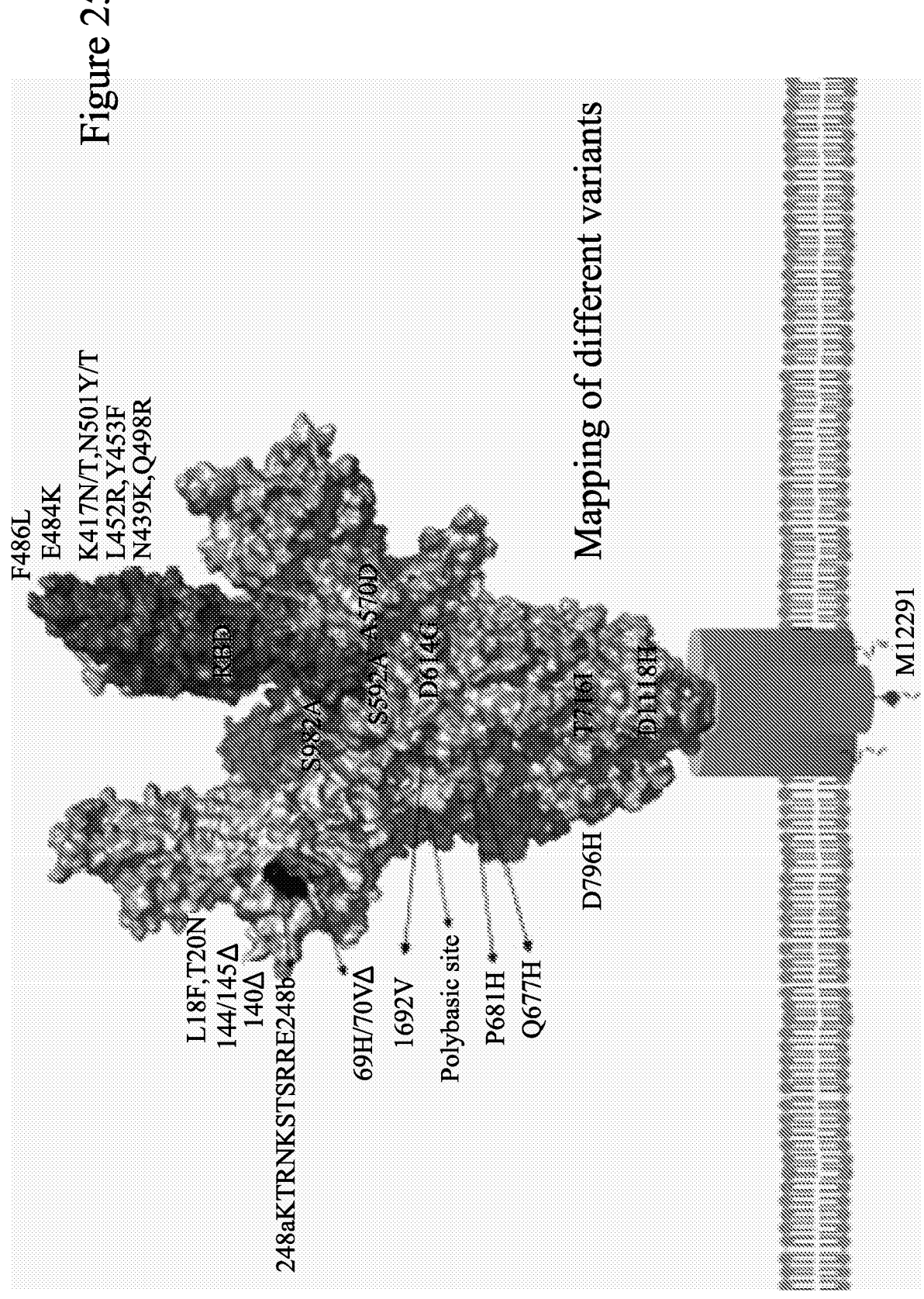
Figure 26:
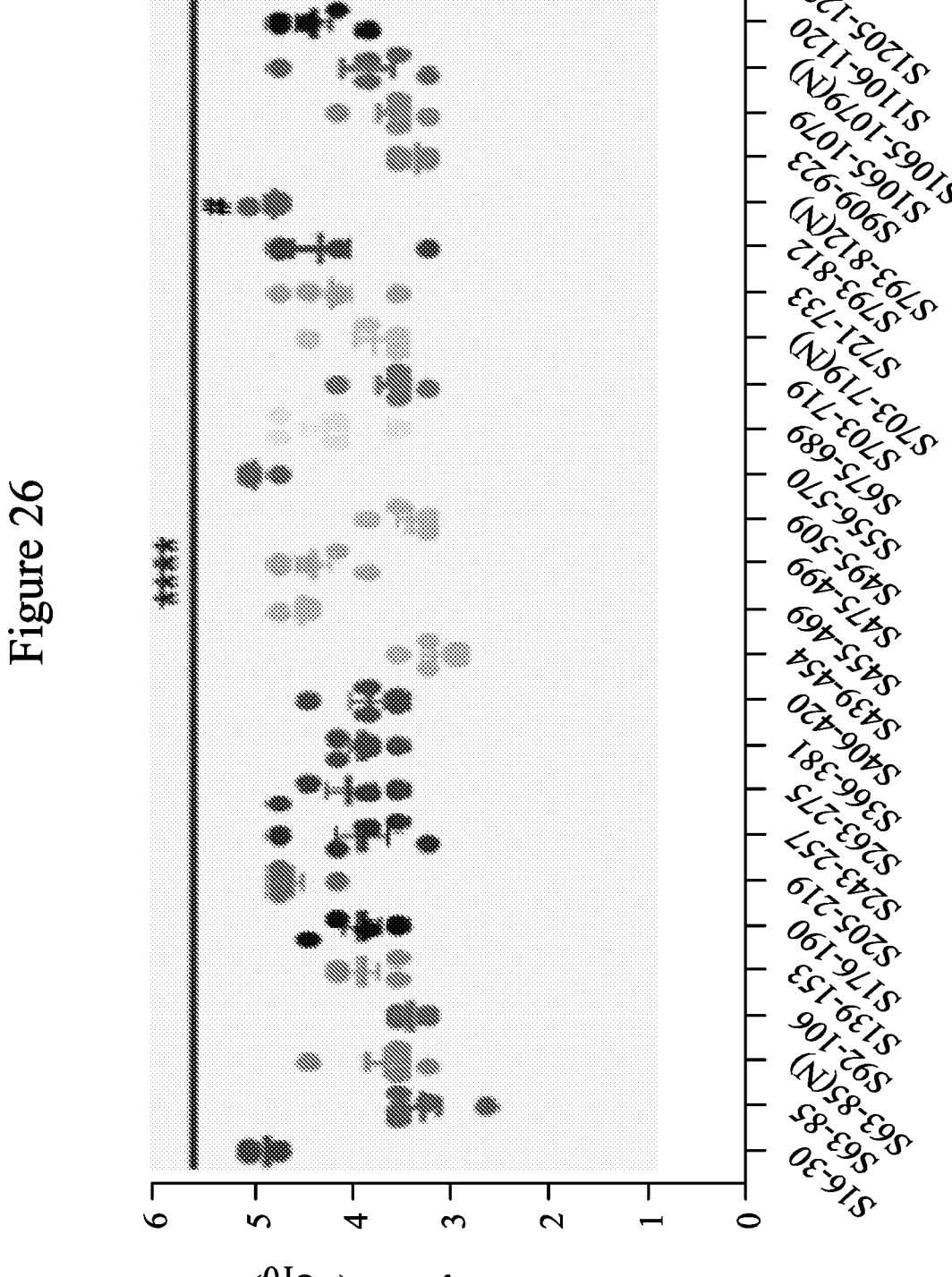

FIG. 4 shows Wuhan_Node1_RBD (CoV_T2_7) amino acid sequence (SEQ ID NO:17) with amino acid residue differences in bold and underline from the respective alignments with AY274119_RBD (COV_T2_5) (SEQ ID NO:5) and EPI_ISL_402119_RBD (COV_T2_6) (SEQ ID NO: 11) amino acid sequences. Common differences from the two alignments are shown highlighted in grey. Amino acid insertions are shown boxed;

FIG. 5 shows dose response curves of antibody binding to full length Spike protein of SARS-CoV-1, or SARS-COV-2 expressed on HEK293T cells. Flow cytometry based cell display assay reported in MFI (Median Fluorescent Intensity). In the left hand figure, the upper to lower curves are SARS-COV-1, DIOS-panSCoV, SARS-COV2; in the right hand figure, the upper to lower curves are DIOS-panSCoV, SARS-COV-1, SARS-COV2;

FIG. 6 shows coronavirus SARS Envelope protein sequence (SEQ ID NO:21), and its significant elements;

FIG. 7 shows a multiple sequence alignment of coronavirus Envelope protein sequences, comparing sequences for isolates of NL63 (SEQ ID NO:93), 229E (SEQ ID NO:94), HKU1 (SEQ ID NOs: 95-96), MERS (SEQ ID NO:97), SARS (SEQ ID NO:21), and SARS2 (SEQ ID NO: 41), and consensus E protein sequences (SEQ ID NOs: 98-100);

FIG. 8 shows a multiple sequence alignment of coronavirus Membrane (M) protein sequences, comparing sequences for a SARS2 reference sequence (isolate NC_045512.2) against CoV_M_T2_1 (Sarbeco_M_root) and CoV_M_T2_2 (Sarbeco_M_Node88b_epitope_optimised);

FIG. 9 shows binding (by ELISA) of mouse sera, collected following immunisation of mice with different full-length S protein genes, to SARS2 RBD;

FIG. 10 shows binding by FACS of mouse sera, collected following immunisation of mice with different DNA vaccines, to SARS1 spike protein and SARS2 spike protein;

FIG. 11 shows the ability of DNA vaccines encoding wild-type SARS1 or SARS2 spike protein (full-length, truncated, or RBD) to induce a neutralisation response to SARS1 and SARS2 pseudotypes—the only SARS2 immunogen which induces SARS2 pseudotype neutralising antibodies is the DNA encoding SARS2 RBD;

FIG. 12 shows the ability of SARS1 and SARS2 RBD protein vaccines to induce antibodies to SARS2 RBD;

FIG. 13 illustrates new RBD antigen designs based on the amino acid sequence of the RBD region (SEQ ID NO:106);

FIG. 14 shows the ability of different S protein RBD DNA vaccines to induce antibodies to SARS2 RBD-M7 DNA vaccine induces a stronger binding response (by ELISA) to SARS2 RBD than wild-type SARS2 RBD DNA vaccine (the uppermost curve, from the left hand end of the figure, is for SARS_2 RBD_mut1 (M7), the next curve down is for SARS_2 RBD);

FIG. 15 shows the results of a competition assay for inhibition of RBD-ACE2 interaction by sera collected following immunisation with M7 and wild-type SARS2 RBD DNA vaccines—the results show that M7 RBD DNA vaccine elicits a faster neutralisation response than wild-type RBD DNA vaccine;

FIG. 16 shows a SARS2 pseudotype neutralisation response induced by M7 and wild-type SARS2 RBD DNA vaccines: FIG. 16(a) bleed at week 2 from the immunised mice, FIG. 16(b) bleed at week 3 from the immunised mice, and FIG. 16(c) bleed at week 4 from the immunised mice—M7 is more neutralising in the early stages (the uppermost curve, from the left hand end of FIGS. 16 (a), (b), (c), is for SARS2 RBD_mut1 (M7), the next curve down is for SARS_2 RBD);

FIG. 17 shows SARS2 pseudotype neutralisation $IC_{50}$ values for sera collected from the mice immunised with wild-type SARS2 RBD DNA vaccine, and M7 SARS2 RBD DNA vaccine. The dots in FIG. 17 show $IC_{50}$ values for individual mice, and the horizontal cross bars show the estimate based on all mice with 95% confidence intervals;

FIG. 18 shows that the supernatant of cells expressing M7 competes with other ACE2 binding viruses for ACE2 cell entry;

FIG. 19 shows the results of an ELISPOT assay showing T cell response to M7 SARS2 RBD DNA vaccine;

FIG. 20 shows an illustration of the M protein (SEQ ID NO:101), and its significant elements;

FIG. 21 shows the spectra overlap (MALDI MS) of supernatants derived from HEK cells transfected with pEVAC plasmid encoding S protein RBD sequences;

FIG. 22 shows spectra for recombinant RBD proteins;

FIG. 23 provides a reference for glycosylation of the S protein;

FIG. 24 shows coronavirus vaccine pan-Sarbecovirus vaccine coverage. Pan-Sarbecovirus protection: Beta-Coronaviruses including SARS-COV-2 (SARS2), -1 (SARS1) & the many ACE2 receptor using Bat SARSr-COV that threaten to spillover into humans. Antigenic coverage achieved by universal Sarbecovirus B-cell and T-cell antigen targets: Part 1. Sarbecoviruses with the SARS1 and SARS2 clades highlighted along with human or bat host species. Part 2. Machine learning predicted MHC class II binding (higher is stronger binding) of predicted epitopes within the insert. Lighter grey is for epitopes conserved within SARS2, darker grey are epitopes grafted in from other Sarbecoviruses such as SARS1;

FIG. 25 illustrates mapping of different SARS-COV-2 variants:

Inclusive list of all the important variants: Pink=exposed mutation; Black=insertion; Yellow=partially buried or fully buried; Purple=in the cytoplasmic tail; Blue colour=RBD; Wheat colour=NTD;

FIG. 26 shows the immunodominant and neutralization linear epitopes for SARS-COV-2:

| EpitopesEpitopes | Variant | Immuno-dominant* |
|---|---|---|
| 16-30 | Japan | Yes |
| 92-106 | | |
| 139-153 | UK, Japan | |

-continued

| EpitopesEpitopes | Variant | Immuno-dominant* |
|---|---|---|
| 243-257 | | |
| 406-420 | Japan, South Africa | |
| 439-454 | | |
| 455-499 | Japan, South Africa | Yes |
| 556-570 | UK | Yes |
| 675-689 | UK | |
| 721-733 | | Yes |

Figure 27:
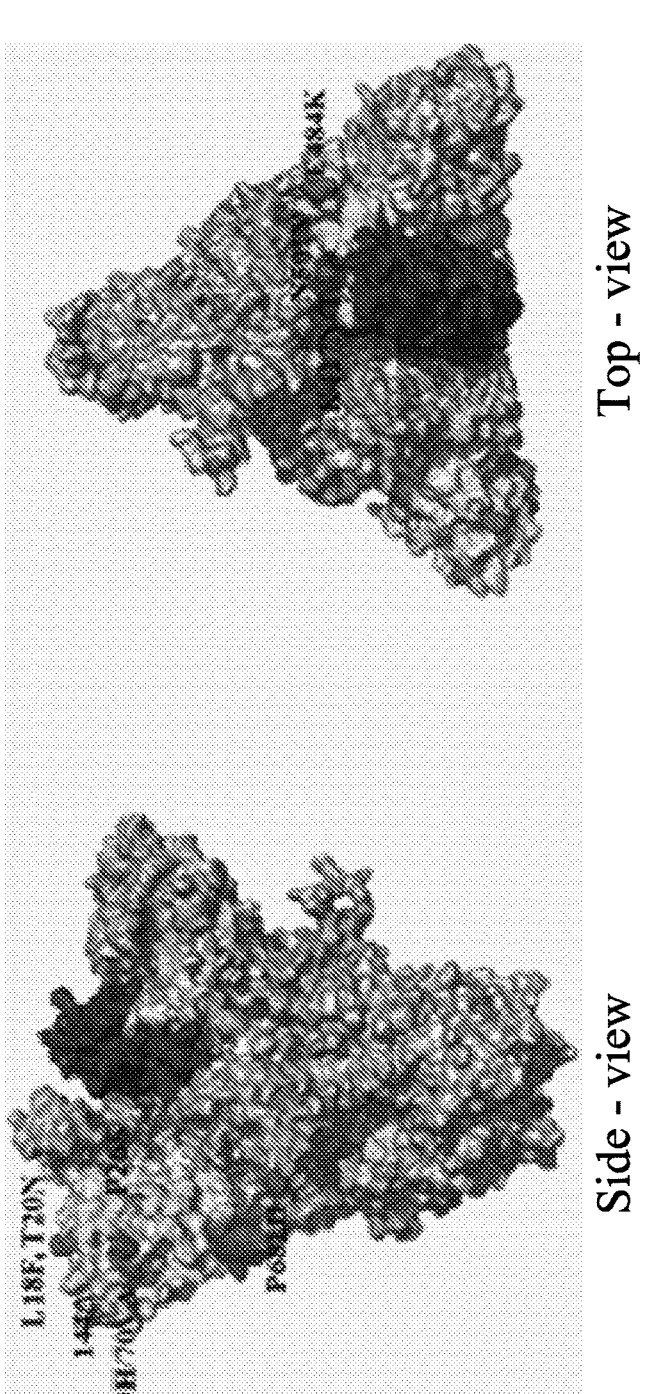
Figure 29:
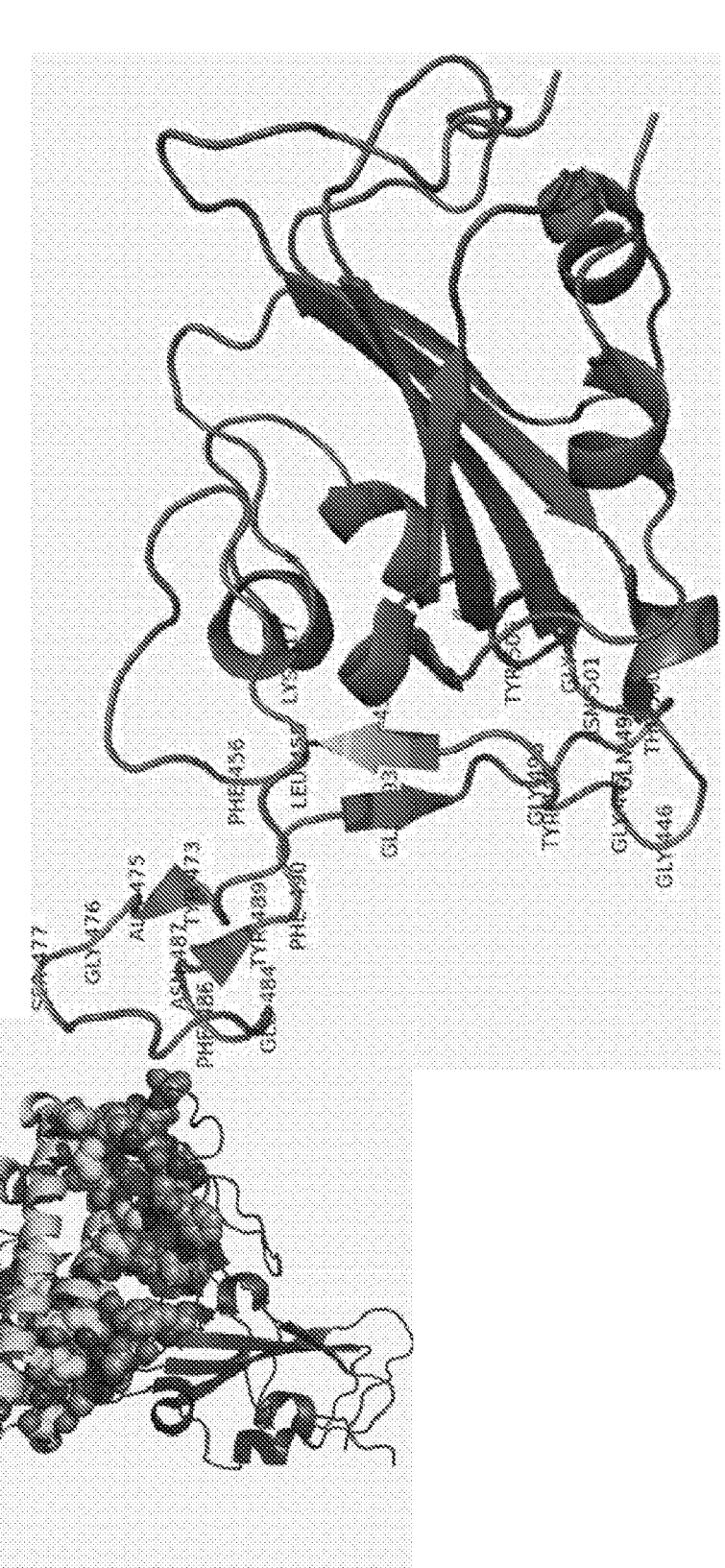
Figure 30:
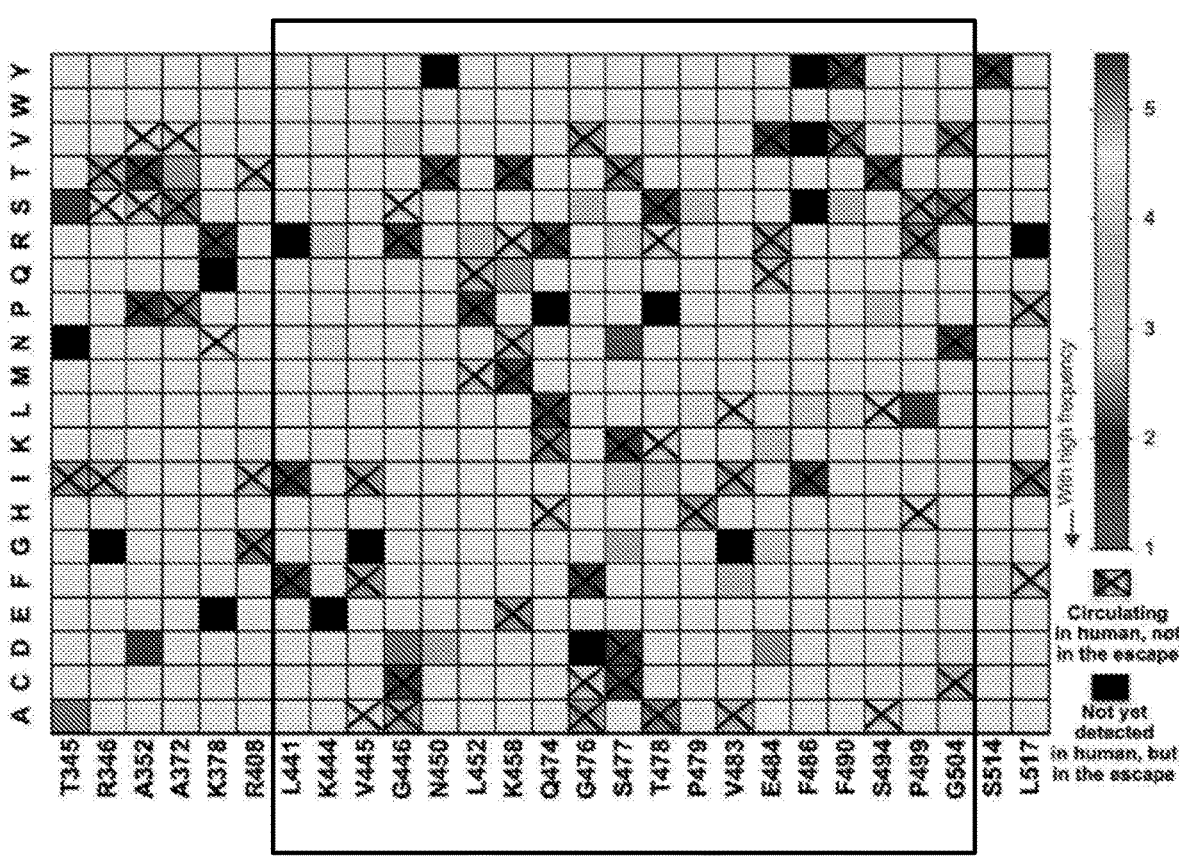
Figure 30:
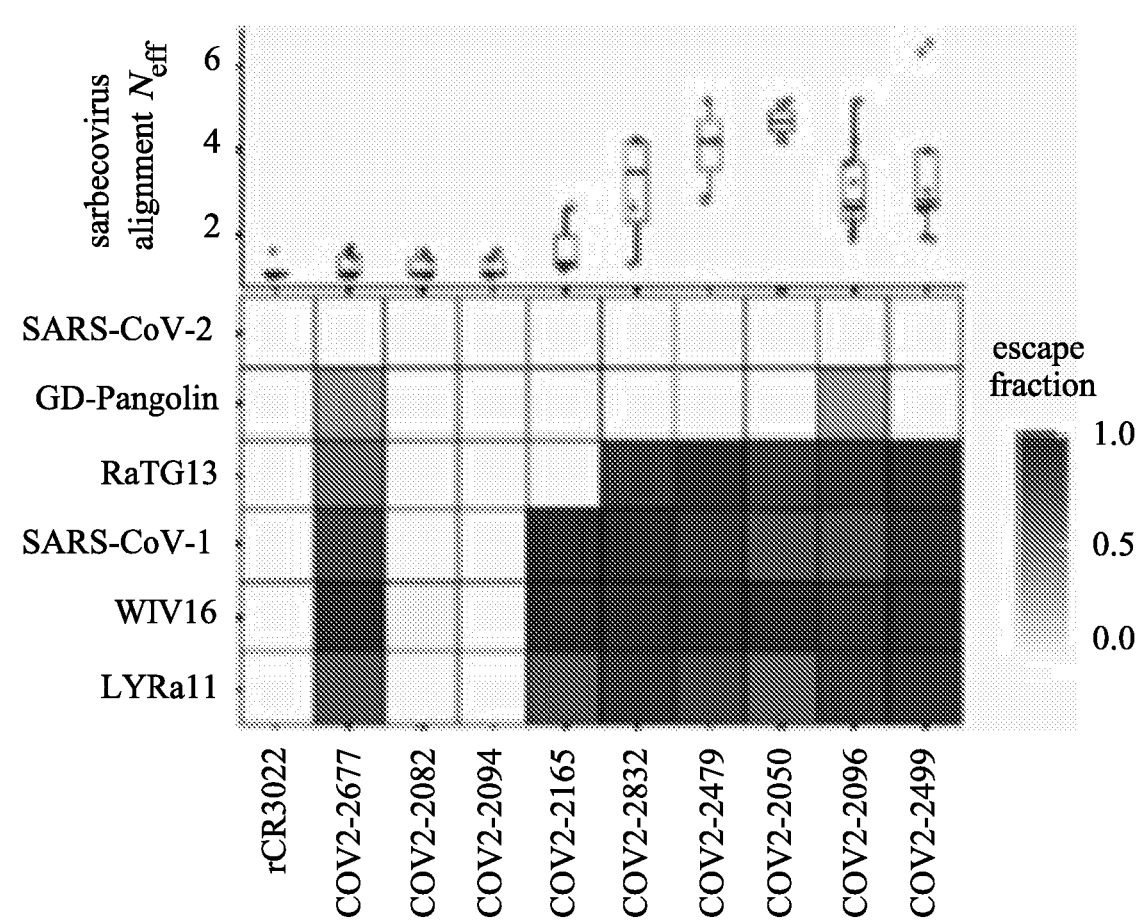
Figure 31:
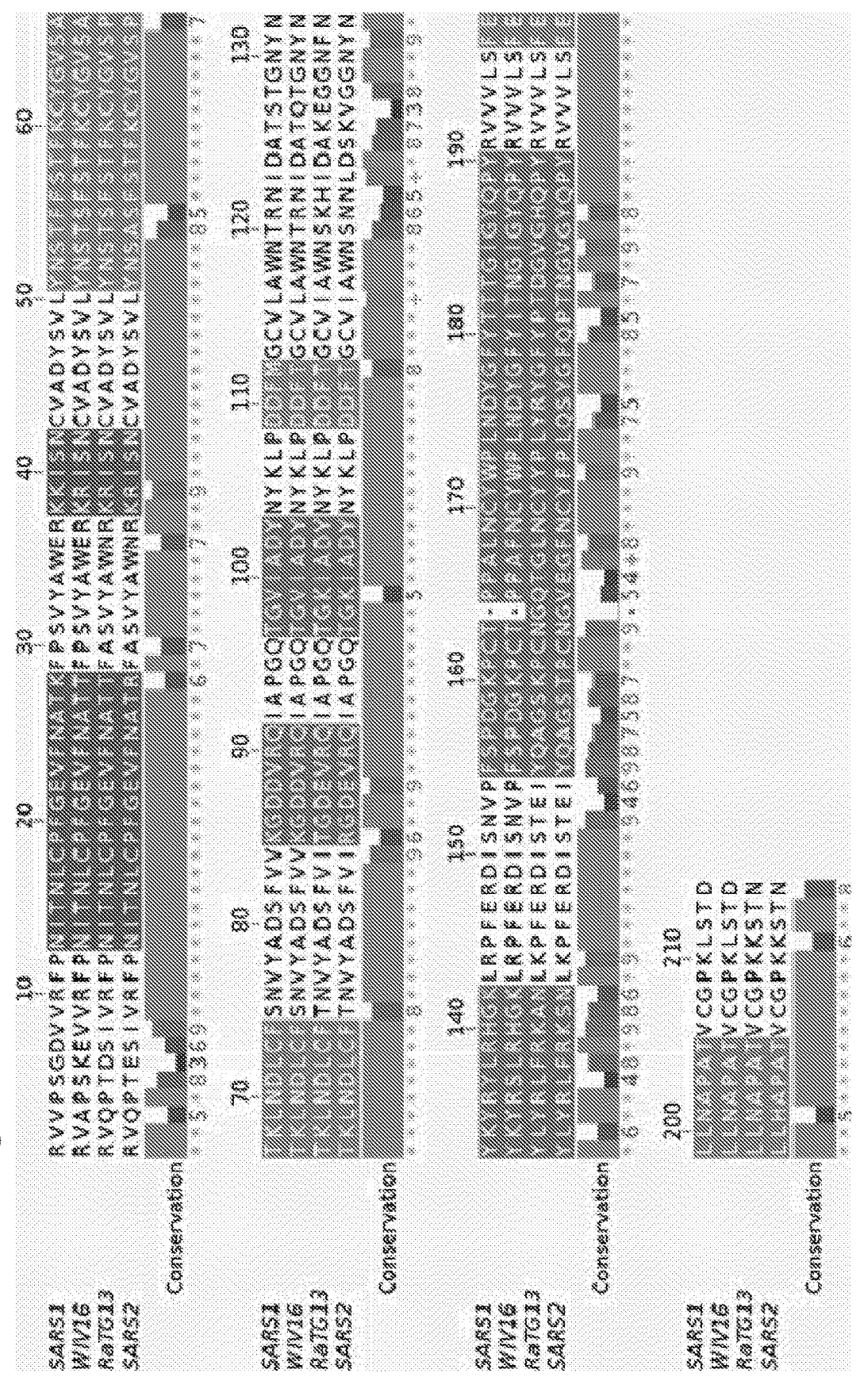
Figure 31:
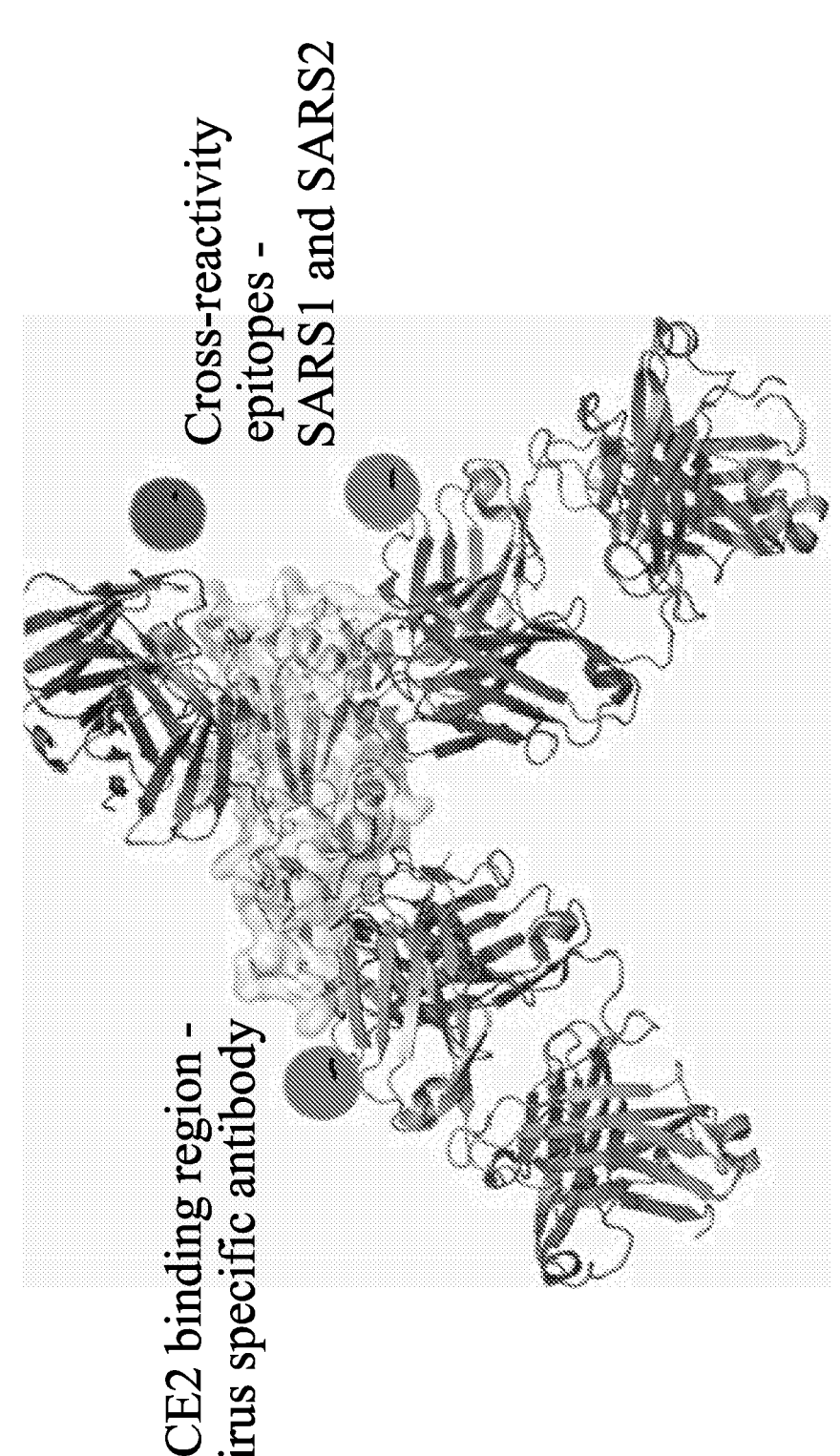
Figure 32:
Figure 34:
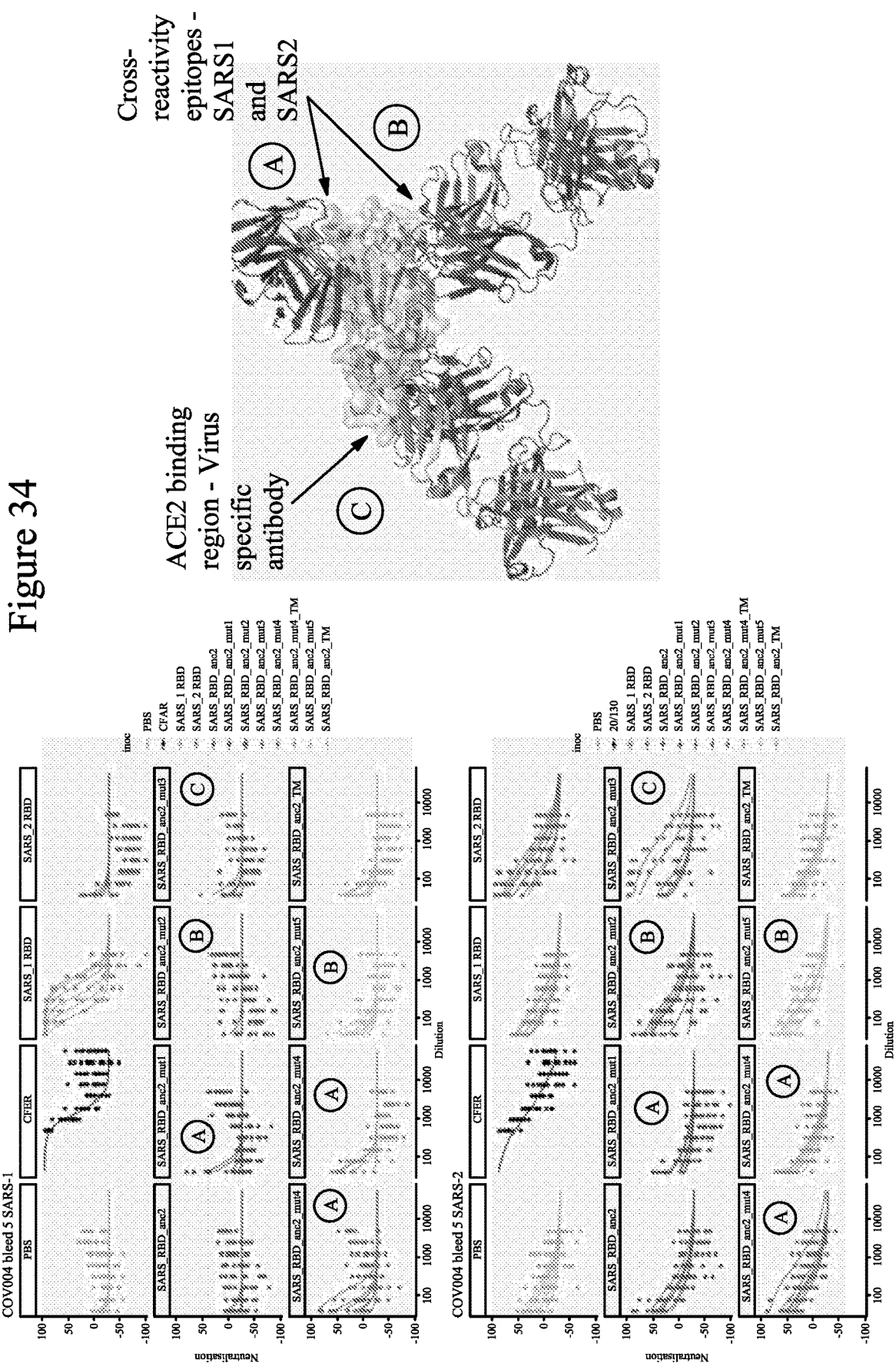

Study limited to Chinese population. Expressed peptides as VSV.
*Against G614 variant FIG. 27 contains a table describing the mutations in the variants of concern (UK, South African, and Brazil), and structural figures with immunodominant epitope coloured teal and mutations shown in red. RBD-Blue; NTD-wheat;

Figure 28:
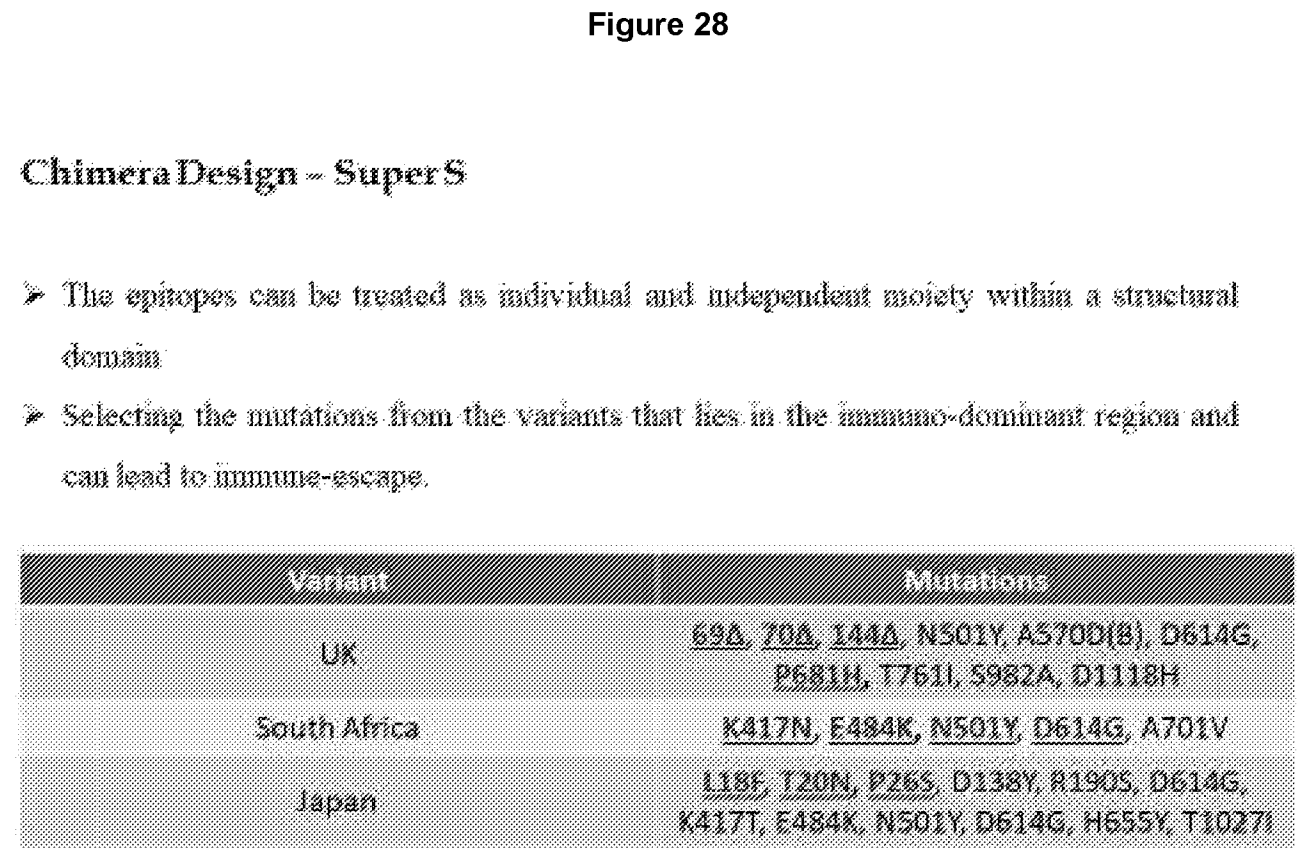

FIG. 28 explains the chimeric design of a super spike protein according to an embodiment of the invention;

FIG. 29 illustrates the positions of the mutations on a structural image of the spike protein;

FIG. 30 shows data taken from the literature, showing maximum of current variants have mutation in RBM region and the other epitopes in RBD are conserved and the antibodies against them cross-react; Boxed is the RBM. Figure D-top is the distribution of entropy. Lower the spread, better conserved in the represented sarbecoviruses. All the antibodies targeting this region show cross-neutralisation (white boxes). Black or grey boxes indicate no neutralisation;

FIGS. 31 and 32 illustrate use of the structural information to identify epitopes, and to include this in the design of S proteins of the invention, and diverting the immune response by glycosylation. FIG. 31 shows RBD sequences of SARS1 (SEQ ID NO:5), WIV16 (SEQ ID NO: 102), RaTG13 (SEQ ID NO:103), and SARS2 (SEQ ID NO:11). In FIG. 32, N1-Phylogenetically optimised design (CoV_S_T2_13) (SEQ ID NO:27), SARS2 N1 (SEQ ID NO: 104), and SARS1 N1 (SEQ ID NO:105);

FIG. 33 summarises designs according to embodiments of the invention;

FIG. 34 summarises data obtained for designs according to embodiments of the invention;

Figure 35:
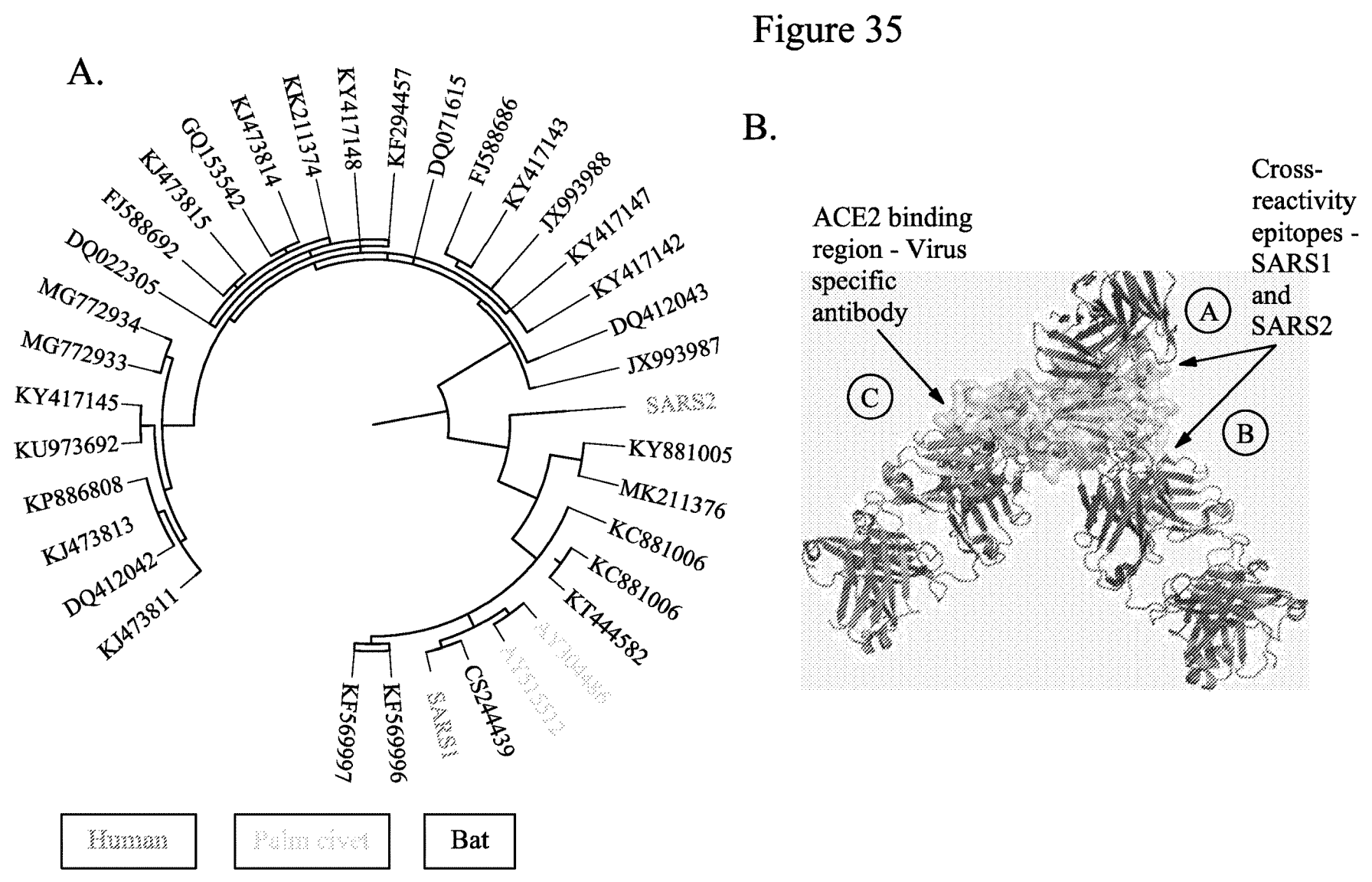
Figure 35:
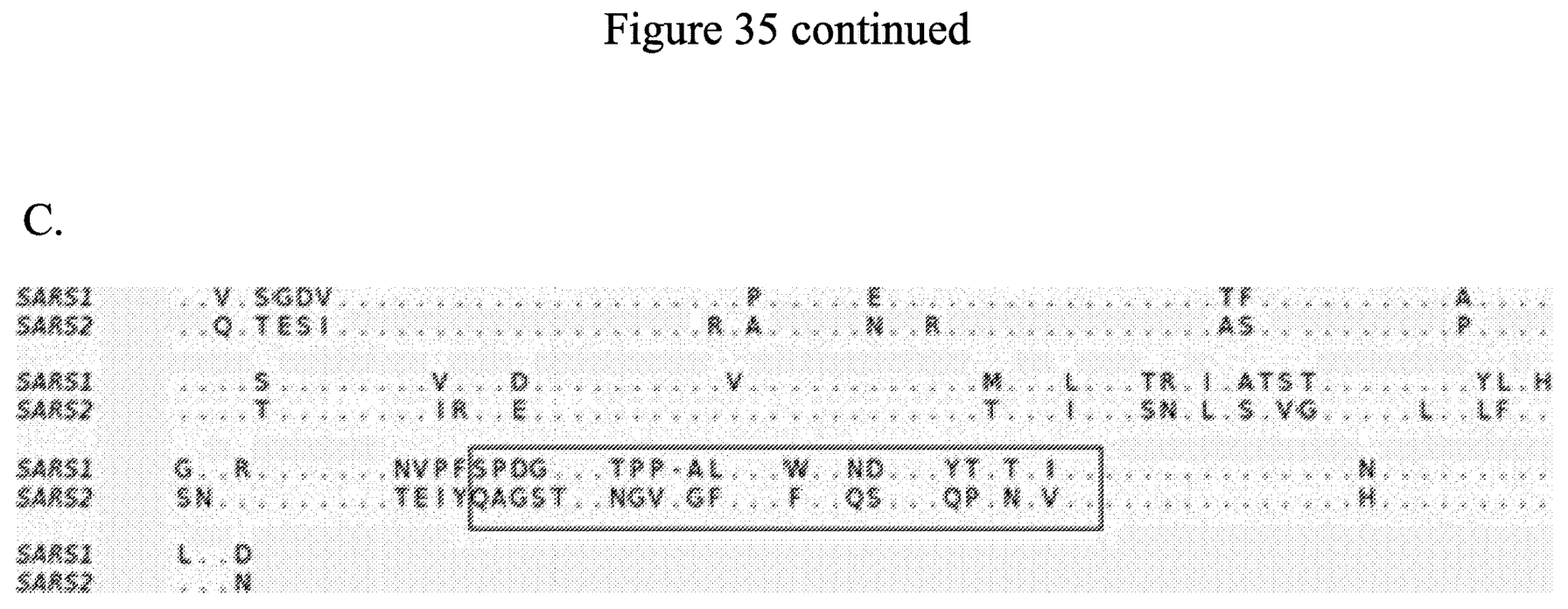

FIG. 35 In-silico design of a vaccine according to an embodiment of the invention:

A. Phylogenetic tree generated for sarbecoviruses using protein sequence of receptor binding domain (RBD) of the spike protein. The tree was generated using IQ-Tree. Human viruses are represented in green, palm civet viruses in pink and bat viruses in dark grey.

B. Structural model of the antibody-RBD complex. The antibodies are represented as cartoon and coloured green and orange and the RBD is represented as both cartoon and surface and coloured pink. The different epitope regions are labelled as A, B and C.

C. Sequence alignment of SARS-1 (SEQ ID NO:5) and SARS-2 (SEQ ID NO:11). Only the non-conserved amino acids are shown. The epitope C is boxed in black.

FIG. 36(A) shows a Western Blot of sera from mice immunised with the vaccine designs of Example 32 (COV_S_T2_13-20). FIG. 36 (B) shows antibody binding responses of Cell Surface expression bleed 2.

Figure 37:
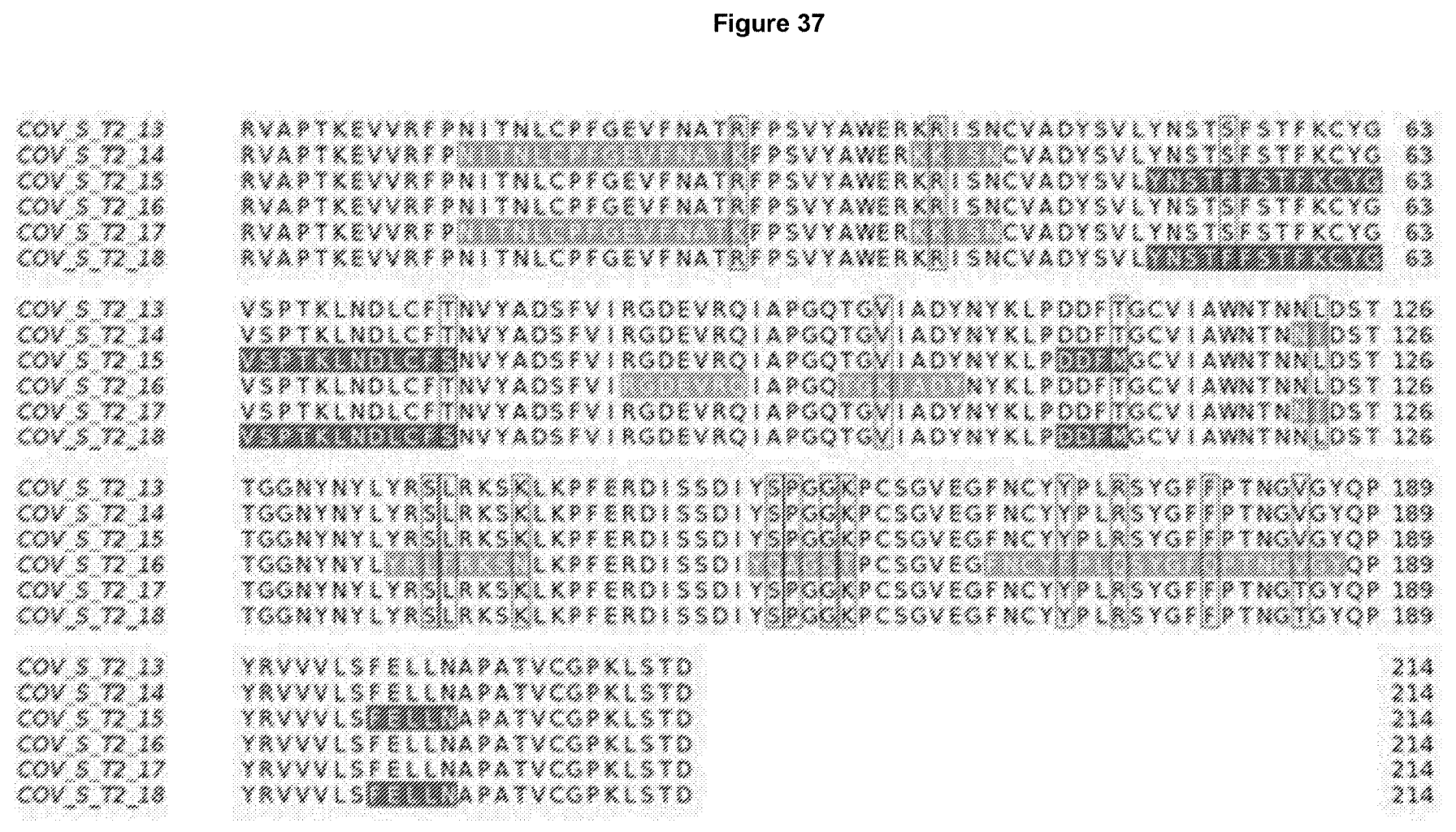

FIG. 37 Neutralisation data:

A. Sequence alignment of the vaccine designs (COV_S_T2_13-18) (SEQ ID NOS: 27-32, respectively). The epitopes are highlighted as coloured blocks. The amino acid residues differing between the designs are boxed in black.

B. Neutralisation curves of vaccine designs, SARS-1 RBD and SARS-2 RBD against SARS1 pseudotype (upper panel) and SARS2 pseudotype (lower panel). The X-axis represents the dilution of the sera and the Y-axis represent the percentage of neutralisation observed. Each curve in the plots represents an individual mouse.

Figure 38:
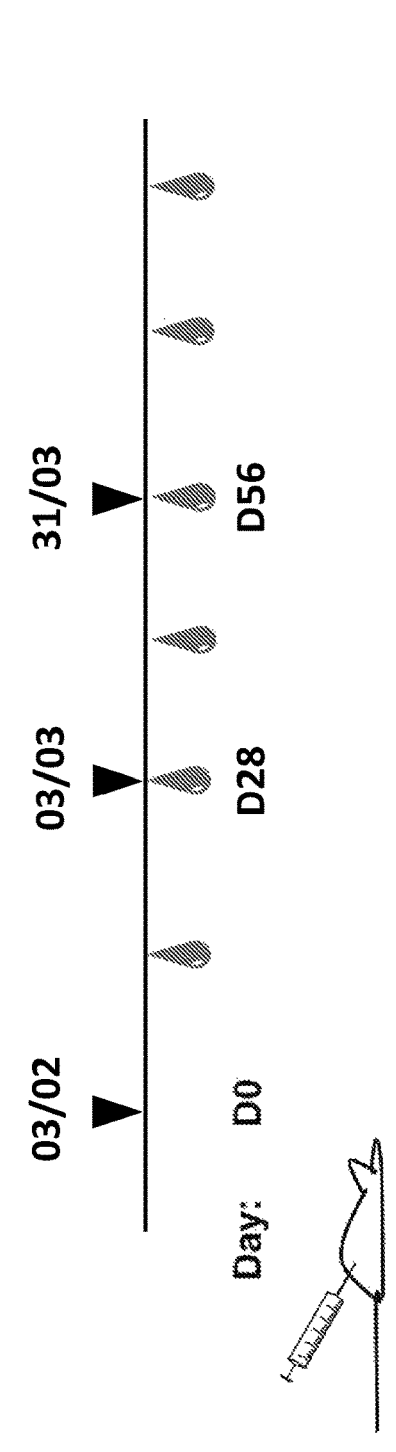
Figure 39:
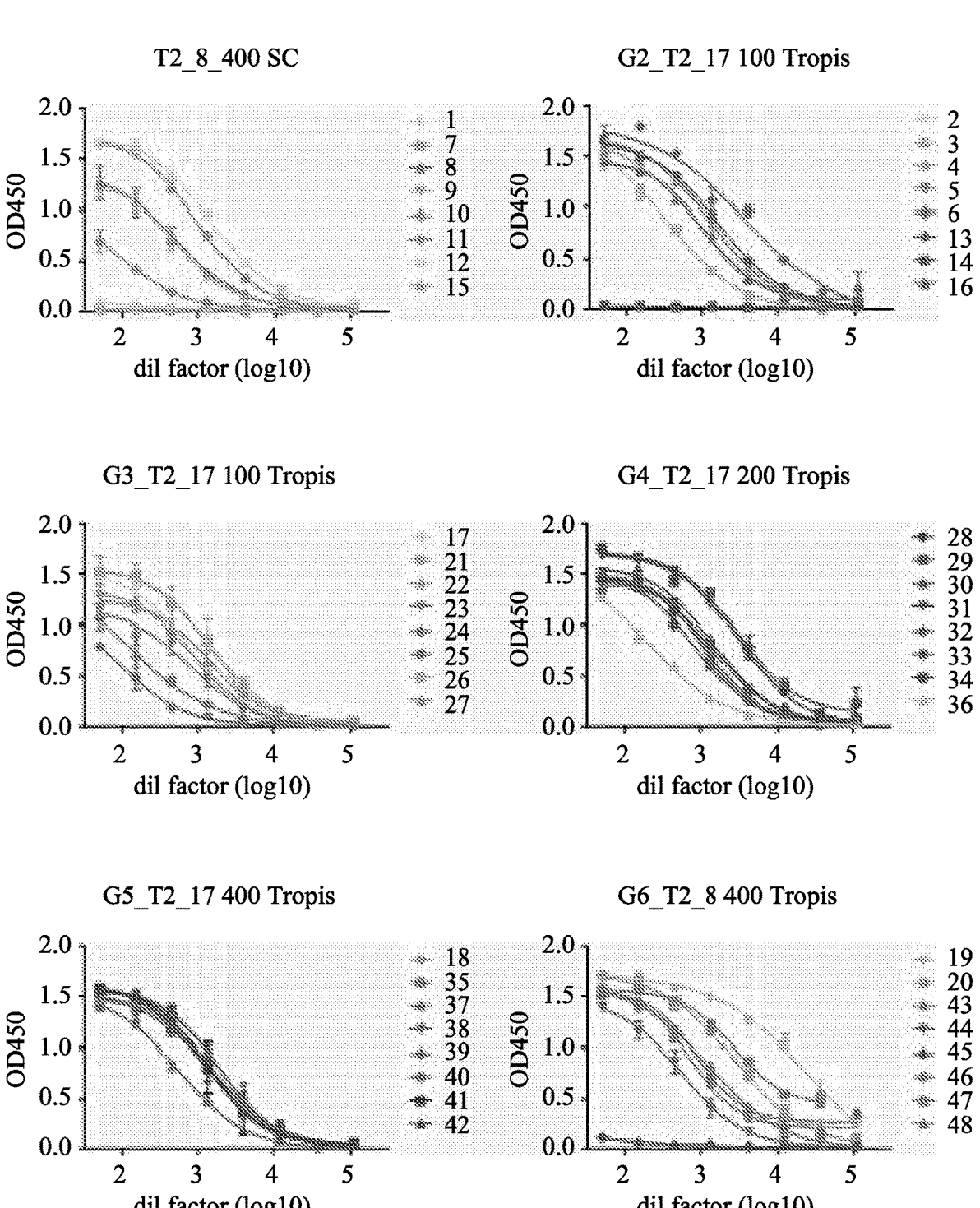
Figure 39:
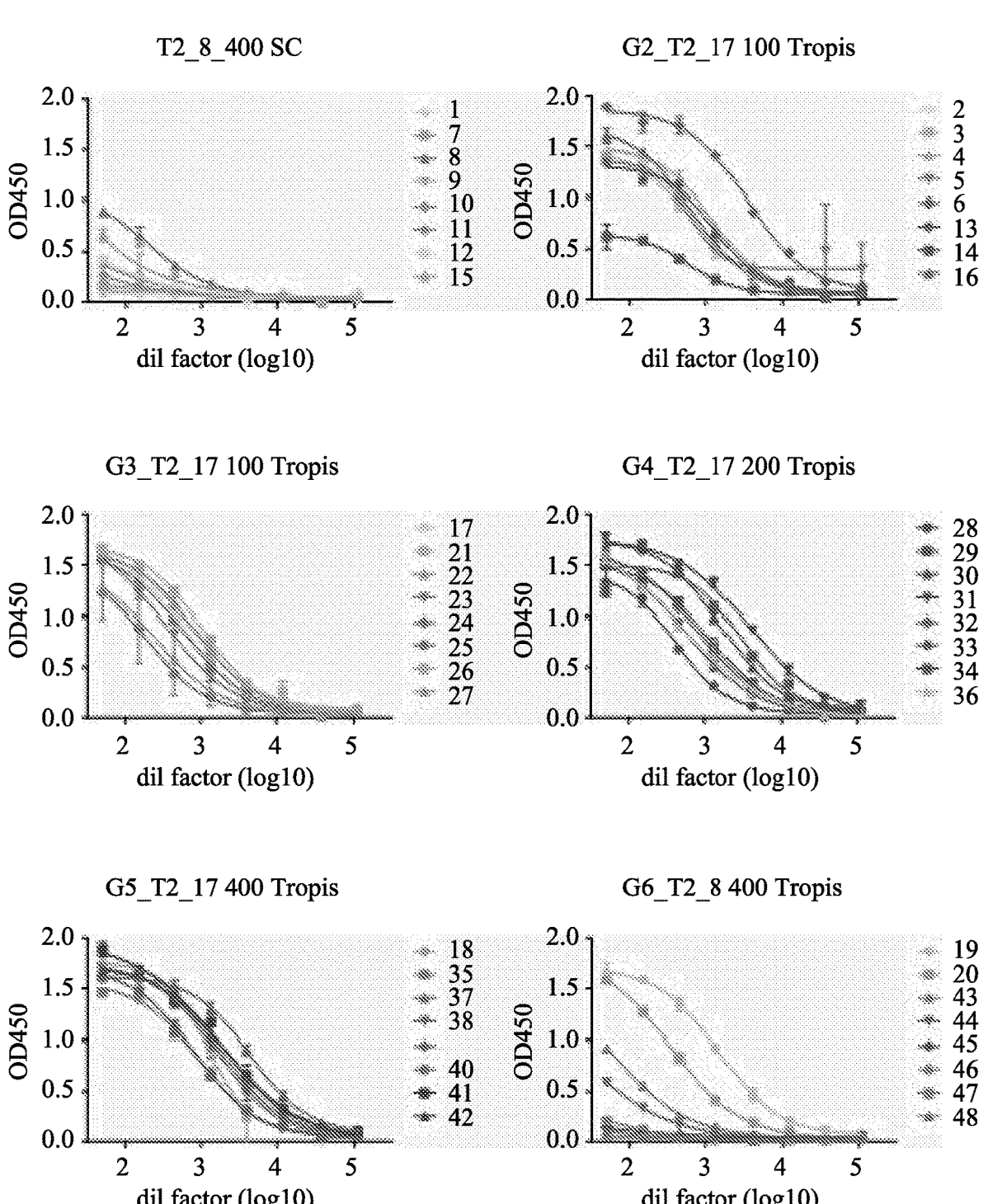

FIG. 38 represents the study protocol of a dose finding study of COV_S_T2_17 (SEQ ID NO: 31), FIG. 39 shows the results of ELISA to determine the level of antibodies to the RBD of SARS-CoV-2, and SARS. Panel A (left) Plates coated with SARS-COV-2 RBD. Panel B (right) Plates coated with SARS RBD;

FIG. 40 shows virus neutralisation at day 28 after 1 immunisation (Pseudotype MicroNeutralisation or pMN assay). Panel A (left) Antibody neutralisation of SARS-COV-2 28 days after 1 dose. Panel B (right) Antibody neutralisation of SARS 28 days after 1 dose.

FIG. 41 shows (for Groups 1, 2, and 3) comparison of virus neutralisation responses after first to second immunisation. Panel A (left SARS-COV-2) Comparing bleeds 2 (pre) and 3 (post) second immunisation (boost). Panel B (right SARS) Comparing bleeds 2 (pre) and 3 (post) second immunisation (boost).

Figure 42:

FIG. 42 shows (for groups 4, 5 and 6) comparison of virus neutralisation responses after first to second immunisation. Panel A (left SARS-COV-2) Comparing bleeds 2 (pre) and 3 (post) second immunisation (boost). Panel B (right SARS) Comparing bleeds 2 (pre) and 3 (post) second immunisation (boost); and FIG. 43 shows neutralisation of variants of concern (B1.351 (SA) & B1.248 (P1 BZ) is superior with T2_17 vs T2_8).

Figure 44A:
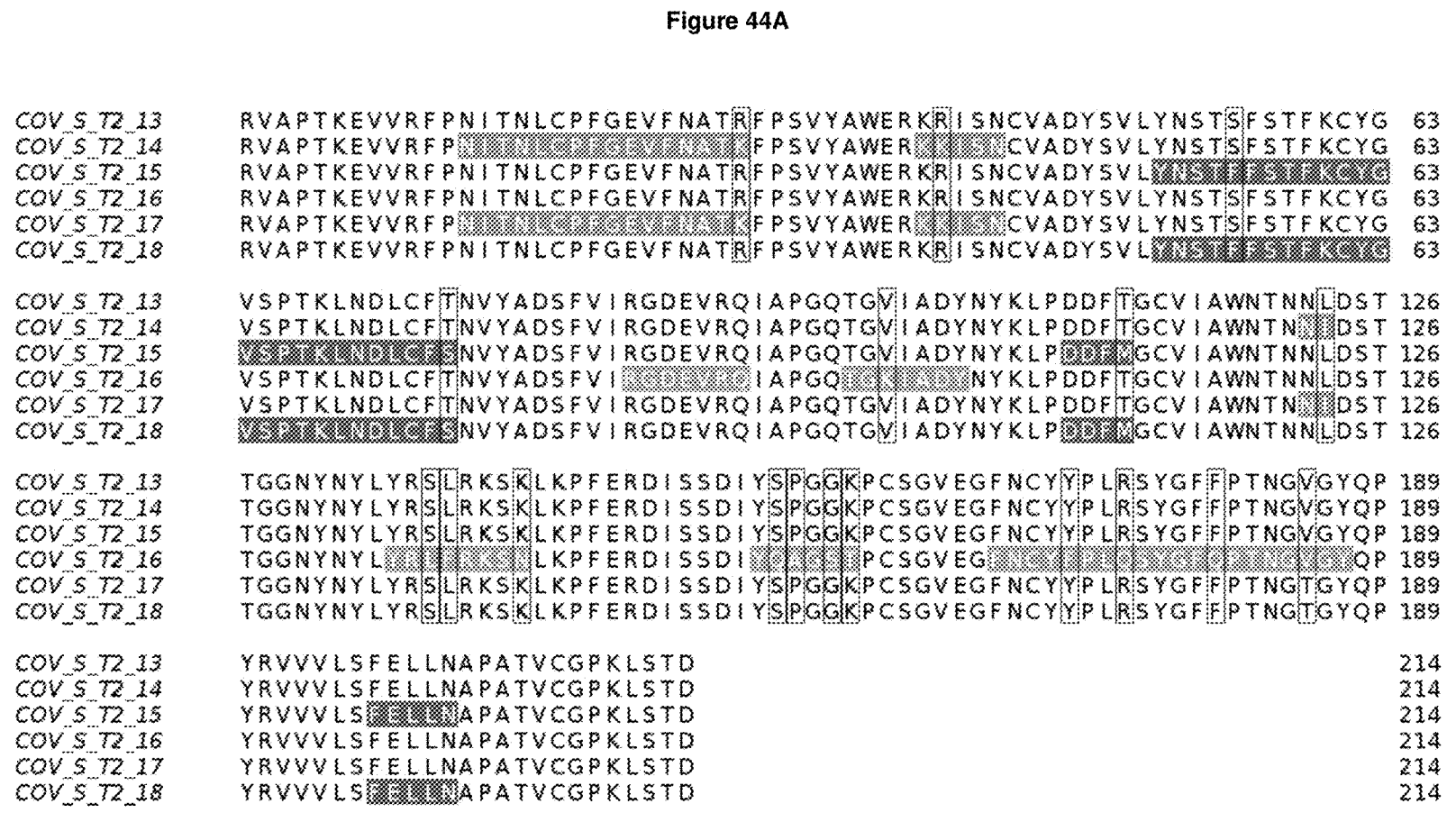

FIG. 44A shows sequence alignment of the designed S protein RBD sequences COV_S_T2_13 (SEQ ID NO: 27), COV_S_T2_14 (SEQ ID NO: 28), COV_S_T2_15 (SEQ ID NO: 29), COV_S_T2_16 (SEQ ID NO: 30), COV_S_T2_17 (SEQ ID NO:31), and COV_S_T2_18 (SEQ ID NO: 32). The coloured boxes show the residues of discontinuous epitopes present in sequences COV_S_T2_14-18 shown in different colour. The changes made relative to the COV_S_T2_13 sequence to provide discontinuous epitopes that elicit a broader or more potent immune response are shown by the boxed regions.

Figure 44B:
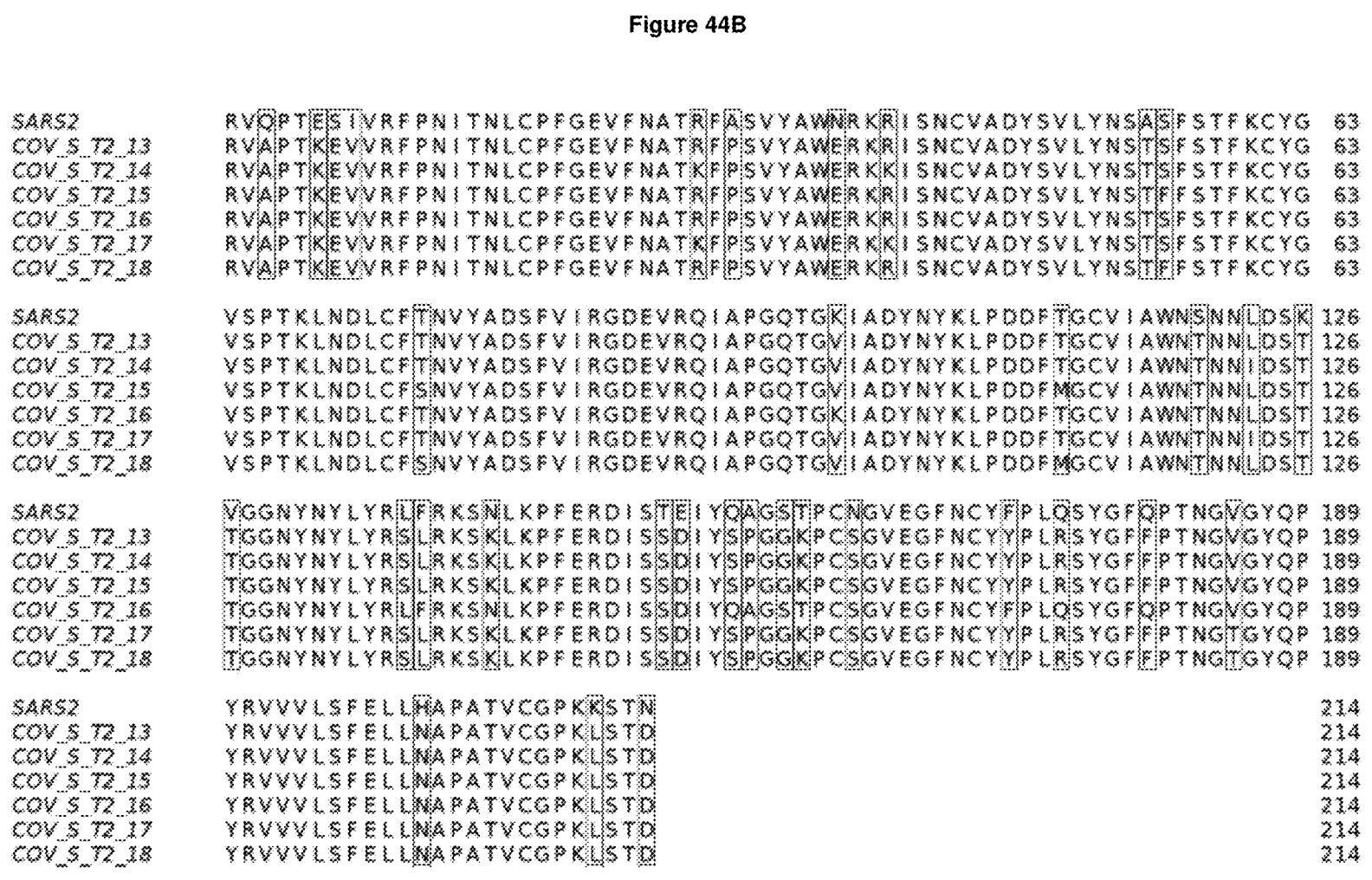

FIG. 44B shows sequence alignment of the SARS2 reference S protein RBD sequence and the designed S protein RBD sequences COV_S_T2_13 (SEQ ID NO:27), COV_S_T2_14 (SEQ ID NO:28), COV_S_T2_15 (SEQ ID NO:29), COV_S_T2_16 (SEQ ID NO:30), COV_S_T2_17 (SEQ ID NO:31), and COV_S_T2_18 (SEQ ID NO:32).

Figure 45:
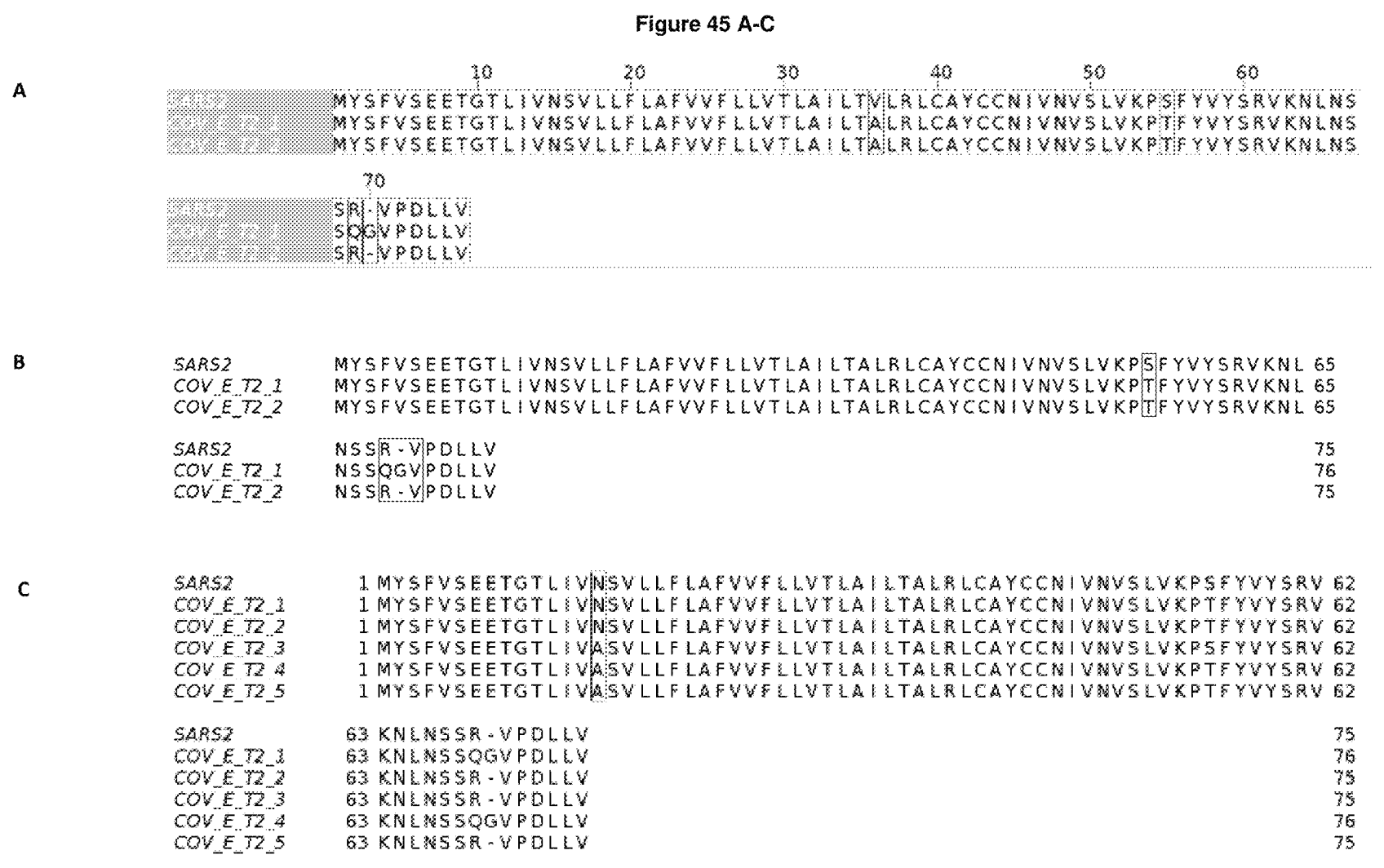

FIG. 45A shows sequence alignment of the SARS2 reference E protein sequence and the COV_E_T2_1 designed sequence (SEQ ID NO:22), and two amino acid differences between the SARS2 reference E protein sequence and the COV_E_T2_2 designed sequence (SEQ ID NO:23).

FIG. 45B shows sequence alignment of the SARS2 reference sequence as correctly shown in FIG. 7 and SEQ ID NO:21 with the designed sequences and highlights that there are three amino acid differences between the alternative SARS2 reference E protein sequence and the COV_E_T2_1 designed sequence (SEQ ID NO:22), and one amino acid difference between the SARS2 reference E protein sequence and the COV_E_T2_2 designed sequence (SEQ ID NO: 23).

FIG. 45C shows sequence alignment of the SARS2 E protein reference sequence (SEQ ID NO: 41) with the COV_E_T2_1 designed sequence (SEQ ID NO:22), the COV_E_T2_2 designed sequence (SEQ ID NO:23), the COV_E_T2_3 designed sequence (SEQ ID NO:42), the COV_E_T2_4 designed sequence (SEQ ID NO:43), and the COV_E_T2_1 designed sequence (SEQ ID NO:44).

FIG. 46 shows sequence alignment of the new M protein designs (COV_M_T2_3 (SEQ ID NO: 48), COV_M_T2_4 (SEQ ID NO: 49), COV_M_T2_5 (SEQ ID NO: 50)) with the previous M protein designs (COV_M_T1_1 (SEQ ID NO: 24), COV_M_T2_1, COV_M_T2_2 (SEQ ID NO: 25)).

FIG. 47 shows sequence alignment of the SARS2 N protein reference sequence (SEQ ID NO: 45) with the N protein designs COV_N_T2_1 1-418 Node1b 321-323 deleted (SEQ ID NO: 46) and COV_N_T2_2/1-417 epitope optimised 321-323 deleted (SEQ ID NO:47).

FIG. 48 presents the SARS2 Reference sequence (EPI_ISL_402119_RBD (COV_T2_6) (SEQ ID NO:11)) aligned with the designed SARS2 RBD design M7 (SEQ ID NO: 33), designed SARS2 RBD design M8 (SEQ ID NO: 34), designed SARS2 RBD design M9 (SEQ ID NO: 35), and designed SARS2 RBD design M10 (SEQ ID NO: 36). The dots represent no difference in amino acid residue from the reference sequence, and the dashes represent positions where amino acid residues have been inserted in the M9 and M10 sequences.

Figure 49:
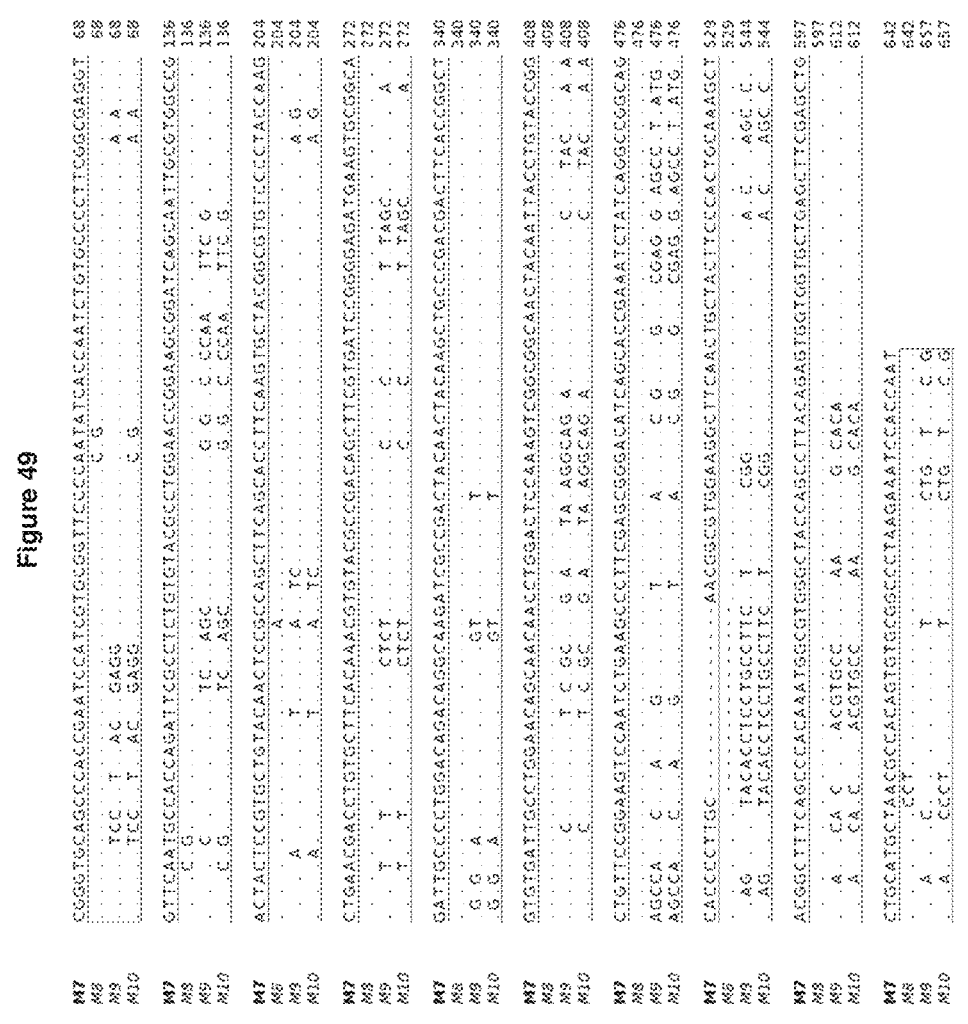

FIG. 49 shows sequence alignment of nucleotide sequences encoding the M7, M8, M9, and M10 SARS2 RBD designs discussed in Example 14 and FIG. 48. Differences between these sequences (SEQ ID NOs: 37-40, respectively) are highlighted in the alignment with the dots indicating that the nucleotide residue is the same as the corresponding SARS RBD reference nucleotide residue).

Figure 50:
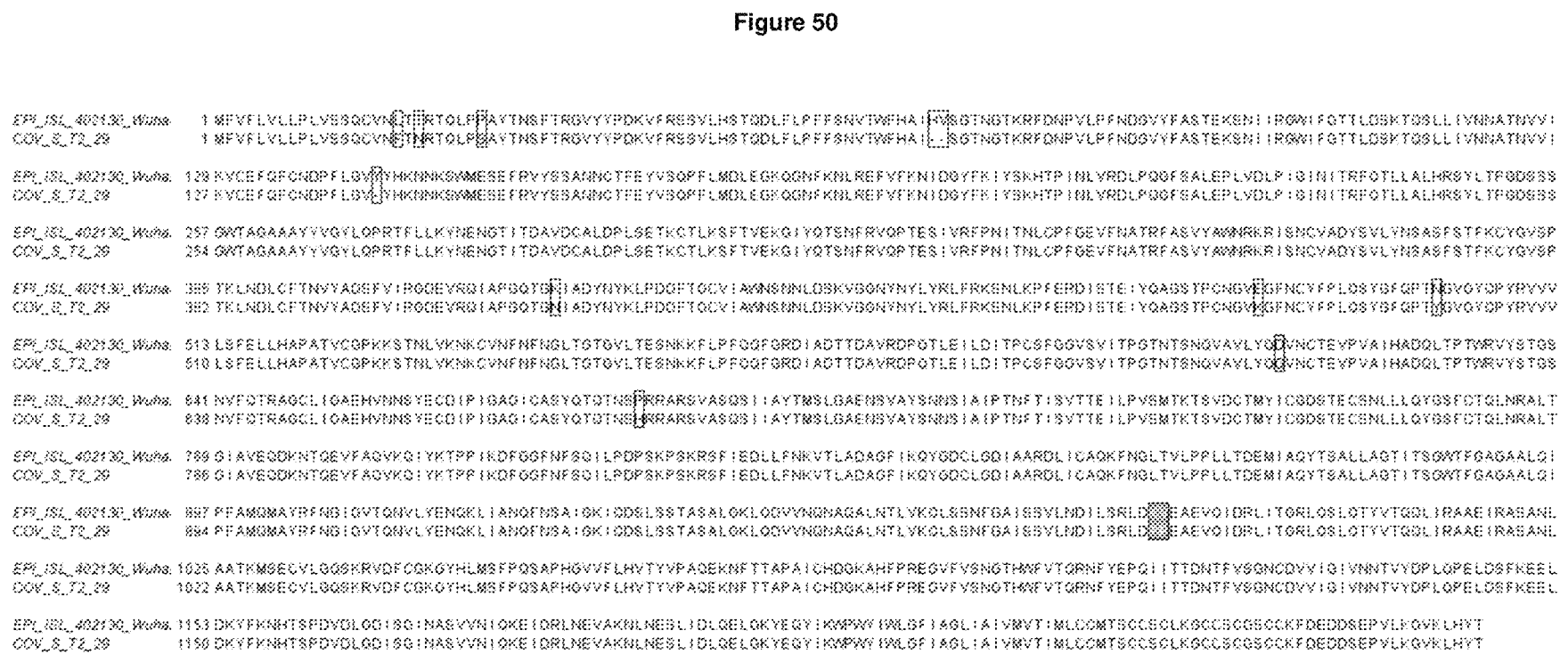

FIG. 50 shows sequence alignment of designed sequence COV_S_T2_29 (SEQ ID NO:53) and the SARS2 S protein reference sequence (EPI_ISL_402130_Wuhan strain (SEQ ID NO: 52)). The amino acid differences between the sequences are shown boxed, with the two amino acid changes made to provide structure stability shown in the shaded box.

Figure 51:
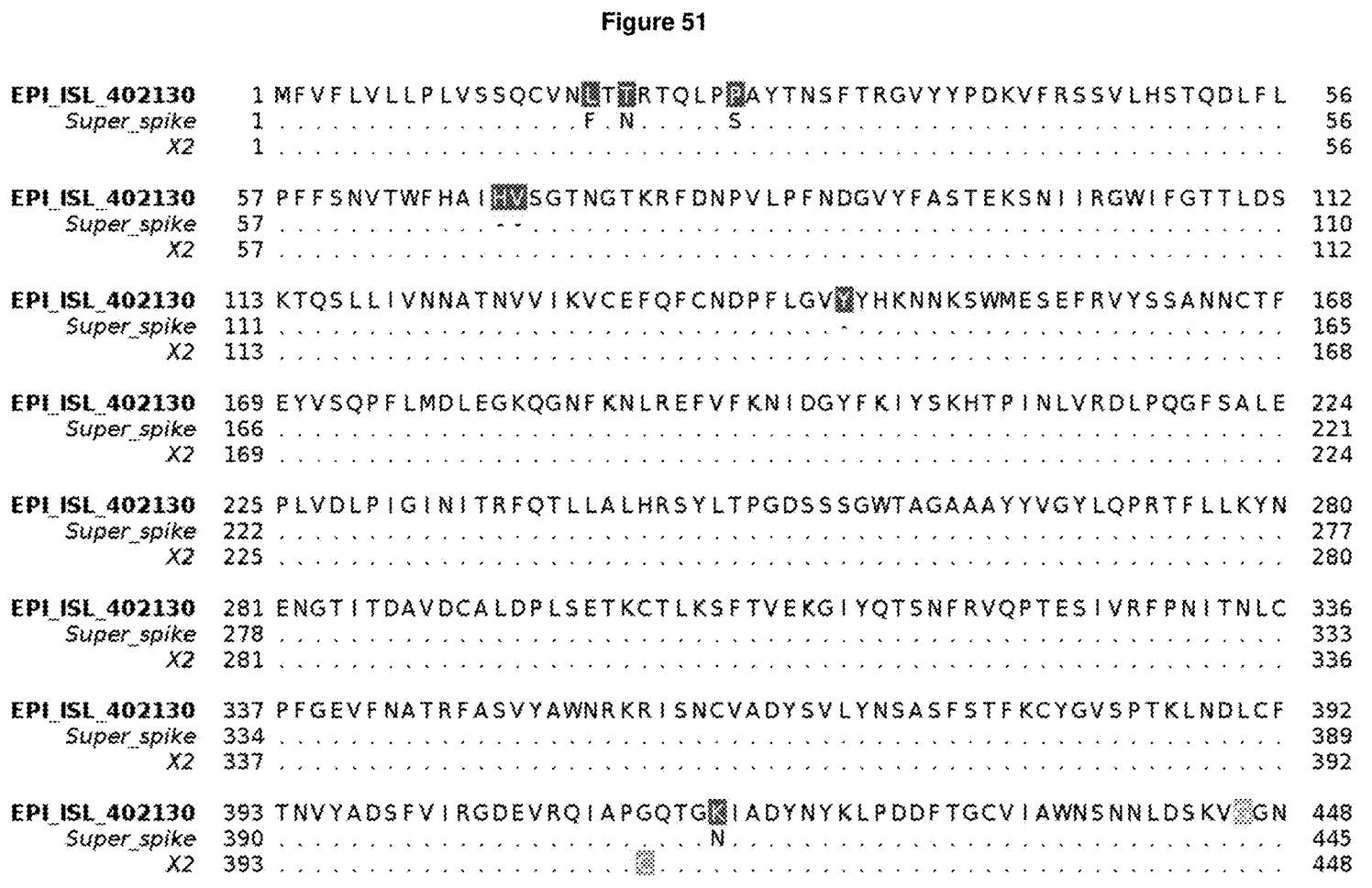

FIG. 51 shows the full-length S protein amino acid sequence of SARS_COV_2 isolate EPI_ISL_402130 (a reference sequence; SEQ ID NO:52) with the amino acid changes made for the designed S protein sequence described in Example 30 ("VOC Chimera", or COV_S_T2_29; SEQ ID NO:53), in the line referred to as "Super_spike". The line underneath the "Super_spike" sequence alignment shows the residues that may be substituted for cysteine residues to allow formation of a disulphide bridge to form a "closed S protein" (SEQ ID NO: 107). Grey shaded amino acids are amino acid residues that have been changed in the "Super-_spike" design. Dark grey shaded amino acids are amino acid residues that may be substituted for a cysteine residue to allow formation of a "closed S protein". Light grey shaded amino acids are amino acid residues that have been predicted to be mutated in future COVID-19 variants and potentially generate a vaccine escape response.

We have developed vaccines that protect against Coronaviruses, such as SARS-COV-2 and SARS-COV-1, which have the potential to cause future outbreaks from zoonotic reservoirs. We have designed antigens to induce immune responses against the Sarbecoviruses (i.e. □-Coronavirus, Lineage B) in order to protect against the current pandemic and future outbreaks of related Coronaviruses.

A major concern for coronavirus vaccines is disease enhancement (Tseng et al. (2012) "*Immunization with SARS Coronavirus Vaccines Leads to Pulmonary Immunopathol-*

US 12,691,172 B2

99

100

*ogy on Challenge with the SARS Virus*". PLOS ONE 7 (4): e35421). We have modified our antigens to avoid antibody dependant enhancement (ADE) (or ADE-like pro-inflammatory responses) and hyper-activation of the complement pathway.

DNA sequences encoding the antigens are optimised for expression in mammalian cells before inserting into a DNA plasmid expression vector, such as pEVAC. The pEVAC vector is a flexible vaccine platform and any combination of antigens can be inserted to produce a different vaccine. A previous version was used in a SARS-1 clinical trial (Martin et al, Vaccine 2008 25:633). This platform is clinically proven and GMP compliant allowing rapid scale-up. The DNA vaccine may be administered using pain-free needless technology causing patients' cells to produce the antigens, which are recognised by the immune system to induce durable protection against SARS-COV-2 and future outbreaks of related Coronaviruses.

While high affinity monoclonal antibodies are capable of protecting animals from SARS virus infection (Traggiai, et al. "*An efficient method to make human monoclonal antibodies from memory B cells: potent neutralization of SARS coronavirus*". Nat Med 10, 871-875 (2004)), a robust antibody response in early infection in humans is associated with COVID-19 disease progression (Zhao et al, medRxiv: doi.org/10.1101/2020.03.02.20030189). Importantly, after recovery from infection and re-challenge of primates with SARS, lung pathology became more severe on secondary exposure, despite limited replication of the virus (Clay et al, "*Primary Severe Acute Respiratory Syndrome Coronavirus Infection Limits Replication but Not Lung Inflammation upon Homologous Rechallenge*", J Virol. 2012 April; 86 (8): 4234-4244). There is a growing body of evidence of adverse effects of vaccine induced Antibody Dependant Enhancement (ADE) due to post-vaccination infection (Peeples, Avoiding pitfalls in the pursuit of a COVID-19 vaccine, PNAS Apr. 14, 2020 117 (15) 8218-8221). Non-neutralizing antibodies to S-protein may enable an alternative infection pathway via Fc receptor-mediated uptake (Wan et al. *Journal of Virology*. 2020, 94 (5): 1-13). These and other reports underline the importance of discriminating between viral antigen structures that induce protective anti-viral effects and those which trigger pro-inflammatory responses. Thus, careful selection and modification of vaccine antigens and the type of vaccine vector that induce protective anti-viral effects, without enhancing lung pathology, is paramount.

Vaccine sequences described herein offer safety from ADE (or ADE-like pro-inflammatory responses), and also increase the breadth of the immune response that can be extended to SARS-COV-2, SARS and related Bat Sarbeco-virus Coronaviruses, which represent future pandemic threats.

Antigens encoded by vaccine sequences described herein have precision immunogenicity, are devoid of ADE sites, and are versatile and compatible with a great number of vaccine vector technologies. DNA molecules may be delivered by PharmaJet's needless-delivery device with demonstrated immunogenicity in advanced clinical trials for other viruses and cancer, or by other DNA delivery such as electroporation or direct injection. Alternatively, the vaccine inserts can be conveniently swapped out to other viral vector, or RNA delivery platforms, which may be easily scaled for greater capacity production or to induce immune responses with different characteristics.

We have designed Coronavirus antigens to induce a highly specific immune response that not only avoids deleterious immune responses induced by the virus, but will provide broader protection, for SARS-COV-2, SARS-1 and other zoonotic Sarbeco-Coronaviruses. By using libraries of multiple antigens, we are able to down-select the optimal antigenic structures of each class (for instance RBD, E, and M proteins) and to combine the best in class to maximise the breadth of protection from Coronaviruses, by recruiting B- and T-cell responses against multiple targets.

Table of SEQ ID NOS:

| SEQ ID NO: | Description |
|---|---|
| 1 | AY274119 (CoV_T1_1): full length S-protein |
| 2 | Nucleic acid sequence encoding amino acid sequence of SEQ ID NO: 1 |
| 3 | AY274119_tr (CoV_T2_2): truncated S-protein |
| 4 | Nucleic acid sequence encoding amino acid sequence of SEQ ID NO: 3 |
| 5 | AY274119_RBD (COV_T2_5): RBD |
| 6 | Nucleic acid sequence encoding amino acid sequence of SEQ ID NO: 5 |
| 7 | EPI_ISL 402119 (CoV_T1_2): full length S-protein |
| 8 | Nucleic acid sequence encoding amino acid sequence of SEQ ID NO: 7 |
| 9 | EPI_ISL 402119_tr (CoV_T2_3): truncated S-protein |
| 10 | Nucleic acid sequence encoding amino acid sequence of SEQ ID NO: 9 |
| 11 | EPI_ISL_402119_RBD (CoV_T2_6): RBD |
| 12 | Nucleic acid sequence encoding amino acid sequence of SEQ ID NO: 11 |
| 13 | Wuhan_Node1 (CoV_T2_1): full length S-protein |
| 14 | Nucleic acid sequence encoding amino acid sequence of SEQ ID NO: 13 |
| 15 | Wuhan_Node1_tr (CoV_T2_4): truncated S-protein |
| 16 | Nucleic acid sequence encoding amino acid sequence of SEQ ID NO: 15 |
| 17 | Wuhan_Node1_RBD (CoV_T2_7): RBD |
| 18 | Nucleic acid sequence encoding amino acid sequence of SEQ ID NO: 17 |
| 19 | Sequence of pEVAC Multiple Cloning Site (MCS) |
| 20 | Entire Sequence of pEVAC |
| 21 | Amino acid sequence of the SARS envelope protein |
| 22 | COV_E_T2_1 (a designed Sarbecovirus sequence) |
| 23 | COV_E_T2_2 (a designed SARS2 sequence) |
| 24 | COV_M_T2_1/1-221 Sarbeco_M_root—Sarbecovirus root ancestor |
| 25 | COV_M_T2_2/1-222 Sarbeco_M_Node88b_epitope_optimised |
| 26 | COV_M_T1_1/1-222 NC_045512.2 SARS2 reference sequence |
| 27 | COV_S_T2_13 (designed S protein RBD sequence) |
| 28 | COV_S_T2_14 (designed S protein RBD sequence) |
| 29 | COV_S_T2_15 (designed S protein RBD sequence) |
| 30 | COV_S_T2_16 (designed S protein RBD sequence) |
| 31 | COV_S_T2_17 (designed S protein RBD sequence) |
| 32 | COV_S_T2_18 (designed S protein RBD sequence) |
| 33 | Designed S protein RBD sequence M7 |
| 34 | Designed S protein RBD sequence M8 |
| 35 | Designed S protein RBD sequence M9 |
| 36 | Designed S protein RBD sequence M10 |
| 37 | Nucleic acid sequence encoding designed S protein RBD sequence M7 |
| 38 | Nucleic acid sequence encoding designed S protein RBD sequence M8 |
| 39 | Nucleic acid sequence encoding designed S protein RBD sequence M9 |
| 40 | Nucleic acid sequence encoding designed S protein RBD sequence M10 |
| 41 | SARS2 reference E protein sequence |
| 42 | COV_E_T2_3 (SARS2_mutant) |
| 43 | COV_E_T2_4 (Env1_mutant) |
| 44 | COV_E_T2_5 (Env2_mutant) |
| 45 | YP_009724397.2/1-419 nucleocapsid phosphoprotein [SARS-COV-2] (reference sequence) |
| 46 | COV_N_T2 _1/1-418 Node1b 321-323 deleted |
| 47 | COV_N_T2_2/1-417 epitope optimised 321-323 deleted |
| 48 | COV_M_T2_3 |
| 49 | COV_M_T2_4 |
| 50 | COV_M_T2_5 |

Table of SEQ ID NOS:

| SEQ ID NO: | Description |
|---|---|
| 51 | Amino acid sequence of "Ralf RBD protein" (Leader-RBD-Tag) |
| 52 | Amino acid sequence of full length S protein for strain EPI_ISL_402130_Wuhan |
| 53 | Amino acid sequence for designed full length S protein COV_S_T2_29 ("VOC Chimera" or "Super_spike") |
| 54 | Amino acid sequence for designed full length S protein COV_S_T2_29, but with cysteine residues at positions 410 and 984 (i.e. G410C and P984C), which correspond to positions 413 and 987, respectively, of SEQ ID NO:52 |
| 55 | COV_S_T2_19 (designed S protein RBD sequence) |
| 56 | COV_S_T2_20 (designed S protein RBD sequence) |
| 57 | residues (i) of a discontinuous epitope present in COV_S_T2_14 and COV_S_T2_17: NITNLCPFGEVFNATK; |
| 58 | residues (ii) of a discontinuous epitope present in COV_S_T2_14 and COV_S_T2_17: KKISN; |
| 59 | residues (iii) of a discontinuous epitope present in COV_S_T2_14 and COV_S_T2_17: NI; |
| 60 | residues (i) of a discontinuous epitope present in COV_S_T2_15 and COV_S_T2_18: YNSTFFSTFKCYGVSPTKLNDLCFS; |
| 61 | residues (ii) of a discontinuous epitope present in COV_S_T2_15 and COV_S_T2_18: DDFM; |
| 62 | residues (iii) of a discontinuous epitope present in COV_S_T2_15 and COV_S_T2_18: FELLN; |
| 63 | residues (i) of a discontinuous epitope present in COV_S_T2_16: RGDEVRQ; |
| 64 | residues (ii) of a discontinuous epitope present in COV_S_T2_16: TGKIADY; |
| 65 | residues (iii) of a discontinuous epitope present in COV_S_T2_16: YRLFRKSN; |
| 66 | residues (iv) of a discontinuous epitope present in COV_S_T2_16: YQAGST; |
| 67 | residues (v) of a discontinuous epitope present in COV_S_T2_16: FNCYFPLQSYGFQPTNGVGY. |
| 68 | residues (i) of a discontinuous epitope present in COV_S_T2_13: NITNLCPFGEVFNATR |
| 69 | residues (ii) of a discontinuous epitope present in COV_S_T2_13: KRISN |
| 70 | residues (iii) of a discontinuous epitope present in COV_S_T2_13: NL |
| 71 | residues (i) of a discontinuous epitope present in COV_S_T2_13: YNSTSFSTFKCYGVSPTKLNDLCFT |
| 72 | residues (ii) of a discontinuous epitope present in COV_S_T2_13: DDFT |
| 73 | residues (ii) of a discontinuous epitope present in COV_S_T2_13: TGVIADY |
| 74 | residues (iii) of a discontinuous epitope present in COV_S_T2_13: YRSLRKSK |
| 75 | residues (iv) of a discontinuous epitope present in COV_S_T2_13: YSPGGK |
| 76 | residues (v) of a discontinuous epitope present in COV_S_T2_13: FNCYYPLRSYGFFPTNGVGY |
| 77 | residues (v) of a discontinuous epitope present in COV_S_T2_17, 18: FNCYYPLRSYGFFPTNGTGY |
| 78-85 | Nucleic acid encoding COV_S_T2_13-20 |
| 86 | SARS S protein—region around the S1 cleavage site |
| 87 | Beta CoV/bat/Yunnan/RaTG13/2013 S protein—region around the S1 cleavage site |
| 88 | Beta CoV/Wuhan/IVDCHB01/2019 S protein—region around the S1 cleavage site |
| 89 | Beta CoV/Wuhan/HBCDCHB01/2019 S protein—region around the S1 cleavage site |
| 90 | Beta CoV/Guangdong/20SF028/2020 S protein—region around the S1 cleavage site |
| 91 | Beta CoV/USA/IL1/2020|EPI_ISL_404253 S protein—region around the S1 cleavage site |
| 92 | Consensus—region around the S1 cleavage site |
| 93 | NL63_Alpha E protein |
| 94 | 229E_Alpha E protein |
| 95 | HKU1_Beta E protein |
| 96 | HKU1_Beta E protein |

Table of SEQ ID NOS:

| SEQ ID NO: | Description |
|---|---|
| 97 | KF600630_MERS_Beta E protein |
| 98 | Consensus E protein sequence (FIG. 7, upper) |
| 99 | Consensus E protein sequence (FIG. 7, middle) |
| 100 | Consensus E protein sequence (FIG. 7, lower) |
| 101 | M protein sequence |
| 102 | WIV16 S protein RBD |
| 103 | RaTG13 S protein RBD |
| 104 | SARS2 N1 protein |
| 105 | SARS1 N protein |
| 106 | RBD region amino acid sequence (FIG. 13) |
| 107 | SARS COV_2 isolate EPI_ISL 402130 (SEQ ID NO: 52) with residues substituted for cysteine residues to allow formation of a disulphide bridge to form a "closed S protein". |

EXAMPLE 1—VACCINE SEQUENCES

The CoV S-protein is a trimeric transmembrane glycoprotein essential for the entry of the virus particles into the host cell. The S-protein comprises two domains, the S1 domain responsible for ACE-2 receptor binding, and the S2 domain, responsible for fusion of the viral and cell membranes. The S-protein is the main target for immunisation. However, evidence has shown antibody dependent enhancement (ADE) of SARS-COV infections, in particular of the S-protein, resulting in enhanced infection and immune evasion, and/or resulting proinflammatory responses. The S-protein contains non-neutralising epitopes which are bound by antibodies. This immune diversion results in enhanced disease progression due to the inability of the immune system to neutralise the pathogen. ADE can also increase infectivity of the pathogen into host cells. Neutralising antibodies produced after an initial infection of SARS-COV may be non-neutralising to a second infection with a different SARS-COV strain.

The high genetic similarity between SARS-COV and SARS-COV-2 means that it is possible to map boundaries of the S1 and S2 domains, as well as the RBD, onto a novel design scaffold. The applicant has generated a novel sequence for an S-protein, called CoV_T2_1 (also referred to as Wuhan-Node-1), which includes modifications to improve its immunogenicity, and to remove or mask epitopes that are responsible for ADE (or ADE-like proinflammatory responses).

This example provides amino acid and nucleic acid sequences of full length S-protein, truncated S-protein (tr, missing the C-terminal part of the S2 sequence), and receptor binding domain (RBD) for:

SARS-TOR2 isolate AY274119;

SARS_COV_2 isolate-hCov-19/Wuhan/LVDC-HB-01/2019 (EPI_ISL_402119); and embodiments of the invention, termed "CoV_T2_1" (or "Wuhan_Node1").

The CoV_T2_1 (Wuhan_Node1) sequences include modifications to provide effective vaccines that induce a broadly neutralising immune response to protect against diseases caused by CoVs, especially β-CoVs, such as SARS-COV and SARS-COV-2. The vaccines also lack non-neutralising epitopes that may result in virus immune evasion and disease progression by ADE (or ADE-like pro-inflammatory responses).

The following amino acid and nucleic acid sequences are provided in this example:

SARS-TOR2 isolate AY274119:
>AY274119 (CoV_T1_1):
full length S-protein (SEQ ID NO: 1) and nucleic acid encoding full length S-protein (SEQ ID NO: 2)
>AY274119_tr (CoV_T2_2):
truncated S-protein (SEQ ID NO: 3) and nucleic acid encoding truncated S-protein (SEQ ID NO: 4)
>AY274119_RBD (COV_T2_5):
RBD (SEQ ID NO: 5) and nucleic acid encoding RBD (SEQ ID NO: 6)

SARS_COV_2 isolate - hCov-19/Wuhan/LVDC-HB-01/2019 (EPI_ISL_402119):
>EPI_ISL_402119 (CoV_T1_2):
full length S-protein (SEQ ID NO: 7) and nucleic acid encoding full length S-protein (SEQ ID NO: 8)
>EPI_ISL_402119_tr (CoV_T2_3):
truncated S-protein (SEQ ID NO: 9) and nucleic acid encoding truncated S-protein (SEQ ID NO: 10)
>EPI_ISL_402119_RBD (COV_T2_6):
RBD (SEQ ID NO: 11) and nucleic acid encoding RBD (SEQ ID NO: 12)

Sequences according to embodiments of the invention: CoV_T2_1 (Wuhan_Node1),
CoV_T2_4 (Wuhan_Node1_tr), or CoV_T2_7 (Wuhan_Node1_RBD):
>Wuhan_Node1 (CoV_T2_1):
full length S-protein (SEQ ID NO: 13) and nucleic acid encoding full length S-protein (SEQ ID NO: 14)
>Wuhan_Node1_tr (CoV_2_4):
truncated S-protein (SEQ ID NO: 15) and nucleic acid encoding truncated S-protein (SEQ ID NO: 16)
>Wuhan_Node1_RBD (CoV_T2_7):
RBD (SEQ ID NO: 17) and nucleic acid encoding RBD (SEQ ID NO:  18)

>AY274119 (CoV_T1_1)

(SEQ ID NO: 1)

Amino acid sequence:
MFIFLLFLTLTSGSDLDRCTTFDDVQAPNYTQHTSSMRGVYYPDEIFRSDTLYLTQDLFLPFYSNVTG
FHTINHTFGNPVIPFKDGIYFAATEKSNVVRGWVFGSTMNNKSQSVIIINNSTNVVIRACNFELCDNP
FFAVSKPMGTQTHTMIFDNAFNCTFEYISDAFSLDVSEKSGNFKHLREFVFKNKDGFLYVYKGYQPID
VVRDLPSGFNTLKPIFKLPLGINITNFRAILTAFSPAQDIWGTSAAAYFVGYLKPTTFMLKYDENGTI
TDAVDCSQNPLAELKCSVKSFEIDKGIYQTSNFRVVPSGDVVRFPNITNLCPFGEVFNATKFPSVYAW
ERKKISNCVADYSVLYNSTFFSTFKCYGVSATKLNDLCFSNVYADSFVVKGDDVRQIAPGQTGVIADY
NYKLPDDFMGCVLAWNTRNIDATSTGNYNYKYRLRHGKLRPFERDISNVPFSPDGKPCTPPALNCYW
PLNDYGFYTTTGIGYQPYRVVVLSFELLNAPATVCGPKLSTDLIKNQCVNFNFNGLTGTGVLTPSSKR
FQPFQQFGRDVSDFTDSVRDPKTSEILDISPCAFGGVSVITPGTNASSEVAVLYQDVNCTDVSTAIHA
DQLTPAWRIYSTGNNVFQTQAGCLIGAEHVDTSYECDIPIGAGICASYHTVSLLRSTSQKSIVAYTMS
LGADSSIAYSNNTIAIPTNFSISITTEVMPVSMAKTSVDCNMYICGDSTECANLLLQYGSFCTQLNRA
LSGIAAEQDRNTREVFAQVKQMYKTPTLKYFGGFNFSQILPDPLKPTKRSFIEDLLFNKVTLADAGFM
KQYGECLGDINARDLICAQKFNGLTVLPPLLTDDMIAAYTAALVSGTATAGWTFGAGAALQIPFAMQM
AYRFNGIGVTQNVLYENQKQIANQFNKAISQIQESLTTTSTALGKLQDVVNQNAQALNTLVKQLSSNF
GAISSVLNDILSRLDKVEAEVQIDRLITGRLQSLQTYVTQQLIRAAEIRASANLAATKMSECVIGQSK
RVDFCGKGYHLMSFPQAAPHGVVFLHVTYVPSQERNFTTAPAICHEGKAYFPREGVFVFNGTSWFITQ
RNFFSPQIITTDNTFVSGNCDVVIGIINNTVYDPLQPELDSFKEELDKYFKNHTSPDVDLGDISGINA
SVVNIQKEIDRINEVAKNLNESLIDLQELGKYEQYIKWPWYVWLGFIAGLIAIVMVTILLCCMTSCCS
CLKGACSCGSCCKFDEDDSEPVLKGVKLHYT >AY274119 (CoV_T1_1)

(SEQ ID NO: 2)

Nucleic acid sequence:
atgtttatctttctgctgtttctgaccctgaccagcggcagcgacctggatagatgcacc
accttcgacgatgtgcaggcccctaactacacccagcacaccagctctatgcggggcgtg
tactaccccgacgagattttcagaagcgacaccctgtatctgacccaggacctgttcctg
cctttctacagcaacgtgaccggcttccacaccatcaaccacaccttcggcaaccctgtg
atcccctttcaaggacggcatctactttgccgccaccgagaagtccaacgtcgtcagagga
tgggtgttcggcagcaccatgaacaacaagagccagagcgtgatcatcatcaacaacagc
accaacgtggtcatccgggcctgcaacttcgagctgtgcgacaacccattcttcgccgtg
tccaagcctatgggcacccagacacacaccatgatcttcgacaacgccttcaactgcacc
ttcgagtacatcagcgacgccttcagcctggacgtgtccgaaaagagcggcaacttcaag
cacctgagggaattcgtgttcaagaacaaggatggcttcctgtacgtgtacaagggctac
cagcctatcgacgtcgtgcgggatctgcccagcggcttcaataccctgaagcctatcttc
aagctgcccctgggcatcaacatcaccaacttcagagccattcgtgggctacctgaagccaacc
gctcaggatatctggggaacaagcgccgctgcctacttcgtgggctacctgaagccaacc
accttcatgctgaagtacgacgagaacggcaccatcaccgacgccgtggactgtagccaa
aatcctctggccgagctgaagtgcagcgtgaagtccttcgagatcgacaagggcatctac
cagaccagcaatttcagagtggtgccctccggggatgtcgtgcggttcccaacatcaca
aatctgtgcccctcggcgaggtgttcaacgccaccaagtttccctctgtgtacggctgg
gagcgcaaaaagatcagcaactgcgtggccgactacagcgtgctgtacaactccacttc
ttcagcacctcaagtgctacggcgtgtccgccacaaagctgaacgacctgtgcttctcc
aacgtgtacgccgacagcttcgtggtcaaaggcgacgacgttcggcagattgccctgga
caaacaggcgtgatcgccgattacaactacaagctgcctgacgacttcatgggctgcgtg -continued

```
ctggcctggaacaccagaaacatcgatgccacctccaccggcaactacaattacaagtac
agatacctgcggcacggcaagctgcggcctttcgagagggatatcagcaatgtgccttt
agccccgacggcaagccctgcacacctcctgctctgaattgctactggcccctgaacgac
tacggcttttacaccaccacaggcatcggctatcagccctatagagtggtggtcctgtcc
tttgagctgctgaatgcccctgccacagtgtgcggacctaagctgtctaccgacctgatc
aagaaccagtgcgtgaacttcaacttcaacggcctgaccggcaccggcgtgctgacacca
agcagcaagagattccagcctttccagcagttcggccgggatgtgtccgacttcacagac
agcgtcagagatcccaagaccagcgagatcctggacatcagcccttgtgcctttggcgga
gtgtccgtgatcacccctggcacaaatgcctctagcgaagtggccgtgctgtatcaggac
gtgaactgcaccgatgtgtccaccgccattcacgccgatcagctgactcccgcttggcgg
atctatagcacaggcaacaacgtgttccagacacaagccggctgtctgatcggagccgag
catgtggataccagctacgagtgcgacatccctatcggcgctggcatctgtgcctcttac
cacaccgtgtctctgctgcggagcaccagccagaaatccatcgtggcctacaccatgagc
ctgggcgccgattcttctatcgcctactccaacaacacaatcgctatccccaccaatttc
agcatctccatcaccaccgaagtgatgcccgtgtccatggccaagacctccgtggattgc
aacatgtacatctgcggcgacagcaccgagtcgcgccaatctgctgctccagtacggcagc
ttctgcacccagctgaatagagccctgtctggaattgccgccgagcaggacagaaacacc
agagaagtgttcgcccaagtgaagcagatgtataagaccccgacactcaagtacttcggc
gggttcaacttctcccagatcctgcctgatcctctgaagcccaccaagcggagcttcatc
gaggacctgctgttcaacaaagtgaccctggccgacgccggctttatgaagcagtatggc
gagtgcctgggcgacatcaacgccagggatctgatttgcgcccagaagtttaacggactg
accgtgctgcctcctctgctgaccgatgatatgatcgccgctaccgccctcacagccgctctggtg
tctggtacagctaccgccggatggacatttggagctggcgccgctctccagattccattc
gctatgcagatggcctaccggttcaacggcatcggagtgacccagaatgtgctgtacgag
aatcagaagcagatcgccaatcagttcaacaaggccatcagccagatccaagagagcctg
accaccacaagcacagccctgggaaagctccaggacgtggtcaaccagaatgctcaggcc
ctgaacaccctggtcaagcagctgagcagcaacttcggcgccatcagctccgtgctgaat
gacatcctgagccggctggacaaggtggaagcagaggtgcagatcgaccggctgatcaca
ggcagactccagagcctccagacctacgtgacacagcagctgatcagagccgccgagatt
agagcctctgccaatctggccgccaccaaaatgagcgagtgtgtccctgggccagagcaag
agagtggactttgcggcaagggctatcacctgatgagcttcccacagccgctcctcat
ggcgtggtctttctgcacgtgacatacgtgcccagccaagagagaaacttcaccaccgct
ccagccatctgccacgagggcaaagcctactttcccagagaaggcgtgttcgtgtttaac
ggcacctcctggtttatcacccagcggaatttcttcagcccgcaaatcatcaccacagac
aacaccttcgtgtccggcaactgtgacgtcgtgatcggcatcattaacaataccgtgtac
gaccctctccagcctgagctggacagcttcaaagaggaactggataagtacttcaagaat
cacacgagccccgatgtggaccctgggcgatatctctggcatcaatgccagcgtcgtgaac
atccagaaagagattgacaggctgaacgaggtggccaagaacctgaacgagtccctgatc
gacctgcaagagctggggaagtacgagcagtacatcaagtggccttggtacgtgtggcgg
ggctttatcgccggactgatcgccatcgtgatggtcaccatcctgctgtgctgcatgacc
agctgttgcagctgtctgaagggcgcctgtagctgtggctcctgctgcaagttcgatgag
gacgactctgagccagtgctgaaaggcgtgaagctgcactacacc
```

>AY274119_tr (CoV_T2_2)
                                                                                    (SEQ ID NO: 3)
Amino acid sequence:
MFIFLLFLTLTSGSDLDRCTTFDDVQAPNYTQHTSSMRGVYYPDEIFRSDTLYLTQDLFLPFYSNVTG
FHTINHTFGNPVIPFKDGIYFAATEKSNVVRGWVFGSTMNNKSQSVIIINNSTNVVIRACNFELCDNP
FFAVSKPMGTQTHTMIFDNAFNCTFEYISDAFSLDVSEKSGNFKHLREFVFKNKDGFLYVYKGYQPID
VVRDLPSGFNTLKPIFKLPLGINITNFRAILTAFSPAQDIWGTSAAAYFVGYLKPTTFMLKYDENGTI
TDAVDCSQNPLAELKCSVKSFEIDKGIYQTSNFRVVPSGDVVRFPNITNLCPFGEVFNATKFPSVYAW
ERKKISNCVADYSVLYNSTFFSTFKCYGVSATKLNDLCFSNVYADSFVVKGDDVRQIAPGQTGVIADY
NYKLPDDFMGCVLAWNTRNIDATSTGNYNYKYRYLRHGKLRPFERDISNVPFSPDGKPCTPPALNCYW
PLNDYGFYTTTGIGYQPYRVVVLSFELLNAPATVCGPKLSTDLIKNQCVNFNFNGLTGTGVLTPSSKR
FQPFQQFGRDVSDFTDSVRDPKTSEILDISPCAFGGVSVITPGTNASSEVAVLYQDVNCTDVSTAIHA
DQLTPAWRIYSTGNNVFQTQAGCLIGAEHVDTSYECDIPIGAGICASYHTVSLLRSTSQKSIVAYTMS
LGADSSIAYSNNTIAIPTNFSISITTEVMPVSMAKTSVDCNMYICGDSTECANLLLQYGSFCTQLNRA
LSGIAAEQDRNTREVFAQVKQMYKTPTLKYFGGFNFSQILPDPLKPTKRSFIEDLLFNKVTLADAGFM
KQYGECLGDINARDLICAQKFNGLTVLPPLLTDDMIAAYTAALVSGTATAGWTFGAGAALQIPFAMQM
AYRFNGIGVTQNVLYENQKQIANQFNKAISQIQESLTTTSTALGKLQDVVNQNAQALNTLVKQLSSNF
GAISSVLNDILSRLDKVEAEVQIDRLITGRLQSLQTYVTQQLIRAAEIRASANLAATKMSECVLGQSK
RVDFCGKGYHLMSFPQAAPHGVVFLHVTYVPSQERNFTTAPAICHEGKAYFPREGVFVFNGTSWFITQ
RNFFSPQIITTDNTFVSGNCDVVIGIINNTVYDPLQPELDSFKEELDKYFKNHTSPDVDLGDIS >AY274119_tr(CoV_T2_2)
                                                                                    (SEQ ID NO: 4)
Nucleic acid sequence:
```
atgtttatctttctgctgtttctgaccctgaccagcggcagcgacctggatagatgcacc
accttcgacgatgtgcaggcccctaactacacccagcacaccagctctatgcggggcgtg
tactaccccgacgagattttcagaagcgacacccgtatctgacccaggacctgttcctg
cctttctacagcaacgtgaccggcttccacaccatcaaccacaccttcggcaaccctgtg
atcccctcaaggacggcatctactttgcgccaccgagaagtccaacgtcgtcagagga
tgggtgttcggcagcaccatgaacaacaagagccagagcgtgatcatcatcaacaacagc
accaacgtggtcatccgggcctgcaacttcgagctgtgcgacaacccattcttcgccgtg
tccaagcctatgggcacccagacacacaccatgatcttcgacaacgccttcaactgcacc
ttcgagtacatcagcgacgccttcagcctggacgtgtccgaaaagagcggcaacttcaag
cacctgagggaattcgtgttcaagaacaaggatggcttcctgtacgtgtacaagggctac
cagcctatcgacgtcgtgcgggatctgcccagcggcttcaataccctgaagcctatcttc
aagctgcccctgggcatcaacatcaccaacttcagagccatcctgaccgctttcagcccc
gctcaggatatctggggaacaagcgccgctgcctacttcgtgggctacctgaagccaacc
accttcatgctgaagtacgacgagaacggcaccatcaccgacgccgtggactgtagccaa
```

-continued

```
aatcctctggccgagctgaagtgcagcgtgaagtccttcgagatcgacaagggcatctac
cagaccagcaatttcagagtggtgccctccggggatgtcgtgcggttccccaacatcaca
aatctgtgcccctcggcgaggtgttcaacgccaccaagtttccctctgtgtacgcctgg
gagcgcaaaaagatcagcaactgcgtggccgactacagcgtgctgtacaactccaccttc
ttcagcaccttcaagtgctacggcgtgtccgccacaaagctgaacgacctgtgcttctcc
aacgtgtacgccgacagcttcgtggtcaaaggcgacgacgttcggcagattgcccctgga
caaacaggcgtgatcgccgattacaactacaagctgcctgacgacttcatgggctgcgtg
ctggcctggaacaccagaaacatcgatgccacctccaccggcaactacaattacaagtac
agatacctgcggcacggcaagctgcggcctttcgagagggatatcagcaatgtgccttttt
agccccgacggcaagccctgcacacctcctgctctgaattgctactggcccctgaacgac
tacggcttttacaccaccacaggcatcggctatcagccctatagagtggtggtcctgtcc
tttgagctgctgaatgcccctgccacagtgtgcggacctaagctgtctaccgacctgatc
aagaaccagtgcgtgaacttcaacttcaacggcctgaccggcaccggcgtgctgacacca
agcagcaagagattccagcctttccagcagttcggccgggatgtgtccagacttcacagac
agcgtcagagatcccaagaccagcgagatcctggacatcagcccttgtgcctttggcgga
gtgtccgtgatcacccctggcacaaatgcctctagcgaagtggccgtgctgtatcaggac
gtgaactgcaccgatgtgtccaccgccattcacgccgatcagctgactcccgcttggcgg
atctatagcacaggcaacaacgtgttccagacacaagccggctgtctgatcggagccgag
catgtggataccagctacgagtgcgacatccctatcggcgctggcatctgtgcctcttac
cacaccgtgtctctgctgcggagcaccagccagaaatccatcgtggcctacaccatgagc
ctgggcgccgattcttctatcgcctactccaacaacacaatcgctatccccaccaatttc
agcatctccatcaccaccgaagtgatgcccgtgtccatggccaagacctccgtggattgc
aacatgtacatctgcggcgacagcaccgagtgcgccaatctgctgctccagtacggcagc
ttctgcacccagctgaatagagccctgtctggaattgccgccgagcaggacagaaacacc
agagaagtgttcgcccaagtgaagcagatgtataagaccccgacactcaagtacticggc
gggttcaacttctcccagatcctgcctgatcctctgaagcccaccaagcggagcttcatc
gaggacctgctgttcaacaaagtgaccctggccgacgccggctttatgaagcagtatggc
gagtgcctgggcgacatcaacgccagggatctgatttgcgcccagaagtttaacggactg
accgtgctgcctcctctgctgaccgatgatatgatcgccgcctacacagccgctctggtg
tctggtacagctaccgccggatggacatttggagctggcgccgctctccagattccattc
gctatgcagatggcctaccggttcaacggcatcggagtgacccagaatgtgctgtacgag
aatcagaagcagatcgccaatcagttcaacaaggccatcagccagatccaagagagcctg
accaccacaagcacagccctgggaaagctccaggacgtggtcaaccagaatgctcaggcc
ctgaacaccctggtcaagcagctgagcagcaacttcggcgccatcagctccgtgctgaat
gacatcctgagccggctggacaaggtggaagcagaggtgcagatcgaccggctgatcaca
ggcagactccagagcctccagacctacgtgacacagcagctgatcagagccgccgagatt
agacctctgccaatctggccgccaccaaaatgagcgagtgtgtcctgggccagagcaag
agagtggacttttgcggcaagggctatcacctgatgagcttcccacaggccgctcctcat
ggcgtggtcttctgcacgtgacatacgtgcccagccaagagagaaacttcaccaccgct
ccagccatctgccacgagggcaaagcctactttcccagagaaggcgtgttcgtgtttaac
ggcacctcctggtttatcacccagcggaatttcttcagcccgcaaatcatcaccacagac
aacaccttcgtgtccggcaactgtgacgtcgtgatcggcatcattaacaataccgtgtac
gaccctctccagcctgagctggacagcttcaaagaggaactggataagtacttcaagaat
cacacgagccccgatgtggacctgggggatatctct
```

>AY274119_RBD (CoV_T2_5)

(SEQ ID NO: 5)

Amino acid sequence:
RVVPSGDVVRFPNITNLCPPGEVFNATKFPSVYAWERKKISNCVADYSVLYNSTFFSTFKCYGVSATK
LNDLCFSNVYADSFVVKGDDVRQIAPGQTGVIADYNYKLPDDFMGCVLAWNTRNIDATSTGNYNYKYR
YLRHGKLRPFERDISNVPFSPDGKPCTPPALNCYWPLNDYGFYTTTGIGYQPYRVVVLSFELLNAPAT
VCGPKLSTD >AY274119_RBD (CoV_T2_5)

(SEQ ID NO: 6)

Nucleic acid sequence:
agagtggtgccctccggggatgtcgtgcggttccccaacatcacaaatctgtgcccctc
ggcgaggtgttcaacgccaccaagtttccctctgtgtacgcctgggagcgcaaaaagatc
agcaactgcgtggccgactacagcgtgctgtacaactccaccttcttcagcaccttcaag
tgctacggcgtgtccgccacaaagctgaacgacctgtgcttctccaacgtgtacgccgac
agcttcgtggtcaaaggcgacgacgttcggcagattgcccctggacaaacaggcgtgatc
gccgattacaactacaagctgcctgacgacttcatgggctgcgtgctggcctggaacacc
agaaacatcgatgccacctccaccggcaactacaattacaagtacagatacctgcggcac
ggcaagctgcggcctttcgagagggatatcagcaatgtgcctttttagccccgacggcaag
ccctgcacacctcctgctctgaattgctactggcccctgaacgactacggcttttacacc
accacaggcatcggctatcagccctatagagtggtggtcctgtcctttgagctgctgaat
gcccctgccacagtgtgcggacctaagctgtctaccgac AY274119 (full length S protein amino acid sequence, with RBD
residues shown in bold, and residues not present in truncated S
protein shown underlined)

(SEQ ID NO: 1)

```
MFIFLLFLTL  TSGSDLDRCT  TFDDVQAPNY  TQHTSSMRGV  YYPDEIFRSD  TLYLTQDLFL       60
PFYSNVTGFH  TINHTFGNPV  IPFKDGIYFA  ATEKSNVVRG  WVFGSTMNNK  SQSVIIINNS      120
TNVVIRACNF  ELCDNPFFAV  SKPMGTQTHT  MIFDNAFNCT  FEYISDAFSL  DVSEKSGNFK      180
HLREFVFKNK  DGFLYVYKGY  QPIDVVRDLP  SGFNTLKPIF  KLPLGINITN  FRAILTAFSP      240
AQDIWGTSAA  AYFVGYLKPT  TFMLKYDENG  TITDAVDCSQ  NPLAELKCSV  KSFEIDKGIY      300
QTSNFRVVPS  GDVVRFPNIT  NLCPFGEVFN  ATKFPSVYAW  ERKKISNCVA  DYSVLYNSTF      360
FSTFKCYGVS  ATKLNDLCFS  NVYADSFVVK  GDDVRQIAPG  QTGVIADYNY  KLPDDFMGCV      420
LAWNTRNIDA  TSTGNYNYKY  RYLRHGKLRP  FERDISNVPF  SPDGKPCTPP  ALNCYWPLND      480
YGFYTTTGIG  YQPYRVVVLS  FELLNAPATV  CGPKLSTDLI  KNQCVNFNFN  GLTGTGVLTP      540
```

-continued

```
SSKRFQPFQQ FGRDVSDFTD SVRDPKTSEI LDISPCAFGG VSVITPGTNA SSEVAVLYQD        600
VNCTDVSTAI HADQLTPAWR IYSTGNNVFQ TQAGCLIGAE HVDTSYECDI PIGAGICASY        660
HTVSLLRSTS QKSIVAYTMS LGADSSIAYS NNTIAIPTNF SISITTEVMP VSMAKTSVDC        720
NMYICGDSTE CANLLLQYGS FCTQLNRALS GIAAEQDRNT REVFAQVKQM YKTPTLKYFG        780
GFNFSQILPD PLKPTKRSFI EDLLFNKVTL ADAGFMKQYG ECLGDINARD LICAQKFNGL        840
TVLPPLLTDD MIAAYTAALV SGTATAGWTF GAGAALQIPF AMQMAYRFNG IGVTQNVLYE        900
NQKQIANQFN KAISQIQESL TTTSTALGKL QDVVNQNAQA LNTLVKQLSS NFGAISSVLN        960
DILSRLDKVE AEVQIDRLIT GRLQSLQTYV TQQLIRAAEI RASANLAATK MSECVLGQSK       1020
RVDFCGKGYH LMSFPQAAPH GVVFLHVTYV PSQERNFTTA PAICHEGKAY FPREGVFVFN       1080
GTSWFITQRN FFSPQIITTD NTFVSGNCDV VIGIINNTVY DPLQPELDSF KEELDKYFKN       1140
HTSPDVDLGD ISGINASVVN IQKEIDRLNE VAKNLNESLI DLQELGKYEQ YIKWPWYVWL       1200
GFIAGLIAIV MVTILLCCMT SCCSCLKGAC SCGSCCKFDE DDSEPVLKGV KLHYT           1255
```

>EPI_ISL_402119 (CoV_T1_2)

(SEQ ID NO: 7)

Amino acid sequence:
```
MFVFLVLLPLVSSQCVNLTTRTQLPPAYTNSFTRGVYYPDKVFRSSVLHSTQDLFLPFFSNVTWFHAI
HVSGTNGTKRFDNPVLPFNDGVYFASTEKSNIIRGWIFGTTLDSKTQSLLIVNNATNVVIKVCEFQFC
NDPFLGVYYHKNNKSWMESEFRVYSSANNCTFEYVSQPFLMDLEGKQGNFKNLREFVFKNIDGYFKIY
SKHTPINLVRDLPQGFSALEPLVDLPIGINITRFQTLLALHRSYLTPGDSSSGWTAGAAAYYVGYLQP
RTFLLKYNENGTITDAVDCALDPLSETKCTLKSFTVEKGIYQTSNFRVQPTESIVRFPNITNLCPFGE
VFNATRFASVYAWNRKRISNCVADYSVLYNSASFSTFKCYGVSPTKLNDLCFTNVYADSFVIRGDEVR
QIAPGQTGKIADYNYKLPDDFTGCVIAWNSNNLDSKVGGNYNYLYRLFRKSNLKPFERDISTEIYQAG
STPCNGVEGFNCYFPLQSYGFQPTNGVGYQPYRVVVLSFELLHAPATVCGPKKSTNLVKNKCVNFNFN
GLTGTGVLTESNKKFLPFQQFGRDIADTTDAVRDPQTLEILDITPCSFGGVSVITPGTNTSNQVAVLY
QDVNCTEVPVAIHADQLTPTWRVYSTGSNVFQTRAGCLIGAEHVNNSYECDIPIGAGICASYQTQTNS
PRRARSVASQSIIAYTMSLGAENSVAYSNNSIAIPTNFTISVTTEILPVSMTKTSVDCTMYICGDSTE
CSNLLLQYGSFCTQLNRALTGIAVEQDKNTQEVFAQVKQIYKTPPIKDFGGFNSQILPDPSKPSKRS
FIEDLLFNKVTLADAGFIKQYGDCLGDIAARDLICAQKFNGLTVLPPLLTDEMIAQYTSALLAGTITS
GWTFGAGAALQIPFAMQMAYRFNGIGVTQNVLYENQKLIANQFNSAIGKIQDSLSSTASALGKLQDVV
NQNAQALNTLVKQLSSNFGAISSVLNDILSRLDKVEAEVQIDRLITGRLQSLQTYVTQQLIRAAEIRA
SANLAATKMSECVLGQSKRVDFCGKGYHLMSFPQSAPHGVVFLHVTYVPAQEKNFTTAPAICHDGKAH
FPREGVFVSNGTHWFVTQRNFYEPQIITTDNTFVSGNCDVVIGIVNNTVYDPLQPELDSFKEELDKYF
KNHTSPDVDLGDISGINASVVNIQKEIDRLNEVAKNLNESLIDLQELGKYEQYIKWPWYIWLGFIAGL
IAIVMVTIMLCCMTSCCSCLKGCCSCGSCCKFDEDDSEPVLKGVKLHYT
```

>EPI_ISL_402119 (CoV_T1_2)

(SEQ ID NO : 8)

Nucleic acid sequence:
```
atgttcgtgtttctggtgctgctgcctctggtgtccagccagtgtgtgaacctgaccacc
agaacacagctgcctccagcctacaccaacagctttaccagaggcgtgtactaccccgac
aaggtgttcagatccagcgtgctgcactctacccaggacctgttcctgccttctcttcagc
aacgtgacctggttccacgccatccacgtgtccggcaccaatggcaccaagagattcgac
aaccccgtgctgcccttcaacgacggggtgtactttgccagcaccgagaagtccaacatc
atcagaggctggatcttcggcaccacactggacagcaagacccagagcctgctgatcgtg
aacaacgccaccaacgtggtcatcaaagtgtgcgagttccagttctgcaacgaccccttc
ctgggcgtgctactaccacaagaacaacaagagctggatggaaagcgagttccgggtgtac
agcagcgccaacaactgcaccttcgagtacgtgtcccagcctttcctgatggacctggaa
ggcaagcagggcaacttcaagaacctgcgcgagttcgtgttcaagaacatcgacggctac
ttcaaaatctacagcaagcacacccctatcaacctcgtgcgggatctgcctcagggcttc
tctgctctggaaccccctggtggatctgcccatcggcatcaacatcaccggtttcagaca
ctgctggccctgcacagaagtacctgacacctggcgatagcagcagcggatggacagct
ggtgccgccgcttactacgtgggataccccagccaagaaccttcctgctgaagtacaac
gagaacggcaccatcaccgacgccgtggattgtgctctggaccctctgagcgagacaaag
tgcaccctgaagtccttcaccgtggaaaagggcatctaccagaccagcaacttccgggtg
cagcccaccgaatccatcgtgcggttccccaatatcaccaatctgtgccccttcggcgag
gtgttcaatgccaccagattcgcctctgtgtacgcctggaaccggaagcggatcagcaat
tgcgtggccgactactccgtgctgtacaactccgccagcttcagcaccttcaagtgctac
ggcgtgtcccctaccaagctgaacgacctgtgcttcacaaacgtgtacgccgacagcttc
gtgatccggggagatgaagtgcggcaagattgcccctggacagacaggcaagatcgccgac
tacaactacaagctgcccgacgacttcaccggctgtgtgattgcctggaacagcaacaac
ctggactccaaagtcggcggcaactacaattacctgtaccggctgttccggaagtccaat
ctgaagcccttcgagcgggacatcagcaccgaaatctatcaggccggcagcacccccttgc
aacggcgtggaaggcttcaactgctacttccctactgcaaagctacggctttcagcccaca
aatggcgtgggctaccagcctacagagtggtggtgctgagcttcgagctgctgcatgct
cctgccacagtgtgcgggcccaagaaatccaccaatctcgtgaagaacaaatgcgtgaac
ttcaacttcaacggcctgaccggcaccggcgtgctgacagagagcaacaagaagttcctg
ccattccagcagttcggccgggatatcgccgataccacagatgccgtcagagtccccag
acactggaaatcctggacatcacccccatgcagcttcggcggagtgtctgtgatcacccct
ggcaccaacaccagcaatcaggtggcagtgctgtaccaggacgtgaactgtaccgaagtg
cccgtggccattcacgccgatcagctgacacctacatggcgggtgtactccaccggcagc
aatgtgtttcagaccagagccggctgtctgatcggagccgacgtgaacaatagctac
gagtgcgacatcccatcggcgctggcatctgcgcctcttaccagacacagacaaacagc
cccagacgggctagaagcgtggccagccagagcatcattgcctacacaatgtctctgggc
gccgagaacagcgtggcctactccaacaactctatcgctatccccaccaacttcaccatc
agtgtgaccaccgagatcctgcctgtgtccatgaccaagaccagcgtggactgcaccatg
tacatctgcggcgattccaccgagtgctccaacctgctgctgccagtacgagcttctgc
acccagctgaatagagccctgacagggatcgccgtggaacaggacaagaacacccaagag
gtgttcgcccaagtgaagcaaatctacaagacccctcctatcaaggacttcggcggcttc
aatttcagccagattctgcccgatcctagcaagcccagcaagcggagcttcatcgaggac
ctgctgttcaacaaagtgacactggccgacgccggcttcatcaagcagtacggcgattgt
```

-continued
```
ctgggcgacattgccgccagggatctgatttgcgcccagaagtttaacggactgacagtg
ctgcctcctctgctgaccgatgagatgatcgcccagtacacatctgccctgctggccggc
acaatcacaagcggctggacatttggagctggcgccgctctccagattccattcgctatg
cagatggcctaccggttcaacggcatcggagtgacccagaatgtgctgtacgagaaccag
aagctgatcgccaaccagttcaacagcgccatcggcaagatccaggacagcctgagcagc
acagcaagcgccctgggaaagctccaggacgtcgtgaaccagaatgcccaggcactgaac
accctggtcaagcagctgtcctccaacttcggcgccatcagctctgtgctgaacgatatc
ctgagcagactggacaaggtggaagccgaggtgcagatcgacagactgatcaccggcaga
ctccagtctctccagacctacgtgacccagcagctgatcagagccgccgagattagagcc
tctgccaatctggccgccaccaagatgtctgagtgtgtgctgggccagagcaagagagtg
gacttttgcggcaagggctaccacctgatgagcttccctcagtctgccctcacggcgtg
gtgtttctgcacgtgacatacgtgcccgctcaagagaagaatttcaccaccgctccagcc
atctgccacgacggcaaagcccacttttcctagagaaggcgtgttcgtgtccaacggcacc
cattggttcgtgacacagcggaacttctacgagccccagatcatcaccaccgacaacacc
ttcgtgtctggcaactgcgacgttgtgatcggcattgtgaacaataccgtgtacgaccct
ctccagcctgaactggactccttcaaagaggaactcgacaagtactttaagaaccacaca
agccccgacgtggacctgggcgatatcagcggaatcaatgccagcgtggtcaacatccag
aaagagatcgaccggctgaacgaggtggccaagaatctgacagagcctgatcacctg
caagaactgggggaagtacgagcagtacatcaagtggccctggtacatctggctgggcttt
atcgccggactgattgccatcgtgatggtcacaatcatgctgtgttgcatgaccagctgc
tgtagctgcctgaagggctgttgtagctgtggctcctgctgcaagttcgacgaggacgat
tctgagcccgtgctgaagggcgtgaaactgcactacacc
```

>EPI_ISL_402119_tr (CoV_T2_3)

(SEQ ID NO: 9)

Amino acid sequence:
```
MFVFLVLLPLVSSQCVNLTTRTQLPPAYTNSFTRGVYYPDKVFRSSVLHSTQDLFLPFFSNVTWFHAI
HVSGTNGTKRFDNPVLPFNDGVYFASTEKSNIIRGWIFGTTLDSKTQSLLIVNNATNVVIKVCEFQFC
NDPFLGVYYHKNNKSWMESEFRVYSSANNCTFEYVSQPFLMDLEGKQGNFKNLREFVFKNIDGYFKIY
SKHTPINLVRDLPQGFSALEPLVDLPIGINITRFQTLLALHRSYLTPGDSSSGWTAGAAAYYVGYLQP
RTFLLKYNENGTITDAVDCALDPLSETKCTLKSFTVEKGIYQTSNFRVQPTESIVRFPNITNLCPFGE
VFNATRFASVYAWNRKRISNCVADYSVLYNSASFSTFKCYGVSPTKLNDLCFTNVYADSFVIRGDEVR
QIAPGQTGKIADYNYKLPDDFTGCVIAWNSNNLDSKVGGNYNYLYRLFRKSNLKPFERDISTEIYQAG
STPCNGVEGFNCYFPLQSYGFQPTNGVGYQPYRVVVLSFELLHAPATVCGPKKSTNLVKNKCVNFNFN
GLTGTGVLTESNKKFLPFQQFGRDIADTTDAVRDPQTLEILDITPCSFGGVSVITPGTNTSNQVAVLY
QDVNCTEVPVAIHADQLTPTWRVYSTGSNVFQTRAGCLIGAEHVNNSYECDIPIGAGICASYQTQTNS
PRRARSVASQSIIAYTMSLGAENSVAYSNNSIAIPTNFTISVTTEILPVSMTKTSVDCTMYICGDSTE
CSNLLLQYGSFCTQLNRALTGIAVEQDKNTQEVFAQVKQIYKTPPIKDFGGFNFSQILPDPSKPSKRS
FIEDLLFNKVTLADAGFIKQYGDCLGDIAARDLICAQKFNGLTVLPPLLTDEMIAQYTSALLAGTITS
GWTFGAGAALQIPFAMQMAYRFNGIGVTQNVLYENQKLIANQFNSAIGKIQDSLSSTASALGKLQDVV
NQNAQALNTLVKQLSSNFGAISSVLNDILSRLDKVEAEVQIDRLITGRLQSLQTYVTQQLIRAAEIRA
SANLAATKMSECVLGQSKRVDFCGKGYHLMSFPQSAPHGVVFLHVTYVPAQEKNFTTAPAICHDGKAH
FPREGVFVSNGTHWFVTQRNFYEPQIITTDNTFVSGNCDVVIGIVNNTVYDPLQPELDSFKEELDKYF
KNHTSPDVDLGDIS
```

>EPI_ISL_402119_tr (CoV_T2_3)

(SEQ ID NO: 10)

Nucleic acid sequence:
```
atgttcgtgtttctggtgctgctgcctctggtgtccagccagtgtgtgaacctgaccacc
agaacacagctgcctccagcctacaccaacagctttaccagaggcgtgtactaccccgac
aaggtgttcagatccagcgtgctgcactctacccaggacctgttcctgcctttcttcagc
aacgtgacctggttccacgccatccacgtgtccggcaccaatggcaccaagagattcgac
aaccccgtgctgcccttcaacgacggggtgtactttgccagcaccgagaagtccaacatc
atcagaggctggatcttcggcaccacactggacagcaagacccagagcctgctgatcgtg
aacaacgccaccaacgtggtcatcaaagtgtgcgagttccagttctgcaacgacccccttc
ctgggcgtctactaccacaagaacaacaagagctggatggaaagcgagttccgggtgtac
agcagcgccaacaactgcaccttcgagtacgtgtcccagcctttcctgatggacctggaa
ggcaagcagggcaacttcaagaacctgcgcgagttcgtgttcaagaacatcgacggctac
ttcaaaatctacagcaagcacacccctatcaacctcgtgcgggatctgcctcagggcttc
tctgctctggaacccctggtggatctgcccatcggcatcaacatcacccggtttcagaca
ctgctggccctgcacagaagctacctgacacctggcgatagcagcagcggatggacagct
ggtgccgccgcttactacgtgggatacctccagccaagaaccttcctgctgaagtacaac
gagaacggcaccatcaccgacgccgtggattgtgctctggaccctctgagcgagacaaag
tgcaccctgaagtccttcaccgtggaaaagggcatctaccagaccagcaacttccgggtg
cagcccaccgaatccatcgtgcggttccccaatatcaccaatctgtgcccccttcggcgag
gtgttcaatgccaccagattcgcctctgtgtacgcctggaaccggaagcggatcagcaat
tgcgtggccgactactccgtgctgtacaactccgccagcttcagcaccttcaagtgctac
ggcgtgtcccctaccaagctgaacgacctgtgcttcacaaacgtgtacgccgacagcttc
gtgatccggggagatgaagtgcggcagattgcccctggacagacaggcaagatcgccgac
tacaactacaagctgcccgacgacttcaccggctgtgtgattgcctggaacagcaacaac
ctggactccaaagtcggcggcaactacaattacctgtaccggctgttccggaagtccaat
ctgaagcccttcgagcgggacatcagcaccgaaatctatcaggccggcagcaccccttgc
aacggcgtggaaggcttcaactgctacttcccactgcaaagctacggctttcagcccaca
aatggcgtgggctaccagccttacagagtggtggtgctgagcttcgagctgctgcatgct
cctgccacagtgtgcgggccctaagaaatccaccaatctcgtgaagaacaaatgcgtgaac
ttcaacttcaacggcctgaccggcaccggccgtgctgacagagacaacaagaagttcctg
ccattccagcagttcggccggggatatcgccgataccacagatgccgtcagagatccccag
acactggaaatcctggacatcacccccatgcagcttcggcggagtgtctgtgatcacccct
ggcaccaacaccagcaatcaggtggcagtgctgtaccaggacgtgaactgtaccgaagtg
cccgtggccattcacgccgatcagctgacacctacatggcgggtgtactccaccggcagc
aatgtgtttcagaccagagccggctgtctgatcggagccgagcacgtgaacaatagctac
```

-continued
```
gagtgcgacatccccatcggcgctggcatctgcgcctcttaccagacacagacaaacagc
cccagacgggctagaagcgtggccagccagagcatcattgcctacacaatgtctctgggc
gccgagaacagcgtggcctactccaacaactctatcgctatccccaccaacttcaccatc
agcgtgaccaccgagatcctgcctgtgtccatgaccaagaccagcgtggactgcaccatg
tacatctgcggcgattccaccgagtgctccaacctgctgctccagtacggcagcttctgc
acccagctgaatagagcccctgacagggatcgccgtggaacaggacaagaacacccaagag
gtgttcgcccaagtgaagcaaatctacaagacccctcctatcaaggacttcggcggcttc
aatttcagccagattctgcccgatcctagcaagcccagcaagcggagcttcatcgaggac
ctgctgttcaacaaagtgacactggccgacgccggcttcatcaagcagtacggcgattgt
ctgggcgacattgccgccagggatctgatttgcgcccagagtttaacggactgacagtg
ctgcctcctctgctgaccgatgagatgatcgcccagtacacatctgccctgctggccggc
acaatcacaagcggctggacatttggagctggcgccgctctccagattccattcgctatg
cagatggcctaccggttcaacggcatcggagtgacccagaatgtgctgtacgagaaccag
aagctgatcgccaaccagttcaacagcgccatcggcaagatccaggacagacctgagcagc
acagcaagcgccctgggaaagctccaggacgtcgtgaaccagaatgcccaggcactgaac
accctggtcaagcagctgtcctccaacttcggcgccatcagctctgtgctgaacgatatc
ctgagcagactggacaaggtggaagccgaggtgcagatcgacagactgatcaccggcaga
ctccagtctctccagacctacgtgacccagcagctgatcagccgcgccgagattagagcc
tctgccaatctggccgccaccaagatgtctgagtgtgtgctgggccagagcaagagagtg
gactttgcggcaagggctaccacctgatgagcttccctcagtctgcccctcacggcgtg
gtgtttctgcacgtgacatacgtgcccgctcaagagaagaatttcaccaccgctccagcc
atctgccacgacggcaaagcccactttcctagagaaggcgtgttcgtgtccaacggcaac
cattggttcgtgacacagcggaacttctacgagccccagatcatcaccaccgacaacacc
ttcgtgtctggcaactgcgacgttgtgatcggcattgtgaacaataccgtgtacgaccct
ctccagcctgaactggactccttcaaagaggaactcgacaagtactttaagaaccacaca
agccccgacgtggacctgggcgatatcagt
```

>EPI_ISL_402119_RBD (CoV_T2_6)

(SEQ ID NO: 11)

Amino acid sequence:
RVQPTESIVRFPNITNLCPFGEVFNATRFASVYAWNRKRISNCVADYSVLYNSASFSTFKCYGVSPTK
LNDLCFTNVYADSFVIRGDEVRQIAPGQTGKIADYNYKLPDDFTGCVIAWNSNNLDSKVGGNYNYLYR
LFRKSNLKPFERDISTEIYQAGSTPCNGVEGFNCYFPLQSYGFQPTNGVGYQPYRVVVLSFELLHAPA
TVCGPKKSTN

>EPI_ISL_402119_RBD (COV_T2_6)

(SEQ ID NO: 12)

Nucleic acid sequence:
```
cgggtgcagcccaccgaatccatcgtgcggttccccaatatcaccaatctgtgccccttc
ggcgaggtgttcaatgccaccagattcgcctctgtgtacgcctggaaccggaagcggatc
agcaattgcgtggccgactactccgtgctgtacaactccgccagcttcagcaccttcaag
tgctacggcgtgtccctaccaagctgaacgacctgtgcttcacaaacgtgtacgccgac
agcttcgtgatccggggagatgaagtgcggcagattgccctggaacagacaggcaagatc
gccgactacaactacaagctgcccgacgacttcaccggctgtgtgattgcctggaacagc
aacaacctggactccaaagtcggcggcaactacaattacctgtaccggctgttccggaag
tccaatctgaagcccttcgagcgggacatcagcaccgaaatctatcaggccggcagcacc
ccttgcaacggcgtggaaggcttcaactgctacttccccactgcaaagctacggctttcag
cccacaaatggcgtgggctaccagccttacagagtggtggtgctgagcttcgagctgctg
catgctcctgccacagtgtgcggccctaagaaatccaccaat
```

EPI_ISL_402119 (full length S protein amino acid sequence, with RBD
residues shown in bold, and residues not present in truncated S
protein shown underlined)

(SEQ ID NO: 7)

```
MFVFLVLLPL  VSSQCVNLTT  RTQLPPAYTN  SFTRGVYYPD  KVFRSSVLHS  TQDLFLPFFS    60
NVTWFHAIHV  SGTNGTKRFD  NPVLPFNDGV  YFASTEKSNI  IRGWIFGTTL  DSKTQSLLIV   120
NNATNVVIKV  CEFQFCNDPF  LGVYYHKNNK  SWMESEFRVY  SSANNCTFEY  VSQPFLMDLE   180
GKQGNFKNLR  EFVFKNIDGY  FKIYSKHTPI  NLVRDLPQGF  SALEPLVDLP  IGINITRFQT   240
LLALHRSYLT  PGDSSSGWTA  GAAAYYVGYL  QPRTFLLKYN  ENGTITDAVD  CALDPLSETK   300
CTLKSFTVEK  GIYQTSNFRV  QPTESIVRFP  NITNLCPFGE  VFNATRFASV  YAWNRKRISN   360
CVADYSVLYN  SASFSTFKCY  GVSPTKLNDL  CFTNVYADSF  VIRGDEVRQI  APGQTGKIAD   420
YNYKLPDDFT  GCVIAWNSNN  LDSKVGGNYN  YLYRLFRKSN  LKPFERDIST  EIYQAGSTPC   480
NGVEGFNCYF  PLQSYGFQPT  NGVGYQPYRV  VVLSFELLHA  PATVCGPKKS  TNLVKNKCVN   540
FNFNGLTGTG  VLTESNKKFL  PFQQFGRDIA  DTTDAVRDPQ  TLEILDITPC  SFGGVSVITP   600
GTNTSNQVAV  LYQDVNCTEV  PVAIHADQLT  PTWRVYSTGS  NVFQTRAGCL  IGAEHVNNSY   660
ECDIPIGAGI  CASYQTQTNS  PRRARSVASQ  SIIAYTMSLG  AENSVAYSNN  SIAIPTNFTI   720
SVTTEILPVS  MTKTSVDCTM  YICGDSTECS  NLLLQYGSFC  TQLNRALTGI  AVEQDKNTQE   780
VFAQVKQIYK  TPPIKDFGGF  NFSQILPDPS  KPSKRSFIED  LLFNKVTLAD  AGFIKQYGDC   840
LGDIAARDLI  CAQKFNGLTV  LPPLLTDEMI  AQYTSALLAG  TITSGWTFGA  GAALQIPFAM   900
QMAYRFNGIG  VTQNVLYENQ  KLIANQFNSA  IGKIQDSLSS  TASALGKLQD  VVNQNAQALN   960
TLVKQLSSNF  GAISSVLNDI  LSRLDKVEAE  VQIDRLITGR  LQSLQTYVTQ  QLIRAAEIRA  1020
SANLAATKMS  ECVLGQSKRV  DFCGKGYHLM  SFPQSAPHGV  VFLHVTYVPA  QEKNFTTAPA  1080
ICHDGKAHFP  REGVFVSNGT  HWFVTQRNFY  EPQIITTDNT  FVSGNCDVVI  GIVNNTVYDP  1140
LQPELDSFKE  ELDKYFKNHT  SPDVDLGDIS  GINASVVNIQ  KEIDRLNEVA  KNLNESLIDL  1200
QELGKYEQYI  KWPWYIWLGF  IAGLIAIVMV  TIMLCCMTSC  CSCLKGCCSC  GSCCKFDEDD  1260
SEPVLKGVKL  HYT                                                         1273
```

>Wuhan_Node1 (CoV_T2_1)

(SEQ ID NO: 13)

Amino acid sequence:
MFLFLFIIIFAFFLLSAKANERCGIFTSKPQPKLAQVSSSRRGVYYPDDIFRSDVLHLTQDYFLPFDS -continued

```
NVTRYFSLNANGPDRIVYFDNPIIPFKDGVYFAATEKSNVIRGWIFGSTLDNTSQSVIIVNNSTNVII
RVCNFDLCNDPFFTVSRPTDKHIKTWSIREFAVYQSAFNCTFEYVSKSFLLDVAEKPGNFKHLREFVF
KNVDGFLNVYSTYKPINVVSGLPTGFSVLKPILKLPLGINITSFRVLLTMFRGDPTPGHTTANWLTAA
AAYYVGYLKPTTFMLKYNENGTITDAVDCSQNPLAELKCTLKNFNVDKGIYQTSNFRVSPTQEVVRFP
NITNLCPFDKVFNATRFPSVYAWERTKISDCVADYTVLYNSTSFSTFKCYGVSPSKLIDLCFTSVYAD
TFLIRCSEVRQVAPGQTGVIADYNYKLPDDFTGCVIAWNTAKQDTGSSGNYNYYRSHRKTKLKPFER
DLSSDECSPDGKPCTPPAFNGVRGFNCYFTLSTYDFNPNVPVEYQATRVVVLSFELLNAPATVCGPKL
STQLVKNQCVNFNFNGLKGTGVLTASSKRFQSFQQFGRDASDFTDSVRDPQTLEILDISPCSFGGVSV
ITPGTNTSSEVAVLYQDVNCTDVPTAIHADQLTPAWRVYSTGVNVFQTQAGCLIGAEHVNASYECDIP
IGAGICASYHTASNSPRILRSTGQKSIVAYTMSLGAENSIAYANNSIAIPTNFSISVTTEVMPVSMAK
TSVDCTMYICGDSLECSNLLLQYGSFCTQLNRALTGIAIEQDKNTQEVFAQVKQMYKTPAIKDFGGFN
FSQILPDPSKPTKRSFIEDLLFNKVTLADAGFMKQYGECLGDISARDLICAQKFNGLTVLPPLLTDEM
IAAYTAALVSGTATAGWTFGAGAALQIPFAMQMAYRFNGIGVTQNVLYENQKQIANQFNKAISQIQES
LTTTSTALGKLQDVVNQNAQALNTLVKQLSSNFGAISSVLNDILSRLDKVEAEVQIDRLITGRLQSLQ
TYVTQQLIRAAEIRASANLAATKMSECVLGQSKRVDFCGKGYHLMSFPQAAPHGVVFLHVTYVPSQER
NFTTAPAICHEGKAYFPREGVFVSNGTSWFITQRNFYSPQIITTDNTFVSGNCDVVIGIINNTVYDPL
QPELDSFKEELDKYFKNHTSPDVDLGDISGINASVVNIQKEIDRLNEVAKNLNESLIDLQELGKYEQY
IKWPWYVWLGFIAGLIAIVMATILLCCMTSCCSCLKGACSCGSCCKFDEDDSEPVLKGVKLHYT
```

>Wuhan_Node1 (CoV_T2_1)

(SEQ ID NO: 14)

Nucleic acid sequence :
```
atgtttctgttcctcttcattattatcttcgcattcttcctgctgagcgccaaggccaac
gagagatgcggcatcttcaccagcaagccccagcctaagctggcccaggtgtccagttct
agacggggcgtgtactaccccgacgacatcttcagatccgacgtgctgcatctgacccag
gactacttcctgcctttcgacagcaacgtgacccggtacttcagcgtgaacgccaacgga
cccgaccggatcgtgtacttcgacaaccctatcatcccctttcaaggacggggtgtacttt
gccgccaccgagaagtccaacgtgatcagaggctggatcttcggcagcaccctggacaat
accagccagagcgtgatcatcgtgaacaacagcaccaacgtcatcatccgcgtgtgcaac
ttcgacctgtgcaacgacccattcttcaccgtgtccagaccaaccgacaagcacatcaag
acctggtccatccgcgagttcgccgtgtaccagagcgccttcaattgcaccttcgagtac
gtgtccaagagcttctctgctggacgtggccgagaagcccggcaactttaagcacctgaga
gaattcgtgttcaagaacgtggacggcttcctgaacgtgtacagcacctacaagcccatc
aacgtggtgtccggcctgcctacaggattcagcgtgctgaagcccatcctgaagctgccc
ctgggcatcaacatcaccagcttcagagtgctgctgaccatgttcagaggcgaccctaca
cctggccacaccaccgctaattggctgacagccgccgctgcctactacgtgggatacctg
aagcctaccacctttcatgctcaagtacaacgagaacggcaccatcaccgacgccgtggac
tgtagccaaaatcctctggccgagctgaagtgcaccctgaagaacttcaacgtggacaag
ggcatctaccagaccagcaacttccggggtgtccctacacaagaggtcgtgcggttcccc
aatatcaccaatctgtgcccccttcgacaaggtgttcaacgccaccagatttcccagcgtg
tacgcctgggagcgcaccaagatttccgattgcgtggccgactacaccgtgctgtataac
tccacctccttcagcacccttcaagtgctacgcgcgtgtccccaagcaagctgatcgatctg
tgcttcacctctgtgtacgccgacaccttcctgatccggtagcgaagtgcgacaggtg
gcacctggacgacaggcgtgatcgccgattacaactacaagctgcccgacgacttcacc
ggctgtgtgatcgcctggaataccgccaagcaggatacaggcagcagcggcaactacaac
tactactacagaagccaccgcaagaccaagctgaagcctttcgagagggacctgagcagc
gacgagtgtagccctgatggcaagcctgtacacctcctgccttcaatggcgtgcggggc
ttcaactgctacttcacccctgagcacctacgacttcaaccccaacgtgcccgtggaatac
caggccacaagagtggtggtgctgagcttcgagctgctgaatgcccctgccacagtgtgt
ggccctaagctgtctacccagctggtcaagaaccagtgcgtgaacttcaatttcaacggc
ctgaaaggcaccggcgtgctgaccgccagcagcaagagattccagagcttccagcagttc
ggcagggacgccagcgatttcacagatagcgtcagagatccccagacactggaaatcctg
gacatcagcccttgcagcttcggcggagtgtctgtgatcaccctggcaccaatacctct
agcgaggtggcagtgctgtaccaggacgtgaactgcaccgatgtgcctacagccatccac
gccgatcagctgacaccagcttggagagtgtactctaccggtgtcaacgtgttccagaca
caagccggctgtctctgattggagccgaacacgtgaacgccagctacgagtggcgacatccct
atcggagccggcatctgtgcctcttaccacaccgcctctaacagccccagaatcctgaga
agcaccggccagaaatccatcgtggcctcacaatgtctctgggcgccgagaactctatc
gcctacgccaacaactccattgctatccccaccaacttcagcatctccgtgaccaccgaa
gtgatgcctgtgtccatggccaagaccagcgtggactgcacaatgtacatctgcggcgac
agcctggaatgcagcaacctgctgctccagtacggcagcttctgtcacccagctgaataga
gccctgaccggaatcgccatcgagcaggacaagaacacccaagaggtgttcgcccaagtg
aagcagatgtataagacccctgccatcaaggacttcggcggctttaacttcagccagatc
ctgcctgatcctagcaagcccaccaagcgggagcttcatcgaggacctgctgttcaacaaa
gtgaccctggccgacgccggcttttatgaagcagtatggcgagtgcctgggcgacatctct
gccagggatctgatttgcgcccagaagttcaacggactgaccgtgctgcctcctctgctg
accgatgagatgatcgccgcctatacagccgctctggtgtctggcacagctaccgccgga
tggacatttggagctggcgccgctctccagattccattcgctatgcagatggcctaccgc
ttcaacggcatcggcgtgacccagaacgtgctgtacgagaaccagaagcagatcgccaac
cagttcaacaaggccatcagtcagatccaagagagcctgaccacaaccagcacagccctg
ggaaagctccaggacgtcgtgaaccagaatgcccaggctctgaacaccctggtcaagcag
ctgagcagcaatttcggcgccatcagctccgtgctgaacgacatcctgagccggctggat
aaggtggaagccgaggtgcagatcgaccggctgattacaggcagactccagtctctccag
acctacgtgacacagcagctgatcagagccgccgagattagagcctctgccaatctggcc
gccaccaagatgtctgagtgtgtgctgggccagtctaagagagtggacttctgcggcaag
ggctaccacctgatgagcttccctcaggctgctcctcacggcgtggtgtttctgcacgtg
acatacgtgcccagccaagagcggaacttcacaactgcccccagccatctgccacgagggc
aaagcctactttcccagagaaggcgtgttcgtgtccaacggcacctcctggttcatcacc
cagagaaacttctacagccctcagatcatcaccaccgacaacaccttcgtgtccggcaac
tgcgacgtggtcatcggcatcatcaacaataccgtgtacgaccctctccagccagaactg
gatagcttcaaagaggaactcgacaagtacttcaagaatcacacaagccccgacgtggac
``` ctgggcgatatcagcggaatcaatgccagcgtggtcaacatccagaaagagatcgacaga
ctgaacgaggtggccaagaacctgaacgagtccctgatcgacctgcaagagctggggaag
tacgagcagtacatcaagtggccttggtacgtgtggctgggctttatcgccggactgatc
gccattgtgatggccaccatcctgctgtgctgcatgacaagctgctgtagctgcctgaag
ggcgcctgtagctgtggcagctgctgcaagttcgacgaggacgattctgagcctgtgctg
aaaggcgtgaagctgcactacacc >Wuhan_Node1_tr (CoV_T2_4)

(SEQ ID NO: 15)

Amino acid sequence:
MFLFLFIIIFAFFLLSAKANERCGIFTSKPQPKLAQVSSSRRGVYYPDDIFRSDVLHLTQDYFLPFDS
NVTRYFSLNANGPDRIVYFDNPIIPFKDGVYFAATEKSNVIRGWIFGSTLDNTSQSVIIVNNSTNVII
RVCNFDLCNDPFFTVSRPTDKHIKTWSIREFAVYQSAFNCTFEYVSKSFLLDVAEKPGNFKHLREFVF
KNVDGFLNVYSTYKPINVVSGLPTGFSVLKPILKLPLGINITSFRVLLTMFRGDPTPGHTTANWLTAA
AAYYVGYLKPTTFMLKYNENGTITDAVDCSQNPLAELKCTLKNFNVDKGIYQTSNFRVSPTQEVVRFP
NITNLCPFDKVFNATRFPSVYAWERTKISDCVADYTVLYNSTSFSTFKCYGVSPSKLIDLCFTSVYAD
TFLIRCSEVRQVAPGQTGVIADYNYKLPDDFTGCVIAWNTAKQDTGSSGNYNYYRSHRKTKLKPFER
DLSSDECSPDGKPCTPPAFNGVRGFNCYFTLSTYDFNPNVPVEYQATRVVVLSFELLNAPATVCGPKL
STQLVKNQCVNFNFNGLKGTGVLTASSKRFQSFQQFGRDASDFTDSVRDPQTLEILDISPCSFGGVSV
ITPGTNTSSEVAVLYQDVNCTDVPTAIHADQLTPAWRVYSTGVNVFQTQAGCLIGAEHVNASYECDIP
IGAGICASYHTASNSPRILRSTGQKSIVAYTMSLGAENSIAYANNSIAIPTNFSISVTTEVMPVSMAK
TSVDCTMYICGDSLECSNLLLQYGSFCTQLNRALTGIAIEQDKNTQEVFAQVKQMYKTPAIKDFGGFN
FSQILPDPSKPTKRSFIEDLLFNKVTLADAGFMKQYGECLGDISARDLICAQKFNGLTVLPPLLTDEM
IAAYTAALVSGTATAGWTFGAGAALQIPFAMQMAYRFNGIGVTQNVLYENQKQIANQFNKAISQIQES
LTTTSTALGKLQDVVNQNAQALNTLVKQLSSNFGAISSVLNDILSRLDKVEAEVQIDRLITGRLQSLQ
TYVTQQLIRAAEIRASANLAATKMSECVLGQSKRVDFCGKGYHLMSFPQAAPHGVVFLHVTYVPSQER
NFTTAPAICHEGKAYFPREGVFVSNGTSWFITQRNFYSPQIITTDNTFVSGNCDVVIGIINNTVYDPL
QPELDSFKEELDKYFKNHTSPDVDLGDIS >Wuhan_Node1_tr (CoV_T2_4)

(SEQ ID NO: 16)

Nucleic acid sequence :
atgtttctgttcctcttcattattatcttcgcattcttcctgctgagcgccaaggccaac
gagagatgcggcatcttcaccagcaagcccagcctaagctggcccaggtgtccagttct
agacggggcgtgtactaccccgacgacatcttcagatccgacgtgctgcatctgacccag
gactacttcctgcctttcgacagcaacgtgacccggtacttcagcctgaacgccaacgga
cccgaccggatcgtgtacttcgacaaccctatcatcccttcaaggacggggtgtactt
gccgccaccgagaagtccaacgtgatcagaggctggatcttcggcagcaccccggacaat
accagccagagcgtgatcatcgtgaacaacagcaccaacgtcatcatccgcgtgtgcaac
ttcgacctgtgcaacgacccattcttcaccgtgtccagaccaaccgacaagcacatcaag
acctggtccatccgcgagttcgccgtgtaccagagcgcctttcaattgcaccttcgagtac
gtgtccaagagctttctgctggacgtggccgagaagcccggcaactttaagcacctgaga
gaattcgtgttcaagaacgtggacggcttcctgaacgtgtactacaccttcaagcccatc
aacgtggtgtccggcctgcctacaggattcagcgtgctgaagcccatcctgaagctgccc
ctgggcatcaacatcaccagcttcagagtgctgctgaccatgttcagaggcgaccctaca
cctggccacaccaccgctaattggctgacagccgccgctgcctactacgtgggatacctg
aagcctaccaccttcatgctcaagtacaacgagaacggcaccatcaccgacgccgtggac
tgtagccaaaatcctctggccgagctgaagtgcaccctgaagaacttcaacgtggacaag
ggcatctaccagaccagcaacttccgggtgtcccctacacaagaggtcgtgcggttcccc
aatatcaccaatctgtgcccttcgacaaggtgttcaacgccaccagatttcccagcgtg
tacgcctgggagcgcaccaagatttccgattgcgtggccgactacacgtgctgtataac
tccacctccttcagcaccttcaagtgctacggcgtgtccccaagcaagctgatcgatctg
tgcttcacctctgtgtacgccgacaccttcctgatccggtgtagcgaagtgcgacaggtg
gcacctggacagacaggcgtgatcgccgattacaactacaagctgcccgacgacttcacc
ggctgtgtgatcgcctggaataccgccaagcaggatacaggcagcagcggcaactacaac
tactactacagaagccaccgcaagaccaagctgaagcctttcgagaggggacctgagcagc
gacgagtgtagccctgatggcaagccttgtacacctcctgcctcaatggcgtgcggggc
ttcaactgctacttcaccctgagcacctacgacttcaaccccaacgtgcccgtggaatac
caggccacaagagtggtggtgctgagcttcgagctgctgaatgccccctgccacagtgtgt
ggccctaagctgtctacccagctggtcaagaaccagtgcgtgaacttcaatttcaacggc
ctgaaaggcaccggcgtgctgaccgccagcagcaagagattccagagcttccagcagttc
ggcagggacgccagcgatttcacagatagcgtcagagatccccgacactggaaatcctg
gacatcagcccttgcagcttcggcggagtgtctgtgatcacccctggcaccaatacctct
agcgaggtggcagtgctgtaccaggacgtgaactgcaccgatgtgcctacagccatccac
gccgatcagctgacaccagcttggagagtgtactctaccggtgtcaacgtgttccagaca
caagccggctgtctgattggagccgaacacgtgaacgccagctacgagtgcgacatccct
atcggagccggcatctgtgcctcttaccacaccgcctctaacagccccagaatcctgaga
agcaccggccagaaatccatcgtggcctacacaatgtctctgggcgccgagaaatctatc
gcctacgccaacaactccattgctatcccaccaactttcagcatctccgtgaccaccgaa
gtgatgcctgtgtccatggccaagaccagcgtggactgcacaatgtacatctgcggcgac
agcctggaatgcagcaacctgctgctccagtacggcagcttctgtcacccagctgaataga
gcctgaccggaatcgccatcgagcaggacaagaacacccaagaggtgttcgcccaagtg
aagcagatgtataagacccctgccatcaaggacttcggcggctttaacttcagccagatc
ctgcctgatcctagcaagcccaccaagcggagcttcatcgaggacctgctgttcaacaaa
gtgaccctggccgacgccggctttatgaagcagtatggcgagtgcctgggcgacatctct
gccagggatctgatttgcgcccagaagttcaacggactgacggtgctgcctctcctgctg
accgatgagatgatcgccgcctatacagccgctctggtgtctggcacagctaccgccgga
tggacatttggagctggcgccgctctccagattccattcgctatgcagatggcctaccgc
ttcaacggcatcggcgtgacccagaacgtgctgtacgagaaccagaagcagatcgccaac
cagttcaacaaggccatcagtcagatccaagagagcctgaccacaaccagcacagccctg
ggaaagctccaggacgtcgtgaaccagaatgcccaggctctgaacaccctggtcaagcag -continued
ctgagcagcaatttcggcgccatcagctccgtgctgaacgacatcctgagccggctggat
aaggtggaagccgaggtgcagatcgaccggctgattacaggcagactccagtctctccag
acctacgtgacacagcagctgatcagagccgccgagattagagcctctgccaatctggcc
gccaccaagatgtctgagtgtgtgctgggccagtctaagagagtggacttctgcggcaag
ggctaccacctgatgagcttccctcaggctgctcctcacggcgtggtgtttctgcacgtg
acatacgtgcccagccaagagcggaacttcacaactgccccagccatctgccacgagggc
aaagcctactttcccagagaaggcgtgttcgtgtccaacggcacctcctggttcatcacc
cagagaaacttctacagccctcagatcatcaccaccgacaacaccttcgtgtccggcaac
tgcgacgtggtcatcggcatcatcaacaataccgtgtacgaccctctccagccagaactg
gatagcttcaaagaggaactcgacaagtacttcaagaatcacacaagccccgacgtggac
ctgggcgatatcagt >Wuhan_Node1_RBD (CoV_T2_7)

(SEQ ID NO: 17)

Amino acid sequence:
RVSPTQEVVRFPNITNLCPFDKVFNATRFPSVYAWERTKISDCVADYTVLYNSTSFSTFKCYGVSPSK
LIDLCFTSVYADTFLIRCSEVRQVAPGQTGVIADYNYKLPDDFTGCVIAWNTAKQDTGSSGNYNYYYR
SHRKTKLKPFERDLSSDECSPDGKPCTPPAFNGVRGFNCYFTLSTYDFNPNVPVEYQATRVVVLSFEL
LNAPATVCGPKLSTQ >Wuhan_Node1_RBD (CoV_T2_7)

(SEQ ID NO: 18)

Nucleic acid sequence:
cgggtgtcccctacacaagaggtcgtgcggttccccaatatcaccaatctgtgccccttc
gacaaggtgttcaacgccaccagatttcccagcgtgtacgcctgggagcgcaccaagatt
tccgattgcgtggccgactacaccgtgctgtataactccacctccttcagcaccttcaag
tgctacggcgtgtccccaagcaagctgatcgatctgtgcttcacctctgtgtacgccgac
accttcctgatccggtgtagcgaagtgcgacaggtggcacctggacagacaggcgtgatc
gccgattacaactacaagctgcccgacgacttcaccggctgtgtgatcgcctggaatacc
gccaagcaggatacaggcagcagcggcaactacaactactactacagaagccaccgcaag
accaagctgaagcctttcgagagggacctgagcagcgacgagtgtagccctgatggcaag
ccttgtacacctcctgccttcaatggcgtgcgggggcttcaactgctacttcaccctgagc
acctacgacttcaaccccaacgtgcccgtggaataccaggccacaagagtggtggtgctg
agcttcgagctgctgaatgcccctgccacagtgtgtggccctaagctgtctacccag Wuhan_Node1 (CoV_T2_1) (full length S protein amino acid sequence,
with RBD residues shown in bold, and residues not present in
truncated S protein shown underlined)

(SEQ ID NO: 13)

| | | | |
|---|---|---|---|---|
| MFLFLFIIIF | AFFLLSAKAN | ERCGIFTSKP | QPKLAQVSSS | RRGVYYPDDI | FRSDVLHLTQ | 60 |
| DYFLPFDSNV | TRYFSLNANG | PDRIVYFDNP | IIPFKDGVYF | AATEKSNVIR | GWIFGSTLDN | 120 |
| TSQSVIIVNN | STNVIIRVCN | FDLCNDPFFT | VSRPTDKHIK | TWSIREFAVY | QSAFNCTFEY | 180 |
| VSKSFLLDVA | EKPGNFKHLR | EFVFKNVDGF | LNVYSTYKPI | NVVSGLPTGF | SVLKPILKLP | 240 |
| LGINITSFRV | LLTMFRGDPT | PGHTTANWLT | AAAAYYVGYL | KPTTFMLKYN | ENGTITDAVD | 300 |
| CSQNPLAELK | CTLKNFNVDK | GIYQTSNFRV | SPTQEVVRFP | NITNLCPFDK | VFNATRFPSV | 360 |
| YAWERTKISD | CVADYTVLYN | STSFSTFKCY | GVSPSKLIDL | CFTSVYADTF | LIRCSEVRQV | 420 |
| APGQTGVIAD | YNYKLPDDFT | GCVIAWNTAK | QDTGSSGNYN | YYRSHRKTK | LKPFERDLSS | 480 |
| DECSPDGKPC | TPPAFNGVRG | FNCYFTLSTY | DFNPNVPVEY | QATRVVVLSF | ELLNAPATVC | 540 |
| GPKLSTQLVK | NQCVNFNFNG | LKGTGVLTAS | SKRFQSFQQF | GRDASDFTDS | VRDPQTLEIL | 600 |
| DISPCSFGGV | SVITPGTNTS | SEVAVLYQDV | NCTDVPTATH | ADQLTPAWRV | YSTGVNVFQT | 660 |
| QAGCLIGAEH | VNASYECDIP | IGAGICASYH | TASNSPRILR | STGQKSIVAY | TMSLGAENSI | 720 |
| AYANNSIAIP | TNFSISVTTE | VMPVSMAKTS | VDCTMYICGD | SLECSNLLLQ | YGSFCTQLNR | 780 |
| ALTGIAIEQD | KNTQEVFAQV | KQMYKTPAIK | DFGGFNFSQI | LPDPSKPTKR | SFIEDLLFNK | 840 |
| VTLADAGFMK | QYGECLGDIS | ARDLICAQKF | NGLTVLPPLL | TDEMIAAYTA | ALVSGTATAG | 900 |
| WTFGAGAALQ | IPFAMQMAYR | FNGIGVTQNV | LYENQKQIAN | QFNKAISQIQ | ESLTTTSTAL | 960 |
| GKLQDVVNQN | AQALNTLVKQ | LSSNFGAISS | VINDILSRLD | KVEAEVQIDR | LITGRLQSLQ | 1020 |
| TYVTQQLIRA | AEIRASANLA | ATKMSECVLG | QSKRVDFCGK | GYHLMSFPQA | APHGVVFLHV | 1080 |
| TYVPSQERNF | TTAPAICHEG | KAYFPREGVF | VSNGTSWFIT | QRNFYSPQII | TTDNTFVSGN | 1140 |
| CDVVIGIINN | TVYDPLQPEL | DSFKEELDKY | FKNHTSPDVD | LGDISGINAS | VVNIQKEIDR | 1200 |
| <u>LNEVAKNLNE</u> | <u>SLIDLQELGK</u> | <u>YEQYIKWPWY</u> | <u>VWLGFIAGLI</u> | <u>AIVMATILLC</u> | <u>CMTSCCSCLK</u> | 1260 |
| <u>GACSCGSCCK</u> | <u>FDEDDSEPVL</u> | <u>KGVKLHYT</u> | | | | 1288 |

EXAMPLE 2

Alignment of full-length S-protein amino acid sequence of CoV_T2_1 (Wuhan_Node1) with
AY274119
Score = 55060.0

Length of alignment = 1284

Sequence Wuhan_Node1/5-1288 (Sequence length = 1288) (SEQ ID NO: 13)

Sequence AY274119/1-1255 (Sequence length = 1255) (SEQ ID NO:1)

```
Wuhan_Node1/5-1288      LFIIIFAFFLLSAKANERCGIFTSKPQPKLAQVSSSRRGVYYPDDIFRSDVLH
                        .||... . || |.   .|| |      |. .| .|| ||||||| .||||| |
AY274119/1-1255         MFIFLLFLTLTSGSDLDRCTTFDDVQAPNYTQHTSSMRGVYYPDEIFRSDTLY
```

-continued

```
Wuhan_Node1/5-1288    LTQDYFLPFDSNVTRYFSLNANGPDRIVYFDNPIIPFKDGVYFAATEKSNVIR
                      ||||  ||||  ||||  . ..|       .   |.||.||||||.|||||||||.|
AY274119/1-1255       LTQDLFLPFYSNVTGFHTIN-----HT--FGNPVIPFKDGIYFAATEKSNVVR Wuhan_Node1/5-1288    GWIFGSTLDNTSQSVIIVNNSINVIIRVCNFDLCNDPFFTVSRPTDKHIKTWS
                      ||.||||..| ||||||.||||||.|| |||.|.|..||.||.|  .    .|.
AY274119/1-1255       GWVFGSTMNNKSQSVIIINNSTNVVIRACNFELCDNPFFAVSKPMG--TQTHT Wuhan_Node1/5-1288    IREFAVYQSAFNCTFEYVSKSFLLDVAEKPGNFKHLREFVFKNVDGFLNVYST
                         ....|||||||||.|  .|  |||.||.|||||||||||  |||| ||
AY274119/1-1255       ----MIFDNAFNCTFEYISDAFSLDVSEKSGNFKHLREFVFKNKDGFLYVYKG Wuhan_Node1/5-1288    YKPINVVSGLPTGFSVLKPILKLPLGINITSFRVLLTMFRGDPTPGHTTANWL
                      |.||.||  .||.||.  |||||.|||||||||.||  .||  |      .|..    |
AY274119/1-1255       YQPIDVVRDLPSGFNTLKPIFKLPLGINITNFRAILTAF----SPAQDI--WG Wuhan_Node1/5-1288    TAAAAYYVGYLKPTTFMLKYNENGTITDAVDCSQNPLAELKCTLKNFNVDKGI
                      |.||||.|||||||||||||.||||||||||||||||||||||..|.|..||||
AY274119/1-1255       TSAAAYFVGYLKPTTFMLKYDENGTITDAVDCSQNPLAELKCSVKSFEIDKGI Wuhan_Node1/5-1288    YQTSNFRVSPTQEVVRFPNITNLCPFDKVFNATRFPSVYAWERTKISDCVADY
                      ||||||| |..|||||||||||||||.  |||||.||||||||  |||.|||||
AY274119/1-1255       YQTSNFRVVPSGDVVRFPNITNLCPFGEVFNATKFPSVYAWERKKISNCVADY Wuhan_Node1/5-1288    TVLYNSTSFSTFKCYGVSPSKLIDLCFTSVYADTFLIRCSEVRQVAPGQTGVI
                      .||||||  |||||||||||..||  ||||..||||.|...    .|||.||||||
AY274119/1-1255       SVLYNSTEFSTFKCYGVSATKLNDLCFSNVYADSFVVKGDDVRQIAPGQTGVI Wuhan_Node1/5-1288    ADYNYKLPDDFTGCVIAWNTAKQDTGSSGNYNYYYRSHRKTKLKPFERDLSSD
                      ||||||||||| |||.||||  .|.  |.|.|||||  ||      ||.|||||.|.
AY274119/1-1255       ADYNYKLPDDFMGCVLAWNTRNIDATSTGNYNYKYRYLRHGKLRPFERDISNV Wuhan_Node1/5-1288    ECSPDGKPCTPPAFNGVRGFNCYFTLSTYDFNPNVPVEYQATRVVVLSFELLN
                      |||||||||||||      .|||  |.|  |.|       ||.  ||||||||||
AY274119/1-1255       PFSPDGKPCTPPA------LNCYWPLNDYGFYTTTGIGYQPYRVVVLSFELLN Wuhan_Node1/5-1288    APATVCGPKLSTQLVKNQCVNFNFNGLKGTGVLTASSKRFQSFQQFGRDASDF
                      |||||||||||||.|.||||||||||||||.|||||||.||||||.|||||||||
AY274119/1-1255       APATVCGPKLSTDLIKNQCVNFNFNGLTGTGVLTPSSKRFQPFQQFGRDVSDF Wuhan_Node1/5-1288    TDSVRDPQTLEILDISPCSFGGVSVITPGTNTSSEVAVLYQDVNCTDVPTAIH
                      ||||||||.| |||||||.||||||||||||||.||||||||||||||||.||||
AY274119/1-1255       TDSVRDPKTSEILDISPCAFGGVSVITPGTNASSEVAVLYQDVNCTDVSTAIH Wuhan_Node1/5-1288    ADQLTPAWRVYSTGVNVFQTQAGCLIGAEHVNASYECDIPIGAGICASYHTAS
                      |||||||||.||||.||||||||||||||||||..||||||||||||||||||.|
AY274119/1-1255       ADQLTPAWRIYSTGNNVFQTQAGCLIGAEHVDTSYECDIPIGAGICASYHTVS Wuhan_Node1/5-1288    NSPRILRSTGQKSIVAYTMSLGAENSIAYANNSIAIPTNFSISVTTEVMPVSM
                          .||||.||||||||||||||||..||||.||.||||||||||.||||||||||
AY274119/1-1255       ----LLRSTSQKSIVAYTMSLGADSSIAYSNNTIAIPTNFSISITTEVMPVSM Wuhan_Node1/5-1288    AKTSVDCTMYICGDSLECSNLLLQYGSFCTQLNRALTGIAIEQDKNTQEVFAQ
                      ||||||| |||||||| ||||.|.|||||||||||.||| |||.||.|.||||||
AY274119/1-1255       AKTSVDCNMYICGDSTECANLLLQYGSFCTQLNRALSGIAAEQDRNTREVFAQ Wuhan_Node1/5-1288    VKQMYKTPAIKDFGGFNFSQILPDPSKPTKRSFIEDLLFNKVTLADAGFMQY
                      ||||||||..| |||||||||||||||| ||||||||||||||||||||||||
AY274119/1-1255       VKQMYKTPTLKYFGGFNFSQILPDPLKPTKRSFIEDLLFNKVTLADAGFMKQY Wuhan_Node1/5-1288    GECLGDISARDLICAQKFNGLTVLPPLLTDEMIAAYTAALVSGTATAGWTFGA
                      |||||||.|||||||||||||||||||||||.|||||||||||||||||||||
AY274119/1-1255       GECLGDINARDLICAQKFNGLTVLPPLLTDDMIAAYTAALVSGTATAGWTFGA Wuhan_Node1/5-1288    GAALQIPFAMQMAYRFNGIGVTQNVLYENQKQIANQFNKAISQIQESLTTTST
                      |||||||||||||||||||||||||||||||||||||||||||||||||||||
AY274119/1-1255       GAALQIPFAMQMAYRFNGIGVTQNVLYENQKQIANQFNKAISQIQESLTTTST Wuhan_Node1/5-1288    ALGKLQDVVNQNAQALNTLVKQLSSNFGAISSVLNDILSRLDKVEAEVQIDRL
                      |||||||||||||||||||||||||||||||||||||||||||||||||||||
AY274119/1-1255       ALGKLQDVVNQNAQALNTLVKQLSSNFGAISSVLNDILSRLDKVEAEVQIDRL Wuhan_Node1/5-1288    ITGRLQSLQTYVTQQLIRAAEIRASANLAATKMSECVLGQSKRVDFCGKGYHL
                      |||||||||||||||||||||||||||||||||||||||||||||||||||||
AY274119/1-1255       ITGRLQSLQTYVTQQLIRAAEIRASANLAATKMSECVLGQSKRVDFCGKGYHL Wuhan_Node1/5-1288    MSFPQAAPHGVVFLHVTYVPSQERNFTTAPAICHEGKAYFPREGVFVSNGTSW
                      |||||||||||||||||||||||||||||||||||||||||||||||.|||||
AY274119/1-1255       MSFPQAAPHGVVFLHVTYVPSQERNFTTAPAICHEGKAYFPREGVFVFNGTSW
```

```
                              -continued
Wuhan_Node1/5-1288       FITQRNFYSPQIITTDNTFVSGNCDVVIGIINNTVYDPLQPELDSFKEELDKY
                         |||||||·|||||||||||||||||||||||||||||||||||||||||||||
AY274119/1-1255          FITQRNFFSPQIITTDNTFVSGNCDVVIGIINNTVYDPLQPELDSFKEELDKY Wuhan_Node1/5-1288       FKNHTSPDVDLGDISGINASVVNIQKEIDRLNEVAKNINESLIDLQELGKYEQ
                         |||||||||||||||||||||||||||||||||||||||||||||||||||||
AY274119/1-1255          FKNHTSPDVDLGDISGINASVVNIQKEIDRLNEVAKNINESLIDLQELGKYEQ Wuhan_Node1/5-1288       YIKWPWYVWLGFIAGLIAIVMATILLCCMTSCCSCLKGACSCGSCCKFDEDDS
                         |||||||||||||||||||||||||·|||||||||||||||||||||||||||
AY274119/1-1255          YIKWPWYVWLGFIAGLIAIVMVTILLCCMTSCCSCLKGACSCGSCCKFDEDDS Wuhan_Node1/5-1288       EPVLKGVKLHYT
                         ||||||||||||
AY274119/1-1255          EPVLKGVKLHYT
```

Percentage ID = 82.32

EXAMPLE 3

Alignment of full-length S-protein amino acid sequence of CoV_T2_1 (Wuhan_Node1) with
EPI_ISL_402119
Score = 53960.0

Length of alignment = 1280

Sequence Wuhan_Node1/9-1288(Sequence length = 1288) (SEQ ID NO: 13)

Sequence EPI_ISL_402119/1-1273(Sequence length = 1273) (SEQ ID NO: 7)

```
Wuhan_Node1/9-1288       IFAFFLLSAKANERCGIFTSKPQPKLAQVSSSRRGVYYPDDIFRSDVLHL
                         ·|·|··|·  ·  ·|  ·|·· |   |   ·|  ||||||||·|||·|||
EPI_ISL_402119/1-1273    MFVFLVLLPLVSSQCVNLTTRTQLPPAYTNSFTRGVYYPDKVFRSSVLHS Wuhan_Node1/9-1288       TQDYFLPFDSNVTRYFSLNANGPDRIVYFDNPIIPFKDGVYFAATEKSNV
                         |||·||||·|||·|||··|··  ···  ·|·      ||||··||·|||||||·||||·
EPI_ISL_402119/1-1273    TQDLFLPFFSNVTWFHAIHVSGINGTKRFDNPVLPFNDGVYFASTEKSNI Wuhan_Node1/9-1288       IRGWIFGSTLDNTSQSVIIVNNSTNVIIRVCNFDLCNDPFFTVSRPTDKH
                         |||||||·|||·  ·||··|||||·|||·|||·|·||·|··|||||· |   ·|·
EPI_ISL_402119/1-1273    IRGWIFGTTLDSKTQSLLIVNNATNVVIKVCEFQFCNDPFLGVY--YHKN Wuhan_Node1/9-1288       IKTWSIREFAVYQSAFNCTFEYVSKSFLLDVAEKPGNFKHLREFVFKNVD
                         |·|    ||·||·||·|| |||||||||··||·|·  |·|||||·|||||||||·|
EPI_ISL_402119/1-1273    NKSWMESEFRVYSSANNCTFEYVSQPFLMDLEGKQGNFKNLREFVFKNID Wuhan_Node1/9-1288       GFLNVYSTYKPINVVSGLPTGFSVLKPILKLPLGINITSFRVLLTMFRGD
                         |····||   |||·|  ·||  |||  |  |··   ||·||||||  |·   ||··   |·
EPI_ISL_402119/1-1273    GYFKIYSKATPINLVRDLPQGFSALEPLVDLPIGINITRFQTLLALHRSY Wuhan_Node1/9-1288       PTPGHTTANWLTAAAAYYVGYLKPTTFMLKYNENGTITDAVDCSQNPLAE
                         |||····  |   ·· |||||||||||·| ||·||||||||||||||||| ·  ·||·|
EPI_ISL_402119/1-1273    LTPGDSSSGWTAGAAAYYVGYLQPRTFLLKYNENGTITDAVDCALDPLSE Wuhan_Node1/9-1288       LKCTLKNFNVDKGIYQTSNFRVSPTQEVVRFPNITNLCPFDKVFNATRFP
                         ||||||·|  |·|||||||||||||  ||·  ·||||||||||||·  |||||||||·
EPI_ISL_402119/1-1273    TKCTLKSFTVEKGIYQTSNFRVQPTESIVRFPNITNLCPFGEVFNATRFA Wuhan_Node1/9-1288       SVYAWERTKISDCVADYTVLYNSTSFSTFKCYGVSPSKLIDLCFTSVYAD
                         ||||||·|  ·||·|||||||·||||| ·||||||||||||||||||·||  ||||||·||||
EPI_ISL_402119/1-1273    SVYAWNRKRISNCVADYSVLYNSASFSTFKCYGVSPTKLNDLCFTNVYAD Wuhan_Node1/9-1288       TFLIRCSEVRQVAPGQTGVIADYNYKLPDDFTGCVIAWNTAKQDTGSSGN
                         ·|·|| ||||·||||||| ||||||||||||||||||||||||||||·  ·  |·  ·||
EPI_ISL_402119/1-1273    SFVIRGDEVRQIAPGQTGKIADYNYKLPDDFTGCVIAWNSNNLDSKVGGN Wuhan_Node1/9-1288       YNYYYRSHRKTKLKPFERDLSSDECSPDGKPCTPPAFNGVRGFNCYFTLS
                         |||  ||   ||··|||||||·|··    ···  ||       |||  |||||| |
EPI_ISL_402119/1-1273    YNYLYRLFRKSNLKPFERDISTEIYQAGSTPC-----NGVEGFNCYFPLQ Wuhan_Node1/9-1288       TYDFNPNVPVEYQATRVVVLSFELLNAPATVCGPKLSTQLVKNQCVNFNF
                         ·|·|·|  |  ||·  ||||||||||||·||||||||·  ||·||||·||||||·
EPI_ISL_402119/1-1273    SYGFQPTNGVGYQPYRVVVLSFELLHAPATVCGPKKSTNLVKNKCVNFNF Wuhan_Node1/9-1288       NGLKGTGVLTASSKRFQSFQQFGRDASDFTDSVRDPQTLEILDISPCSFG
                         ||| |||||||·|·|  ·||||||||·|  ||·||·||||||||||||·|||||
EPI_ISL_402119/1-1273    NGLTGTGVLTESNKKFLPFQQFGRDIADTTDAVRDPQTLEILDITPCSFG
```

-continued

```
Wuhan_Node1/9-1288        GVSVITPGTNTSSEVAVLYQDVNCTDVPTAIHADQLTPAWRVYSTGVNVF
                          |||||||||||||..|||||||||||.||.|||||||||.||||||.|||
EPI_ISL_402119/1-1273     GVSVITPGTNTSNQVAVLYQDVNCTEVPVAIHADQLTPTWRVYSTGSNVF Wuhan_Node1/9-1288        QTQAGCLIGAEHVNASYECDIPIGAGICASYHTASNSPRILRSTGQKSIV
                          ||.|||||||||||.||||||||||||||||||.|.|||||.||..||.
EPI_ISL_402119/1-1273     QTRAGCLIGAEHVNNSYECDIPIGAGICASYQTQTNSPRRARSVASQSII Wuhan_Node1/9-1288        AYTMSLGAENSIAYANNSIAIPTNFSISVTTEVMPVSMAKTSVDCTMYIC
                          |||||||||||.||.||||||||.||||||..||||.||||||||||||
EPI_ISL_402119/1-1273     AYTMSLGAENSVAYSNNSIAIPTNFTISVTTEILPVSMTKTSVDCTMYIC Wuhan_Node1/9-1288        GDSLECSNLLLQYGSFCTQLNRALTGIAIEQDKNTQEVFAQVKQMYKTPA
                          |||.|||||||||||||||||||||||.|||||||||||||||.||||.
EPI_ISL_402119/1-1273     GDSTECSNLLLQYGSFCTQLNRALTGIAVEQDKNTQEVFAQVKQIYKTPP Wuhan_Node1/9-1288        IKDFGGFNFSQILPDPSKPTKRSFIEDLLFNKVTLADAGFMKQYGECLGD
                          ||||||||||||||||||||.|||||||||||||||||||.||||.||||
EPI_ISL_402119/1-1273     IKDFGGFNFSQILPDPSKPSKRSFIEDLLFNKVTLADAGFIKQYGDCLGD Wuhan_Node1/9-1288        ISARDLICAQKFNGLTVLPPLLTDEMIAAYTAALVSGTATAGWTFGAGAA
                          |.|||||||||||||||||||||||||.||.||..||.|.||||||||||
EPI_ISL_402119/1-1273     IAARDLICAQKFNGLTVLPPLLTDEMIAQYTSALLAGTITSGWTFGAGAA Wuhan_Node1/9-1288        LQIPFAMQMAYRFNGIGVTQNVLYENQKQIANQFNKAISQIQESLITTST
                          |||||||||||||||||||||||||||||.||||||||||.||.||..|..
EPI_ISL_402119/1-1273     LQIPFAMQMAYRFNGIGVTQNVLYENQKLIANQFNSAIGKIQDSLSSTAS Wuhan_Node1/9-1288        ALGKLQDVVNQNAQALNTLVKQLSSNFGAISSVLNDILSRLDKVEAEVQI
                          ||||||||||||||||||||||||||||||||||||||||||||||||||
EPI_ISL_402119/1-1273     ALGKLQDVVNQNAQALNTLVKQLSSNFGAISSVLNDILSRLDKVEAEVQI Wuhan_Node1/9-1288        DRLITGRLQSLQTYVTQQLIRAAEIRASANLAATKMSECVLGQSKRVDFC
                          ||||||||||||||||||||||||||||||||||||||||||||||||||
EPI_ISL_402119/1-1273     DRLITGRLQSLQTYVTQQLIRAAEIRASANLAATKMSECVLGQSKRVDFC Wuhan_Node1/9-1288        GKGYHLMSFPQAAPHGVVFLHVTYVPSQERNFTTAPAICHECKAYFPREG
                          |||||||||||.||||||||||||||||.||.||||||||||.|||.|||
EPI_ISL_402119/1-1273     GKGYHLMSFPQSAPHGVVFLHVTYVPAQEKNFTTAPAICHDGKAHFPREG Wuhan_Node1/9-1288        VFVSNGTSWFITQRNFYSPQIITTDNTFVSGNCDVVIGIINNTVYDPLQP
                          ||||||.||.||||||.|||||||||||||||||||||.|||||||||||
EPI_ISL_402119/1-1273     VFVSNGTHWFVTQRNFYEPQIITTDNTFVSGNCDVVIGIVNNTVYDPLQP Wuhan_Node1/9-1288        ELDSFKEELDKYFKNHTSPDVDLGDISGINASVVNIQKEIDRINEVAKNL
                          ||||||||||||||||||||||||||||||||||||||||||||.|||||
EPI_ISL_402119/1-1273     ELDSFKEELDKYFKNHTSPDVDLGDISGINASVVNIQKEIDRLNEVAKNL Wuhan_Node1/9-1288        NESLIDLQELGKYEQYIKWPWYVWLGFIAGLIAIVMATILLCCMTSCCSC
                          |||||||||||||||||||||||||.||||||||||||||.|||||||||
EPI_ISL_402119/1-1273     NESLIDLQELGKYEQYIKWPWYIWLGFIAGLIAIVMVTIMLCCMTSCCSC Wuhan_Node1/9-1288        LKGACSCGSCCKFDEDDSEPVLKGVKLHYT
                          |||.||||||||||||||||||||||||||
EPI_ISL_402119/1-1273     LKGCCSCGSCCKFDEDDSEPVLKGVKLHYT Percentage ID = 78.98
```

EXAMPLE 4

```
Alignment of truncated S-protein amino acid sequence of CoV_T2_4 (Wuhan_Node1_tr)
with AY274119
Score = 49480.0

Length of alignment = 1181

Sequence Wuhan_Node1_tr/5-1185 (Sequence length = 1185) (SEQ ID NO: 15)

Sequence AY274119_tr (CoV_T2_2)/1-1152(Sequence length = 1152) (SEQ ID NO: 3)

Wuhan_Node1_tr/5-1185              LFIIIFAFFLLSAKANERCGIFTSKPQPKLAQVSSSRRGVYYP
                                  .||...,.||.,.||,|,,,,,|..|.,|||,||||||
AY274119_tr (CoV_T2_2)/1-1152     MFIFLLFLTLTSGSDLDRCTTFDDVQAPNYTQHTSSMRGVYYP Wuhan_Node1_tr/5-1185             DDIFRSDVLALTQDYFLPFDSNVTRYFSLNANGPDRIVYFDNP
                                 |.|||||.|,||||,||||,||||,.,,|,       .   |.||
```

```
                        -continued
AY274119_tr (CoV_T2_2)/1-1152   DEIFRSDTLYLTQDLFLPFYSNVTGFHTIN-----HT--FGNP Wuhan_Node1_tr/5-1185           IIPFKDGVYFAATEKSNVIRGWIFGSTLDNTSQSVIIVNNSTN
                                .||||||.||||||||||.|||.||||..| ||||||.|||||
AY274119_tr(CoV_T2_2)/1-1152    VIPFKDGIYFAATEKSNVVRGWVFGSTMNNKSQSVIIINNSTN Wuhan_Node1_tr/5-1185           VIIRVCNFDLCNDPFFTVSRPTDKHIKTWSIREFAVYQSAFNC
                                |.|| |||.||..|||.||.| .    .| .     ....||||
AY274119_tr (CoV_T2_2)/1-1152   VVIRACNFELCDNPFFAVSKPMG--TQTHT----MIFDNAFNC Wuhan_Node1_tr/5-1185           TFEYVSKSFLLDVAEKPGNFKHLREFVFKNVDGFLNVYSTYKP
                                ||||.| .| |||.||.|||||||||||| |||| || |.|
AY274119_tr (CoV_T2_2)/1-1152   TFEYISDAFSLDVSEKSGNFKHLREFVFKNKDGFLYVYKGYQP Wuhan_Node1_tr/5-1185           INVVSGLPTGFSVLKPILKLPLGINITSFRVLLTMFRGDPTPG
                                |.|| .||.||. ||||.|||||||||.|| .|| |    .|.
AY274119_tr (CoV_T2_2)/1-1152   IDVVRDLPSGFNTLKPIFKLPLGINITNFRAILTAF----SPA Wuhan_Node1_tr/5-1185           HTTANWLTAAAAYYVGYLKPTTFMLKYNENGTITDAVDCSQNP
                                .    | |.||||.|||||||||||||.||||||||||||||||
AY274119_tr (CoV_T2_2)/1-1152   QDI--WGTSAAAYFVGYLKPTTFMLKYDENGTITDAVDCSQNP Wuhan_Node1_tr/5-1185           LAELKCTLKNFNVDKGIYQTSNFRVSPTQEVVRFPNITNLCPF
                                ||||||..|.|..||||||||||||| |. .|||||||||||||
AY274119_tr(CoV_T2_2)/1-1152    LAELKCSVKSFEIDKGIYQTSNFRVVPSGDVVRFPNITNLCPF Wuhan_Node1_tr/5-1185           DKVFNATRFPSVYAWERTKISDCVADYTVLYNSTSFSTFKCYG
                                . |||||.|||||||| |||.||||.||||||| ||||||||
AY274119_tr(CoV_T2_2)/1-1152    GEVFNATKFPSVYAWERKKISNCVADYSVLYNSTFFSTFKCYG Wuhan_Node1_tr/5-1185           VSPSKLIDLCFTSVYADTFLIRCSEVRQVAPGQTGVIADYNYK
                                ||..|| ||||..||||.|... .|||.|||||||||||||||
AY274119_tr(CoV_T2_2)/1-1152    VSATKLNDLCFSNVYADSFVVKGDDVRQIAPGQTGVIADYNYK Wuhan_Node1_tr/5-1185           LPDDFTGCVIAWNTAKQDTGSSGNYNYYYRSHRKTKLKPFERD
                                ||||| |||.||||  . |. |.|||||| ||   |.||.||||
AY274119_tr (CoV_T2_2)/1-1152   LPDDFMGCVLAWNTRNIDATSTGNYNYKYRYLRHGKLRPFERD Wuhan_Node1_tr/5-1185           LSSDECSPDGKPCTPPAFNGVRGFNCYFTLSTYDFNPNVPVEY
                                .|.  |||||||||||       .||| |.|.|.|      .|
AY274119_tr (CoV_T2_2)/1-1152   ISNVPFSPDGKPCTPPA------LNCYWPLNDYGFYTTTGIGY Wuhan_Node1_tr/5-1185           QATRVVVLSFELLNAPATVCGPKLSTQLVKNQCVNFNFNGLKG
                                |. |||||||||||||||||||||||||.|.|.||||||||||| |
AY274119_tr (CoV_T2_2)/1-1152   QPYRVVVLSFELLNAPATVCGPKLSTDLIKNQCVNFNFNGLTG Wuhan_Node1_tr/5-1185           TGVLTASSKRFQSFQQFGRDASDFTDSVRDPQTLEILDISPCS
                                |||||.|||||.||||||| |||||||||||.| |||||||||.
AY274119_tr (CoV_T2_2)/1-1152   TGVLTPSSKRFQPFQQFGRDVSDFTDSVRDPKTSEILDISPCA Wuhan_Node1_tr/5-1185           FGGVSVITPGTNTSSEVAVLYQDVNCTDVPTAIHADQLTPAWR
                                ||||||||||||.||||||||||||||||||.|||||||||||||
AY274119_tr(CoV_T2_2)/1-1152    FGGVSVITPGTNASSEVAVLYQDVNCTDVSTAIHADQLTPAWR Wuhan_Node1_tr/5-1185           VYSTGVNVFQTQAGCLIGAEHVNASYECDIPIGAGICASYHTA
                                .||||  ||||||||||||||||.||||||||||||||||||
AY274119_tr(CoV_T2_2)/1-1152    IYSTGNNVFQTQAGCLIGAEHVDTSYECDIPIGAGICASYHTV Wuhan_Node1_tr/5-1185           SNSPRILRSTGQKSIVAYTMSLGAENSIAYANNSIAIPTNFSI
                                |     .||||.|||||||||||||..||||.||.|||||||||
AY274119_tr (CoV_T2_2)/1-1152   S----LLRSTSQKSIVAYTMSLGADSSIAYSNNTIAIPTNFSI Wuhan_Node1_tr/5-1185           SVTTEVMPVSMAKTSVDCTMYICGDSLECSNLLLQYGSFCTQL
                                |.||||||||||||||||||.||||||.|||.||||||||||||
AY274119_tr (CoV_T2_2)/1-1152   SITTEVMPVSMAKTSVDCNMYICGDSTECANLLLQYGSFCTQL Wuhan_Node1_tr/5-1185           NRALTGIAIEQDKNTQEVFAQVKQMYKTPAIKDFGGFNFSQIL
                                ||||.||| |||.||.|||||||||||||||.| |||||||||||
AY274119_tr (CoV_T2_2)/1-1152   NRALSGIAAEQDRNTREVFAQVKQMYKTPTLKYFGGFNFSQIL Wuhan_Node1_tr/5-1185           PDPSKPTKRSFIEDLLFNKVTLADAGFMKQYGECLGDISARDL
                                ||| ||||||||||||||||||||||||||||||.||||.||||
AY274119_tr (CoV_T2_2)/1-1152   PDPLKPTKRSFIEDLLFNKVTLADAGFMKQYGECLGDINARDL Wuhan_Node1_tr/5-1185           ICAQKFNGLTVLPPLLTDEMIAAYTAALVSGTATAGWTFGAGA
                                ||||||||||||||||||.|||||||||||||||||||||||||
AY274119_tr (CoV_T2_2)/1-1152   ICAQKFNGLTVLPPLLTDDMIAAYTAALVSGTATAGWTFGAGA Wuhan_Node1_tr/5-1185           ALQIPFAMQMAYRFNGIGVTQNVLYENQKQIANQFNKAISQIQ
                                |||||||||||||||||||||||||||||||||||||||||||
AY274119_tr (CoV_T2_2)/1-1152   ALQIPFAMQMAYRFNGIGVTQNVLYENQKQIANQFNKAISQIQ
```

-continued

```
Wuhan_Node1_tr/5-1185              ESLTTTSTALGKLQDVVNQNAQALNTLVKQLSSNFGAISSVLN
                                   ||||||||||||||||||||||||||||||||||||||||||||
AY274119_tr (CoV_T2_2)/1-1152      ESLTTTSTALGKLQDVVNQNAQALNTLVKQLSSNFGAISSVLN Wuhan_Node1_tr/5-1185              DILSRLDKVEAEVQIDRLITGRLQSLQTYVTQQLIRAAEIRAS
                                   ||||||||||||||||||||||||||||||||||||||||||||
AY274119_tr (CoV_T2_2)/1-1152      DILSRLDKVEAEVQIDRLITGRLQSLQTYVTQQLIRAAEIRAS Wuhan_Node1_tr/5-1185              ANLAATKMSECVLGQSKRVDFCGKGYHLMSFPQAAPHGVVFLH
                                   |||||||||||||||||||||||||||||.||||||||||||||
AY274119_tr (CoV_T2_2)/1-1152      ANLAATKMSECVLGQSKRVDFCGKGYHIMSFPQAAPHGVVFLH Wuhan_Node1_tr/5-1185              VTYVPSQERNFTTAPAICHEGKAYFPREGVFVSNGTSWFITQR
                                   ||||||||||||||||||||||||||||||||.||||||||||||
AY274119_tr (CoV_T2_2)/1-1152      VTYVPSQERNFTTAPAICHEGKAYFPREGVFVFNGTSWFITQR Wuhan_Node1_tr/5-1185              NFYSPQIITTDNTFVSGNCDVVIGIINNTVYDPLQPELDSFKE
                                   ||.|||||||||||||||||||||||||||||||||||||||||
AY274119_tr (CoV_T2_2)/1-1152      NFFSPQIITTDNTFVSGNCDVVIGIINNTVYDPLQPELDSFKE Wuhan_Node1_tr/5-1185              ELDKYFKNHTSPDVDLGDIS
                                   ||||||||||||||||||||
AY274119_tr (CoV_T2_2)/1-1152      ELDKYFKNHTSPDVDLGDIS
```

Percentage ID = 80.86

EXAMPLE 5

```
Alignment of truncated S-protein amino acid sequence of CoV_T2_4 (Wuhan_Node1_tr)
with EPI_ISL_402119
Score = 48450.0

Length of alignment = 1177

Sequence Wuhan_Node1_tr/9-1185 (Sequence length = 1185) (SEQ ID NO: 15)

Sequence EPI_ISL_402119_tr/1-1170 (Sequence length = 1170) (SEQ ID NO: 9)

Wuhan_Node1_tr/9-1185              IFAFFLLSAKANERCGIFTSKPQPKLAQVSSSRRGVYYPDDIFRSDV
                                  .| |..|.   . .|  .|..|    |     |  .|  ||||||| .||| |
EPI_ISL_402119_tr/1-1170          MFVFLVLLPLVSSQCVNLTTRTQLPPAYTNSFTRGVYYPDKVFRSSV Wuhan_Node1_tr/9-1185             LHLTQDYFLPFDSNVTRYFSLNANGPDRIVYFDNPIIPFKDGVYFAA
                                  || |||  ||||  ||||..  ...  .|  .    ||||..||.||||||.
EPI_ISL_402119_tr/1-1170          LHSTQDLFLPFFSNVTWFHAIHVSGTNGTKRFDNPVLPFNDGVYFAS Wuhan_Node1_tr/9-1185             TEKSNVIRGWIFGSTLDNTSQSVIIVNNSTNVIIRVCNFDLCNDPFF
                                  |||||.||||||||.|||. .||..|||||.|||.|.||.|..|||||.
EPI_ISL_402119_tr/1-1170          TEKSNIIRGWIFGTTLDSKTQSLLIVNNATNVVIKVCEFQFQNDPFL Wuhan_Node1_tr/9-1185             TVSRPTDKHIKTWSIREFAVYQSAFNCTFEYVSKSFLLDVAEKPGNF
                                  |    .|. |.|   || || || |||||||||..||.|.  | |||
EPI_ISL_402119_tr/1-1170          GVY--YHKNNKSWMESEFRVYSSANNCTFEYVSQPFLMDLEGKQGNF Wuhan_Node1_tr/9-1185             KHLREFVFKNVDGFLNVYSTYKPINVVSGLPTGFSVLKPILKLPLGI
                                  |.|||||||.||....||   |||.|  .|| ||| | |..  ||.||
EPI_ISL_402119_tr/1-1170          KNLREFVFKNIDGYFKIYSKHTPINLVRDLPQGFSALEPLVDLPIGI Wuhan_Node1_tr/9-1185             NITSFRVLLTMFRGDPTPGHTTANWLTAAAAYYVGYLKPTTFMLKYN
                                  ||| |. ||.. |.  |||....  |  ..||||||||||.| ||.||||
EPI_ISL_402119_tr/1-1170          NITRFQTLLALHRSYLTPGDSSSGWTAGAAAYYVGYLQPRTFLLKYN Wuhan_Node1_tr/9-1185             ENGTITDAVDCSQNPLAELKCTLKNFNVDKGIYQTSNFRVSPTQEVV
                                  ||||||||||.  .||.| ||||||.| |.||||||||||| ||. .|
EPI_ISL_402119_tr/1-1170          ENGTITDAVDCALDPLSETKCTLKSFTVEKGIYQTSNFRVQPTESIV Wuhan_Node1_tr/9-1185             RFPNITNLCPFDKVFNATRFPSVYAWERTKISDCVADYTVLYNSTSF
                                  ||||||||||.  ||||||.|||||.| .||.|||||.|||||.||
EPI_ISL_402119_tr/1-1170          RFPNITNLCPFGEVFNATRFASVYAWNRKRISNCVADYSVLYNSASF Wuhan_Node1_tr/9-1185             STFKCYGVSPSKLIDLCFTSVYADTFLIRCSEVRQVAPGQTGVIADY
                                  ||||||||||.|| ||||.||||.|.|| |||| .|||||||||| ||||
EPI_ISL_402119_tr/1-1170          STFKCYGVSPTKLNDLCFTNVYADSFVIRGDEVRQIAPGQTGKIADY Wuhan_Node1_tr/9-1185             NYKLPDDFTGCVIAWNTAKQDTGSSGNYNYYYRSHRKTKLKPFERDL
                                  |||||||||||||||| .  |.   .||||| ||   ||..||||||.
```

```
                              -continued
EPI_ISL_402119_tr/1-1170    NYKLPDDFTGCVIAWNSNNLDSKVGGNYNYLYRLFRKSNLKPFERDI Wuhan_Node1_tr/9-1185       SSDECSPDGKPCTPPAFNGVRGFNCYFTLSTYDFNPNVPVEYQATRV
                            |..    ... ||      ||| |||||| | .|.|.|   | ||. ||
EPI_ISL_402119_tr/1-1170    STEIYQAGSTPC-----NGVEGFNCYFPLQSYGFQPTNGVGYQPYRV Wuhan_Node1_tr/9-1185       VVLSFELLNAPATVCGPKLSTQLVKNQCVNFNFNGLKGTGVLTASSK
                            ||||||||.|||||||||| ||.||||.|||||||||| |||||| |.|
EPI_ISL_402119_tr/1-1170    VVLSFELLHAPATVCGPKKSTNLVKNKCVNFNFNGLTGTGVLTESNK Wuhan_Node1_tr/9-1185       RFQSFQQFGRDASDFTDSVRDPQTLEILDISPCSFGGVSVITPGTNT
                            .|  .||||||| .| ||.||||||||||||.|||||||||||||||||
EPI_ISL_402119_tr/1-1170    KFLPFQQFGRDIADTTDAVRDPQTLEILDITPCSFGGVSVITPGTNT Wuhan_Node1_tr/9-1185       SSEVAVLYQDVNCTDVPTAIHADQLTPAWRVYSTGVNVFQTQAGCLI
                            |..|||||||||||.|| |||||||||.|||||||  ||||| .|||||
EPI_ISL_402119_tr/1-1170    SNQVAVLYQDVNCTEVPVAIHADQLTPTWRVYSTGSNVFQTRAGCLI Wuhan_Node1_tr/9-1185       GAEHVNASYECDIPIGAGICASYHTASNSPRILRSTGQKSIVAYTMS
                            |||||| |||||||||||||||.| .|||| || . .||.|||||
EPI_ISL_402119_tr/1-1170    GAEHVNNSYECDIPIGAGICASYQTQTNSPRRARSVASQSIIAYTMS Wuhan_Node1_tr/9-1185       LGAENSIAYANNSIAIPTNFSISVTTEVMPVSMAKTSVDCTMYICGD
                            |||||||.||.|||||||||||.||||||..||||.|||||||||||
EPI_ISL_402119_tr/1-1170    LGAENSVAYSNNSIAIPTNFTISVTTEILPVSMTKTSVDCTMYICGD Wuhan_Node1_tr/9-1185       SLECSNELLQYGSFCTQLNRALTGIAIEQDKNTQEVFAQVKQMYKTP
                            | |||||||||||||||||||||||||.||||||||||||||.||||
EPI_ISL_402119_tr/1-1170    STECSNLLLQYGSFCTQLNRALTGIAVEQDKNTQEVFAQVKQIYKTP Wuhan_Node1_tr/9-1185       AIKDFGGFNFSQILPDPSKPTKRSFIEDLLFNKVTLADAGFMKQYGE
                            .|||||||||||||||||||.|||||||||||||||||||.||||.
EPI_ISL_402119_tr/1-1170    PIKDFGGFNFSQILPDPSKPSKRSFIEDLLFNKVTLADAGFIKQYGD Wuhan_Node1_tr/9-1185       CLGDISARDLICAQKFNGLTVLPPLLTDEMIAAYTAALVSGTATAGW
                            |||||.|||||||||||||||||||||||||||| ||.||..|| |.||
EPI_ISL_402119_tr/1-1170    CLGDIAARDLICAQKFNGLTVLPPLLTDEMIAQYTSALLAGTITSGW Wuhan_Node1_tr/9-1185       TFGAGAALQIPFAMQMAYRFNGIGVTQNVLYENQKQIANQFNKAISQ
                            |||||||||||||||||||||||||||||||||||| |||||| ||..
EPI_ISL_402119_tr/1-1170    TFGAGAALQIPFAMQMAYRFNGIGVTQNVLYENQKLIANQFNSAIGK Wuhan_Node1_tr/9-1185       IQESLTTTSTALGKLQDVVNQNAQALNTLVKQLSSNFGAISSVLNDI
                            ||.||..|..|||||||||||||||||||||||||||||||||||||
EPI_ISL_402119_tr/1-1170    IQDSLSSTASALGKLQDVVNQNAQALNTLVKQLSSNFGAISSVLNDI Wuhan_Node1_tr/9-1185       LSRLDKVEAEVQIDRLITGRLQSLQTYVTQQLIRAAEIRASANLAAT
                            |||||||||||||||||||||||||||||||||||||||||||||||
EPI_ISL_402119_tr/1-1170    LSRLDKVEAEVQIDRLITGRLQSLQTYVEQQLIRAAEIRASANLAAT Wuhan_Node1_tr/9-1185       KMSECVLGQSKRVDFCGKGYHLMSFPQAAPHGVVFLHVTYVPSQERN
                            |||||||||||||||||||||||||||.|||||||||||||.||.|
EPI_ISL_402119_tr/1-1170    KMSECVLGQSKRVDFCGKGYHLMSFPQSAPHGVVFLHVTYVPAQEKN Wuhan_Node1_tr/9-1185       FTTAPAICHEGKAYFPREGVFVSNGTSWFITQRNFYSPQIITTDNTF
                            ||||||||.||| |||||||||||||| ||.|||||| ||||||||
EPI_ISL_402119_tr/1-1170    FTTAPAICHDGKAHFPREGVFVSNGTHWFVTQRNFYEPQIITTDNTF Wuhan_Node1_tr/9-1185       VSGNCDVVIGIINNTVYDPLQPELDSFKEELDKYFKNHTSPDVDLGD
                            |||||||||||.||||||||||||||||||||||||||||||||||
EPI_ISL_402119_tr/1-1170    VSGNCDVVIGIVNNTVYDPLQPELDSFKEELDKYFKNHTSPDVDLGD Wuhan_Node1_tr/9-1185       IS
                            ||
EPI_ISL_402119_tr/1-1170    IS Percentage ID = 77.49
```

EXAMPLE 6

```
Alignment of S-protein RBD amino acid sequence
of CoV_T2_7 (Wuhan_Node1_RBD) with
Score = 8170.0
Length of alignment = 219
Sequence Wuhan Node1 RBD/1-219 (Sequence length = 219) (SEQ ID NO: 17)
Sequence AY274119 RBD/1-213 (Sequence length = 213) (SEQ ID NO: 5)
Wuhan_Model_RBD/1-219   RVSPTQEVVREPNITNLCPEDKVENATREPSVYAWERTKISDCVADYTVL
```

```
                        -continued
                  || |. .|||||||||||||. ||||||.||||||||| |||.|||||.||
AY274119_RBD/1-213  RVVPSGDVVRFPNITNLCPFGEVENATKEPSVYAWERKKISNCVADYSVL Wuhan_Model_RBD/1-219  YNSTSFSTEKCYGVSPSKLIDLCFTSVYADTFLIRCSEVRQVAPGQTGVI
                       |||| ||||||||||..|| ||||..||||.|... .|||.|||||||||
AY274119_RBD/1-213     YNSTFFSTFKCYGVSATKLNDLCFSNVYADSFVVKGDDVRQIAPGQTGVI Wuhan_Node1_RBD/1-219  ADYNYKLPDDETGCVIAWNTAKQDTGSSGNYNYYYRSHRKTKLKPFERDL
                       |||||||||||| |||.|||| . |. |.|||||| || | ||.|||||.
AY274119_RBD/1-213     ADYNYKLPDDFMGCVLAWNTRNIDATSTGNYNYKYRYLRHGKLRPFERDI Wuhan_Node1_RBD/1-219  SSDECSPDGKPCTPPAENGVRGENCYFTLSTYDENPNVPVEYQATRVVVL
                       |. |||||||||||     .||| |.|.| . ||. |||||
AY274119_RBD/1-213     SNVPFSPDGKPCTPPA------LNCYWPLNDYGFYTTTGIGYQPYRVVVL Wuhan_Node1_RBD/1-219  SFELLNAPATVCGPKLSTQ
                       |||||||||||||||||||.
AY274119_RBD/1-213     SFELLNAPATVCGPKLSTD
Percentage ID = 70.32
```

EXAMPLE 7

```
Alignment of S-protein RBD amino acid sequence
of CoV_T2_7 (Wuhan_Node1_RBD) with
EPI_ISL_402119
Score = 8150.0
Length of alignment = 219
Sequence Wuhan Node1 RBD/1-219 (Sequence length = 219) (SEQ ID NO: 17)
Sequence EPI_ISL_402119 RBD/1-214 (Sequence length = 214) (SEQ ID NO: 11)
Wuhan_Node1_RBD/1-219    RVSPTQEVVRFPNITNLCPFDKVFNATRFPSVYAWERTKISDCVADY
                         || ||. .||||||||||||. ||||||.|||||.| .||.|||||
EPI_ISL_402119_RBD/1-214 RVQPTESIVRFPNITNLCPFGEVFNATRFASVYAWNRKRISNCVADY Wuhan_Node1_RBD/1-219    TVLYNSTSESTEKCYGVSPSKLIDLCFTSVYADTFLIRCSEVRQVAP
                         .|||||.|||||||||||||.|| |||||.||||.|.|| ||||.||
EPI_ISL_402119_RBD/1-214 SVLYNSASFSTEKCYGVSPTKLNDLCFTNVYADSFVIRGDEVRQIAP Wuhan_Node1_RBD/1-219    GQTGVIADYNYKLPDDETGCVIAWNTAKQDTGSSGNYNYYYRSHRKT
                         |||| ||||||||||||||||||||. . |. .||||| || ||.
EPI_ISL_402119_RBD/1-214 GQTGKIADYNYKLPDDETGCVIAWNSNNLDSKVGGNYNYLYRLERKS Wuhan_Node1_RBD/1-219    KLKPFERDLSSDECSPDGKPCTPPAFNGVRGENCYFTLSTYDENPNV
                         .||||||.|.. ... || ||| ||||| | .|.|.|
EPI_ISL_402119_RBD/1-214 NLKPFERDISTEIYQAGSTPC-----NGVEGENCYFPLQSYGFQPTN Wuhan_Node1_RBD/1-219    PVEYQATRVVVLSFELLNAPATVCGPKLSTQ
                         | ||. |||||||||||.||||||||| ||.
EPI_ISL_402119_RBD/1-214 GVGYQPYRVVVLSFELLHAPATVCGPKKSTN
Percentage ID = 70.32
```

EXAMPLE 8

45

--- pEVAC Expression Vector

---

Figure 1:
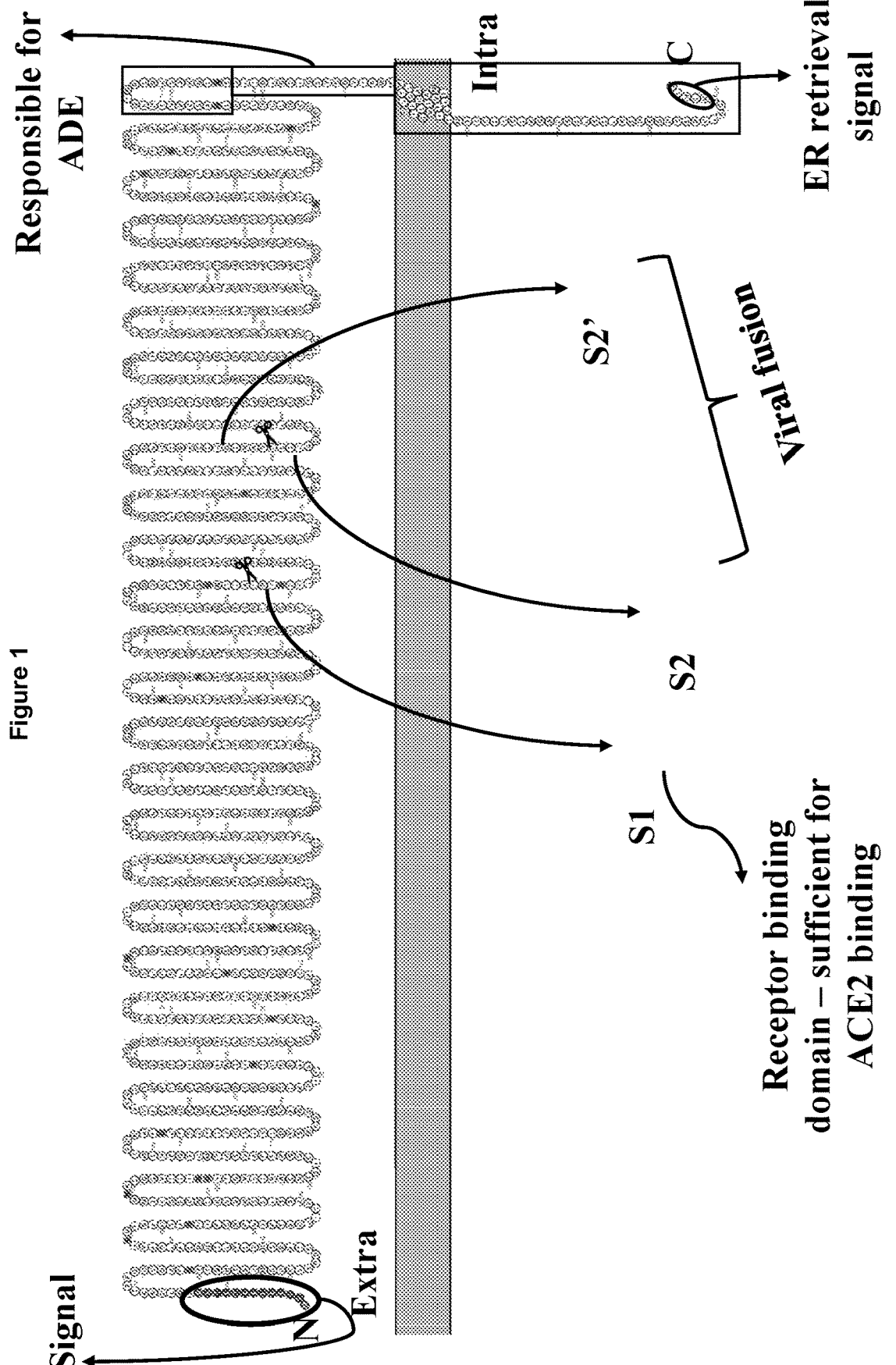
FIG. 1 shows SARS S-protein architecture.
Figure 2:
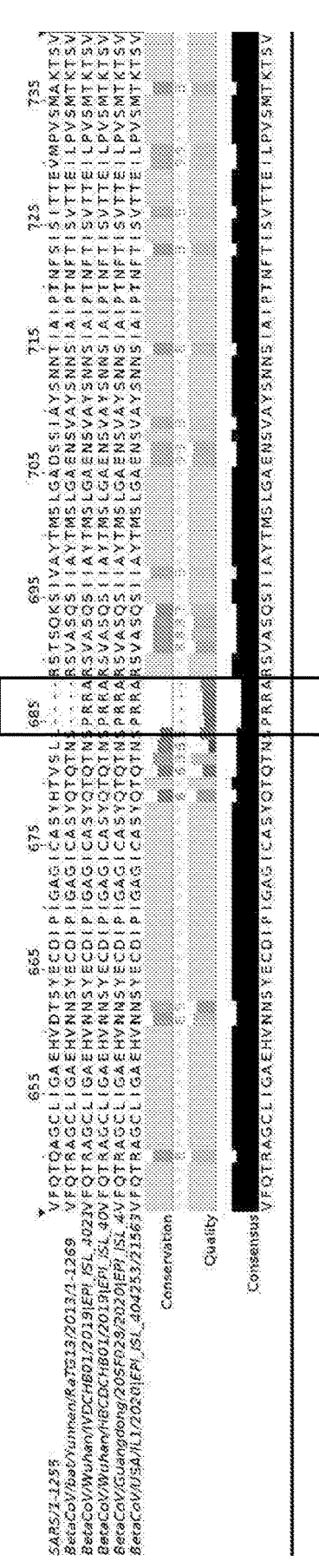
FIG. 2 shows a multiple sequence alignment of the S-protein (region around the S1 cleavage site) comparing SARS-COV-1 isolate (SEQ ID NO:86) and closely related bat betacoronavirus isolate (SEQ ID NO:87) with four SARS-COV-2 isolates (SEQ ID NO:88-91), and a consensus sequence (SEQ ID NO:92)
Figure 3:
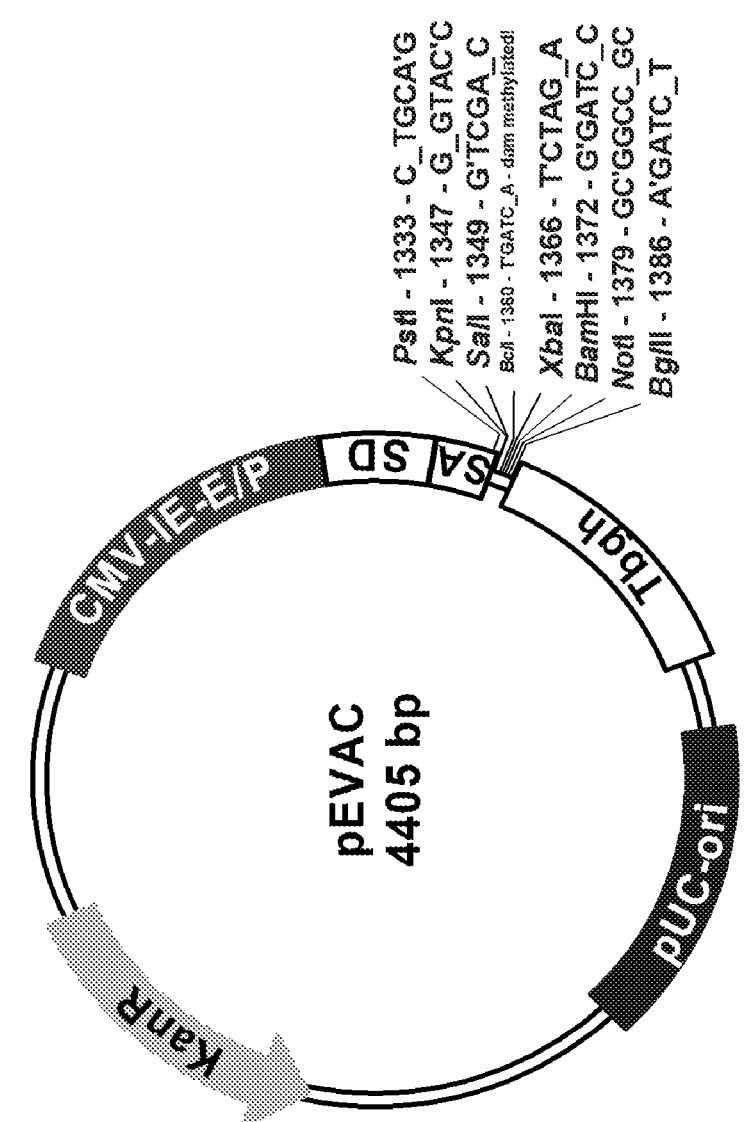
FIG. 3 shows a plasmid map for pEVAC DNA vector.

FIG. 3 shows a map of the pEVAC expression vector. The sequence
of the multiple cloning site of the vector is given below,
followed by its entire nucleotide sequence.
Sequence of pEVAC Multiple Cloning Site (MCS) (SEQ ID NO: 19):

```
           Pstl   Kpnl Sall
pEVAC 1301 ACAGACTGTT CCTTTCCATG GGTCTTTTCT GCAGTCACCG TCGGTACCGT Bcll Xbal BamHl Notl Bglll
pEVAC 1351 CGACACGTGT GATCATCTAG AGGATCCGCG GCCGCAGATC T
```

Entire Sequence of pEVAC (SEQ ID NO:20):

```
CMV-IE-E/   248 -   989 CMV immediate early 1 enhancer/promoter
P:
KanR:      3445 - 4098 Kanamycin resistance
SD:         990 - 1220 Splice donor
SA:        1221 - 1343 Splice acceptor
Tbgh:      1392 - 1942 Terminator signal from bovine growth hormone
pUC-ori:   2096 - 2769 pUC-plasmid origin of replication
```

-continued

| pEVAC Expression Vector |
| --- |

```
   1 TCGCGCGTTT CGGTGATGAC GGTGAAAACC TCTGACACAT GCAGCTCCCG

51 GAGACGGTCA CAGCTTGTCT GTAAGCGGAT GCCGGGAGCA GACAAGCCCG

101 TCAGGGCGCG TCAGCGGGTG TTGGGGGGTG TCGGGGCTGG CTTAACTATG

151 CGGCATCAGA GCAGATTGTA CTGAGAGTGC ACCATATGCG GTGTGAAATA

201 CCGCACAGAT GCGTAAGGAG AAAATACCGC ATCAGATTGG CTATTGGCCA

251 TTGCATACGT TGTATCCATA TCATAATATG TACATTTATA TTGGCTCATG

301 TCCAACATTA CCGCCATGTT GACATTGATT ATTGACTAGT TATTAATAGT

351 AATCAATTAC GGGGTCATTA GTTCATAGCC CATATATGGA GTTCCGCGTT

401 ACATAACTTA CGGTAAATGG CCCGCCTGGC TGACCGCCCA ACGACCCCCG

451 CCCATTGACG TCAATAATGA CGTATGTTCC CATAGTAACG CCAATAGGGA

501 CTTTCCATTG ACGTCAATGG GTGGAGTATT TACGGTAAAC TGCCCACTTG

551 GCAGTACATC AAGTGTATCA TATGCCAAGT ACGCCCCCTA TTGACGTCAA

601 TGACGGTAAA TGGCCCGCCT GGCATTATGC CCAGTACATG ACCTTATGGG

651 ACTTTCCTAC TTGGCAGTAC ATCTACGTAT TAGTCATCGC TATTACCATG

701 GTGATGCGGT TTTGGCAGTA CATCAATGGG CGTGGATAGC GGTTTGACTC

751 ACGGGGATTT CCAAGTCTCC ACCCCATTGA CGTCAATGGG AGTTTGTTTT

801 GGCACCAAAA TCAACGGGAC TTTCCAAAAT GTCGTAACAA CTCCGCCCCA

851 TTGACGCAAA TGGGGGGTAG GCGTGTACGG TGGGAGGTCT ATATAAGCAG

901 AGCTCGTTTA GTGAACCGTC AGATCGCCTG GAGACGCCAT CCACGCTGTT

951 TTGACCTCCA TAGAAGACAC CGGGACCGAT CCAGCCTCCA TCGGCTCGCA

1001 TCTCTCCTTC ACGCGCCCGC CGCCCTACCT GAGGCCGCCA TCCACGCCGG

1051 TTGAGTCGCG TTCTGCCGCC TCCCGCCTGT GGTGCCTCCT GAACTGCGTC

1101 CGCCGTCTAG GTAAGTTTAA AGCTCAGGTC GAGACCGGGC CTTTGTCCGG

1151 CGCTCCCTTG GAGCCTACCT AGACTCAGCC GGCTCTCCAC GCTTTGCCTG

1201 ACCCTGCTTG CTCAACTCTA GTTAACGGTG GAGGGCAGTG TAGTCTGAGC

1251 AGTACTCGTT GCTGCCGCGC GCGCCACCAG ACATAATAGC TGACAGACTA

1301 ACAGACTGTT CCTTTCCATG GGTCTTTTCT GCAGTCACCG TCGGTACCGT

1351 CGACACGTGT GATCATCTAG AGGATCCGCG CCGCAGATC TGCTGTGCCT

1401 TCTAGTTGCC AGCCATCTGT TGTTTGCCCC TCCCCCGTGC CTTCCTTGAC

1451 CCTGGAAGGT GCCACTCCCA CTGTCCTTTC CTAATAAAAT GAGGAAATTG

1501 CATCGCATTG TCTGAGTAGG TGTCATTCTA TTCTGGGGGG TGGGGTGGGG

1551 CAGGACAGCA AGGGGGAGGA TTGGGAAGAC AATAGCAGGC ATGCTGGGGA

1601 TGCGGTGGGC TCTATGGCTA CCCAGGTGCT GAAGAATTGA CCCGGTTCCT

1651 CCTGGGCCAG AAAGAAGCAG GCACATCCCC TTCTCTGTGA CACACCCTGT

1701 CCACGCCCCT GGTTCTTAGT TCCAGCCCCA CTCATAGGAC ACTCATAGCT

1751 CAGGAGGGCT CCGCCTTCAA TCCCACCCGC TAAAGTACTT GGAGCGGTCT

1801 CTCCCTCCCT CATCAGCCCA CCAAACCAAA CCTAGCCTCC AAGAGTGGGA

1851 AGAAATTAAA GCAAGATAGG CTATTAAGTG CAGAGGGAGA GAAAATGCCT
```

138

-continued

| pEVAC Expression Vector |
| --- |

```
1901 CCAACATGTG AGGAAGTAAT GAGAGAAATC ATAGAATTTT AAGGCCATGA

1951 TTTAAGGCCA TCATGGCCTT AATCTTCCGC TTCCTCGCTC ACTGACTCGC

2001 TGCGCTCGGT CGTTCGGCTG CGGCGAGCGG TATCAGCTCA CTCAAAGGCG

2051 GTAATACGGT TATCCACAGA ATCAGGGGAT AACGCAGGAA AGAACATGTG

2101 AGCAAAAGGC CAGCAAAAGG CCAGGAACCG TAAAAAGGCC GCGTTGCTGG

2151 CGTTTTTCCA TAGGCTCCGC CCCCCTGACG AGCATCACAA AAATCGACGC

2201 TCAAGTCAGA GGTGGCGAAA CCCGACAGGA CTATAAAGAT ACCAGGCGTT

2251 TCCCCCTGGA AGCTCCCTCG TGCGCTCTCC TGTTCCGACC CTGCCGCTTA

2301 CCGGATACCT GTCCGCCTTT CTCCCTTCGG GAAGCGTGGC GCTTTCTCAT

2351 AGCTCACGCT GTAGGTATCT CAGTTCGGTG TAGGTCGTTC GCTCCAAGCT

2401 GGGCTGTGTG CACGAACCCC CCGTTCAGCC CGACCGCTGC GCCTTATCCG

2451 GTAACTATCG TCTTGAGTCC AACCCGGTAA GACACGACTT ATCGCCACTG

2501 GCAGCAGCCA CTGGTAACAG GATTAGCAGA GCGAGGTATG TAGGCGGTGC

2551 TACAGAGTTC TTGAAGTGGT GGCCTAACTA CGGCTACACT AGAAGAACAG

2601 TATTTGGTAT CTGCGCTCTG CTGAAGCCAG TTACCTTCGG AAAAAGAGTT

2651 GGTAGCTCTT GATCCGGCAA ACAAACCACC GCTGGTAGCG GTGGTTTTTT

2701 TGTTTGCAAG CAGCAGATTA CGCGCAGAAA AAAGGATCT CAAGAAGATC

2751 CTTTGATCTT TTCTACGGGG TCTGACGCTC AGTGGAACGA AAACTCACGT

2801 TAAGGGATTT TGGTCATGAG ATTATCAAAA AGGATCTTCA CCTAGATCCT

2851 TTTAAATTAA AAATGAAGTT TTAAATCAAT CTAAAGTATA TATGAGTAAA

2901 CTTGGTCTGA CAGTTACCAA TGCTTAATCA GTGAGGCACC TATCTCAGCG

2951 ATCTGTCTAT TTCGTTCATC CATAGTTGCC TGACTCGGGG GGGGGGGCG

3001 CTGAGGTCTG CCTCGTGAAG AAGGTGTTGC TGACTCATAC CAGGCCTGAA

3051 TCGCCCCATC ATCCAGCCAG AAAGTGAGGG AGCCACGGTT GATGAGAGCT

3101 TTGTTGTAGG TGGACCAGTT GGTGATTTTG AACTTTTGCT TTGCCACGGA

3151 ACGGTCTGCG TTGTCGGGAA GATGCGTGAT CTGATCCTTC AACTCAGCAA

3201 AAGTTCGATT TATTCAACAA AGCCGCCGTC CCGTCAAGTC AGCGTAATGC

3251 TCTGCCAGTG TTACAACCAA TTAACCAATT CTGATTAGAA AAACTCATCG

3301 AGCATCAAAT GAAACTGCAA TTTATTCATA TCAGGATTAT CAATACCATA

3351 TTTTTGAAAA AGCCGTTTCT GTAATGAAGG AGAAAACTCA CCGAGGCAGT

3401 TCCATAGGAT GGCAAGATCC TGGTATCGGT CTGCGATTCC GACTCGTCCA

3451 ACATCAATAC AACCTATTAA TTTCCCCTCG TCAAAAATAA GGTTATCAAG

3501 TGAGAAATCA CCATGAGTGA CGACTGAATC CGGTGAGAAT GGCAAAAGCT

3551 TATGCATTTC TTTCCAGACT TGTTCAACAG GCCAGCCATT ACGCTCGTCA

3601 TCAAAATCAC TCGCATCAAC CAAACCGTTA TTCATTCGTG ATTGCGCCTG

3651 AGCGAGACGA AATACGCGAT CGCTGTTAAA AGGACAATTA CAAACAGGAA

3701 TCGAATGCAA CCGGCGCAGG AACACTGCCA GCGCATCAAC AATATTTTCA

3751 CCTGAATCAG GATATTCTTC TAATACCTGG AATGCTGTTT TCCCGGGGAT

3801 CGCAGTGGTG AGTAACCATG CATCATCAGG AGTACGGATA AAATGCTTGA
```

-continued

| pEVAC Expression Vector |
| --- |

```
3851 TGGTCGGAAG AGGCATAAAT TCCGTCAGCC AGTTTAGTCT GACCATCTCA

3901 TCTGTAACAT CATTGGCAAC GCTACCTTTG CCATGTTTCA GAAACAACTC

3951 TGGCGCATCG GGCTTCCCAT ACAATCGATA GATTGTCGCA CCTGATTGCC

4001 CGACATTATC GCGAGCCCAT TTATACCCAT ATAAATCAGC ATCCATGTTG

4051 GAATTTAATC GCGGCCTCGA GCAAGACGTT TCCCGTTGAA TATGGCTCAT

4101 AACACCCCTT GTATTACTGT TTATGTAAGC AGACAGTTTT ATTGTTCATG

4151 ATGTATATATT TTTATCTTGT GCAATGTAAC ATCAGAGATT TTGAGACACA

4201 ACGTGGCTTT CCCCCCCCCC CCATTATTGA AGCATTTATC AGGGTTATTG

4251 TCTCATGAGC GGATACATAT TTGAATGTAT TTAGAAAAAT AAACAAATAG

4301 GGGTTCCGCG CACATTTCCC CGAAAAGTGC CACCTGACGT CTAAGAAACC

4351 ATTATTATCA TGACATTAAC CTATAAAAAT AGGCGTATCA CGAGGCCCTT

4401 TCGTC
```

EXAMPLE 9

Common Amino Acid Differences of Wuhan Node1 RBD (CoV_T2_7) Amino Acid Sequence (SEQ ID NO:17) with AY274119 RBD (CoV_T2_5) (SEQ ID NO:5) and EPI_ISL 402119 RBD (CoV_T2_6) (SEQ ID NO:11) Amino Acid Sequences FIG. 4 shows Wuhan_Node1_RBD (CoV_T2_7) amino acid sequence (SEQ ID NO:17) with amino acid residue differences in bold and underline from the respective alignments with AY274119_RBD (COV_T2_5) (SEQ ID NO:5) and EPI_ISL_402119_RBD (COV_T2_6) (SEQ ID NO: 11) amino acid sequences (Examples 6 and 7, respectively).

The amino acid residue differences from the two alignments are listed in the table below (the numbering of residue positions corresponds to positions of the Wuhan_Node1_RBD (CoV_T2_7) (SEQ ID NO:17) amino acid sequence. The common differences from the two alignments are at amino acid residues: 3, 6, 7, 21, 22, 38, 42, 48, 67, 70, 76, 81, 83, 86, 87, 92, 121, 122, 123, 125, 126, 128, 134, 137, 138, 141, 150, 152, 153, 154, 155, 167, 171, 178, 180, 181, 183, 185, 187, 188, 189, 191, 194, 195, 219 (shown with grey highlighting in FIG. 4, and as centered in the table below):

| Wuhan_Node1_RBD (CoV_T2_7) residue position | Amino acid residue difference vs AY274119_RBD | Amino acid residue difference vs EPI_ISL_402119_RBD |
| --- | --- | --- |
| 3 | S | S |
| 5 | T | — |
| 6 | Q | Q |
| 7 | E | E |
| 8 | — | V |
| 21 | D | D |
| 22 | K | K |
| 28 | R | — |
| 30 | — | P |
| 36 | — | E |
| 38 | T | T |
| 39 | — | K |
| 42 | D | D |

-continued

| Wuhan_Node1_RBD (CoV_T2_7) residue position | Amino acid residue difference vs AY274119_RBD | Amino acid residue difference vs EPI_ISL_402119_RBD |
| --- | --- | --- |
| 48 | T | T |
| 54 | — | T |
| 55 | S | — |
| 66 | P | — |
| 67 | S | S |
| 70 | I | I |
| 75 | T | — |
| 76 | S | S |
| 81 | T | T |
| 83 | L | L |
| 84 | I | — |
| 85 | R | — |
| 86 | C | C |
| 87 | S | S |
| 88 | E | — |
| 92 | V | V |
| 99 | — | V |
| 112 | T | — |
| 116 | I | — |
| 120 | — | T |
| 121 | A | A |
| 122 | K | K |
| 123 | Q | Q |
| 125 | T | T |
| 126 | G | G |
| 127 | — | S |
| 128 | S | S |
| 134 | Y | Y |
| 137 | S | S |
| 138 | H | H |
| 140 | K | — |
| 141 | T | T |
| 142 | — | K |
| 144 | K | — |
| 150 | L | L |
| 152 | S | S |
| 153 | D | D |
| 154 | E | E |
| 155 | C | C |
| 156 | — | S |
| 157 | — | P |
| 158 | — | D |
| 159 | — | G |
| 160 | — | K |

-continued

| Wuhan_Node1_RBD (CoV_T2_7) residue position | Amino acid residue difference vs AY274119_RBD | Amino acid residue difference vs EPI_ISL_402119_RBD |
|---|---|---|
| 163 | — | T |
| 164 | — | P |
| 165 | — | P |
| 166 | — | A |
| 167 | F | F |
| 168 | N | — |
| 169 | G | — |
| 170 | V | — |
| 171 | R | R |
| 172 | G | — |
| 173 | F | — |
| 177 | F | — |
| 178 | T | T |
| 180 | S | S |
| 181 | T | T |
| 183 | D | D |
| 185 | N | N |
| 186 | P | — |
| 187 | N | N |
| 188 | V | V |
| 189 | P | P |
| 190 | V | — |
| 191 | E | E |
| 194 | A | A |
| 195 | T | T |
| 206 | — | N |
| 216 | — | L |
| 219 | Q | Q |

Amino acid insertions are at positions 167-172 (compared to AY274119_RBD), and 163-167 (compared to EPI_ISL_402119_RBD) (shown boxed in FIG. 4).

EXAMPLE 9

Immune Response Induced by DNA Vaccine Encoding "panS" Antigen

Mice (n=6) were immunised with DNA encoding a "panS" antigen according to an embodiment of the invention (Wuhan_Node1 (CoV_T2_1), nucleic acid of SEQ ID NO:13, encoding full length S-protein of amino acid SEQ ID NO:14), full-length S gene from SARS-Cov-1, or full-length S gene from SARS-COV-2.

Antibodies in serum obtained from the mice were compared for their ability to bind wild-type antigens through FACS.

FIG. 5 shows dose response curves of antibody binding to SARS-COV-1 (A) or SARS-COV-2 (B) full length Spike protein expressed on HEK293T cells. Flow cytometry based cell display assay reported in MFI (Median Fluorescent Intensity).

Serum from mice immunised with either wildtype S gene show weak binding to heterologous protein. In contrast, serum from mice immunised with the "panS" antigen binds to both SARS-CoV-1 and SARS-COV-2 Spike proteins.

It was concluded that the "panS" antigen induces an immune response that is more cross-reactive than wild-type antigens, indicating protection against future Sarbecovirus outbreaks not conferred by using naturally occurring antigens.

EXAMPLE 10

Envelope (E) Protein Vaccine Sequences

FIG. 6 shows an amino acid sequence of the SARS envelope protein (SEQ ID NO:21), and illustrates key features of the sequence:

```
                                        (SEQ ID NO: 21)
MYSFVSEETG TLIVNSVLLF LAFVVFLLVT LAILTALRLC

AYCCNIVNVS LVKPTVYVYS RVKNINSSEG VPDLLV
```

FIG. 7 shows a multiple sequence alignment of coronavirus Envelope (E) protein sequences, comparing sequences for isolates of NL63 and 229E (alpha-coronaviruses), and HKU1, MERS, SARS, and SARS2 (beta-coronaviruses). The alignment shows that the C-terminal end of the E protein for the SARS2 and SARS sequences (beta-coronaviruses of subgenus Sarbeco) includes a deletion, compared with the other sequences, and that the SARS2 E protein sequence includes a deletion, and an Arginine (positively charged) amino acid residue, compared with the SARS sequence.

We have generated novel sequences for the Envelope (E) protein, called COV_E_T2_1 (a designed Sarbecovirus sequence) (SEQ ID NO:22) and COV_E_T2_2 (a designed SARS2 sequence) (SEQ ID NO:23):

```
>COV_E_T2_1
                                        (SEQ ID NO: 22)
MYSFVSEETG TLIVNSVLLF LAFVVFLLVT LAILTALRLC

AYCCNIVNVS LVKPTFYVYS RVKNENSSQG VPDLLV

>COV_E_T2_2
                                        (SEQ ID NO: 23)
MYSFVSEETG TLIVNSVLLF LAFVVFLLVT LAILTALRLC

AYCCNIVNVS LVKPTFYVYS RVKNENSSR- VPDLLV
```

Alignment of the SARS2 reference E protein sequence in FIG. 7 with these designed sequences highlights that there are four amino acid differences between the SARS2 reference E protein sequence and the COV_E_T2_1 designed sequence (SEQ ID NO:22), and two amino acid differences between the SARS2 reference E protein sequence and the COV_E_T2_2 designed sequence (SEQ ID NO:23) (see the boxed amino acid residues in the amino acid sequence alignment shown in FIG. 45A).

The C-terminal sequence of the COV_E_T2_2 sequence is identical to the SARS2 reference sequence. The C-terminal of the E protein is one of the identified epitopes for E-protein, so the amino acid deletion and the substitution with an Arginine residue present in the SARS2 reference sequence (compared with the SARS reference sequence in FIG. 6) have been retained in the COV_E_T2_2 designed sequence. The amino acid differences at the other positions are optimised to maximise induction of an immune response that recognises all Sarbeco viruses.

The amino acid differences are summarised in the table below:

| SARS2 E protein residue position | SARS2 Reference Amino acid residue | COV_E_T2_1 Amino acid residue | COV_E_T2_2 Amino acid residue |
|---|---|---|---|
| 36 | V | A | A |
| 55 | S | T | T |
| 69 | R | Q | R |
| 70 | — | G | — |

In the alignment shown in FIG. 45A, residue 36 of the SARS2 reference sequence is shown as V, but is actually A (as correctly shown in FIG. 7 and SEQ ID NO:21). FIG. 45B shows the alignment of SEQ ID NO:21 with the designed sequences and highlights that there are three amino acid differences between the alternative SARS2 reference E protein sequence and the COV_E_T2_1 designed sequence (SEQ ID NO:22), and one amino acid difference between the SARS2 reference E protein sequence and the COV_E_T2_2 designed sequence (SEQ ID NO:23):

The amino acid differences are summarised in the table below:

| SARS2 E protein residue position | SARS2 Reference Amino acid residue | COV_E_ T2_1 Amino acid residue | COV_E_ T2_2 Amino acid residue |
|---|---|---|---|
| 55 | S | T | T |
| 69 | R | Q | R |
| 70 | — | G | — |

EXAMPLE 11

Membrane (M) Protein Vaccine Sequences

We have generated novel sequences for the coronavirus membrane (M) protein:

COV_M_T2_1 Sarbecovirus root ancestor (SEQ ID NO:24);

COV_M_T2_2 Epitope optimised version of SARS2 clade ancestor Node88b (D4 removed), SARS2 equivalent of B cell epitope from start and end added, and then T cell epitopes added whilst observing coevolving site constraints (SEQ ID NO:25).

The amino acid sequences of these designed sequences are:

```
>COV_M_T2_1/1-221 Sarbeco_M_root:
                          (SEQ ID NO: 24)
MADNGTITVE ELKQLLEQWN EVIGFLFLAW

IMLLQFAYSN RNRFLYIIKL VFLWLLWPVT

LACFVLAAVY RINWVIGGIA IAMACIVGLM

WLSYEVASER LFARTRSMWS FNPETNILLN

VPLRGTILTR PLMESELVIG AVIIRGHLRM

AGHSLGRCDI KDLPKEITVA TSRTLSYYKL

GASQRVGTDS GEAAYNRYRI GNYKINTDHA

GSNDNIALLV Q

>COV_M_T2_2/1-222 Sarbeco_M_Node88b_
epitope_optimised:
                          (SEQ ID NO: 25)
MADSNGTITV EELKKLLEQW NLVIGELFLT

WICLLQFAYS NRNRFLYIIK LIFLWLLWPV

TLACFVLAAV YRINWVIGGI AIAMACIVGL

MWLSYFVASF RLFARTRSMW SENPETNILL

NVPLRGSIIT RPLMESELVI GAVILRGHLR

MAGHSIGRCD IKDLPKEITV ATSRTLSYYK

LGASQRVASD SGFAVYNRYR IGNYKINTDH

SSSSDNIALL VQ
```

Alignment of the following SARS2 reference M protein sequence (SEQ ID NO:26) with the designed sequences is shown in FIG. 8. The reference M protein sequence is:

>COV_M_T1_1/1-222 NC_045512.2 SARS2 reference sequence:

```
                          (SEQ ID NO: 26)
MADSNGTITV EELKKLLEQW NIVIGFLFLT

WICLLQFAYA NRNRFLYIIK LIFLWLLWPV

TLACFVLAAV YRINWITGGI AIAMACIVGL

MWLSYFIASF RLFARTRSMW SENPETNILL

NVPLHGTILT RPLLESELVI GAVILRGHLR

IAGHHLGRCD IKDLPKEITV ATSRTLSYYK

LGASQRVAGD SGFAAYSRYR IGNYKINTDH

SSSSDNIALL VQ
```

The alignment shown in FIG. 8 highlights the amino acid differences between the SARS2 reference M protein sequence and the COV_M_T2_1 and COV_M_T2_2 designed sequences, as shown in the table below:

| SARS2 M protein residue position | SARS2 Reference Amino acid residue | COV_M_T2_1 Amino acid residue | COV_M_ T2_2 Amino acid residue |
|---|---|---|---|
| 4 | S | — | S |
| 15 | K | Q | K |
| 30 | T | A | T |
| 33 | C | M | C |
| 40 | A | S | S |
| 52 | I | V | I |
| 76 | I | V | V |
| 87 | L | I | I |
| 97 | I | V | V |
| 125 | H | R | R |
| 127 | T | T | S |
| 134 | L | M | M |
| 145 | L | I | L |
| 151 | I | M | M |
| 155 | H | S | S |
| 188 | A | G | A |
| 189 | G | T | S |
| 195 | A | A | V |
| 197 | S | N | N |
| 211 | S | A | S |
| 212 | S | G | S |
| 214 | S | N | S |

EXAMPLE 12

Clinical Trial Design

The study will consist of thirty SARS-COV-2 PCR, antibody and T-cell negative healthy human volunteers enrolled for this trial, who agree to self-isolate and report back during the three immunisations, in order to demonstrate safety and immunogenicity.

The first of 3 study Groups will consist of:

Group 1; n=6 dose escalation;

Group 2; 12 healthy human volunteers with the needless PharmaJet delivery;

Group 3; 12 healthy human volunteers receiving direct intramuscular (IM) administration of DNA to benchmark the results by Martin et al (Vaccine, 2008).

The PharmaJet arm of the trial uses a dose-sparing needless delivery system, which minimises the barriers to people taking the vaccine. Power calculations are based on an estimated standard deviation of 0.27 log 10 units, using the ELISA data from the SARS clinical Trial (Martin et al, Vaccine, 2008).

Due to the pandemic emergency, primary and secondary endpoints will be analysed when the last patient has completed 3 months following primary immunisation (complete safety data for 28 days, and immunogenicity primary and key secondary endpoints to 3 months).

Secondary Objective/Endpoints to Assess the Immunogenicity of the Vaccine:

Key immunogenicity endpoints to be analysed and reported at 3 months: Serology (t=0, 14 days, 28 days, 2 months, 3 months). In addition to antigen specific IgM and IgG ELISAs, ADE and ADCC assays will be performed at all time points. Standardised microneutralization assays to measure neutralizing capacity of vaccine antigen-specific antibodies in sera collected pre- and post-immunization at the defined time points.

Antigen-specific T cellular immune responses will be measured at t=0, 14 days, 28 days, 2 months, 3 months). Antigen-specific T cell immune responses will be evaluated in cryopreserved PBMC from vaccinees by proliferation assay (CFSE) and IFN gamma ELISPOT as a preliminary screening of positive responders. A detailed phenotypic analysis of the vaccine-induced T cell responses performed by flow cytometry will follow to determine subpopulations induced by the vaccine candidates [Central memory T-cells (TCM), Effector memory T-cells (TEM) and regulatory T-cells (Treg)] coupled to functional analysis of T cells by intracellular staining for different cytokines (IFN gamma, TNF-α, IL-17, IL-2 and IL-10). Ex vivo nCOV-specific CD8+ and CD4+ T cell subsets, tested for their expression of CD3, CD4, CD8, CD45RA/RO, CD62L, CCR7, CD127, CD25 and nuclear FoxP3, will be identified by multiparametric flow cytometry with fluorochrome-labelled dextramers. If necessary, dextramer analysis will be coupled to a 12-15 day in vitro re-stimulation with vaccine-specific synthetic peptides (20 amino acids overlapped by 12 amino-acids) spanning the Spike(S) protein. Moreover, supernatants of secondary cultures will be also assessed for a large panel of cytokines (IFN-gamma IL-4, IL-5, IL-2, IL-10, IL-13, IL-17, IL-21 and TNF-α) in order to precisely define T cell polarization allowing the identification of T helper subsets and poly-functionality by using the Bio-Plex Pro™ Human Cytokine plex Assay (Biorad).

EXAMPLE 13

Further Designed S Protein RBD Sequences

We have generated further novel S protein RBD sequences by modifying the previous input alignment to our design algorithm: CoV_S_T2_13-COV_S_T2_18. CoV_S_T2_13 is the direct output of the design algorithm, and CoV_S_T2_14-COV_S_T2_18 are epitope-enriched versions of COV_S_T2_13.

The amino acid sequences of these designed sequences are:

```
>COV_S_T2_13
                              (SEQ ID NO: 27)
RVAPTKEVVR FPNITNLCPF GEVENATRFP SVYAWERKRI

SNCVADYSVL YNSTSFSTEK CYGVSPTKLN DLCFINVYAD

SFVIRGDEVR QIAPGQTGVI ADYNYKLPDD FTGCVIAWNT
```

```
NNLDSTTGGN YNYLYRSLRK SKLKPFERDI SSDIYSPGGK

PCSGVEGENC YYPLRSYGFF PINGVGYQPY RVVVLSFELL

NAPATVCGPK LSTD

>COV_S T2_14
                              (SEQ ID NO: 28)
RVAPTKEVVR FPNITNLCPF GEVENATKEP SVYAWERKKI

SNCVADYSVL YNSTSESTEK CYGVSPTKLN DLCFTNVYAD

SFVIRGDEVR QIAPGQTGVI ADYNYKLPDD FTGCVIAWNT

NNIDSTTGGN YNYLYRSLRK SKLKPFERDI SSDIYSPGGK

PCSGVEGENC YYPLRSYGFF PINGVGYQPY RVVVLSFELL

NAPATVCGPK LSTD

>COV_S T2 15
                              (SEQ ID NO: 29)
RVAPTKEVVR FPNITNLCPF GEVENATREP SVYAWERKRI

SNCVADYSVL YNSTFFSTEK CYGVSPTKLN DLCFSNVYAD

SFVIRGDEVR QIAPGQTGVI ADYNYKLPDD FMGCVIAWNT

NNLDSTTGGN YNYLYRSLRK SKLKPFERDI SSDIYSPGGK

PCSGVEGENC YYPLRSYGFF PINGVGYQPY RVVVLSFELL

NAPATVCGPK LSTD

>COV_S_T2_16
                              (SEQ ID NO: 30)
RVAPTKEVVR FPNITNLCPF GEVENATREP SVYAWERKRI

SNCVADYSVL YNSTSFSTFK CYGVSPTKLN DLCFINVYAD

SFVIRGDEVR QIAPGQTGKI ADYNYKLPDD FTGCVIAWNT

NNLDSTTGGN YNYLYRLERK SNLKPFERDI SSDIYQAGST

PCSGVEGENC YFPLQSYGFQ PINGVGYQPY RVVVLSFELL

NAPATVCGPK LSTD

>COV_S T2 17
                              (SEQ ID NO: 31)
RVAPTKEVVR FPNITNLCPF GEVENATKEP SVYAWERKKI

SNCVADYSVL YNSTSFSTEK CYGVSPTKLN DLCFINVYAD

SFVIRGDEVR QIAPGQTGVI ADYNYKLPDD FTGCVIAWNT

NNIDSTTGGN YNYLYRSLRK SKLKPFERDI SSDIYSPGGK

PCSGVEGENC YYPLRSYGFF PINGTGYQPY RVVVLSFELL

NAPATVCGPK LSTD

>COV_S_T2_18
                              (SEQ ID NO: 32)
RVAPTKEVVR FPNITNLCPF GEVENATRFP SVYAWERKRI

SNCVADYSVL YNSTFFSTEK CYGVSPTKLN DLCFSNVYAD

SFVIRGDEVR QIAPGQTGVI ADYNYKLPDD EMGCVIAWNT

NNLDSTTGGN YNYLYRSLRK SKLKPFERDI SSDIYSPGGK

PCSGVEGENC YYPLRSYGFF PINGTGYQPY RVVVLSFELL

NAPATVCGPK LSTD
```

Alignment of these sequences (SEQ ID NO:27-32) with SARS2 Reference sequence (EPI_ISL_402119_RBD (COV_T2_6) (SEQ ID NO:11)) is shown in FIG. 44 B (the boxed regions highlight sequence differences in the alignments).

EXAMPLE 14

Further Designed S Protein RBD Sequences (with Altered Glycosylation Sites)

Masking/de-masking of epitopes has been shown to alter the immune response by masking non-neutralising epitopes, or by de-masking important epitopes in MERS (Du L et. al., Nat. Comm, 2016).

We have prepared additional designed S protein RBD sequences in which we have deleted a glycosylation site of, or introduced a glycosylation site to, the SARS2 RBD sequence. The changes made are illustrated in FIG. 13. The figure shows amino acid sequence of the RBD region. The circled numbers show the positions at which a glycosylation site has been deleted or introduced. Numbers circled in light grey represent deletion of a glycosylation site. Numbers circled in dark grey represent introduction of a glycosylation site. At the position marked by circled number 3, a glycosylation site is present in the SARS wild-type sequence, but absent in the SARS-2 wild-type sequence. This may be important for non-neutralising epitope masking. The introduced glycosylation site is only present in the M8 design. Modifications in the RBD:

designs M7 and M9 include a glycosylation site introduced at the position indicated by circled number 4 (residue position 203);

designs M8 and M10 include a deleted glycosylation site at each of the positions indicated by circled numbers 1 and 2 (residue positions 13 and 25, respectively). The M8 design also includes an introduced glycosylation site at the position indicated by circled number 3 (residue position 54).

The amino acid sequences of SARS2 RBD designs M7, M8, M9, and M10 are shown below:

```
>M7
                              (SEQ ID NO:  33)
RVQPTESIVR FPNITNLCPF GEVENATREA SVYAWNRKRI

SNCVADYSVL YNSASESTEK CYGVSPTKLN DLCFINVYAD

SFVIRGDEVR QIAPGQTGKI ADYNYKLPDD ETGCVIAWNS

NNLDSKVGGN YNYLYRLERK SNLKPFERDI STEIYQAGST
```

-continued

```
PCNGVEGENC YFPLQSYGFQ PINGVGYQPY RVVVLSFELL

HANATVCGPK KSTN

>M8
                              (SEQ ID NO:  34)
RVQPTESIVR FPQITNLCPF GEVEQATREA SVYAWNRKRI

SNCVADYSVL YNSTSESTEK CYGVSPTKLN DLCFINVYAD

SFVIRGDEVR QIAPGQTGKI ADYNYKLPDD FTGCVIAWNS

NNLDSKVGGN YNYLYRLFRK SNLKPFERDI STEIYQAGST

PCNGVEGENC YFPLQSYGFQ PINGVGYQPY RVVVLSFELL

HAPATVCGPK KSTN

>M9
                              (SEQ ID NO:  35)
RVSPTQEVVR FPNITNLCPF DKVENATREP SVYAWERTKI

SDCVADYTVL YNSTSESTEK CYGVSPSKLI DLCFTSVYAD

TFLIRCSEVR QVAPGQTGVI ADYNYKLPDD FTGCVIAWNT

AKQDTGSSGN YNYYYRSHRK TKLKPFERDL SSDECSPDGK

PCTPPAENGV RGENCYFTLS TYDENPNVPV EYQATRVVVL

SFELLNANAT VCGPKLSTQ

>M10
                              (SEQ ID NO:  36)
RVSPTQEVVR FPQITNLCPF DKVFQATREP SVYAWERTKI

SDCVADYTVL YNSTSESTEK CYGVSPSKLI DLCFTSVYAD

TFLIRCSEVR QVAPGQTGVI ADYNYKLPDD FTGCVIAWNT

AKQDTGSSGN YNYYYRSHRK TKLKPFERDL SSDECSPDGK

PCTPPAENGV RGENCYFTLS TYDENPNVPV EYQATRVVVL

SFELLNAPAT VCGPKLSTQ
```

Alignment of these sequences (SEQ ID NOs: 33-36) with the SARS2 Reference sequence (EPI_ISL_402119_RBD (COV_T2_6) (SEQ ID NO:11)) is shown in FIG. 48 (with the dots representing no difference in amino acid residue from the reference sequence, and the dashes representing positions where amino acid residues have been inserted in the M9 and M10 sequences).

The amino acid differences of the designed sequences from the SARS2 reference sequence are summarised in the table below (with differences from the reference sequence in bold):

| Circled number of FIG. 13 | SARS2 RBD residue position | Reference residue | M7 residue | M8 residue | M9 residue | M10 residue |
|---|---|---|---|---|---|---|
| | 3 | Q | | | S | S |
| | 6 | E | | | Q | Q |
| | 7 | S | | | E | E |
| | 8 | I | | | V | V |
| 1 | 13 | N | | Q | | Q |
| | 21 | G | | | D | K |
| | 22 | E | | | D | K |
| 2 | 25 | N | | Q | | Q |
| | 30 | A | | | P | P |
| | 36 | N | | | E | E |
| | 38 | K | | | T | K |
| | 39 | R | | | T | K |
| | 42 | N | | | D | D |
| | 48 | S | | | T | T |

-continued

| Circled number of FIG. 13 | SARS2 RBD residue position | Reference residue | M7 residue | M8 residue | M9 residue | M10 residue |
|---|---|---|---|---|---|---|
| 3 | 54 | A | | T | T | T |
| | 67 | T | | | S | S |
| | 70 | N | | | I | I |
| | 76 | N | | | S | S |
| | 81 | S | | | T | T |
| | 83 | V | | | L | L |
| | 86 | G | | | C | C |
| | 87 | D | | | S | S |
| | 92 | 1 | | | V | V |
| | 99 | K | | | V | V |
| | 120 | S | | | T | T |
| | 121 | N | | | A | A |
| | 122 | N | | | K | K |
| | 123 | L | | | Q | Q |
| | 125 | S | | | T | T |
| | 126 | K | | | G | G |
| | 127 | V | | | S | S |
| | 128 | G | | | S | S |
| | 134 | L | | | Y | Y |
| | 137 | L | | | S | S |
| | 138 | F | | | H | H |
| | 141 | S | | | T | T |
| | 142 | N | | | K | K |
| | 150 | I | | | L | L |
| | 152 | T | | | S | S |
| | 153 | E | | | D | D |
| | 154 | I | | | E | E |
| | 155 | Y | | | C | C |
| | 156 | Q | | | S | S |
| | 157 | A | | | P | P |
| | 158 | G | | | D | D |
| | 159 | S | | | G | G |
| | 160 | T | | | K | K |
| | | — | | | T | T |
| | | — | | | P | P |
| | | — | | | P | P |
| | | — | | | A | A |
| | | — | | | F | F |
| | 166 | E | | | R | R |
| | 173 | P | | | T | T |
| | 175 | Q | | | S | S |
| | 176 | S | | | T | T |
| | 178 | G | | | D | D |
| | 180 | Q | | | N | N |
| | 182 | T | | | N | N |
| | 183 | N | | | V | V |
| | 184 | G | | | P | P |
| | 186 | E | | | E | E |
| | 189 | P | | | A | A |
| | 190 | Y | | | T | T |
| | 201 | H | | | N | N |
| 4 | 203 | P | N | | N | — |
| | 211 | K | | | L | L |
| | 214 | Q | | | Q | Q |

EXAMPLE 15

Nucleotide Sequences of Further Designed S Protein RBD Sequences

Nucleotide sequences encoding the M7, M8, M9, and M10 SARS2 RBD designs discussed in Example 14 are shown below:

>M7

(SEQ ID NO: 37)

```
cgggtgcagc ccaccgaatc catcgtgcgg ttccccaata tcaccaatct gtgcccccttc   60 ggcgaggtgt tcaatgccac cagattcgcc tctgtgtacg cctggaaccg gaagcggatc  120
agcaattgcg tggccgacta ctccgtgctg tacaactccg ccagcttcag caccttcaag  180
```

-continued

```
tgctacggcg tgtcccctac caagctgaac gacctgtgct tcacaaacgt gtacgccgac 240
agcttcgtga tccgggggaga tgaagtgcgg cagattgccc ctggacagac aggcaagatc 300
gccgactaca actacaagct gcccgacgac ttcaccggct gtgtgattgc ctggaacagc 360
aacaacctgg actccaaagt cggcggcaac tacaattacc tgtaccggct gttccggaag 420
tccaatctga agcccttcga gcgggacatc agcaccgaaa tctatcaggc cggcagcacc 480
ccttgcaacg gcgtggaagg cttcaactgc tacttcccac tgcaaagcta cggctttcag 540
cccacaaatg gcgtgggcta ccagccttac agagtggtgg tgctgagctt cgagctgctg 600
catgctaacg ccacagtgtg cggccctaag aaatccacca at              642
```

>M8
(SEQ ID NO: 38)
```
cgggtgcagc ccaccgaatc catcgtgcgg ttcccccaga tcaccaatct gtgccccttc  60
ggcgaggtgt tccaggccac cagattcgcc tctgtgtacg cctggaaccg gaagcggatc 120
agcaattgcg tggccgacta ctccgtgctg tacaactcca ccagcttcag caccttcaag 180
tgctacggcg tgtcccctac caagctgaac gacctgtgct tcacaaacgt gtacgccgac 240
agcttcgtga tccgggggaga tgaagtgcgg cagattgccc ctggacagac aggcaagatc 300
gccgactaca actacaagct gcccgacgac ttcaccggct gtgtgattgc ctggaacagc 360
aacaacctgg actccaaagt cggcggcaac tacaattacc tgtaccggct gttccggaag 420
tccaatctga agcccttcga gcgggacatc agcaccgaaa tctatcaggc cggcagcacc 480
ccttgcaacg gcgtggaagg cttcaactgc tacttcccac tgcaaagcta cggctttcag 540
cccacaaatg gcgtgggcta ccagccttac agagtggtgg tgctgagctt cgagctgctg 600
catgctcctg ccacagtgtg cggccctaag aaatccacca at              642
```

>M9
                                                      (SEQ ID NO: 39)
```
cgggtgtccc ctacacaaga ggtcgtgcgg ttccccaata tcaccaatct gtgccccttc  60
gacaaggtgt tcaacgccac cagatttccc agcgtgtacg cctgggagcg caccaagatt 120
tccgattgcg tggccgacta caccgtgctg tataactcca cctccttcag caccttcaag 180
tgctacggcg tgtccccaag caagctgatc gatctgtgct tcacctctgt gtacgccgac 240
accttcctga tccggtgtag cgaagtgcga caggtggcac ctggacagac aggcgtgatc 300
gccgattaca actacaagct gcccgacgac ttcaccggct gtgtgatcgc ctggaatacc 360
gccaagcagg atacaggcag cagcggcaac tacaactact actacagaag ccaccgcaag 420
accaagctga agcctttcga gagggacctg agcagcgacg agtgtagccc tgatggcaag 480
ccttgtacac ctcctgcctt caatggcgtg cggggcttca actgctactt caccctgagc 540
acctacgact tcaaccccaa cgtgcccgtg aataccaggg ccacaagagt ggtggtgctg 600
agcttcgagc tgctgaatgc caacgccaca gtgtgtggcc ctaagctgtc tacccag    657
```

>M10
                                                      (SEQ ID NO: 40)
```
cgggtgtccc ctacacaaga ggtcgtgcgg ttcccccaga tcaccaatct gtgccccttc  60
gacaaggtgt tccaggccac cagatttccc agcgtgtacg cctgggagcg caccaagatt 120
tccgattgcg tggccgacta caccgtgctg tataactcca cctccttcag caccttcaag 180
tgctacggcg tgtccccaag caagctgatc gatctgtgct tcacctctgt gtacgccgac 240
accttcctga tccggtgtag cgaagtgcga caggtggcac ctggacagac aggcgtgatc 300
gccgattaca actacaagct gcccgacgac ttcaccggct gtgtgatcgc ctggaatacc 360
gccaagcagg atacaggcag cagcggcaac tacaactact actacagaag ccaccgcaag 420
```

-continued

```
accaagctga agcctttcga gagggacctg agcagcgacg agtgtagccc tgatggcaag 480
ccttgtacac ctcctgcctt caatggcgtg cggggcttca actgctactt caccctgagc 540
acctacgact tcaaccccaa cgtgcccgtg gaataccagg ccacaagagt ggtggtgctg 600
agcttcgagc tgctgaatgc ccctgccaca gtgtgtggcc ctaagctgtc tacccag    657
```

Differences between these sequences (SEQ ID NOs: 37-40) are highlighted in the alignment shown in FIG. 49 (with the dots indicating that the nucleotide residue is the same as the corresponding M7 nucleotide residue).

EXAMPLE 16

Ability of Different Full-Length S Protein Genes to Induce Antibodies to SARS2 RBD Mice were immunised with different full-length Coronavirus S protein genes (from SARS-1 and SARS-2), and the sera was collected and tested at different dilutions for binding (by ELISA) to SARS2 RBD. The sera were heat inactivated (HI) to check for non-specific interactions in the ELISA.

The results are shown in FIG. 9.

The binding of the sera to SARS-2 RBD was tested using ELISA. The ELISA protocol is as follows:

Materials and Reagents:

F96 Nunc Maxisorp flat-bottom plates (Cat #: 44-2404-21, Thermo Scientific)

Plate sealers (Cat #: 676001, Greiner Bio-one)

Shaker (Cat #: 544-11200-00, Heidolph Instruments Titramax 100)

50 mL and 100 mL reservoirs (Cat #4870 Corning and #B3110-100 Argos)

U-bottom dilution plates (Cat #: 650201, Greiner bio-one)

1×PBS (—Ca/—Mg):

Add 2 PBS tablets (Cat #: 18912-014, Gibco) to 1 L milliQ water

1×PBS (—Ca/—Mg)+0.1% Tween-20 (PBST):

Add 4 PBS tablets (Cat #: 18912-014, Gibco) and 2 mL Tween-20 (Cat #: P1379-500 ML, Sigma Aldrich) to 2 L milliQ water 3% (w/v) non-fat milk in 1×PBST (blocking solution):

Add 1.5 g of semi-skimmed milk powder (Cat #: 70166-500G, Sigma Aldrich) in 50 mL of PBST 1% (w/v) non-fat milk in 1×PBST (serum dilution solution):

0.5 g of milk powder (Cat #: 70166-500G, Sigma Aldrich) in 50 ml of PBST

HRP-conjugated secondary antibodies:

Anti-mouse IgG-horseradish peroxidase (HRP) conjugated secondary antibody (Cat #: 715-035-150, Jackson ImmunoResearch)

Anti-human IgG/IgM/IgA-horseradish peroxidase (HRP) conjugated secondary antibody (Cat #: 109-035-064, Jackson ImmunoResearch)

1-Step™ Ultra TMB (Cat #34029, Thermo Scientific)

Stop solution of $H_2SO_4$ (add 28 mL of 1.84 kg/L $H_2SO_4$ to 472 mL milliQ water)

Serum samples (about 4 ul is needed to run a duplicate, starting at 1:50 dilution with 10-fold serial dilutions; about 5.5 ul is needed to run a duplicated, starting at 1:50 dilution with 2-fold serial dilutions)

Human positive control: strong antibody positive plasma from Covid-19 patient (Cat #20/130, NIBSC)

Human negative control: WHO Reference Anti-EBOV Negative human plasma (Cat #: 15/288, NIBSC)

Method:

Day 0

1. Coat ninety-six well Nunc Maxisorp plates with 50 μl (per well) of 1 μg/mL of protein diluted in PBS–/–. Tap the plates gently against the counter to ensure that the liquid has fully coated the bottom of the plate.

2. Seal the plates tightly with plate sealer. Store plates in –4° C. fridge overnight, to a maximum of 4 days. Ensure that the liquid has not evaporated when using.

3. Prepare 3% and 1% non-fat milk, vortex and leave to dissolve on the shaker at 1350 rpm at room temperature. Leave to dissolve for at least one hour. Store in the –4° C. fridge overnight.

Day 1

4. Prepare the negative and positive controls

Mouse Negative control: Prepare a pool of all six mice from the PBS-immunized group (usually Group 1) from the corresponding bleed, at a final dilution of 1:50 in 1% non-fat milk in PBST Mouse Positive control: Prepare a 1:500 dilution of a known strong positive in 1% non-fat milk in PBST Human Negative control: Prepare a 1:50 dilution of the required amount of anti-EBOV plasma in 1% non-fat milk in PBST Human Positive control: Prepare a 1:500 dilution of the required amount of 20/130 in 1% non-fat milk in PBST 5. Decant the protein from the 96-well plate and add 100 μl of 3% non-fat milk per well. Incubate for 1 hour at room temperature on the shaker at 200-400 rpm.

6. During the blocking step, prepare serial dilutions of the serum in 1% non-fat milk in PBST using the U-bottom dilution plates.

For a two-fold serial dilution starting at 1:50-Add 130 μl 1% non-fat milk to the first row with 2.6 μl of serum (in duplicates). Add 65 μl 1% non-fat milk to the remaining rows. Transfer 65 μl for the serial dilutions.

For a ten-fold serial dilution starting at 1:50-Add 75 μl 1% non-fat milk to the first row with 1.5 μl of serum (in duplicates). Add 63 μl 1% non-fat milk to the remaining rows. Transfer 7 μl for the serial dilutions.

7. After the 1-hour blocking, decant the blocking solution and add 50 μl of the serial dilutions to the corresponding plates. Incubate on the shaker at 200-400 rpm for two hours at room temperature.

8. During the incubation, dilute the HRP-conjugated anti-mouse IgG secondary antibody 1:3000 in PBST. Make up 5 mL of diluted secondary per 96-well plate.

9. After the 2-hour primary antibody incubation, wash the plates three times with 200 μl (per well) of PBST. Tap dry after the last wash. Then add 50 μl (per well) of the diluted secondary antibody. Incubate on the shaker at 200-400 rpm at room temperature for 1 hour.

10. After adding the secondary antibody, take the appropriate volume of TMB and leave it on the counter to come to room temperature. Take 5 mL of TMB per 96-well plate.

11. After the 1-hour secondary antibody incubation, wash the plates three times with 200 μl (per well) of PBST. Tap dry after the last wash.

12. Add 50 μl (per well) of room temperature TMB. Agitate the plate gently. Leave for approximately 2-3 mins. Monitor the plate to ensure that the colour change does not become saturated. Add TMB to a maximum of 5 plates at a time.

13. Add 50 μl (per well) of room temperature stop solution. Agitate the plate gently. Read immediately.

14. Read endpoint optical density at 450 nm.

The following DNA vaccines were used:

Heat Inactivation (HI)

SARS-1 (DNA encoding full length SARS-1 S protein)

SARS-2 (DNA encoding full length SARS-2 S protein)

DIOS-ancestor (Wuhan Node 1 full length)

Not HI

SARS-1

SARS-2

DIOS-ancestor

Human sera against SARS-2 and anti-SARS1 spike monoclonal antibody were used as positive controls, and anti-MERS human sera was used as a negative control.

The figure shows that all the full-length S protein genes tested induced a relatively poor or negligible binding response to SARS2 RBD.

EXAMPLE 17

Ability of DNA Vaccines Encoding SARS1 and SARS2 Truncated Spike(s) Protein and RBD to Induce Antibodies to SARS1 and SARS2 S Protein Mice were immunised with different DNA vaccines, and sera collected from the mice was used to test binding by FACS to SARS1 and SARS2 spike protein.

1—Reagents and Consumables

HEK293T/17 cells

DMEM with 10% FBS and 1% Pen/strep

OptiMEM

1×PBS

FuGENE-HD pEVAC expressing plasmid

2—Protocol

Day 1—Seeding Cells

1. Seed 6-well plates with ~150,000 cells per well for next day transfection (2 six well plates are enough for one 96 well plate)

2. Incubate overnight at 37° C., 5% $CO_2$.

Day 2—Cell Transfection

1. Thaw producer cell plasmid DNA and pre-warm DMEM and OptiMEM to 37° C.

2. Prepare DNA mix in 600 μl OptiMEM (amount per plate; see table 1) in a labelled 1.5 ml tube 3. Incubate DNA mix for 5 minutes at room temperature 4. Add 9 μl of FuGENE-HD transfection reagent per 3 μg DNA in the transfection complex (see table below)

5. Incubate at room temperature for 20 minutes; mix by gently flicking the tube.

6. During incubation, remove depleted media from each well of the 6 well plate and replace with 2 ml DMEM per well.

7. After incubation, add the transfection complex to cells in a dropwise manner, and swirl to ensure even distribution.

8. Return cells to tissue culture incubator (37° C., 5% $CO_2$)

| Transfection complex | Glycoprotein plasmid (ng) | OptiMEM (μl) | FuGENE HD (μl) |
|---|---|---|---|
| pEVAC SARS1 | 3000 | 600 | 9.0 |
| pEVAC SARS2 | 3000 | 600 | 9.0 |

Day 3—Antibody/Serum Dilution

1. Perform 1:2 serial dilution of serum or antibodies in cold PBS 1% FBS (e.g. 6 μl of serum in 300 μl of buffer, aliquot 150 μl for a duplicate. (6-well U-plate is preferred)

2. Human serum or IgG isotype controls must be included in the experimental plan Day 4—Flow Cytometry 3. Remove media and collect cells in a falcon 4. Centrifuge 5' at 300×g 5. Resuspend cell pellet in 10 ml PBS (per plate)

6. Aliquot 100 μl of cell suspension per well in a 96 well plate V-bottom, using P100 multichannel and reservoir.

7. Centrifuge the plate 2' at 300×g (R2 rotor in 227)

8. Flick out the plate in the sink

9. By using a multichannel, transfer 75 μl of diluted serum or antibodies from dilution plate to the FCAS plate and resuspend cells 10. Incubate RT 40'

11. Wash plate by adding 100 μl of PBS

12. Centrifuge the plate 2' at 300×g

13. Flick out the plate in the sink

14. Wash plate by adding 180 μl of PBS and resuspend cell pellet

15. Flick out the plate

17. Incubate RT 40' 16. Add 60 μl/well of secondary antibody (20 μl/ml) and resuspend cells 18. Wash plate by adding 100 μl of PBS 19. Centrifuge the plate 2' at 300×g 20. Flick out the plate in the sink 21. Wash plate by adding 180 μl of PBS and resuspend cells 22. Flick out the plate 23. Resuspend cells in 200 μl of PBS The DNA Vaccines Used were:

| | |
|---|---|
| COV_S_T2_2 | AY274119_tr (CoV_T2_2): nucleic acid encoding truncated S-protein (SEQ ID NO: 4) |
| COV_S_T2_3 | EPI_ISL_402119_tr (CoV_T2_3): nucleic acid encoding truncated S-protein (SEQ ID NO: 10) |
| COV_S_T2_5 | AY274119_RBD (CoV_T2_5): nucleic acid encoding RBD (SEQ ID NO: 6) |
| COV_S_T2_6 | EPI_ISL_402119_RBD (COV_T2_6): nucleic acid encoding RBD (SEQ ID NO: 12) |
| COV_S_T2_7 | Wuhan_Node1_RBD (CoV_T2_7): nucleic acid encoding RBD (SEQ ID NO: 18) |
| COV_S_T2_8 | "SARS_2 RBD_mut1" (the M7 construct, SEQ ID NO: 37) |
| COV_S_T2_10 | "SARS_an RBD_mut1" (the M9 construct, SEQ ID NO: 39) |

Binding of the sera obtained following the immunisations to SARS1 spike protein and SARS2 spike protein, at different dilutions, was assessed by FACS. The results are shown in FIG. 10.

The results show that the sera collected following immunisation with DNA encoding truncated spike protein and the RBD domains binds to the respective SARS protein. The M7 construct induced sera with better binding than the corresponding wild type SARS2 RBD.

EXAMPLE 18

Ability of DNA Vaccines Encoding Wild-Type SARS1 or SARS2 Spike Protein (Full-Length, Truncated, or RBD) to Induce a Neutralisation Response to SARS1 and SARS2 Pseudotypes Mice were immunised with DNA vaccine encoding wild-type full-length SARS1 or SARS2 spike protein, DNA vaccine encoding wild-type truncated SARS1 or SARS2 spike protein, DNA vaccine encoding wild-type SARS1 or SARS2 spike RBD protein, or wild-type SARS1 or SARS2 RBD protein. Sera collected from the immunised mice were tested at different dilutions for their ability to neutralise SARS1 or SARS2 pseudotypes.

The vaccines used were:
DNA encoding full-length SARS1 or SARS2 spike protein;
DNA encoding truncated SARS1 or SARS2 spike protein;
DNA encoding SARS1 or SARS2 spike RBD; and
SARS1 or SARS2 RBD protein.

PBS was used as a negative control, and 20/130 (a National Institute for Biological Standards and Control (NIBSC) standard) and serum from patient 4 (a COVID-19 patient with strongly neutralising antibodies) were used as positive controls.

The results are shown in FIG. 11.

The results show that mice immunised with the SARS1 immunogens (DNA or protein) induce antibodies which neutralise SARS1 pseudotypes. However, the only SARS2 immunogen which induces SARS2 pseudotype neutralising antibodies is the DNA encoding SARS2 RBD.

EXAMPLE 19

Ability of SARS1 and SARS2 RBD Protein Vaccines to Induce Antibodies to SARS2 RBD Mice were immunised with different protein vaccines. The sera were collected and tested for binding to SARS2 RBD at different dilutions.

The vaccines used were:
P-RBD-CoV1 (wild-type SARS1 RBD protein)
P-RBD-CoV2 (wild-type SARS2 RBD protein)
P-S_Stab_CoV2 (full-length spike protein stabilised by two proline mutations and removal of transmembrane region)

The results are shown in FIG. 12.

The results show that all of the protein vaccines tested induced SARS2 RBD-binding antibodies, including the SARS1 RBD (P-RBD-CoV1).

EXAMPLE 20

Ability of Different S Protein RBD DNA Vaccines to Induce Antibodies to SARS2 RBD Mice were immunised with different S protein (truncated or RBD) DNA vaccines, then sera was collected and tested for binding to SARS2 RBD by ELISA (using the protocol described in Example 16).

The vaccines used were:
Ancestor RBD
Conv373 (positive control-sera from a Covid positive patient; data not shown)
Human_s (negative control, pre-Covid serum from Sigma)

SARS_1 RBD
SARS_1 trunc
SARS_2 RBD
SARS_2 RBD_mut1 (M7)
SARS_2 trunc
SARS_anc RBD_mut1 (M9)

The results are shown in FIG. 14.

The results show that the M7 SARS2 RBD DNA vaccine induced an immune response with stronger binding to SARS2 RBD than wild-type SARS2 RBD DNA in the early bleed.

EXAMPLE 21

Inhibition of RBD-ACE2 Interaction by Sera Collected Following Immunisation with M7 and Wild-Type SARS2 RBD DNA Vaccines A competition assay was used to show to what extent mouse sera, after immunisation of mice with M7 and wild-type RBD DNA vaccines, prevents binding of SARS2 pseudotypes to ACE2 receptors, using sera collected 2 and 8 weeks after immunisation.

The DNA vaccines used were:
D-RBD-CoV2 (DNA encoding wild-type SARS2 RBD);
D-RBD-M7_CoV2 (DNA encoding M7 SARS2 RBD)
D-RBD-TM_CoV2 (DNA encoding wild type RBD with a transmembrane domain, so that it remains tethered to the cell membrane rather than released as soluble protein like other RBD constructs)

The results are shown in FIG. 15.

The results presented in the left hand figure (a) (week 2) show that sera collected 2 weeks after immunisation with DNA encoding wild-type RBD and tethered wild-type RBD has no effect on binding of SARS2 pseudotypes to ACE2 receptors, but the sera collected 2 weeks after immunisation with DNA encoding M7 RBD does inhibit binding of SARS2 pseudotypes to ACE2 receptors.

The results presented in the right hand figure (b) (week 8) show that sera collected 8 weeks after immunisation with DNA encoding wild-type RBD and M7 RBD both show strong neutralisation.

It was concluded from these results that the DNA vaccine encoding wild-type RBD and M7 RBD elicit a neutralising immune response 8 weeks after immunisation, but that DNA vaccine encoding M7 SARS2 RBD elicits a neutralising immune response more rapidly than DNA vaccine encoding wild-type SARS2 RBD.

Methods:

The competition assay was carried out using the GenScript SARS-COV-2 Surrogate Virus Neutralization Test (SVNT) Kit, according to the manufacturer's protocol. The kit can detect circulating neutralizing antibodies against SARS-COV-2 that block the interaction between the receptor binding domain of the viral spike glycoprotein (RBD) with the ACE2 cell surface receptor. The assay detects any antibodies in serum and plasma that neutralize the RBD-ACE2 interaction. The test is both species and isotype independent.

First, the samples and controls are pre-incubated with the HRP-RBD to allow the binding of the circulating neutralization antibodies to HRP-RBD. The mixture is then added to the capture plate which is pre-coated with the hACE2 protein. The unbound HRP-RBD as well as any HRP-RBD bound to non-neutralizing antibody will be captured on the plate, while the circulating neutralization antibodies-HRP-RBD complexes remain in the supernatant and get removed during washing. After washing steps, TMB solution is added, making the colour blue. By adding Stop Solution, the reaction is quenched and the colour turns yellow. This final solution can be read at 450 nm in a microtiter plate reader. The absorbance of the sample is inversely dependent on the titre of the anti-SARS-COV-2 neutralizing antibodies.

EXAMPLE 22

Neutralisation of SARS2 Pseudotype Induced by M7 and Wild-Type SARS2 RBD DNA Vaccines Mice were immunised with different RBD DNA vaccines listed below, then sera was collected and tested for SARS2 pseudotype neutralisation. Two studies were carried out (COV002.1 and COV002.2).
The DNA Vaccines Used were:
  Ancestor RBD (DNA encoding ancestor RBD);
  SARS_1 RBD (DNA encoding wild-type SARS1 RBD);
  SARS_1 trunc (DNA encoding wild-type SARS1 truncated S protein);
  SARS_2 RBD (DNA encoding wild-type SARS2 RBD)
  SARS_2 RBD_mut1 (M7) (DNA encoding M7 SARS2 RBD)
  SARS_2 trunc (DNA encoding wild-type SARS2 truncated S protein)
  SARS_anc RBD_mut1 (M9) (DNA encoding M9 SARS ancestor RBD)
  The results are shown in FIGS. 16 and 17.
The results from study COV002.1 and COV002.2 are shown in FIG. 16(a) (bleed at week 2 from the immunised mice), and the results from study COV002.1 and COV002.2 are shown in FIG. 16(b) (bleed at week 3 from the immunised mice), and 16(c) (bleed at week 4 from the immunised mice).
FIG. 17 shows SARS2 pseudotype neutralisation $IC_{50}$ values for sera collected from the mice immunised with wild-type SARS2 RBD DNA vaccine, and M7 SARS2 RBD DNA vaccine. The dots in FIG. 17 show $IC_{50}$ values for individual mice, and the horizontal cross bars show the estimate based on all mice with 95% confidence intervals. The results shown in FIG. 17(a) are from study COV002.1 and COV002.2. The results shown in FIG. 17(b) are from study COV002.2.
The results in FIGS. 16 and 17 show that the M7 SARS2 RBD DNA vaccine induces a more neutralising response than the wild-type SARS2 RBD DNA vaccine in sera collected from bleeds at weeks 1 and 2, but that by later bleeds there appears to be little difference between the two vaccines.

EXAMPLE 23

Supernatant of Cells Expressing M7 SARS2 RBD Competes with Other ACE2 Binding Viruses for ACE2 Cell Entry Supernatant of cells was used to compete with one of three coronavirus pseudotypes (NL63, SARS1, SARS2) for ACE2 receptors. The supernatant was either from cells expressing M7 or from cells transfected with the empty pEVAC. The results are shown in FIG. 18.
The results show that the M7 supernatant competes effectively with the three ACE2 binding viruses, although possibly to a lesser extent with SARS1.

EXAMPLE 24

M7 SARS2 RBD DNA Vaccine Induces T Cell Responses

An enzyme-linked immunospot (ELISPOT) assay against an RBD peptide pool was used to determine T cell responses induced by the M7 SARS2 RBD DNA vaccine (compared with PBS as a negative control). The results are shown in FIG. 19. The results show that T cell responses were induced by the M7 DNA vaccine that were reactive against peptides of the RBD peptide pool. The medium is used as the negative control.
The ELISPOT assay is a highly sensitive immunoassay that measures the frequency of cytokine-secreting cells (in this case, murine T cells secreting IFN-γ) at the single-cell level. In this assay, cells are cultured on a surface coated with a specific capture antibody in the presence or absence of stimuli. Proteins, such as cytokines, that are secreted by the cells will be captured by the specific antibodies on the surface. After an appropriate incubation time, cells are removed and the secreted molecule is detected using a detection antibody in a similar procedure to that employed by the enzyme-linked immunoassay (ELISA). The detection antibody is either biotinylated and followed by a streptavidin-enzyme conjugate or the antibody is directly conjugated to an enzyme. By using a substrate with a precipitating rather than a soluble product, the end result is visible spots on the surface. Each spot corresponds to an individual cytokine-secreting cell.
The ELISPOT assay was carried out according to the manufacturer's protocol (Cellular Technology Limited, CTL) repeated below:
Murine IFN-γ Single-Color Enzymatic ELISPOT Assay:
  PROCEDURE (If using precoated plates, start at Day 1)
Day 0—Sterile Conditions
  Prepare Murine IFN-γ Capture Solution (see Solutions).
  Pipette 80 μl/well Murine IFN-γ Capture Solution. Seal plate with parafilm and incubate at 4° C. overnight. (Prewetting of plates with ethanol is not required but in some instances where a large response is expected, the assay can benefit from removing the underdrain, adding 15 μl of 70% ethanol/well for less than one minute, washing three times with 150 μl of PBS/well, replacing the underdrain, and immediately [before plate dries], add the Capture Solution. If using strip plates, there is no underdrain to remove before prewetting. As an alternative, one can purchase CTL precoated plates.) Note: Activation of the membrane with ethanol is instantaneous and can be seen visually as a graying of the membrane. Ethanol should be washed off as quickly as possible following activation.
Day 1—Sterile Conditions
  Prepare CTL-Test™ Medium (see Solutions).
  Prepare antigen/mitogen solutions at two times final concentration in CTL-Test™ Medium.
  Decant plate containing Capture Solution from Day 0 and wash one time with 150 μl PBS.
  Plate antigen/mitogen solutions, 100 μl/well. Ensure the pH and temperature are ideal for cells by placing the plate containing antigens into a 37° C. incubator for 10-20 minutes before plating cells.
  Adjust cells to desired concentration in CTL-Test™ Medium, e.g.: 3 million/ml corresponding to 300,000 cells/well (cell numbers can be adjusted according to expected spot counts since 100,000-800,000 cells/well will provide linear results). Keep cells at 37° C. in humidified incubator, 9% $CO_2$ while processing cells and until plating.

Plate cells 100 μl/well using large orifice tips. Once completed, gently tap the sides of the plate and immediately place into a 37° C. humidified incubator, 9% $CO_2$.

Incubate for 24 hours. Do not stack plates. Avoid shaking plates by carefully opening and closing incubator door. Do not touch plates during incubation.

Day 2

Prepare Buffer Solutions: PBS, distilled water and Tween-PBS (see Wash Buffers).

Prepare Anti-murine IFN-γ Detection Solution (see Solutions).

Wash plate two times with PBS and then two times with 0.05% Tween-PBS, 200 μl/well each time.

Add 80 μl/well Anti-murine IFN-γ Detection Solution. Incubate at room temperature, two hours.

Prepare Tertiary Solution (see Solutions).

Wash plate three times with 0.05% Tween-PBS, 200 μl/well.

Add 80 μl/well of Tertiary Solution. Incubate at room temperature, 30 minutes.

During incubation, prepare Blue Developer Solution (see Solutions).

Wash plate two times with 0.05% Tween-PBS, and then two times with distilled water, 200 μl/well each time.

Add Blue Developer Solution, 80 μl/well. Incubate at room temperature, 15 minutes.

Stop reaction by gently rinsing membrane with tap water, decant, and repeat three times.

Remove protective underdrain from the plate and rinse back of plate with tap water.

Air-dry plate for two hours in running laminar flow hood or for 24 hours face down on paper towels on bench top.

Scan and count plate. (CTL has scanning and analysis services available and offers a trial version of ImmunoSpot® Software with the purchase of any kit. Email kitscanningservices@immunospot.com for more info.)

Solutions

All solutions should be freshly-made prior to use. It is important to quick-spin the vials before use to ensure content volumes.

70% Ethanol (if prewetting—not included): Dilute 190-200 proof ethanol. For 10 ml, add 7 ml of ethanol to 3 ml of distilled water.

CTL-Test™ Medium: Prepare medium by adding 1% fresh L-glutamine. The amount of medium needed will depend on variables such as cell yield and number of samples tested but will be no less than 20 ml for one full plate.

Capture Solution: Dilute Murine IFN-γ Capture Antibody in Diluent A. For one plate, add 60 μl of Murine IFN-γ Capture Antibody to 10 ml of Diluent A.

Detection Solution: Dilute Anti-murine IFN-γ (Biotin) Detection Antibody in Diluent B. For one plate, add 10 μl of Anti-murine IFN-γ (Biotin) Detection Antibody to 10 ml of Diluent B.

Tertiary Solution: Dilute Strep-AP Solution in Diluent C, 1:1000. For one plate, add 10 μl of Strep-AP to 10 ml of Diluent C.

Blue Developer Solution: Add the Substrate Solutions in sequential steps to 10 ml of Diluent Blue.

For one plate:

Step 1—Add 160 μl of S1 to 10 ml of Diluent Blue. Mix well!

Step 2—Add 160 μl of S2. Mix well!

Step 3—Add 92 μl of S3. Mix well!

It is recommended to make the Blue Developer Solution within ten minutes of use and to keep it protected from direct light.

Wash Buffers (not included)

For each plate prepare:

0.05% Tween-PBS: 100 μl Tween-20 in 200 ml PBS

PBS, sterile, 100 ml

Distilled water, 100 ml

Cryopreservation of Mouse Splenocytes

This was carried out according to the protocol of CELLULAR TECHNOLOGY LIMITED, repeated below:

Cell permeability, reagent toxicity, and cooling rates must be considered for each cell type when freezing. The osmotic pressure caused by DMSO (more than DMSO's intrinsic toxicity) is one of the primary factors that need to be controlled for successful freezing and thawing of splenocytes. To maintain the metabolic activity of the cells and their membrane lipid fluidity (so they can compensate for the osmotic pressure), all reagents should be at room temperature (preferably at 37° C.).

Preparation:

1. Mix CTL-Cryo™ A with CTL-Cryo™ B in an 80% to 20% (v/v) ratio (4+1) by slowly adding CTL-Cryo™ B into CTL-Cryo™ A.

(CTL-Cryo™ B contains DMSO as a component. Please refer to MSDS, included.)

2. Warm the resulting CTL-Cryo™ A-B Mix and CTL-Cryo™ C in a 37° C. $CO_2$ incubator. (It is advised to start with this step while counting cells).

3. Each cryotube should contain approximately $10 \times 10^6$ cells (10-15 million). Freezing more cells per tube may lead to cell loss.

After Washing:

1. After counting, centrifuge the cell suspension at room temperature at 330 g for 10 minutes with rapid acceleration and brake on high.

2. Decant supernatant and mix cells gently by tapping the tube with your finger. Do not use a pipette and avoid foam formation!

3. Slowly, over a time period of ~2 minutes, add an equal volume of warm CTL-Cryo™ A-B Mix to the CTL-Cryo™ C containing the splenocytes. (Add CTL-Cryo™ A-B mix drop-by-drop while gently whirling the tube to ensure complete mixing of the two solutions.

4. Aliquot the resulting CTL-Cryo™ A-B-C suspension containing the splenocytes into pre-labeled 1.8 ml cryovials, 1 ml into each vial.

Pipette gently and slowly to minimize shear forces; do not attempt additional mixing with the pipette. The cells can remain in the completed CTL-Cryo™ A-B-C medium for 10-20 minutes without loss of viability or function.

5. Place cryovials into a room temperature Nalgene® cryofreezing container (Mr. Frosty™) filled with propanol and transfer into a –80° C. freezer for a minimum of 12 hours. Do not open the freezer during this time period. Use a dedicated –80° C. freezer in order to prevent shaking the samples and fluctuation of the freezer's temperature due to opening and closing of the freezer door.

6. After a minimum of 12 hours and no more than 48 hours, transfer the cryovials into vapor/liquid nitrogen tanks for storage.

EXAMPLE 25

Further Designed E Protein Sequences (with Abrogated Ion Channel Activity)

SARS-COV envelope (E) gene encodes a 76-amino acid transmembrane protein with ion channel (IC) activity, an important function in virus-host interaction. Infection of mice with viruses lacking or displaying E protein IC activity revealed that activation of the inflammasome pathway, and the exacerbated inflammatory response induced by SARS-COV, was decreased in infections by ion channel-deficient viruses (Nieto-Torres et al., 2014, Severe Acute Respiratory Syndrome Coronavirus Envelope Protein Ion Channel Activity Promotes Virus Fitness and Pathogenesis. PLOS Pathog 10 (5): e1004077).

We have made new E protein designs Cov_E_T2_3, CoV_E_T2_4 and CoV_E_T2_5, which correspond to SARS2, CoV_E_T2_1 and CoV_E_T2_2 (see Example 10), respectively. The new designs have a point mutation, N15A, which abrogates the ion channel activity, but does not influence the stability of the structure. Nieto-Torres et al., supra, discusses this mutation as well as the toxicity and inflammatory action of SARS E on the host cell.

The amino acid sequences of the new E protein designs are shown below:

```
>COV_E_T2_3 (SARS2_mutant)
                          (SEQ ID NO: 42)
MYSFVSEETG TLIVASVLLF LAFVVELLVT LAILTALRLC

AYCCNIVNVS LVKPSFYVYS RVKNLNSSR-VPDLLV

>COV_E_T2_4 (Env1_mutant)
                          (SEQ ID NO: 43)
MYSFVSEETG TLIVASVLLF LAFVVFLLVT LAILTALRLC

AYCCNIVNVS LVKPTFYVYS RVKNLNSSQGVPDLLV

>COV_E_T2_5 (Env2_mutant)
                          (SEQ ID NO: 44)
MYSFVSEETG TLIVASVLLF LAFVVELLVT LAILTALRLC

AYCCNIVNVS LVKPTFYVYS RVKNLNSSR-VPDLLV
```

Alignment of the E protein designs (SEQ ID NOs: 22-23, and SEQ ID NOs: 41-44) with SARS2 E protein reference sequence is shown in FIG. 45C.

The amino acid differences of the designed sequences from the SARS2 reference sequence are shown in the table below (with differences from the reference sequence in bold):

EXAMPLE 26

Nucleoprotein (N) Protein Vaccine Sequences

We have made new N protein designs, COV_N_T2_1 and COV_N_T2_2. The amino acid sequences of these designs is shown below. Sequence COV_N_T2_2 was designed using a methodology and algorithm which selected predicted epitopes to include based on their conservation across the sarbecoviruses (whilst minimising redundancy), the frequency and number of MHC alleles the epitope is restricted by the predicted epitope quality, and a handful of user specified weightings.

```
>YP 009724397.2/1-419 nucleocapsid phosphoprotein
(SARS-CoV-2) (reference sequence)
                          (SEQ ID NO: 45)
MSDNGPQ-NQ RNAPRITFGG PSDSTGSNQN GERSGARSKQ

RRPQGLPNNT ASWFTALTQH GKEDLKEPRG QGVPININSS

PDDQIGYYRR ATRRIRGGDG KMKDLSPRWY FYYLGTGPEA

GLPYGANKDG IIWVATEGAL NTPKDHIGTR NPANNAAIVL

QLPQGTTLPK GFYAEGSRGG SQASSRSSSR SRNSSRNSTP

GSSRGTSPAR MAGNGGDAAL ALLLLDRINQ LESKMSGKGQ

QQQGQTVTKK SAAEASKKPR QKRTATKAYN VTQAFGRRGP

EQTQGNFGDQ ELIRQGTDYK HWPQIAQFAP SASAFFGMSR

IGMEVTPSGT WLTYTGAIKL DDKDPNEKDQ VILLNKHIDA

YKTEPPTEPK KDKKKKADET QALPQRQKKQ QTVILLPAAD

LDDESKQLQQ SMSSA--DST

>CoV N T2 1/1-418 Node1b 321-323 deleted
                          (SEQ ID NO: 46)
MSDNGPQ-NQ RSAPRITEGG PSDSTDNNQN GERSGARPKQ

RRPQGLPNNT ASWFTALTQH GKEDLREPRG QGVPINTNSG

KDDQIGYYRR ATRRVRGGDG KMKELSPRWY FYYLGTGPEA

ALPYGANKEG IVWVATEGAL NTPKDHIGTR NPNNNAAIVL

QLPQGTTLPK GFYAEGSRGG SQASSRSSSR SRGNSRNSTP

GSSRGTSPAR MASGGGDTAL ALLLLDRLNQ LESKVSGKGQ

QQQGQTVTKK SAAEASKKPR QKRTATKQYN VTQAFGRRGP

EQTQGNEGDQ ELIRQGTDYK HWPQIAQFAP SASAFFGMSR

---EVTPSGT WLTYHGAIKL DDKDPQEKDN VILLNKHIDA

YKTFPPTEPK KDKKKKADEA QPLPQRQKKQ PTVTLLPAAD
```

| SARS2 E protein residue position | SARS2 Reference Amino acid residue | COV_E_T2_1 Amino acid residue | COV_E_T2_2 Amino acid residue | COV_E_T2_3 Amino acid residue | COV_E_T2_4 Amino acid residue | COV_E_T2_5 Amino acid residue |
|---|---|---|---|---|---|---|
| 15 | N | N | N | A | A | A |
| 55 | S | T | T | S | T | T |
| 69 | R | Q | R | R | Q | R |
| 70 | — | G | — | — | G | — |

-continued

```
LDDESKQLQN SMSGASADST QA

>CoV N T2 2/1-417 epitope optimised 321-323
deleted
                            (SEQ ID NO: 47)
MTDNGQQ-GP RNAPRITF-G VSDNEDNNQD GGRSGARPKQ

RRPQGLPNNT ASWFTALTQH GKEDLREPRG QGVPINTNSS

PDDQIGYYRR ATRRIRGGDG KMKDLSPRWY FYYLGTGPEA

ALPYGANKEG IVWVATEGAL NTPKDHIGTR NPNNNAAIVL

QLPQGTTLPK GFYAEGSRGG SQASSRSSSR SRNSSRNSTP

GSSRGTSPAR NLQAGGDTAL ALLLLDRINQ LESKMSGKGQ

QQQGQTVTKK SAAEASKKPR QKRTATKQYN VTQAFGRRGP

EQTQGNEGDQ ELIRQGTDYK QWPQIAQFAP SASAFFGMSR

---EVTPSGT WLTYTGAIKL DDKDPQEKDN VILLNKHIDA

YKTEPPTEPK KDKKKKADEA QPLPQRQKKQ QTVILLPAAD

LDDESRQLQN SMSGASADST QA
```

Alignment of the N protein designs with SARS2 N protein reference sequence is shown in FIG. 47.

The amino acid differences of the designed sequences from the SARS2 reference sequence are shown in the table below (with differences from the reference sequence in bold, and differences that are common to all the designed sequences underlined):

| SARS2 N protein residue position (SEQ ID NO: 45) | SARS2 Reference amino acid residue (SEQ ID NO: 45) | N_T2_1 amino acid residue (SEQ ID NO: 46) | N_T2_2 amino acid residue (SEQ ID NO: 47) |
|---|---|---|---|
| 2 | S | S | T |
| 6 | P | P | Q |
| 8 | N | N | G |
| 9 | Q | Q | P |
| 11 | N | S | N |
| 18 | G | G | — |
| 20 | P | P | V |
| 23 | S | S | N |
| 24 | T | T | F |
| 25 | G | D | D |
| 26 | S | N | N |
| 29 | N | N | D |
| 31 | E | E | G |
| 37 | S | P | P |
| 65 | K | R | R |
| 79 | S | G | S |
| 80 | P | K | P |
| 94 | I | V | I |
| 103 | D | E | D |
| 120 | G | A | A |
| 128 | D | E | E |
| 131 | I | V | V |
| 152 | A | N | N |
| 192 | N | G | N |
| 193 | S | N | S |
| 211 | A | A | L |
| 212 | G | S | Q |
| 213 | Z | G | A |
| 217 | A | T | T |
| 234 | M | V | M |
| 267 | A | Q | Q |
| 300 | H | H | Q |
| 320 | I | — | — |
| 321 | G | — | — |
| 322 | M | — | — |

-continued

| SARS2 N protein residue position (SEQ ID NO: 45) | SARS2 Reference amino acid residue (SEQ ID NO: 45) | N_T2_1 amino acid residue (SEQ ID NO: 46) | N_T2_2 amino acid residue (SEQ ID NO: 47) |
|---|---|---|---|
| 334 | T | H | T |
| 345 | N | Q | Q |
| 349 | Q | N | N |
| 379 | T | A | A |
| 390 | Q | P | Q |
| 406 | K | K | R |
| 409 | Q | N | N |
| 413 | S | G | G |
| *415* | — | S | S |
| *416* | — | A | A |

Positions 415 and 416 are italicised as they are not residues of the reference sequences, but include insertions in the N_T2_1 and N_T2_2 sequences.

EXAMPLE 27

Membrane (M) Protein Vaccine Sequences

We have made further new M protein designs. In these designs, we have deleted the 1st and the 2nd transmembrane region of the membrane protein to abrogate its interaction with the S protein:

The string construct with S, M and E was showing higher order aggregates.

Abrogation of interaction between S and M-can reduce aggregation.

M-del constructs (Cov_M_T2_(3-5)) designed to abrogate the interaction with S.

FIG. 20 shows an illustration of the M protein. Interaction between the M, E and N proteins is important for viral assembly. The M protein also binds to the nucleocapsid, and this interaction promotes the completion of virion assembly. These interactions have been mapped to the C-terminus of the endo-domain of the M protein, and the C-terminal domain of the N-protein. In FIG. 20, * denotes identification of immunodominant epitopes on the membrane protein of the Severe Acute Respiratory Syndrome-Associated Coronavirus, and ** denotes mapping of the Coronavirus membrane protein domains involved in interaction with the Spike protein.

The amino acid sequences of the new M protein designs are given below:

```
>COV_M_T2_3
                            (SEQ ID NO: 48)
MADSNGTITV EELKKLLEQI TGGIAIAMAC LVGLMWLSYF

IASFRLFART RSMWSENPET NILLNVPLHG TILTRPLLES

ELVIGAVILR GHLRIAGHHL GRCDIKDLPK EITVATSRTL

SYYKLGASQR VAGDSGFAAY SRYRIGNGKL NTDHSSSSDN

IALLVQ

>COV_M_T2_4
                            (SEQ ID NO: 49)
MADNGTITVE ELKQLLEQVT GGIAIAMACI VGLMWLSYFV

ASFRLFARTR SMWSENPETN ILLNVPLRGT ILTRPLMESE
```

-continued

```
LVIGAVIIRG HLRMAGHSLG RCDIKDLPKE ITVATSRTLS

YYKLGASQRV GTDSGFAAYN RYRIGNGKLN TDHAGSNDNI

ALLVQ

>COV_M_T2_5
                                    (SEQ ID NO: 50)
MADSNGTITV EELKKLLEQV TGGIAIAMAC IVGLMWLSYF

VASFRLFART RSMWSENPET NILLNVPLRG SIITRPLMES

ELVIGAVILR GHLRMAGHSL GRCDIKDLPK EITVATSRTL

SYYKLGASQR VASDSGFAVY NRYRIGNGKL NTDHSSSSDN

IALLVQ
```

Sequence alignment of the new M protein designs (COV_M_T2_3, COV_M_T2_4, COV_M_T2_5) (SEQ ID NO:48-50) with the previous M protein designs (COV_M_T1_1, COV_M_T2_1, COV_M_T2_2) (SEQ ID NO:24-26) is shown in FIG. 46.

The amino acid differences of the designed sequences from the SARS2 M protein reference sequence are shown in the table below (with differences from the reference sequence in bold):

COV_S_T2_18
COV_S_T2_19
COV_S_T2_20
M7 RBD
TM RBD

The results show that the RBD is peaking at 25-26 KDa, and a second peak appears at 29 KDa.

FIG. 22 shows the spectra for the following examples of recombinant RBD proteins:

RBD (one sample labelled "LMB");

His-tagged RBD;

Another RBD protein sample labelled "Ralph".

The amino acid sequence of COV_S_T2_19 is below:

```
>COV_S_T2_19
                                    (SEQ ID NO: 55)
RVAPTKEVVRFPNITNLCPFGEVFNATRFPSVYAWERKRISNCVA

DYSVLYNSTSFSTFKCYGVSPTKLNDLCFTNVYADSFVIRGDEVR

QIAPGQTGVIADYNYKLPDDFTGCVIAWNTNNLDSTTGGNYNYLY

RSLRKSKLKPFERDISSDIYSPGGKPCSGVEGFNCYYPLRSYGFF
```

| SARS2 M protein residue position | SARS2 Reference Amino acid residue (COV_M_T1_1) | COV_M_T2_1 Amino acid residue | COV_M_T2_2 Amino acid residue | COV_M_T2_3 Amino acid residue | COV_M_T2_4 Amino acid residue | COV_M_T2_5 Amino acid residue |
|---|---|---|---|---|---|---|
| 4 | S | Deleted | S | S | Deleted | S |
| 15 | K | Q | K | K | Q | K |
| 20-75 | | | | Deleted | Deleted | Deleted |
| 30 | T | A | T | | | |
| 33 | C | M | C | | | |
| 40 | A | S | S | | | |
| 52 | I | V | I | | | |
| 76 | I | V | V | | V | V |
| 87 | L | I | I | L | I | I |
| 97 | I | V | V | 1 | V | V |
| 125 | H | R | R | H | R | R |
| 127 | T | T | S | T | T | S |
| 129 | L | L | I | L | L | I |
| 134 | L | M | M | L | M | M |
| 145 | L | I | L | L | I | L |
| 151 | I | M | M | I | M | M |
| 155 | H | S | S | H | S | S |
| 188 | A | G | A | A | G | A |
| 189 | G | T | S | G | T | S |
| 195 | A | A | V | A | A | V |
| 197 | S | N | N | S | N | N |
| 204 | Y | Y | Y | G | G | G |
| 211 | S | A | S | S | A | S |
| 212 | S | G | S | S | G | S |
| 214 | S | N | S | S | N | S |

EXAMPLE 28

Glycosylation of S Protein RBD Proteins

FIG. 21 shows the spectra overlap (MALDI MS) of supernatants derived from HEK cells transfected with pEVAC plasmid encoding the following S protein RBD sequences:

COV_S_T2_5 (wild-type SARS1 RBD)
COV_S_T2_6 (wild-type SARS2 RBD)
COV_S_T2_13
COV_S_T2_14
COV_S_T2_15
COV_S_T2_16
COV_S_T2_17

-continued

```
PTNGVGYQPYRVVVLSFELLNAPATVCGPKLSTDGGGGSGGGGSG

GGGGGGGSKSSIASFFFIIGLIIGLFLVLRVGIHLCIKLKHTKKR

QIYTDIEMNRLGK
```

The amino acid sequence of COV_S_T2_20 is below:

```
>COV_S_T2_20
                                    (SEQ ID NO: 56)
RVAPTKEVVRFPNITNLCPFGEVFNATKFPSVYAWERKKISNCVA

DYSVLYNSTSFSTFKCYGVSPTKLNDLCFTNVYADSFVIRGDEVR

QIAPGQTGVIADYNYKLPDDFTGCVIAWNTNNIDSTTGGNYNYLY
```

US 12,691,172 B2

169

-continued

RSLRKSKLKPFERDISSDIYSPGGKPCSGVEGFNCYYPLRSYGFF

PTNGTGYQPYRVVVLSFELLNAPATVCGPKLSTDGGGGSGGGGSG

GGGSGGGGSKSSIASFFFIIGLIIGLFLVLRVGIHLCIKLKHTKK

RQIYTDIEMNRLGK

COV_S_T2_19 is essentially COV_S_T2_13 with a transmembrane domain, and COV_S_T2_20 is COV_S_T2_17 with a transmembrane domain.

The amino acid sequence of RBD protein (Leader-RBD-Tag) is below:

(SEQ ID NO: 51)
MKRGLCCVLLLCGAVFVSPSAARVQPTESIVRFPNITNLCPFGEV

FNATRFASVYAWNRKRISNCVADYSVLYNSASFSTFKCYGVSPTK

LNDLCFTNVYADSFVIRGDEVRQIAPGQTGKIADYNYKLPDDFTG

CVIAWNSNNLDSKVGGNYNYLYRLFRKSNLKPFERDISTEIYQAG

STPCNGVEGFNCYFPLQSYGFQPTNGVGYQPYRVVVLSFELLHAP

ATVCGPKKSTNGGSGLNDIFEAQKIEWHEGSHHHHHH

FIG. 22 shows that the LMB and His-tagged RBD proteins peak at ~26 KDa (LMB is the higher peak in the figure), and that the Ralph RBD sample peaks at ~31-32 KDa. Peaks are also seen at ~52 KDa for "LMB" and "his RBD" (LMB is the higher peak), and at ~62-64 KDa for the Ralph RBD sample.

It was concluded from these results that there are two main glycosylated forms of the proteins obtained from the supernatant, in comparison to purified (recombinant) protein. The purified protein is non-glycosylated or sparsely glycosylated. This difference in glycosylation is believed to be important, as the glycosylation sites surround the epitope region and are conserved in most sarbecoviruses. These glycosylation sites are also important for interaction with some of the antibodies.

FIG. 23 provides a reference for glycosylation of the "S" Spike protein. As can be seen from the spectra, the glycosylation pattern of the spike protein is mixed. On average, the mass for each glycan is ~2 kDa. There are three sites of glycosylation for four of the S protein RBD designs (COV_T2_13, COV_T2_14, COV_T2_15, and COV_T2_16) and wild-type SARS1 RBD, two for wild-type SARS2 RBD, and four for S protein RBD designs COV_T2_17, COV_T2_18.

The mass of "Ralf RBD protein" is 29.2 kDa. The mass of the designed RBD proteins, and wild-type RBD is ~24 kDa.

EXAMPLE 29

Pan-Sarbecovirus Vaccine Coverage

Pan-Sarbecovirus protection: Beta-Coronaviruses including SARS-COV-2 (SARS2), -1 (SARS1) & the many Bat SARSr-COV (ACE2 receptor using) that threaten to spillover into humans.

FIG. 24 illustrates antigenic coverage achieved by universal Sarbecovirus B-cell and T-cell antigen targets. Part 1 shows Sarbecoviruses with the SARS1 and SARS2 clades highlighted along with human or bat host species. Part 2 shows machine learning predicted MHC class II binding (higher is stronger binding) of predicted epitopes within the insert. Lighter grey is for epitopes conserved within SARS2, darker grey are epitopes grafted in from other Sarbecoviruses such as SARS1.

EXAMPLE 30

Designed S Protein Sequence to Protect Against COVID-19 Variants

Multiple SARS-COV-2 variants are circulating globally. Several new variants emerged in the fall of 2020, most notably:

In the United Kingdom (UK), a new variant of SARS-COV-2 (known as 201/501Y.V1, VOC 202012/01, or B.1.1.7) emerged with a large number of mutations. This variant has since been detected in numerous countries around the world, including the United States (US). In January 2021, scientists from UK reported evidence that suggests the B.1.1.7 variant may be associated with an increased risk of death compared with other variants, although more studies are needed to confirm this finding. This variant was reported in the US at the end of December 2020.

In South Africa, another variant of SARS-COV-2 (known as 20H/501Y.V2 or B.1.351) emerged independently of B.1.1.7. This variant shares some mutations with B.1.1.7. Cases attributed to this variant have been detected in multiple countries outside of South Africa. This variant was reported in the US at the end of January 2021.

In Brazil, a variant of SARS-COV-2 (known as P.1) emerged that was first was identified in four travelers from Brazil, who were tested during routine screening at Haneda airport outside Tokyo, Japan. This variant has 17 unique mutations, including three in the receptor binding domain of the spike protein. This variant was detected in the US at the end of January 2021.

Scientists are working to learn more about these variants to better understand how easily they might be transmitted and the effectiveness of currently authorized vaccines against them. New information about the virologic, epidemiologic, and clinical characteristics of these variants is rapidly emerging.

B.1.1.7 Lineage (a.k.a. 201/501Y.V1 Variant of Concern (VOC) 202012/01)

This variant has a mutation in the receptor binding domain (RBD) of the spike protein at position 501, where the amino acid asparagine (N) has been replaced with tyrosine (Y). The shorthand for this mutation is N501Y. This variant also has several other mutations, including:

69/70 deletion: occurred spontaneously many times and likely leads to a conformational change in the spike protein P681H: near the S1/S2 furin cleavage site, a site with high variability in coronaviruses. This mutation has also emerged spontaneously multiple times.

This variant is estimated to have first emerged in the UK during September 2020.

Since Dec. 20, 2020, several countries have reported cases of the B.1.1.7 lineage, including the United States.

This variant is associated with increased transmissibility (i.e., more efficient and rapid transmission).

In January 2021, scientists from UK reported evidence (Horby P, Huntley C, Davies N, et al. NERVTAG note on B.1.1.7 severity. SAGE meeting report. Jan. 21, 2021) that suggests the B.1.1.7 variant may be associated with an increased risk of death compared with other variants.

Early reports found no evidence to suggest that the variant has any impact on the severity of disease or vaccine efficacy (Wu K, Werner A P, Moliva J I, et al. mRNA-1273 vaccine induces neutralizing antibodies against spike mutants from global SARS-COV-2 variants. bioRxiv. Posted Jan. 25, 2021; Xie X, Zou J, Fontes-Garfias C R, et al. Neutralization of N501Y mutant SARS-COV-2 by BNT162b2 vaccine-elicited sera. bioRxiv. Posted Jan. 7, 2021; Greaney A J, Loes A N, Crawford K H D, et al. Comprehensive mapping of mutations to the SARS-COV-2 receptor-binding domain that affect recognition by polyclonal human serum antibodies. bioRxiv. [Preprint posted online Jan. 4, 2021]; Weisblum Y, Schmidt F, Zhang F, et al. Escape from neutralizing antibodies by SARS-COV-2 spike protein variants. eLife 2020; 9: e61312.)

B.1.351 lineage (a.k.a. 20H/501Y.V2)

This variant has multiple mutations in the spike protein, including K417N, E484K, N501Y. Unlike the B.1.1.7 lineage detected in the UK, this variant does not contain the deletion at 69/70.

This variant was first identified in Nelson Mandela Bay, South Africa, in samples dating back to the beginning of October 2020, and cases have since been detected outside of South Africa, including the United States.

The variant also was identified in Zambia in late December 2020, at which time it appeared to be the predominant variant in the country.

Currently there is no evidence to suggest that this variant has any impact on disease severity.

There is some evidence to indicate that one of the spike protein mutations, E484K, may affect neutralization by some polyclonal and monoclonal antibodies (Weisblum Y, Schmidt F, Zhang F, et al. Escape from neutralizing antibodies by SARS-COV-2 spike protein variants. eLife 2020; 9: e61312; Resende P C, Bezerra J F, de Vasconcelos R H T, at al. Spike E484K mutation in the first SARS-COV-2 reinfection case confirmed in Brazil, 2020. [Posted on www.virological.org on Jan. 10, 2021])

P.1 lineage (a.k.a. 20J/501Y.V3)

The P.1 variant is a branch off the B.1.1.28 lineage that was first reported by the National Institute of Infectious Diseases (NIID) in Japan in four travelers from Brazil, sampled during routine screening at Haneda airport outside Tokyo.

The P.1 lineage contains three mutations in the spike protein receptor binding domain: K417T, E484K, and N501Y.

There is evidence to suggest that some of the mutations in the P.1 variant may affect its transmissibility and antigenic profile, which may affect the ability of antibodies generated through a previous natural infection or through vaccination to recognize and neutralize the virus. —A recent study reported on a cluster of cases in Manaus, the largest city in the Amazon region, in which the P.1 variant was identified in 42% of the specimens sequenced from late December (Resende P C, Bezerra J F, de Vasconcelos R H T, at al. Spike E484K mutation in the first SARS-COV-2 reinfection case confirmed in Brazil, 2020. [Posted on www.virological.org on Jan. 10, 2021]). In this region, it is estimated that approximately 75% of the population had been infected with SARS-COV2 as of October 2020. However, since mid-December the region has observed a surge in cases. The emergence of this variant raises concerns of a potential increase in transmissibility or propensity for SARS-COV-2 re-infection of individuals.

This variant was identified in the United States at the end of January 2021.

One specific mutation, called D614G, is shared by these three variants. It gives the variants the ability to spread more quickly than the predominant viruses, as described in a non-peer-reviewed preprint article (1Bin Zhou, Tran Thi Nhu Thao, Donata Hoffmann, et al. SARS-CoV-2 spike D614G variant confers enhanced replication and transmissibility bioRxiv 2020.10.27 doi.org/10.1101/2020.10.27.357558; Volz E, Hill V, McCrone J, et al. Evaluating the Effects of SARS-COV-2 Spike Mutation D614G on Transmissibility and Pathogenicity. Cell 2021; 184 (64-75). doi.org/10.1016/j.cell.2020.11.020). There also is epidemiologic evidence that variants with this specific mutation spread more quickly than viruses without the mutation (Korber B, Fischer W M, Gnanakaran S, et al. Tracking Changes in SARS-COV-2 Spike: Evidence that D614G Increases Infectivity of the COVID-19 Virus. Cell 2021; 182 (812-7). doi.org/10.1016/j.cell.2020.06.043). This mutation was one of the first documented in the US in the initial stages of the pandemic, after having initially circulated in Europe (Yurkovetskiy L, Wang X, Pascal K E, et al. Structural and Functional Analysis of the D614G SARS-COV-2 Spike Protein Variant. Cell 2020; 183 (3): 739-1. doi.org/10.1016/j.cell.2020.09.032).

The variants are summarised in the table below (www.cdc.gov/coronavirus/2019-ncov/cases-updates/variant-surveillance/variant-info.html):

| Name | Name (Nextstrain) | First Detected | Countries Reporting Cases | Key Mutations | Transmissibility Rate |
|---|---|---|---|---|---|
| B.1.1.7 | 20I/ 501Y.V1 | United Kingdom | 70 | 69/70 deletion 144Y deletion N501Y A570D D614G P681H | ~50% increase |
| P.1 | 20J/ 501Y.V3 | Japan/ Brazil | >4 | E484K K417N/T N501Y D614G | Not determined |
| B.1.351 | 20H/ 501.V2 | South Africa | >30 | K417N E484K N501Y D614G | Not determined |

We have designed a new full-length S protein sequence (referred to as "VOC Chimera", or COV_S_T2_29) for use as a COVID-19 vaccine insert to protect against variants B.1.1.7, P.1, and B.1.351.

The full-length S protein amino acid sequence of SARS_COV_2 isolate EPI_ISL_402130 (a reference sequence) is given below:

```
>EPI_ISL_402130 (Wuhan strain)
                                                          (SEQ ID NO: 52)
MFVELVLLPL VSSQCVNLTT RTQLPPAYEN SFTRGVYYPD KVERSSVLHS TQDLFLPEES    60

NVTWFHAIHV SGTNGTKRED NPVLPENDGV YFASTEKSNI IRGWIFGTTL DSKTQSLLIV   120
```

-continued

```
NNATNVVIKV CEFQFCNDPF LGVYYHKNNK SWMESEERVY SSANNCTFEY VSQPFLMDLE  180

GKQGNEKNLR EFVEKNIDGY FKIYSKHTPI NLVRDLPQGF SALEPLVDLP IGINITRFQT  240

LLALHRSYLT PGDSSSGWTA GAAAYYVGYL QPRTELLKYN ENGTITDAVD CALDPLSETK  300

CTLKSFTVEK GIYQTSNERV QPTESIVREP NITNLCPEGE VENATREASV YAWNRKRISN  360

CVADYSVLYN SASFSTEKCY GVSPTKLNDL CFTNVYADSF VIRGDEVRQI APGQTGKIAD  420

YNYKLPDDFT GCVIAWNSNN LDSKVGGNYN YLYRLERKSN LKPFERDIST EIYQAGSTPC  480

NGVEGENCYF PLQSYGFQPT NGVGYQPYRV VVLSFELLHA PATVCGPKKS TNLVKNKCVN  540

ENENGLIGTG VLTESNKKEL PFQQFGRDIA DTTDAVRDPQ TLEILDITPC SEGGVSVITP  600

GTNTSNQVAV LYQDVNCTEV PVAIHADQLT PTWRVYSTGS NVFQTRAGCL IGAEHVNNSY  660

ECDIPIGAGI CASYQTQTNS PRRARSVASQ SIIAYTMSLG AENSVAYSNN SIAIPTNFTI  720

SVTTEILPVS MTKTSVDCTM YICGDSTECS NLLLQYGSFC TQLNRALTGI AVEQDKNTQE  780

VEAQVKQIYK TPPIKDEGGF NESQILPDPS KPSKRSFIED LLENKVTLAD AGFIKQYGDC  840

LGDIAARDLI CAQKENGLTV LPPLLTDEMI AQYTSALLAG TITSGWTFGA GAALQIPFAM  900

QMAYRENGIG VTQNVLYENQ KLIANQFNSA IGKIQDSLSS TASALGKLQD VVNQNAQALN  960

TLVKQLSSNF GAISSVENDI LSRLDKVEAE VQIDRLITGR LQSLQTYVTQ QLIRAAEIRA 1020

SANLAATKMS ECVLGQSKRV DECGKGYHLM SFPQSAPHGV VELHVTYVPA QEKNETTAPA 1080

ICHDGKAHFP REGVFVSNGT HWFVTQRNFY EPQIITTDNT FVSGNCDVVI GIVNNTVYDP 1140

LQPELDSEKE ELDKYEKNHT SPDVDLGDIS GINASVVNIQ KEIDRLNEVA KNLNESLIDL 1200

QELGKYEQYI KWPWYIWLGF IAGLIAIVMV TIMLCCMTSC CSCLKGCCSC GSCCKEDEDD 1260

SEPVLKGVKL HYT                                                    1273
```

The amino acid sequence of the designed full-length S[35] protein sequence is given below:

```
>COV_S_T2_29 (VOC chimera)
                                              (SEQ ID NO: 53)
MEVELVLLPL VSSQCVNETN RTQLPSAYIN SETRGVYYPD KVERSSVLHS TQDLFLPFES   60

NVTWFHAISG TNGTKREDNP VLPENDGVYF ASTEKSNIIR GWIEGTTLDS KTQSLLIVNN  120

ATNVVIKVCE FQFCNDPFLG VYHKNNKSWM ESEFRVYSSA NNCTFEYVSQ PELMDLEGKQ  180

GNFKNLREFV FKNIDGYFKI YSKHTPINLV RDLPQGESAL EPLVDLPIGI NITRFQTLLA  240

LHRSYLTPGD SSSGWTAGAA AYYVGYLQPR TELLKYNENG TITDAVDCAL DPLSETKCTL  300

KSFTVEKGIY QTSNERVQPT ESIVREPNIT NLCPFGEVEN ATREASVYAW NRKRISNCVA  360

DYSVLYNSAS ESTEKCYGVS PTKLNDLCFT NVYADSEVIR GDEVRQIAPG QTGNIADYNY  420

KLPDDFTGCV IAWNSNNLDS KVGGNYNYLY RLERKSNLKP FERDISTEIY QAGSTPCNGV  480

KGENCYFPLQ SYGFQPTYGV GYQPYRVVVL SFELLHAPAT VCGPKKSTNL VKNKCVNENE  540

NGLIGTGVLT ESNKKELPFQ QFGRDIADTT DAVRDPQTLE ILDITPCSFG GVSVITPGIN  600

TSNQVAVLYQ GVNCTEVPVA IHADQLTPTW RVYSTGSNVE QTRAGCLIGA EHVNNSYECD  660

IPIGAGICAS YQTQTNSHRR ARSVASQSII AYTMSLGAEN SVAYSNNSIA IPTNFTISVT  720

TEILPVSMTK TSVDCTMYIC GDSTECSNLL LQYGSFCTQL NRALTGIAVE QDKNTQEVEA  780

QVKQIYKTPP IKDEGGENFS QILPDPSKPS KRSFIEDLLE NKVTLADAGE IKQYGDCLGD  840

IAARDLICAQ KENGLTVLPP LLTDEMIAQY TSALLAGTIT SGWTFGAGAA LQIPFAMQMA  900

YRENGIGVTQ NVLYENQKLI ANQFNSAIGK IQDSLSSTAS ALGKLQDVVN QNAQALNTLV  960
```

```
                                          -continued
KQLSSNFGAI SSVINDILSR LDPPEAEVQI DRLITGRLQS LQTYVTQQLI RAAEIRASAN 1020

LAATKMSECV LGQSKRVDFC GKGYHLMSFP QSAPHGVVFL HVTYVPAQEK NFTTAPAICH 1080

DGKAHFPREG VEVSNGTHWF VTQRNFYEPQ IITTDNTEVS GNCDVVIGIV NNTVYDPLQP 1140

ELDSFKEELD KYFKNHTSPD VDLGDISGIN ASVVNIQKEI DRINEVAKNL NESLIDLQEL 1200

GKYEQYIKWP WYIWLGFIAG LIAIVMVTIM LCCMTSCCSC LKGCCSCGSC CKEDEDDSEP 1260

VLKGVKLHYT                                                       1270
```

Alignment of these two sequences is shown in FIG. 50. The amino acid differences between the sequences are shown boxed, with the two amino acid changes made to provide structure stability shown in the shaded box.

The amino acid differences of the designed sequence COV_S_T2_29 from the SARS2 S protein reference sequence (EPI_ISL_402130_Wuhan strain) are summarised in the table below:

| SARS2 S protein residue position (SEQ ID NO: 52) | SARS2 Reference amino acid residue (SEQ ID NO: 52) | COV_S_T2_29 amino acid residue (SEQ ID NO: 53) |
| --- | --- | --- |
| 18 | L | F |
| 20 | T | N |
| 26 | P | S |
| 69 | H | Deletion |
| 70 | V | Deletion |
| 144 | Y | Deletion |
| 417 | K | N |
| 484 | E | K |
| 501 | N | Y |
| 614 | D | G |
| 681 | P | H |
| 986 | K | P |
| 987 | V | P |

EXAMPLE 31

Designed S Protein Sequence in Closed State to Protect Against Known COVID-19 Variants, and Predicted Future Variants The majority of SARS-COV-2 vaccines in use or in advanced clinical development are based on the viral spike protein(S) as their immunogen. S is present on virions as pre-fusion trimers in which the receptor binding domain (RBD) is stochastically open or closed. Neutralizing antibodies have been described that act against both open and closed conformations. The long-term success of vaccination strategies will depend upon inducing antibodies that provide long-lasting broad immunity against evolving, circulating SARS-COV-2 strains, while avoiding the risk of antibody dependent enhancement as observed with other Coronavirus vaccines.

Carnell et al. ("*SARS-COV-2 spike protein arrested in the closed state induces potent neutralizing responses*"; doi.org/10.1101/2021.01.14.426695, posted 14 Jan. 2021) have assessed the results of immunization in a mouse model using an S protein trimer that is arrested in the closed state to prevent exposure of the receptor binding site and therefore interaction with the receptor. The authors compared this with a range of other modified S protein constructs, including representatives used in current vaccines. They found that all trimeric S proteins induce a long-lived, strongly neutralizing antibody response as well as T-cell responses. Notably, the protein binding properties of sera induced by the closed spike differed from those induced by standard S protein constructs. Closed S proteins induced more potent neutralising responses than expected based on the degree to which they inhibit interactions between the RBD and ACE2. The authors conclude that these observations suggest that closed spikes recruit different, but equally potent, virus-inhibiting immune responses than open spikes, and that this is likely to include neutralizing antibodies against conformational epitopes present in the closed conformation.

We have appreciated that the amino acid changes of the designed S protein sequences disclosed herein (and especially in Example 30 above) may optionally be present in a designed S protein that is arrested in the closed state, and thereby further improve the antibody response of the designed sequences. In particular, use of such structural constraints may reduce immunodominance to key regions, and spread the antibody response to focus on other, or less immunodominant sites.

SARS-COV-2 is continually evolving, with more contagious mutations spreading rapidly. Zahradník et al., 2021 ("*SARS-COV-2 RBD in vitro evolution follows contagious mutation spread, yet generates an able infection inhibitor*"; doi.org/10.1101/2021.01.06.425392, posted 29 Jan. 2021) recently reported using in vitro evolution to affinity maturate the receptor-binding domain (RBD) of the spike protein towards ACE2 resulting in the more contagious mutations, S477N, E484K, and N501Y, to be among the first selected, explaining the convergent evolution of the "European" (20E-EU1), "British" (501.V1), "South African" (501.V2), and "Brazilian" variants (501.V3). The authors report that further in vitro evolution enhancing binding by 600-fold provides guidelines towards potentially new evolving mutations with even higher infectivity. For example, Q498R epistatic to N501Y.

We have also appreciated that the designed S protein sequences (RBD, truncated, or full-length) disclosed herein (and especially in Example 30 above) may optionally also include amino acid substitutions at residue positions predicted to be mutated in future COVID-19 variants with a vaccine escape response.

The amino acid sequence alignment of FIG. 51 shows the full-length S protein amino acid sequence of SARS_COV_2 isolate EPI_ISL_402130 (a reference sequence; SEQ ID NO:52) with the amino acid changes made for the designed S protein sequence described in Example 30 above ("VOC Chimera", or COV_S_T2_29; SEQ ID NO:53), shown underneath the isolate sequence (in the line referred to as "Super_spike"). This designed ("Super_spike") S protein sequence may optionally also include one or more amino acid changes (a substitution or deletion) at one or more of the residue positions predicted to be mutated in future COVID-19 variants with a vaccine escape response.

The line underneath the "Super_spike" sequence alignment shows the residues that may be substituted for cysteine residues to allow formation of a disulphide bridge to form a "closed S protein" (SEQ ID NO:107). These cysteine substitutions may be combined with one or more (or all) of the amino acid changes made in the designed S protein sequence of the "Super_spike" sequence (COV_S_T2_29; SEQ ID NO:53), and optionally with one or more (or all) amino acid changes at the residue positions predicted to be mutated in future COVID-19 variants with a vaccine escape response (especially including, for example, Q498R).

The table below summarises the amino acid changes.

The shaded residues in the alignment in FIG. 51 are as follows:

Grey—amino acid residues that have been changed in the "Super_spike" design;

Dark grey—amino acid residues that may be substituted for a cysteine residue to allow formation of a "closed S protein";

Light grey—amino acid residues that have been predicted to be mutated in future COVID-19 variants and potentially generate a vaccine escape response.

| SARS2 S protein residue position NO:52) | SARS2 Reference amino acid residue NO:52) | COV_S_T2_29 amino acid NO:53) | Residues at which mutations have been predicted to arise and generate response | Residue at which cysteine substitution can be made to form protein |
|---|---|---|---|---|
| 18 | L | F | | |
| 20 | T | N | | |
| 26 | P | S | | |
| 69 | H | Deletion | | |
| 70 | V | Deletion | | |
| 144 | Y | Deletion | | |
| 413 | G | | | C |
| 417 | K | N | | |
| 446 | G | | * | |
| 452 | L | | * | |
| 477 | S | | * | |
| 484 | E | K | | |
| 498 | Q | | * (for example Q498R) | |
| 501 | N | Y | | |
| 614 | D | G | | |
| 681 | P | H | | |
| 986 | K | P | | |
| 987 | V | P | | C |

Optionally G413C and V987C is combined with one or more (or all) of the amino acid changes listed in the table below:

| SARS2 S protein residue position (SEQ ID NO: 52 | COV_S_T2_29 amino acid residue (SEQ ID NO: 53) |
|---|---|
| 18 | F |
| 20 | N |
| 26 | S |
| 69 | (deletion) |
| 70 | — (deletion) |
| 144 | — (deletion) |
| 417 | N |
| 484 | K |
| 501 | Y |
| 614 | G |
| 681 | H |

A further amino acid change that may optionally be included is K986P.

EXAMPLE 32

Epitope Optimised Broad Coverage Vaccine Designs for Sarbecoviruses

Overview

To increase the coverage of our receptor binding domain (RBD) based vaccine designs to all the extant sarbecovirus sub-genus of Beta-coronaviruses, a phylogenetically optimised vaccine design is constructed. This design is further used as backbone for designing both epitope optimised and immune re-focussed designs. The epitope information is derived largely from the known high-resolution structural data of spike protein-antibody complex. Few of these epitopes are reported to cross protect SARS-1 and SARS-2 and were included in the designs to increase the coverage of the vaccine designs. On further analysis of the sequence divergence of the epitopes, it was observed that one of the epitopes shows maximum divergence among sarbecovirus in comparison to other regions/epitopes of RBD. To enhance the immune response toward better conserved epitopes, post-translation modification-glycosylation was introduced at this epitope.

Results

Design of Broad Coverage Vaccine Antigens

To achieve broader response towards sarbecoviruses, we first generated a phylogenetically optimised design (COV_S_T2_13) (SEQ ID NO:27) where the amino acid sequence of RBD is optimised for all the extant sequences represented in FIG. 35A. Such a design is expected to generate broader antibody response compared to individual antigen from the extant species. To further understand the contribution of each epitope to antibody response, we modified the epitope sequences of COV_S_T2_13 to match the epitope sequences from SARS-1 and SARS-2. Three conformational epitopes (also referred to herein as "discontinuous epitopes") are identified through structural analyses of RBD-antibody complex (FIG. 35B). Two of these epitopes (henceforth termed as A and B) are reported to bind antibodies that neutralise both SARS-1 and SARS-2. These epitopes on COV_S_T2_13 designs are modified to match the SARS-1 epitope sequence (COV_S_T2_14 (SEQ ID NO: 28) and COV_S_T2_15 (SEQ ID NO:29)) to understand the contribution of these epitopes to generate neutralising antibody response against both SARS-1 and SARS-2. The third epitope (henceforth termed as C) is in and around the receptor binding region. This epitope shows maximum divergence (FIG. 35C) and is expected to generate a virus specific antibody response. To understand the importance of the amino acid composition of this epitope in generating neutralising antibody response, this epitope is modified to match the epitope from SARS-2 (COV_S_T2_16) (SEQ ID NO:30). Further to broaden the antibody response to both SARS-1 and SARS-2, a glycosylation site is introduced at the third epitope for both COV_S_T2_14 and COV_S_T2_15 (COV_S_T2_17 (SEQ ID NO:31) and COV_S_T2_18 (SEQ ID NO:32) respectively). To compare the efficacy in generating neutralising antibody response in soluble or membrane bound form, a membrane bound form for COV_S_T2_13 and COV_S_T2_17 (COV_S_T2_19 (SEQ ID NO:55) and COV_S_T2_20 (SEQ ID NO:56) respectively) is designed. All the designs are tabulated in the Table below. The sequence alignment of all the vaccine designs is shown in FIG. 37A. The residues that differ between the vaccine designs are boxed in black.

TABLE

Description of the vaccine designs used in the study.

| DESIGN | DESCRIPTION |
| --- | --- |
| COV_S_T2_13 | Phylogenetic optimised |
| COV_S_T2_14 | COV_S_T2_13 with epitope A and epitope |
| COV_S_T2_15 | B from SARS-1 |
| COV_S_T2_16 | COV_S_T2_13 with epitope C from SARS-2 |
| COV_S_T2_17 | COV_S_T2_13 with glycosylation site at |
| COV_S_T2_18 | epitope C |
| COV_S_T2_19 | Membrane bound version of COV_S_T2_13 |
| COV_S_T2_20 | Membrane bound version of COV_S_T2_17 |

FIG. 36(A) shows a Western Blot of sera from mice immunised with the vaccine designs.

FIG. 36 (B) shows antibody binding responses of Cell Surface expression bleed 2.

Neutralisation Data

Sera from mice injected with the vaccine designs (COV_S_TFeb. 13, 2020), SARS-1 RBD and SARS-2 RBD are checked for neutralisation of SARS-1 and SARS-2 pseudotypes. As a positive control, human sera from an infected individual are used. The neutralisation curves are shown in FIG. 37B. The phylogenetically optimised design (COV_S_T2_13) could generate neutralising antibody against SARS-2 but not for SARS-1. On comparing the sequence of the COV_S_T2_13 with SARS-1 and SARS-2, it is observed that the epitope C was enriched with amino acids from SARS-2 in comparison to other sarbecoviruses represented in phylogenetic tree (FIG. 35A). Sera from mice vaccinated with COV_S_T2_14, COV_S_T2_15, and COV_S_T2_16 showed data like COV_S_T2_13 for SARS-1, suggesting strongly that the epitope C is an immunodominant epitope and epitope A and B are immune sub-dominant epitope. Better neutralisation of SARS-2 by COV_S_T2_16 in comparison to COV_S_T2_13 suggests that the mutations at epitope C can lead to lower neutralisation of SARS-2. Substitution made in COV_S_T2_15 enhances the immunogenic response for SARS-2. The difference in immunogenic response could be due to the substitution of a small amino acid serine by bulky phenylalanine group.

Sera from COV_T2_S_17 and COV_T2_S_18 designs could neutralise both SARS-1 and SARS-2, suggesting that the introduction of glycosylation at epitope C successfully focused the immune response towards epitope A and epitope B. Thus, validating our design strategy. Comparison of neutralisation data of COV_T2_S_13 and COV_T2_S_17 with COV_S_T2_19 and COV_S_T2_20 respectively suggest that the membrane bound and soluble form similar immunogenic response in mice.

Neutralisation data for bat viruses (not shown) shows broader coverage. This rationalises the usage of phylogenetic optimised sequence as the template for further designs.

Competition data (not shown) shows that all the designs generate antibodies that block receptor binding.

Discussion

A vaccine design which can generate antibody response against diverse sarbecovirus is desirable. To achieve this, we first generated a novel protein sequence (COV_S_T2_13) for the receptor binding domain of the spike protein by using sequence information for all the know extant sarbecoviruses. Each amino acid position in the sequence is chosen based on the phylogenetic relatedness of the input sequences. The novel sequence generated neutralising response against SARS-2 but not much against SARS-1. On comparison of the epitopes in the COV_S_T2_13 and SARS-1 and SARS-2, it was observed that the epitopes were more biased towards SARS-2 compared to SARS-1. To expand the reactivity towards SARS-1, two of the epitopes (which were also conserved between SARS-1 and SARS-2) were mutated to match the sequence from SARS-1 (COV_S_T2_14 and COV_S_T2_15) and the third epitope was mutated to match SARS-2 (COV_S_T2_16). Comparison of the neutralisation from these designs suggested that the two conserved epitopes are sub-dominant in nature compared to the third epitope. Also, comparison of COV_S_T2_16 with COV_S_T2_13 suggested that conservative mutations in the third epitope can cause immune escape. To focus the immune response towards the conserved epitopes, a glycosylation site was introduced at the more diverged third epitope (COV_S_T2_17 and COV_S_T2_18). The introduction of the glycosylation site indeed broadened the immune response to both SARS-1 and SARS-2, with cross-neutralisation observed for both the designs. The data presented here strongly supports the design strategy to broaden the coverage of vaccine designs by re-focussing the immune response to better conserved epitopes by introducing modifications in epitopes that more diverged.

Methodology

Phylogenetic Analysis

Protein sequences of spike proteins were downloaded from the NCBI virus database for all the known sarbecoviruses. Multiple sequence alignment (MSA) was generated using the MUSCLE algorithm. The resulting MSA was pruned to the RBD region and used as input for phylogenetic tree reconstruction. The phylogenetic tree was generated using IQTREE algorithm using protein model with best AIC score. The resultant tree was used for generation of phylogenetically optimised design using FASTML algorithm.

Epitope Identification

Available structural data for Spike protein-antibody complexes for SARS-1 and SARS-2 were downloaded from the Protein Databank (PDB). These structural data were further pruned for antigen-antibody complexes where the epitope region is in the RBD. Amino acid residues of antigen that have at least one atom within 5 Å radii of at least one atom of amino acid of antibody are defined as epitope residues. An epitope region is defined as contiguous stretch of at least 5 amino acids.

Molecular Modelling

Structural models were generated for COV_S_T2_13 using MODELLER algorithm. The structural model with the highest DOPE score was chosen as the working model for the further molecular modelling. The side chains for the model were further optimised using SCWRL library and energy minimised using GROMACS package. Structural stability of the COV_S_T2_14-COV_S_T2_18 designs was checked for using POSSCAN and BUILD module of FOLDX algorithm using the optimised structural model of COV_S_T2_13.

EXAMPLE 33

Dose Finding Study of COV_S_T2_17 (SEQ ID NO:31), a Pan-Sarbeco Coronavirus Vaccine DNA Candidate, Delivered by Needleless Intradermal Administration Study Protocol in Brief (FIG. 38):

To determine the optimal dose of DNA, a pre-clinical vaccine study was undertaken in mature Hartley Guinea pigs. Animals were randomised into six groups of eight animals and pre-bled to determine the absence of anti-SARS-COV-2 antibodies.

Group 1 (control) group received the high dose of 400 µg (2 mg/ml) of the modified SARS-COV-2 RBD COV_S_T2_8 DNA subcutaneously, to compare to a second group the same control DNA of COV_S_T2_8 at 400 µg administered intradermally (ID) by the PharmaJet Tropis device. The remaining four groups received the pan-Sarbeco vaccine candidate, COV_S_T2_17 at 100 µg (0.5 mg/ml), 200 µg (1 mg/ml) (two groups, one receiving 2, the other 3 doses) or 400 µg (400 µg/ml) intradermally at day 0 and 28. Animals were bled at days 14, 28, 42, 56 and 70.

ELISA to Determine the Level of Antibodies to the RBD of SARS-COV-2, and SARS (FIG. 39):

Panel A (Left) Plates Coated with SARS-COV-2 RBD.

28 days following the first immunisation an ELISA assay was performed to determine the titre of anti-SARS-COV-2 RBD, or anti-SARS RBD antibodies induced 28 days after one DNA immunisation. The top left panel (T2_8 at 400 µg sc) demonstrates the antibody responses to SARS-COV-2 in 5 out of 8 animals, compared to the bottom right hand panel (T2_8 at 400 µg DNA administered ID by the Tropis PharmaJet) where 7 of 8 animals respond strongly to SARS-COV-2 RBD. The 4 remaining groups receiving COV_S_T2_17 ID by PharmaJet delivery, showed similar anti-SARS-COV-2 responses to 400 µg of the SARS-COV-2 RBD DNA administered at the maximal dose.

Panel B (Right) Plates Coated with SARS RBD.

The same 28 day serum samples at serial dilutions were tested for binding to the SARS RBD.

The top left panel (T2_8 at 400 µg sc) demonstrates low titre antibodies, with only 2 of 8 animals reaching an OD of 0.5. The same dose of the SARS-COV-2 RBD vaccine given by the PharmaJet device (bottom right hand panel) demonstrates slightly improved but weak cross-reactive responses to the SARS RBD in contrast to its homotypic response to the SARS-CoV-2 RBD (panel A, left). In contrast all of the pan-Sarbeco T2_17 groups respond strongly to the SARS RBD in a dose-dependent manor, with all animals in the high (400 µg) (bottom row left in panel B) and medium doses (200 µg) groups (middle row panel B) responding strongly, and a more variable but distinct response in all 8 animals in the lowest (100 µg) T2_17 group (top right, panel B).

Virus Neutralisation at Day 28 after 1 Immunisation (Pseudotype MicroNeutralisation or pMN Assay) (FIG. 40):

Panel A (Left) Antibody Neutralisation of SARS-COV-2 28 Days after 1 Dose.

Similar to RBD antibody responses, neutralising antibodies to SARS-COV-2 were identified. In all groups 28 days following the first immunisation. The top left panel (T2_8 at 400 µg sc) had low level responses compared to the same vaccine candidate (T2_8 at 400 µg DNA) administered ID by the Tropis Pharmajet device, which was the strongest of all the groups. T2_17 ID by PharmaJet delivery, showed lower but significant responses to SARS-COV-2.

Panel B (Right) Antibody Neutralisation of SARS 28 Days after 1 Dose.

The same 28 day serum samples at serial dilutions were tested for neutralising to SARS pseudotyped viruses. At this time point, after 1 administration, responses were absent in the T2_8 groups (top left and bottom right of panel B (right).

The pan-Sarbeco T2_17 groups respond at low and variable levels after 1 dose of vaccine, again with the best but weak response in the highest dose group (400 µg) (bottom row left in panel B)

Groups 1 to 3, Comparison of Virus Neutralisation Responses after First to Second Immunisation (FIG. 41):

Panel A (Left SARS-COV-2) Comparing Bleeds 2 (Pre) and 3 (Post) Second Immunisation (Boost)

There was significant boost effect with increased neutralising responses to SARS-COV-2 in all groups, though not all animals in group 1 (T2_8 at 400 µg) administered subcutaneously. Groups 2 and 3, middle and lower rows of panel A, left, were more uniform and comparably boosted neutralising titres to SARS-COV-2.

Panel B (Right SARS) Comparing Bleeds 2 (Pre) and 3 (Post) Second Immunisation (Boost).

There was weak and variable boost effect in 5 of 8 animals to SARS in group 1 (T2_8 at 400 µg). Groups 2 and 3, middle and lower rows of panel A, left, were uniform and comparably strongly boosted with significant neutralising titres to SARS.

Groups 4, 5 and 6, Comparison of Virus Neutralisation Responses after First to Second Immunisation (FIG. 42):

Panel A (Left SARS-COV-2) Comparing Bleeds 2 (Pre) and 3 (Post) Second Immunisation (Boost).

Comparing the left hand column of groups 4, 5 and 6, there was significant boost effect with increased neutralising responses to SARS-COV-2 in Group 4 200 µg T_17 Tropis, group 5 400 µg T_17 Tropis, and the SARS-COV-2 specific 400 µg T2_8 also delivered by Tropis.

Panel B (Right SARS) Comparing Bleeds 2 (Pre) and 3 (Post) Second Immunisation (Boost).

Comparing the left to the right hand column of groups 4, 5 and 6, there was clear boost effect with increased neutralising responses to SARS in all 3 groups, but most significantly in the two T2_17 immunised groups (4 and 5, upper right hand graphs) that received 200 µg (top row panel B), and 400 µg of T2_17 (middle row panel B), with a possible dose effect in the 400 µg dose. In contrast, the 400 µg T2_8 group was boosted to a much lower and variable effect.

Neutralisation of Variants of Concern (FIG. 43):

Selected high, middle and low neutralising antibody responders from T2_8 and T2_17 guinea pig groups were tested for pseudotype based viral neutralisation of the original Wuhan strain (control), as well as variants of concern (VOC) lineages B1.248 (Brazil P1 lineage) and B1.351 (South Africa). Both these VOCs contain the E484K mutation that confers resistance to current vaccines in use (Astra-Zeneca, Pfizer, Moderna). High responding T2_8 guinea pig (8 and 11) antisera do not neutralise the VOCs, whereas high responders from the T2_17 group (31 and 34) still neutralise strongly.

EXAMPLE 34

Nucleic Acid Sequences Encoding COV S T2 13-20
>COV_S_T2_13 encoding nucleic acid
                                        (SEQ ID NO: 78)
AGAGTGGCCCCTACCAAAGAAGTCGTGCGGTTCCCCAACATCACC

AATCTGTGCCCTTTCGGCGAGGTGTTCAACGCCACCAGATTTCCC

TCTGTGTACGCCTGGGAGAGAAAGCGGATCAGCAACTGCGTGGCC

GACTACAGCGTGCTGTACAACAGCACCAGCTTCAGCACCTTCAAG

TGCTACGGCGTGTCACCCACCAAGCTGAACGACCTGTGCTTCACC

AACGTGTACGCCGACAGCTTCGTGATCAGAGGCGACGAAGTGCGG

CAGATTGCCCCTGGACAAACAGGCGTGATCGCCGATTACAACTAC

AAGCTGCCCGACGACTTCACCGGCTGTGTGATCGCCTGGAACACC

AACAACCTGGACAGCACCACCGGCGGCAACTACAACTACCTGTAC

AGAAGCCTGCGGAAGTCTAAGCTGAAGCCCTTCGAGCGGGACATC

AGCAGCGACATCTATAGCCCTGGCGGCAAGCCTTGTTCTGGCGTG

GAAGGCTTCAACTGCTACTACCCTCTGCGGGAGCTACGGCTTCTTC

CCCACAAATGGCGTGGGCTACCAGCCTTACAGAGTGGTGGTCCTG

AGCTTCGAGCTGCTGAATGCCCCTGCCACAGTGTGTGGCCCTAAG

CTGTCTACCGAC

>COV_S_T2_14 encoding nucleic acid
                                        (SEQ ID NO: 79)
AGAGTGGCCCCTACCAAAGAAGTCGTGCGGTTCCCCAACATCACC

AATCTGTGCCCTTTCGGCGAGGTGTTCAACGCCACCAAGTTTCCC

TCTGTGTACGCCTGGGAGCGCAAAAAGATCAGCAACTGCGTGGCC

GACTACAGCGTGCTGTACAACAGCACCAGCTTCAGCACCTTCAAG

TGCTACGGCGTGTCACCCACCAAGCTGAACGACCTGTGCTTCACC

AACGTGTACGCCGACAGCTTCGTGATCAGAGGCGACGAAGTGCGG

CAGATTGCCCCTGGACAAACAGGCGTGATCGCCGATTACAACTAC

AAGCTGCCCGACGACTTCACCGGCTGTGTGATCGCCTGGAACACC

AACAACATCGACAGCACCACCGGCGGCAACTACAACTACCTGTAC

AGAAGCCTGCGGAAGTCTAAGCTGAAGCCCTTCGAGCGGGACATC

AGCAGCGACATCTATAGCCCTGGCGGCAAGCCTTGTTCTGGCGTG

GAAGGCTTCAACTGCTACTACCCTCTGCGGGAGCTACGGCTTCTTC

CCCACAAATGGCGTGGGCTACCAGCCTTACAGAGTGGTGGTCCTG

AGCTTCGAGCTGCTGAATGCCCCTGCCACAGTGTGTGGCCCTAAG

CTGTCTACCGAC

>COV_S_T2_15 encoding nucleic acid
                                        (SEQ ID NO: 80)
AGAGTGGCCCCTACCAAAGAAGTCGTGCGGTTCCCCAACATCACC

AATCTGTGCCCTTTCGGCGAGGTGTTCAACGCCACCAGATTTCCC

-continued

TCTGTGTACGCCTGGGAGAGAAAGCGGATCAGCAACTGCGTGGCC

GACTACAGCGTGCTGTACAACAGCACCTTCTTCAGCACCTTTAAG

TGCTACGGCGTGTCACCCACCAAGCTGAACGACCTGTGCTTCAGC

AACGTGTACGCCGACAGCTTCGTGATCAGAGGCGACGAAGTGCGG

CAGATTGCCCCTGGACAAACAGGCGTGATCGCCGATTACAACTAC

AAGCTGCCCGACGACTTCATGGGCTGTGTGATCGCCTGGAACACC

AACAACCTGGACAGCACCACCGGCGGCAACTACAACTACCTGTAC

AGAAGCCTGCGGAAGTCTAAGCTGAAGCCCTTCGAGCGGGACATC

AGCAGCGACATCTATAGCCCTGGCGGCAAGCCTTGTTCTGGCGTG

GAAGGCTTCAACTGCTACTACCCTCTGCGGGAGCTACGGCTTCTTC

CCCACAAATGGCGTGGGCTACCAGCCTTACAGAGTGGTGGTCCTG

AGCTTCGAGCTGCTGAATGCCCCTGCCACAGTGTGTGGCCCTAAG

CTGTCTACCGAC

>COV_S_T2_16 encoding nucleic acid
                                        (SEQ ID NO: 81)
AGAGTGGCCCCTACCAAAGAAGTCGTGCGGTTCCCCAACATCACC

AATCTGTGCCCTTTCGGCGAGGTGTTCAACGCCACCAGATTTCCC

TCTGTGTACGCCTGGGAGAGAAAGCGGATCAGCAACTGCGTGGCC

GACTACAGCGTGCTGTACAACAGCACCAGTTCAGCACCTTCAAG

TGCTACGGCGTGTCACCCACCAAGCTGAACGACCTGTGCTTCACC

AACGTGTACGCCGACAGCTTCGTGATCAGAGGCGACGAAGTGCGG

CAGATTGCCCCTGGACAGACAGGCAAGATCGCCGATTACAACTAC

AAGCTGCCCGACGACTTCACCGGCTGTGTGATCGCCTGGAACACC

AACAACCTGGACAGCACCACCGGCGGCAACTACAACTACCTGTAC

CGGCTGTTCCGGAAGTCCAACCTGAAGCCTTTCGAGCGGGACATC

AGCAGCGACATCTATCAGGCCGGCAGCACACCTTGTTCTGGCGTG

GAAGGCTTCAACTGCTACTTCCCACTGCAAAGCTACGGCTTCCAG

CCTACCAACGGCGTGGGCTACCAGCCTTATAGAGTGGTGGTCCTG

AGCTTCGAGCTGCTGAATGCCCCTGCCACAGTGTGTGGCCCTAAG

CTGTGTACCGAC

>COV_S_T2_17 encoding nucleic acid
                                        (SEQ ID NO: 82)
AGAGTGGCCCCTACCAAAGAAGTCGTGCGGTTCCCCAACATCACC

AATCTGTGCCCTTTCGGCGAGGTGTTCAACGCCACCAAGTTTCCC

TCTGTGTACGCCTGGGAGCGCAAAAAGATCAGCAACTGCGTGGCC

GACTACAGCGTGCTGTACAACAGCACCAGCTTCAGCACCTTCAAG

TGCTACGGCGTGTCACCCACCAAGCTGAACGACCTGTGCTTCACC

AACGTGTACGCCGACAGCTTCGTGATCAGAGGCGACGAAGTGCGG

CAGATTGCCCCTGGACAAACAGGCGTGATCGCCGATTACAACTAC

AAGCTGCCCGACGACTTCACCGGCTGTGTGATCGCCTGGAACACC

AACAACATCGACAGCACCACCGGCGGCAACTACAACTACCTGTAC

AGAAGCCTGCGGGAAGTCTAAGCTGAAGCCCTTCGAGCGGGACATC

AGCAGCGACATCTATAGCCCTGGCGGCAAGCCTTGTTCTGGCGTG

GAAGGCTTCAACTGCTACTACCCTCTGCGGAGCTACGGCTTCTTC

CCCACAAATGGCACAGGCTACCAGCCTTACAGAGTGGTGGTCCTG

AGCTTCGAGCTGCTGAATGCCCCTGCCACAGTGTGTGGCCCTAAG

CTGTCTACCGAC

>COV_S_T2_18 encoding nucleic acid
                                 (SEQ ID NO: 83)
AGAGTGGCCCCTACCAAAGAAGTCGTGCGGTTCCCCAACATCACC

AATCTGTGCCCTTTCGGCGAGGTGTTCAACGCCACCAGATTTCCC

TCTGTGTACGCCTGGGAGAGAAAGCGGATCAGCAACTGCGTGGCC

GACTACAGCGTGCTGTACAACAGCACCTTCTTCAGCACCTTTAAG

TGCTACGGCGTGTCACCCACCAAGCTGAACGACCTGTGCTTCAGC

AACGTGTACGCCGACAGCTTCGTGATCAGAGGCGACGAAGTGCGG

CAGATTGCCCCTGGACAAACAGGCGTGATCGCCGATTACAACTAC

AAGCTGCCCGACGACTTCATGGGCTGTGTGATCGCCTGGAACACC

AACAACCTGGACAGCACCACCGGCGGCAACTACAACTACCTGTAC

AGAAGCCTGCGGAAGTCTAAGCTGAAGCCCTTCGAGCGGGACATC

AGCAGCGACATCTATAGCCCTGGCGGCAAGCCTTGTTCTGGCGTG

GAAGGCTTCAACTGCTACTACCCTCTGCGGAGCTACGGCTTCTTC

CCCACAAATGGCACAGGCTACCAGCCTTACAGAGTGGTGGTCCTG

AGCTTCGAGCTGCTGAATGCCCCTGCCACAGTGTGTGGCCCTAAG

CTGTCTACCGAC

>COV_S_T2 19 encoding nucleic acid
                                 (SEQ ID NO: 84)
AGAGTGGCCCCTACCAAAGAAGTCGTGCGGTTCCCCAACATCACC

AATCTGTGCCCTTTCGGCGAGGTGTTCAACGCCACCAGATTTCCC

TCTGTGTACGCCTGGGAGAGAAAGCGGGATCAGCAACTGCGTGGCC

GACTACAGCGTGCTGTACAACAGCACCAGCTTCAGCACCTTCAAG

TGCTACGGCGTGTCACCCACCAAGCTGAACGACCTGTGCTTCACC

AACGTGTACGCCGACAGCTTCGTGATCAGAGGCGACGAAGTGCGG

CAGATTGCCCCTGGACAAACAGGCGTGATCGCCGATTACAACTAC

AAGCTGCCCGACGACTTCACCGGCTGTGTGATCGCCTGGAACACC

AACAACCTGGACAGCACCACCGGCGGCAACTACAACTACCTGTAC

AGAAGCCTGCGGAAGTCTAAGCTGAAGCCCTTCGAGCGGGACATC

AGCAGCGACATCTATAGCCCTGGCGGCAAGCCTTGTTCTGGCGTG

GAAGGCTTCAACTGCTACTACCCTCTGCGGAGCTACGGCTTCTTC

CCCACAAATGGCGTGGGCTACCAGCCTTACAGAGTGGTGGTCCTG

AGCTTCGAGCTGCTGAATGCCCCTGCCACAGTGTGTGGCCCTAAG

CTGTCTACAGATGGCGGCGGAGGATCTGGCGGAGGTGGAAGCGGA

GGCGGAGGAÅGCGGTGGCGGOGGATCTAAATCTTCTATCGCCAGC

TTCTTCTTCATCATCGGCCTGATTATCGGCCTGTTCCTGGTGCTG

AGAGTGGGCATCCACCTGTGCATCAAGCTGAAACACACCAAGAAG

CGGCAAATCTACACCGACATCGAGATGAACCGGCTGGGCAAA

>COV_S_T2_20 encoding nucleic acid
                                 (SEQ ID NO: 85)
AGAGTGGCCCCTACCAAAGAAGTCGTGCGGTTCCCCAACATCACC

AATCTGTGCCCTTTCGGCGAGGTGTTCAACGCCACCAAGTTTCCC

TCTGTGTACGCCTGGGAGCGCAAAAAGATCAGCAACTGCGTGGCC

GACTACAGCGTGCTGTACAACAGCACCAGCTTCAGCACCTTCAAG

TGCTACGGCGTGTCACCCACCAAGCTGAACGACCTGTGCTTCACC

AACGTGTACGCCGACAGCTTCGTGATCAGAGGCGACGAAGTGCGG

CAGATTGCCCCTGGACAAACAGGCGTGATCGCCGATTACAACTAC

AAGCTGCCCGACGACTTCACCGGCTGTGTGATCGCCTGGAACACC

AACAACATCGACAGCACCACCGGCGGCAACTACAACTACCTGTAC

AGAAGCCTGCGGAAGTCTAAGCTGAAGCCCTTCGAGCGGGACATC

AGCAGCGACATCTATAGCCCTGGCGGCAAGCCTTGTTCTGGCGTG

GAAGGCTTCAACTGCTACTACCCTCTGCGGAGCTACGGCTTCTTC

CCCACAAATGGCACAGGCTACCAGCCTTACAGAGTGGTGGTCCTG

AGCTTCGAGCTGCTGAATGCCCCTGCCACAGTGTGTGGCCCTAAG

CTGTCTACAGATGGGGGGGGAGGATCTGGCGGAGGTGGAAGCGGA

GGCGGAGGAAGCGGTGGGGGGGGGATCTAAATCTTCTATCGCCAGC

TTCTTCTTCATCATCGGCCTGATTATCGGCCTGTTCCTGGTGCTG

AGAGTGGGCATCCACCTGTGCATCAAGCTGAAACACACCAAGAAG

CGGCAAATCTACACCGACATCGAGATGAACCGGCTGGGCAAA

The invention claimed is:

1. An isolated polypeptide, which comprises an amino acid sequence of SEQ ID NO: 31 (COV_S_T2_17), or an amino acid sequence which has at least 95%, 96%, 97%, 98%, or 99% amino acid identity over its entire length with the amino acid sequence of SEQ ID NO:31.

2. A polypeptide according to claim 1, which comprises at least one, or all of the amino acid residues, optionally at least five, at least ten, or at least fifteen of the amino acid residues, at the following positions: A at a position corresponding to residue position 3 of SEQ ID NO:11; K at a position corresponding to residue position 6 of SEQ ID NO:11; E at a position corresponding to residue position 7 of SEQ ID NO:11, V at a position corresponding to residue position 8 of SEQ ID NO:11; P at a position corresponding to residue position 30 of SEQ ID NO: 11; E at a position corresponding to residue position 36 of SEQ ID NO:11; T at a position corresponding to residue position 54 of SEQ ID NO: 11; T at a position corresponding to residue position 120 of SEQ ID NO: 11; T at a position corresponding to residue position 126 of SEQ ID NO: 11; T at a position corresponding to residue position 127 of SEQ ID NO:11; S at a position corresponding to residue position 152 of SEQ ID NO: 11; D at a position corresponding to residue position 153 of SEQ ID NO:11; S at a position corresponding to residue position 163 of SEQ ID NO:11; N at a position corresponding to residue position 201 of SEQ ID NO:11; L at a position corresponding to residue position 211 of SEQ ID NO:11; and D at a position corresponding to residue position 214 of SEQ ID NO:11.

3. A polypeptide according to claim 1, which comprises at least one, or all of the amino acid residues at the following positions: V at a position corresponding to residue position 99 of SEQ ID NO:11; S at a position corresponding to residue position 137 of SEQ ID NO: 11; L at a position corresponding to residue position 138 of SEQ ID NO:11; K at a position corresponding to residue position 142 of SEQ ID NO:11; S at a position corresponding to residue position 156 of SEQ ID NO: 11; P at a position corresponding to residue position 157 of SEQ ID NO: 11; G at a position corresponding to residue position 159 of SEQ ID NO:11; K at a position corresponding to residue position 160 of SEQ ID NO:11; Y at a position corresponding to residue position 172 of SEQ ID NO:11; R at a position corresponding to residue position 175 of SEQ ID NO: 11; and F at a position corresponding to residue position 180 of SEQ ID NO: 11.

4. A polypeptide according to claim 1, which comprises at least one, or all of the amino acid residues at the following positions: K at a position corresponding to residue position 28 of SEQ ID NO: 11; K at a position corresponding to residue position 39 of SEQ ID NO: 11; and I at a position corresponding to residue position 123 of SEQ ID NO:11.

5. A polypeptide according to claim 1, which comprises amino acid residue T at the position corresponding to the amino acid residue position 185 of SEQ ID NO:11.

6. A polypeptide according to claim 1, which comprises the following discontinuous amino acid sequences:

```
a)
(i)
                         (SEQ ID NO: 57)
NITNLCPFGEVENATK;

(ii)
                         (SEQ ID NO: 58)
KKISN;

(iii)
                         (SEQ ID NO: 59)
NI;

b)
(i)
                         (SEQ ID NO: 71)
YNSTSFSTFKCYGVSPTKLNDLCFT;

(ii)
                         (SEQ ID NO: 72)
DDFT;

iii)
                         (SEQ ID NO: 62)
FELLN;
or c)
(i)
                         (SEQ ID NO: 63)
RGDEVRQ;

(SEQ ID NO: 73)
TGVIADY
```

```
-continued iii)
                         (SEQ ID NO: 74)
YRSLRKSK;
(iv)
                         (SEQ ID NO: 75)
YSPGGK;
(v)
                         (SEQ ID NO: 77)
FNCYYPLRSYGFFPTNGTGY;
``` wherein the discontinuous amino acid sequences of (a) (i)-(iii) are present in the order recited, the discontinuous amino acid sequences of (b) (i)-(iii) are present in the order recited, and the discontinuous amino acid sequences of (c) (i)-(v) are present in the order recited.

7. An isolated nucleic acid molecule encoding a polypeptide according to claim 1, or the complement thereof.

8. A vector comprising a nucleic acid molecule of claim 7, optionally which further comprises a promoter operably linked to the nucleic acid.

9. A vector according to claim 8, wherein the promoter is for expression of a polypeptide encoded by the nucleic acid in mammalian cells.

10. A vector according to claim 8, which is a vaccine vector.

11. An isolated cell comprising a vector of claim 8.

12. A fusion protein comprising a polypeptide according to claim 1.

13. A pharmaceutical composition comprising:

a polypeptide which comprises an amino acid sequence of SEQ ID NO: 31 (COV_S_T2_17), or an amino acid sequence which has at least 95%, 96%, 97%, 98%, or 99% amino acid identity over its entire length with the amino acid sequence of SEQ ID NO:31;

a nucleic acid molecule encoding a polypeptide which comprises an amino acid sequence of SEQ ID NO: 31 (COV_S_T2_17), or an amino acid sequence which has at least 95%, 96%, 97%, 98%, or 99% amino acid identity over its entire length with the amino acid sequence of SEQ ID NO:31, or the complement thereof, or a vector comprising a nucleic acid molecule encoding a polypeptide which comprises an amino acid sequence of SEQ ID NO: 31 (COV_S_T2_17), or an amino acid sequence which has at least 95%, 96%, 97%, 98%, or 99% amino acid identity over its entire length with the amino acid sequence of SEQ ID NO:31, or the complement thereof, optionally which further comprises a promoter operably linked to the nucleic acid;

and a pharmaceutically acceptable carrier, excipient, or diluent.

14. A pharmaceutical composition according to claim 13, which further comprises an adjuvant for enhancing an immune response in a subject to the polypeptide, or to a polypeptide encoded by the nucleic acid, of the composition.

15. A pseudotyped virus comprising a polypeptide according to claim 1.

16. A method of inducing an immune response to a coronavirus in a subject, which comprises administering to the subject an effective amount of:

i) a polypeptide which comprises an amino acid sequence of SEQ ID NO: 31 (COV_S_T2_17), or an amino acid sequence which has at least 95%, 96%, 97%, 98%, or 99% amino acid identity over its entire length with the amino acid sequence of SEQ ID NO:31;

ii) a nucleic acid molecule encoding a polypeptide which comprises an amino acid sequence of SEQ ID NO: 31 (COV_S_T2_17), or an amino acid sequence which has at least 95%, 96%, 97%, 98%, or 99% amino acid identity over its entire length with the amino acid sequence of SEQ ID NO:31, or the complement thereof;

iii) a vector comprising a nucleic acid molecule encoding a polypeptide which comprises an amino acid sequence of SEQ ID NO: 31 (COV_S_T2_17), or an amino acid sequence which has at least 95%, 96%, 97%, 98%, or 99% amino acid identity over its entire length with the amino acid sequence of SEQ ID NO:31, or the complement thereof; or iv) a pharmaceutical composition comprising:

a) a polypeptide which comprises an amino acid sequence of SEQ ID NO: 31 (COV_S_T2_17), or an amino acid sequence which has at least 95%, 96%, 97%, 98%, or 99% amino acid identity over its entire length with the amino acid sequence of SEQ ID NO:31, and a pharmaceutically acceptable carrier, excipient, or diluent;

b) a nucleic acid molecule encoding a polypeptide which comprises an amino acid sequence of SEQ ID NO: 31 (COV_S_T2_17), or an amino acid sequence which has at least 95%, 96%, 97%, 98%, or 99% amino acid identity over its entire length with the amino acid sequence of SEQ ID NO:31, or the complement thereof, and a pharmaceutically acceptable carrier, excipient, or diluent; or c) a vector comprising a nucleic acid molecule encoding a polypeptide which comprises an amino acid sequence of SEQ ID NO: 31 (COV_S_T2_17), or an amino acid sequence which has at least 95%, 96%, 97%, 98%, or 99% amino acid identity over its entire length with the amino acid sequence of SEQ ID NO: 31, or the complement thereof, and a pharmaceutically acceptable carrier, excipient, or diluent.

18. A method according to claim 16, wherein the coronavirus is a β-coronavirus.

19. A method according to claim 18, wherein the β-coronavirus is a lineage B β-coronavirus.

20. A vector according to claim 10, wherein the vaccine vector is a viral vaccine vector, a bacterial vaccine vector, an RNA vaccine vector, or a DNA vaccine vector.

21. A method according to claim 18, wherein the β-coronavirus is a lineage B or C β-coronavirus.

22. A method according to claim 19, wherein lineage B β-coronavirus is SARS-COV or SARS-COV-2.

\* \* \* \* \*

--- ii) a nucleic acid molecule encoding a polypeptide which comprises an amino acid sequence of SEQ ID NO: 31 (COV_S_T2_17), or an amino acid sequence which has at least 95%, 96%, 97%, 98%, or 99% amino acid identity over its entire length with the amino acid sequence of SEQ ID NO:31, or the complement thereof;

iii) a vector comprising a nucleic acid molecule encoding a polypeptide which comprises an amino acid sequence of SEQ ID NO: 31 (COV_S_T2_17), or an amino acid sequence which has at least 95%, 96%, 97%, 98%, or 99% amino acid identity over its entire length with the amino acid sequence of SEQ ID NO:31, or the complement thereof; or iv) a pharmaceutical composition comprising:

a) a polypeptide which comprises an amino acid sequence of SEQ ID NO: 31 (COV_S_T2_17), or an amino acid sequence which has at least 95%, 96%, 97%, 98%, or 99% amino acid identity over its entire length with the amino acid sequence of SEQ ID NO:31, and a pharmaceutically acceptable carrier, excipient, or diluent;

b) a nucleic acid molecule encoding a polypeptide which comprises an amino acid sequence of SEQ ID NO: 31 (COV_S_T2_17), or an amino acid sequence which has at least 95%, 96%, 97%, 98%, or 99% amino acid identity over its entire length with the amino acid sequence of SEQ ID NO:31, or the complement thereof, and a pharmaceutically acceptable carrier, excipient, or diluent; or c) a vector comprising a nucleic acid molecule encoding a polypeptide which comprises an amino acid sequence of SEQ ID NO: 31 (COV_S_T2_17), or an amino acid sequence which has at least 95%, 96%, 97%, 98%, or 99% amino acid identity over its entire length with the amino acid sequence of SEQ ID NO:31, or the complement thereof, optionally which further comprises a promoter operably linked to the nucleic acid; or

SEQUENCE LISTING

<160> NUMBER OF SEQ ID NOS: 85

<210> SEQ ID NO 1
<211> LENGTH: 1255
<212> TYPE: PRT
<213> ORGANISM: Artificial Sequence
<220> FEATURE:
<223> OTHER INFORMATION: Coronavirus wild-type S-protein sequence

<400> SEQUENCE: 1

Met Phe Ile Phe Leu Leu Phe Leu Thr Leu Thr Ser Gly Ser Asp Leu
1               5                   10                  15

-continued

```
Asp Arg Cys Thr Thr Phe Asp Asp Val Gln Ala Pro Asn Tyr Thr Gln
            20                  25                  30

His Thr Ser Ser Met Arg Gly Val Tyr Tyr Pro Asp Glu Ile Phe Arg
            35                  40                  45

Ser Asp Thr Leu Tyr Leu Thr Gln Asp Leu Phe Leu Pro Phe Tyr Ser
        50                  55                  60

Asn Val Thr Gly Phe His Thr Ile Asn His Thr Phe Gly Asn Pro Val
    65                  70                  75                  80

Ile Pro Phe Lys Asp Gly Ile Tyr Phe Ala Ala Thr Glu Lys Ser Asn
                85                  90                  95

Val Val Arg Gly Trp Val Phe Gly Ser Thr Met Asn Asn Lys Ser Gln
                100                 105                 110

Ser Val Ile Ile Ile Asn Asn Ser Thr Asn Val Val Ile Arg Ala Cys
            115                 120                 125

Asn Phe Glu Leu Cys Asp Asn Pro Phe Phe Ala Val Ser Lys Pro Met
        130                 135                 140

Gly Thr Gln Thr His Thr Met Ile Phe Asp Asn Ala Phe Asn Cys Thr
145                 150                 155                 160

Phe Glu Tyr Ile Ser Asp Ala Phe Ser Leu Asp Val Ser Glu Lys Ser
                165                 170                 175

Gly Asn Phe Lys His Leu Arg Glu Phe Val Phe Lys Asn Lys Asp Gly
            180                 185                 190

Phe Leu Tyr Val Tyr Lys Gly Tyr Gln Pro Ile Asp Val Val Arg Asp
            195                 200                 205

Leu Pro Ser Gly Phe Asn Thr Leu Lys Pro Ile Phe Lys Leu Pro Leu
        210                 215                 220

Gly Ile Asn Ile Thr Asn Phe Arg Ala Ile Leu Thr Ala Phe Ser Pro
225                 230                 235                 240

Ala Gln Asp Ile Trp Gly Thr Ser Ala Ala Ala Tyr Phe Val Gly Tyr
                245                 250                 255

Leu Lys Pro Thr Thr Phe Met Leu Lys Tyr Asp Glu Asn Gly Thr Ile
                260                 265                 270

Thr Asp Ala Val Asp Cys Ser Gln Asn Pro Leu Ala Glu Leu Lys Cys
            275                 280                 285

Ser Val Lys Ser Phe Glu Ile Asp Lys Gly Ile Tyr Gln Thr Ser Asn
        290                 295                 300

Phe Arg Val Val Pro Ser Gly Asp Val Val Arg Phe Pro Asn Ile Thr
305                 310                 315                 320

Asn Leu Cys Pro Phe Gly Glu Val Phe Asn Ala Thr Lys Phe Pro Ser
                325                 330                 335

Val Tyr Ala Trp Glu Arg Lys Lys Ile Ser Asn Cys Val Ala Asp Tyr
                340                 345                 350

Ser Val Leu Tyr Asn Ser Thr Phe Phe Ser Thr Phe Lys Cys Tyr Gly
            355                 360                 365

Val Ser Ala Thr Lys Leu Asn Asp Leu Cys Phe Ser Asn Val Tyr Ala
        370                 375                 380

Asp Ser Phe Val Val Lys Gly Asp Asp Val Arg Gln Ile Ala Pro Gly
385                 390                 395                 400

Gln Thr Gly Val Ile Ala Asp Tyr Asn Tyr Lys Leu Pro Asp Asp Phe
                405                 410                 415

Met Gly Cys Val Leu Ala Trp Asn Thr Arg Asn Ile Asp Ala Thr Ser
                420                 425                 430
```

```
Thr Gly Asn Tyr Asn Tyr Lys Tyr Arg Tyr Leu Arg His Gly Lys Leu
        435             440             445

Arg Pro Phe Glu Arg Asp Ile Ser Asn Val Pro Phe Ser Pro Asp Gly
    450             455             460

Lys Pro Cys Thr Pro Pro Ala Leu Asn Cys Tyr Trp Pro Leu Asn Asp
465             470             475             480

Tyr Gly Phe Tyr Thr Thr Thr Gly Ile Gly Tyr Gln Pro Tyr Arg Val
                485             490             495

Val Val Leu Ser Phe Glu Leu Leu Asn Ala Pro Ala Thr Val Cys Gly
            500             505             510

Pro Lys Leu Ser Thr Asp Leu Ile Lys Asn Gln Cys Val Asn Phe Asn
        515             520             525

Phe Asn Gly Leu Thr Gly Thr Gly Val Leu Thr Pro Ser Ser Lys Arg
    530             535             540

Phe Gln Pro Phe Gln Gln Phe Gly Arg Asp Val Ser Asp Phe Thr Asp
545             550             555             560

Ser Val Arg Asp Pro Lys Thr Ser Glu Ile Leu Asp Ile Ser Pro Cys
                565             570             575

Ala Phe Gly Gly Val Ser Val Ile Thr Pro Gly Thr Asn Ala Ser Ser
            580             585             590

Glu Val Ala Val Leu Tyr Gln Asp Val Asn Cys Thr Asp Val Ser Thr
        595             600             605

Ala Ile His Ala Asp Gln Leu Thr Pro Ala Trp Arg Ile Tyr Ser Thr
    610             615             620

Gly Asn Asn Val Phe Gln Thr Gln Ala Gly Cys Leu Ile Gly Ala Glu
625             630             635             640

His Val Asp Thr Ser Tyr Glu Cys Asp Ile Pro Ile Gly Ala Gly Ile
                645             650             655

Cys Ala Ser Tyr His Thr Val Ser Leu Leu Arg Ser Thr Ser Gln Lys
            660             665             670

Ser Ile Val Ala Tyr Thr Met Ser Leu Gly Ala Asp Ser Ser Ile Ala
        675             680             685

Tyr Ser Asn Asn Thr Ile Ala Ile Pro Thr Asn Phe Ser Ile Ser Ile
    690             695             700

Thr Thr Glu Val Met Pro Val Ser Met Ala Lys Thr Ser Val Asp Cys
705             710             715             720

Asn Met Tyr Ile Cys Gly Asp Ser Thr Glu Cys Ala Asn Leu Leu Leu
                725             730             735

Gln Tyr Gly Ser Phe Cys Thr Gln Leu Asn Arg Ala Leu Ser Gly Ile
            740             745             750

Ala Ala Glu Gln Asp Arg Asn Thr Arg Glu Val Phe Ala Gln Val Lys
        755             760             765

Gln Met Tyr Lys Thr Pro Thr Leu Lys Tyr Phe Gly Gly Phe Asn Phe
    770             775             780

Ser Gln Ile Leu Pro Asp Pro Leu Lys Pro Thr Lys Arg Ser Phe Ile
785             790             795             800

Glu Asp Leu Leu Phe Asn Lys Val Thr Leu Ala Asp Ala Gly Phe Met
                805             810             815

Lys Gln Tyr Gly Glu Cys Leu Gly Asp Ile Asn Ala Arg Asp Leu Ile
            820             825             830

Cys Ala Gln Lys Phe Asn Gly Leu Thr Val Leu Pro Pro Leu Leu Thr
        835             840             845

Asp Asp Met Ile Ala Ala Tyr Thr Ala Ala Leu Val Ser Gly Thr Ala
```

```
                850             855             860

Thr Ala Gly Trp Thr Phe Gly Ala Gly Ala Ala Leu Gln Ile Pro Phe
865                 870             875             880

Ala Met Gln Met Ala Tyr Arg Phe Asn Gly Ile Gly Val Thr Gln Asn
                885             890             895

Val Leu Tyr Glu Asn Gln Lys Gln Ile Ala Asn Gln Phe Asn Lys Ala
            900             905             910

Ile Ser Gln Ile Gln Glu Ser Leu Thr Thr Thr Ser Thr Ala Leu Gly
        915             920             925

Lys Leu Gln Asp Val Val Asn Gln Asn Ala Gln Ala Leu Asn Thr Leu
    930             935             940

Val Lys Gln Leu Ser Ser Asn Phe Gly Ala Ile Ser Ser Val Leu Asn
945             950             955             960

Asp Ile Leu Ser Arg Leu Asp Lys Val Glu Ala Glu Val Gln Ile Asp
                965             970             975

Arg Leu Ile Thr Gly Arg Leu Gln Ser Leu Gln Thr Tyr Val Thr Gln
            980             985             990

Gln Leu Ile Arg Ala Ala Glu Ile  Arg Ala Ser Ala Asn  Leu Ala Ala
        995             1000            1005

Thr Lys  Met Ser Glu Cys Val  Leu Gly Gln Ser Lys  Arg Val Asp
    1010            1015            1020

Phe Cys  Gly Lys Gly Tyr His  Leu Met Ser Phe Pro  Gln Ala Ala
    1025            1030            1035

Pro His  Gly Val Val Phe Leu  His Val Thr Tyr Val  Pro Ser Gln
    1040            1045            1050

Glu Arg  Asn Phe Thr Thr Ala  Pro Ala Ile Cys His  Glu Gly Lys
    1055            1060            1065

Ala Tyr  Phe Pro Arg Glu Gly  Val Phe Val Phe Asn  Gly Thr Ser
    1070            1075            1080

Trp Phe  Ile Thr Gln Arg Asn  Phe Phe Ser Pro Gln  Ile Ile Thr
    1085            1090            1095

Thr Asp  Asn Thr Phe Val Ser  Gly Asn Cys Asp Val  Val Ile Gly
    1100            1105            1110

Ile Ile  Asn Asn Thr Val Tyr  Asp Pro Leu Gln Pro  Glu Leu Asp
    1115            1120            1125

Ser Phe  Lys Glu Glu Leu Asp  Lys Tyr Phe Lys Asn  His Thr Ser
    1130            1135            1140

Pro Asp  Val Asp Leu Gly Asp  Ile Ser Gly Ile Asn  Ala Ser Val
    1145            1150            1155

Val Asn  Ile Gln Lys Glu Ile  Asp Arg Leu Asn Glu  Val Ala Lys
    1160            1165            1170

Asn Leu  Asn Glu Ser Leu Ile  Asp Leu Gln Glu Leu  Gly Lys Tyr
    1175            1180            1185

Glu Gln  Tyr Ile Lys Trp Pro  Trp Tyr Val Trp Leu  Gly Phe Ile
    1190            1195            1200

Ala Gly  Leu Ile Ala Ile Val  Met Val Thr Ile Leu  Leu Cys Cys
    1205            1210            1215

Met Thr  Ser Cys Cys Ser Cys  Leu Lys Gly Ala Cys  Ser Cys Gly
    1220            1225            1230

Ser Cys  Cys Lys Phe Asp Glu  Asp Asp Ser Glu Pro  Val Leu Lys
    1235            1240            1245

Gly Val  Lys Leu His Tyr Thr
    1250            1255
```

-continued

```
<210> SEQ ID NO 2
<211> LENGTH: 3765
<212> TYPE: DNA
<213> ORGANISM: Artificial Sequence
<220> FEATURE:
<223> OTHER INFORMATION: Coronavirus wild-type S-protein sequence

<400> SEQUENCE: 2
atgtttatct ttctgctgtt tctgaccctg accagcggca gcgacctgga tagatgcacc      60
accttcgacg atgtgcaggc ccctaactac acccagcaca ccagctctat gcggggcgtg     120
tactaccccg acgagatttt cagaagcgac accctgtatc tgacccagga cctgttcctg     180
cctttctaca gcaacgtgac cggcttccac accatcaacc acaccttcgg caaccctgtg     240
atccccttca aggacggcat ctactttgcc gccaccgaga gtccaacgt cgtcagagga     300 tgggtgttcg gcagcaccat gaacaacaag agccagagcg tgatcatcat caacaacagc     360
accaacgtgg tcatccgggc ctgcaacttc gagctgtgcg acaacccatt cttcgccgtg     420
tccaagccta tgggcaccca gacacacacc atgatcttcg acaacgcctt caactgcacc     480
ttcgagtaca tcagcgacgc cttcagcctg gacgtgtccg aaaagagcgg caacttcaag     540
cacctgaggg aattcgtgtt caagaacaag gatggcttcc tgtacgtgta caagggctac     600
cagcctatcg acgtcgtgcg ggatctgccc agcggcttca ataccctgaa gcctatcttc     660
aagctgcccc tgggcatcaa catcaccaac ttcagagcca tcctgaccgc tttcagcccc     720
gctcaggata tctggggaac aagcgccgct gcctacttcg tgggctacct gaagccaacc     780
accttcatgc tgaagtacga cgagaacggc accatcaccg acgccgtgga ctgtagccaa     840
aatcctctgg ccgagctgaa gtgcagcgtg aagtccttcg agatcgacaa gggcatctac     900
cagaccagca atttcagagt ggtgccctcc ggggatgtcg tgcggttccc caacatcaca     960
aatctgtgcc ccttcggcga ggtgttcaac gccaccaagt ttccctctgt gtacgcctgg    1020
gagcgcaaaa agatcagcaa ctgcgtggcc gactacagcg tgctgtacaa ctccacccttc    1080 ttcagcacct tcaagtgcta cggcgtgtcc gccacaaagc tgaacgacct gtgcttctcc    1140
aacgtgtacg ccgacagctt cgtggtcaaa ggcgacgacg ttcggcagat gcccctggga    1200
caaacaggcg tgatcgccga ttacaactac aagctgcctg acgacttcat gggctgcgtg    1260
ctggcctgga acaccagaaa catcgatgcc acctccaccg gcaactacaa ttacaagtac    1320
agatacctgc ggcacggcaa gctgcggcct ttcgagaggg atatcagcaa tgtgcctttt    1380
agccccgacg gcaagccctg cacacctcct gctctgaatt gctactggcc cctgaacgac    1440
tacggctttt acaccaccac aggcatcggc tatcagccct atagagtggt ggtcctgtcc    1500
tttgagctgc tgaatgcccc tgccacagtg tgcggaccta gctgtctac cgacctgatc    1560 aagaaccagt gcgtgaactt caacttcaac ggcctgaccg gcaccggcgt gctgacacca    1620
agcagcaaga gattccagcc tttccagcag ttcggccggg atgtgtccga cttcacagac    1680
agcgtcagag atcccaagac cagcgagatc ctggacatca gcccttgtgc ctttggcgga    1740
gtgtccgtga tcacccctgg cacaaatgcc tctagcgaag tggccgtgct gtatcaggac    1800
gtgaactgca cgatgtgtc caccgccatt cacgccgatc agctgactcc cgcttggcgg    1860
atctatagca caggcaacaa cgtgttccag acacaagccg gctgtctgat cggagccgag    1920
catgtggata ccagctacga gtgcgacatc cctatcggcg ctggcatctg tgcctcttac    1980
cacaccgtgt ctctgctgcg gagcaccagc cagaaatcca tcgtggccta caccatgagc    2040
```

-continued

```
ctgggcgccg attcttctat cgcctactcc aacaacacaa tcgctatccc caccaatttc      2100
agcatctcca tcaccaccga agtgatgccc gtgtccatgg ccaagacctc cgtggattgc      2160
aacatgtaca tctgcggcga cagcaccgag tgcgccaatc tgctgctcca gtacggcagc      2220
ttctgcaccc agctgaatag agccctgtct ggaattgccg ccgagcagga cagaaacacc      2280
agagaagtgt tcgcccaagt gaagcagatg tataagaccc cgacactcaa gtacttcggc      2340
gggttcaact tctcccagat cctgcctgat cctctgaagc ccaccaagcg gagcttcatc      2400
gaggacctgc tgttcaacaa agtgaccctg gccgacgccg gctttatgaa gcagtatggc      2460
gagtgcctgg gcgacatcaa cgccagggat ctgatttgcg cccagaagtt taacggactg      2520
accgtgctgc ctcctctgct gaccgatgat atgatcgccg cctacacagc cgctctggtg      2580
tctggtacag ctaccgccgg atggacattt ggagctggcg ccgctctcca gattccattc      2640
gctatgcaga tggcctaccg gttcaacggc atcggagtga cccagaatgt gctgtacgag      2700
aatcagaagc agatcgccaa tcagttcaac aaggccatca gccagatcca agagagcctg      2760
accaccacaa gcacagccct gggaaagctc caggacgtgg tcaaccagaa tgctcaggcc      2820
ctgaacaccc tggtcaagca gctgagcagc aacttcggcg ccatcagctc cgtgctgaat      2880
gacatcctga gccggctgga caaggtggaa gcagaggtgc agatcgaccg gctgatcaca      2940
ggcagactcc agagcctcca gacctacgtg acacagcagc tgatcagagc cgccgagatt      3000
agagcctctg ccaatctggc cgccaccaaa atgagcgagt gtgtcctggg ccagagcaag      3060
agagtggact tttgcggcaa gggctatcac ctgatgagct tcccacaggc cgctcctcat      3120
ggcgtggtct ttctgcacgt gacatacgtg cccagccaag agagaaactt caccaccgct      3180
ccagccatct gccacgaggg caaagcctac tttcccagag aaggcgtgtt cgtgtttaac      3240
ggcacctcct ggtttatcac ccagcggaat ttcttcagcc cgcaaatcat caccacagac      3300
aacaccttcg tgtccggcaa ctgtgacgtc gtgatcggca tcattaacaa taccgtgtac      3360
gaccctctcc agcctgagct ggacagcttc aaagaggaac tggataagta cttcaagaat      3420
cacacgagcc ccgatgtgga cctgggcgat atctctggca tcaatgccag cgtcgtgaac      3480
atccagaaag agattgacag gctgaacgag gtggccaaga acctgaacga gtccctgatc      3540
gacctgcaag agctggggaa gtacgagcag tacatcaagt ggccttggta cgtgtggctg      3600
ggctttatcg ccggactgat cgccatcgtg atggtcacca tcctgctgtg ctgcatgacc      3660
agctgttgca gctgtctgaa gggcgcctgt agctgtggct cctgctgcaa gttcgatgag      3720
gacgactctg agccagtgct gaaaggcgtg aagctgcact acacc                     3765
```

```
<210> SEQ ID NO 3
<211> LENGTH: 1152
<212> TYPE: PRT
<213> ORGANISM: Artificial Sequence
<220> FEATURE:
<223> OTHER INFORMATION: Coronavirus wild-type trS-protein sequence

<400> SEQUENCE: 3

Met Phe Ile Phe Leu Leu Phe Leu Thr Leu Thr Ser Gly Ser Asp Leu
1               5                   10                  15

Asp Arg Cys Thr Thr Phe Asp Asp Val Gln Ala Pro Asn Tyr Thr Gln
            20                  25                  30

His Thr Ser Ser Met Arg Gly Val Tyr Tyr Pro Asp Glu Ile Phe Arg
        35                  40                  45

Ser Asp Thr Leu Tyr Leu Thr Gln Asp Leu Phe Leu Pro Phe Tyr Ser
    50                  55                  60
```

-continued

```
Asn Val Thr Gly Phe His Thr Ile Asn His Thr Phe Gly Asn Pro Val
65              70                  75                  80

Ile Pro Phe Lys Asp Gly Ile Tyr Phe Ala Ala Thr Glu Lys Ser Asn
                85              90                  95

Val Val Arg Gly Trp Val Phe Gly Ser Thr Met Asn Asn Lys Ser Gln
            100             105                 110

Ser Val Ile Ile Ile Asn Asn Ser Thr Asn Val Val Ile Arg Ala Cys
        115                 120                 125

Asn Phe Glu Leu Cys Asp Asn Pro Phe Phe Ala Val Ser Lys Pro Met
    130                 135                 140

Gly Thr Gln Thr His Thr Met Ile Phe Asp Asn Ala Phe Asn Cys Thr
145                 150                 155                 160

Phe Glu Tyr Ile Ser Asp Ala Phe Ser Leu Asp Val Ser Glu Lys Ser
            165                 170                 175

Gly Asn Phe Lys His Leu Arg Glu Phe Val Phe Lys Asn Lys Asp Gly
        180                 185                 190

Phe Leu Tyr Val Tyr Lys Gly Tyr Gln Pro Ile Asp Val Val Arg Asp
        195                 200                 205

Leu Pro Ser Gly Phe Asn Thr Leu Lys Pro Ile Phe Lys Leu Pro Leu
    210                 215                 220

Gly Ile Asn Ile Thr Asn Phe Arg Ala Ile Leu Thr Ala Phe Ser Pro
225                 230                 235                 240

Ala Gln Asp Ile Trp Gly Thr Ser Ala Ala Ala Tyr Phe Val Gly Tyr
            245                 250                 255

Leu Lys Pro Thr Thr Phe Met Leu Lys Tyr Asp Glu Asn Gly Thr Ile
        260                 265                 270

Thr Asp Ala Val Asp Cys Ser Gln Asn Pro Leu Ala Glu Leu Lys Cys
        275                 280                 285

Ser Val Lys Ser Phe Glu Ile Asp Lys Gly Ile Tyr Gln Thr Ser Asn
    290                 295                 300

Phe Arg Val Val Pro Ser Gly Asp Val Val Arg Phe Pro Asn Ile Thr
305                 310                 315                 320

Asn Leu Cys Pro Phe Gly Glu Val Phe Asn Ala Thr Lys Phe Pro Ser
            325                 330                 335

Val Tyr Ala Trp Glu Arg Lys Lys Ile Ser Asn Cys Val Ala Asp Tyr
        340                 345                 350

Ser Val Leu Tyr Asn Ser Thr Phe Phe Ser Thr Phe Lys Cys Tyr Gly
        355                 360                 365

Val Ser Ala Thr Lys Leu Asn Asp Leu Cys Phe Ser Asn Val Tyr Ala
    370                 375                 380

Asp Ser Phe Val Val Lys Gly Asp Asp Val Arg Gln Ile Ala Pro Gly
385                 390                 395                 400

Gln Thr Gly Val Ile Ala Asp Tyr Asn Tyr Lys Leu Pro Asp Asp Phe
            405                 410                 415

Met Gly Cys Val Leu Ala Trp Asn Thr Arg Asn Ile Asp Ala Thr Ser
        420                 425                 430

Thr Gly Asn Tyr Asn Tyr Lys Tyr Arg Tyr Leu Arg His Gly Lys Leu
        435                 440                 445

Arg Pro Phe Glu Arg Asp Ile Ser Asn Val Pro Phe Ser Pro Asp Gly
    450                 455                 460

Lys Pro Cys Thr Pro Pro Ala Leu Asn Cys Tyr Trp Pro Leu Asn Asp
465                 470                 475                 480
```

-continued

Tyr Gly Phe Tyr Thr Thr Thr Gly Ile Gly Tyr Gln Pro Tyr Arg Val
            485                 490                 495

Val Val Leu Ser Phe Glu Leu Leu Asn Ala Pro Ala Thr Val Cys Gly
            500                 505                 510

Pro Lys Leu Ser Thr Asp Leu Ile Lys Asn Gln Cys Val Asn Phe Asn
            515                 520                 525

Phe Asn Gly Leu Thr Gly Thr Gly Val Leu Thr Pro Ser Ser Lys Arg
    530                 535                 540

Phe Gln Pro Phe Gln Gln Phe Gly Arg Asp Val Ser Asp Phe Thr Asp
545                 550                 555                 560

Ser Val Arg Asp Pro Lys Thr Ser Glu Ile Leu Asp Ile Ser Pro Cys
                565                 570                 575

Ala Phe Gly Gly Val Ser Val Ile Thr Pro Gly Thr Asn Ala Ser Ser
            580                 585                 590

Glu Val Ala Val Leu Tyr Gln Asp Val Asn Cys Thr Asp Val Ser Thr
            595                 600                 605

Ala Ile His Ala Asp Gln Leu Thr Pro Ala Trp Arg Ile Tyr Ser Thr
    610                 615                 620

Gly Asn Asn Val Phe Gln Thr Gln Ala Gly Cys Leu Ile Gly Ala Glu
625                 630                 635                 640

His Val Asp Thr Ser Tyr Glu Cys Asp Ile Pro Ile Gly Ala Gly Ile
                645                 650                 655

Cys Ala Ser Tyr His Thr Val Ser Leu Leu Arg Ser Thr Ser Gln Lys
            660                 665                 670

Ser Ile Val Ala Tyr Thr Met Ser Leu Gly Ala Asp Ser Ser Ile Ala
            675                 680                 685

Tyr Ser Asn Asn Thr Ile Ala Ile Pro Thr Asn Phe Ser Ile Ser Ile
    690                 695                 700

Thr Thr Glu Val Met Pro Val Ser Met Ala Lys Thr Ser Val Asp Cys
705                 710                 715                 720

Asn Met Tyr Ile Cys Gly Asp Ser Thr Glu Cys Ala Asn Leu Leu Leu
                725                 730                 735

Gln Tyr Gly Ser Phe Cys Thr Gln Leu Asn Arg Ala Leu Ser Gly Ile
            740                 745                 750

Ala Ala Glu Gln Asp Arg Asn Thr Arg Glu Val Phe Ala Gln Val Lys
            755                 760                 765

Gln Met Tyr Lys Thr Pro Thr Leu Lys Tyr Phe Gly Gly Phe Asn Phe
    770                 775                 780

Ser Gln Ile Leu Pro Asp Pro Leu Lys Pro Thr Lys Arg Ser Phe Ile
785                 790                 795                 800

Glu Asp Leu Leu Phe Asn Lys Val Thr Leu Ala Asp Ala Gly Phe Met
                805                 810                 815

Lys Gln Tyr Gly Glu Cys Leu Gly Asp Ile Asn Ala Arg Asp Leu Ile
            820                 825                 830

Cys Ala Gln Lys Phe Asn Gly Leu Thr Val Leu Pro Pro Leu Leu Thr
            835                 840                 845

Asp Asp Met Ile Ala Ala Tyr Thr Ala Ala Leu Val Ser Gly Thr Ala
    850                 855                 860

Thr Ala Gly Trp Thr Phe Gly Ala Gly Ala Ala Leu Gln Ile Pro Phe
865                 870                 875                 880

Ala Met Gln Met Ala Tyr Arg Phe Asn Gly Ile Gly Val Thr Gln Asn
                885                 890                 895

Val Leu Tyr Glu Asn Gln Lys Gln Ile Ala Asn Gln Phe Asn Lys Ala

-continued

```
              900              905              910
Ile Ser Gln Ile Gln Glu Ser Leu Thr Thr Thr Ser Thr Ala Leu Gly
         915              920              925

Lys Leu Gln Asp Val Val Asn Gln Asn Ala Gln Ala Leu Asn Thr Leu
     930              935              940

Val Lys Gln Leu Ser Ser Asn Phe Gly Ala Ile Ser Ser Val Leu Asn
945              950              955              960

Asp Ile Leu Ser Arg Leu Asp Lys Val Glu Ala Glu Val Gln Ile Asp
             965              970              975

Arg Leu Ile Thr Gly Arg Leu Gln Ser Leu Gln Thr Tyr Val Thr Gln
             980              985              990

Gln Leu Ile Arg Ala Ala Glu Ile  Arg Ala Ser Ala Asn  Leu Ala Ala
         995              1000              1005

Thr Lys  Met Ser Glu Cys Val  Leu Gly Gln Ser Lys  Arg Val Asp
    1010              1015              1020

Phe Cys  Gly Lys Gly Tyr His  Leu Met Ser Phe Pro  Gln Ala Ala
    1025              1030              1035

Pro His  Gly Val Val Phe Leu  His Val Thr Tyr Val  Pro Ser Gln
    1040              1045              1050

Glu Arg  Asn Phe Thr Thr Ala  Pro Ala Ile Cys His  Glu Gly Lys
    1055              1060              1065

Ala Tyr  Phe Pro Arg Glu Gly  Val Phe Val Phe Asn  Gly Thr Ser
    1070              1075              1080

Trp Phe  Ile Thr Gln Arg Asn  Phe Phe Ser Pro Gln  Ile Ile Thr
    1085              1090              1095

Thr Asp  Asn Thr Phe Val Ser  Gly Asn Cys Asp Val  Val Ile Gly
    1100              1105              1110

Ile Ile  Asn Asn Thr Val Tyr  Asp Pro Leu Gln Pro  Glu Leu Asp
    1115              1120              1125

Ser Phe  Lys Glu Glu Leu Asp  Lys Tyr Phe Lys Asn  His Thr Ser
    1130              1135              1140

Pro Asp  Val Asp Leu Gly Asp  Ile Ser
    1145              1150
```

```
<210> SEQ ID NO 4
<211> LENGTH: 3456
<212> TYPE: DNA
<213> ORGANISM: Artificial Sequence
<220> FEATURE:
<223> OTHER INFORMATION: Coronavirus wild-type tr-S-protein sequence

<400> SEQUENCE: 4
atgtttatct ttctgctgtt tctgaccctg accagcggca gcgacctgga tagatgcacc      60
accttcgacg atgtgcaggc ccctaactac acccagcaca ccagctctat gcggggcgtg     120
tactaccccg acgagatttt cagaagcgac accctgtatc tgacccagga cctgttcctg     180 ccttttctaca gcaacgtgac cggcttccac accatcaacc acaccttcgg caaccctgtg     240
atccccttca aggacggcat ctactttgcc gccaccgaga gtccaacgt cgtcagagga     300 tgggtgttcg gcagcaccat gaacaacaag agccagagcg tgatcatcat caacaacagc     360
accaacgtgg tcatccgggc ctgcaacttc gagctgtgcg acaacccatt cttcgccgtg     420
tccaagccta tgggcaccca gacacacacc atgatcttcg acaacgcctt caactgcacc     480
ttcgagtaca tcagcgacgc cttcagcctg gacgtgtccg aaaagagcgg caacttcaag     540
cacctgaggg aattcgtgtt caagaacaag gatggcttcc tgtacgtgta caagggctac     600
```

-continued

```
cagcctatcg acgtcgtgcg ggatctgccc agcggcttca ataccctgaa gcctatcttc    660
aagctgcccc tgggcatcaa catcaccaac ttcagagcca tcctgaccgc tttcagcccc    720
gctcaggata tctggggaac aagcgccgct gcctacttcg tgggctacct gaagccaacc    780
accttcatgc tgaagtacga cgagaacggc accatcaccg acgccgtgga ctgtagccaa    840
aatcctctgg ccgagctgaa gtgcagcgtg aagtccttcg agatcgacaa gggcatctac    900
cagaccagca atttcagagt ggtgccctcc ggggatgtcg tgcggttccc caacatcaca    960
aatctgtgcc ccttcggcga ggtgttcaac gccaccaagt ttccctctgt gtacgcctgg   1020
gagcgcaaaa agatcagcaa ctgccgtggc gactacagcg tgctgtacaa ctccaccttc   1080
ttcagcacct tcaagtgcta cggcgtgtcc gccacaaagc tgaacgacct gtgcttctcc   1140
aacgtgtacg ccgacagctt cgtggtcaaa ggcgacgacg ttcggcagat tgcccctgga   1200
caaacaggcg tgatcgccga ttacaactac aagctgcctg acgacttcat gggctgcgtg   1260
ctggcctgga acaccagaaa catcgatgcc acctccaccg gcaactacaa ttacaagtac   1320
agatacctgc ggcacggcaa gctgcggcct ttcgagaggg atatcagcaa tgtgcctttt   1380
agcccccacg gcaagcccctg cacacctcct gctctgaatt gctactggcc cctgaacgac   1440
tacggctttt acaccaccac aggcatcggc tatcagccct atagagtggt ggtcctgtcc   1500
tttgagctgc tgaatgcccc tgccacagtg tgcggaccta agctgtctac cgacctgatc   1560
aagaaccagt gcgtgaactt caacttcaac ggcctgaccg gcaccggcgt gctgacacca   1620
agcagcaaga gattccagcc tttccagcag ttcggccggg atgtgtccga cttcacagac   1680
agcgtcagag atcccaagac cagcgagatc ctggacatca gcccttgtgc ctttggcgga   1740
gtgtccgtga tcacccctgg cacaaatgcc tctagcgaag tggccgtgct gtatcaggac   1800
gtgaactgca ccgatgtgtc caccgccatt cacgccgatc agctgactcc cgcttggcgg   1860
atctatagca caggcaacaa cgtgttccag acacaagccg gctgtctgat cggagccgag   1920
catgtggata ccagctacga gtgcgacatc cctatcggcg ctggcatctg tgcctcttac   1980
cacaccgtgt ctctgctgcg gagcaccagc cagaaatcca tcgtggccta caccatgagc   2040
ctgggcgccg attcttctat cgcctactcc aacaacacaa tcgctatccc caccaatttc   2100
agcatctcca tcaccaccga agtgatgccc gtgtccatgg ccaagacctc cgtggattgc   2160
aacatgtaca tctgcggcga cagcaccgag tgcgccaatc tgctgctcca gtacggcagc   2220
ttctgcaccc agctgaatag agccctgtct ggaattgccg ccgagcagga cagaaacacc   2280
agagaagtgt tcgcccaagt gaagcagatg tataagaccc cgacactcaa gtacttcggc   2340
gggttcaact tctcccagat cctgcctgat cctctgaagc ccaccaagcg gagcttcatc   2400
gaggacctgc tgttcaacaa agtgaccctg gccgacgccg gctttatgaa gcagtatggc   2460
gagtgcctgg gcgacatcaa cgccagggat ctgatttgcg cccagaagtt taacggactg   2520
accgtgctgc ctcctctgct gaccgatgat atgatcgccg cctacacagc cgctctggtg   2580
tctggtacag ctaccgccgg atggacattt ggagctggcg ccgctctcca gattccattc   2640
gctatgcaga tggcctaccg gttcaacggc atcggagtga cccagaatgt gctgtacgag   2700
aatcagaagc agatcgccaa tcagttcaac aaggccatca gccagatcca agagagcctg   2760
accaccacaa gcacagccct gggaaagctc caggacgtgg tcaaccagaa tgctcaggcc   2820
ctgaacaccc tggtcaagca gctgagcagc aacttcggcg ccatcagctc cgtgctgaat   2880
gacatcctga gccggctgga caaggtggaa gcagaggtgc agatcgaccg gctgatcaca   2940
```

-continued

```
ggcagactcc agagcctcca gacctacgtg acacagcagc tgatcagagc cgccgagatt      3000
agagcctctg ccaatctggc cgccaccaaa atgagcgagt gtgtcctggg ccagagcaag      3060
agagtggact tttgcggcaa gggctatcac ctgatgagct cccacaggc cgctcctcat       3120 ggcgtggtct ttctgcacgt gacatacgtg cccagccaag agagaaactt caccaccgct      3180
ccagccatct gccacgaggg caaagcctac tttcccagag aaggcgtgtt cgtgtttaac      3240
ggcacctcct ggtttatcac ccagcggaat ttcttcagcc cgcaaatcat caccacagac      3300
aacaccttcg tgtccggcaa ctgtgacgtc gtgatcggca tcattaacaa taccgtgtac      3360
gaccctctcc agcctgagct ggacagcttc aaagaggaac tggataagta cttcaagaat      3420
cacacgagcc ccgatgtgga cctgggcgat atctct                                3456
```

```
<210> SEQ ID NO 5
<211> LENGTH: 213
<212> TYPE: PRT
<213> ORGANISM: Artificial Sequence
<220> FEATURE:
<223> OTHER INFORMATION: Coronavirus wild-type S-protein RBD sequence

<400> SEQUENCE: 5

Arg Val Val Pro Ser Gly Asp Val Val Arg Phe Pro Asn Ile Thr Asn
1               5                   10                  15

Leu Cys Pro Phe Gly Glu Val Phe Asn Ala Thr Lys Phe Pro Ser Val
            20                  25                  30

Tyr Ala Trp Glu Arg Lys Lys Ile Ser Asn Cys Val Ala Asp Tyr Ser
        35                  40                  45

Val Leu Tyr Asn Ser Thr Phe Phe Ser Thr Phe Lys Cys Tyr Gly Val
    50                  55                  60

Ser Ala Thr Lys Leu Asn Asp Leu Cys Phe Ser Asn Val Tyr Ala Asp
65                  70                  75                  80

Ser Phe Val Val Lys Gly Asp Asp Val Arg Gln Ile Ala Pro Gly Gln
                85                  90                  95

Thr Gly Val Ile Ala Asp Tyr Asn Tyr Lys Leu Pro Asp Asp Phe Met
            100                 105                 110

Gly Cys Val Leu Ala Trp Asn Thr Arg Asn Ile Asp Ala Thr Ser Thr
            115                 120                 125

Gly Asn Tyr Asn Tyr Lys Tyr Arg Tyr Leu Arg His Gly Lys Leu Arg
        130                 135                 140

Pro Phe Glu Arg Asp Ile Ser Asn Val Pro Phe Ser Pro Asp Gly Lys
145                 150                 155                 160

Pro Cys Thr Pro Pro Ala Leu Asn Cys Tyr Trp Pro Leu Asn Asp Tyr
                165                 170                 175

Gly Phe Tyr Thr Thr Thr Gly Ile Gly Tyr Gln Pro Tyr Arg Val Val
            180                 185                 190

Val Leu Ser Phe Glu Leu Leu Asn Ala Pro Ala Thr Val Cys Gly Pro
        195                 200                 205

Lys Leu Ser Thr Asp
    210
```

```
<210> SEQ ID NO 6
<211> LENGTH: 639
<212> TYPE: DNA
<213> ORGANISM: Artificial Sequence
<220> FEATURE:
<223> OTHER INFORMATION: Coronavirus wild-type S-protein RBD sequence

<400> SEQUENCE: 6
```

```
agagtggtgc cctccgggga tgtcgtgcgg ttccccaaca tcacaaatct gtgcccttc      60 ggcgaggtgt tcaacgccac caagtttccc tctgtgtacg cctgggagcg caaaaagatc     120
agcaactgcg tggccgacta cagcgtgctg tacaactcca ccttcttcag caccttcaag     180
tgctacggcg tgtccgccac aaagctgaac gacctgtgct ctccaacgt gtacgccgac      240 agcttcgtgg tcaaaggcga cgacgttcgg cagattgccc ctggacaaac aggcgtgatc     300
gccgattaca actacaagct gcctgacgac ttcatgggct gcgtgctggc ctggaacacc     360
agaaacatcg atgccacctc caccggcaac tacaattaca gtacagata cctgcggcac      420 ggcaagctgc ggcctttcga gaggdatatc agcaatgtgc cttttagccc cgacggcaag     480
ccctgcacac tcctgctct gaattgctac tggcccctga cgactacgg cttttacacc       540 accacaggca tcggctatca gccctataga gtggtggtcc tgtcctttga gctgctgaat     600 gccccctgcca cagtgtgcgg acctaagctg tctaccgac                            639
```

<210> SEQ ID NO 7
<211> LENGTH: 1273
<212> TYPE: PRT
<213> ORGANISM: Artificial Sequence
<220> FEATURE:
<223> OTHER INFORMATION: Coronavirus wild-type S-protein sequence

<400> SEQUENCE: 7

```
Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
```

-continued

```
                 245               250               255

Gly Trp Thr Ala Gly Ala Ala Ala Tyr Tyr Val Gly Tyr Leu Gln Pro
            260               265               270

Arg Thr Phe Leu Leu Lys Tyr Asn Glu Asn Gly Thr Ile Thr Asp Ala
            275               280               285

Val Asp Cys Ala Leu Asp Pro Leu Ser Glu Thr Lys Cys Thr Leu Lys
            290               295               300

Ser Phe Thr Val Glu Lys Gly Ile Tyr Gln Thr Ser Asn Phe Arg Val
305               310               315               320

Gln Pro Thr Glu Ser Ile Val Arg Phe Pro Asn Ile Thr Asn Leu Cys
                 325               330               335

Pro Phe Gly Glu Val Phe Asn Ala Thr Arg Phe Ala Ser Val Tyr Ala
            340               345               350

Trp Asn Arg Lys Arg Ile Ser Asn Cys Val Ala Asp Tyr Ser Val Leu
            355               360               365

Tyr Asn Ser Ala Ser Phe Ser Thr Phe Lys Cys Tyr Gly Val Ser Pro
            370               375               380

Thr Lys Leu Asn Asp Leu Cys Phe Thr Asn Val Tyr Ala Asp Ser Phe
385               390               395               400

Val Ile Arg Gly Asp Glu Val Arg Gln Ile Ala Pro Gly Gln Thr Gly
                 405               410               415

Lys Ile Ala Asp Tyr Asn Tyr Lys Leu Pro Asp Asp Phe Thr Gly Cys
                 420               425               430

Val Ile Ala Trp Asn Ser Asn Asn Leu Asp Ser Lys Val Gly Gly Asn
            435               440               445

Tyr Asn Tyr Leu Tyr Arg Leu Phe Arg Lys Ser Asn Leu Lys Pro Phe
            450               455               460

Glu Arg Asp Ile Ser Thr Glu Ile Tyr Gln Ala Gly Ser Thr Pro Cys
465               470               475               480

Asn Gly Val Glu Gly Phe Asn Cys Tyr Phe Pro Leu Gln Ser Tyr Gly
            485               490               495

Phe Gln Pro Thr Asn Gly Val Gly Tyr Gln Pro Tyr Arg Val Val Val
            500               505               510

Leu Ser Phe Glu Leu Leu His Ala Pro Ala Thr Val Cys Gly Pro Lys
            515               520               525

Lys Ser Thr Asn Leu Val Lys Asn Lys Cys Val Asn Phe Asn Phe Asn
            530               535               540

Gly Leu Thr Gly Thr Gly Val Leu Thr Glu Ser Asn Lys Lys Phe Leu
545               550               555               560

Pro Phe Gln Gln Phe Gly Arg Asp Ile Ala Asp Thr Thr Asp Ala Val
            565               570               575

Arg Asp Pro Gln Thr Leu Glu Ile Leu Asp Ile Thr Pro Cys Ser Phe
            580               585               590

Gly Gly Val Ser Val Ile Thr Pro Gly Thr Asn Thr Ser Asn Gln Val
            595               600               605

Ala Val Leu Tyr Gln Asp Val Asn Cys Thr Glu Val Pro Val Ala Ile
            610               615               620

His Ala Asp Gln Leu Thr Pro Thr Trp Arg Val Tyr Ser Thr Gly Ser
625               630               635               640

Asn Val Phe Gln Thr Arg Ala Gly Cys Leu Ile Gly Ala Glu His Val
            645               650               655

Asn Asn Ser Tyr Glu Cys Asp Ile Pro Ile Gly Ala Gly Ile Cys Ala
            660               665               670
```

-continued

```
Ser Tyr Gln Thr Gln Thr Asn Ser Pro Arg Arg Ala Arg Ser Val Ala
        675             680             685

Ser Gln Ser Ile Ile Ala Tyr Thr Met Ser Leu Gly Ala Glu Asn Ser
    690             695             700

Val Ala Tyr Ser Asn Asn Ser Ile Ala Ile Pro Thr Asn Phe Thr Ile
705             710             715             720

Ser Val Thr Thr Glu Ile Leu Pro Val Ser Met Thr Lys Thr Ser Val
            725             730             735

Asp Cys Thr Met Tyr Ile Cys Gly Asp Ser Thr Glu Cys Ser Asn Leu
            740             745             750

Leu Leu Gln Tyr Gly Ser Phe Cys Thr Gln Leu Asn Arg Ala Leu Thr
        755             760             765

Gly Ile Ala Val Glu Gln Asp Lys Asn Thr Gln Glu Val Phe Ala Gln
        770             775             780

Val Lys Gln Ile Tyr Lys Thr Pro Pro Ile Lys Asp Phe Gly Gly Phe
785             790             795             800

Asn Phe Ser Gln Ile Leu Pro Asp Pro Ser Lys Pro Ser Lys Arg Ser
            805             810             815

Phe Ile Glu Asp Leu Leu Phe Asn Lys Val Thr Leu Ala Asp Ala Gly
            820             825             830

Phe Ile Lys Gln Tyr Gly Asp Cys Leu Gly Asp Ile Ala Ala Arg Asp
        835             840             845

Leu Ile Cys Ala Gln Lys Phe Asn Gly Leu Thr Val Leu Pro Pro Leu
    850             855             860

Leu Thr Asp Glu Met Ile Ala Gln Tyr Thr Ser Ala Leu Leu Ala Gly
865             870             875             880

Thr Ile Thr Ser Gly Trp Thr Phe Gly Ala Gly Ala Ala Leu Gln Ile
            885             890             895

Pro Phe Ala Met Gln Met Ala Tyr Arg Phe Asn Gly Ile Gly Val Thr
            900             905             910

Gln Asn Val Leu Tyr Glu Asn Gln Lys Leu Ile Ala Asn Gln Phe Asn
        915             920             925

Ser Ala Ile Gly Lys Ile Gln Asp Ser Leu Ser Ser Thr Ala Ser Ala
    930             935             940

Leu Gly Lys Leu Gln Asp Val Val Asn Gln Asn Ala Gln Ala Leu Asn
945             950             955             960

Thr Leu Val Lys Gln Leu Ser Ser Asn Phe Gly Ala Ile Ser Ser Val
            965             970             975

Leu Asn Asp Ile Leu Ser Arg Leu Asp Lys Val Glu Ala Glu Val Gln
            980             985             990

Ile Asp Arg Leu Ile Thr Gly Arg  Leu Gln Ser Leu Gln  Thr Tyr Val
        995             1000                1005

Thr Gln  Gln Leu Ile Arg Ala  Ala Glu Ile Arg Ala  Ser Ala Asn
    1010            1015                1020

Leu Ala  Ala Thr Lys Met Ser  Glu Cys Val Leu Gly  Gln Ser Lys
    1025            1030                1035

Arg Val  Asp Phe Cys Gly Lys  Gly Tyr His Leu Met  Ser Phe Pro
    1040            1045                1050

Gln Ser  Ala Pro His Gly Val  Val Phe Leu His Val  Thr Tyr Val
    1055            1060                1065

Pro Ala  Gln Glu Lys Asn Phe  Thr Thr Ala Pro Ala  Ile Cys His
    1070            1075                1080
```

-continued

```
Asp Gly  Lys Ala His Phe Pro  Arg Glu Gly Val Phe  Val Ser Asn
    1085             1090              1095

Gly Thr  His Trp Phe Val Thr  Gln Arg Asn Phe Tyr  Glu Pro Gln
    1100             1105              1110

Ile Ile  Thr Thr Asp Asn Thr  Phe Val Ser Gly Asn  Cys Asp Val
    1115             1120              1125

Val Ile  Gly Ile Val Asn Asn  Thr Val Tyr Asp Pro  Leu Gln Pro
    1130             1135              1140

Glu Leu  Asp Ser Phe Lys Glu  Glu Leu Asp Lys Tyr  Phe Lys Asn
    1145             1150              1155

His Thr  Ser Pro Asp Val Asp  Leu Gly Asp Ile Ser  Gly Ile Asn
    1160             1165              1170

Ala Ser  Val Val Asn Ile Gln  Lys Glu Ile Asp Arg  Leu Asn Glu
    1175             1180              1185

Val Ala  Lys Asn Leu Asn Glu  Ser Leu Ile Asp Leu  Gln Glu Leu
    1190             1195              1200

Gly Lys  Tyr Glu Gln Tyr Ile  Lys Trp Pro Trp Tyr  Ile Trp Leu
    1205             1210              1215

Gly Phe  Ile Ala Gly Leu Ile  Ala Ile Val Met Val  Thr Ile Met
    1220             1225              1230

Leu Cys  Cys Met Thr Ser Cys  Cys Ser Cys Leu Lys  Gly Cys Cys
    1235             1240              1245

Ser Cys  Gly Ser Cys Cys Lys  Phe Asp Glu Asp Asp  Ser Glu Pro
    1250             1255              1260

Val Leu  Lys Gly Val Lys Leu  His Tyr Thr
    1265             1270
```

```
<210> SEQ ID NO 8
<211> LENGTH: 3819
<212> TYPE: DNA
<213> ORGANISM: Artificial Sequence
<220> FEATURE:
<223> OTHER INFORMATION: Coronavirus wild-type S-protein sequence

<400> SEQUENCE: 8
atgttcgtgt ttctggtgct gctgcctctg gtgtccagcc agtgtgtgaa cctgaccacc      60
agaacacagc tgcctccagc ctacaccaac agctttacca gaggcgtgta ctaccccgac     120
aaggtgttca gatccagcgt gctgcactct acccaggacc tgttcctgcc tttcttcagc     180
aacgtgacct ggttccacgc catccacgtg tccggcacca atggcaccaa gagattcgac     240
aaccccgtgc tgcccttcaa cgacggggtg tactttgcca gcaccgagaa gtccaacatc     300
atcagaggct ggatcttcgg caccacactg gacagcaaga cccagagcct gctgatcgtg     360
aacaacgcca ccaacgtggt catcaaagtg tgcgagttcc agttctgcaa cgacccttc      420 ctgggcgtct actaccacaa gaacaacaag agctggatgg aaagcgagtt ccgggtgtac     480
agcagcgcca caactgcac cttcgagtac gtgtcccagc cttcctgat ggacctggaa      540 ggcaagcagg gcaacttcaa gaacctgcgc gagttcgtgt tcaagaacat cgacggctac     600
ttcaaaatct acagcaagca caccctatc aacctcgtgc gggatctgcc tcagggcttc     660
tctgctctgg aacccctggt ggatctgccc atcggcatca acatcacccg gtttcagaca     720
ctgctggccc tgcacagaag ctacctgaca cctggcgata gcagcagcgg atggacagct     780
ggtgccgccg cttactacgt gggatacctc cagccaagaa ccttcctgct gaagtacaac     840
gagaacggca ccatcaccga cgccgtggat tgtgctctgg accctctgag cgagacaaag     900
```

-continued

```
tgcaccctga agtccttcac cgtggaaaag ggcatctacc agaccagcaa cttccgggtg     960
cagcccaccg aatccatcgt gcggttcccc aatatcacca atctgtgccc cttcggcgag    1020
gtgttcaatg ccaccagatt cgcctctgtg tacgcctgga accggaagcg gatcagcaat    1080
tgcgtggccg actactccgt gctgtacaac tccgccagct tcagcacctt caagtgctac    1140
ggcgtgtccc ctaccaagct gaacgacctg tgcttcacaa acgtgtacgc cgacagcttc    1200
gtgatccggg gagatgaagt gcggcagatt gccctggac agacaggcaa gatcgccgac    1260
tacaactaca agctgcccga cgacttcacc ggctgtgtga ttgcctggaa cagcaacaac    1320
ctggactcca aagtcggcgg caactacaat tacctgtacc ggctgttccg gaagtccaat    1380
ctgaagccct tcgagcggga catcagcacc gaaatctatc aggccggcag caccccttgc    1440
aacggcgtgg aaggcttcaa ctgctacttc ccactgcaaa gctacggctt tcagcccaca    1500
aatggcgtgg gctaccagcc ttacagagtg gtggtgctga gcttcgagct gctgcatgct    1560
cctgccacag tgtgcggccc taagaaatcc accaatctcg tgaagaacaa atgcgtgaac    1620
ttcaacttca acggcctgac cggcaccggc gtgctgacag agagcaacaa gaagttcctg    1680
ccattccagc agttcggccg ggatatcgcc gataccacag atgccgtcag agatccccag    1740
acactggaaa tcctggacat cacccc atgc agcttcggcg gagtgtctgt gatcaccct    1800 ggcaccaaca ccagcaatca ggtggcagtg ctgtaccagg acgtgaactg taccgaagtg    1860
cccgtggcca ttcacgccga tcagctgaca cctacatggc gggtgtactc caccggcagc    1920
aatgtgtttc agaccagagc cggctgtctg atcggagccg agcacgtgaa caatagctac    1980
gagtgcgaca tccccatcgg cgctggcatc tgcgcctctt accagacaca gacaaacagc    2040
cccagacggg ctagaagcgt ggccagccag agcatcattg cctacacaat gtctctgggc    2100
gccgagaaca gcgtggccta ctccaacaac tctatcgcta tcccccaccaa cttcaccatc    2160 agcgtgacca ccgagatcct gcctgtgtcc atgaccaaga ccagcgtgga ctgcaccatg    2220
tacatctgcg gcgattccac cgagtgctcc aacctgctgc tccagtacgg cagcttctgc    2280
acccagctga atagagccct gacagggatc gccgtggaac aggacaagaa cacccaagag    2340
gtgttcgccc aagtgaagca aatctacaag acccctccta tcaaggactt cggcggcttc    2400
aatttcagcc agattctgcc cgatcctagc aagcccagca agcggagctt catcgaggac    2460
ctgctgttca caaaagtgac actggccgac gccggcttca tcaagcagta cggcgattgt    2520
ctgggcgaca ttgccgccag ggatctgatt tgcgcccaga gtttaacgg actgacagtg    2580 ctgcctcctc tgctgaccga tgagatgatc gcccagtaca catctgccct gctggccggc    2640
acaatcacaa gcggctggac atttggagct ggcgccgctc tccagattcc attcgctatg    2700
cagatggcct accggttcaa cggcatcgga gtgacccaga atgtgctgta cgagaaccag    2760
aagctgatcg ccaaccagtt caacagcgcc atcggcaaga tccaggacag cctgagcagc    2820
acagcaagcg ccctgggaaa gctccaggac gtcgtgaacc agaatgccca ggcactgaac    2880
accctggtca agcagctgtc ctccaacttc ggcgccatca gctctgtgct gaacgatatc    2940
ctgagcagac tggacaaggt ggaagccgag gtgcagatcg acagactgat caccggcaga    3000
ctccagtctc tccagaccta cgtgacccag cagctgatca gagccgccga gattagagcc    3060
tctgccaatc tggccgccac caagatgtct gagtgtgtgc tgggccagag caagagagtg    3120
gacttttgcg gcaagggcta ccacctgatg agcttccctc agtctgcccc tcacggcgtg    3180
gtgtttctgc acgtgacata cgtgcccgct caagagaaga atttcaccac cgctccagcc    3240
atctgccacg acggcaaagc ccactttcct agagaaggcg tgttcgtgtc caacggcacc    3300
```

-continued

```
cattggttcg tgacacagcg gaacttctac gagccccaga tcatcaccac cgacaacacc    3360
ttcgtgtctg gcaactgcga cgttgtgatc ggcattgtga acaataccgt gtacgaccct    3420
ctccagcctg aactggactc cttcaaagag gaactcgaca agtactttaa gaaccacaca    3480
agccccgacg tggacctggg cgatatcagc ggaatcaatg ccagcgtggt caacatccag    3540
aaagagatcg accggctgaa cgaggtggcc aagaatctga cgagagcct gatcgacctg     3600 caagaactgg ggaagtacga gcagtacatc aagtggccct ggtacatctg gctgggcttt    3660
atcgccggac tgattgccat cgtgatggtc acaatcatgc tgtgttgcat gaccagctgc    3720
tgtagctgcc tgaagggctg ttgtagctgt ggctcctgct gcaagttcga cgaggacgat    3780
tctgagcccg tgctgaaggg cgtgaaactg cactacacc                           3819
```

<210> SEQ ID NO 9
<211> LENGTH: 1170
<212> TYPE: PRT
<213> ORGANISM: Artificial Sequence
<220> FEATURE:
<223> OTHER INFORMATION: Coronavirus wild-type trS-protein sequence

<400> SEQUENCE: 9

```
Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
            85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
            165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
            245                 250                 255

Gly Trp Thr Ala Gly Ala Ala Ala Tyr Tyr Val Gly Tyr Leu Gln Pro
            260                 265                 270
```

-continued

```
Arg Thr Phe Leu Leu Lys Tyr Asn Glu Asn Gly Thr Ile Thr Asp Ala
    275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
                340                 345                 350

Trp Asn Arg Lys Arg Ile Ser Asn Cys Val Ala Asp Tyr Ser Val Leu
    355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
                420                 425                 430

Val Ile Ala Trp Asn Ser Asn Asn Leu Asp Ser Lys Val Gly Gly Asn
                435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
                500                 505                 510

Leu Ser Phe Glu Leu Leu His Ala Pro Ala Thr Val Cys Gly Pro Lys
                515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
                580                 585                 590

Gly Gly Val Ser Val Ile Thr Pro Gly Thr Asn Thr Ser Asn Gln Val
                595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
                660                 665                 670

Ser Tyr Gln Thr Gln Thr Asn Ser Pro Arg Arg Ala Arg Ser Val Ala
    675                 680                 685
```

-continued

```
Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
            755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
            805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
            835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
    915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg Leu Gln Ser Leu Gln Thr Tyr Val
            995                 1000                1005

Thr Gln Gln Leu Ile Arg Ala Ala Glu Ile Arg Ala Ser Ala Asn
    1010                1015                1020

Leu Ala Ala Thr Lys Met Ser Glu Cys Val Leu Gly Gln Ser Lys
    1025                1030                1035

Arg Val Asp Phe Cys Gly Lys Gly Tyr His Leu Met Ser Phe Pro
    1040                1045                1050

Gln Ser Ala Pro His Gly Val Val Phe Leu His Val Thr Tyr Val
    1055                1060                1065

Pro Ala Gln Glu Lys Asn Phe Thr Thr Ala Pro Ala Ile Cys His
    1070                1075                1080

Asp Gly Lys Ala His Phe Pro Arg Glu Gly Val Phe Val Ser Asn
    1085                1090                1095

Gly Thr His Trp Phe Val Thr Gln Arg Asn Phe Tyr Glu Pro Gln
```

-continued

```
       1100              1105              1110

Ile Ile  Thr Thr Asp Asn Thr  Phe Val Ser Gly Asn  Cys Asp Val
       1115              1120              1125

Val Ile  Gly Ile Val Asn Asn  Thr Val Tyr Asp Pro  Leu Gln Pro
       1130              1135              1140

Glu Leu  Asp Ser Phe Lys Glu  Glu Leu Asp Lys Tyr  Phe Lys Asn
       1145              1150              1155

His Thr  Ser Pro Asp Val Asp  Leu Gly Asp Ile Ser
       1160              1165              1170
```

```
<210> SEQ ID NO 10
<211> LENGTH: 3510
<212> TYPE: DNA
<213> ORGANISM: Artificial Sequence
<220> FEATURE:
<223> OTHER INFORMATION: Coronavirus wild-type trS-protein sequence

<400> SEQUENCE: 10
atgttcgtgt ttctggtgct gctgcctctg gtgtccagcc agtgtgtgaa cctgaccacc      60
agaacacagc tgcctccagc ctacaccaac agctttacca gaggcgtgta ctaccccgac     120
aaggtgttca gatccagcgt gctgcactct acccaggacc tgttcctgcc tttcttcagc     180
aacgtgacct ggttccacgc catccacgtg tccggcacca atggcaccaa gagattcgac     240
aaccccgtgc tgcccttcaa cgacggggtg tactttgcca gcaccgagaa gtccaacatc     300
atcagaggct ggatcttcgg caccacactg gacagcaaga cccagagcct gctgatcgtg     360
aacaacgcca ccaacgtggt catcaaagtg tgcgagttcc agttctgcaa cgacccccttc     420 ctgggcgtct actaccacaa gaacaacaag agctggatgg aaagcgagtt ccgggtgtac     480
agcagcgcca caactgcac cttcgagtac gtgtcccagc cttcctgat ggacctggaa     540 ggcaagcagg gcaacttcaa gaacctgcgc gagttcgtgt tcaagaacat cgacggctac     600
ttcaaaatct acagcaagca cacccctatc aacctcgtgc gggatctgcc tcagggcttc     660
tctgctctgg aaccctggt ggatctgccc atcggcatca acatcacccg gtttcagaca     720
ctgctggccc tgcacagaag ctacctgaca cctggcgata gcagcagcgg atggacagct     780
ggtgccgccg cttactacgt gggatacctc agccaagaa ccttcctgct gaagtacaac     840
gagaacggca ccatcaccga cgccgtggat tgtgctctgg accctctgag cgagacaaag     900
tgcaccctga gtccttcac cgtggaaaag ggcatctacc agaccagcaa cttccgggtg     960
cagcccaccg aatccatcgt gcggttcccc aatatcacca atctgtgccc cttcggcgag    1020
gtgttcaatg ccaccagatt cgcctctgtg tacgcctgga accggaagcg gatcagcaat    1080
tgcgtggccg actactccgt gctgtacaac tccgccagct tcagcacctt caagtgctac    1140
ggcgtgtccc ctaccaagct gaacgacctg tgcttcacaa acgtgtacgc cgacagcttc    1200
gtgatccggg gagatgaagt gcggcagatt gcccctggac agacaggcaa gatcgccgac    1260
tacaactaca agctgcccga cgacttcacc ggctgtgtga ttgcctggaa cagcaacaac    1320
ctggactcca aagtcggcgg caactacaat tacctgtacc ggctgttccg gaagtccaat    1380
ctgaagccct cgagcggga catcagcacc gaaatctatc aggccggcag caccccttgc    1440
aacggcgtgg aaggcttcaa ctgctacttc ccactgcaaa gctacggctt tcagccaca    1500 aatggcgtgg ctaccagcc ttacagagtg gtggtgctga gcttcgagct gctgcatgct    1560
cctgccacag tgtgcggccc taagaaatcc accaatctcg tgaagaacaa atgcgtgaac    1620
ttcaacttca cggcctgac cggcaccggc gtgctgacag agagcaacaa gaagttcctg    1680
```

-continued

```
ccattccagc agttcggccg ggatatcgcc gataccacag atgccgtcag agatccccag      1740
acactggaaa tcctggacat cacccccatgc agcttcggcg gagtgtctgt gatcacccct      1800
ggcaccaaca ccagcaatca ggtggcagtg ctgtaccagg acgtgaactg taccgaagtg      1860
cccgtggcca ttcacgccga tcagctgaca cctacatggc gggtgtactc caccggcagc      1920
aatgtgtttc agaccagagc cggctgtctg atcggagccg agcacgtgaa caatagctac      1980
gagtgcgaca tccccatcgg cgctggcatc tgcgcctctt accagacaca gacaaacagc      2040
cccagacggg ctagaagcgt ggccagccag agcatcattg cctacacaat gtctctgggc      2100
gccgagaaca gcgtggccta ctccaacaac tctatcgcta tccccaccaa cttcaccatc      2160
agcgtgacca ccgagatcct gcctgtgtcc atgaccaaga ccagcgtgga ctgcaccatg      2220
tacatctgcg gcgattccac cgagtgctcc aacctgctgc tccagtacgg cagcttctgc      2280
acccagctga atagagccct gacagggatc gccgtggaac aggacaagaa cacccaagag      2340
gtgttcgccc aagtgaagca aatctacaag acccctccta tcaaggactt cggcggcttc      2400
aatttcagcc agattctgcc cgatcctagc aagcccagca agcggagctt catcgaggac      2460
ctgctgttca acaaagtgac actggccgac gccggcttca tcaagcagta cggcgattgt      2520
ctgggcgaca ttgccgccag ggatctgatt tgcgcccaga agtttaacgg actgacagtg      2580
ctgcctcctc tgctgaccga tgagatgatc gcccagtaca catctgccct gctggccggc      2640
acaatcacaa gcggctggac atttggagct ggcgccgctc tccagattcc attcgctatg      2700
cagatggcct accggttcaa cggcatcgga gtgacccaga atgtgctgta cgagaaccag      2760
aagctgatcg ccaaccagtt caacagcgcc atcggcaaga tccaggacag cctgagcagc      2820
acagcaagcg ccctgggaaa gctccaggac gtcgtgaacc agaatgccca ggcactgaac      2880
accctggtca agcagctgtc ctccaacttc ggcgccatca gctctgtgct gaacgatatc      2940
ctgagcagac tggacaaggt ggaagccgag gtgcagatcg acagactgat caccggcaga      3000
ctccagtctc tccagaccta cgtgacccag cagctgatca gagccgccga gattagagcc      3060
tctgccaatc tggccgccac caagatgtct gagtgtgtgc tgggccagag caagagagtg      3120 gactttgcg gcaagggcta ccacctgatg agcttccctc agtctgcccc tcacggcgtg      3180
gtgtttctgc acgtgacata cgtgcccgct caagagaaga atttcaccac cgctccagcc      3240
atctgccacg acggcaaagc ccactttcct agagaaggcg tgttcgtgtc caacggcacc      3300
cattggttcg tgacacagcg gaacttctac gagccccaga tcatcaccac cgacaacacc      3360
ttcgtgtctg gcaactgcga cgttgtgatc ggcattgtga acaataccgt gtacgaccct      3420
ctccagcctg aactggactc cttcaaagag gaactcgaca gtactttaa gaaccacaca      3480 agccccgacg tggacctggg cgatatcagt                                      3510
```

<210> SEQ ID NO 11
<211> LENGTH: 214
<212> TYPE: PRT
<213> ORGANISM: Artificial Sequence
<220> FEATURE:
<223> OTHER INFORMATION: Coronavirus wild-type S-protein RBD sequence

<400> SEQUENCE: 11

```
Arg Val Gln Pro Thr Glu Ser Ile Val Arg Phe Pro Asn Ile Thr Asn
1               5                   10                  15

Leu Cys Pro Phe Gly Glu Val Phe Asn Ala Thr Arg Phe Ala Ser Val
            20                  25                  30
```

-continued

```
Tyr Ala Trp Asn Arg Lys Arg Ile Ser Asn Cys Val Ala Asp Tyr Ser
    35              40              45

Val Leu Tyr Asn Ser Ala Ser Phe Ser Thr Phe Lys Cys Tyr Gly Val
    50              55              60

Ser Pro Thr Lys Leu Asn Asp Leu Cys Phe Thr Asn Val Tyr Ala Asp
65              70              75              80

Ser Phe Val Ile Arg Gly Asp Glu Val Arg Gln Ile Ala Pro Gly Gln
                85              90              95

Thr Gly Lys Ile Ala Asp Tyr Asn Tyr Lys Leu Pro Asp Asp Phe Thr
            100             105             110

Gly Cys Val Ile Ala Trp Asn Ser Asn Asn Leu Asp Ser Lys Val Gly
            115             120             125

Gly Asn Tyr Asn Tyr Leu Tyr Arg Leu Phe Arg Lys Ser Asn Leu Lys
    130             135             140

Pro Phe Glu Arg Asp Ile Ser Thr Glu Ile Tyr Gln Ala Gly Ser Thr
145             150             155             160

Pro Cys Asn Gly Val Glu Gly Phe Asn Cys Tyr Phe Pro Leu Gln Ser
                165             170             175

Tyr Gly Phe Gln Pro Thr Asn Gly Val Gly Tyr Gln Pro Tyr Arg Val
            180             185             190

Val Val Leu Ser Phe Glu Leu Leu His Ala Pro Ala Thr Val Cys Gly
        195             200             205

Pro Lys Lys Ser Thr Asn
    210
```

```
<210> SEQ ID NO 12
<211> LENGTH: 642
<212> TYPE: DNA
<213> ORGANISM: Artificial Sequence
<220> FEATURE:
<223> OTHER INFORMATION: Coronavirus S-protein RBD sequence

<400> SEQUENCE: 12
cgggtgcagc ccaccgaatc catcgtgcgg ttccccaata tcaccaatct gtgccccttc      60
ggcgaggtgt tcaatgccac cagattcgcc tctgtgtacg cctggaaccg gaagcggatc     120
agcaattgcg tggccgacta ctccgtgctg tacaactccg ccagcttcag caccttcaag     180
tgctacggcg tgtcccctac caagctgaac gacctgtgct tcacaaacgt gtacgccgac     240
agcttcgtga tccggggaga tgaagtgcgg cagattgccc ctggacagac aggcaagatc     300
gccgactaca actacaagct gcccgacgac ttcaccggct gtgtgattgc ctggaacagc     360
aacaacctgg actccaaagt cggcggcaac tacaattacc tgtaccggct gttccggaag     420
tccaatctga gcccttcga gcgggacatc agcaccgaaa tctatcaggc cggcagcacc     480
ccttgcaacg gcgtggaagg cttcaactgc tacttccac tgcaaagcta cggctttcag     540
cccacaaatg gcgtgggcta ccagccttac agagtggtgg tgctgagctt cgagctgctg     600
catgctcctg ccacagtgtg cggccctaag aaatccacca at                       642
```

```
<210> SEQ ID NO 13
<211> LENGTH: 1288
<212> TYPE: PRT
<213> ORGANISM: Artificial Sequence
<220> FEATURE:
<223> OTHER INFORMATION: Coronavirus S-protein designed sequence

<400> SEQUENCE: 13

Met Phe Leu Phe Leu Phe Ile Ile Ile Phe Ala Phe Phe Leu Leu Ser
```

```
1              5              10             15

Ala Lys Ala Asn Glu Arg Cys Gly Ile Phe Thr Ser Lys Pro Gln Pro
            20             25             30

Lys Leu Ala Gln Val Ser Ser Ser Arg Arg Gly Val Tyr Tyr Pro Asp
            35             40             45

Asp Ile Phe Arg Ser Asp Val Leu His Leu Thr Gln Asp Tyr Phe Leu
    50             55             60

Pro Phe Asp Ser Asn Val Thr Arg Tyr Phe Ser Leu Asn Ala Asn Gly
65             70             75             80

Pro Asp Arg Ile Val Tyr Phe Asp Asn Pro Ile Ile Pro Phe Lys Asp
            85             90             95

Gly Val Tyr Phe Ala Ala Thr Glu Lys Ser Asn Val Ile Arg Gly Trp
            100            105            110

Ile Phe Gly Ser Thr Leu Asp Asn Thr Ser Gln Ser Val Ile Ile Val
            115            120            125

Asn Asn Ser Thr Asn Val Ile Ile Arg Val Cys Asn Phe Asp Leu Cys
    130            135            140

Asn Asp Pro Phe Phe Thr Val Ser Arg Pro Thr Asp Lys His Ile Lys
145            150            155            160

Thr Trp Ser Ile Arg Glu Phe Ala Val Tyr Gln Ser Ala Phe Asn Cys
            165            170            175

Thr Phe Glu Tyr Val Ser Lys Ser Phe Leu Leu Asp Val Ala Glu Lys
            180            185            190

Pro Gly Asn Phe Lys His Leu Arg Glu Phe Val Phe Lys Asn Val Asp
            195            200            205

Gly Phe Leu Asn Val Tyr Ser Thr Tyr Lys Pro Ile Asn Val Val Ser
    210            215            220

Gly Leu Pro Thr Gly Phe Ser Val Leu Lys Pro Ile Leu Lys Leu Pro
225            230            235            240

Leu Gly Ile Asn Ile Thr Ser Phe Arg Val Leu Leu Thr Met Phe Arg
            245            250            255

Gly Asp Pro Thr Pro Gly His Thr Thr Ala Asn Trp Leu Thr Ala Ala
            260            265            270

Ala Ala Tyr Tyr Val Gly Tyr Leu Lys Pro Thr Thr Phe Met Leu Lys
            275            280            285

Tyr Asn Glu Asn Gly Thr Ile Thr Asp Ala Val Asp Cys Ser Gln Asn
    290            295            300

Pro Leu Ala Glu Leu Lys Cys Thr Leu Lys Asn Phe Asn Val Asp Lys
305            310            315            320

Gly Ile Tyr Gln Thr Ser Asn Phe Arg Val Ser Pro Thr Gln Glu Val
            325            330            335

Val Arg Phe Pro Asn Ile Thr Asn Leu Cys Pro Phe Asp Lys Val Phe
            340            345            350

Asn Ala Thr Arg Phe Pro Ser Val Tyr Ala Trp Glu Arg Thr Lys Ile
            355            360            365

Ser Asp Cys Val Ala Asp Tyr Thr Val Leu Tyr Asn Ser Thr Ser Phe
    370            375            380

Ser Thr Phe Lys Cys Tyr Gly Val Ser Pro Ser Lys Leu Ile Asp Leu
385            390            395            400

Cys Phe Thr Ser Val Tyr Ala Asp Thr Phe Leu Ile Arg Cys Ser Glu
            405            410            415

Val Arg Gln Val Ala Pro Gly Gln Thr Gly Val Ile Ala Asp Tyr Asn
            420            425            430
```

-continued

```
Tyr Lys Leu Pro Asp Asp Phe Thr Gly Cys Val Ile Ala Trp Asn Thr
        435                 440                 445

Ala Lys Gln Asp Thr Gly Ser Ser Gly Asn Tyr Asn Tyr Tyr Tyr Arg
    450                 455                 460

Ser His Arg Lys Thr Lys Leu Lys Pro Phe Glu Arg Asp Leu Ser Ser
465                 470                 475                 480

Asp Glu Cys Ser Pro Asp Gly Lys Pro Cys Thr Pro Pro Ala Phe Asn
                485                 490                 495

Gly Val Arg Gly Phe Asn Cys Tyr Phe Thr Leu Ser Thr Tyr Asp Phe
                500                 505                 510

Asn Pro Asn Val Pro Val Glu Tyr Gln Ala Thr Arg Val Val Val Leu
        515                 520                 525

Ser Phe Glu Leu Leu Asn Ala Pro Ala Thr Val Cys Gly Pro Lys Leu
        530                 535                 540

Ser Thr Gln Leu Val Lys Asn Gln Cys Val Asn Phe Asn Phe Asn Gly
545                 550                 555                 560

Leu Lys Gly Thr Gly Val Leu Thr Ala Ser Ser Lys Arg Phe Gln Ser
                565                 570                 575

Phe Gln Gln Phe Gly Arg Asp Ala Ser Asp Phe Thr Asp Ser Val Arg
                580                 585                 590

Asp Pro Gln Thr Leu Glu Ile Leu Asp Ile Ser Pro Cys Ser Phe Gly
        595                 600                 605

Gly Val Ser Val Ile Thr Pro Gly Thr Asn Thr Ser Ser Glu Val Ala
        610                 615                 620

Val Leu Tyr Gln Asp Val Asn Cys Thr Asp Val Pro Thr Ala Ile His
625                 630                 635                 640

Ala Asp Gln Leu Thr Pro Ala Trp Arg Val Tyr Ser Thr Gly Val Asn
                645                 650                 655

Val Phe Gln Thr Gln Ala Gly Cys Leu Ile Gly Ala Glu His Val Asn
                660                 665                 670

Ala Ser Tyr Glu Cys Asp Ile Pro Ile Gly Ala Gly Ile Cys Ala Ser
            675                 680                 685

Tyr His Thr Ala Ser Asn Ser Pro Arg Ile Leu Arg Ser Thr Gly Gln
        690                 695                 700

Lys Ser Ile Val Ala Tyr Thr Met Ser Leu Gly Ala Glu Asn Ser Ile
705                 710                 715                 720

Ala Tyr Ala Asn Asn Ser Ile Ala Ile Pro Thr Asn Phe Ser Ile Ser
                725                 730                 735

Val Thr Thr Glu Val Met Pro Val Ser Met Ala Lys Thr Ser Val Asp
                740                 745                 750

Cys Thr Met Tyr Ile Cys Gly Asp Ser Leu Glu Cys Ser Asn Leu Leu
        755                 760                 765

Leu Gln Tyr Gly Ser Phe Cys Thr Gln Leu Asn Arg Ala Leu Thr Gly
    770                 775                 780

Ile Ala Ile Glu Gln Asp Lys Asn Thr Gln Glu Val Phe Ala Gln Val
785                 790                 795                 800

Lys Gln Met Tyr Lys Thr Pro Ala Ile Lys Asp Phe Gly Gly Phe Asn
                805                 810                 815

Phe Ser Gln Ile Leu Pro Asp Pro Ser Lys Pro Thr Lys Arg Ser Phe
                820                 825                 830

Ile Glu Asp Leu Leu Phe Asn Lys Val Thr Leu Ala Asp Ala Gly Phe
        835                 840                 845
```

-continued

```
Met Lys Gln Tyr Gly Glu Cys Leu Gly Asp Ile Ser Ala Arg Asp Leu
    850             855             860

Ile Cys Ala Gln Lys Phe Asn Gly Leu Thr Val Leu Pro Pro Leu Leu
865             870             875             880

Thr Asp Glu Met Ile Ala Ala Tyr Thr Ala Ala Leu Val Ser Gly Thr
            885             890             895

Ala Thr Ala Gly Trp Thr Phe Gly Ala Gly Ala Ala Leu Gln Ile Pro
        900             905             910

Phe Ala Met Gln Met Ala Tyr Arg Phe Asn Gly Ile Gly Val Thr Gln
        915             920             925

Asn Val Leu Tyr Glu Asn Gln Lys Gln Ile Ala Asn Gln Phe Asn Lys
    930             935             940

Ala Ile Ser Gln Ile Gln Glu Ser Leu Thr Thr Thr Ser Thr Ala Leu
945             950             955             960

Gly Lys Leu Gln Asp Val Val Asn Gln Asn Ala Gln Ala Leu Asn Thr
            965             970             975

Leu Val Lys Gln Leu Ser Ser Asn Phe Gly Ala Ile Ser Ser Val Leu
        980             985             990

Asn Asp Ile Leu Ser Arg Leu Asp Lys Val Glu Ala Glu Val Gln Ile
        995             1000            1005

Asp Arg Leu Ile Thr Gly Arg Leu Gln Ser Leu Gln Thr Tyr Val
    1010            1015            1020

Thr Gln Gln Leu Ile Arg Ala Ala Glu Ile Arg Ala Ser Ala Asn
    1025            1030            1035

Leu Ala Ala Thr Lys Met Ser Glu Cys Val Leu Gly Gln Ser Lys
    1040            1045            1050

Arg Val Asp Phe Cys Gly Lys Gly Tyr His Leu Met Ser Phe Pro
    1055            1060            1065

Gln Ala Ala Pro His Gly Val Val Phe Leu His Val Thr Tyr Val
    1070            1075            1080

Pro Ser Gln Glu Arg Asn Phe Thr Thr Ala Pro Ala Ile Cys His
    1085            1090            1095

Glu Gly Lys Ala Tyr Phe Pro Arg Glu Gly Val Phe Val Ser Asn
    1100            1105            1110

Gly Thr Ser Trp Phe Ile Thr Gln Arg Asn Phe Tyr Ser Pro Gln
    1115            1120            1125

Ile Ile Thr Thr Asp Asn Thr Phe Val Ser Gly Asn Cys Asp Val
    1130            1135            1140

Val Ile Gly Ile Ile Asn Asn Thr Val Tyr Asp Pro Leu Gln Pro
    1145            1150            1155

Glu Leu Asp Ser Phe Lys Glu Glu Leu Asp Lys Tyr Phe Lys Asn
    1160            1165            1170

His Thr Ser Pro Asp Val Asp Leu Gly Asp Ile Ser Gly Ile Asn
    1175            1180            1185

Ala Ser Val Val Asn Ile Gln Lys Glu Ile Asp Arg Leu Asn Glu
    1190            1195            1200

Val Ala Lys Asn Leu Asn Glu Ser Leu Ile Asp Leu Gln Glu Leu
    1205            1210            1215

Gly Lys Tyr Glu Gln Tyr Ile Lys Trp Pro Trp Tyr Val Trp Leu
    1220            1225            1230

Gly Phe Ile Ala Gly Leu Ile Ala Ile Val Met Ala Thr Ile Leu
    1235            1240            1245

Leu Cys Cys Met Thr Ser Cys Cys Ser Cys Leu Lys Gly Ala Cys
```

-continued

```
        1250            1255            1260

Ser Cys  Gly Ser Cys Cys Lys  Phe Asp Glu Asp  Ser Glu Pro
    1265            1270            1275

Val Leu  Lys Gly Val Lys Leu  His Tyr Thr
    1280            1285

<210> SEQ ID NO 14
<211> LENGTH: 3864
<212> TYPE: DNA
<213> ORGANISM: Artificial Sequence
<220> FEATURE:
<223> OTHER INFORMATION: Coronavirus S-protein designed sequence

<400> SEQUENCE: 14
atgtttctgt tcctcttcat tattatcttc gcattcttcc tgctgagcgc caaggccaac    60
gagagatgcg gcatcttcac cagcaagccc cagcctaagc tggcccaggt gtccagttct    120
agacggggcg tgtactaccc cgacgacatc ttcagatccg acgtgctgca tctgacccag    180
gactacttcc tgcctttcga cagcaacgtg acccggtact tcagcctgaa cgccaacgga    240
cccgaccgga tcgtgtactt cgacaaccct atcatcccct tcaaggacgg ggtgtacttt    300
gccgccaccg agaagtccaa cgtgatcaga ggctggatct tcggcagcac cctggacaat    360
accagccaga gcgtgatcat cgtgaacaac agcaccaacg tcatcatccg cgtgtgcaac    420
ttcgacctgt gcaacgaccc cattcttacc gtgtccagac aaccgacaa gcacatcaag    480 acctggtcca tccgcgagtt cgccgtgtac cagagcgcct tcaattgcac cttcgagtac    540
gtgtccaaga gctttctgct ggacgtggcc gagaagcccg caactttaa gcacctgaga    600 gaattcgtgt tcaagaacgt ggacggcttc ctgaacgtgt acagcaccta caagcccatc    660
aacgtggtgt ccggcctgcc tacaggattc agcgtgctga gcccatcct gaagctgccc    720 ctgggcatca acatcaccag cttcagagtg ctgctgacca tgttcagagg cgaccctaca    780
cctggccaca ccaccgctaa ttggctgaca gccgccgctg cctactacgt gggatacctg    840
aagcctacca ccttcatgct caagtacaac gagaacggca ccatcaccga cgccgtggac    900
tgtagccaaa tcctctggcc cgagctgaag tgcacctga agaacttcaa cgtggacaag    960
ggcatctacc agaccagcaa cttccgggtg tcccctacac aagaggtcgt gcggttcccc   1020
aatatcacca atctgtgccc cttcgacaag gtgttcaacg ccaccagatt tcccagcgtg   1080
tacgcctggg agcgcaccaa gatttccgat tgcgtggccg actacaccgt gctgtataac   1140
tccacctcct tcagcacctt caagtgctac ggcgtgtccc aagcaagct gatcgatctg   1200 tgcttcacct ctgtgtacgc cgacaccttc ctgatccggt gtagcgaagt cgacaggtg   1260 gcacctggac agacaggcgt gatcgccgat tacaactaca gctgcccga cgacttcacc   1320 ggctgtgtga tcgcctggaa taccgccaag caggatacag gcagcagcgg caactacaac   1380
tactactaca gaagccaccg caagaccaag ctgaagcctt cgagaggga cctgagcagc   1440 gacgagtgta gccctgatgg caagccttgt acacctcctg ccttcaatgg cgtgcggggc   1500
ttcaactgct acttcacccct gagcacctac gacttcaacc ccaacgtgcc cgtggaatac   1560
caggccacaa gagtggtggt gctgagcttc gagctgctga atgcccctgc acagtgtgt   1620 ggccctaagc tgtctaccca gctggtcaag aaccagtgcg tgaacttcaa tttcaacggc   1680
ctgaaaggca ccggcgtgct gaccgccagc agcaagagat ccagagctt ccagcagttc   1740 ggcagggacg ccagcgattt cacagatagc gtcagagatc ccagacact ggaaatcctg   1800 gacatcagcc cttgcagctt cggcggagtg tctgtgatca cccctggcac caatacctct   1860
```

-continued

```
agcgaggtgg cagtgctgta ccaggacgtg aactgcaccg atgtgcctac agccatccac     1920
gccgatcagc tgacaccagc ttggagagtg tactctaccg gtgtcaacgt gttccagaca     1980
caagccggct gtctgattgg agccgaacac gtgaacgcca gctacgagtg cgacatccct     2040
atcggagccg gcatctgtgc ctcttaccac accgcctcta acagccccag aatcctgaga     2100
agcaccggcc agaaatccat cgtggcctac acaatgtctc tgggcgccga gaactctatc     2160
gcctacgcca acaactccat tgctatcccc accaacttca gcatctccgt gaccaccgaa     2220
gtgatgcctg tgtccatggc caagaccagc gtggactgca caatgtacat ctgcggcgac     2280
agcctggaat gcagcaacct gctgctccag tacggcagct tctgcaccca gctgaataga     2340
gccctgaccg gaatcgccat cgagcaggac aagaacaccc aagaggtgtt cgcccaagtg     2400
aagcagatgt ataagacccc tgccatcaag gacttcggcg gctttaactt cagccagatc     2460
ctgcctgatc ctagcaagcc caccaagcgg agcttcatcg aggacctgct gttcaacaaa     2520
gtgaccctgg ccgacgccgg ctttatgaag cagtatggcg agtgcctggg cgacatctct     2580
gccagggatc tgatttgcgc ccagaagttc aacggactga ccgtgctgcc tcctctgctg     2640
accgatgaga tgatcgccgc ctatacagcc gctctggtgt ctggcacagc taccgccgga     2700
tggacatttg gagctggcgc cgctctccag attccattcg ctatgcagat ggcctaccgc     2760
ttcaacggca tcggcgtgac ccagaacgtg ctgtacgaga accagaagca gatcgccaac     2820
cagttcaaca aggccatcag tcagatccaa gagagcctga ccacaaccag cacagccctg     2880
ggaaagctcc aggacgtcgt gaaccagaat gcccaggctc tgaacaccct ggtcaagcag     2940
ctgagcagca atttcggcgc catcagctcc gtgctgaacg acatcctgag ccggctggat     3000
aaggtggaag ccgaggtgca gatcgaccgg ctgattacag gcagactcca gtctctccag     3060
acctacgtga cacagcagct gatcagagcc gccgagatta gagcctctgc caatctggcc     3120
gccaccaaga tgtctgagtg tgtgctgggc cagtctaaga gagtggactt ctgcggcaag     3180
ggctaccacc tgatgagctt ccctcaggct gctcctcacg gcgtggtgtt tctgcacgtg     3240
acatacgtgc ccagccaaga gcggaacttc acaactgccc cagccatctg ccacgagggc     3300
aaagcctact ttcccagaga aggcgtgttc gtgtccaacg gcacctcctg gttcatcacc     3360
cagagaaact tctacagccc tcagatcatc accaccgaca acaccttcgt gtccggcaac     3420
tgcgacgtgg tcatcggcat catcaacaat accgtgtacg accctctcca gccagaactg     3480
gatagcttca agaggaact cgacaagtac ttcaagaatc acacaagccc cgacgtggac     3540
ctgggcgata tcagcggaat caatgccagc gtggtcaaca tccagaaaga gatcgacaga     3600
ctgaacgagg tggccaagaa cctgaacgag tccctgatcg acctgcaaga gctggggaag     3660
tacgagcagt acatcaagtg gccttggtac gtgtggctgg gctttatcgc cggactgatc     3720
gccattgtga tggccaccat cctgctgtgc tgcatgacaa gctgctgtag ctgcctgaag     3780
ggcgcctgta gctgtggcag ctgctgcaag ttcgacgagg acgattctga gcctgtgctg     3840
aaaggcgtga agctgcacta cacc                                           3864
```

<210> SEQ ID NO 15
<211> LENGTH: 1185
<212> TYPE: PRT
<213> ORGANISM: Artificial Sequence
<220> FEATURE:
<223> OTHER INFORMATION: Coronavirus trS-protein designed sequence

<400> SEQUENCE: 15

-continued

```
Met Phe Leu Phe Leu Phe Ile Ile Ile Phe Ala Phe Phe Leu Leu Ser
1               5                   10                  15

Ala Lys Ala Asn Glu Arg Cys Gly Ile Phe Thr Ser Lys Pro Gln Pro
            20                  25                  30

Lys Leu Ala Gln Val Ser Ser Ser Arg Arg Gly Val Tyr Tyr Pro Asp
        35                  40                  45

Asp Ile Phe Arg Ser Asp Val Leu His Leu Thr Gln Asp Tyr Phe Leu
    50                  55                  60

Pro Phe Asp Ser Asn Val Thr Arg Tyr Phe Ser Leu Asn Ala Asn Gly
65                  70                  75                  80

Pro Asp Arg Ile Val Tyr Phe Asp Asn Pro Ile Ile Pro Phe Lys Asp
                85                  90                  95

Gly Val Tyr Phe Ala Ala Thr Glu Lys Ser Asn Val Ile Arg Gly Trp
            100                 105                 110

Ile Phe Gly Ser Thr Leu Asp Asn Thr Ser Gln Ser Val Ile Ile Val
        115                 120                 125

Asn Asn Ser Thr Asn Val Ile Ile Arg Val Cys Asn Phe Asp Leu Cys
    130                 135                 140

Asn Asp Pro Phe Phe Thr Val Ser Arg Pro Thr Asp Lys His Ile Lys
145                 150                 155                 160

Thr Trp Ser Ile Arg Glu Phe Ala Val Tyr Gln Ser Ala Phe Asn Cys
                165                 170                 175

Thr Phe Glu Tyr Val Ser Lys Ser Phe Leu Leu Asp Val Ala Glu Lys
            180                 185                 190

Pro Gly Asn Phe Lys His Leu Arg Glu Phe Val Phe Lys Asn Val Asp
            195                 200                 205

Gly Phe Leu Asn Val Tyr Ser Thr Tyr Lys Pro Ile Asn Val Val Ser
    210                 215                 220

Gly Leu Pro Thr Gly Phe Ser Val Leu Lys Pro Ile Leu Lys Leu Pro
225                 230                 235                 240

Leu Gly Ile Asn Ile Thr Ser Phe Arg Val Leu Leu Thr Met Phe Arg
                245                 250                 255

Gly Asp Pro Thr Pro Gly His Thr Thr Ala Asn Trp Leu Thr Ala Ala
            260                 265                 270

Ala Ala Tyr Tyr Val Gly Tyr Leu Lys Pro Thr Thr Phe Met Leu Lys
        275                 280                 285

Tyr Asn Glu Asn Gly Thr Ile Thr Asp Ala Val Asp Cys Ser Gln Asn
    290                 295                 300

Pro Leu Ala Glu Leu Lys Cys Thr Leu Lys Asn Phe Asn Val Asp Lys
305                 310                 315                 320

Gly Ile Tyr Gln Thr Ser Asn Phe Arg Val Ser Pro Thr Gln Glu Val
                325                 330                 335

Val Arg Phe Pro Asn Ile Thr Asn Leu Cys Pro Phe Asp Lys Val Phe
            340                 345                 350

Asn Ala Thr Arg Phe Pro Ser Val Tyr Ala Trp Glu Arg Thr Lys Ile
        355                 360                 365

Ser Asp Cys Val Ala Asp Tyr Thr Val Leu Tyr Asn Ser Thr Ser Phe
    370                 375                 380

Ser Thr Phe Lys Cys Tyr Gly Val Ser Pro Ser Lys Leu Ile Asp Leu
385                 390                 395                 400

Cys Phe Thr Ser Val Tyr Ala Asp Thr Phe Leu Ile Arg Cys Ser Glu
                405                 410                 415

Val Arg Gln Val Ala Pro Gly Gln Thr Gly Val Ile Ala Asp Tyr Asn
```

-continued

```
               420               425               430

Tyr Lys Leu Pro Asp Asp Phe Thr Gly Cys Val Ile Ala Trp Asn Thr
        435               440               445

Ala Lys Gln Asp Thr Gly Ser Ser Gly Asn Tyr Asn Tyr Tyr Tyr Arg
        450               455               460

Ser His Arg Lys Thr Lys Leu Lys Pro Phe Glu Arg Asp Leu Ser Ser
465               470               475               480

Asp Glu Cys Ser Pro Asp Gly Lys Pro Cys Thr Pro Pro Ala Phe Asn
                485               490               495

Gly Val Arg Gly Phe Asn Cys Tyr Phe Thr Leu Ser Thr Tyr Asp Phe
                500               505               510

Asn Pro Asn Val Pro Val Glu Tyr Gln Ala Thr Arg Val Val Val Leu
        515               520               525

Ser Phe Glu Leu Leu Asn Ala Pro Ala Thr Val Cys Gly Pro Lys Leu
        530               535               540

Ser Thr Gln Leu Val Lys Asn Gln Cys Val Asn Phe Asn Phe Asn Gly
545               550               555               560

Leu Lys Gly Thr Gly Val Leu Thr Ala Ser Ser Lys Arg Phe Gln Ser
                565               570               575

Phe Gln Gln Phe Gly Arg Asp Ala Ser Asp Phe Thr Asp Ser Val Arg
                580               585               590

Asp Pro Gln Thr Leu Glu Ile Leu Asp Ile Ser Pro Cys Ser Phe Gly
        595               600               605

Gly Val Ser Val Ile Thr Pro Gly Thr Asn Thr Ser Ser Glu Val Ala
        610               615               620

Val Leu Tyr Gln Asp Val Asn Cys Thr Asp Val Pro Thr Ala Ile His
625               630               635               640

Ala Asp Gln Leu Thr Pro Ala Trp Arg Val Tyr Ser Thr Gly Val Asn
                645               650               655

Val Phe Gln Thr Gln Ala Gly Cys Leu Ile Gly Ala Glu His Val Asn
                660               665               670

Ala Ser Tyr Glu Cys Asp Ile Pro Ile Gly Ala Gly Ile Cys Ala Ser
                675               680               685

Tyr His Thr Ala Ser Asn Ser Pro Arg Ile Leu Arg Ser Thr Gly Gln
        690               695               700

Lys Ser Ile Val Ala Tyr Thr Met Ser Leu Gly Ala Glu Asn Ser Ile
705               710               715               720

Ala Tyr Ala Asn Asn Ser Ile Ala Ile Pro Thr Asn Phe Ser Ile Ser
                725               730               735

Val Thr Thr Glu Val Met Pro Val Ser Met Ala Lys Thr Ser Val Asp
                740               745               750

Cys Thr Met Tyr Ile Cys Gly Asp Ser Leu Glu Cys Ser Asn Leu Leu
                755               760               765

Leu Gln Tyr Gly Ser Phe Cys Thr Gln Leu Asn Arg Ala Leu Thr Gly
        770               775               780

Ile Ala Ile Glu Gln Asp Lys Asn Thr Gln Glu Val Phe Ala Gln Val
785               790               795               800

Lys Gln Met Tyr Lys Thr Pro Ala Ile Lys Asp Phe Gly Gly Phe Asn
                805               810               815

Phe Ser Gln Ile Leu Pro Asp Pro Ser Lys Pro Thr Lys Arg Ser Phe
                820               825               830

Ile Glu Asp Leu Leu Phe Asn Lys Val Thr Leu Ala Asp Ala Gly Phe
        835               840               845
```

-continued

```
Met Lys Gln Tyr Gly Glu Cys Leu Gly Asp Ile Ser Ala Arg Asp Leu
    850             855             860

Ile Cys Ala Gln Lys Phe Asn Gly Leu Thr Val Leu Pro Pro Leu Leu
865             870             875             880

Thr Asp Glu Met Ile Ala Ala Tyr Thr Ala Ala Leu Val Ser Gly Thr
                885             890             895

Ala Thr Ala Gly Trp Thr Phe Gly Ala Gly Ala Ala Leu Gln Ile Pro
            900             905             910

Phe Ala Met Gln Met Ala Tyr Arg Phe Asn Gly Ile Gly Val Thr Gln
        915             920             925

Asn Val Leu Tyr Glu Asn Gln Lys Gln Ile Ala Asn Gln Phe Asn Lys
    930             935             940

Ala Ile Ser Gln Ile Gln Glu Ser Leu Thr Thr Thr Ser Thr Ala Leu
945             950             955             960

Gly Lys Leu Gln Asp Val Val Asn Gln Asn Ala Gln Ala Leu Asn Thr
            965             970             975

Leu Val Lys Gln Leu Ser Ser Asn Phe Gly Ala Ile Ser Ser Val Leu
            980             985             990

Asn Asp Ile Leu Ser Arg Leu Asp  Lys Val Glu Ala Glu  Val Gln Ile
        995             1000            1005

Asp Arg  Leu Ile Thr Gly Arg  Leu Gln Ser Leu Gln  Thr Tyr Val
    1010            1015            1020

Thr Gln  Gln Leu Ile Arg Ala  Ala Glu Ile Arg Ala  Ser Ala Asn
    1025            1030            1035

Leu Ala  Ala Thr Lys Met Ser  Glu Cys Val Leu Gly  Gln Ser Lys
    1040            1045            1050

Arg Val  Asp Phe Cys Gly Lys  Gly Tyr His Leu Met  Ser Phe Pro
    1055            1060            1065

Gln Ala  Ala Pro His Gly Val  Val Phe Leu His Val  Thr Tyr Val
    1070            1075            1080

Pro Ser  Gln Glu Arg Asn Phe  Thr Thr Ala Pro Ala  Ile Cys His
    1085            1090            1095

Glu Gly  Lys Ala Tyr Phe Pro  Arg Glu Gly Val Phe  Val Ser Asn
    1100            1105            1110

Gly Thr  Ser Trp Phe Ile Thr  Gln Arg Asn Phe Tyr  Ser Pro Gln
    1115            1120            1125

Ile Ile  Thr Thr Asp Asn Thr  Phe Val Ser Gly Asn  Cys Asp Val
    1130            1135            1140

Val Ile  Gly Ile Ile Asn Asn  Thr Val Tyr Asp Pro  Leu Gln Pro
    1145            1150            1155

Glu Leu  Asp Ser Phe Lys Glu  Glu Leu Asp Lys Tyr  Phe Lys Asn
    1160            1165            1170

His Thr  Ser Pro Asp Val Asp  Leu Gly Asp Ile Ser
    1175            1180            1185
```

<210> SEQ ID NO 16
<211> LENGTH: 3555
<212> TYPE: DNA
<213> ORGANISM: Artificial Sequence
<220> FEATURE:
<223> OTHER INFORMATION: Coronavirus trS-protein designed sequence

<400> SEQUENCE: 16
atgtttctgt tcctcttcat tattatcttc gcattcttcc tgctgagcgc caaggccaac     60

-continued

```
gagagatgcg gcatcttcac cagcaagccc cagcctaagc tggcccaggt gtccagttct     120 agacgggcg tgtactaccc cgacgacatc ttcagatccg acgtgctgca tctgacccag     180
gactacttcc tgcctttcga cagcaacgtg acccggtact tcagcctgaa cgccaacgga     240
cccgaccgga tcgtgtactt cgacaaccct atcatcccct tcaaggacgg ggtgtacttt     300
gccgccaccg agaagtccaa cgtgatcaga ggctggatct tcggcagcac cctggacaat     360
accagccaga gcgtgatcat cgtgaacaac agcaccaacg tcatcatccg cgtgtgcaac     420
ttcgacctgt gcaacgaccc attcttcacc gtgtccagac caaccgacaa gcacatcaag     480
acctggtcca tccgcgagtt cgccgtgtac cagagcgcct tcaattgcac cttcgagtac     540
gtgtccaaga gctttctgct ggacgtggcc gagaagcccg gcaactttaa gcacctgaga     600
gaattcgtgt tcaagaacgt ggacggcttc ctgaacgtgt acagcaccta caagcccatc     660
aacgtggtgt ccggcctgcc tacaggattc agcgtgctga gcccatcct gaagctgccc     720 ctgggcatca acatcaccag cttcagagtg ctgctgacca tgttcagagg cgaccctaca     780
cctggccaca ccaccgctaa ttggctgaca gccgccgctg cctactacgt gggatacctg     840
aagcctacca ccttcatgct caagtacaac gagaacggca ccatcaccga cgccgtggac     900
tgtagccaaa atcctctggc cgagctgaag tgcaccctga agaacttcaa cgtggacaag     960
ggcatctacc agaccagcaa cttccgggtg tccctacac aagaggtcgt gcggttcccc    1020
aatatcacca atctgtgccc cttcgacaag gtgttcaacg ccaccagatt tcccagcgtg    1080
tacgcctggg agcgcaccaa gatttccgat tgcgtggccg actacaccgt gctgtataac    1140
tccacctcct tcagcacctt caagtgctac ggcgtgtccc caagcaagct gatcgatctg    1200
tgcttcacct ctgtgtacgc cgacaccttc ctgatccggt gtagcgaagt gcgacaggtg    1260
gcacctggac agacaggcgt gatcgccgat tacaactaca agctgcccga cgacttcacc    1320
ggctgtgtga tcgcctggaa taccgccaag caggatacag gcagcagcgg caactacaac    1380
tactactaca gaagccaccg caagaccaag ctgaagcctt cgagaggga cctgagcagc    1440 gacgagtgta gccctgatgg caagccttgt acacctcctg ccttcaatgg cgtgcggggc    1500
ttcaactgct acttcacct gagcacctac gacttcaacc ccaacgtgcc cgtggaatac    1560
caggccacaa gagtggtggt gctgagcttc gagctgctga atgcccctgc cacagtgtgt    1620
ggccctaagc tgtctaccca gctggtcaag aaccagtgcg tgaacttcaa tttcaacggc    1680
ctgaaaggca ccggcgtgct gaccgccagc agcaagagat tccagagctt ccagcagttc    1740
ggcagggacg ccagcgattt cacagatagc gtcagagatc cccagacact ggaaatcctg    1800
gacatcagcc cttgcagctt cggcggagtg tctgtgatca cccctggcac caatacctct    1860
agcgaggtgg cagtgctgta ccaggacgtg aactgcaccg atgtgcctac agccatccac    1920
gccgatcagc tgacaccagc ttggagagtg tactctaccg gtgtcaacgt gttccagaca    1980
caagccggct gtctgattgg agccaacac gtgaacgcca gctacgagtg cgacatccct    2040
atcggagccg gcatctgtgc ctcttaccac accgcctcta acagcccag aatcctgaga    2100 agcaccggcc agaaatccat cgtggcctac acaatgtctc tgggcgccga gaactctatc    2160
gcctacgcca acaactccat tgctatcccc accaacttca gcatctccgt gaccaccgaa    2220
gtgatgcctg tgtccatggc caagaccagc gtggactgca caatgtacat ctgcggcgac    2280
agcctggaat gcagcaacct gctgctccag tacggcagct tctgcaccca gctgaataga    2340
gccctgaccg gaatcgccat cgagcaggac aagaacaccc aagaggtgtt cgcccaagtg    2400
aagcagatgt ataagacccc tgccatcaag gacttcggcg gctttaactt cagccagatc    2460
```

-continued

```
ctgcctgatc ctagcaagcc caccaagcgg agcttcatcg aggacctgct gttcaacaaa    2520
gtgaccctgg ccgacgccgg ctttatgaag cagtatggcg agtgcctggg cgacatctct    2580
gccagggatc tgatttgcgc ccagaagttc aacggactga ccgtgctgcc tcctctgctg    2640
accgatgaga tgatcgccgc ctatacagcc gctctggtgt ctggcacagc taccgccgga    2700
tggacatttg agctggccgc cgctctccag attccattcg ctatgcagat ggcctaccgc    2760
ttcaacggca tcggcgtgac ccagaacgtg ctgtacgaga accagaagca gatcgccaac    2820
cagttcaaca aggccatcag tcagatccaa gagagcctga ccacaaccag cacagccctg    2880
ggaaagctcc aggacgtcgt gaaccagaat gcccaggctc tgaacaccct ggtcaagcag    2940
ctgagcagca atttcggcgc catcagctcc gtgctgaacg acatcctgag ccggctggat    3000
aaggtggaag ccgaggtgca gatcgaccgg ctgattacag cagactcca gtctctccag    3060 acctacgtga cacagcagct gatcagagcc gccgagatta gagcctctgc caatctggcc    3120
gccaccaaga tgtctgagtg tgtgctgggc cagtctaaga gagtggactt ctgcggcaag    3180
ggctaccacc tgatgagctt ccctcaggct gctcctcacg gcgtggtgtt tctgcacgtg    3240
acatacgtgc ccagccaaga gcggaacttc acaactgccc cagccatctg ccacgagggc    3300
aaagcctact ttcccagaga aggcgtgttc gtgtccaacg gcacctcctg gttcatcacc    3360
cagagaaact tctacagccc tcagatcatc accaccgaca acaccttcgt gtccggcaac    3420
tgcgacgtgg tcatcggcat catcaacaat accgtgtacg accctctcca gccagaactg    3480
gatagcttca agaggaact cgacaagtac ttcaagaatc acacaagccc cgacgtggac    3540
ctgggcgata tcagt                                                   3555
```

<210> SEQ ID NO 17
<211> LENGTH: 219
<212> TYPE: PRT
<213> ORGANISM: Artificial Sequence
<220> FEATURE:
<223> OTHER INFORMATION: Coronavirus S-protein RBD designed sequence

<400> SEQUENCE: 17

```
Arg Val Ser Pro Thr Gln Glu Val Val Arg Phe Pro Asn Ile Thr Asn
1               5                   10                  15

Leu Cys Pro Phe Asp Lys Val Phe Asn Ala Thr Arg Phe Pro Ser Val
            20                  25                  30

Tyr Ala Trp Glu Arg Thr Lys Ile Ser Asp Cys Val Ala Asp Tyr Thr
        35                  40                  45

Val Leu Tyr Asn Ser Thr Ser Phe Ser Thr Phe Lys Cys Tyr Gly Val
    50                  55                  60

Ser Pro Ser Lys Leu Ile Asp Leu Cys Phe Thr Ser Val Tyr Ala Asp
65                  70                  75                  80

Thr Phe Leu Ile Arg Cys Ser Glu Val Arg Gln Val Ala Pro Gly Gln
                85                  90                  95

Thr Gly Val Ile Ala Asp Tyr Asn Tyr Lys Leu Pro Asp Asp Phe Thr
            100                 105                 110

Gly Cys Val Ile Ala Trp Asn Thr Ala Lys Gln Asp Thr Gly Ser Ser
        115                 120                 125

Gly Asn Tyr Asn Tyr Tyr Tyr Arg Ser His Arg Lys Thr Lys Leu Lys
    130                 135                 140

Pro Phe Glu Arg Asp Leu Ser Ser Asp Glu Cys Ser Pro Asp Gly Lys
145                 150                 155                 160
```

-continued

```
Pro Cys Thr Pro Pro Ala Phe Asn Gly Val Arg Gly Phe Asn Cys Tyr
            165                 170                 175

Phe Thr Leu Ser Thr Tyr Asp Phe Asn Pro Asn Val Pro Val Glu Tyr
        180                 185                 190

Gln Ala Thr Arg Val Val Val Leu Ser Phe Glu Leu Leu Asn Ala Pro
    195                 200                 205

Ala Thr Val Cys Gly Pro Lys Leu Ser Thr Gln
    210                 215
```

```
<210> SEQ ID NO 18
<211> LENGTH: 657
<212> TYPE: DNA
<213> ORGANISM: Artificial Sequence
<220> FEATURE:
<223> OTHER INFORMATION: Coronavirus S-protein RBD designed sequence

<400> SEQUENCE: 18
cgggtgtccc ctacacaaga ggtcgtgcgg ttccccaata tcaccaatct gtgccccttc      60
gacaaggtgt tcaacgccac cagatttccc agcgtgtacg cctgggagcg caccaagatt     120
tccgattgcg tggccgacta caccgtgctg tataactcca cctccttcag caccttcaag     180
tgctacggcg tgtccccaag caagctgatc gatctgtgct tcacctctgt gtacgccgac     240
accttcctga tccggtgtag cgaagtgcga caggtggcac ctggacagac aggcgtgatc     300
gccgattaca actacaagct gcccgacgac ttcaccggct gtgtgatcgc ctggaatacc     360
gccaagcagg atacaggcag cagcggcaac tacaactact actacagaag ccaccgcaag     420
accaagctga agcctttcga gaggggacctg agcagcgacg agtgtagccc tgatggcaag     480
ccttgtacac ctcctgcctt caatggcgtg cggggcttca actgctactt caccctgagc     540
acctacgact tcaaccccaa cgtgcccgtg aataccaggg ccacaagagt ggtggtgctg     600
agcttcgagc tgctgaatgc ccctgccaca gtgtgtggcc ctaagctgtc taccccag      657
```

```
<210> SEQ ID NO 19
<211> LENGTH: 91
<212> TYPE: DNA
<213> ORGANISM: Artificial Sequence
<220> FEATURE:
<223> OTHER INFORMATION: pEVAC Multiple Cloning Site sequence

<400> SEQUENCE: 19
acagactgtt cctttccatg ggtcttttct gcagtcaccg tcggtaccgt cgacacgtgt      60
gatcatctag aggatccgcg gccgcagatc t                                     91
```

```
<210> SEQ ID NO 20
<211> LENGTH: 4405
<212> TYPE: DNA
<213> ORGANISM: Artificial Sequence
<220> FEATURE:
<223> OTHER INFORMATION: pEVAC sequence

<400> SEQUENCE: 20
tcgcgcgttt cggtgatgac ggtgaaaacc tctgacacat gcagctcccg gagacggtca      60
cagcttgtct gtaagcggat gccgggagca gacaagcccg tcaggcgcgc tcagcgggtg     120
ttggcgggtg tcgggctgg cttaactatg cggcatcaga gcagattgta ctgagagtgc     180
accatatgcg gtgtgaaata ccgcacagat gcgtaaggag aaaataccgc atcagattgg     240
ctattggcca ttgcatacgt tgtatccata tcataatatg tacatttata ttggctcatg     300
tccaacatta ccgccatgtt gacattgatt attgactagt tattaatagt aatcaattac     360
```

```
ggggtcatta gttcatagcc catatatgga gttccgcgtt acataactta cggtaaatgg      420
cccgcctggc tgaccgccca acgacccccg cccattgacg tcaataatga cgtatgttcc      480
catagtaacg ccaatacggga cttttccattg acgtcaatgg gtggagtatt tacggtaaac    540
tgcccacttg gcagtacatc aagtgtatca tatgccaagt acgcccccta ttgacgtcaa      600
tgacggtaaa tggcccgcct ggcattatgc ccagtacatg accttatggg actttcctac      660
ttggcagtac atctacgtat tagtcatcgc tattaccatg gtgatgcggt tttggcagta      720
catcaatggg cgtggatagc ggtttgactc acggggattt ccaagtctcc accccattga      780
cgtcaatggg agtttgtttt ggcaccaaaa tcaacgggac tttccaaaat gtcgtaacaa      840
ctccgcccca ttgacgcaaa tgggcggtag gcgtgtacgg tgggaggtct atataagcag      900
agctcgttta gtgaaccgtc agatcgcctg gagacgccat ccacgctgtt ttgacctcca      960
tagaagacac cgggaccgat ccagcctcca tcggctcgca tctctccttc acgcgcccgc     1020
cgccctacct gaggccgcca tccacgccgg ttgagtcgcg ttctgccgcc tcccgcctgt     1080
ggtgcctcct gaactgcgtc cgccgtctag gtaagtttaa agctcaggtc gagaccgggc     1140
ctttgtccgg cgctcccttg gagcctacct agactcagcc ggctctccac gctttgcctg     1200
accctgcttg ctcaactcta gttaacggtg gagggcagtg tagtctgagc agtactcgtt     1260
gctgccgcgc gcgccaccag acataatagc tgacagacta acagactgtt cctttccatg     1320
ggtcttttct gcagtcaccg tcggtaccgt cgacacgtgt gatcatctag aggatccgcg     1380
gccgcagatc tgctgtgcct tctagttgcc agccatctgt tgtttgcccc tccccgtgc      1440 cttccttgac cctggaaggt gccactccca ctgtcctttc ctaataaaat gaggaaattg     1500
catcgcattg tctgagtagg tgtcattcta ttctgggggg tggggtgggg caggacagca     1560 aggggagga ttgggaagac aatagcaggc atgctgggga tgcggtgggc tctatggcta     1620
cccaggtgct gaagaattga cccggttcct cctgggccag aaagaagcag gcacatcccc     1680
ttctctgtga cacaccctgt ccacgcccct ggttcttagt tccagcccca ctcataggac    1740
actcatagct caggagggct ccgccttcaa tcccacccgc taaagtactt ggagcggtct    1800
ctccctccct catcagccca ccaaaccaaa cctagcctcc aagagtggga agaaattaaa    1860
gcaagatagg ctattaagtg cagagggaga gaaaatgcct ccaacatgtg aggaagtaat    1920
gagagaaatc atagaatttt aaggccatga tttaaggcca tcatggcctt aatcttccgc    1980
ttcctcgctc actgactcgc tgcgctcggt cgttcggctg cggcgagcgg tatcagctca    2040
ctcaaaggcg gtaatacggt tatccacaga atcaggggat aacgcaggaa agaacatgtg    2100
agcaaaaggc cagcaaaagg ccaggaaccg taaaaaggcc gcgttgctgg cgtttttcca    2160
taggctccgc cccctgacg agcatcacaa aaatcgacgc tcaagtcaga ggtggcgaaa     2220
cccgacagga ctataaagat accaggcgtt tccccctgga agctccctcg tgcgctctcc    2280
tgttccgacc ctgccgctta ccggatacct gtccgccttt ctcccttcgg gaagcgtggc    2340
gctttctcat agctcacgct gtaggtatct cagttcggtg taggtcgttc gctccaagct    2400
gggctgtgtg cacgaacccc ccgttcagcc cgaccgctgc gccttatccg gtaactatcg    2460
tcttgagtcc aacccggtaa gacacgactt atcgccactg gcagcagcca ctggtaacag    2520
gattagcaga gcgaggtatg taggcggtgc tacagagttc ttgaagtggt ggcctaacta    2580
cggctacact agaagaacag tatttggtat ctgcgctctg ctgaagccag ttaccttcgg    2640
aaaaagagtt ggtagctctt gatccggcaa acaaaccacc gctggtagcg gtggtttttt    2700
```

-continued

```
tgtttgcaag cagcagatta cgcgcagaaa aaaaggatct caagaagatc ctttgatctt    2760
ttctacgggg tctgacgctc agtggaacga aaactcacgt taagggattt tggtcatgag    2820
attatcaaaa aggatcttca cctagatcct tttaaattaa aaatgaagtt ttaaatcaat    2880
ctaaagtata tatgagtaaa cttggtctga cagttaccaa tgcttaatca gtgaggcacc    2940
tatctcagcg atctgtctat ttcgttcatc catagttgcc tgactcgggg ggggggggcg    3000
ctgaggtctg cctcgtgaag aaggtgttgc tgactcatac caggcctgaa tcgccccatc    3060
atccagccag aaagtgaggg agccacggtt gatgagagct ttgttgtagg tggaccagtt    3120
ggtgattttg aacttttgct ttgccacgga acggtctgcg ttgtcgggaa gatgcgtgat    3180
ctgatccttc aactcagcaa aagttcgatt tattcaacaa agccgccgtc ccgtcaagtc    3240
agcgtaatgc tctgccagtg ttacaaccaa ttaaccaatt ctgattagaa aaactcatcg    3300
agcatcaaat gaaactgcaa tttattcata tcaggattat caataccata ttttttgaaaa    3360 agccgtttct gtaatgaagg agaaaactca ccgaggcagt tccataggat ggcaagatcc    3420
tggtatcggt ctgcgattcc gactcgtcca acatcaatac aacctattaa tttcccctcg    3480
tcaaaaataa ggttatcaag tgagaaatca ccatgagtga cgactgaatc cggtgagaat    3540
ggcaaaagct tatgcatttc tttccagact tgttcaacag gccagccatt acgctcgtca    3600
tcaaaatcac tcgcatcaac caaaccgtta ttcattcgtg attgcgcctg agcgagacga    3660
aatacgcgat cgctgttaaa aggacaatta caaacaggat cgaatgcaa ccggcgcagg    3720 aacactgcca gcgcatcaac aatattttca cctgaatcag gatattcttc taatacctgg    3780
aatgctgttt tcccggggat cgcagtggtg agtaaccatg catcatcagg agtacggata    3840
aaatgcttga tggtcggaag aggcataaat tccgtcagcc agtttagtct gaccatctca    3900
tctgtaacat cattggcaac gctacctttg ccatgtttca gaaacaactc tggcgcatcg    3960
ggcttcccat acaatcgata gattgtcgca cctgattgcc cgacattatc gcgagcccat    4020
ttatacccat ataaatcagc atccatgttg gaatttaatc gcggcctcga gcaagacgtt    4080
tcccgttgaa tatggctcat aacacccctt gtattactgt ttatgtaagc agacagtttt    4140
attgttcatg atgatatatt tttatcttgt gcaatgtaac atcagagatt ttgagacaca    4200
acgtggcttt cccccccccc ccattattga agcatttatc agggttattg tctcatgagc    4260
ggatacatat ttgaatgtat ttagaaaaat aaacaaatag gggttccgcg cacatttccc    4320
cgaaaagtgc cacctgacgt ctaagaaacc attattatca tgacattaac ctataaaaat    4380
aggcgtatca cgaggccctt cgtc                                           4405
```

<210> SEQ ID NO 21
<211> LENGTH: 76
<212> TYPE: PRT
<213> ORGANISM: Artificial Sequence
<220> FEATURE:
<223> OTHER INFORMATION: SARS envelope protein sequence

<400> SEQUENCE: 21

```
Met Tyr Ser Phe Val Ser Glu Glu Thr Gly Thr Leu Ile Val Asn Ser
1               5                   10                  15

Val Leu Leu Phe Leu Ala Phe Val Val Phe Leu Leu Val Thr Leu Ala
            20                  25                  30

Ile Leu Thr Ala Leu Arg Leu Cys Ala Tyr Cys Cys Asn Ile Val Asn
        35                  40                  45

Val Ser Leu Val Lys Pro Thr Val Tyr Val Tyr Ser Arg Val Lys Asn
    50                  55                  60
```

```
Leu Asn Ser Ser Glu Gly Val Pro Asp Leu Leu Val
65                  70              75

<210> SEQ ID NO 22
<211> LENGTH: 76
<212> TYPE: PRT
<213> ORGANISM: Artificial Sequence
<220> FEATURE:
<223> OTHER INFORMATION: Coronavirus envelope protein designed sequence

<400> SEQUENCE: 22

Met Tyr Ser Phe Val Ser Glu Glu Thr Gly Thr Leu Ile Val Asn Ser
1               5                   10                  15

Val Leu Leu Phe Leu Ala Phe Val Val Phe Leu Leu Val Thr Leu Ala
                20                  25                  30

Ile Leu Thr Ala Leu Arg Leu Cys Ala Tyr Cys Cys Asn Ile Val Asn
            35                  40                  45

Val Ser Leu Val Lys Pro Thr Phe Tyr Val Tyr Ser Arg Val Lys Asn
        50                  55                  60

Leu Asn Ser Ser Gln Gly Val Pro Asp Leu Leu Val
65                  70              75

<210> SEQ ID NO 23
<211> LENGTH: 75
<212> TYPE: PRT
<213> ORGANISM: Artificial Sequence
<220> FEATURE:
<223> OTHER INFORMATION: Coronavirus envelope protein designed sequence

<400> SEQUENCE: 23

Met Tyr Ser Phe Val Ser Glu Glu Thr Gly Thr Leu Ile Val Asn Ser
1               5                   10                  15

Val Leu Leu Phe Leu Ala Phe Val Val Phe Leu Leu Val Thr Leu Ala
                20                  25                  30

Ile Leu Thr Ala Leu Arg Leu Cys Ala Tyr Cys Cys Asn Ile Val Asn
            35                  40                  45

Val Ser Leu Val Lys Pro Thr Phe Tyr Val Tyr Ser Arg Val Lys Asn
        50                  55                  60

Leu Asn Ser Ser Arg Val Pro Asp Leu Leu Val
65                  70              75

<210> SEQ ID NO 24
<211> LENGTH: 221
<212> TYPE: PRT
<213> ORGANISM: Artificial Sequence
<220> FEATURE:
<223> OTHER INFORMATION: Coronavirus M protein designed sequence

<400> SEQUENCE: 24

Met Ala Asp Asn Gly Thr Ile Thr Val Glu Glu Leu Lys Gln Leu Leu
1               5                   10                  15

Glu Gln Trp Asn Leu Val Ile Gly Phe Leu Phe Leu Ala Trp Ile Met
                20                  25                  30

Leu Leu Gln Phe Ala Tyr Ser Asn Arg Asn Arg Phe Leu Tyr Ile Ile
            35                  40                  45

Lys Leu Val Phe Leu Trp Leu Leu Trp Pro Val Thr Leu Ala Cys Phe
        50                  55                  60

Val Leu Ala Ala Val Tyr Arg Ile Asn Trp Val Thr Gly Gly Ile Ala
65                  70                  75                  80
```

```
Ile Ala Met Ala Cys Ile Val Gly Leu Met Trp Leu Ser Tyr Phe Val
            85                  90                  95

Ala Ser Phe Arg Leu Phe Ala Arg Thr Arg Ser Met Trp Ser Phe Asn
            100                 105                 110

Pro Glu Thr Asn Ile Leu Leu Asn Val Pro Leu Arg Gly Thr Ile Leu
            115                 120                 125

Thr Arg Pro Leu Met Glu Ser Glu Leu Val Ile Gly Ala Val Ile Ile
    130                 135                 140

Arg Gly His Leu Arg Met Ala Gly His Ser Leu Gly Arg Cys Asp Ile
145                 150                 155                 160

Lys Asp Leu Pro Lys Glu Ile Thr Val Ala Thr Ser Arg Thr Leu Ser
            165                 170                 175

Tyr Tyr Lys Leu Gly Ala Ser Gln Arg Val Gly Thr Asp Ser Gly Phe
            180                 185                 190

Ala Ala Tyr Asn Arg Tyr Arg Ile Gly Asn Tyr Lys Leu Asn Thr Asp
            195                 200                 205

His Ala Gly Ser Asn Asp Asn Ile Ala Leu Leu Val Gln
    210                 215                 220

<210> SEQ ID NO 25
<211> LENGTH: 222
<212> TYPE: PRT
<213> ORGANISM: Artificial Sequence
<220> FEATURE:
<223> OTHER INFORMATION: Coronavirus M protein designed sequence

<400> SEQUENCE: 25

Met Ala Asp Ser Asn Gly Thr Ile Thr Val Glu Glu Leu Lys Lys Leu
1               5                   10                  15

Leu Glu Gln Trp Asn Leu Val Ile Gly Phe Leu Phe Leu Thr Trp Ile
            20                  25                  30

Cys Leu Leu Gln Phe Ala Tyr Ser Asn Arg Asn Arg Phe Leu Tyr Ile
            35                  40                  45

Ile Lys Leu Ile Phe Leu Trp Leu Leu Trp Pro Val Thr Leu Ala Cys
    50                  55                  60

Phe Val Leu Ala Ala Val Tyr Arg Ile Asn Trp Val Thr Gly Gly Ile
65                  70                  75                  80

Ala Ile Ala Met Ala Cys Ile Val Gly Leu Met Trp Leu Ser Tyr Phe
            85                  90                  95

Val Ala Ser Phe Arg Leu Phe Ala Arg Thr Arg Ser Met Trp Ser Phe
            100                 105                 110

Asn Pro Glu Thr Asn Ile Leu Leu Asn Val Pro Leu Arg Gly Ser Ile
            115                 120                 125

Ile Thr Arg Pro Leu Met Glu Ser Glu Leu Val Ile Gly Ala Val Ile
    130                 135                 140

Leu Arg Gly His Leu Arg Met Ala Gly His Ser Leu Gly Arg Cys Asp
145                 150                 155                 160

Ile Lys Asp Leu Pro Lys Glu Ile Thr Val Ala Thr Ser Arg Thr Leu
            165                 170                 175

Ser Tyr Tyr Lys Leu Gly Ala Ser Gln Arg Val Ala Ser Asp Ser Gly
            180                 185                 190

Phe Ala Val Tyr Asn Arg Tyr Arg Ile Gly Asn Tyr Lys Leu Asn Thr
            195                 200                 205

Asp His Ser Ser Ser Ser Asp Asn Ile Ala Leu Leu Val Gln
    210                 215                 220
```

-continued

```
<210> SEQ ID NO 26
<211> LENGTH: 222
<212> TYPE: PRT
<213> ORGANISM: Artificial Sequence
<220> FEATURE:
<223> OTHER INFORMATION: Coronavirus M protein reference sequence

<400> SEQUENCE: 26

Met Ala Asp Ser Asn Gly Thr Ile Thr Val Glu Glu Leu Lys Lys Leu
1               5                   10                  15

Leu Glu Gln Trp Asn Leu Val Ile Gly Phe Leu Phe Leu Thr Trp Ile
            20                  25                  30

Cys Leu Leu Gln Phe Ala Tyr Ala Asn Arg Asn Arg Phe Leu Tyr Ile
            35                  40                  45

Ile Lys Leu Ile Phe Leu Trp Leu Leu Trp Pro Val Thr Leu Ala Cys
        50                  55                  60

Phe Val Leu Ala Ala Val Tyr Arg Ile Asn Trp Ile Thr Gly Gly Ile
65                  70                  75                  80

Ala Ile Ala Met Ala Cys Leu Val Gly Leu Met Trp Leu Ser Tyr Phe
                85                  90                  95

Ile Ala Ser Phe Arg Leu Phe Ala Arg Thr Arg Ser Met Trp Ser Phe
                100                 105                 110

Asn Pro Glu Thr Asn Ile Leu Leu Asn Val Pro Leu His Gly Thr Ile
            115                 120                 125

Leu Thr Arg Pro Leu Leu Glu Ser Glu Leu Val Ile Gly Ala Val Ile
        130                 135                 140

Leu Arg Gly His Leu Arg Ile Ala Gly His His Leu Gly Arg Cys Asp
145                 150                 155                 160

Ile Lys Asp Leu Pro Lys Glu Ile Thr Val Ala Thr Ser Arg Thr Leu
                165                 170                 175

Ser Tyr Tyr Lys Leu Gly Ala Ser Gln Arg Val Ala Gly Asp Ser Gly
                180                 185                 190

Phe Ala Ala Tyr Ser Arg Tyr Arg Ile Gly Asn Tyr Lys Leu Asn Thr
            195                 200                 205

Asp His Ser Ser Ser Ser Asp Asn Ile Ala Leu Leu Val Gln
        210                 215                 220

<210> SEQ ID NO 27
<211> LENGTH: 214
<212> TYPE: PRT
<213> ORGANISM: Artificial Sequence
<220> FEATURE:
<223> OTHER INFORMATION: Coronavirus S-protein RBD designed sequence

<400> SEQUENCE: 27

Arg Val Ala Pro Thr Lys Glu Val Val Arg Phe Pro Asn Ile Thr Asn
1               5                   10                  15

Leu Cys Pro Phe Gly Glu Val Phe Asn Ala Thr Arg Phe Pro Ser Val
            20                  25                  30

Tyr Ala Trp Glu Arg Lys Arg Ile Ser Asn Cys Val Ala Asp Tyr Ser
            35                  40                  45

Val Leu Tyr Asn Ser Thr Ser Phe Ser Thr Phe Lys Cys Tyr Gly Val
        50                  55                  60

Ser Pro Thr Lys Leu Asn Asp Leu Cys Phe Thr Asn Val Tyr Ala Asp
65                  70                  75                  80

Ser Phe Val Ile Arg Gly Asp Glu Val Arg Gln Ile Ala Pro Gly Gln
                85                  90                  95
```

-continued

```
Thr Gly Val Ile Ala Asp Tyr Asn Tyr Lys Leu Pro Asp Asp Phe Thr
            100                 105                 110

Gly Cys Val Ile Ala Trp Asn Thr Asn Asn Leu Asp Ser Thr Thr Gly
            115                 120                 125

Gly Asn Tyr Asn Tyr Leu Tyr Arg Ser Leu Arg Lys Ser Lys Leu Lys
        130                 135                 140

Pro Phe Glu Arg Asp Ile Ser Ser Asp Ile Tyr Ser Pro Gly Gly Lys
145                 150                 155                 160

Pro Cys Ser Gly Val Glu Gly Phe Asn Cys Tyr Tyr Pro Leu Arg Ser
                165                 170                 175

Tyr Gly Phe Phe Pro Thr Asn Gly Val Gly Tyr Gln Pro Tyr Arg Val
            180                 185                 190

Val Val Leu Ser Phe Glu Leu Leu Asn Ala Pro Ala Thr Val Cys Gly
            195                 200                 205

Pro Lys Leu Ser Thr Asp
    210
```

```
<210> SEQ ID NO 28
<211> LENGTH: 214
<212> TYPE: PRT
<213> ORGANISM: Artificial Sequence
<220> FEATURE:
<223> OTHER INFORMATION: Coronavirus S-protein RBD designed sequence

<400> SEQUENCE: 28

Arg Val Ala Pro Thr Lys Glu Val Val Arg Phe Pro Asn Ile Thr Asn
1                 5                 10                 15

Leu Cys Pro Phe Gly Glu Val Phe Asn Ala Thr Lys Phe Pro Ser Val
            20                 25                 30

Tyr Ala Trp Glu Arg Lys Lys Ile Ser Asn Cys Val Ala Asp Tyr Ser
        35                 40                 45

Val Leu Tyr Asn Ser Thr Ser Phe Ser Thr Phe Lys Cys Tyr Gly Val
    50                 55                 60

Ser Pro Thr Lys Leu Asn Asp Leu Cys Phe Thr Asn Val Tyr Ala Asp
65                 70                 75                 80

Ser Phe Val Ile Arg Gly Asp Glu Val Arg Gln Ile Ala Pro Gly Gln
                85                 90                 95

Thr Gly Val Ile Ala Asp Tyr Asn Tyr Lys Leu Pro Asp Asp Phe Thr
            100                 105                 110

Gly Cys Val Ile Ala Trp Asn Thr Asn Asn Ile Asp Ser Thr Thr Gly
            115                 120                 125

Gly Asn Tyr Asn Tyr Leu Tyr Arg Ser Leu Arg Lys Ser Lys Leu Lys
        130                 135                 140

Pro Phe Glu Arg Asp Ile Ser Ser Asp Ile Tyr Ser Pro Gly Gly Lys
145                 150                 155                 160

Pro Cys Ser Gly Val Glu Gly Phe Asn Cys Tyr Tyr Pro Leu Arg Ser
                165                 170                 175

Tyr Gly Phe Phe Pro Thr Asn Gly Val Gly Tyr Gln Pro Tyr Arg Val
            180                 185                 190

Val Val Leu Ser Phe Glu Leu Leu Asn Ala Pro Ala Thr Val Cys Gly
            195                 200                 205

Pro Lys Leu Ser Thr Asp
    210
```

```
<210> SEQ ID NO 29
```

-continued

```
<211> LENGTH: 214
<212> TYPE: PRT
<213> ORGANISM: Artificial Sequence
<220> FEATURE:
<223> OTHER INFORMATION: Coronavirus S-protein RBD designed sequence

<400> SEQUENCE: 29

Arg Val Ala Pro Thr Lys Glu Val Val Arg Phe Pro Asn Ile Thr Asn
1               5                   10                  15

Leu Cys Pro Phe Gly Glu Val Phe Asn Ala Thr Arg Phe Pro Ser Val
            20                  25                  30

Tyr Ala Trp Glu Arg Lys Arg Ile Ser Asn Cys Val Ala Asp Tyr Ser
        35                  40                  45

Val Leu Tyr Asn Ser Thr Phe Phe Ser Thr Phe Lys Cys Tyr Gly Val
    50                  55                  60

Ser Pro Thr Lys Leu Asn Asp Leu Cys Phe Ser Asn Val Tyr Ala Asp
65                  70                  75                  80

Ser Phe Val Ile Arg Gly Asp Glu Val Arg Gln Ile Ala Pro Gly Gln
                85                  90                  95

Thr Gly Val Ile Ala Asp Tyr Asn Tyr Lys Leu Pro Asp Asp Phe Met
            100                 105                 110

Gly Cys Val Ile Ala Trp Asn Thr Asn Asn Leu Asp Ser Thr Thr Gly
        115                 120                 125

Gly Asn Tyr Asn Tyr Leu Tyr Arg Ser Leu Arg Lys Ser Lys Leu Lys
    130                 135                 140

Pro Phe Glu Arg Asp Ile Ser Ser Asp Ile Tyr Ser Pro Gly Gly Lys
145                 150                 155                 160

Pro Cys Ser Gly Val Glu Gly Phe Asn Cys Tyr Tyr Pro Leu Arg Ser
            165                 170                 175

Tyr Gly Phe Phe Pro Thr Asn Gly Val Gly Tyr Gln Pro Tyr Arg Val
        180                 185                 190

Val Val Leu Ser Phe Glu Leu Leu Asn Ala Pro Ala Thr Val Cys Gly
        195                 200                 205

Pro Lys Leu Ser Thr Asp
    210

<210> SEQ ID NO 30
<211> LENGTH: 214
<212> TYPE: PRT
<213> ORGANISM: Artificial Sequence
<220> FEATURE:
<223> OTHER INFORMATION: Coronavirus S-protein RBD designed sequence

<400> SEQUENCE: 30

Arg Val Ala Pro Thr Lys Glu Val Val Arg Phe Pro Asn Ile Thr Asn
1               5                   10                  15

Leu Cys Pro Phe Gly Glu Val Phe Asn Ala Thr Arg Phe Pro Ser Val
            20                  25                  30

Tyr Ala Trp Glu Arg Lys Arg Ile Ser Asn Cys Val Ala Asp Tyr Ser
        35                  40                  45

Val Leu Tyr Asn Ser Thr Ser Phe Ser Thr Phe Lys Cys Tyr Gly Val
    50                  55                  60

Ser Pro Thr Lys Leu Asn Asp Leu Cys Phe Thr Asn Val Tyr Ala Asp
65                  70                  75                  80

Ser Phe Val Ile Arg Gly Asp Glu Val Arg Gln Ile Ala Pro Gly Gln
                85                  90                  95

Thr Gly Lys Ile Ala Asp Tyr Asn Tyr Lys Leu Pro Asp Asp Phe Thr
```

-continued

```
              100               105                110

Gly Cys Val Ile Ala Trp Asn Thr Asn Asn Leu Asp Ser Thr Thr Gly
         115               120               125

Gly Asn Tyr Asn Tyr Leu Tyr Arg Leu Phe Arg Lys Ser Asn Leu Lys
     130               135               140

Pro Phe Glu Arg Asp Ile Ser Ser Asp Ile Tyr Gln Ala Gly Ser Thr
145               150               155               160

Pro Cys Ser Gly Val Glu Gly Phe Asn Cys Tyr Phe Pro Leu Gln Ser
             165               170               175

Tyr Gly Phe Gln Pro Thr Asn Gly Val Gly Tyr Gln Pro Tyr Arg Val
             180               185               190

Val Val Leu Ser Phe Glu Leu Leu Asn Ala Pro Ala Thr Val Cys Gly
         195               200               205

Pro Lys Leu Ser Thr Asp
    210

<210> SEQ ID NO 31
<211> LENGTH: 214
<212> TYPE: PRT
<213> ORGANISM: Artificial Sequence
<220> FEATURE:
<223> OTHER INFORMATION: Coronavirus S-protein RBD designed sequence

<400> SEQUENCE: 31

Arg Val Ala Pro Thr Lys Glu Val Val Arg Phe Pro Asn Ile Thr Asn
1               5                10                15

Leu Cys Pro Phe Gly Glu Val Phe Asn Ala Thr Lys Phe Pro Ser Val
         20                25                30

Tyr Ala Trp Glu Arg Lys Lys Ile Ser Asn Cys Val Ala Asp Tyr Ser
         35                40                45

Val Leu Tyr Asn Ser Thr Ser Phe Ser Thr Phe Lys Cys Tyr Gly Val
     50                55                60

Ser Pro Thr Lys Leu Asn Asp Leu Cys Phe Thr Asn Val Tyr Ala Asp
65                70                75                80

Ser Phe Val Ile Arg Gly Asp Glu Val Arg Gln Ile Ala Pro Gly Gln
             85                90                95

Thr Gly Val Ile Ala Asp Tyr Asn Tyr Lys Leu Pro Asp Asp Phe Thr
             100               105               110

Gly Cys Val Ile Ala Trp Asn Thr Asn Asn Ile Asp Ser Thr Thr Gly
         115               120               125

Gly Asn Tyr Asn Tyr Leu Tyr Arg Ser Leu Arg Lys Ser Lys Leu Lys
     130               135               140

Pro Phe Glu Arg Asp Ile Ser Ser Asp Ile Tyr Ser Pro Gly Gly Lys
145               150               155               160

Pro Cys Ser Gly Val Glu Gly Phe Asn Cys Tyr Tyr Pro Leu Arg Ser
             165               170               175

Tyr Gly Phe Phe Pro Thr Asn Gly Thr Gly Tyr Gln Pro Tyr Arg Val
             180               185               190

Val Val Leu Ser Phe Glu Leu Leu Asn Ala Pro Ala Thr Val Cys Gly
         195               200               205

Pro Lys Leu Ser Thr Asp
    210

<210> SEQ ID NO 32
<211> LENGTH: 214
<212> TYPE: PRT
```

-continued

```
<213> ORGANISM: Artificial Sequence
<220> FEATURE:
<223> OTHER INFORMATION: Coronavirus S-protein RBD designed sequence

<400> SEQUENCE: 32

Arg Val Ala Pro Thr Lys Glu Val Val Arg Phe Pro Asn Ile Thr Asn
1               5                   10                  15

Leu Cys Pro Phe Gly Glu Val Phe Asn Ala Thr Arg Phe Pro Ser Val
            20                  25                  30

Tyr Ala Trp Glu Arg Lys Arg Ile Ser Asn Cys Val Ala Asp Tyr Ser
            35                  40                  45

Val Leu Tyr Asn Ser Thr Phe Phe Ser Thr Phe Lys Cys Tyr Gly Val
    50                  55                  60

Ser Pro Thr Lys Leu Asn Asp Leu Cys Phe Ser Asn Val Tyr Ala Asp
65                  70                  75                  80

Ser Phe Val Ile Arg Gly Asp Glu Val Arg Gln Ile Ala Pro Gly Gln
                85                  90                  95

Thr Gly Val Ile Ala Asp Tyr Asn Tyr Lys Leu Pro Asp Asp Phe Met
            100                 105                 110

Gly Cys Val Ile Ala Trp Asn Thr Asn Asn Leu Asp Ser Thr Thr Gly
            115                 120                 125

Gly Asn Tyr Asn Tyr Leu Tyr Arg Ser Leu Arg Lys Ser Lys Leu Lys
    130                 135                 140

Pro Phe Glu Arg Asp Ile Ser Ser Asp Ile Tyr Ser Pro Gly Gly Lys
145                 150                 155                 160

Pro Cys Ser Gly Val Glu Gly Phe Asn Cys Tyr Tyr Pro Leu Arg Ser
            165                 170                 175

Tyr Gly Phe Phe Pro Thr Asn Gly Thr Gly Tyr Gln Pro Tyr Arg Val
            180                 185                 190

Val Val Leu Ser Phe Glu Leu Leu Asn Ala Pro Ala Thr Val Cys Gly
        195                 200                 205

Pro Lys Leu Ser Thr Asp
    210

<210> SEQ ID NO 33
<211> LENGTH: 214
<212> TYPE: PRT
<213> ORGANISM: Artificial Sequence
<220> FEATURE:
<223> OTHER INFORMATION: Coronavirus S-protein RBD designed sequence
<220> FEATURE:
<221> NAME/KEY: MISC_FEATURE
<222> LOCATION: (203)..(203)
<223> OTHER INFORMATION: Glycosylation site introduced at this residue

<400> SEQUENCE: 33

Arg Val Gln Pro Thr Glu Ser Ile Val Arg Phe Pro Asn Ile Thr Asn
1               5                   10                  15

Leu Cys Pro Phe Gly Glu Val Phe Asn Ala Thr Arg Phe Ala Ser Val
            20                  25                  30

Tyr Ala Trp Asn Arg Lys Arg Ile Ser Asn Cys Val Ala Asp Tyr Ser
            35                  40                  45

Val Leu Tyr Asn Ser Ala Ser Phe Ser Thr Phe Lys Cys Tyr Gly Val
    50                  55                  60

Ser Pro Thr Lys Leu Asn Asp Leu Cys Phe Thr Asn Val Tyr Ala Asp
65                  70                  75                  80

Ser Phe Val Ile Arg Gly Asp Glu Val Arg Gln Ile Ala Pro Gly Gln
                85                  90                  95
```

```
Thr Gly Lys Ile Ala Asp Tyr Asn Tyr Lys Leu Pro Asp Asp Phe Thr
            100                 105                 110

Gly Cys Val Ile Ala Trp Asn Ser Asn Asn Leu Asp Ser Lys Val Gly
            115                 120                 125

Gly Asn Tyr Asn Tyr Leu Tyr Arg Leu Phe Arg Lys Ser Asn Leu Lys
    130                 135                 140

Pro Phe Glu Arg Asp Ile Ser Thr Glu Ile Tyr Gln Ala Gly Ser Thr
145                 150                 155                 160

Pro Cys Asn Gly Val Glu Gly Phe Asn Cys Tyr Phe Pro Leu Gln Ser
                165                 170                 175

Tyr Gly Phe Gln Pro Thr Asn Gly Val Gly Tyr Gln Pro Tyr Arg Val
            180                 185                 190

Val Val Leu Ser Phe Glu Leu Leu His Ala Asn Ala Thr Val Cys Gly
            195                 200                 205

Pro Lys Lys Ser Thr Asn
    210
```

<210> SEQ ID NO 34
<211> LENGTH: 214
<212> TYPE: PRT
<213> ORGANISM: Artificial Sequence
<220> FEATURE:
<223> OTHER INFORMATION: Coronavirus S-protein RBD designed sequence
<220> FEATURE:
<221> NAME/KEY: MISC_FEATURE
<222> LOCATION: (13)..(13)
<223> OTHER INFORMATION: Glycosylation site deleted at this residue
<220> FEATURE:
<221> NAME/KEY: MISC_FEATURE
<222> LOCATION: (25)..(25)
<223> OTHER INFORMATION: Glycosylation site deleted at this residue
<220> FEATURE:
<221> NAME/KEY: MISC_FEATURE
<222> LOCATION: (54)..(54)
<223> OTHER INFORMATION: Glycosylation site introduced at this residue

<400> SEQUENCE: 34

```
Arg Val Gln Pro Thr Glu Ser Ile Val Arg Phe Pro Gln Ile Thr Asn
1               5                   10                  15

Leu Cys Pro Phe Gly Glu Val Phe Gln Ala Thr Arg Phe Ala Ser Val
            20                  25                  30

Tyr Ala Trp Asn Arg Lys Arg Ile Ser Asn Cys Val Ala Asp Tyr Ser
            35                  40                  45

Val Leu Tyr Asn Ser Thr Ser Phe Ser Thr Phe Lys Cys Tyr Gly Val
    50                  55                  60

Ser Pro Thr Lys Leu Asn Asp Leu Cys Phe Thr Asn Val Tyr Ala Asp
65                  70                  75                  80

Ser Phe Val Ile Arg Gly Asp Glu Val Arg Gln Ile Ala Pro Gly Gln
                85                  90                  95

Thr Gly Lys Ile Ala Asp Tyr Asn Tyr Lys Leu Pro Asp Asp Phe Thr
            100                 105                 110

Gly Cys Val Ile Ala Trp Asn Ser Asn Asn Leu Asp Ser Lys Val Gly
            115                 120                 125

Gly Asn Tyr Asn Tyr Leu Tyr Arg Leu Phe Arg Lys Ser Asn Leu Lys
    130                 135                 140

Pro Phe Glu Arg Asp Ile Ser Thr Glu Ile Tyr Gln Ala Gly Ser Thr
145                 150                 155                 160

Pro Cys Asn Gly Val Glu Gly Phe Asn Cys Tyr Phe Pro Leu Gln Ser
                165                 170                 175
```

-continued

```
Tyr Gly Phe Gln Pro Thr Asn Gly Val Gly Tyr Gln Pro Tyr Arg Val
            180                 185                 190

Val Val Leu Ser Phe Glu Leu Leu His Ala Pro Ala Thr Val Cys Gly
        195                 200                 205

Pro Lys Lys Ser Thr Asn
    210

<210> SEQ ID NO 35
<211> LENGTH: 219
<212> TYPE: PRT
<213> ORGANISM: Artificial Sequence
<220> FEATURE:
<223> OTHER INFORMATION: Coronavirus S-protein RBD designed sequence
<220> FEATURE:
<221> NAME/KEY: MISC_FEATURE
<222> LOCATION: (203)..(203)
<223> OTHER INFORMATION: Glycosylation site introduced at this residue

<400> SEQUENCE: 35

Arg Val Ser Pro Thr Gln Glu Val Val Arg Phe Pro Asn Ile Thr Asn
1               5                   10                  15

Leu Cys Pro Phe Asp Lys Val Phe Asn Ala Thr Arg Phe Pro Ser Val
            20                  25                  30

Tyr Ala Trp Glu Arg Thr Lys Ile Ser Asp Cys Val Ala Asp Tyr Thr
        35                  40                  45

Val Leu Tyr Asn Ser Thr Ser Phe Ser Thr Phe Lys Cys Tyr Gly Val
    50                  55                  60

Ser Pro Ser Lys Leu Ile Asp Leu Cys Phe Thr Ser Val Tyr Ala Asp
65                  70                  75                  80

Thr Phe Leu Ile Arg Cys Ser Glu Val Arg Gln Val Ala Pro Gly Gln
            85                  90                  95

Thr Gly Val Ile Ala Asp Tyr Asn Tyr Lys Leu Pro Asp Asp Phe Thr
            100                 105                 110

Gly Cys Val Ile Ala Trp Asn Thr Ala Lys Gln Asp Thr Gly Ser Ser
            115                 120                 125

Gly Asn Tyr Asn Tyr Tyr Tyr Arg Ser His Arg Lys Thr Lys Leu Lys
        130                 135                 140

Pro Phe Glu Arg Asp Leu Ser Ser Asp Glu Cys Ser Pro Asp Gly Lys
145                 150                 155                 160

Pro Cys Thr Pro Pro Ala Phe Asn Gly Val Arg Gly Phe Asn Cys Tyr
                165                 170                 175

Phe Thr Leu Ser Thr Tyr Asp Phe Asn Pro Asn Val Pro Val Glu Tyr
            180                 185                 190

Gln Ala Thr Arg Val Val Val Leu Ser Phe Glu Leu Leu Asn Ala Asn
        195                 200                 205

Ala Thr Val Cys Gly Pro Lys Leu Ser Thr Gln
    210                 215

<210> SEQ ID NO 36
<211> LENGTH: 219
<212> TYPE: PRT
<213> ORGANISM: Artificial Sequence
<220> FEATURE:
<223> OTHER INFORMATION: Coronavirus S-protein RBD designed sequence
<220> FEATURE:
<221> NAME/KEY: MISC_FEATURE
<222> LOCATION: (13)..(13)
<223> OTHER INFORMATION: Glycosylation site deleted at this residue
<220> FEATURE:
<221> NAME/KEY: MISC_FEATURE
```

-continued

```
<222> LOCATION: (25)..(25)
<223> OTHER INFORMATION: Glycosylation site deleted at this residue

<400> SEQUENCE: 36

Arg Val Ser Pro Thr Gln Glu Val Val Arg Phe Pro Gln Ile Thr Asn
1               5                   10                  15

Leu Cys Pro Phe Asp Lys Val Phe Gln Ala Thr Arg Phe Pro Ser Val
            20                  25                  30

Tyr Ala Trp Glu Arg Thr Lys Ile Ser Asp Cys Val Ala Asp Tyr Thr
        35                  40                  45

Val Leu Tyr Asn Ser Thr Ser Phe Ser Thr Phe Lys Cys Tyr Gly Val
    50                  55                  60

Ser Pro Ser Lys Leu Ile Asp Leu Cys Phe Thr Ser Val Tyr Ala Asp
65                  70                  75                  80

Thr Phe Leu Ile Arg Cys Ser Glu Val Arg Gln Val Ala Pro Gly Gln
                85                  90                  95

Thr Gly Val Ile Ala Asp Tyr Asn Tyr Lys Leu Pro Asp Asp Phe Thr
            100                 105                 110

Gly Cys Val Ile Ala Trp Asn Thr Ala Lys Gln Asp Thr Gly Ser Ser
            115                 120                 125

Gly Asn Tyr Asn Tyr Tyr Tyr Arg Ser His Arg Lys Thr Lys Leu Lys
        130                 135                 140

Pro Phe Glu Arg Asp Leu Ser Ser Asp Glu Cys Ser Pro Asp Gly Lys
145                 150                 155                 160

Pro Cys Thr Pro Pro Ala Phe Asn Gly Val Arg Gly Phe Asn Cys Tyr
                165                 170                 175

Phe Thr Leu Ser Thr Tyr Asp Phe Asn Pro Asn Val Pro Val Glu Tyr
            180                 185                 190

Gln Ala Thr Arg Val Val Val Leu Ser Phe Glu Leu Leu Asn Ala Pro
        195                 200                 205

Ala Thr Val Cys Gly Pro Lys Leu Ser Thr Gln
    210                 215

<210> SEQ ID NO 37
<211> LENGTH: 642
<212> TYPE: DNA
<213> ORGANISM: Artificial Sequence
<220> FEATURE:
<223> OTHER INFORMATION: Coronavirus S-protein RBD designed sequence

<400> SEQUENCE: 37
cgggtgcagc caccgaatc catcgtgcgg ttccccaata tcaccaatct gtgcccttc       60 ggcgaggtgt tcaatgccac cagattcgcc tctgtgtacg cctggaaccg gaagcggatc     120
agcaattgcg tggccgacta ctccgtgctg tacaactccg ccagcttcag caccttcaag     180
tgctacggcg tgtcccctac caagctgaac gacctgtgct tcacaaacgt gtacgccgac     240
agcttcgtga tccggggaga tgaagtgcgg cagattgccc ctggacgac aggcaagatc      300 gccgactaca actacaagct gcccgacgac ttcaccggct gtgtgattgc ctggaacagc     360
aacaacctgg actccaaagt cggcggcaac tacaattacc tgtaccggct gttccggaag     420
tccaatctga gcccttcga gcgggacatc agcaccgaaa tctatcaggc cggcagcacc      480
ccttgcaacg gcgtggaagg cttcaactgc tacttccac tgcaaagcta cggctttcag      540
cccacaaatg gcgtgggcta ccagccttac agagtggtgg tgctgagctt cgagctgctg     600
catgctaacg ccacagtgtg cggccctaag aaatccacca at                       642
```

```
<210> SEQ ID NO 38
<211> LENGTH: 642
<212> TYPE: DNA
<213> ORGANISM: Artificial Sequence
<220> FEATURE:
<223> OTHER INFORMATION: Coronavirus S-protein RBD designed sequence

<400> SEQUENCE: 38
cgggtgcagc ccaccgaatc catcgtgcgg ttcccccaga tcaccaatct gtgccccttc      60
ggcgaggtgt tccaggccac cagattcgcc tctgtgtacg cctggaaccg gaagcggatc     120
agcaattgcg tggccgacta ctccgtgctg tacaactcca ccagcttcag caccttcaag     180
tgctacggcg tgtcccctac caagctgaac gacctgtgct tcacaaacgt gtacgccgac     240
agcttcgtga tccgggggaga tgaagtgcgg cagattgccc ctggacagac aggcaagatc     300
gccgactaca actacaagct gcccgacgac ttcaccggct gtgtgattgc ctggaacagc     360
aacaacctgg actccaaagt cggcggcaac tacaattacc tgtaccggct gttccggaag     420
tccaatctga gcccttcga gcgggacatc agcaccgaaa tctatcaggc cggcagcacc     480
ccttgcaacg gcgtggaagg cttcaactgc tacttccac tgcaaagcta cggctttcag     540
cccacaaatg gcgtgggcta ccagccttac agagtggtgg tgctgagctt cgagctgctg     600
catgctcctg ccacagtgtg cggccctaag aaatccacca at                       642

<210> SEQ ID NO 39
<211> LENGTH: 657
<212> TYPE: DNA
<213> ORGANISM: Artificial Sequence
<220> FEATURE:
<223> OTHER INFORMATION: Coronavirus S-protein RBD designed sequence

<400> SEQUENCE: 39
cgggtgtccc ctacacaaga ggtcgtgcgg ttccccaata tcaccaatct gtgcccccttc    60 gacaaggtgt tcaacgccac cagatttccc agcgtgtacg cctgggagcg caccaagatt    120
tccgattgcg tggccgacta caccgtgctg tataactcca cctccttcag caccttcaag    180
tgctacggcg tgtccccaag caagctgatc gatctgtgct tcacctctgt gtacgccgac    240
accttcctga tccggtgtag cgaagtgcga caggtggcac ctggacagac aggcgtgatc    300
gccgattaca actacaagct gcccgacgac ttcaccggct gtgtgatcgc ctggaatacc    360
gccaagcagg atacaggcag cagcggcaac tacaactact actacagaag ccaccgcaag    420
accaagctga gcctttcga gagggacctg agcagcgacg agtgtagccc tgatggcaag    480
ccttgtacac ctcctgcctt caatggcgtg cggggcttca actgctactt caccctgagc    540
acctacgact tcaacccca cgtgcccgtg aataccagg ccacaagagt ggtggtgctg      600
agcttcgagc tgctgaatgc caacgccaca gtgtgtggcc ctaagctgtc tacccag       657

<210> SEQ ID NO 40
<211> LENGTH: 657
<212> TYPE: DNA
<213> ORGANISM: Artificial Sequence
<220> FEATURE:
<223> OTHER INFORMATION: Coronavirus S-protein RBD designed sequence

<400> SEQUENCE: 40
cgggtgtccc ctacacaaga ggtcgtgcgg ttcccccaga tcaccaatct gtgccccttc     60
gacaaggtgt tccaggccac cagatttccc agcgtgtacg cctgggagcg caccaagatt    120
tccgattgcg tggccgacta caccgtgctg tataactcca cctccttcag caccttcaag    180
```

-continued

```
tgctacggcg tgtccccaag caagctgatc gatctgtgct tcacctctgt gtacgccgac    240
accttcctga tccggtgtag cgaagtgcga caggtggcac ctggacagac aggcgtgatc    300
gccgattaca actacaagct gcccgacgac ttcaccggct gtgtgatcgc ctggaatacc    360
gccaagcagg atacaggcag cagcggcaac tacaactact actacagaag ccaccgcaag    420
accaagctga agcctttcga gagggacctg agcagcgacg agtgtagccc tgatggcaag    480
ccttgtacac ctcctgcctt caatggcgtg cggggcttca actgctactt caccctgagc    540
acctacgact tcaaccccaa cgtgcccgtg aataccagg ccacaagagt ggtggtgctg     600
agcttcgagc tgctgaatgc ccctgccaca gtgtgtggcc ctaagctgtc tacccag      657
```

```
<210> SEQ ID NO 41
<211> LENGTH: 75
<212> TYPE: PRT
<213> ORGANISM: Artificial Sequence
<220> FEATURE:
<223> OTHER INFORMATION: SARS2 envelope protein reference sequence

<400> SEQUENCE: 41

Met Tyr Ser Phe Val Ser Glu Glu Thr Gly Thr Leu Ile Val Asn Ser
1               5                   10                  15

Val Leu Leu Phe Leu Ala Phe Val Val Phe Leu Leu Val Thr Leu Ala
            20                  25                  30

Ile Leu Thr Ala Leu Arg Leu Cys Ala Tyr Cys Cys Asn Ile Val Asn
        35                  40                  45

Val Ser Leu Val Lys Pro Ser Phe Tyr Val Tyr Ser Arg Val Lys Asn
    50                  55                  60

Leu Asn Ser Ser Arg Val Pro Asp Leu Leu Val
65                  70                  75
```

```
<210> SEQ ID NO 42
<211> LENGTH: 75
<212> TYPE: PRT
<213> ORGANISM: Artificial Sequence
<220> FEATURE:
<223> OTHER INFORMATION: Coronavirus envelope protein designed sequence

<400> SEQUENCE: 42

Met Tyr Ser Phe Val Ser Glu Glu Thr Gly Thr Leu Ile Val Ala Ser
1               5                   10                  15

Val Leu Leu Phe Leu Ala Phe Val Val Phe Leu Leu Val Thr Leu Ala
            20                  25                  30

Ile Leu Thr Ala Leu Arg Leu Cys Ala Tyr Cys Cys Asn Ile Val Asn
        35                  40                  45

Val Ser Leu Val Lys Pro Ser Phe Tyr Val Tyr Ser Arg Val Lys Asn
    50                  55                  60

Leu Asn Ser Ser Arg Val Pro Asp Leu Leu Val
65                  70                  75
```

```
<210> SEQ ID NO 43
<211> LENGTH: 76
<212> TYPE: PRT
<213> ORGANISM: Artificial Sequence
<220> FEATURE:
<223> OTHER INFORMATION: Coronavirus envelope protein designed sequence

<400> SEQUENCE: 43

Met Tyr Ser Phe Val Ser Glu Glu Thr Gly Thr Leu Ile Val Ala Ser
1               5                   10                  15
```

```
Val Leu Leu Phe Leu Ala Phe Val Val Phe Leu Leu Val Thr Leu Ala
            20                  25                  30

Ile Leu Thr Ala Leu Arg Leu Cys Ala Tyr Cys Cys Asn Ile Val Asn
            35                  40                  45

Val Ser Leu Val Lys Pro Thr Phe Tyr Val Tyr Ser Arg Val Lys Asn
        50                  55                  60

Leu Asn Ser Ser Gln Gly Val Pro Asp Leu Leu Val
65                  70                  75

<210> SEQ ID NO 44
<211> LENGTH: 75
<212> TYPE: PRT
<213> ORGANISM: Artificial Sequence
<220> FEATURE:
<223> OTHER INFORMATION: Coronavirus envelope protein designed sequence

<400> SEQUENCE: 44

Met Tyr Ser Phe Val Ser Glu Glu Thr Gly Thr Leu Ile Val Ala Ser
1               5                  10                  15

Val Leu Leu Phe Leu Ala Phe Val Val Phe Leu Leu Val Thr Leu Ala
            20                  25                  30

Ile Leu Thr Ala Leu Arg Leu Cys Ala Tyr Cys Cys Asn Ile Val Asn
            35                  40                  45

Val Ser Leu Val Lys Pro Thr Phe Tyr Val Tyr Ser Arg Val Lys Asn
        50                  55                  60

Leu Asn Ser Ser Arg Val Pro Asp Leu Leu Val
65                  70                  75

<210> SEQ ID NO 45
<211> LENGTH: 419
<212> TYPE: PRT
<213> ORGANISM: Artificial Sequence
<220> FEATURE:
<223> OTHER INFORMATION: Coronavirus nucleoprotein reference sequence

<400> SEQUENCE: 45

Met Ser Asp Asn Gly Pro Gln Asn Gln Arg Asn Ala Pro Arg Ile Thr
1               5                  10                  15

Phe Gly Gly Pro Ser Asp Ser Thr Gly Ser Asn Gln Asn Gly Glu Arg
            20                  25                  30

Ser Gly Ala Arg Ser Lys Gln Arg Arg Pro Gln Gly Leu Pro Asn Asn
            35                  40                  45

Thr Ala Ser Trp Phe Thr Ala Leu Thr Gln His Gly Lys Glu Asp Leu
        50                  55                  60

Lys Phe Pro Arg Gly Gln Gly Val Pro Ile Asn Thr Asn Ser Ser Pro
65                  70                  75                  80

Asp Asp Gln Ile Gly Tyr Tyr Arg Arg Ala Thr Arg Arg Ile Arg Gly
                85                  90                  95

Gly Asp Gly Lys Met Lys Asp Leu Ser Pro Arg Trp Tyr Phe Tyr Tyr
            100                 105                 110

Leu Gly Thr Gly Pro Glu Ala Gly Leu Pro Tyr Gly Ala Asn Lys Asp
        115                 120                 125

Gly Ile Ile Trp Val Ala Thr Glu Gly Ala Leu Asn Thr Pro Lys Asp
        130                 135                 140

His Ile Gly Thr Arg Asn Pro Ala Asn Asn Ala Ala Ile Val Leu Gln
145                 150                 155                 160

Leu Pro Gln Gly Thr Thr Leu Pro Lys Gly Phe Tyr Ala Glu Gly Ser
```

-continued

```
                    165                   170                   175
Arg Gly Gly Ser Gln Ala Ser Ser Arg Ser Ser Ser Arg Ser Arg Asn
                180                   185                   190

Ser Ser Arg Asn Ser Thr Pro Gly Ser Ser Arg Gly Thr Ser Pro Ala
            195                   200                   205

Arg Met Ala Gly Asn Gly Gly Asp Ala Ala Leu Ala Leu Leu Leu Leu
        210                   215                   220

Asp Arg Leu Asn Gln Leu Glu Ser Lys Met Ser Gly Lys Gly Gln Gln
225                   230                   235                   240

Gln Gln Gly Gln Thr Val Thr Lys Lys Ser Ala Ala Glu Ala Ser Lys
                245                   250                   255

Lys Pro Arg Gln Lys Arg Thr Ala Thr Lys Ala Tyr Asn Val Thr Gln
                260                   265                   270

Ala Phe Gly Arg Arg Gly Pro Glu Gln Thr Gln Gly Asn Phe Gly Asp
                275                   280                   285

Gln Glu Leu Ile Arg Gln Gly Thr Asp Tyr Lys His Trp Pro Gln Ile
        290                   295                   300

Ala Gln Phe Ala Pro Ser Ala Ser Ala Phe Phe Gly Met Ser Arg Ile
305                   310                   315                   320

Gly Met Glu Val Thr Pro Ser Gly Thr Trp Leu Thr Tyr Thr Gly Ala
                325                   330                   335

Ile Lys Leu Asp Asp Lys Asp Pro Asn Phe Lys Asp Gln Val Ile Leu
                340                   345                   350

Leu Asn Lys His Ile Asp Ala Tyr Lys Thr Phe Pro Pro Thr Glu Pro
            355                   360                   365

Lys Lys Asp Lys Lys Lys Lys Ala Asp Glu Thr Gln Ala Leu Pro Gln
        370                   375                   380

Arg Gln Lys Lys Gln Gln Thr Val Thr Leu Leu Pro Ala Ala Asp Leu
385                   390                   395                   400

Asp Asp Phe Ser Lys Gln Leu Gln Gln Ser Met Ser Ser Ala Asp Ser
                405                   410                   415

Thr Gln Ala
```

<210> SEQ ID NO 46
<211> LENGTH: 418
<212> TYPE: PRT
<213> ORGANISM: Artificial Sequence
<220> FEATURE:
<223> OTHER INFORMATION: Coronavirus nucleoprotein designed sequence

<400> SEQUENCE: 46

```
Met Ser Asp Asn Gly Pro Gln Asn Gln Arg Ser Ala Pro Arg Ile Thr
1                   5                   10                  15

Phe Gly Gly Pro Ser Asp Ser Thr Asp Asn Asn Gln Asn Gly Glu Arg
                20                  25                  30

Ser Gly Ala Arg Pro Lys Gln Arg Arg Pro Gln Gly Leu Pro Asn Asn
            35                  40                  45

Thr Ala Ser Trp Phe Thr Ala Leu Thr Gln His Gly Lys Glu Asp Leu
        50                  55                  60

Arg Phe Pro Arg Gly Gln Gly Val Pro Ile Asn Thr Asn Ser Gly Lys
65                  70                  75                  80

Asp Asp Gln Ile Gly Tyr Tyr Arg Arg Ala Thr Arg Arg Val Arg Gly
                85                  90                  95

Gly Asp Gly Lys Met Lys Glu Leu Ser Pro Arg Trp Tyr Phe Tyr Tyr
                100                 105                 110
```

Leu Gly Thr Gly Pro Glu Ala Ala Leu Pro Tyr Gly Ala Asn Lys Glu
        115                 120                 125

Gly Ile Val Trp Val Ala Thr Glu Gly Ala Leu Asn Thr Pro Lys Asp
        130                 135                 140

His Ile Gly Thr Arg Asn Pro Asn Asn Asn Ala Ala Ile Val Leu Gln
145                 150                 155                 160

Leu Pro Gln Gly Thr Thr Leu Pro Lys Gly Phe Tyr Ala Glu Gly Ser
                165                 170                 175

Arg Gly Gly Ser Gln Ala Ser Ser Arg Ser Ser Ser Arg Ser Arg Gly
                180                 185                 190

Asn Ser Arg Asn Ser Thr Pro Gly Ser Ser Arg Gly Thr Ser Pro Ala
                195                 200                 205

Arg Met Ala Ser Gly Gly Gly Asp Thr Ala Leu Ala Leu Leu Leu Leu
        210                 215                 220

Asp Arg Leu Asn Gln Leu Glu Ser Lys Val Ser Gly Lys Gly Gln Gln
225                 230                 235                 240

Gln Gln Gly Gln Thr Val Thr Lys Lys Ser Ala Ala Glu Ala Ser Lys
                245                 250                 255

Lys Pro Arg Gln Lys Arg Thr Ala Thr Lys Gln Tyr Asn Val Thr Gln
        260                 265                 270

Ala Phe Gly Arg Arg Gly Pro Glu Gln Thr Gln Gly Asn Phe Gly Asp
        275                 280                 285

Gln Glu Leu Ile Arg Gln Gly Thr Asp Tyr Lys His Trp Pro Gln Ile
    290                 295                 300

Ala Gln Phe Ala Pro Ser Ala Ser Ala Phe Phe Gly Met Ser Arg Glu
305                 310                 315                 320

Val Thr Pro Ser Gly Thr Trp Leu Thr Tyr His Gly Ala Ile Lys Leu
                325                 330                 335

Asp Asp Lys Asp Pro Gln Phe Lys Asp Asn Val Ile Leu Leu Asn Lys
                340                 345                 350

His Ile Asp Ala Tyr Lys Thr Phe Pro Pro Thr Glu Pro Lys Lys Asp
        355                 360                 365

Lys Lys Lys Lys Ala Asp Glu Ala Gln Pro Leu Pro Gln Arg Gln Lys
    370                 375                 380

Lys Gln Pro Thr Val Thr Leu Leu Pro Ala Ala Asp Leu Asp Asp Phe
385                 390                 395                 400

Ser Lys Gln Leu Gln Asn Ser Met Ser Gly Ala Ser Ala Asp Ser Thr
                405                 410                 415

Gln Ala

<210> SEQ ID NO 47
<211> LENGTH: 417
<212> TYPE: PRT
<213> ORGANISM: Artificial Sequence
<220> FEATURE:
<223> OTHER INFORMATION: Coronavirus nucleoprotein designed sequence

<400> SEQUENCE: 47

Met Thr Asp Asn Gly Gln Gln Gly Pro Arg Asn Ala Pro Arg Ile Thr
1               5                   10                  15

Phe Gly Val Ser Asp Asn Phe Asp Asn Asn Gln Asp Gly Gly Arg Ser
                20                  25                  30

Gly Ala Arg Pro Lys Gln Arg Arg Pro Gln Gly Leu Pro Asn Asn Thr
        35                  40                  45

-continued

```
Ala Ser Trp Phe Thr Ala Leu Thr Gln His Gly Lys Glu Asp Leu Arg
    50              55              60

Phe Pro Arg Gly Gln Gly Val Pro Ile Asn Thr Asn Ser Ser Pro Asp
65              70              75              80

Asp Gln Ile Gly Tyr Tyr Arg Arg Ala Thr Arg Arg Ile Arg Gly Gly
                85              90              95

Asp Gly Lys Met Lys Asp Leu Ser Pro Arg Trp Tyr Phe Tyr Tyr Leu
            100             105             110

Gly Thr Gly Pro Glu Ala Ala Leu Pro Tyr Gly Ala Asn Lys Glu Gly
            115             120             125

Ile Val Trp Val Ala Thr Glu Gly Ala Leu Asn Thr Pro Lys Asp His
    130             135             140

Ile Gly Thr Arg Asn Pro Asn Asn Asn Ala Ala Ile Val Leu Gln Leu
145             150             155             160

Pro Gln Gly Thr Thr Leu Pro Lys Gly Phe Tyr Ala Glu Gly Ser Arg
                165             170             175

Gly Gly Ser Gln Ala Ser Ser Arg Ser Ser Ser Arg Ser Arg Asn Ser
            180             185             190

Ser Arg Asn Ser Thr Pro Gly Ser Ser Arg Gly Thr Ser Pro Ala Arg
            195             200             205

Asn Leu Gln Ala Gly Gly Asp Thr Ala Leu Ala Leu Leu Leu Leu Asp
    210             215             220

Arg Leu Asn Gln Leu Glu Ser Lys Met Ser Gly Lys Gly Gln Gln Gln
225             230             235             240

Gln Gly Gln Thr Val Thr Lys Lys Ser Ala Ala Glu Ala Ser Lys Lys
                245             250             255

Pro Arg Gln Lys Arg Thr Ala Thr Lys Gln Tyr Asn Val Thr Gln Ala
            260             265             270

Phe Gly Arg Arg Gly Pro Glu Gln Thr Gln Gly Asn Phe Gly Asp Gln
            275             280             285

Glu Leu Ile Arg Gln Gly Thr Asp Tyr Lys Gln Trp Pro Gln Ile Ala
    290             295             300

Gln Phe Ala Pro Ser Ala Ser Ala Phe Phe Gly Met Ser Arg Glu Val
305             310             315             320

Thr Pro Ser Gly Thr Trp Leu Thr Tyr Thr Gly Ala Ile Lys Leu Asp
            325             330             335

Asp Lys Asp Pro Gln Phe Lys Asp Asn Val Ile Leu Leu Asn Lys His
            340             345             350

Ile Asp Ala Tyr Lys Thr Phe Pro Pro Thr Glu Pro Lys Lys Asp Lys
            355             360             365

Lys Lys Lys Ala Asp Glu Ala Gln Pro Leu Pro Gln Arg Gln Lys Lys
    370             375             380

Gln Gln Thr Val Thr Leu Leu Pro Ala Ala Asp Leu Asp Asp Phe Ser
385             390             395             400

Arg Gln Leu Gln Asn Ser Met Ser Gly Ala Ser Ala Asp Ser Thr Gln
                405             410             415

Ala
```

<210> SEQ ID NO 48
<211> LENGTH: 166
<212> TYPE: PRT
<213> ORGANISM: Artificial Sequence
<220> FEATURE:
<223> OTHER INFORMATION: Coronavirus membrane protein designed sequence -continued

<400> SEQUENCE: 48

Met Ala Asp Ser Asn Gly Thr Ile Thr Val Glu Glu Leu Lys Lys Leu
1               5                   10                  15

Leu Glu Gln Ile Thr Gly Gly Ile Ala Ile Ala Met Ala Cys Leu Val
                20                  25                  30

Gly Leu Met Trp Leu Ser Tyr Phe Ile Ala Ser Phe Arg Leu Phe Ala
            35                  40                  45

Arg Thr Arg Ser Met Trp Ser Phe Asn Pro Glu Thr Asn Ile Leu Leu
        50                  55                  60

Asn Val Pro Leu His Gly Thr Ile Leu Thr Arg Pro Leu Leu Glu Ser
65                  70                  75                  80

Glu Leu Val Ile Gly Ala Val Ile Leu Arg Gly His Leu Arg Ile Ala
                85                  90                  95

Gly His His Leu Gly Arg Cys Asp Ile Lys Asp Leu Pro Lys Glu Ile
            100                 105                 110

Thr Val Ala Thr Ser Arg Thr Leu Ser Tyr Tyr Lys Leu Gly Ala Ser
            115                 120                 125

Gln Arg Val Ala Gly Asp Ser Gly Phe Ala Ala Tyr Ser Arg Tyr Arg
        130                 135                 140

Ile Gly Asn Gly Lys Leu Asn Thr Asp His Ser Ser Ser Ser Asp Asn
145                 150                 155                 160

Ile Ala Leu Leu Val Gln
                165

<210> SEQ ID NO 49
<211> LENGTH: 165
<212> TYPE: PRT
<213> ORGANISM: Artificial Sequence
<220> FEATURE:
<223> OTHER INFORMATION: Coronavirus membrane protein designed sequence

<400> SEQUENCE: 49

Met Ala Asp Asn Gly Thr Ile Thr Val Glu Glu Leu Lys Gln Leu Leu
1               5                   10                  15

Glu Gln Val Thr Gly Gly Ile Ala Ile Ala Met Ala Cys Ile Val Gly
                20                  25                  30

Leu Met Trp Leu Ser Tyr Phe Val Ala Ser Phe Arg Leu Phe Ala Arg
        35                  40                  45

Thr Arg Ser Met Trp Ser Phe Asn Pro Glu Thr Asn Ile Leu Leu Asn
        50                  55                  60

Val Pro Leu Arg Gly Thr Ile Leu Thr Arg Pro Leu Met Glu Ser Glu
65                  70                  75                  80

Leu Val Ile Gly Ala Val Ile Ile Arg Gly His Leu Arg Met Ala Gly
                85                  90                  95

His Ser Leu Gly Arg Cys Asp Ile Lys Asp Leu Pro Lys Glu Ile Thr
            100                 105                 110

Val Ala Thr Ser Arg Thr Leu Ser Tyr Tyr Lys Leu Gly Ala Ser Gln
            115                 120                 125

Arg Val Gly Thr Asp Ser Gly Phe Ala Ala Tyr Asn Arg Tyr Arg Ile
        130                 135                 140

Gly Asn Gly Lys Leu Asn Thr Asp His Ala Gly Ser Asn Asp Asn Ile
145                 150                 155                 160

Ala Leu Leu Val Gln
                165

```
<210> SEQ ID NO 50
<211> LENGTH: 166
<212> TYPE: PRT
<213> ORGANISM: Artificial Sequence
<220> FEATURE:
<223> OTHER INFORMATION: Coronavirus membrane protein designed sequence

<400> SEQUENCE: 50

Met Ala Asp Ser Asn Gly Thr Ile Thr Val Glu Glu Leu Lys Lys Leu
1               5                   10                  15

Leu Glu Gln Val Thr Gly Gly Ile Ala Ile Ala Met Ala Cys Ile Val
                20                  25                  30

Gly Leu Met Trp Leu Ser Tyr Phe Val Ala Ser Phe Arg Leu Phe Ala
            35                  40                  45

Arg Thr Arg Ser Met Trp Ser Phe Asn Pro Glu Thr Asn Ile Leu Leu
        50                  55                  60

Asn Val Pro Leu Arg Gly Ser Ile Ile Thr Arg Pro Leu Met Glu Ser
65                  70                  75                  80

Glu Leu Val Ile Gly Ala Val Ile Leu Arg Gly His Leu Arg Met Ala
                85                  90                  95

Gly His Ser Leu Gly Arg Cys Asp Ile Lys Asp Leu Pro Lys Glu Ile
            100                 105                 110

Thr Val Ala Thr Ser Arg Thr Leu Ser Tyr Tyr Lys Leu Gly Ala Ser
            115                 120                 125

Gln Arg Val Ala Ser Asp Ser Gly Phe Ala Val Tyr Asn Arg Tyr Arg
        130                 135                 140

Ile Gly Asn Gly Lys Leu Asn Thr Asp His Ser Ser Ser Ser Asp Asn
145                 150                 155                 160

Ile Ala Leu Leu Val Gln
                165

<210> SEQ ID NO 51
<211> LENGTH: 262
<212> TYPE: PRT
<213> ORGANISM: Artificial Sequence
<220> FEATURE:
<223> OTHER INFORMATION: Coronavirus S-protein RBD designed protein

<400> SEQUENCE: 51

Met Lys Arg Gly Leu Cys Cys Val Leu Leu Leu Cys Gly Ala Val Phe
1               5                   10                  15

Val Ser Pro Ser Ala Ala Arg Val Gln Pro Thr Glu Ser Ile Val Arg
                20                  25                  30

Phe Pro Asn Ile Thr Asn Leu Cys Pro Phe Gly Glu Val Phe Asn Ala
            35                  40                  45

Thr Arg Phe Ala Ser Val Tyr Ala Trp Asn Arg Lys Arg Ile Ser Asn
        50                  55                  60

Cys Val Ala Asp Tyr Ser Val Leu Tyr Asn Ser Ala Ser Phe Ser Thr
65                  70                  75                  80

Phe Lys Cys Tyr Gly Val Ser Pro Thr Lys Leu Asn Asp Leu Cys Phe
                85                  90                  95

Thr Asn Val Tyr Ala Asp Ser Phe Val Ile Arg Gly Asp Glu Val Arg
            100                 105                 110

Gln Ile Ala Pro Gly Gln Thr Gly Lys Ile Ala Asp Tyr Asn Tyr Lys
            115                 120                 125

Leu Pro Asp Asp Phe Thr Gly Cys Val Ile Ala Trp Asn Ser Asn Asn
        130                 135                 140
```

-continued

```
Leu Asp Ser Lys Val Gly Gly Asn Tyr Asn Tyr Leu Tyr Arg Leu Phe
145             150                 155                 160

Arg Lys Ser Asn Leu Lys Pro Phe Glu Arg Asp Ile Ser Thr Glu Ile
                165                 170                 175

Tyr Gln Ala Gly Ser Thr Pro Cys Asn Gly Val Glu Gly Phe Asn Cys
                180                 185                 190

Tyr Phe Pro Leu Gln Ser Tyr Gly Phe Gln Pro Thr Asn Gly Val Gly
                195                 200                 205

Tyr Gln Pro Tyr Arg Val Val Val Leu Ser Phe Glu Leu Leu His Ala
        210                 215                 220

Pro Ala Thr Val Cys Gly Pro Lys Lys Ser Thr Asn Gly Gly Ser Gly
225                 230                 235                 240

Leu Asn Asp Ile Phe Glu Ala Gln Lys Ile Glu Trp His Glu Gly Ser
                245                 250                 255

His His His His His His
                260
```

<210> SEQ ID NO 52
<211> LENGTH: 1273
<212> TYPE: PRT
<213> ORGANISM: Artificial Sequence
<220> FEATURE:
<223> OTHER INFORMATION: Coronavirus S-protein mutant sequence

<400> SEQUENCE: 52

```
Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
                20                  25                  30

Thr Arg Gly Val Tyr Tyr Pro Asp Lys Val Phe Arg Ser Ser Val Leu
            35                  40                  45

His Ser Thr Gln Asp Leu Phe Leu Pro Phe Phe Ser Asn Val Thr Trp
        50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
                100                 105                 110

Lys Thr Gln Ser Leu Leu Ile Val Asn Asn Ala Thr Asn Val Val Ile
                115                 120                 125

Lys Val Cys Glu Phe Gln Phe Cys Asn Asp Pro Phe Leu Gly Val Tyr
                130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
                180                 185                 190

Val Phe Lys Asn Ile Asp Gly Tyr Phe Lys Ile Tyr Ser Lys His Thr
                195                 200                 205

Pro Ile Asn Leu Val Arg Asp Leu Pro Gln Gly Phe Ser Ala Leu Glu
        210                 215                 220

Pro Leu Val Asp Leu Pro Ile Gly Ile Asn Ile Thr Arg Phe Gln Thr
225                 230                 235                 240
```

-continued

```
Leu Leu Ala Leu His Arg Ser Tyr Leu Thr Pro Gly Asp Ser Ser Ser
            245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
            275                 280                 285

Val Asp Cys Ala Leu Asp Pro Leu Ser Glu Thr Lys Cys Thr Leu Lys
            290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
                340                 345                 350

Trp Asn Arg Lys Arg Ile Ser Asn Cys Val Ala Asp Tyr Ser Val Leu
                355                 360                 365

Tyr Asn Ser Ala Ser Phe Ser Thr Phe Lys Cys Tyr Gly Val Ser Pro
            370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
                420                 425                 430

Val Ile Ala Trp Asn Ser Asn Asn Leu Asp Ser Lys Val Gly Gly Asn
                435                 440                 445

Tyr Asn Tyr Leu Tyr Arg Leu Phe Arg Lys Ser Asn Leu Lys Pro Phe
            450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
                500                 505                 510

Leu Ser Phe Glu Leu Leu His Ala Pro Ala Thr Val Cys Gly Pro Lys
            515                 520                 525

Lys Ser Thr Asn Leu Val Lys Asn Lys Cys Val Asn Phe Asn Phe Asn
            530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
                580                 585                 590

Gly Gly Val Ser Val Ile Thr Pro Gly Thr Asn Thr Ser Asn Gln Val
                595                 600                 605

Ala Val Leu Tyr Gln Asp Val Asn Cys Thr Glu Val Pro Val Ala Ile
            610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
```

-continued

```
                 660              665              670
Ser Tyr Gln Thr Gln Thr Asn Ser Pro Arg Arg Ala Arg Ser Val Ala
            675              680              685

Ser Gln Ser Ile Ile Ala Tyr Thr Met Ser Leu Gly Ala Glu Asn Ser
        690              695              700

Val Ala Tyr Ser Asn Asn Ser Ile Ala Ile Pro Thr Asn Phe Thr Ile
705              710              715              720

Ser Val Thr Thr Glu Ile Leu Pro Val Ser Met Thr Lys Thr Ser Val
                725              730              735

Asp Cys Thr Met Tyr Ile Cys Gly Asp Ser Thr Glu Cys Ser Asn Leu
            740              745              750

Leu Leu Gln Tyr Gly Ser Phe Cys Thr Gln Leu Asn Arg Ala Leu Thr
        755              760              765

Gly Ile Ala Val Glu Gln Asp Lys Asn Thr Gln Glu Val Phe Ala Gln
        770              775              780

Val Lys Gln Ile Tyr Lys Thr Pro Pro Ile Lys Asp Phe Gly Gly Phe
785              790              795              800

Asn Phe Ser Gln Ile Leu Pro Asp Pro Ser Lys Pro Ser Lys Arg Ser
            805              810              815

Phe Ile Glu Asp Leu Leu Phe Asn Lys Val Thr Leu Ala Asp Ala Gly
            820              825              830

Phe Ile Lys Gln Tyr Gly Asp Cys Leu Gly Asp Ile Ala Ala Arg Asp
            835              840              845

Leu Ile Cys Ala Gln Lys Phe Asn Gly Leu Thr Val Leu Pro Pro Leu
        850              855              860

Leu Thr Asp Glu Met Ile Ala Gln Tyr Thr Ser Ala Leu Leu Ala Gly
865              870              875              880

Thr Ile Thr Ser Gly Trp Thr Phe Gly Ala Gly Ala Ala Leu Gln Ile
                885              890              895

Pro Phe Ala Met Gln Met Ala Tyr Arg Phe Asn Gly Ile Gly Val Thr
            900              905              910

Gln Asn Val Leu Tyr Glu Asn Gln Lys Leu Ile Ala Asn Gln Phe Asn
        915              920              925

Ser Ala Ile Gly Lys Ile Gln Asp Ser Leu Ser Ser Thr Ala Ser Ala
        930              935              940

Leu Gly Lys Leu Gln Asp Val Val Asn Gln Asn Ala Gln Ala Leu Asn
945              950              955              960

Thr Leu Val Lys Gln Leu Ser Ser Asn Phe Gly Ala Ile Ser Ser Val
                965              970              975

Leu Asn Asp Ile Leu Ser Arg Leu Asp Lys Val Glu Ala Glu Val Gln
            980              985              990

Ile Asp Arg Leu Ile Thr Gly Arg  Leu Gln Ser Leu Gln  Thr Tyr Val
            995              1000             1005

Thr Gln  Gln Leu Ile Arg Ala  Ala Glu Ile Arg Ala  Ser Ala Asn
    1010             1015             1020

Leu Ala  Ala Thr Lys Met Ser  Glu Cys Val Leu Gly  Gln Ser Lys
    1025             1030             1035

Arg Val  Asp Phe Cys Gly Lys  Gly Tyr His Leu Met  Ser Phe Pro
    1040             1045             1050

Gln Ser  Ala Pro His Gly Val  Val Phe Leu His Val  Thr Tyr Val
    1055             1060             1065

Pro Ala  Gln Glu Lys Asn Phe  Thr Thr Ala Pro Ala  Ile Cys His
    1070             1075             1080
```

-continued

```
Asp Gly Lys Ala His Phe Pro  Arg Glu Gly Val Phe  Val Ser Asn
    1085              1090              1095

Gly Thr  His Trp Phe Val Thr  Gln Arg Asn Phe Tyr  Glu Pro Gln
    1100              1105              1110

Ile Ile  Thr Thr Asp Asn Thr  Phe Val Ser Gly Asn  Cys Asp Val
    1115              1120              1125

Val Ile  Gly Ile Val Asn Asn  Thr Val Tyr Asp Pro  Leu Gln Pro
    1130              1135              1140

Glu Leu  Asp Ser Phe Lys Glu  Glu Leu Asp Lys Tyr  Phe Lys Asn
    1145              1150              1155

His Thr  Ser Pro Asp Val Asp  Leu Gly Asp Ile Ser  Gly Ile Asn
    1160              1165              1170

Ala Ser  Val Val Asn Ile Gln  Lys Glu Ile Asp Arg  Leu Asn Glu
    1175              1180              1185

Val Ala  Lys Asn Leu Asn Glu  Ser Leu Ile Asp Leu  Gln Glu Leu
    1190              1195              1200

Gly Lys  Tyr Glu Gln Tyr Ile  Lys Trp Pro Trp Tyr  Ile Trp Leu
    1205              1210              1215

Gly Phe  Ile Ala Gly Leu Ile  Ala Ile Val Met Val  Thr Ile Met
    1220              1225              1230

Leu Cys  Cys Met Thr Ser Cys  Cys Ser Cys Leu Lys  Gly Cys Cys
    1235              1240              1245

Ser Cys  Gly Ser Cys Cys Lys  Phe Asp Glu Asp Asp  Ser Glu Pro
    1250              1255              1260

Val Leu  Lys Gly Val Lys Leu  His Tyr Thr
    1265              1270

<210> SEQ ID NO 53
<211> LENGTH: 1270
<212> TYPE: PRT
<213> ORGANISM: Artificial Sequence
<220> FEATURE:
<223> OTHER INFORMATION: Coronavirus S-protein designed sequence

<400> SEQUENCE: 53

Met Phe Val Phe Leu Val Leu Leu Pro Leu Val Ser Ser Gln Cys Val
1               5               10              15

Asn Phe Thr Asn Arg Thr Gln Leu Pro Ser Ala Tyr Thr Asn Ser Phe
            20              25              30

Thr Arg Gly Val Tyr Tyr Pro Asp Lys Val Phe Arg Ser Ser Val Leu
        35              40              45

His Ser Thr Gln Asp Leu Phe Leu Pro Phe Phe Ser Asn Val Thr Trp
    50              55              60

Phe His Ala Ile Ser Gly Thr Asn Gly Thr Lys Arg Phe Asp Asn Pro
65              70              75              80

Val Leu Pro Phe Asn Asp Gly Val Tyr Phe Ala Ser Thr Glu Lys Ser
            85              90              95

Asn Ile Ile Arg Gly Trp Ile Phe Gly Thr Thr Leu Asp Ser Lys Thr
            100             105             110

Gln Ser Leu Leu Ile Val Asn Asn Ala Thr Asn Val Val Ile Lys Val
        115             120             125

Cys Glu Phe Gln Phe Cys Asn Asp Pro Phe Leu Gly Val Tyr His Lys
        130             135             140

Asn Asn Lys Ser Trp Met Glu Ser Glu Phe Arg Val Tyr Ser Ser Ala
145             150             155             160
```

```
Asn Asn Cys Thr Phe Glu Tyr Val Ser Gln Pro Phe Leu Met Asp Leu
              165                 170                 175

Glu Gly Lys Gln Gly Asn Phe Lys Asn Leu Arg Glu Phe Val Phe Lys
              180                 185                 190

Asn Ile Asp Gly Tyr Phe Lys Ile Tyr Ser Lys His Thr Pro Ile Asn
              195                 200                 205

Leu Val Arg Asp Leu Pro Gln Gly Phe Ser Ala Leu Glu Pro Leu Val
          210                 215                 220

Asp Leu Pro Ile Gly Ile Asn Ile Thr Arg Phe Gln Thr Leu Leu Ala
225                 230                 235                 240

Leu His Arg Ser Tyr Leu Thr Pro Gly Asp Ser Ser Ser Gly Trp Thr
              245                 250                 255

Ala Gly Ala Ala Ala Tyr Tyr Val Gly Tyr Leu Gln Pro Arg Thr Phe
              260                 265                 270

Leu Leu Lys Tyr Asn Glu Asn Gly Thr Ile Thr Asp Ala Val Asp Cys
              275                 280                 285

Ala Leu Asp Pro Leu Ser Glu Thr Lys Cys Thr Leu Lys Ser Phe Thr
          290                 295                 300

Val Glu Lys Gly Ile Tyr Gln Thr Ser Asn Phe Arg Val Gln Pro Thr
305                 310                 315                 320

Glu Ser Ile Val Arg Phe Pro Asn Ile Thr Asn Leu Cys Pro Phe Gly
              325                 330                 335

Glu Val Phe Asn Ala Thr Arg Phe Ala Ser Val Tyr Ala Trp Asn Arg
              340                 345                 350

Lys Arg Ile Ser Asn Cys Val Ala Asp Tyr Ser Val Leu Tyr Asn Ser
              355                 360                 365

Ala Ser Phe Ser Thr Phe Lys Cys Tyr Gly Val Ser Pro Thr Lys Leu
          370                 375                 380

Asn Asp Leu Cys Phe Thr Asn Val Tyr Ala Asp Ser Phe Val Ile Arg
385                 390                 395                 400

Gly Asp Glu Val Arg Gln Ile Ala Pro Gly Gln Thr Gly Asn Ile Ala
              405                 410                 415

Asp Tyr Asn Tyr Lys Leu Pro Asp Asp Phe Thr Gly Cys Val Ile Ala
              420                 425                 430

Trp Asn Ser Asn Asn Leu Asp Ser Lys Val Gly Gly Asn Tyr Asn Tyr
              435                 440                 445

Leu Tyr Arg Leu Phe Arg Lys Ser Asn Leu Lys Pro Phe Glu Arg Asp
          450                 455                 460

Ile Ser Thr Glu Ile Tyr Gln Ala Gly Ser Thr Pro Cys Asn Gly Val
465                 470                 475                 480

Lys Gly Phe Asn Cys Tyr Phe Pro Leu Gln Ser Tyr Gly Phe Gln Pro
              485                 490                 495

Thr Tyr Gly Val Gly Tyr Gln Pro Tyr Arg Val Val Val Leu Ser Phe
              500                 505                 510

Glu Leu Leu His Ala Pro Ala Thr Val Cys Gly Pro Lys Lys Ser Thr
              515                 520                 525

Asn Leu Val Lys Asn Lys Cys Val Asn Phe Asn Phe Asn Gly Leu Thr
          530                 535                 540

Gly Thr Gly Val Leu Thr Glu Ser Asn Lys Lys Phe Leu Pro Phe Gln
545                 550                 555                 560

Gln Phe Gly Arg Asp Ile Ala Asp Thr Thr Asp Ala Val Arg Asp Pro
              565                 570                 575
```

-continued

```
Gln Thr Leu Glu Ile Leu Asp Ile Thr Pro Cys Ser Phe Gly Gly Val
            580                 585                 590

Ser Val Ile Thr Pro Gly Thr Asn Thr Ser Asn Gln Val Ala Val Leu
            595                 600                 605

Tyr Gln Gly Val Asn Cys Thr Glu Val Pro Val Ala Ile His Ala Asp
    610                 615                 620

Gln Leu Thr Pro Thr Trp Arg Val Tyr Ser Thr Gly Ser Asn Val Phe
625                 630                 635                 640

Gln Thr Arg Ala Gly Cys Leu Ile Gly Ala Glu His Val Asn Asn Ser
            645                 650                 655

Tyr Glu Cys Asp Ile Pro Ile Gly Ala Gly Ile Cys Ala Ser Tyr Gln
            660                 665                 670

Thr Gln Thr Asn Ser His Arg Arg Ala Arg Ser Val Ala Ser Gln Ser
            675                 680                 685

Ile Ile Ala Tyr Thr Met Ser Leu Gly Ala Glu Asn Ser Val Ala Tyr
    690                 695                 700

Ser Asn Asn Ser Ile Ala Ile Pro Thr Asn Phe Thr Ile Ser Val Thr
705                 710                 715                 720

Thr Glu Ile Leu Pro Val Ser Met Thr Lys Thr Ser Val Asp Cys Thr
            725                 730                 735

Met Tyr Ile Cys Gly Asp Ser Thr Glu Cys Ser Asn Leu Leu Leu Gln
            740                 745                 750

Tyr Gly Ser Phe Cys Thr Gln Leu Asn Arg Ala Leu Thr Gly Ile Ala
            755                 760                 765

Val Glu Gln Asp Lys Asn Thr Gln Glu Val Phe Ala Gln Val Lys Gln
    770                 775                 780

Ile Tyr Lys Thr Pro Pro Ile Lys Asp Phe Gly Gly Phe Asn Phe Ser
785                 790                 795                 800

Gln Ile Leu Pro Asp Pro Ser Lys Pro Ser Lys Arg Ser Phe Ile Glu
            805                 810                 815

Asp Leu Leu Phe Asn Lys Val Thr Leu Ala Asp Ala Gly Phe Ile Lys
            820                 825                 830

Gln Tyr Gly Asp Cys Leu Gly Asp Ile Ala Ala Arg Asp Leu Ile Cys
            835                 840                 845

Ala Gln Lys Phe Asn Gly Leu Thr Val Leu Pro Pro Leu Leu Thr Asp
    850                 855                 860

Glu Met Ile Ala Gln Tyr Thr Ser Ala Leu Leu Ala Gly Thr Ile Thr
865                 870                 875                 880

Ser Gly Trp Thr Phe Gly Ala Gly Ala Ala Leu Gln Ile Pro Phe Ala
            885                 890                 895

Met Gln Met Ala Tyr Arg Phe Asn Gly Ile Gly Val Thr Gln Asn Val
            900                 905                 910

Leu Tyr Glu Asn Gln Lys Leu Ile Ala Asn Gln Phe Asn Ser Ala Ile
            915                 920                 925

Gly Lys Ile Gln Asp Ser Leu Ser Ser Thr Ala Ser Ala Leu Gly Lys
    930                 935                 940

Leu Gln Asp Val Val Asn Gln Asn Ala Gln Ala Leu Asn Thr Leu Val
945                 950                 955                 960

Lys Gln Leu Ser Ser Asn Phe Gly Ala Ile Ser Ser Val Leu Asn Asp
            965                 970                 975

Ile Leu Ser Arg Leu Asp Pro Pro Glu Ala Glu Val Gln Ile Asp Arg
            980                 985                 990

Leu Ile Thr Gly Arg Leu Gln Ser  Leu Gln Thr Tyr Val  Thr Gln Gln
```

-continued

```
         995                1000               1005
Leu Ile  Arg Ala Ala Glu Ile  Arg Ala Ser Ala Asn  Leu Ala Ala
    1010               1015               1020

Thr Lys  Met Ser Glu Cys Val  Leu Gly Gln Ser Lys  Arg Val Asp
    1025               1030               1035

Phe Cys  Gly Lys Gly Tyr His  Leu Met Ser Phe Pro  Gln Ser Ala
    1040               1045               1050

Pro His  Gly Val Val Phe Leu  His Val Thr Tyr Val  Pro Ala Gln
    1055               1060               1065

Glu Lys  Asn Phe Thr Thr Ala  Pro Ala Ile Cys His  Asp Gly Lys
    1070               1075               1080

Ala His  Phe Pro Arg Glu Gly  Val Phe Val Ser Asn  Gly Thr His
    1085               1090               1095

Trp Phe  Val Thr Gln Arg Asn  Phe Tyr Glu Pro Gln  Ile Ile Thr
    1100               1105               1110

Thr Asp  Asn Thr Phe Val Ser  Gly Asn Cys Asp Val  Val Ile Gly
    1115               1120               1125

Ile Val  Asn Asn Thr Val Tyr  Asp Pro Leu Gln Pro  Glu Leu Asp
    1130               1135               1140

Ser Phe  Lys Glu Glu Leu Asp  Lys Tyr Phe Lys Asn  His Thr Ser
    1145               1150               1155

Pro Asp  Val Asp Leu Gly Asp  Ile Ser Gly Ile Asn  Ala Ser Val
    1160               1165               1170

Val Asn  Ile Gln Lys Glu Ile  Asp Arg Leu Asn Glu  Val Ala Lys
    1175               1180               1185

Asn Leu  Asn Glu Ser Leu Ile  Asp Leu Gln Glu Leu  Gly Lys Tyr
    1190               1195               1200

Glu Gln  Tyr Ile Lys Trp Pro  Trp Tyr Ile Trp Leu  Gly Phe Ile
    1205               1210               1215

Ala Gly  Leu Ile Ala Ile Val  Met Val Thr Ile Met  Leu Cys Cys
    1220               1225               1230

Met Thr  Ser Cys Cys Ser Cys  Leu Lys Gly Cys Cys  Ser Cys Gly
    1235               1240               1245

Ser Cys  Cys Lys Phe Asp Glu  Asp Asp Ser Glu Pro  Val Leu Lys
    1250               1255               1260

Gly Val  Lys Leu His Tyr Thr
    1265               1270

<210> SEQ ID NO 54
<211> LENGTH: 1270
<212> TYPE: PRT
<213> ORGANISM: Artificial Sequence
<220> FEATURE:
<223> OTHER INFORMATION: Coronavirus S-protein designed sequence

<400> SEQUENCE: 54

Met Phe Val Phe Leu Val Leu Leu Pro Leu Val Ser Ser Gln Cys Val
1               5                  10                  15

Asn Phe Thr Asn Arg Thr Gln Leu Pro Ser Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile Ser Gly Thr Asn Gly Thr Lys Arg Phe Asp Asn Pro
```

-continued

```
65                    70                    75                    80

Val Leu Pro Phe Asn Asp Gly Val Tyr Phe Ala Ser Thr Glu Lys Ser
                85                    90                    95

Asn Ile Ile Arg Gly Trp Ile Phe Gly Thr Thr Leu Asp Ser Lys Thr
                100                   105                   110

Gln Ser Leu Leu Ile Val Asn Ala Thr Asn Val Val Ile Lys Val
            115                   120                   125

Cys Glu Phe Gln Phe Cys Asn Asp Pro Phe Leu Gly Val Tyr His Lys
        130                   135                   140

Asn Asn Lys Ser Trp Met Glu Ser Glu Phe Arg Val Tyr Ser Ser Ala
145                   150                   155                   160

Asn Asn Cys Thr Phe Glu Tyr Val Ser Gln Pro Phe Leu Met Asp Leu
                165                   170                   175

Glu Gly Lys Gln Gly Asn Phe Lys Asn Leu Arg Glu Phe Val Phe Lys
                180                   185                   190

Asn Ile Asp Gly Tyr Phe Lys Ile Tyr Ser Lys His Thr Pro Ile Asn
                195                   200                   205

Leu Val Arg Asp Leu Pro Gln Gly Phe Ser Ala Leu Glu Pro Leu Val
        210                   215                   220

Asp Leu Pro Ile Gly Ile Asn Ile Thr Arg Phe Gln Thr Leu Leu Ala
225                   230                   235                   240

Leu His Arg Ser Tyr Leu Thr Pro Gly Asp Ser Ser Ser Gly Trp Thr
                245                   250                   255

Ala Gly Ala Ala Ala Tyr Tyr Val Gly Tyr Leu Gln Pro Arg Thr Phe
                260                   265                   270

Leu Leu Lys Tyr Asn Glu Asn Gly Thr Ile Thr Asp Ala Val Asp Cys
            275                   280                   285

Ala Leu Asp Pro Leu Ser Glu Thr Lys Cys Thr Leu Lys Ser Phe Thr
        290                   295                   300

Val Glu Lys Gly Ile Tyr Gln Thr Ser Asn Phe Arg Val Gln Pro Thr
305                   310                   315                   320

Glu Ser Ile Val Arg Phe Pro Asn Ile Thr Asn Leu Cys Pro Phe Gly
                325                   330                   335

Glu Val Phe Asn Ala Thr Arg Phe Ala Ser Val Tyr Ala Trp Asn Arg
                340                   345                   350

Lys Arg Ile Ser Asn Cys Val Ala Asp Tyr Ser Val Leu Tyr Asn Ser
            355                   360                   365

Ala Ser Phe Ser Thr Phe Lys Cys Tyr Gly Val Ser Pro Thr Lys Leu
        370                   375                   380

Asn Asp Leu Cys Phe Thr Asn Val Tyr Ala Asp Ser Phe Val Ile Arg
385                   390                   395                   400

Gly Asp Glu Val Arg Gln Ile Ala Pro Cys Gln Thr Gly Asn Ile Ala
                405                   410                   415

Asp Tyr Asn Tyr Lys Leu Pro Asp Asp Phe Thr Gly Cys Val Ile Ala
                420                   425                   430

Trp Asn Ser Asn Asn Leu Asp Ser Lys Val Gly Gly Asn Tyr Asn Tyr
            435                   440                   445

Leu Tyr Arg Leu Phe Arg Lys Ser Asn Leu Lys Pro Phe Glu Arg Asp
        450                   455                   460

Ile Ser Thr Glu Ile Tyr Gln Ala Gly Ser Thr Pro Cys Asn Gly Val
465                   470                   475                   480

Lys Gly Phe Asn Cys Tyr Phe Pro Leu Gln Ser Tyr Gly Phe Gln Pro
                485                   490                   495
```

-continued

```
Thr Tyr Gly Val Gly Tyr Gln Pro Tyr Arg Val Val Val Leu Ser Phe
            500                 505                 510

Glu Leu Leu His Ala Pro Ala Thr Val Cys Gly Pro Lys Lys Ser Thr
            515                 520                 525

Asn Leu Val Lys Asn Lys Cys Val Asn Phe Asn Phe Asn Gly Leu Thr
            530                 535                 540

Gly Thr Gly Val Leu Thr Glu Ser Asn Lys Lys Phe Leu Pro Phe Gln
545                 550                 555                 560

Gln Phe Gly Arg Asp Ile Ala Asp Thr Thr Asp Ala Val Arg Asp Pro
                565                 570                 575

Gln Thr Leu Glu Ile Leu Asp Ile Thr Pro Cys Ser Phe Gly Gly Val
            580                 585                 590

Ser Val Ile Thr Pro Gly Thr Asn Thr Ser Asn Gln Val Ala Val Leu
            595                 600                 605

Tyr Gln Gly Val Asn Cys Thr Glu Val Pro Val Ala Ile His Ala Asp
            610                 615                 620

Gln Leu Thr Pro Thr Trp Arg Val Tyr Ser Thr Gly Ser Asn Val Phe
625                 630                 635                 640

Gln Thr Arg Ala Gly Cys Leu Ile Gly Ala Glu His Val Asn Asn Ser
                645                 650                 655

Tyr Glu Cys Asp Ile Pro Ile Gly Ala Gly Ile Cys Ala Ser Tyr Gln
                660                 665                 670

Thr Gln Thr Asn Ser His Arg Arg Ala Arg Ser Val Ala Ser Gln Ser
            675                 680                 685

Ile Ile Ala Tyr Thr Met Ser Leu Gly Ala Glu Asn Ser Val Ala Tyr
            690                 695                 700

Ser Asn Asn Ser Ile Ala Ile Pro Thr Asn Phe Thr Ile Ser Val Thr
705                 710                 715                 720

Thr Glu Ile Leu Pro Val Ser Met Thr Lys Thr Ser Val Asp Cys Thr
                725                 730                 735

Met Tyr Ile Cys Gly Asp Ser Thr Glu Cys Ser Asn Leu Leu Leu Gln
                740                 745                 750

Tyr Gly Ser Phe Cys Thr Gln Leu Asn Arg Ala Leu Thr Gly Ile Ala
            755                 760                 765

Val Glu Gln Asp Lys Asn Thr Gln Glu Val Phe Ala Gln Val Lys Gln
770                 775                 780

Ile Tyr Lys Thr Pro Pro Ile Lys Asp Phe Gly Gly Phe Asn Phe Ser
785                 790                 795                 800

Gln Ile Leu Pro Asp Pro Ser Lys Pro Ser Lys Arg Ser Phe Ile Glu
                805                 810                 815

Asp Leu Leu Phe Asn Lys Val Thr Leu Ala Asp Ala Gly Phe Ile Lys
                820                 825                 830

Gln Tyr Gly Asp Cys Leu Gly Asp Ile Ala Ala Arg Asp Leu Ile Cys
            835                 840                 845

Ala Gln Lys Phe Asn Gly Leu Thr Val Leu Pro Pro Leu Leu Thr Asp
            850                 855                 860

Glu Met Ile Ala Gln Tyr Thr Ser Ala Leu Leu Ala Gly Thr Ile Thr
865                 870                 875                 880

Ser Gly Trp Thr Phe Gly Ala Gly Ala Ala Leu Gln Ile Pro Phe Ala
                885                 890                 895

Met Gln Met Ala Tyr Arg Phe Asn Gly Ile Gly Val Thr Gln Asn Val
            900                 905                 910
```

-continued

```
Leu Tyr Glu Asn Gln Lys Leu Ile Ala Asn Gln Phe Asn Ser Ala Ile
        915                 920                 925

Gly Lys Ile Gln Asp Ser Leu Ser Ser Thr Ala Ser Ala Leu Gly Lys
        930                 935                 940

Leu Gln Asp Val Val Asn Gln Asn Ala Gln Ala Leu Asn Thr Leu Val
945                 950                 955                 960

Lys Gln Leu Ser Ser Asn Phe Gly Ala Ile Ser Ser Val Leu Asn Asp
                965                 970                 975

Ile Leu Ser Arg Leu Asp Pro Cys Glu Ala Glu Val Gln Ile Asp Arg
                980                 985                 990

Leu Ile Thr Gly Arg Leu Gln Ser  Leu Gln Thr Tyr Val  Thr Gln Gln
        995                 1000                1005

Leu Ile  Arg Ala Ala Glu Ile  Arg Ala Ser Ala Asn  Leu Ala Ala
        1010                1015                1020

Thr Lys  Met Ser Glu Cys Val  Leu Gly Gln Ser Lys  Arg Val Asp
        1025                1030                1035

Phe Cys  Gly Lys Gly Tyr His  Leu Met Ser Phe Pro  Gln Ser Ala
        1040                1045                1050

Pro His  Gly Val Val Phe Leu  His Val Thr Tyr Val  Pro Ala Gln
        1055                1060                1065

Glu Lys  Asn Phe Thr Thr Ala  Pro Ala Ile Cys His  Asp Gly Lys
        1070                1075                1080

Ala His  Phe Pro Arg Glu Gly  Val Phe Val Ser Asn  Gly Thr His
        1085                1090                1095

Trp Phe  Val Thr Gln Arg Asn  Phe Tyr Glu Pro Gln  Ile Ile Thr
        1100                1105                1110

Thr Asp  Asn Thr Phe Val Ser  Gly Asn Cys Asp Val  Val Ile Gly
        1115                1120                1125

Ile Val  Asn Asn Thr Val Tyr  Asp Pro Leu Gln Pro  Glu Leu Asp
        1130                1135                1140

Ser Phe  Lys Glu Glu Leu Asp  Lys Tyr Phe Lys Asn  His Thr Ser
        1145                1150                1155

Pro Asp  Val Asp Leu Gly Asp  Ile Ser Gly Ile Asn  Ala Ser Val
        1160                1165                1170

Val Asn  Ile Gln Lys Glu Ile  Asp Arg Leu Asn Glu  Val Ala Lys
        1175                1180                1185

Asn Leu  Asn Glu Ser Leu Ile  Asp Leu Gln Glu Leu  Gly Lys Tyr
        1190                1195                1200

Glu Gln  Tyr Ile Lys Trp Pro  Trp Tyr Ile Trp Leu  Gly Phe Ile
        1205                1210                1215

Ala Gly  Leu Ile Ala Ile Val  Met Val Thr Ile Met  Leu Cys Cys
        1220                1225                1230

Met Thr  Ser Cys Cys Ser Cys  Leu Lys Gly Cys Cys  Ser Cys Gly
        1235                1240                1245

Ser Cys  Cys Lys Phe Asp Glu  Asp Asp Ser Glu Pro  Val Leu Lys
        1250                1255                1260

Gly Val  Lys Leu His Tyr Thr
        1265                1270
```

<210> SEQ ID NO 55
<211> LENGTH: 284
<212> TYPE: PRT
<213> ORGANISM: Artificial Sequence
<220> FEATURE:
<223> OTHER INFORMATION: Designed S protein RBD sequence COV_S_T2_19

-continued

<400> SEQUENCE: 55

Arg Val Ala Pro Thr Lys Glu Val Val Arg Phe Pro Asn Ile Thr Asn
1               5                   10                  15

Leu Cys Pro Phe Gly Glu Val Phe Asn Ala Thr Arg Phe Pro Ser Val
            20                  25                  30

Tyr Ala Trp Glu Arg Lys Arg Ile Ser Asn Cys Val Ala Asp Tyr Ser
        35                  40                  45

Val Leu Tyr Asn Ser Thr Ser Phe Ser Thr Phe Lys Cys Tyr Gly Val
    50                  55                  60

Ser Pro Thr Lys Leu Asn Asp Leu Cys Phe Thr Asn Val Tyr Ala Asp
65                  70                  75                  80

Ser Phe Val Ile Arg Gly Asp Glu Val Arg Gln Ile Ala Pro Gly Gln
                85                  90                  95

Thr Gly Val Ile Ala Asp Tyr Asn Tyr Lys Leu Pro Asp Asp Phe Thr
            100                 105                 110

Gly Cys Val Ile Ala Trp Asn Thr Asn Asn Leu Asp Ser Thr Thr Gly
            115                 120                 125

Gly Asn Tyr Asn Tyr Leu Tyr Arg Ser Leu Arg Lys Ser Lys Leu Lys
    130                 135                 140

Pro Phe Glu Arg Asp Ile Ser Ser Asp Ile Tyr Ser Pro Gly Gly Lys
145                 150                 155                 160

Pro Cys Ser Gly Val Glu Gly Phe Asn Cys Tyr Tyr Pro Leu Arg Ser
            165                 170                 175

Tyr Gly Phe Phe Pro Thr Asn Gly Val Gly Tyr Gln Pro Tyr Arg Val
            180                 185                 190

Val Val Leu Ser Phe Glu Leu Leu Asn Ala Pro Ala Thr Val Cys Gly
            195                 200                 205

Pro Lys Leu Ser Thr Asp Gly Gly Gly Ser Gly Gly Gly Gly Ser
    210                 215                 220

Gly Gly Gly Gly Ser Gly Gly Gly Gly Ser Lys Ser Ser Ile Ala Ser
225                 230                 235                 240

Phe Phe Phe Ile Ile Gly Leu Ile Ile Gly Leu Phe Leu Val Leu Arg
            245                 250                 255

Val Gly Ile His Leu Cys Ile Lys Leu Lys His Thr Lys Lys Arg Gln
            260                 265                 270

Ile Tyr Thr Asp Ile Glu Met Asn Arg Leu Gly Lys
        275                 280

<210> SEQ ID NO 56
<211> LENGTH: 284
<212> TYPE: PRT
<213> ORGANISM: Artificial Sequence
<220> FEATURE:
<223> OTHER INFORMATION: Designed S protein RBD sequence COV_S_T2_20

<400> SEQUENCE: 56

Arg Val Ala Pro Thr Lys Glu Val Val Arg Phe Pro Asn Ile Thr Asn
1               5                   10                  15

Leu Cys Pro Phe Gly Glu Val Phe Asn Ala Thr Lys Phe Pro Ser Val
            20                  25                  30

Tyr Ala Trp Glu Arg Lys Lys Ile Ser Asn Cys Val Ala Asp Tyr Ser
        35                  40                  45

Val Leu Tyr Asn Ser Thr Ser Phe Ser Thr Phe Lys Cys Tyr Gly Val
    50                  55                  60

-continued

```
Ser Pro Thr Lys Leu Asn Asp Leu Cys Phe Thr Asn Val Tyr Ala Asp
65                  70                  75                  80

Ser Phe Val Ile Arg Gly Asp Glu Val Arg Gln Ile Ala Pro Gly Gln
                85                  90                  95

Thr Gly Val Ile Ala Asp Tyr Asn Tyr Lys Leu Pro Asp Asp Phe Thr
            100                 105                 110

Gly Cys Val Ile Ala Trp Asn Thr Asn Asn Ile Asp Ser Thr Thr Gly
        115                 120                 125

Gly Asn Tyr Asn Tyr Leu Tyr Arg Ser Leu Arg Lys Ser Lys Leu Lys
    130                 135                 140

Pro Phe Glu Arg Asp Ile Ser Ser Asp Ile Tyr Ser Pro Gly Gly Lys
145                 150                 155                 160

Pro Cys Ser Gly Val Glu Gly Phe Asn Cys Tyr Tyr Pro Leu Arg Ser
                165                 170                 175

Tyr Gly Phe Phe Pro Thr Asn Gly Thr Gly Tyr Gln Pro Tyr Arg Val
                180                 185                 190

Val Val Leu Ser Phe Glu Leu Leu Asn Ala Pro Ala Thr Val Cys Gly
            195                 200                 205

Pro Lys Leu Ser Thr Asp Gly Gly Gly Gly Ser Gly Gly Gly Gly Ser
    210                 215                 220

Gly Gly Gly Gly Ser Gly Gly Gly Gly Ser Lys Ser Ser Ile Ala Ser
225                 230                 235                 240

Phe Phe Phe Ile Ile Gly Leu Ile Ile Gly Leu Phe Leu Val Leu Arg
                245                 250                 255

Val Gly Ile His Leu Cys Ile Lys Leu Lys His Thr Lys Lys Arg Gln
            260                 265                 270

Ile Tyr Thr Asp Ile Glu Met Asn Arg Leu Gly Lys
            275                 280
```

```
<210> SEQ ID NO 57
<211> LENGTH: 16
<212> TYPE: PRT
<213> ORGANISM: Artificial Sequence
<220> FEATURE:
<223> OTHER INFORMATION: Part of discontinuous epitope of COV_S_T2_14
      and Part of discontinuous epitope of COV_S_T2_17

<400> SEQUENCE: 57

Asn Ile Thr Asn Leu Cys Pro Phe Gly Glu Val Phe Asn Ala Thr Lys
1               5                   10                  15
```

```
<210> SEQ ID NO 58
<211> LENGTH: 5
<212> TYPE: PRT
<213> ORGANISM: Artificial Sequence
<220> FEATURE:
<223> OTHER INFORMATION: Part of discontinuous epitope of COV_S_T2_14
      and COV_S_T2_17

<400> SEQUENCE: 58

Lys Lys Ile Ser Asn
1               5
```

```
<210> SEQ ID NO 59
<211> LENGTH: 2
<212> TYPE: PRT
<213> ORGANISM: Artificial Sequence
<220> FEATURE:
<223> OTHER INFORMATION: Part of discontinuous epitope of COV_S_T2_14
      and COV_S_T2_17
```

-continued

```
<400> SEQUENCE: 59

Asn Ile
1

<210> SEQ ID NO 60
<211> LENGTH: 25
<212> TYPE: PRT
<213> ORGANISM: Artificial Sequence
<220> FEATURE:
<223> OTHER INFORMATION: Part of discontinuous epitope of COV_S_T2_15
      and COV_S_T2_18

<400> SEQUENCE: 60

Tyr Asn Ser Thr Phe Phe Ser Thr Phe Lys Cys Tyr Gly Val Ser Pro
1               5                   10                  15

Thr Lys Leu Asn Asp Leu Cys Phe Ser
            20                  25

<210> SEQ ID NO 61
<211> LENGTH: 4
<212> TYPE: PRT
<213> ORGANISM: Artificial Sequence
<220> FEATURE:
<223> OTHER INFORMATION: Part of discontinuous epitope of COV_S_T2_15
      and COV_S_T2_18

<400> SEQUENCE: 61

Asp Asp Phe Met
1

<210> SEQ ID NO 62
<211> LENGTH: 5
<212> TYPE: PRT
<213> ORGANISM: Artificial Sequence
<220> FEATURE:
<223> OTHER INFORMATION: Part of discontinuous epitope of COV_S_T2_15
      and COV_S_T2_18

<400> SEQUENCE: 62

Phe Glu Leu Leu Asn
1               5

<210> SEQ ID NO 63
<211> LENGTH: 7
<212> TYPE: PRT
<213> ORGANISM: Artificial Sequence
<220> FEATURE:
<223> OTHER INFORMATION: Part of discontinuous epitope of COV_S_T2_16

<400> SEQUENCE: 63

Arg Gly Asp Glu Val Arg Gln
1               5

<210> SEQ ID NO 64
<211> LENGTH: 7
<212> TYPE: PRT
<213> ORGANISM: Artificial Sequence
<220> FEATURE:
<223> OTHER INFORMATION: Part of discontinuous epitope of COV_S_T2_16

<400> SEQUENCE: 64

Thr Gly Lys Ile Ala Asp Tyr
1               5

<210> SEQ ID NO 65
<211> LENGTH: 8
```

-continued

```
<212> TYPE: PRT
<213> ORGANISM: Artificial Sequence
<220> FEATURE:
<223> OTHER INFORMATION: Part of discontinuous epitope of COV_S_T2_16

<400> SEQUENCE: 65

Tyr Arg Leu Phe Arg Lys Ser Asn
1               5

<210> SEQ ID NO 66
<211> LENGTH: 6
<212> TYPE: PRT
<213> ORGANISM: Artificial Sequence
<220> FEATURE:
<223> OTHER INFORMATION: Part of discontinuous epitope of COV_S_T2_16

<400> SEQUENCE: 66

Tyr Gln Ala Gly Ser Thr
1               5

<210> SEQ ID NO 67
<211> LENGTH: 20
<212> TYPE: PRT
<213> ORGANISM: Artificial Sequence
<220> FEATURE:
<223> OTHER INFORMATION: Part of discontinuous epitope of COV_S_T2_16

<400> SEQUENCE: 67

Phe Asn Cys Tyr Phe Pro Leu Gln Ser Tyr Gly Phe Gln Pro Thr Asn
1               5                   10                  15

Gly Val Gly Tyr
            20

<210> SEQ ID NO 68
<211> LENGTH: 16
<212> TYPE: PRT
<213> ORGANISM: Artificial Sequence
<220> FEATURE:
<223> OTHER INFORMATION: Part of discontinuous epitope present in
      COV_S_T2_13

<400> SEQUENCE: 68

Asn Ile Thr Asn Leu Cys Pro Phe Gly Glu Val Phe Asn Ala Thr Arg
1               5                   10                  15

<210> SEQ ID NO 69
<211> LENGTH: 5
<212> TYPE: PRT
<213> ORGANISM: Artificial Sequence
<220> FEATURE:
<223> OTHER INFORMATION: Part of discontinuous epitope present in
      COV_S_T2_13

<400> SEQUENCE: 69

Lys Arg Ile Ser Asn
1               5

<210> SEQ ID NO 70
<211> LENGTH: 2
<212> TYPE: PRT
<213> ORGANISM: Artificial Sequence
<220> FEATURE:
<223> OTHER INFORMATION: Part of discontinuous epitope present in
      COV_S_T2_13

<400> SEQUENCE: 70

Asn Leu
```

-continued

1

```
<210> SEQ ID NO 71
<211> LENGTH: 25
<212> TYPE: PRT
<213> ORGANISM: Artificial Sequence
<220> FEATURE:
<223> OTHER INFORMATION: Part of discontinuous epitope present in
      COV_S_T2_13

<400> SEQUENCE: 71

Tyr Asn Ser Thr Ser Phe Ser Thr Phe Lys Cys Tyr Gly Val Ser Pro
1               5                   10                  15

Thr Lys Leu Asn Asp Leu Cys Phe Thr
            20                  25

<210> SEQ ID NO 72
<211> LENGTH: 4
<212> TYPE: PRT
<213> ORGANISM: Artificial Sequence
<220> FEATURE:
<223> OTHER INFORMATION: Part of discontinuous epitope present in
      COV_S_T2_13

<400> SEQUENCE: 72

Asp Asp Phe Thr
1

<210> SEQ ID NO 73
<211> LENGTH: 7
<212> TYPE: PRT
<213> ORGANISM: Artificial Sequence
<220> FEATURE:
<223> OTHER INFORMATION: Part of discontinuous epitope present in
      COV_S_T2_13

<400> SEQUENCE: 73

Thr Gly Val Ile Ala Asp Tyr
1               5

<210> SEQ ID NO 74
<211> LENGTH: 8
<212> TYPE: PRT
<213> ORGANISM: Artificial Sequence
<220> FEATURE:
<223> OTHER INFORMATION: Part of discontinuous epitope present in
      COV_S_T2_13

<400> SEQUENCE: 74

Tyr Arg Ser Leu Arg Lys Ser Lys
1               5

<210> SEQ ID NO 75
<211> LENGTH: 6
<212> TYPE: PRT
<213> ORGANISM: Artificial Sequence
<220> FEATURE:
<223> OTHER INFORMATION: Part of discontinuous epitope present in
      COV_S_T2_13

<400> SEQUENCE: 75

Tyr Ser Pro Gly Gly Lys
1               5

<210> SEQ ID NO 76
<211> LENGTH: 20
<212> TYPE: PRT
```

-continued

<213> ORGANISM: Artificial Sequence
<220> FEATURE:
<223> OTHER INFORMATION: Part of discontinuous epitope present in
      COV_S_T2_13

<400> SEQUENCE: 76

Phe Asn Cys Tyr Tyr Pro Leu Arg Ser Tyr Gly Phe Phe Pro Thr Asn
1               5                   10                  15

Gly Val Gly Tyr
            20

<210> SEQ ID NO 77
<211> LENGTH: 20
<212> TYPE: PRT
<213> ORGANISM: Artificial Sequence
<220> FEATURE:
<223> OTHER INFORMATION: Part of discontinuous epitope present in
      COV_S_T2_13

<400> SEQUENCE: 77

Phe Asn Cys Tyr Tyr Pro Leu Arg Ser Tyr Gly Phe Phe Pro Thr Asn
1               5                   10                  15

Gly Thr Gly Tyr
            20

<210> SEQ ID NO 78
<211> LENGTH: 642
<212> TYPE: DNA
<213> ORGANISM: Artificial Sequence
<220> FEATURE:
<223> OTHER INFORMATION: COV_S_T2_13 encoding nucleic acid

<400> SEQUENCE: 78
agagtggccc ctaccaaaga agtcgtgcgg ttccccaaca tcaccaatct gtgccctttc      60
ggcgaggtgt tcaacgccac cagatttccc tctgtgtacg cctgggagag aaagcggatc     120
agcaactgcg tggccgacta cagcgtgctg tacaacagca ccagcttcag caccttcaag     180
tgctacggcg tgtcacccac caagctgaac gacctgtgct tcaccaacgt gtacgccgac     240
agcttcgtga tcagaggcga cgaagtgcgg cagattgccc ctggacaaac aggcgtgatc     300
gccgattaca actacaagct gcccgacgac ttcaccggct gtgtgatcgc ctggaacacc     360
aacaacctgg acagcaccac cggcggcaac tacaactacc tgtacagaag cctgcggaag     420
tctaagctga agcccttcga gcgggacatc agcagcgaca tctatagccc tggcggcaag     480
ccttgttctg gcgtggaagg cttcaactgc tactaccctc tgcggagcta cggcttcttc     540
cccacaaatg gcgtgggcta ccagccttac agagtggtgg tcctgagctt cgagctgctg     600
aatgcccctg ccacagtgtg tggccctaag ctgtctaccg ac                        642

<210> SEQ ID NO 79
<211> LENGTH: 642
<212> TYPE: DNA
<213> ORGANISM: Artificial Sequence
<220> FEATURE:
<223> OTHER INFORMATION: COV_S_T2_14 encoding nucleic acid

<400> SEQUENCE: 79
agagtggccc ctaccaaaga agtcgtgcgg ttccccaaca tcaccaatct gtgccctttc      60
ggcgaggtgt tcaacgccac caagtttccc tctgtgtacg cctgggagcg caaaaagatc     120
agcaactgcg tggccgacta cagcgtgctg tacaacagca ccagcttcag caccttcaag     180
tgctacggcg tgtcacccac caagctgaac gacctgtgct tcaccaacgt gtacgccgac     240

-continued

```
agcttcgtga tcagaggcga cgaagtgcgg cagattgccc ctggacaaac aggcgtgatc      300
gccgattaca actacaagct gcccgacgac ttcaccggct gtgtgatcgc ctggaacacc      360
aacaacatcg acagcaccac cggcggcaac tacaactacc tgtacagaag cctgcggaag      420
tctaagctga agcccttcga gcgggacatc agcagcgaca tctatagccc tggcggcaag      480
ccttgttctg gcgtggaagg cttcaactgc tactaccctc tgcggagcta cggcttcttc      540
cccacaaatg gcgtgggcta ccagccttac agagtggtgg tcctgagctt cgagctgctg      600
aatgcccctg ccacagtgtg tggccctaag ctgtctaccg ac                        642
```

<210> SEQ ID NO 80
<211> LENGTH: 642
<212> TYPE: DNA
<213> ORGANISM: Artificial Sequence
<220> FEATURE:
<223> OTHER INFORMATION: COV_S_T2_15 encoding nucleic acid

<400> SEQUENCE: 80

```
agagtggccc ctaccaaaga agtcgtgcgg ttccccaaca tcaccaatct gtgccctttc       60
ggcgaggtgt tcaacgccac cagatttccc tctgtgtacg cctgggagag aaagcggatc      120
agcaactgcg tggccgacta cagcgtgctg tacaacagca ccttcttcag caccttta ag    180 tgctacggcg tgtcacccac caagctgaac gacctgtgct tcagcaacgt gtacgccgac      240
agcttcgtga tcagaggcga cgaagtgcgg cagattgccc ctggacaaac aggcgtgatc      300
gccgattaca actacaagct gcccgacgac ttcatgggct gtgtgatcgc ctggaacacc      360
aacaacctgg acagcaccac cggcggcaac tacaactacc tgtacagaag cctgcggaag      420
tctaagctga agcccttcga gcgggacatc agcagcgaca tctatagccc tggcggcaag      480
ccttgttctg gcgtggaagg cttcaactgc tactaccctc tgcggagcta cggcttcttc      540
cccacaaatg gcgtgggcta ccagccttac agagtggtgg tcctgagctt cgagctgctg      600
aatgcccctg ccacagtgtg tggccctaag ctgtctaccg ac                        642
```

<210> SEQ ID NO 81
<211> LENGTH: 642
<212> TYPE: DNA
<213> ORGANISM: Artificial Sequence
<220> FEATURE:
<223> OTHER INFORMATION: COV_S_T2_16 encoding nucleic acid

<400> SEQUENCE: 81

```
agagtggccc ctaccaaaga agtcgtgcgg ttccccaaca tcaccaatct gtgccctttc       60
ggcgaggtgt tcaacgccac cagatttccc tctgtgtacg cctgggagag aaagcggatc      120
agcaactgcg tggccgacta cagcgtgctg tacaacagca ccagcttcag caccttcaag      180
tgctacggcg tgtcacccac caagctgaac gacctgtgct tcaccaacgt gtacgccgac      240
agcttcgtga tcagaggcga cgaagtgcgg cagattgccc ctggacagac aggcaagatc      300
gccgattaca actacaagct gcccgacgac ttcaccggct gtgtgatcgc ctggaacacc      360
aacaacctgg acagcaccac cggcggcaac tacaactacc tgtaccggct gttccggaag      420
tccaacctga agcctttcga gcgggacatc agcagcgaca tctatcaggc cggcagcaca      480
ccttgttctg gcgtggaagg cttcaactgc tacttccac tgcaaagcta cggcttccag       540
cctaccaacg gcgtgggcta ccagccttat agagtggtgg tcctgagctt cgagctgctg      600
aatgcccctg ccacagtgtg tggccctaag ctgtctaccg ac                        642
```

```
<210> SEQ ID NO 82
<211> LENGTH: 642
<212> TYPE: DNA
<213> ORGANISM: Artificial Sequence
<220> FEATURE:
<223> OTHER INFORMATION: COV_S_T2_17 encoding nucleic acid

<400> SEQUENCE: 82
agagtggccc ctaccaaaga agtcgtgcgg ttccccaaca tcaccaatct gtgccctttc      60
ggcgaggtgt tcaacgccac caagtttccc tctgtgtacg cctgggagcg caaaaagatc     120
agcaactgcg tggccgacta cagcgtgctg tacaacagca ccagcttcag caccttcaag     180
tgctacggcg tgtcacccac caagctgaac gacctgtgct tcaccaacgt gtacgccgac     240
agcttcgtga tcagaggcga cgaagtgcgg cagattgccc ctggacaaac aggcgtgatc     300
gccgattaca actacaagct gcccgacgac ttcaccggct gtgtgatcgc ctggaacacc     360
aacaacatcg acagcaccac cggcggcaac tacaactacc tgtacagaag cctgcggaag     420
tctaagctga agcccttcga gcgggacatc agcagcgaca tctatagccc tggcggcaag     480
ccttgttctg gcgtggaagg cttcaactgc tactaccctc tgcggagcta cggcttcttc     540
cccacaaatg gcacaggcta ccagccttac agagtggtgg tcctgagctt cgagctgctg     600
aatgcccctg ccacagtgtg tggccctaag ctgtctaccg ac                        642

<210> SEQ ID NO 83
<211> LENGTH: 642
<212> TYPE: DNA
<213> ORGANISM: Artificial Sequence
<220> FEATURE:
<223> OTHER INFORMATION: COV_S_T2_18 encoding nucleic acid

<400> SEQUENCE: 83
agagtggccc ctaccaaaga agtcgtgcgg ttccccaaca tcaccaatct gtgccctttc      60
ggcgaggtgt tcaacgccac cagatttccc tctgtgtacg cctgggagag aaagcggatc     120
agcaactgcg tggccgacta cagcgtgctg tacaacagca ccttcttcag cacctttaag     180
tgctacggcg tgtcacccac caagctgaac gacctgtgct tcagcaacgt gtacgccgac     240
agcttcgtga tcagaggcga cgaagtgcgg cagattgccc ctggacaaac aggcgtgatc     300
gccgattaca actacaagct gcccgacgac ttcatgggct gtgtgatcgc ctggaacacc     360
aacaacctgg acagcaccac cggcggcaac tacaactacc tgtacagaag cctgcggaag     420
tctaagctga agcccttcga gcgggacatc agcagcgaca tctatagccc tggcggcaag     480
ccttgttctg gcgtggaagg cttcaactgc tactaccctc tgcggagcta cggcttcttc     540
cccacaaatg gcacaggcta ccagccttac agagtggtgg tcctgagctt cgagctgctg     600
aatgcccctg ccacagtgtg tggccctaag ctgtctaccg ac                        642

<210> SEQ ID NO 84
<211> LENGTH: 852
<212> TYPE: DNA
<213> ORGANISM: Artificial Sequence
<220> FEATURE:
<223> OTHER INFORMATION: COV_S_T2_19 encoding nucleic acid

<400> SEQUENCE: 84
agagtggccc ctaccaaaga agtcgtgcgg ttccccaaca tcaccaatct gtgccctttc      60
ggcgaggtgt tcaacgccac cagatttccc tctgtgtacg cctgggagag aaagcggatc     120
agcaactgcg tggccgacta cagcgtgctg tacaacagca ccagcttcag caccttcaag     180
```

-continued

```
tgctacggcg tgtcacccac caagctgaac gacctgtgct tcaccaacgt gtacgccgac      240
agcttcgtga tcagaggcga cgaagtgcgg cagattgccc ctggacaaac aggcgtgatc      300
gccgattaca actacaagct gcccgacgac ttcaccggct gtgtgatcgc ctggaacacc      360
aacaacctgg acagcaccac cggcggcaac tacaactacc tgtacagaag cctgcggaag      420
tctaagctga agcccttcga gcgggacatc agcagcgaca tctatagccc tggcggcaag      480
ccttgttctg gcgtggaagg cttcaactgc tactaccctc tgcggagcta cggcttcttc      540
cccacaaatg gcgtgggcta ccagccttac agagtggtgg tcctgagctt cgagctgctg      600
aatgcccctg ccacagtgtg tggccctaag ctgtctacag atggcggcgg aggatctggc      660
ggaggtggaa gcggaggcgg aggaagcggt ggcggcggat ctaaatcttc tatcgccagc      720
ttcttcttca tcatcggcct gattatcggc ctgttcctgg tgctgagagt gggcatccac      780
ctgtgcatca agctgaaaca caccaagaag cggcaaatct acaccgacat cgagatgaac      840
cggctgggca aa                                                          852
```

```
<210> SEQ ID NO 85
<211> LENGTH: 852
<212> TYPE: DNA
<213> ORGANISM: Artificial Sequence
<220> FEATURE:
<223> OTHER INFORMATION: COV_S_T2_20 encoding nucleic acid

<400> SEQUENCE: 85
agagtggccc ctaccaaaga agtcgtgcgg ttccccaaca tcaccaatct gtgccctttc       60
ggcgaggtgt tcaacgccac caagtttccc tctgtgtacg cctgggagcg caaaaagatc      120
agcaactgcg tggccgacta cagcgtgctg tacaacagca ccagcttcag caccttcaag      180
tgctacggcg tgtcacccac caagctgaac gacctgtgct tcaccaacgt gtacgccgac      240
agcttcgtga tcagaggcga cgaagtgcgg cagattgccc ctggacaaac aggcgtgatc      300
gccgattaca actacaagct gcccgacgac ttcaccggct gtgtgatcgc ctggaacacc      360
aacaacatcg acagcaccac cggcggcaac tacaactacc tgtacagaag cctgcggaag      420
tctaagctga agcccttcga gcgggacatc agcagcgaca tctatagccc tggcggcaag      480
ccttgttctg gcgtggaagg cttcaactgc tactaccctc tgcggagcta cggcttcttc      540
cccacaaatg gcacaggcta ccagccttac agagtggtgg tcctgagctt cgagctgctg      600
aatgcccctg ccacagtgtg tggccctaag ctgtctacag atggcggcgg aggatctggc      660
ggaggtggaa gcggaggcgg aggaagcggt ggcggcggat ctaaatcttc tatcgccagc      720
ttcttcttca tcatcggcct gattatcggc ctgttcctgg tgctgagagt gggcatccac      780
ctgtgcatca agctgaaaca caccaagaag cggcaaatct acaccgacat cgagatgaac      840
cggctgggca aa                                                          852
```